US009938267B2

(12) United States Patent
Li et al.

(10) Patent No.: US 9,938,267 B2
(45) Date of Patent: *Apr. 10, 2018

(54) HETEROCYCLIC INHIBITORS OF GLUTAMINASE

(71) Applicant: Calithera Biosciences, Inc., South San Francisco, CA (US)

(72) Inventors: Jim Li, San Francisco, CA (US); Lijing Chen, Cupertino, CA (US); Bindu Goyal, Fremont, CA (US); Guy Laidig, Woodside, CA (US); Timothy F. Stanton, Daly City, CA (US); Eric B. Sjogren, Mountain View, CA (US)

(73) Assignee: Calithera Biosciences, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/700,796

(22) Filed: Sep. 11, 2017

(65) Prior Publication Data

US 2017/0369485 A1    Dec. 28, 2017

Related U.S. Application Data

(60) Continuation of application No. 14/471,476, filed on Aug. 28, 2014, which is a continuation of application No. 14/051,216, filed on Oct. 10, 2013, now Pat. No. 8,865,718, which is a division of application No. 13/680,582, filed on Nov. 19, 2012, now Pat. No. 8,604,016.

(60) Provisional application No. 61/665,370, filed on Jun. 28, 2012, provisional application No. 61/562,266, filed on Nov. 21, 2011.

(51) Int. Cl.
| | | |
|---|---|---|
| *C07D 417/14* | (2006.01) | |
| *C07D 285/135* | (2006.01) | |
| *C07D 285/125* | (2006.01) | |
| *A61N 7/00* | (2006.01) | |
| *A61N 5/10* | (2006.01) | |
| *A61N 5/00* | (2006.01) | |
| *A61K 45/06* | (2006.01) | |
| *A61K 31/5377* | (2006.01) | |
| *A61K 31/506* | (2006.01) | |
| *A61K 31/501* | (2006.01) | |
| *A61K 31/433* | (2006.01) | |
| *C07D 417/06* | (2006.01) | |
| *A61B 18/02* | (2006.01) | |

(52) U.S. Cl.
CPC .......... *C07D 417/14* (2013.01); *A61B 18/02* (2013.01); *A61K 31/433* (2013.01); *A61K 31/501* (2013.01); *A61K 31/506* (2013.01); *A61K 31/5377* (2013.01); *A61K 45/06* (2013.01); *A61N 5/00* (2013.01); *A61N 5/10* (2013.01); *A61N 7/00* (2013.01); *C07D 285/125* (2013.01); *C07D 285/135* (2013.01); *C07D 417/06* (2013.01)

(58) Field of Classification Search
None
See application file for complete search history.

(56) References Cited

U.S. PATENT DOCUMENTS

| | | |
|---|---|---|
| 6,451,828 B1 | 9/2002 | Newcomb et al. |
| 8,604,016 B2 | 12/2013 | Li et al. |
| 8,865,718 B2 | 10/2014 | Li et al. |
| 9,687,485 B2 | 6/2017 | Steggerda et al. |
| 2005/0260697 A1 | 11/2005 | Wang et al. |
| 2010/0330197 A1 | 12/2010 | Higashiguchi et al. |
| 2012/0302605 A1 | 11/2012 | DeWitt |
| 2013/0109643 A1 | 5/2013 | Riggins et al. |
| 2013/0157998 A1 | 6/2013 | Li et al. |
| 2014/0050699 A1 | 2/2014 | Li et al. |
| 2014/0142081 A1 | 5/2014 | Lemieux et al. |
| 2014/0142146 A1 | 5/2014 | Lemieux et al. |
| 2014/0194421 A1 | 7/2014 | Li et al. |
| 2014/0369961 A1 | 12/2014 | Li et al. |
| 2015/0004134 A1 | 1/2015 | Bennett et al. |
| 2015/0258082 A1 | 9/2015 | Parlati et al. |
| 2016/0010158 A1 | 1/2016 | Wang et al. |
| 2016/0022674 A1 | 1/2016 | Steggerda et al. |
| 2016/0287564 A1 | 10/2016 | Gross et al. |

FOREIGN PATENT DOCUMENTS

| | | |
|---|---|---|
| WO | WO-2011/143160 A2 | 11/2011 |
| WO | WO-2012/006506 A1 | 1/2012 |
| WO | WO-2013/044596 A1 | 4/2013 |
| WO | WO-2013/078123 A1 | 5/2013 |
| WO | WO-2014/039960 A1 | 3/2014 |
| WO | WO-2014/078645 A1 | 5/2014 |
| WO | WO-2014/079136 A1 | 5/2014 |
| WO | WO-2014/079150 A1 | 5/2014 |

(Continued)

OTHER PUBLICATIONS

Chemical Abstract Registry No. 666208-63-5, indexed in the Registry File On STN CAS Online Mar. 22, 2004.*
Borodovsky et al., "5-azacytidine reduces methylation, promotes differentiation and induces tumor regression in a patient-derived IDH1 mutant glioma xenograft," Oncotarget, 4(10): 1737-1737 (Sep. 16, 2013).
CAS RN 1400068-83-8 STN Entry Date Oct. 8, 2012; N,N1-(5,51-(pentane-1,5-diyl)]bis(1,3,4-thiadiazole-5,2-diyl))bis(2-methoxybenzamide).
CAS RN 331234-76-5, STN Entry Date Apr. 13, 2001; N,N1-[thiobis(2,1-ethanediyl-1,3,4-thiadiazole-5,2-diyl)]bis-1H-1,2,4-triazole-3-carboxmide.
Chemical Abstract Registry No. 296888-91-0, indexed in the Registry File on STN CAS Online Oct. 18, 2000.

(Continued)

*Primary Examiner* — Alicia L Otton
*Assistant Examiner* — Po-Chih Chen
(74) *Attorney, Agent, or Firm* — Foley Hoag LLP; David P. Halstead

(57) ABSTRACT

The invention relates to novel heterocyclic compounds and pharmaceutical preparations thereof. The invention further relates to methods of treatment using the novel heterocyclic compounds of the invention.

21 Claims, 1 Drawing Sheet

(56) References Cited

FOREIGN PATENT DOCUMENTS

| WO | WO-2014/081925 A1 | 5/2014 |
|---|---|---|
| WO | WO-2014/089048 A1 | 6/2014 |
| WO | WO-2015/061432 A1 | 4/2015 |
| WO | WO-2015/061752 A1 | 4/2015 |
| WO | WO-2015/138902 A1 | 9/2015 |
| WO | WO-2015/192014 A1 | 12/2015 |
| WO | WO-2016/004418 A1 | 1/2016 |
| WO | WO-2016/014690 A1 | 1/2016 |
| WO | WO-2016/022969 A1 | 2/2016 |
| WO | WO-2016/054388 A1 | 4/2016 |
| WO | WO-2016/077632 A2 | 5/2016 |
| WO | WO-2016/160980 A1 | 10/2016 |
| WO | WO-2016/164401 A1 | 10/2016 |

OTHER PUBLICATIONS

Costello et al., "Evidence for changes in RREB-1, ZIP3, and zinc in the early development of pancreatic adenocarcinoma," J Gastrointest Cancer, 43:570-8 (2012).
Dai et al., "Studies on the novel a-glucosidase inhibitory activity and structure-activity relationships for andrographolide analogues," Bioorg Med Chem Lett, 16:2710-13 (2006).
DeLabarre B. a et al., "Full-Length Human Glutaminase in Complex with an Allosteric Inhibitor", Biochem, 50:1-27 (2011).
Extended European Search Report from European Application No. 15761424.9 dated Jul. 31, 2017.
Gehlen, H., et al. "Uber die Acylierung der 2-Amino-5-(alkyl, aryl)-1.3.4-oxidazole," Leibeigs Ann. Chem. 703: 131-135 (1967).
Gross et al., "Antitumor Activity of the Glutaminase Inhibitor CB-839 in Triple-Negative Breast Cancer", Mol. Cancer Ther., 13(4):890-901 (2014).
Hensley et al., "Glutamine and cancer: Cell biology, physiology, and clinical opportunities," J Clin Investig, 123(9):3678-84 (2013).
Holliday et al., "Choosing the right cell line for breast cancer research," Breast Cancer Res, 13:215 (2011).
Horig et al., "From bench to clinic and back: Perspective on the 1st IQPC Translational Research conference", Journal of Translational Medicine, vol. 2, p. 44 (2004).
International Search Report and Written Opinion for Application No. PCT/US2016/055316 dated Jan. 12, 2017.
International Search Report and Written Opinion for PCT/US2015/035577 dated Sep. 20, 2015.
International Search Report for Application No. PCT/US2016/026127, dated Jul. 27, 2016.
International Search Report for PCT/US2012/065816 dated Feb. 1, 2013.
International Search Report from International Application No. PCT/US2013/070277 dated Feb. 13, 2014.
International Search Report from International Application No. PCT/US2013/072830 dated Mar. 4, 2014.
Ito et al., "A medium-term rat liver bioassay for rapid in vivo detection of carcinogenic potential of chemicals," Cancer Science, 94(1):3-8 (2003).
Jacque, et al., "Targeting glutaminolysis has antileukemic activity in acute myeloid leukemia and synergizes with BCL-2 inhibition," Blood, 126(11): 1346-1356 (2015).
Johnson et al., "Relationships between drug activity and NCI preclinical in vitro and in vivo models and early clinical trials," Brit J Cancer, 84(10):1424-31 (2001).
Kim, A., "Clinical impact of gene expression profiling on oncology diagnosis, prognosis, and treatment," Combinatorial Chem & High Throughput Screening, 7:183-206 (2004).
Kung et al., "Glutamine synthetase is a genetic determinant of cell type-specific glutamine independence in breast epithelia," PLOS Genetics, 7(8):e1002229 (2011).
Lacy et al., "Pomalidomide (CC4047) plus low dose dexamethasone (Pom/dex) is active and well tolerated in lenalidomide refractory multiple myeloma (MM)," Leukemia, 24(11): 1934-1939 (2010).
Liu et al., "Screening for EGFR and KRAS Mutations in Non-Small Cell Lung Carcinomas using DNA Extraction by Hydrothermal Pressure Coupled with PCR-based Direct Sequencing," Int J Clin Exp Pathol, 6(9): 1860-1689 (2013).
Lopez-Girona et al., "Cereblon is a direct protein target for immunomodulatory and antiproliferative activities of lenalidomide and pomalidomide," Leukemia, 26(11):2326-2335 (2012).
Martin et al., "Do structurally similar molecules have similar biological activity?" J Med Chem, 45:4350-8 (2002).
McCleland, et al., "Lactate dehydrogenase B is required for the growth of KRAS-Dependent lung adenocarcinomas," Clin Cancer Res, 19(4): 773-784 (2013).
Medina, M., "Glutamine and cancer," J Nutr, 131(9 Suppl):2539S-42S (2001).
Nars et al., "Immunomodulatory effects of low dose chemotherapy and perspectives of its combination with immunotherapy," Int J Cancer, 132(11):2471-2478 (2013).
Osol, A. [Editor]. "Chapter 27: Structure-activity relationship and drug design," Remington's Pharmaceutical Sciences (Sixteenth Edition). 1980. pp. 420-435.
Pajic et al., "Cell cycle activation by c-myc in a Burkitt's lymphoma model cell ine", International Journal of Cancer, vol. 87, pp. 787-793 (2000).
Parlati et al., "Antitumor Activity of the Glutaminase Inhibitor CB-839 in Hematological Malignances", 55th ASH Annual Meeting and Exposition, Dec. 9, 2013, New Orleans, LA, abstract No. 4226.
Parlati et al., "Glutaminase inhibitor CB-839 synergizes with pomalidomide in preclinical multiple myeloma models," American Society of Hematology Annual Meeting—Dec. 6-9, 2014.
Prat et al., "Phenotypic and molecular characterization of the claudin-low intrinsic subtype of breast cancer," Breast Cancer Res, 12(5):R68 (2010).
Rajagopalan K.N. et al., "Role of Glutamine in Cancer: Therapeutic and Imaging Implications", Journal of Nuclear Medicine, vol. 52, pp. 1005-1008 (2011).
Robinson et al., "Novel mechanism of inhibition of rat kidney-type glutaminase by bis-2-(5-phenylacetamido-1,2,4-thiadiazol-2-yl)ethyl sulfide (BPTES)," Biochem. J., 406:407-414 (2007).
Schäfer et al., "Failure is an option: learning from unsuccessful proof-of-concept trials", Drug Discovery Today, vol. 13, pp. 913-916 (2008).
Seltzer et al., "Inhibition of glutaminase preferentially slows growth of glioma cells with mutant IDH1", Cancer Research, vol. 70, pp. 8981-8987 (2010).
Sharma et al., "Anti-myeloma activity of a novel glutaminase inhibitor CB-839," Blood, vol. 124(21): 4226 (2014).
Shimano Y. et al., "Synthesis of Poly(diacylthiosemicarbazide)s from Diacylisothiocyanates and Dihydrazides, and Their Thermal Cyclodehydration" Kobunshi Ronbunshu, vol. 37, No. 2, pp. 131-137 (1980).
Shukla, K., et al, "Design, Synthesis and Pharmacological Evaluation of Bis-2-(5-phenylacetamido-1-2, 4-thiadiazol-2-yl)ethyl 1 sulphide 3 (BPTES) Analogs as Glutaminase Inhibitors", Journal of Medicinal Chemistry, vol. 55, No. 23, pp. 10551-10563 (2012).
Simpson et al., "Modifying metabollically sensitive histone marks by inhibiting glutamine metabolism affects gene expression and alters cancer cell phenotype," Epigenetics, 7(12):1413-20 (2012).
Sporn et al., "Chemoprevention of cancer," Carcinogenesis, 21(3):525-30 (2000).
Thangavelu, K. et al., "Structural basis for the allosteric inhibitory mechanism of human kidney-type glutaminase (KGA) and its regulation by Raf-Mek-Erk signaling in cancer cell metabolism", Proceedings of the National Acedemy of Sciences of the United States of America, vol. 109, No. 20, pp. 7705-7710 (2012).
Thoppil et al., "Terpenoids as potential chemopreventive and therapeutic agents in liver cancer," World J Hepatol, 3(9):228-249 (2011).
Tseng, et al., "The synthesis of daidzein derivatives," J Natural Taiwan Normal University, 30: 537-545 (1985).
Voskoglou-Nomikos et al., "Clinical predictive value of the in vitro cell line, human xenograft, and mouse allograft preclinical cancer models," Clin Cancer Res, 9:4227-39 (2003).
Wang et al., "Targeting mitochondrial glutaminase activity inhibits oncogenic transformation," Cancer Cell, 18(3):207-19 (2010).

(56) References Cited

OTHER PUBLICATIONS

Written Opinion of the International Searching Authority for Application No. PCT/US2016/026127, dated Jul. 27, 2016.
Zimmerman, et al., "Allosteric glutaminase inhibitors based on a 1,4-Di(5-amino-1,3,4-thiadiazol-2-yl) butane scaffold," ACS Med Chem Lett, 7(5): 520-524 (2016).

* cited by examiner

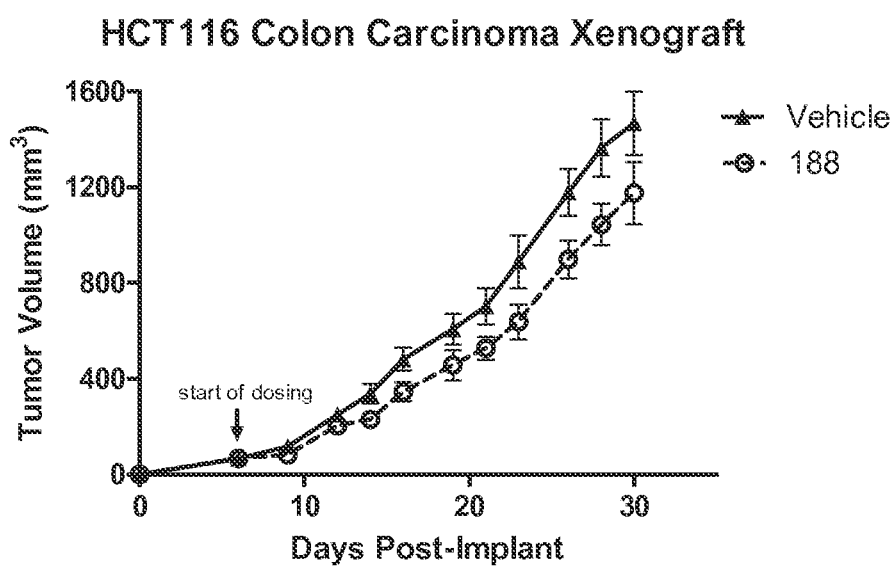

HETEROCYCLIC INHIBITORS OF GLUTAMINASE

RELATED APPLICATIONS

This application is a continuation of U.S. application Ser. No. 14/471,476, filed Aug. 28, 2014, which is a continuation of U.S. application Ser. No. 14/051,216, filed Oct. 10, 2013, which is a divisional of U.S. application Ser. No. 13/680,582, filed Nov. 19, 2012, which claims the benefit of priority to U.S. Provisional Patent Application No. 61/562,266, filed Nov. 21, 2011, and U.S. Provisional Patent Application No. 61/665,370, filed Jun. 28, 2012. All the teachings of the above-referenced applications are incorporated herein by reference.

BACKGROUND

Glutamine supports cell survival, growth and proliferation through metabolic and non-metabolic mechanisms. In actively proliferating cells, the metabolism of glutamine to lactate, also referred to as "glutaminolysis" is a major source of energy in the form of NADPH. The first step in glutaminolysis is the deamination of glutamine to form glutamate and ammonia, which is catalyzed by the glutaminase enzyme. Thus, deamination via glutaminase is a control point for glutamine metabolism.

Ever since Warburg's observation that ascites tumor cells exhibited high rates of glucose consumption and lactate secretion in the presence of oxygen (Warburg, 1956), researchers have been exploring how cancer cells utilize metabolic pathways to be able to continue actively proliferating. Several reports have demonstrated how glutamine metabolism supports macromolecular synthesis necessary for cells to replicate (Curthoys, 1995; DeBardinis, 2008).

Thus, glutaminase has been theorized to be a potential therapeutic target for the treatment of diseases characterized by actively proliferating cells, such as cancer. The lack of suitable glutaminase inhibitors has made validation of this target impossible. Therefore, the creation of glutaminase inhibitors that are specific and capable of being formulated for in vivo use could lead to a new class of therapeutics.

SUMMARY OF INVENTION

The present invention provides a compound of formula I,

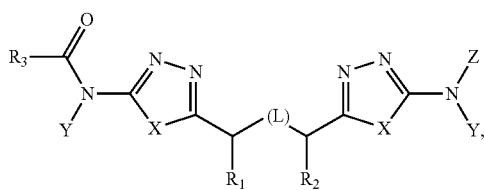

(I)

or a pharmaceutically acceptable salt thereof, wherein:
L represents $CH_2SCH_2$, $CH_2CH_2$, $CH_2CH_2CH_2$, $CH_2$, $CH_2S$, $SCH_2$, $CH_2NHCH_2$, $CH=CH$, or

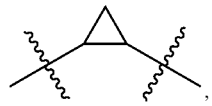 [SMILES: *C1CC1*]

preferably $CH_2CH_2$, wherein any hydrogen atom of a CH or $CH_2$ unit may be replaced by alkyl or alkoxy, any hydrogen of an NH unit may be replaced by alkyl, and any hydrogen atom of a $CH_2$ unit of $CH_2CH_2$, $CH_2CH_2CH_2$ or $CH_2$ may be replaced by hydroxy;

X, independently for each occurrence, represents S, O or CH=CH, preferably S or CH=CH, wherein any hydrogen atom of a CH unit may be replaced by alkyl;

Y, independently for each occurrence, represents H or $CH_2O(CO)R_7$;

$R_7$, independently for each occurrence, represents H or substituted or unsubstituted alkyl, alkoxy, aminoalkyl, alkylaminoalkyl, heterocyclylalkyl, arylalkyl, or heterocyclylalkoxy;

Z represents H or $R_3(CO)$;

$R_1$ and $R_2$ each independently represent H, alkyl, alkoxy or hydroxy;

$R_3$, independently for each occurrence, represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or $C(R_8)(R_9)(R_{10})$, $N(R_4)(R_5)$ or $OR_6$, wherein any free hydroxyl group may be acylated to form $C(O)R_7$;

$R_4$ and $R_5$ each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$;

$R_6$, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$; and $R_8$, $R_9$ and $R_{10}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or $R_8$ and $R_9$ together with the carbon to which they are attached, form a carbocyclic or heterocyclic ring system, wherein any free hydroxyl group may be acylated to form $C(O)R_7$, and wherein at least two of $R_8$, $R_9$ and $R_{10}$ are not H.

In certain embodiments, the present invention provides a pharmaceutical preparation suitable for use in a human patient, comprising an effective amount of any of the compounds described herein (e.g., a compound of the invention, such as a compound of formula I), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for intravenous use in a human patient.

The present invention further provides methods of treating or preventing cancer, immunological or neurological diseases as described herein, comprising administering a compound of the invention.

DETAILED DESCRIPTION OF THE DRAWINGS

FIG. 1 shows that intraperitoneal administration of compound 188 to mice results in reduced tumor size in a HCT116 colon carcinoma xenograft model.

DETAILED DESCRIPTION OF THE INVENTION

The present invention provides a compound of formula I,

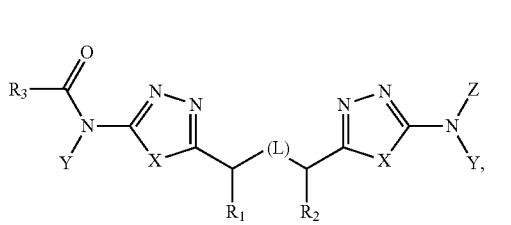
(I)

or a pharmaceutically acceptable salt thereof, wherein:
L represents $CH_2SCH_2$, $CH_2CH_2$, $CH_2CH_2CH_2$, $CH_2$, $CH_2S$, $SCH_2$, $CH_2NHCH_2$, $CH{=}CH$, or

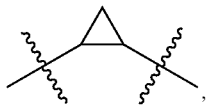 [SMILES: *C1CC1*]
, preferably $CH_2CH_2$, wherein any hydrogen atom of a CH or $CH_2$ unit may be replaced by alkyl or alkoxy, any hydrogen of an NH unit may be replaced by alkyl, and any hydrogen atom of a $CH_2$ unit of $CH_2CH_2$, $CH_2CH_2CH_2$ or $CH_2$ may be replaced by hydroxy;
X, independently for each occurrence, represents S, O or $CH{=}CH$, preferably S or $CH{=}CH$, wherein any hydrogen atom of a CH unit may be replaced by alkyl;
Y, independently for each occurrence, represents H or $CH_2O(CO)R_7$;
$R_7$, independently for each occurrence, represents H or substituted or unsubstituted alkyl, alkoxy, aminoalkyl, alkylaminoalkyl, heterocyclylalkyl, arylalkyl, or heterocyclylalkoxy;
Z represents H or $R_3(CO)$;
$R_1$ and $R_2$ each independently represent H, alkyl, alkoxy or hydroxy;
$R_3$, independently for each occurrence, represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or $C(R_8)(R_9)(R_{10})$, $N(R_4)(R_5)$ or $OR_6$, wherein any free hydroxyl group may be acylated to form $C(O)R_7$;
$R_4$ and $R_5$ each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$;
$R_6$, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$; and
$R_8$, $R_9$ and $R_{10}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or $R_8$ and $R_9$ together with the carbon to which they are attached, form a carbocyclic or heterocyclic ring system, wherein any free hydroxyl group may be acylated to form $C(O)R_7$, and wherein at least two of $R_8$, $R_9$ and $R_{10}$ are not H.

In certain embodiments wherein alkyl, hydroxyalkyl, amino, acylamino, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl are substituted, they are substituted with one or more substituents selected from substituted or unsubstituted alkyl, such as perfluoroalkyl (e.g., trifluoromethyl), alkenyl, alkoxy, alkoxyalkyl, aryl, aralkyl, arylalkoxy, aryloxy, aryloxyalkyl, hydroxyl, halo, alkoxy, such as perfluoroalkoxy (e.g., trifluoromethoxy), alkoxyalkoxy, hydroxyalkyl, hydroxyalkylamino, hydroxyalkoxy, amino, aminoalkyl, alkylamino, aminoalkylalkoxy, aminoalkoxy, acylamino, acylaminoalkyl, such as perfluoro acylaminoalkyl (e.g., trifluoromethylacylaminoalkyl), acyloxy, cycloalkyl, cycloalkylalkyl, cycloalkylalkoxy, heterocyclyl, heterocyclylalkyl, heterocyclyloxy, heterocyclylalkoxy, heteroaryl, heteroarylalkyl, heteroarylalkoxy, heteroaryloxy, heteroaryloxyalkyl, heterocyclylaminoalkyl, heterocyclylaminoalkoxy, amido, amidoalkyl, amidine, imine, oxo, carbonyl (such as carboxyl, alkoxycarbonyl, formyl, or acyl, including perfluoroacyl (e.g., $C(O)CF_3$)), carbonylalkyl (such as carboxyalkyl, alkoxycarbonylalkyl, formylalkyl, or acylalkyl, including perfluoroacylalkyl (e.g., -alkylC(O)CF$_3$)), carbamate, carbamatealkyl, urea, ureaalkyl, sulfate, sulfonate, sulfamoyl, sulfone, sulfonamide, sulfonamidealkyl, cyano, nitro, azido, sulfhydryl, alkylthio, thiocarbonyl (such as thioester, thioacetate, or thioformate), phosphoryl, phosphate, phosphonate or phosphinate.

In certain embodiments, L represents $CH_2SCH_2$, $CH_2CH_2$, $CH_2CH_2CH_2$, $CH_2$, $CH_2S$, $SCH_2$, or $CH_2NHCH_2$, wherein any hydrogen atom of a $CH_2$ unit may be replaced by alkyl or alkoxy, and any hydrogen atom of a $CH_2$ unit of $CH_2CH_2$, $CH_2CH_2CH_2$ or $CH_2$ may be replaced by hydroxyl. In certain embodiments, L represents $CH_2SCH_2$, $CH_2CH_2$, $CH_2S$ or $SCH_2$. In certain embodiments, L represents $CH_2CH_2$. In certain embodiments, L is not $CH_2SCH_2$.

In certain embodiments, Y represents H.

In certain embodiments, X represents S or $CH{=}CH$. In certain embodiments, one or both X represents $CH{=}CH$. In certain embodiments, each X represents S. In certain embodiments, one X represents S and the other X represents $CH{=}CH$.

In certain embodiments, Z represents $R_3(CO)$. In certain embodiments wherein Z is $R_3(CO)$, each occurrence of $R_3$ is not identical (e.g., the compound of formula I is not symmetrical).

In certain embodiments, $R_1$ and $R_2$ each represent H.

In certain embodiments, $R_3$ represents arylalkyl, heteroarylalkyl, cycloalkyl or heterocycloalkyl. In certain embodiments, $R_3$ represents $C(R_8)(R_9)(R_{10})$, wherein $R_8$ represents aryl, arylalkyl, heteroaryl or heteroarylalkyl, such as aryl, arylalkyl or heteroaryl, $R_9$ represents H, and $R_{10}$ represents hydroxy, hydroxyalkyl, alkoxy or alkoxyalkyl, such as hydroxy, hydroxyalkyl or alkoxy.

In certain embodiments, L represents $CH_2SCH_2$, $CH_2CH_2$, $CH_2S$ or $SCH_2$, such as $CH_2CH_2$, $CH_2S$ or $SCH_2$, Y represents H, X represents S, Z represents $R_3(CO)$, $R_1$ and $R_2$ each represent H, and each $R_3$ represents arylalkyl, heteroarylalkyl, cycloalkyl or heterocycloalkyl. In certain such embodiments, each occurrence of $R_3$ is identical.

In certain embodiments, L represents $CH_2SCH_2$, $CH_2CH_2$, $CH_2S$ or $SCH_2$, Y represents H, X represents S, Z represents $R_3(CO)$, $R_1$ and $R_2$ each represent H, and each $R_3$ represents $C(R_8)(R_9)(R_{10})$, wherein $R_8$ represents aryl, arylalkyl, heteroaryl or heteroarylalkyl, such as aryl, arylalkyl or heteroaryl, $R_9$ represents H, and $R_{10}$ represents hydroxy, hydroxyalkyl, alkoxy or alkoxyalkyl, such as hydroxy, hydroxyalkyl or alkoxy. In certain such embodiments, each occurrence of $R_3$ is identical.

In certain embodiments, L represents $CH_2CH_2$, Y represents H, X represents S or CH=CH, Z represents $R_3(CO)$, $R_1$ and $R_2$ each represent H, and each $R_3$ represents substituted or unsubstituted arylalkyl, heteroarylalkyl, cycloalkyl or heterocycloalkyl. In certain such embodiments, each X represents S. In other embodiments, one or both occurrences of X represents CH=CH, such as one occurrence of X represents S and the other occurrence of X represents CH=CH. In certain embodiments of the foregoing, each occurrence of $R_3$ is identical. In other embodiments of the foregoing wherein one occurrence of X represents S and the other occurrence of X represents CH=CH, the two occurrences of $R_3$ are not identical.

In certain embodiments, L represents $CH_2CH_2$, Y represents H, X represents S, Z represents $R_3(CO)$, $R_1$ and $R_2$ each represent H, and each $R_3$ represents $C(R_8)(R_9)(R_{10})$, wherein $R_8$ represents aryl, arylalkyl or heteroaryl, $R_9$ represents H, and $R_{10}$ represents hydroxy, hydroxyalkyl or alkoxy. In certain such embodiments, $R_8$ represents aryl and $R_{10}$ represents hydroxyalkyl. In certain such embodiments, each occurrence of $R_3$ is identical.

In certain embodiments wherein L represents $CH_2$, $CH_2CH_2CH_2$ or $CH_2CH_2$, X represents O, and Z represents $R_3(CO)$, both $R_3$ groups are not alkyl, such as methyl, or $C(R_8)(R_9)(R_{10})$, wherein $R_8$, $R_9$ and $R_{10}$ are each independently hydrogen or alkyl.

In certain embodiments wherein L represents $CH_2CH_2$, X represents S, and Z represents $R_3(CO)$, both $R_3$ groups are not phenyl or heteroaryl, such as 2-furyl.

In certain embodiments wherein L represents $CH_2CH_2$, X represents O, and Z represents $R_3(CO)$, both $R_3$ groups are not $N(R_4)(R_5)$ wherein $R_4$ is aryl, such as phenyl, and $R_5$ is H.

In certain embodiments wherein L represents $CH_2SCH_2$, X represents S, and Z represents $R_3(CO)$, both $R_3$ groups are not aryl, such as optionally substituted phenyl, aralkyl, such as benzyl, heteroaryl, such as 2-furyl, 2-thienyl or 1,2,4-trizole, substituted or unsubstituted alkyl, such as methyl, chloromethyl, dichloromethyl, n-propyl, n-butyl, t-butyl or hexyl, heterocyclyl, such as pyrimidine-2,4(1H,3H)-dione, or alkoxy, such as methoxy, pentyloxy or ethoxy.

In certain embodiments wherein L represents $CH_2SCH_2$, X represents S, and Z represents $R_3(CO)$, both $R_3$ groups are not $N(R_4)(R_5)$ wherein $R_4$ is aryl, such as substituted or unsubstituted phenyl (e.g., phenyl, 3-tolyl, 4-tolyl, 4-bromophenyl or 4-nitrophenyl), and $R_5$ is H.

In certain embodiments wherein L represents $CH_2CH_2CH_2$, X represents S, and Z represents $R_3(CO)$, both $R_3$ groups are not alkyl, such as methyl, ethyl, or propyl, cycloalkyl, such as cyclohexyl, or $C(R_8)(R_9)(R_{10})$, wherein any of $R_8$, $R_9$ and $R_{10}$ together with the C to which they are attached, form any of the foregoing.

In certain embodiments, the compound is not one of the following:

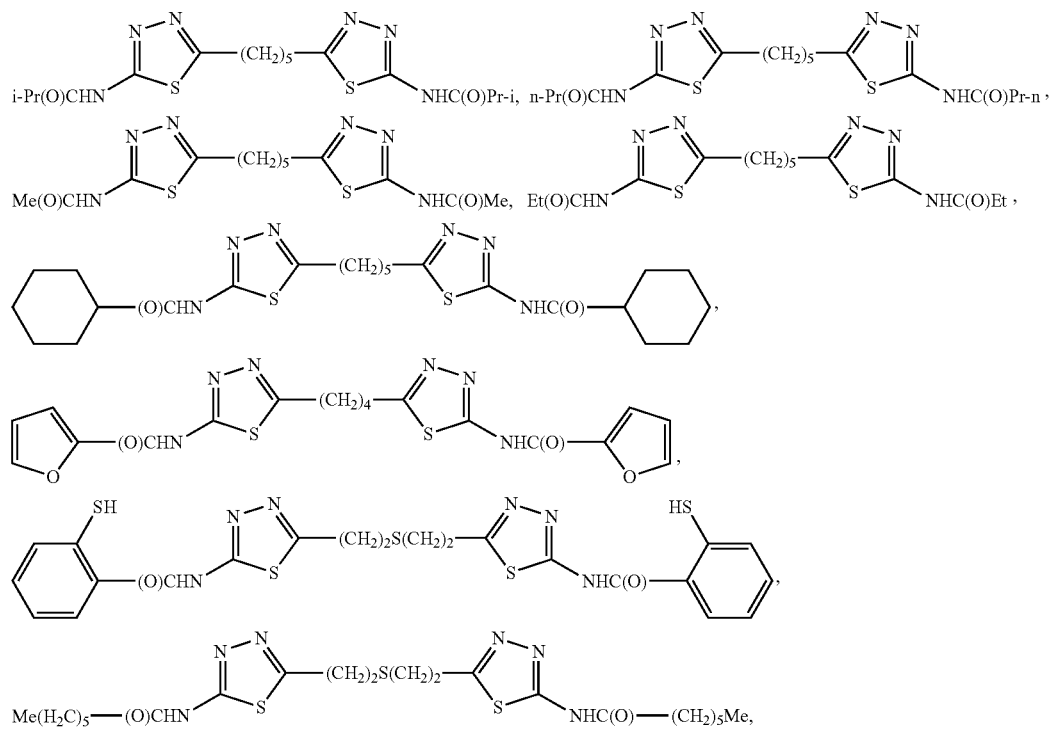

-continued
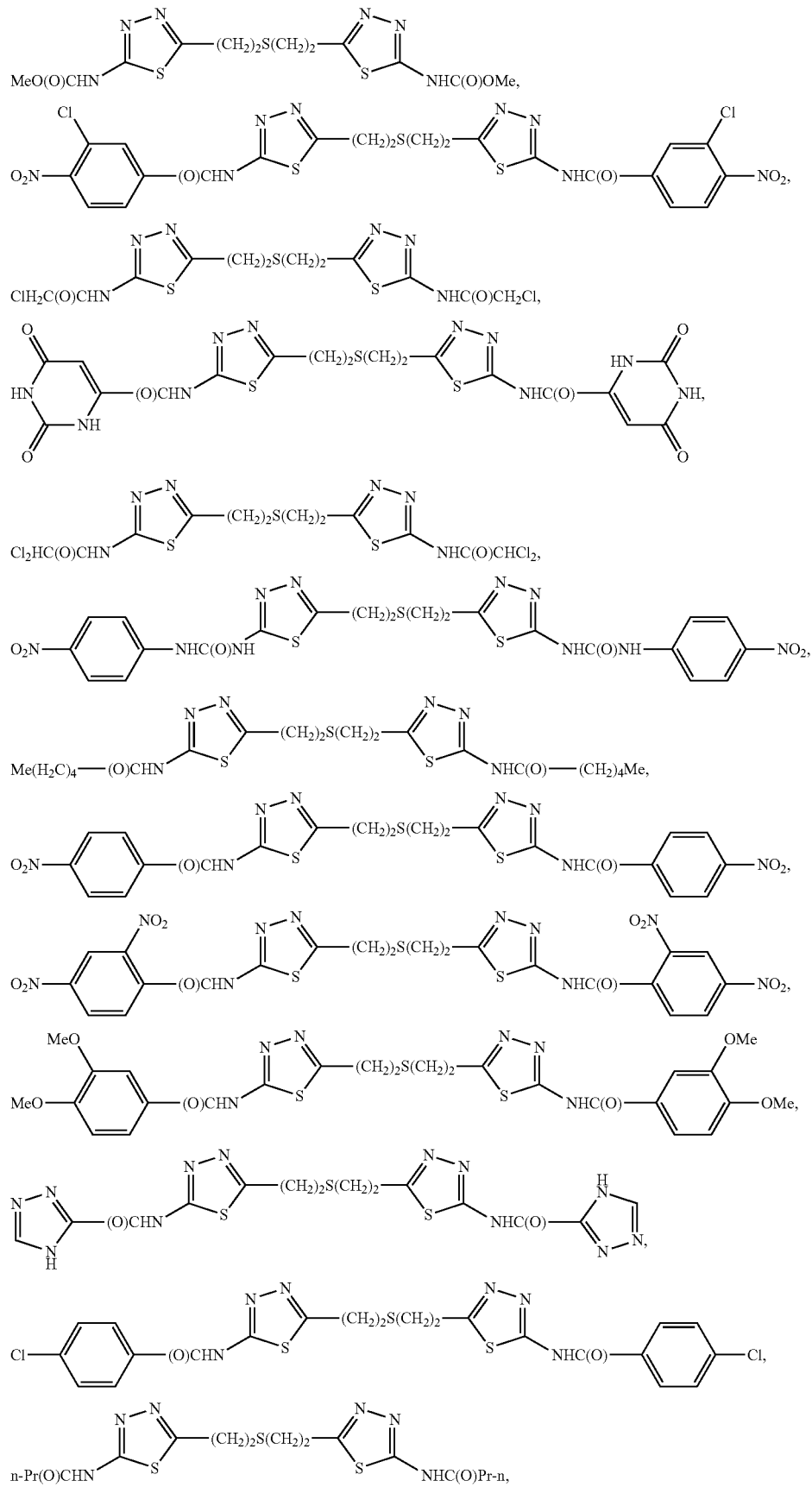

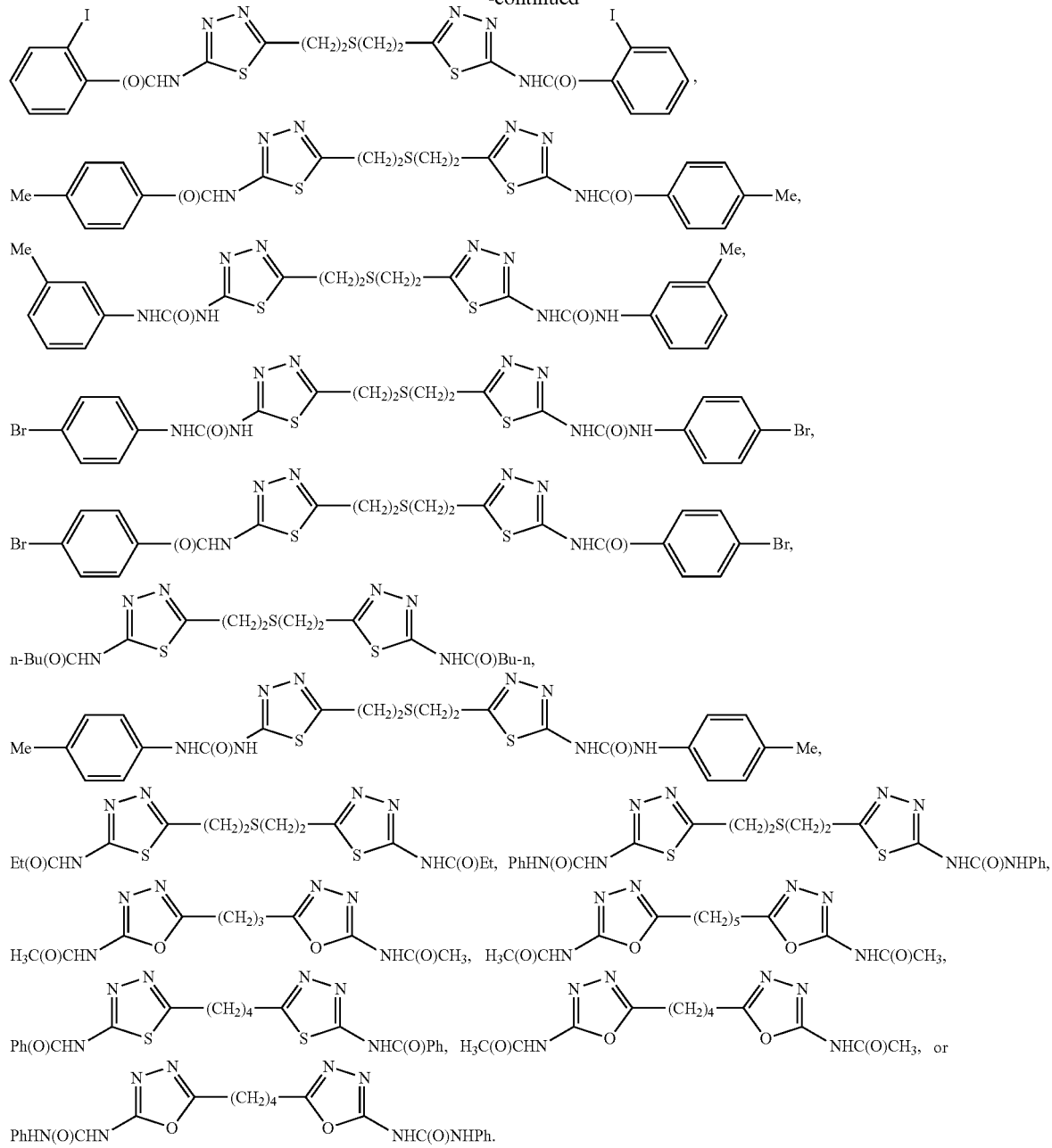

The present invention further provides a compound of formula Ia,

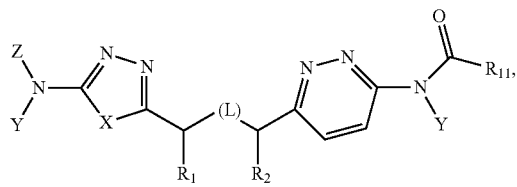

or a pharmaceutically acceptable salt thereof, wherein:
L represents $CH_2SCH_2$, $CH_2CH_2$, $CH_2CH_2CH_2$, $CH_2$, $CH_2S$, $SCH_2$, $CH_2NHCH_2$, $CH=CH$, or

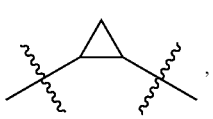

preferably $CH_2CH_2$, wherein any hydrogen atom of a CH or $CH_2$ unit may be replaced by alkyl or alkoxy, any hydrogen of an NH unit may be replaced by alkyl, and any hydrogen atom of a $CH_2$ unit of $CH_2CH_2$, $CH_2CH_2CH_2$ or $CH_2$ may be replaced by hydroxy;

X represents S, O or CH=CH, preferably S or CH=CH, wherein any hydrogen atom of a CH unit may be replaced by alkyl;

Y, independently for each occurrence, represents H or CH$_2$O(CO)R$_7$;

R$_7$, independently for each occurrence, represents H or substituted or unsubstituted alkyl, alkoxy, aminoalkyl, alkylaminoalkyl, heterocyclylalkyl, arylalkyl, or heterocyclylalkoxy;

Z represents H or R$_3$(CO);

R$_1$ and R$_2$ each independently represent H, alkyl, alkoxy or hydroxy, preferably H;

R$_3$ represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or C(R$_8$)(R$_9$)(R$_{10}$), N(R$_4$)(R$_5$) or OR$_6$, wherein any free hydroxyl group may be acylated to form C(O)R$_7$;

R$_4$ and R$_5$ each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form C(O)R$_7$;

R$_6$, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form C(O)R$_7$; and R$_8$, R$_9$ and R$_{10}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or R$_8$ and R$_9$ together with the carbon to which they are attached, form a carbocyclic or heterocyclic ring system, wherein any free hydroxyl group may be acylated to form C(O)R$_7$, and wherein at least two of R$_8$, R$_9$ and R$_{10}$ are not H;

R$_{11}$ represents substituted or unsubstituted aryl, arylalkyl, aryloxy, aryloxyalkyl, heteroaryl, heteroarylalkyl, heteroaryloxy, or heteroaryloxyalkyl, or C(R$_{12}$)(R$_{13}$)(R$_{14}$), N(R$_4$)(R$_{14}$) or OR$_{14}$, wherein any free hydroxyl group may be acylated to form C(O)R$_7$;

R$_{12}$ and R$_{13}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form C(O)R$_7$, and wherein both of R$_{12}$ and R$_{13}$ are not H; and R$_{14}$ represents substituted or unsubstituted aryl, arylalkyl, aryloxy, aryloxyalkyl, heteroaryl, heteroarylalkyl, heteroaryloxy, or heteroaryloxyalkyl.

In certain embodiments wherein alkyl, hydroxyalkyl, amino, acylamino, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl are substituted, they are substituted with one or more substituents selected from substituted or unsubstituted alkyl, such as perfluoroalkyl (e.g., trifluoromethyl), alkenyl, alkoxy, alkoxyalkyl, aryl, aralkyl, arylalkoxy, aryloxy, aryloxyalkyl, hydroxyl, halo, alkoxy, such as perfluoroalkoxy (e.g., trifluoromethylalkoxy), alkoxyalkoxy, hydroxyalkyl, hydroxyalkylamino, hydroxyalkoxy, amino, aminoalkyl, alkylamino, aminoalkylalkoxy, aminoalkoxy, acylamino, acylaminoalkyl, such as perfluoro acylaminoalkyl (e.g., trifluoromethylacylaminoalkyl), acyloxy, cycloalkyl, cycloalkylalkyl, cycloalkylalkoxy, heterocyclyl, heterocyclylalkyl, heterocyclyloxy, heterocyclylalkoxy, heteroaryl, heteroarylalkyl, heteroarylalkoxy, heteroaryloxy, heteroaryloxyalkyl, heterocyclylaminoalkyl, heterocyclylaminoalkoxy, amido, amidoalkyl, amidine, imine, oxo, carbonyl (such as carboxyl, alkoxycarbonyl, formyl, or acyl, including perfluoroacyl (e.g., C(O)CF$_3$)), carbonylalkyl (such as carboxyalkyl, alkoxycarbonylalkyl, formylalkyl, or acylalkyl, including perfluoroacylalkyl (e.g., -alkylC(O)CF$_3$)), carbamate, carbamatealkyl, urea, ureaalkyl, sulfate, sulfonate, sulfamoyl, sulfone, sulfonamide, sulfonamidealkyl, cyano, nitro, azido, sulfhydryl, alkylthio, thiocarbonyl (such as thioester, thioacetate, or thioformate), phosphoryl, phosphate, phosphonate or phosphinate.

In certain embodiments, R$_{11}$ represents substituted or unsubstituted arylalkyl, such as substituted or unsubstituted benzyl.

In certain embodiments, L represents CH$_2$SCH$_2$, CH$_2$CH$_2$, CH$_2$CH$_2$CH$_2$, CH$_2$, CH$_2$S, SCH$_2$, or CH$_2$NHCH$_2$, wherein any hydrogen atom of a CH$_2$ unit may be replaced by alkyl or alkoxy, and any hydrogen atom of a CH$_2$ unit of CH$_2$CH$_2$, CH$_2$CH$_2$CH$_2$ or CH$_2$ may be replaced by hydroxyl. In certain embodiments, L represents CH$_2$SCH$_2$, CH$_2$CH$_2$, CH$_2$S or SCH$_2$, preferably CH$_2$CH$_2$. In certain embodiments, L is not CH$_2$SCH$_2$.

In certain embodiments, each Y represents H. In other embodiments, at least one Y is CH$_2$O(CO)R$_7$.

In certain embodiments, X represents S or CH=CH. In certain embodiments, X represents S.

In certain embodiments, R$_1$ and R$_2$ each represent H.

In certain embodiments, Z represents R$_3$(CO). In certain embodiments wherein Z is R$_3$(CO), R$_3$ and R$_{11}$ are not identical (e.g., the compound of formula I is not symmetrical).

In certain embodiments, Z represents R$_3$(CO) and R$_3$ represents arylalkyl, heteroarylalkyl, cycloalkyl or heterocycloalkyl. In certain embodiments, Z represents R$_3$(CO) and R$_3$ represents C(R$_8$)(R$_9$)(R$_{10}$), wherein R$_8$ represents aryl, arylalkyl, heteroaryl or heteroaralkyl, such as aryl, arylalkyl or heteroaryl, R$_9$ represents H, and R$_{10}$ represents hydroxy, hydroxyalkyl, alkoxy or alkoxyalkyl, such as hydroxy, hydroxyalkyl or alkoxy. In certain embodiments, Z represents R$_3$(CO) and R$_3$ represents heteroarylalkyl.

In certain embodiments, L represents CH$_2$SCH$_2$, CH$_2$CH$_2$, CH$_2$S or SCH$_2$, such as CH$_2$CH$_2$, Y represents H, X represents S, Z represents R$_3$(CO), R$_1$ and R$_2$ each represent H, R$_3$ represents arylalkyl, heteroarylalkyl, cycloalkyl or heterocycloalkyl, and R$_{11}$ represents arylalkyl. In certain such embodiments, R$_3$ represents heteroarylalkyl.

In certain embodiments, L represents CH$_2$SCH$_2$, CH$_2$CH$_2$, CH$_2$S or SCH$_2$, such as CH$_2$CH$_2$, Y represents H, X represents S, Z represents R$_3$(CO), R$_1$ and R$_2$ each represent H, and each R$_3$ represents C(R$_8$)(R$_9$)(R$_{10}$), wherein R$_8$ represents aryl, arylalkyl, heteroaryl or heteroaralkyl, such as aryl, arylalkyl or heteroaryl, R$_9$ represents H, and R$_{10}$ represents hydroxy, hydroxyalkyl, alkoxy or alkoxyalkyl, such as hydroxy, hydroxyalkyl or alkoxy, and $R_{11}$ represents arylalkyl. In certain such embodiments, $R_8$ represents heteroaryl.

In certain embodiments, L represents $CH_2CH_2$, Y represents H, X represents S or CH=CH, such as S, Z represents $R_3(CO)$, $R_1$ and $R_2$ each represent H, $R_3$ represents substituted or unsubstituted arylalkyl, heteroarylalkyl, cycloalkyl or heterocycloalkyl, and $R_{11}$ represents arylalkyl. In certain such embodiments, $R_3$ represents heteroarylalkyl.

In certain embodiments, L represents $CH_2CH_2$, Y represents H, X represents S, Z represents $R_3(CO)$, $R_1$ and $R_2$ each represent H, $R_3$ represents $C(R_8)(R_9)(R_{10})$, wherein $R_8$ represents aryl, arylalkyl or heteroaryl, $R_9$ represents H, and $R_{10}$ represents hydroxy, hydroxyalkyl or alkoxy, and $R_{11}$ represents arylalkyl. In certain such embodiments, $R_8$ represents aryl and $R_{10}$ represents hydroxyalkyl. In certain other embodiments, $R_8$ represents heteroaryl.

In certain embodiments, the compound is selected from any one of the compounds disclosed in Table 3. Preferably, the compound is selected from compound 1, 2, 6, 7, 8, 11, 13, 14, 15, 16, 17, 18, 19, 20, 21, 24, 25, 26, 27, 28, 29, 30, 31, 32, 33, 35, 36, 38, 39, 40, 41, 43, 44, 47, 48, 50, 51, 52, 54, 55, 58, 63, 64, 65, 67, 68, 69, 70, 71, 72, 73, 77, 78, 79, 80, 81, 82, 83, 84, 85, 86, 87, 88, 92, 93, 94, 95, 97, 99, 100, 102, 105, 107, 111, 112, 114, 115, 116, 117, 118, 120, 121, 122, 123, 126, 127, 133, 135, 136, 138, 140, 141, 143, 146, 147, 148, 152, 153, 155, 156, 157, 158, 159, 160, 161, 162, 163, 164, 165, 166, 168, 169, 170, 172, 173, 174, 175, 176, 177, 178, 179, 180, 181, 182, 185, 186, 187, 188, 189, 190, 193, 194, 195, 196, 197, 198, 199, 200, 201, 202, 203, 204, 205, 208, 210, 211, 213, 214, 216, 217, 219, 220, 226, 227, 228, 229, 231, 232, 234, 235, 236, 237, 239, 240, 241, 242, 243, 244, 245, 246, 247, 248, 249, 250, 251, 252, 255, 256, 257, 258, 259, 260, 261, 262, 263, 264, 265, 266, 267, 268, 269, 270, 271, 273, 274, 275, 276, 278, 279, 280, 281, 282, 283, 285, 286, 287, 288, 290, 291, 292, 293, 294, 295, 296, 297, 298, 299, 300, 302, 304, 1038, 306, 307, 308, 309, 310, 311, 313, 314, 315, 316, 317, 318, 319, 320, 321, 322, 323, 324, 325, 327, 329, 332, 333, 334, 335, 336, 337, 338, 339, 340, 341, 342, 343, 344, 345, 346, 527, 347, 348, 349, 350, 351, 352, 353, 354, 355, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 638, 639, 640, 641, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 692, 693, 694, 695, 696, 697, 698, 699, 700, 701, 702, 703, 704, 705, 707, 708, or 709.

In certain embodiments, compounds of the invention may be prodrugs of the compounds of formula I, e.g., wherein a hydroxyl in the parent compound is presented as an ester or a carbonate, or carboxylic acid present in the parent compound is presented as an ester. In certain such embodiments, the prodrug is metabolized to the active parent compound in vivo (e.g., the ester is hydrolyzed to the corresponding hydroxyl, or carboxylic acid).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. In certain embodiments, compounds of the invention may have more than one stereocenter. In certain such embodiments, compounds of the invention may be enriched in one or more diastereomer. For example, a compound of the invention may have greater than 30% de, 40% de, 50% de, 60% de, 70% de, 80% de, 90% de, or even 95% or greater de.

In certain embodiments, the present invention relates to methods of treatment with a compound of formula I, or a pharmaceutically acceptable salt thereof. In certain embodiments, the therapeutic preparation may be enriched to provide predominantly one enantiomer of a compound (e.g., of formula I). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound (e.g., of formula I). A diastereomerically enriched mixture may comprise, for example, at least 60 mol percent of one diastereomer, or more preferably at least 75, 90, 95, or even 99 mol percent.

In certain embodiments, the present invention relates to methods of treatment with a compound of formula I, or a pharmaceutically acceptable salt thereof. In certain embodiments, the therapeutic preparation may be enriched to provide predominantly one enantiomer of a compound (e.g., of formula I). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound (e.g., of formula I). A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient, comprising any of the compounds shown above (e.g., a compound of the invention, such as a compound of formula I), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

Uses of Enzyme Inhibitors

Glutamine plays an important role as a carrier of nitrogen, carbon, and energy. It is used for hepatic urea synthesis, for renal ammoniagenesis, for gluconeogenesis, and as respiratory fuel for many cells. The conversion of glutamine into glutamate is initiated by the mitochondrial enzyme, glutaminase ("GLS"). There are two major forms of the enzyme, K-type and L-type, which are distinguished by their Km values for glutamine and response to glutamate, wherein the Km value, or Michaelis constant, is the concentration of substrate required to reach half the maximal velocity. The L-type, also known as "liver-type" or GLS2, has a high Km for glutamine and is glutamate resistant. The K-type, also known as "kidney-type or GLS1, has a low Km for glutamine and is inhibited by glutamate. An alternative splice form of GLS1, referred to as glutmainase C or "GAC", has been identified recently and has similar activity characteristics of GLS1. In certain embodiments, the compounds may selectively inhibit GLS1, GLS2 and GAC. In a preferred embodiment, the compounds selectively inhibit GLS1 and GAC.

In addition to serving as the basic building blocks of protein synthesis, amino acids have been shown to contribute to many processes critical for growing and dividing cells, and this is particularly true for cancer cells. Nearly all definitions of cancer include reference to dysregulated proliferation. Numerous studies on glutamine metabolism in cancer indicate that many tumors are avid glutamine consumers (Souba, Ann. Surg., 1993; Collins et al., J. Cell. Physiol., 1998; Medina, J. Nutr., 2001; Shanware et al., J. Mol. Med., 2011). An embodiment of the invention is the use of the compounds described herein for the treatment of cancer.

In certain embodiments, the cancer may be one or a variant of Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma) Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sezary Syndrome), Hodgkin, Non-Hodgkin, Primary Central Nervous System (CNS), Macroglobulinemia, Waldenström, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, and Low Malignant Potential Tumor), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sezary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenström Macroglobulinemia and Wilms Tumor.

In some instances, oncogenic mutations promote glutamine metabolism. Cells expressing oncogenic K-Ras exhibt increased ultilization of glutamine (Weinberg et al., Proc. Natl. Acad. Sci. USA, 2010; Gaglio et al., Mol. Syst. Biol., 2011). In certain embodiments, the cancer cells have a mutated K-Ras gene. In certain embodiments, the cancer is associated with tissue of the bladder, bone marrow, breast, colon, kidney, liver, lung, ovary, pancreas, prostate, skin or thyroid. The c-Myc gene is known to be altered in numerous cancers (Zeller et al., Genome biology, 2003). Increased Myc protein expression has been correlated with increased expression of glutaminase, leading to up-regulation of glutamine metabolism (Dang et al., Clin. Cancer Res., 2009; Gao et al., Nature, 2009). In certain embodiments, the cancer cells have an oncogenic c-Myc gene or elevated Myc protein expression. In some embodiments, the cancer is associated with tissue of the bladder, bone, bowel, breast, central nervous system (like brain), colon, gastric system (such as stomach and intestine), liver, lung, ovary, prostate, muscle, and skin.

While many cancer cells depend on exogenous glutamine for survival, the degree of glutamine dependence among tumor cell subtypes may make a population of cells more susceptible to the reduction of glutamine. As an example, gene expression analysis of breast cancers has identified five intrinsic subtypes (luminal A, luminal B, basal, HER2+, and normal-like) (Sorlie et al., Proc Natl Acad Sci USA, 2001). Although glutamine deprivation has an impact on cell growth and viability, basal-like cells appear to be more sensitive to the reduction of exogenous glutamine (Kung et al., PLoS Genetics, 2011). This supports the concept that glutamine is a very important energy source in basal-like breast cancer cell lines, and suggests that inhibition of the glutaminase enzyme would be beneficial in the treatment of breast cancers comprised of basal-like cells. Triple-negative breast cancer (TNBC) is characterized by a lack of estrogen receptor, progesterone receptor and human epidermal growth factor receptor 2 expression. It has a higher rate of relapse following chemotherapy, and a poorer prognosis than with the other breast cancer subtypes (Dent et al., Clin Cancer res, 2007). Interestingly, there appears to be significant similarities in metabolic profiling between TNBC cells and basal-like breast cancer cells (unpublished data). Therefore, an embodiment of the invention is the use of the compounds described herein for the treatment of TNBC and basal-type breast cancers.

Cachexia, the massive loss of muscle mass, is often associated with poor performance status and high mortality rate of cancer patients. A theory behind this process is that tumors require more glutamine than is normally supplied by diet, so muscle, a major source of glutamine, starts to breakdown in order to supply enough nutrient to the tumor. Thus, inhibition of glutaminase may reduce the need to breakdown muscle. An embodiment of the invention is the use of the present compounds to prevent, inhibit or reduce cachexia.

The most common neurotransmitter is glutamate, derived from the enzymatic conversion of glutamine via glutaminase. High levels of glutamate have been shown to be neurotoxic. Following traumatic insult to neuronal cells, there occurs a rise in neurotransmitter release, particularly glutamate. Accordingly, inhibition of glutaminase has been hypothesized as a means of treatment following an ischemic insult, such as stroke (Newcomb, PCT WO 99/09825, Kostandy, Neurol. Sci., 2011). Huntington's disease is a progressive, fatal neurological condition. In genetic mouse models of Huntington's disease, it was observed that the early manifestation of the disease correlated with dysregulated glutamate release (Raymond et al., Neuroscience, 2011). In HIV-associated dementia, HIV infected macrophages exhibit upregulated glutaminase activity and increased glutamate release, leading to neuronal damage (Huang et al., J Neurosci., 2011). Similarly, in another neurological disease, the activated microglia in Rett Syndrome release glutamate causing neuronal damage. The release of excess glutamate has been associated with the up-regulation of glutaminase (Maezawa et al., J. Neurosci, 2010). In mice bred to have reduced glutaminase levels, sensitivity to psychotic-stimulating drugs, such as amphetamines, was dramatically reduced, thus suggesting that glutaminase inhibition may be beneficial in the treatment of schizophrenia (Gaisler-Salomon et al., Neuropsychopharmacology, 2009). Bipolar disorder is a devastating illness that is marked by recurrent episodes of mania and depression. This disease is treated with mood stabilizers such as lithium and valproate; however, chronic use of these drugs appear to increase the abundance of glutamate receptors (Nanavati et al., J. Neurochem., 2011), which may lead to a decrease in the drug's effectiveness over time. Thus, an alternative treatment may be to reduce the amount of glutamate by inhibiting glutaminase. This may or may not be in conjunction with the mood stabilizers. Memantine, a partial antagonist of N-methyl-D-aspartate receptor (NMDAR), is an approved therapeutic in the treatment of Alzheimer's disease. Currently, research is being conducted looking at memantine as a means of treating vascular dementia and Parkinson's disease (Oliverares et al., Curr. Alzheimer Res., 2011). Since memantine has been shown to partially block the NMDA glutamate receptor also, it is not unresasonable to speculate that decreasing glutamate levels by inhibiting glutaminase could also treat Alzheimer's disease, vascular dementia and Parkinson's disease. Alzheimer's disease, bipolar disorder, HIV-associated dementia, Huntington's disease, ischemic insult, Parkinson's disease, schizophrenia, stroke, traumatic insult and vascular dementia are but a few of the neurological diseases that have been correlated to increased levels of glutamate. Thus, inhibiting glutaminase with a compound described herein can reduce or prevent neurological diseases. Therefore, in one embodiment, the compounds may be used for the treatment or prevention of neurological diseases.

Activation of T lymphocytes induces cell growth, proliferation, and cytokine production, thereby placing energetic and biosynthetic demands on the cell. Glutamine serves as an amine group donor for nucleotide synthesis, and glutamate, the first component in glutamine metabolism, plays a direct role in amino acid and glutathione synthesis, as well as being able to enter the Krebs cycle for energy production (Carr et al., J. Immunol., 2010). Mitogen-induced T cell proliferation and cytokine production require high levels of glutamine metabolism, thus inhibiting glutaminase may serve as a means of immune modulation. In multiple sclerosis, an inflammatory autoimmune disease, the activated microglia exhibit up-regulated glutaminase and release increased levels of extracellular glutamate. Glutamine levels are lowered by sepsis, injury, burns, surgery and endurance exercise (Calder et al., Amino Acids, 1999). These situations put the individual at risk of immunosuppression. In fact, in general, glutaminase gene expression and enzyme activity are both increased during T cell activity. Patients given glutamine following bone marrow transplantation resulted in a lower level of infection and reduced graft v. host disease (Crowther, Proc. Nutr. Soc., 2009). T cell proliferation and activation is involved in many immunological diseases, such as inflammatory bowel disease, Crohn's disease, sepsis, psoriasis, arthritis (including rheumatoid arthritis), multiple sclerosis, graft v. host disease, infections, lupus and diabetes. In an embodiment of the invention, the compounds described herein can be used to treat or prevent immunological diseases.

Hepatic encephalopathy (HE) represents a series of transient and reversible neurologic and psychiatric dysfunction in patients with liver disease or portosystemic shunting. HE is not a single clinical entity and may reflect reversible metabolic encephalopathy, brain atrophy, brain edema, or a combination of these factors; however, the current hypothesis is that the accumulation of ammonia, mostly derived from the intestine, plays a key role in the pathophysiology (Khunger et al., Clin Liver Dis, 2012). The deamination of glutamine in small intestine, renal and muscle synthesis all contribute to ammonia production. Impaired hepatic clearance caused by hepatocellular clearance or portosystemic shunting causes increased accumulation of ammonia. Ammonia toxicity affects astrocytes in the brain via glutamine synthetase, which metabolizes the ammonia to produce increased glutamine. Glutamine, in turn, attracts water into the astrocytes, leading to swelling and oxidative dysfunction of the mitochondria. The resulting cerebral edema is thought to contribute to neurologic dysfunction seen in HE (Kavitt et al., Clin Gastroenterol Hepatol, 2008). In an embodiment of the invention, the compounds described herein can be used to treat or prevent HE.

Primary sensory neurons in the dorsal root ganglion have been shown to elevate their glutaminase enzyme activity following inflammation (Miller et al., Pain Research and Treatment, 2012). It is believed that the resulting increased glutamate production contributes to both central and peripheral sensitization, identified as pain. An aspect of the invention is the use of the present compounds herein for the treatment or diminishment of pain. In certain embodiments, the pain can be neuropathic pain, chemotherapy-induced pain or inflammatory pain.

High blood glucose levels, high insulin levels, and insulin resistance are risk factors for developing diabetes mellitus. Similarly, high blood pressure is a risk factor for developing cardiovascular disease. In a recent report from a large human cohort study, these four risk factors were inversely correlated with glutamine-to-glutamate ratios in the blood stream (Chen et al, Circulation, 2012). Furthermore, plasma glutamine-to-glutamate ratios were inversely correlated with the eventual incidence of diabetes mellitus over 12 years (Cheng et al, Circulation, 2012). Experiments with animal models were consistent with these findings. Mice fed glutamine-rich diets exhibited lower blood glucose levels in a glucose tolerance test after 6 hours of fasting, and intraperitoneal injection of glutamine into mice rapidly decreased their blood pressure (Cheng et al, Circulation, 2012). Therefore, it is plausible that glutaminase inhibitors, which cause increased glutamine levels and decrease glutamate levels, would decrease the incidence of diabetes mellitus and cardiovascular disease. In particular, the liver and small intestine are major sites of glutamine utilization in diabetic animals, and glutaminase activity is higher than normal in these organs in streptozotocin-induced diabetic rats (Watford et al, Biochem J, 1984; Mithieux et al, Am J Physiol Endrocrinol Metab, 2004). In an embodiment of the invention, the compounds described herein can be used to treat diabetes. In another embodiment of the invention, the present compounds can be used to reduce high blood pressure.

In one embodiment, the method of treating or preventing cancer, immunological and neurological diseases may comprise administering a compound of the invention conjointly with a chemotherapeutic agent. Chemotherapeutic agents that may be conjointly administered with compounds of the invention include: aminoglutethimide, amsacrine, anastrozole, asparaginase, bcg, bicalutamide, bleomycin, buserelin, busulfan, campothecin, capecitabine, carboplatin, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, octreotide, oxaliplatin, paclitaxel, pamidronate, pentostatin, perifosine, plicamycin, porfimer, procarbazine, raltitrexed, rituximab, sorafenib, streptozocin, sunitinib, suramin, tamoxifen, temozolomide, temsirolimus, teniposide, testosterone, thioguanine, thiotepa, titanocene dichloride, topotecan, trastuzumab, tretinoin, vinblastine, vincristine, vindesine, and vinorelbine.

Many combination therapies have been developed for the treatment of cancer. In certain embodiments, compounds of the invention may be conjointly administered with a combination therapy. Examples of combination therapies with which compounds of the invention may be conjointly administered are included in Table 1.

TABLE 1

Exemplary combinatorial therapies for the treatment of cancer.

| Name | Therapeutic agents |
| --- | --- |
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |

TABLE 1-continued

Exemplary combinatorial therapies for the treatment of cancer.

| Name | Therapeutic agents |
|---|---|
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |

TABLE 1-continued

Exemplary combinatorial therapies for the treatment of cancer.

| Name | Therapeutic agents |
|---|---|
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

The proliferation of cancer cells requires lipid synthesis. Normally, acetyl-coA used for lipid synthesis is formed from a mitochondrial pool of pyruvate that is derived from glycolysis. Yet under hypoxic conditions, such as those normally found in a tumor environment, the conversion of pyruvate to acetyl-coA within the mitochondria is down-regulated. Recent studies from Metallo et al. (2011) and Mullen et al. (2011) revealed that under such hypoxic conditions, cells instead largely switch to using a pathway involving the reductive carboxylation of alpha-ketoglutarate to make acetyl-coA for lipid synthesis. The first step in this pathway involves converting glutamine to glutamate via glutaminase enzymes. Subsequently, glutamate is converting to alpha-ketoglutarate, and the resulting alpha-ketoglutarate is converted to isocitrate in a reductive carboxylation step mediated by the isocitrate dehydrogenase enzymes. A switch to this reductive carboxylation pathway also occurs in some renal carcinoma cell lines that contain either impaired mitochondria or an impaired signal for induction of the enzyme responsible for converting glycolytic pyruvate to acetyl-coA (Mullen et al 2011). A similar switch occurs in cells exposed to mitochondrial respiratory chain inhibitors such as metformin, rotenone, and antimycin (Mullen at al. 2011). Therefore, in some embodiments of this invention, we propose using combinations of mitochondrial respiratory chain inhibitors and glutaminase inhibitors to simultaneously increase cancer cells' dependence on glutaminase-dependent pathways for lipid synthesis while inhibiting those very pathways.

The increased dependence on glycolysis in tumor cells is likely because the hypoxic tumor environment impairs mitochondrial respiration. Furthermore, depletion of glucose induces apoptosis in cells transformed with the MYC oncogene. These findings suggest that inhibiting glycolysis would have a therapeutic value in preventing cancer cell proliferation. There are currently many documented glycolytic inhibitors (Pelicano et al. 2006). However, as pointed out by Zhao et al. (2012), "available glycolytic inhibitors are generally not very potent, and high doses are required, which may cause high levels of systemic toxicity." Since cancer cells typically use both glucose and glutamine at higher levels than normal cells, impairing utilization of each of those metabolites will likely have a synergistic effect. Therefore, in some embodiments of this invention, we propose using combinations of glycolytic pathway inhibitors and glutaminase inhibitors. Such glycolytic inhibitors include 2-deoxyglucose, lonidamine, 3-bromopyruvate, imatinib, oxythiamine, rapamycin, and their pharmacological equivalents. Glycolysis can be inhibited indirectly by depleting NAD+ via DNA damage induced by DNA alkylating agents through a pathway activated by poly(ADP-ribose) polymerase (Zong et al. 2004). Therefore, in one embodiment of this invention, we propose using a combination of DNA alkylating agents and glutaminase inhibitors. Cancer cells use the pentose phosphate pathway along with the glycolytic pathway to create metabolic intermediates derived from glucose. Therefore, in another embodiment of this invention, we propose using a combination of pentose phosphate inhibitors such as 6-aminonicotinamide along with glutaminase inhibitors.

In certain embodiments, a compound of the invention may be conjointly administered with non-chemical methods of cancer treatment. In certain embodiments, a compound of the invention may be conjointly administered with radiation therapy. In certain embodiments, a compound of the invention may be conjointly administered with surgery, with thermoablation, with focused ultrasound therapy, with cryotherapy, or with any combination of these.

In certain embodiments, different compounds of the invention may be conjointly administered with one or more other compounds of the invention. Moreover, such combinations may be conjointly administered with other therapeutic agents, such as other agents suitable for the treatment of cancer, immunological or neurological diseases, such as the agents identified above.

In certain embodiments, the present invention provides a kit comprising: a) one or more single dosage forms of a compound of the invention; b) one or more single dosage forms of a chemotherapeutic agent as mentioned above; and c) instructions for the administration of the compound of the invention and the chemotherapeutic agent.

The present invention provides a kit comprising:
  a) a pharmaceutical formulation (e.g., one or more single dosage forms) comprising a compound of the invention; and b) instructions for the administration of the pharmaceutical formulation, e.g., for treating or preventing any of the conditions discussed above.

In certain embodiments, the kit further comprises instructions for the administration of the pharmaceutical formulation comprising a compound of the invention conjointly with a chemotherapeutic agent as mentioned above. In certain embodiments, the kit further comprises a second pharmaceutical formulation (e.g., as one or more single dosage forms) comprising a chemotherapeutic agent as mentioned above.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

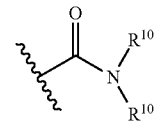

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

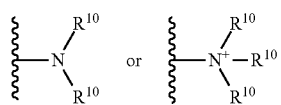

wherein each R¹⁰ independently represents a hydrogen or a hydrocarbyl group, or two R¹⁰ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

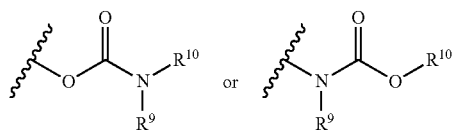

wherein R⁹ and R¹⁰ independently represent hydrogen or a hydrocarbyl group, such as an alkyl group, or R⁹ and R¹⁰ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO₂—R¹⁰, wherein R¹⁰ represents a hydrocarbyl group.

The term "carboxy", as used herein, refers to a group represented by the formula —CO₂H.

The term "ester", as used herein, refers to a group —C(O)OR¹⁰ wherein R¹⁰ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

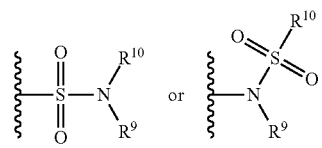

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

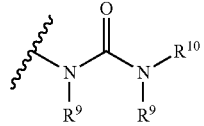

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters.

In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In certain embodiments, the invention relates to a method for conducting a pharmaceutical business, by manufacturing a formulation of a compound of the invention, or a kit as described herein, and marketing to healthcare providers the benefits of using the formulation or kit for treating or preventing any of the diseases or conditions as described herein.

In certain embodiments, the invention relates to a method for conducting a pharmaceutical business, by providing a distribution network for selling a formulation of a compound of the invention, or kit as described herein, and providing instruction material to patients or physicians for using the formulation for treating or preventing any of the diseases or conditions as described herein.

In certain embodiments, the invention comprises a method for conducting a pharmaceutical business, by determining an appropriate formulation and dosage of a compound of the invention for treating or preventing any of the diseases or conditions as described herein, conducting therapeutic profiling of identified formulations for efficacy and toxicity in animals, and providing a distribution network for selling an identified preparation as having an acceptable therapeutic profile. In certain embodiments, the method further includes providing a sales group for marketing the preparation to healthcare providers.

In certain embodiments, the invention relates to a method for conducting a pharmaceutical business by determining an appropriate formulation and dosage of a compound of the invention for treating or preventing any of the disease or conditions as described herein, and licensing, to a third party, the rights for further development and sale of the formulation.

EXAMPLES

Example 1: Synthetic Protocols

Synthesis of Linker Cores:

5,5'-(butane-1,4-diyl)-bis(1,3,4-thiadiazol-2-amine) (1001)

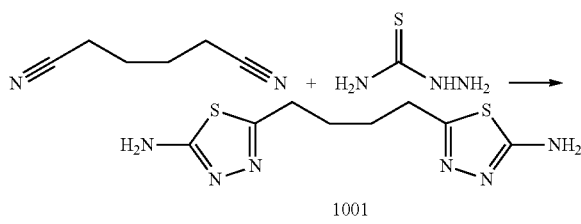

1001

A mixture of adiponitrile (8.00 g, 73.98 mmol) and thiosemicarbazide (13.48 g, 147.96 mmol) in trifluoroacetic acid (TFA) (75 mL) was heated at 80° C. for 17 hours. The reaction was cooled to room temperature and poured into a mixture of ice and water. Sodium hydroxide pellets were added to the mixture until it was basic (pH 14). The white precipitate was collected by suction filtration, rinsed with water and dried to provide 5,5'-(butane-1,4-diyl)-bis(1,3,4-thiadiazol-2-amine) (1001, 13.07 g). $^1$H NMR (300 MHz, DMSO-d$_6$) δ 7.00 (s, 4H), 2.84 (bs, 4H), 1.68 (bs, 4H).

Synthesis of 5,5'-(thiobis(ethane-2,1-diyl))bis(1,3,4-thiadiazol-2-amine) (1002)

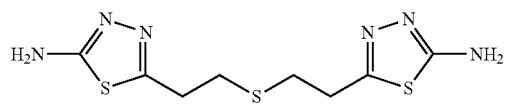

1002

Compound 1002 was prepared as described in US/2002/0115698 A1

5,5'-(2-methylbutane-1,4-diyl)-bis(1,3,4-thiadiazol-2-amine) (1003)

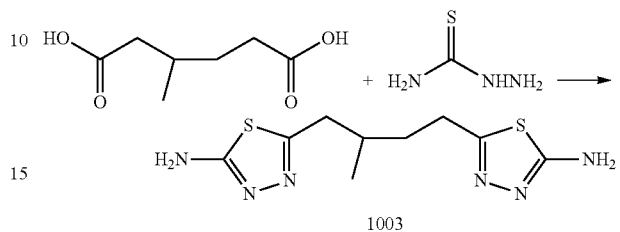

1003

A mixture of 3-methyl adipic acid (5.00 g, 31.22 mmol) and thiosemicarbazide (5.69 g, 62.43 mmol) in POCl$_3$ (45 mL) was heated at 90° C. for 4 h. The reaction was cooled to room temperature and poured into a mixture of ice and water. Sodium hydroxide pellets were added to the mixture until it was basic (pH 14). The white precipitate was collected by suction filtration, rinsed with water and dried to provide 5,5'-(2-methylbutane-1,4-diyl)-bis(1,3,4-thiadiazol-2-amine) (1003, 8.97 g). $^1$H NMR (300 MHz, DMSO-d$_6$) δ 7.00 (s, 4H), 2.89-2.81 (m, 3H), 2.89-2.81 (m, 3H), 2.69 (dd, J=7.6, 7.6 Hz, 1H), 1.89-1.46 (m, 3H), 0.94 (d, J=6.6 Hz, 3H).

5,5'-(propane-1,3-diyl)-bis(1,3,4-thiadiazol-2-amine) (1004)

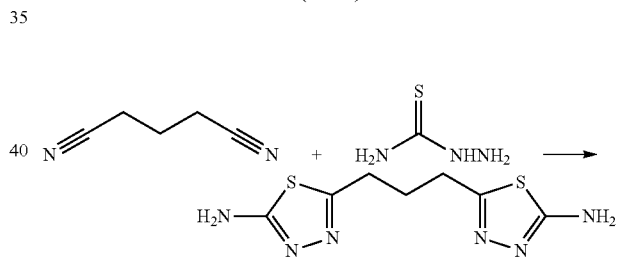

1004

A mixture of glutaronitrile (5.00 g, 53.13 mmol) and thiosemicarbazide (9.68 g, 106.26 mmol) in TFA (50 mL) was heated at 85° C. for 4 h. The reaction was cooled to room temperature and poured into a mixture of ice and water. Sodium hydroxide pellets were added to the mixture until it was basic (pH 14). The white precipitate was collected by suction filtration, rinsed with water and dried to provide 5,5'-(propane-1,3-diyl)-bis(1,3,4-thiadiazol-2-amine) (1004, 13.72 g). $^1$H NMR (300 MHz, DMSO-d$_6$) δ 7.06-7.03 (s, 4H), 2.87 (t, J=7.5 Hz, 4H), 2.02-1.95 (m, 2H).

5-(2-((2-(5-amino-1,3,4-thiadiazol-2-yl)ethyl)amino)ethyl)-1,3,4-thiadiazol-2-amine (1005)

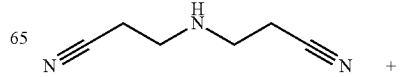

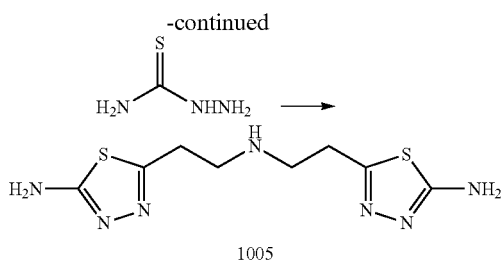

1005

A mixture of 3,3'-iminodipropionitrile (1.50 g, 12.18 mmol) and thiosemicarbazide (2.22 g, 24.36 mmol) in TFA (10 mL) was heated at 85 for 4.5 h. The reaction was cooled to room temperature and poured into a mixture of ice and water. Sodium hydroxide pellets were added to the mixture until it was basic (pH 14). The white precipitate was collected by suction filtration, rinsed with water and dried to provide 5-(2-((2-(5-amino-1,3,4-thiadiazol-2-yl)ethyl) amino)ethyl)-1,3,4-thiadiazol-2-amine (1005, 1.47 g). $^1$H NMR (300 MHz, DMSO-d$_6$) δ 6.95 (s, 4H), 2.90 (d, J=6.0 Hz, 4H), 2.83 (d, J=6.3 Hz, 4H).

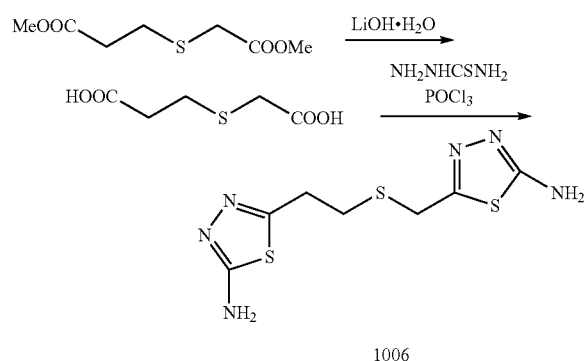

1006

To a solution of methyl 3-((2-methoxy-2-oxoethyl)thio) propanoate (5.0 g, 26 mmol) in THF/MeOH/water (60 mL, 4:1:1) was added lithium hydroxide monohydrate (4.375 g, 101 mmol). The resulting mixture was stirred at room temperature overnight before it was concentrated under reduced pressure. The residue obtained was diluted with water (~100 mL) and the resulting solution was acidified with 6N HCl. The mixture was partitioned between water and ethyl acetate. The organic extract was washed with more water, separated, dried over sodium sulfate, filtered and evaporated to afford 3-((carboxymethyl)thio)propanoic acid (3.64 g, 85%) as a white solid. $^1$H NMR (300 MHz, DMSO-d6) δ ppm 2.55-2.57 (t, 2H) 2.75-2.79 (t, 2H) 3.27 (s, 2H) 12.41 (s, 2H)

To a mixture of 3-((carboxymethyl)thio)propanoic acid (3.64 g, 22.2 mmol) and thiosemicarbazide (4.1 g, 45 mmol) was added phosphorus oxychloride (25 mL) slowly. The resulting mixture was stirred at 90° C. for 3 hr before it was poured over crushed ice slowly. The solid separated was filtered and the filtrate was basified to pH~13 by solid sodium hydroxide. The solid separated was filtered, washed with water and dried at 45° C. under vacuum overnight to afford 1006 (~3 g, 50%) as a tan solid. $^1$H NMR (300 MHz, DMSO-d6) δ ppm 2.79-2.83 (t, 2H) 3.06-3.10 (t, 2H) 3.99 (s, 2H) 7.04 (s, 2H) 7.16 (s, 2H)

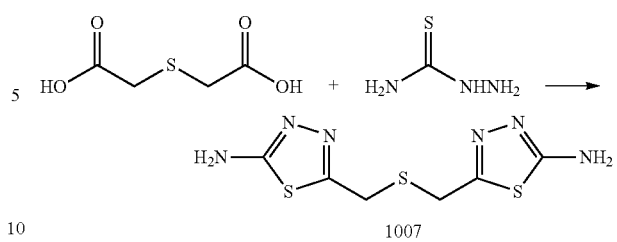

1007

A mixture of 2,2'-Thiodiacetic acid (5.00 g, 33.3 mmol) and thiosemicarbazide (6.07 g, 66.6 mmol) in POCl$_3$ (40 mL) was heated at 90° C. for 5 h. The reaction was cooled to room temperature and carefully poured it onto a mixture of ice and water. Sodium hydroxide pellets were added to the mixture until it was basic (pH 14). The white precipitate was collected by suction filtration, rinsed with water and dried to afford 1007. $^1$H NMR (300 MHz, DMSO-d$_6$) δ 7.18 (s, 4H), 3.96 (s, 4H).

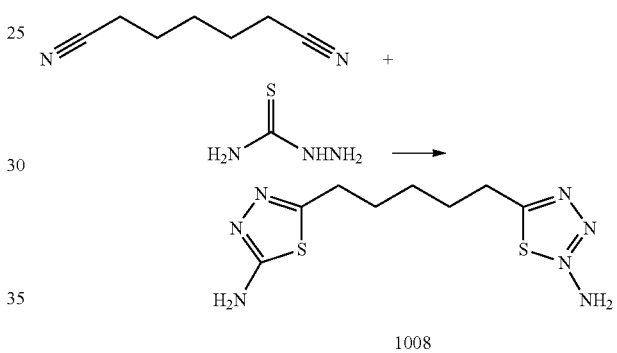

1008

A mixture of 1,5-dicyanopentane (1.00 g, 8.19 mmol) and thiosemicarbazide (1.5 g, 16.40 mmol) in TFA (3 mL) was heated at 85° C. for 5 h. The reaction was cooled to room temperature and poured into a mixture of ice and water. Sodium hydroxide pellets were added to the mixture until it was basic (pH 14). The white precipitate was collected by suction filtration, rinsed with water and dried to afford 1008. $^1$H NMR (300 MHz, DMSO-d$_6$) δ 6.98 (s, 4H), 2.81 (t, 4H), 1.67 (m, 4H), 1.20 (m, 2H).

Acylation of Diamino Core:

Method A: Via Acid Chloride

N,N'-[5,5'-(butane-1,4-diyl)-bis(1,3,4-thiadiazole-5, 2-diyl)]-bis(2-phenylacetamide) (21)

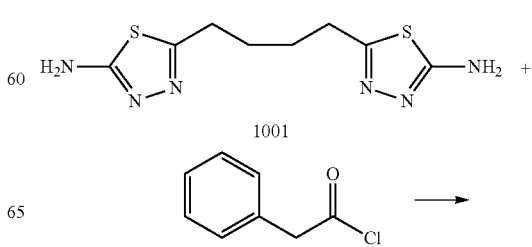

-continued

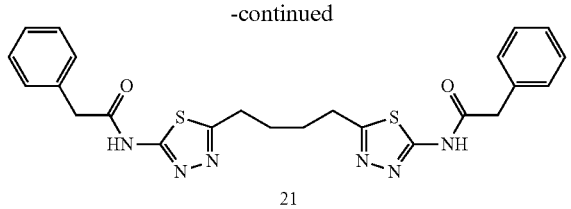
21

To a suspension of 1001 (8.00 g, 31.21 mmol) in 1-Methyl-2-pyrrolidinone (NMP) 100 mL) at 0° C. was added phenylacetyl chloride (10.25 mL, 77.54 mmol) dropwise. The resulting mixture was stirred at 0° C. for 1 h before it was quenched by addition of water (~200 mL). The white precipitate was collected by suction filtration, rinsed with water and dried to provide N,N'-[5,5'-(butane-1,4-diyl)-bis(1,3,4-thiadiazole-5,2-diyl)]-bis(2-phenylacetamide) (21, 14.02 g). $^1$H NMR (300 MHz, DMSO-$d_6$) δ 12.66 (s, 2H), 7.34 (m, 10H), 3.81 (s, 4H), 3.01 (bs, 4H), 1.76 (bs, 4H).

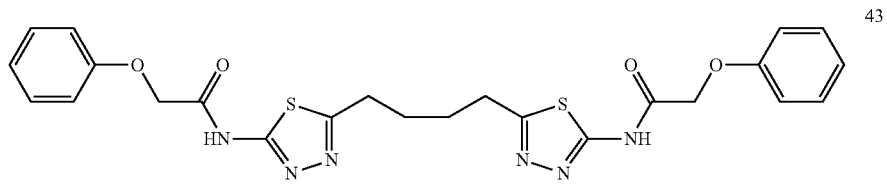 [SMILES: O=C(COc1ccccc1)Nc1nnc(CCCCc2nnc(NC(=O)COc3ccccc3)s2)s1]
43

Compound 43 was prepared following Method A using phenoxyacetyl chloride. $^1$H NMR (300 MHz, DMSO-$d_6$) δ 12.68 (s, 2H), 7.35-7.30 (m, 4H), 6.99-6.97 (m, 6H), 4.90 (s, 4H), 3.05 (bs, 4H), 1.79 (bs, 4H).

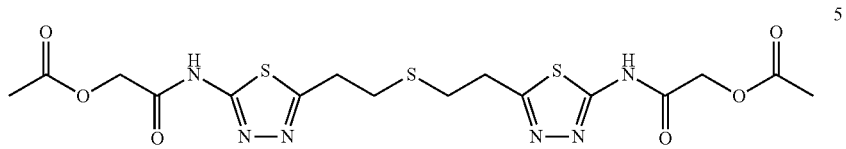 [SMILES: CC(=O)OCC(=O)Nc1nnc(CCSCCc2nnc(NC(=O)COC(C)=O)s2)s1]
100

Compound 100 was prepared following Method A. $^1$H NMR (300 MHz, DMSO-$d_6$) δ 12.42 (s, 2H), 3.64 (t, J=5.6 Hz, 4H), 3.24 (s, 6H), 3.01 (bs, 4H), 2.72 (t, J=6.2 Hz, 4H), 1.79 (bs, 4H).

Compound 5 was prepared according to Method A: $^1$H NMR (300 MHz, DMSO-$d_6$) δ 12.66 (s, 4H), 3.27 (t, J=6.99 Hz, 4H), 2.95 (t, J=7.02 Hz, 4H), 2.12 (s, 6H).

1001

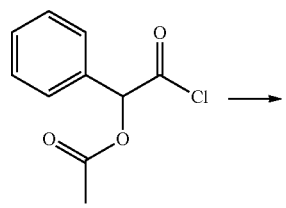

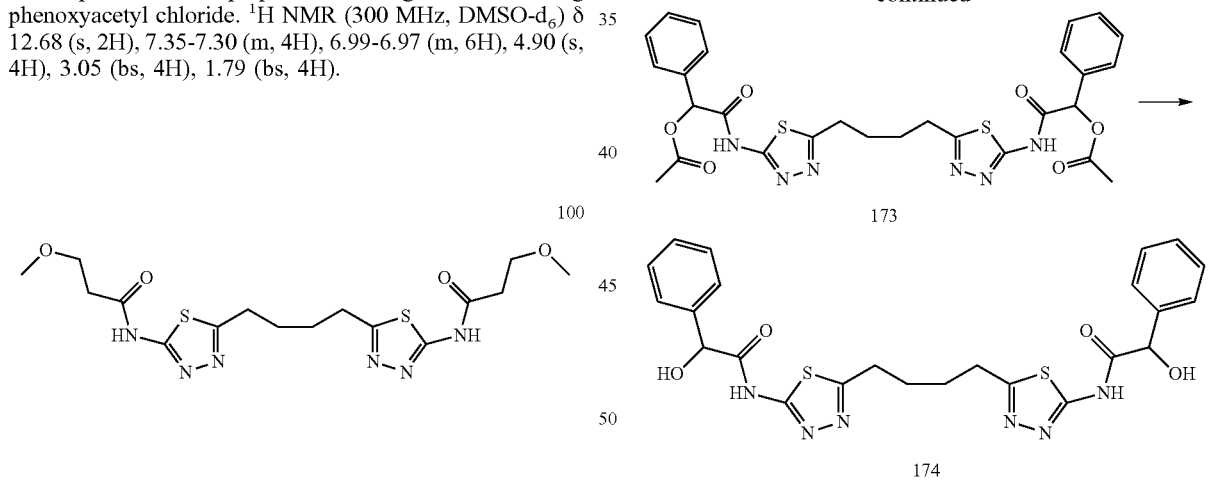

To a suspension of 1001 (200 mg, 0.78 mmol) in NMP (2 mL) at 0° C. was added 0-acetylmandelic acid chloride (0.44 mL, 1.95 mmol) dropwise. The resulting mixture was stirred at 0° C. for 1.5 h before it was quenched by addition of water (~10 mL). The white precipitate was collected by suction filtration, rinsed with more water and dried. The crude material was purified by recrystallization with a mixture of DMSO and MeOH to afford 173.

A flask was charged with 173 and 2N ammonia in MeOH (3 ml) and the resulting mixture was stirred at room temperature for 6 h. The solvent was removed and the resulting material was dried in the oven to afford 174. $^1$H NMR (300 MHz, DMSO-$d_6$) δ 12.42 (s, 2H), 7.53-7.31 (m, 10H), 6.35 (s, 2H), 5.34 (d, J=1.14 Hz, 2H), 3.01 (bs, 4H), 1.76 (bs, 4H).

Compound 306 was prepared according to the procedure for compound 174 above.

To a suspension of 1001 (400 mg, 1.56 mmol) in NMP (4 mL) at 0° C. was added (R)—(−)—O-formylmandeloyl chloride (0.61 mL, 3.90 mmol) dropwise. The resulting mixture was stirred at 0° C. for 1.5 h before it was quenched by addition of water (~10 mL). The white precipitate was collected by suction filtration, rinsed with more water and dried. The crude material was purified by recrystallization with a mixture of DMSO and MeOH to afford 68.

A flask was charged with 68 and 2N ammonia in MeOH (5 ml) and the resulting mixture was stirred at room temperature for 2 h. The solvent was removed and the resulting material was dried in the oven to afford 80. $^1$H NMR (300 MHz, DMSO-$d_6$) δ 7.53-7.31 (m, 10H), 6.34 (s, 2H), 5.33 (s, 2H), 3.01 (bs, 4H), 1.75 (bs, 4H).

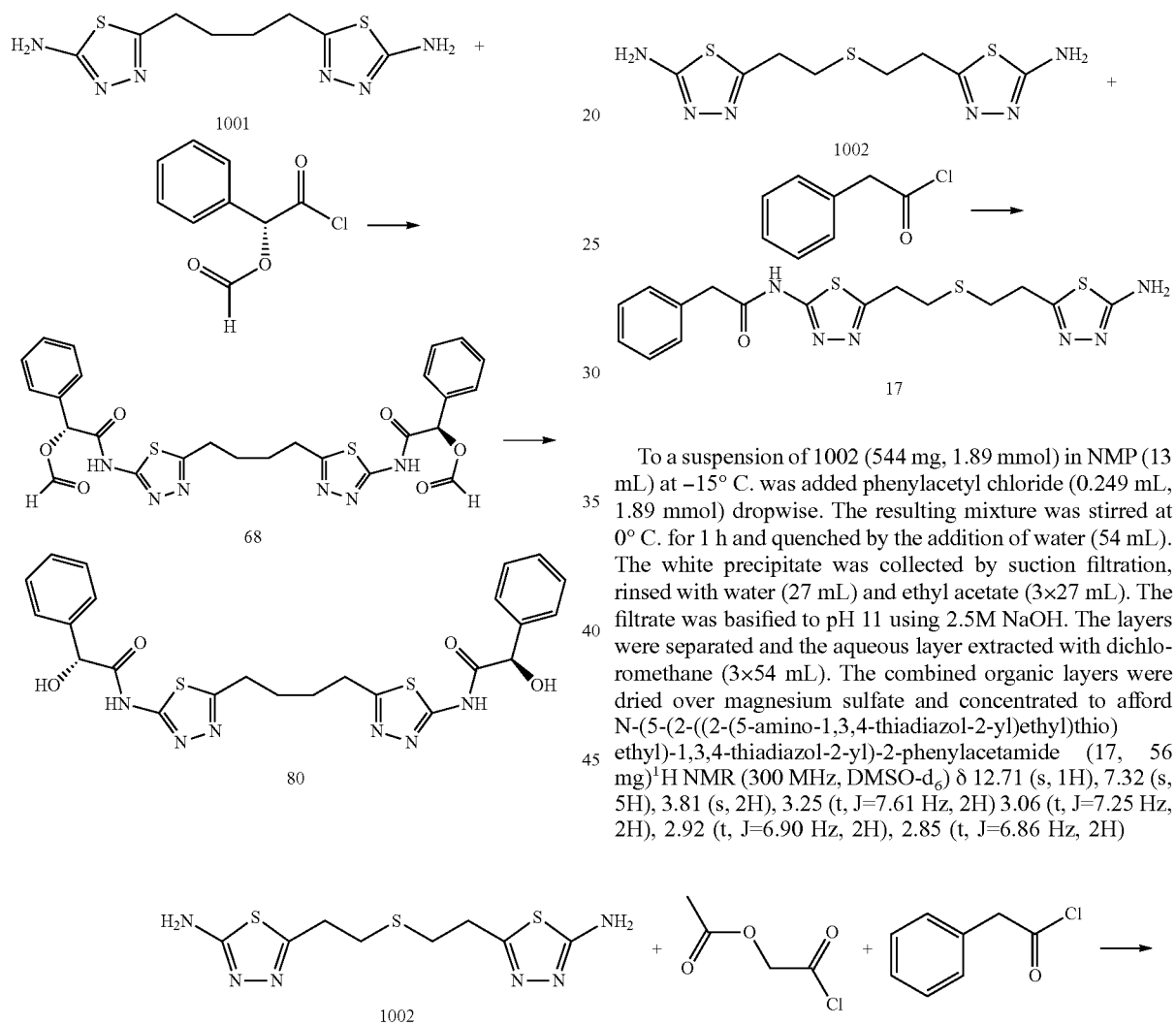

To a suspension of 1002 (544 mg, 1.89 mmol) in NMP (13 mL) at −15° C. was added phenylacetyl chloride (0.249 mL, 1.89 mmol) dropwise. The resulting mixture was stirred at 0° C. for 1 h and quenched by the addition of water (54 mL). The white precipitate was collected by suction filtration, rinsed with water (27 mL) and ethyl acetate (3×27 mL). The filtrate was basified to pH 11 using 2.5M NaOH. The layers were separated and the aqueous layer extracted with dichloromethane (3×54 mL). The combined organic layers were dried over magnesium sulfate and concentrated to afford N-(5-(2-((2-(5-amino-1,3,4-thiadiazol-2-yl)ethyl)thio) ethyl)-1,3,4-thiadiazol-2-yl)-2-phenylacetamide (17, 56 mg)$^1$H NMR (300 MHz, DMSO-$d_6$) δ 12.71 (s, 1H), 7.32 (s, 5H), 3.81 (s, 2H), 3.25 (t, J=7.61 Hz, 2H) 3.06 (t, J=7.25 Hz, 2H), 2.92 (t, J=6.90 Hz, 2H), 2.85 (t, J=6.86 Hz, 2H)

Phenylacetyl chloride (0.134 mL, 1.01 mmol) and acetoxyacetyl chloride (0.109 mL, 1.01 mmol) were mixed together in NMP (0.5 mL). This mixture was slowly added to a suspension of 1002 (292 mg, 1.01 mmol) in NMP (7 mL) at RT. The resulting mixture was stirred at RT for 1 h and quenched by the addition of water (20 mL). The white precipitate was collected by suction filtration, rinsed with water and dried under high vacuum. The crude material was purified by preparative HPLC. Compound 26: $^1$H NMR (300 MHz, DMSO-$d_6$) δ 12.69 (s, 2H), 7.34 (3, 5H), 4.81 (s, 2H), 3.82 (s, 2H), 2.96 (bs, 4H), 2.14 (s, 3H).

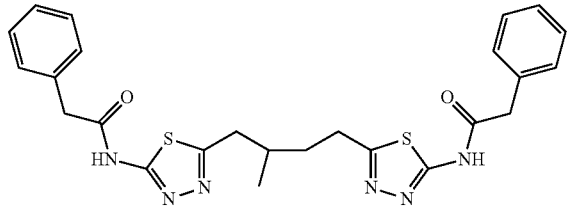

44

Compound 44 was prepared following the procedure for compound 21 described previously. $^1$H NMR (300 MHz,

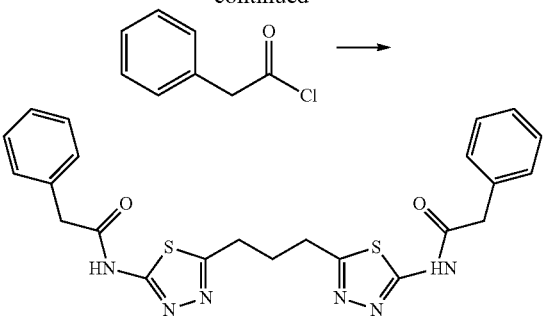

72

Compound 72 was prepared following the procedure for compound 21 described previously. To a suspension of diamine 1004 (0.70 g, 3.07 mmol) in NMP (15 mL) at 0° C. was added phenylacetyl chloride (811 μL, 6.13 mmol) dropwise. The resulting mixture was stirred at 0° C. for 1 h before it was quenched by addition of water. The white precipitate was collected by suction filtration, rinsed with water and dried to provide N,N'-[5,5'-(propane-1,3-diyl)-bis (1,3,4-thiadiazole-5,2-diyl)]-bis(2-phenylacetamide) (72, 1.37 g). $^1$H NMR (300 MHz, DMSO-$d_6$) δ 12.68 (s, 2H), 7.38-7.27 (m, 10H), 3.82 (s, 4H), 3.06 (t, J=7.2 Hz, 4H), 2.17-2.12 (m, 2H).

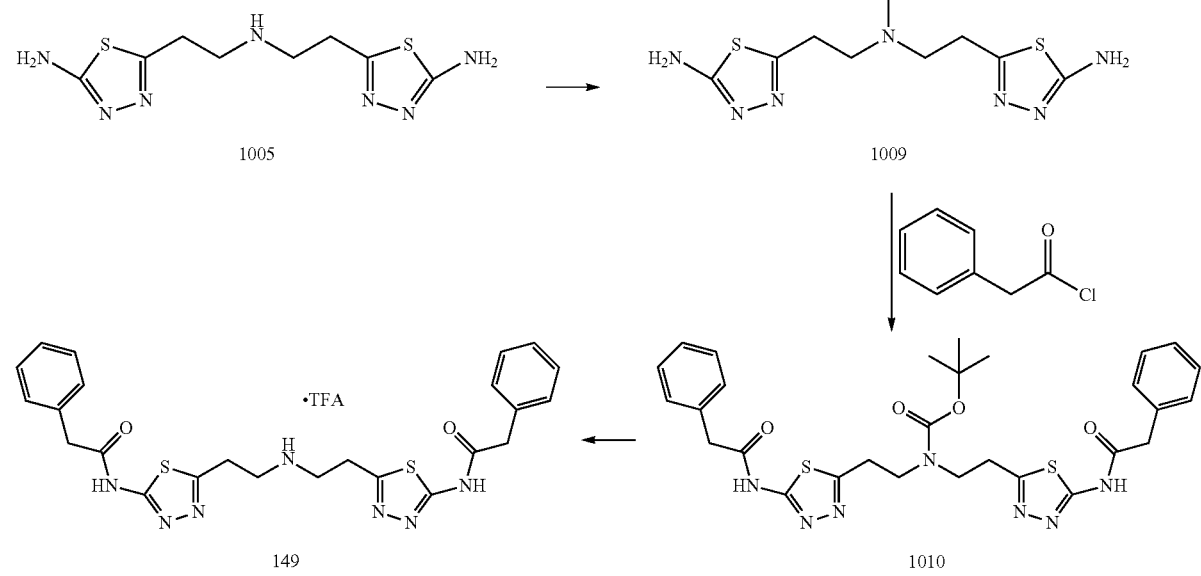

DMSO-$d_6$) δ 12.66 (s, 2H), 7.34-7.28 (m, 10H), 3.81 (s, 4H), 3.05-3.00 (m, 3H), 2.87 (dd, J=7.9, 8.2 Hz, 1H), 1.95-1.77 (m, 3H), 0.94 (d, J=6.5 Hz, 3H).

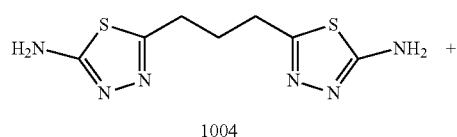

1004

To a suspension of compound 1005 (100 mg, 0.37 mmol) in DMF (12 mL) at room temperature was added a solution of (t-Boc)$_2$O (88 mg, 0.41 mmol) in DMF (2 mL). The mixture was stirred at room temperature for 24 h. To this reaction mixture was added NMP (2 mL) and followed by addition of phenylacetyl chloride (97 μL, 0.74 mmol). The reaction was stirred for 1 h before it was poured into a mixture of ice-water. The solid was collected by suction filtration, rinsed with water and dried to provide 1010 (180 mg).

The above product 1010 (160 mg, 0.26 mmol) in a mixture of TFA (1.5 mL) and CH₂Cl₂ (10 mL) was stirred at room temperature for 4 h before it was concentrated. The residue was re-taken up in CH₂Cl₂ (3×) and concentrated to provide N,N'-(5,5'-(azanediyl-bis(ethane-2,1-diyl))-bis(1,3,4-thiadiazole-5,2-diyl))-bis(2-phenylacetamide) trifluoroacetic acid (149, 122 mg). ¹H NMR (300 MHz, DMSO-d₆) δ 12.81 (s, 2H), 8.75 (bs, 2H), 7.38-7.27 (m, 10H), 3.84 (s, 4H), 3.45 (d, J=2.9 Hz, 4H), 3.39 (d, J=6.0 Hz, 4H).

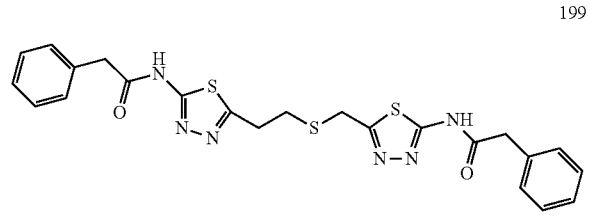 [SMILES: O=C(Cc1ccccc1)Nc1nnc(CCSCc2nnc(NC(=O)Cc3ccccc3)s2)s1]

199

To a suspension of 1006 (0.274 g, 1 mmol) in NMP (5 mL) was added phenyl acetyl chloride (0.263 mL, 2 mmol) dropwise. The mixture was stirred at room temperature for 1 hr and afterwards it was diluted with water. Solid separated was filtered, washed with more water and dried. The crude material was purified by prep HPLC to afford 199 as a white solid. ¹H NMR (300 MHz, Dimethylsulfoxide-d6) δ ppm 2.87-2.91 (t, 2H) 3.25-3.29 (t, 2H) 3.82 (s, 4H) 4.19 (s, 2H) 7.26-7.33 (m, 10H) 12.71-12.72 (br s, 2H).

Method B: Via Acid Using Peptide Coupling Reagents multiplet, 4H), 3.34 (dd, 4H, J=7.2 Hz), 3.28 (s, 4H), 3.00 (dd, 4H, J=7.1 Hz), 2.63 (broad multiplet, 4H).

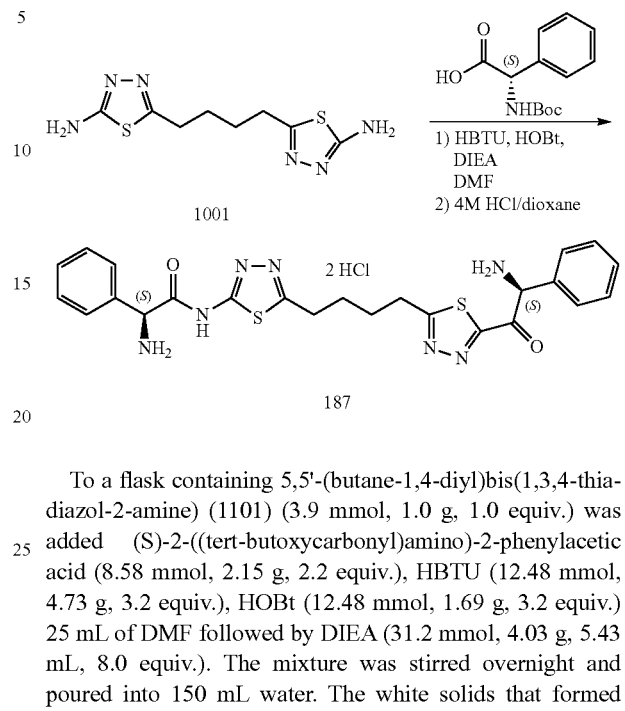

To a flask containing 5,5'-(butane-1,4-diyl)bis(1,3,4-thiadiazol-2-amine) (1101) (3.9 mmol, 1.0 g, 1.0 equiv.) was added (S)-2-((tert-butoxycarbonyl)amino)-2-phenylacetic acid (8.58 mmol, 2.15 g, 2.2 equiv.), HBTU (12.48 mmol, 4.73 g, 3.2 equiv.), HOBt (12.48 mmol, 1.69 g, 3.2 equiv.) 25 mL of DMF followed by DIEA (31.2 mmol, 4.03 g, 5.43 mL, 8.0 equiv.). The mixture was stirred overnight and poured into 150 mL water. The white solids that formed

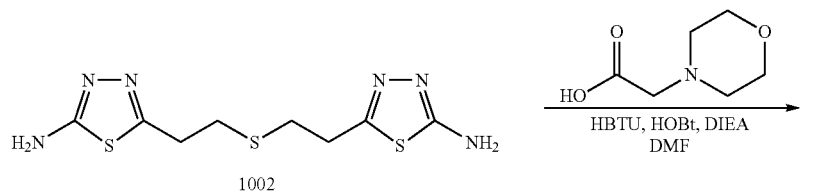

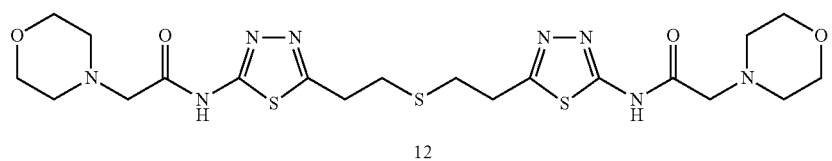

12

To a flask containing 5,5'-(thiobis(ethane-2,1-diyl))bis(1,3,4-thiadiazol-2-amine) (1002) (0.69 mmol, 0.20 g, 1.0 equiv.) was added 2-morpholinoacetic acid (1.52 mmol, 0.22 g, 2.2 equiv.), O-(Benzotriazol-1-yl)-N,N,N',N'-tetramethyluronium hexafluorophosphate (HBTU) (2.20 mmol, 0.83 g, 3.2 equiv.), 1-Hydroxybenzotriazole (HOBT) (2.2 mmol, 0.29 g, 3.2 equiv.) 5 mL of DMF followed by N,N-Diisopropylethylamine (DIEA) (5.52 mmol, 0.71 g, 0.960 mL, 8.0 equiv.). The mixture was stirred overnight at room temperature and then diluted with 15 mL water. The mixture was extracted with EtOAc and the organic layers combined, washed with water, brine and dried over Na₂SO₄. The Na₂SO₄ was removed by filtration and the volatiles removed under reduced pressure to give 0.04 g of compound 12. ¹HNMR (300 MHz, CDCl₃) Compound 12: δ 3.80 (broad were collected by vacuum filtration, washed with water and dried under vacuum giving 2.47 g of the bis-Boc protected intermediate.

To a slurry of the bis-Boc protected intermediate (2.76 mmol, 2.0 g, 1.0 equiv.) in 20 mL of dichloromethane (DCM) was added 4 M HCl in dioxane (40 mmol, 10 mL) with vigorous stirring. The mixture briefly became clear and homogeneous then a white precipitate formed. The mixture was stirred overnight and diluted with 20 mL diethyl ether. The solids were collected by vacuum filtration washed with additional diethyl ether and dried under vacuum giving 0.9 g 187. ¹HNMR (300 MHz, DMSO, d₆) Compound 187: δ 9.13 (s, 4H), 7.61 (m, 4H), 7.48 (m, 6H), 6.2 (broad singlet, 4H), 5.32 (s, 2H), 3.04 (broad multiplet, 4H), 1.77 (broad multiplet, 4H).

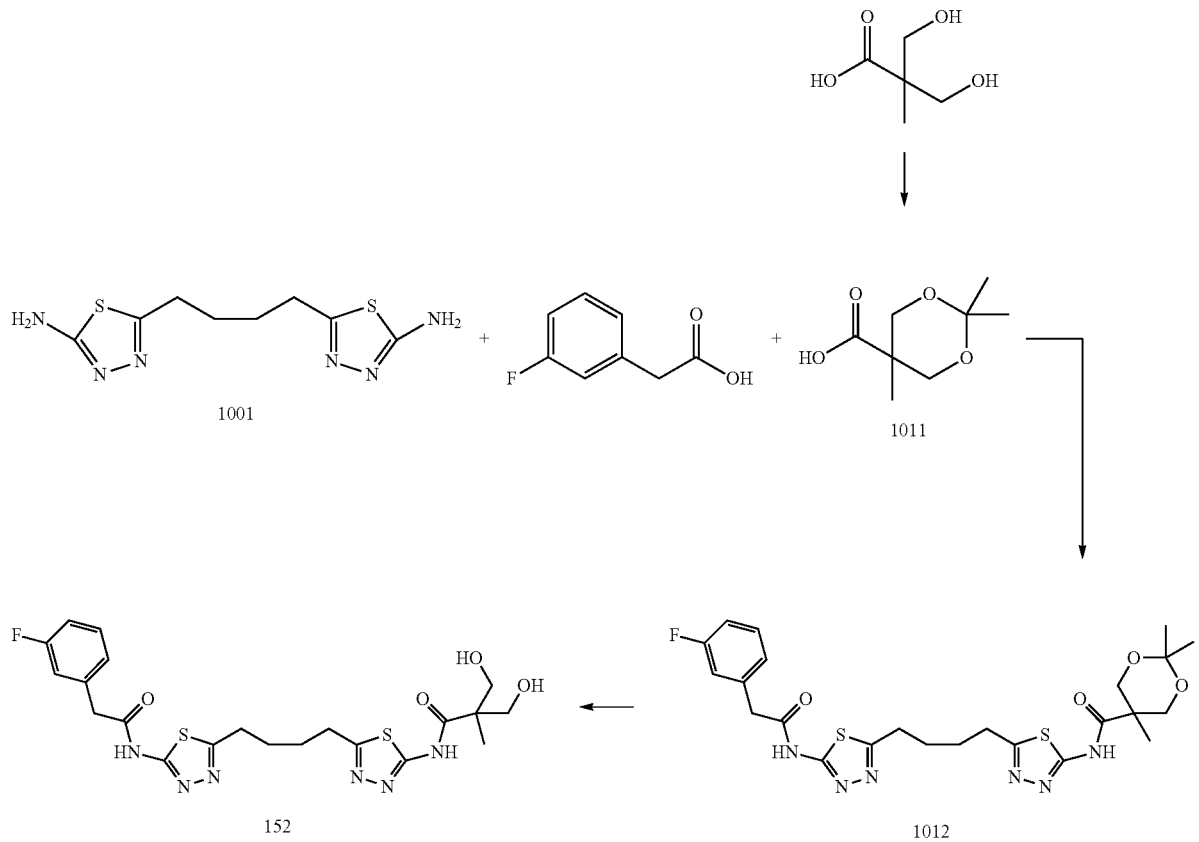

To a solution of 2,2-bis(hydroxymethyl)propionic acid (5.00 g, 37.28 mmol) in acetone (80 mL) at room temperature was added 2,2-dimethoxypropane (6.88 mL, 55.92 mmol) and p-TsOH.H$_2$O (0.36 g, 1.86 mmol). The reaction was stirred for 2 h before it was quenched with Et$_3$N (0.30 mL). The organic volatile was removed under reduced pressure. The residue was partitioned between EtOAc and water. The organic layer was washed with brine, dried (MgSO$_4$) and concentrated to provide the desired product 1011 (5.17 g) as a white solid.

To a suspension of diamine 1001 (500 mg, 1.95 mmol), 3-fluorophenylacetic acid (361 mg, 2.34 mmol) and acid 1011 (442 mg, 2.54 mmol) in DMF (20 mL) at 0° C. was added HOBt (791 mg, 5.85 mmol) and followed by N-(3-Dimethylaminopropyl)-N'-ethylcarbodiimide hydrochloride (EDC) (1.12 g, 5.85 mmol). The mixture was stirred from 0° C. to room temperature over 18 h before it was diluted with water. The precipitate was collected by suction filtration, washed with water and dried. The crude product was purified by silica gel chromatography eluting with 1-10% MeOH in CH$_2$Cl$_2$ to provide N-(5-(4-(5-(2-(3-fluorophenyl)acetamido)-1,3,4-thiadiazol-2-yl)butyl)-1,3,4-thiadiazol-2-yl)-2,2,5-trimethyl-1,3-dioxane-5-carboxamide (1012, 208 mg).

The above product 1012 (87 mg, 0.16 mmol) and TFA (2 mL) in a mixture of THF (8 mL) and water (2 mL) was heated at 50° C. for 5 h before it was concentrated under reduced pressure. The crude residue was purified by HPLC to provide N,N'-(5-(4-(5-(2-(3-fluorophenyl)acetamido)-1,3,4-thiadiazol-2-yl)butyl)-1,3,4-thiadiazol-2-yl)-3-hydroxy-2-(hydroxymethyl)-2-methylpropanamide (152). $^1$H NMR (300 MHz, DMSO-d$_6$) δ 12.68 (s, 1H), 11.77 (s, 1H), 7.04-7.38 (m, 1H), 7.18-7.09 (m, 4H), 4.98 (s, 2H), 3.86 (s, 2H), 3.62 (dd, J=10.7, 29.0 Hz, 4H), 3.03 (bs, 4H), 1.77 (bs, 4H), 1.14 (s, 3H).

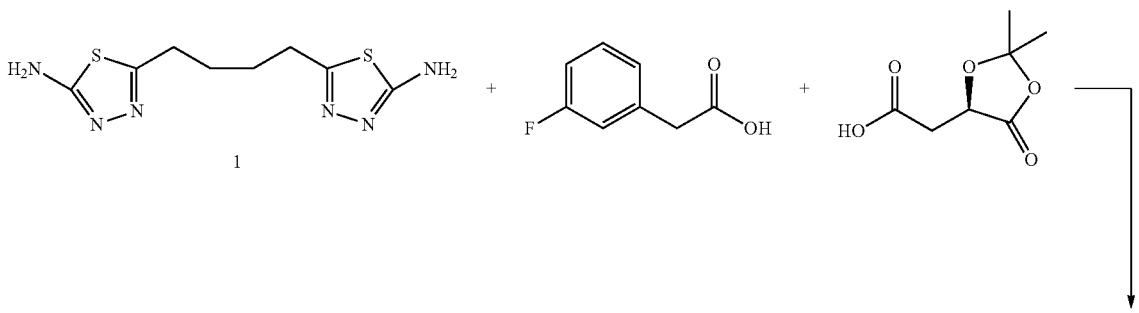

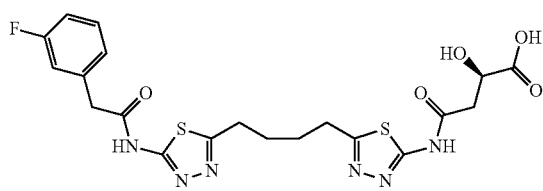 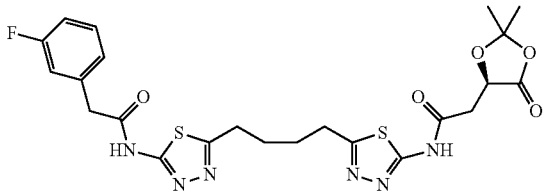

To a suspension of diamine 1001 (400 mg, 1.56 mmol), 3-fluorophenylacetic acid (313 mg, 2.03 mmol), (R)-(−)-2,2-dimethyl-5-oxo-1,3-dioxolane-4-acetic acid (353 mg, 2.03 mmol) and Et$_3$N (200 μL) in DMF (20 mL) at 0° C. was added HOBt (633 mg, 4.68 mmol) and followed by EDC (897 mg, 4.68 mmol). The mixture was stirred from 0° C. to room temperature over 18 h before it was diluted with water. The precipitate was collected by suction filtration and washed with water. The solid was further rinsed with a mixture of hot MeOH-THF. The combined filtrate was concentrated and purified by silica gel chromatography eluting with 1-10% MeOH in CH$_2$Cl$_2$ to provide (R)—N-(5-(4-(5-(2-(3-fluorophenyl)acetamido)-1,3,4-thiadiazol-2-yl)butyl)-1,3,4-thiadiazol-2-yl)-3,4-dihydroxybutanamide (1013, 93 mg).

The above product 1013 (87 mg, 0.16 mmol) and TFA (2 mL) in a mixture of THF (8 mL) and water (2 mL) was heated at 50° C. for 5 h before it was concentrated under reduced pressure. The crude residue was purified by HPLC to provide (R)—N-(5-(4-(5-(2-(3-fluorophenyl)acetamido)-1,3,4-thiadiazol-2-yl)butyl)-1,3,4-thiadiazol-2-yl)-3,4-dihydroxybutanamide (153). $^1$H NMR (300 MHz, DMSO-d$_6$) δ 12.67 (s, 1H), 12.43 (s, 1H), 7.41-7.38 (m, 1H), 7.20-7.12 (m, 4H), 4.45-4.40 (m, 1H), 3.86 (s, 2H), 3.03 (bs, 4H), 2.85-2.77 (m, 2H), 1.78 (bs, 4H).

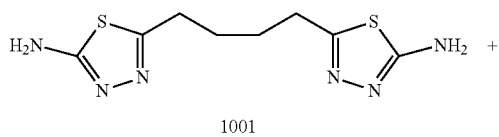

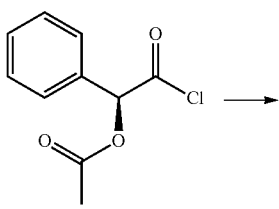

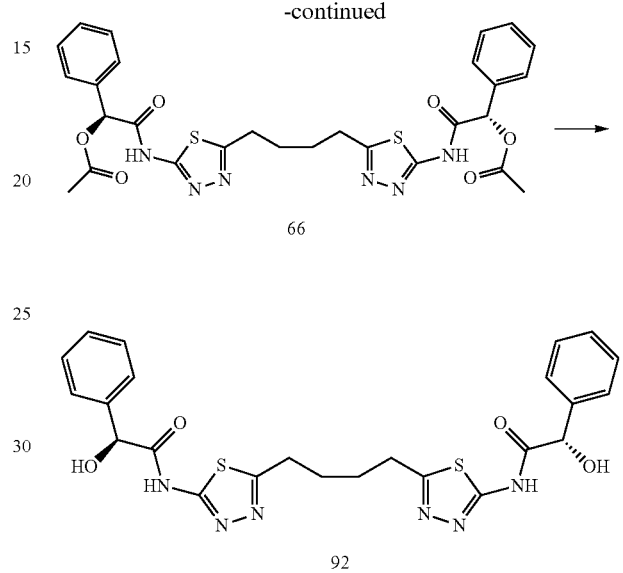

To a suspension of (S)—(+)—O-acetylmandelic acid (666 mg, 3.43 mmol) and O-(7-Azabenzotriazol-1-yl)-N,N,N',N'-tetramethyluronium hexafluorophosphate (HATU) (1.47 g, 3.86 mmol) in DMF (4 mL) was added DIEA (0.672 ml, 3.86 mmol) followed by 1001 (400 mg, 1.56 mmol). The resulting mixture was stirred at room temperature overnight before it was quenched by addition of water (~10 mL). The white precipitate was collected by suction filtration, rinsed with more water and dried. The crude material was purified by recrystallization with a mixture of DMSO and MeOH to afford 66.

A flask was charged with 66 and 2N ammonia in MeOH (5 ml) and the resulting mixture was stirred at room temperature for 6 h. The solvent was removed and the resulting material was dried in the oven to afford 92. $^1$H NMR (300 MHz, DMSO-d$_6$) δ 12.42 (s, 2H), 7.53-7.31 (m, 10H), 6.35 (s, 2H), 5.33 (s, 2H), 3.01 (bs, 4H), 1.76 (bs, 4H).

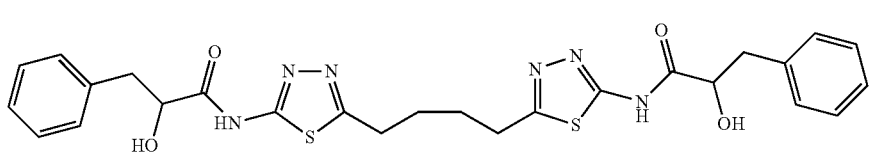

A flask was charged with 1001 (200 mg, 0.78 mmol), DL-3-phenyllactic acid (285 mg, 1.716 mmol), and HOBT (527 mg, 3.9 mmol) in DMF (3 ml) was added EDC (897 mg, 4.68 mmol) followed by triethylamine (0.87 ml, 6.24 mmol). The resulting mixture was stirred at room temperature overnight before it was quenched by addition of water (~5 mL). The mixture was partitioned between water and EtOAc. The organic extract was washed with water, dried over sodium sulfate, filtered and evaporated. The crude material was purified by silica gel chromatography eluting with 0-6% MeOH in $CH_2Cl_2$ to afford 69. $^1$H NMR (300 MHz, DMSO-$d_6$) δ 12.20 (s, 2H), 7.24 (m, 10H), 5.75 (d, J=6.87 Hz, 2H), 4.43 (m, 2H), 3.10 (m, 6H), 2.89-2.81 (m, 2H), 1.80 (bs, 4H).

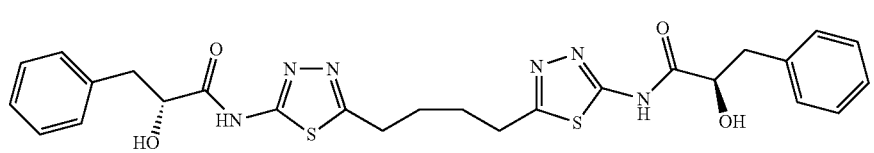

169

A flask was charged with 1001 (200 mg, 0.78 mmol), D-(+)-3-phenyllactic acid (285 mg, 1.716 mmol), and HOBt (464 mg, 3.43 mmol) in DMF (3 ml) was added EDC (822 mg, 4.28 mmol) followed by triethylamine (0.718 ml, 5.15 mmol). The resulting mixture was stirred at room temperature overnight before it was quenched by addition of water (~5 mL). The mixture was partitioned between water and EtOAc. The organic extract was washed with water, dried over sodium sulfate, filtered and evaporated. The crude material was purified by silica gel chromatography eluting with 0-6% MeOH in $CH_2Cl_2$ to afford 169. $^1$H NMR (300 MHz, DMSO-$d_6$) δ 12.20 (s, 2H), 7.24 (m, 10H), 5.75 (d, J=6.87 Hz, 2H), 4.43 (m, 2H), 3.03 (m, 6H), 2.89-2.81 (m, 2H), 1.80 (bs, 4H).

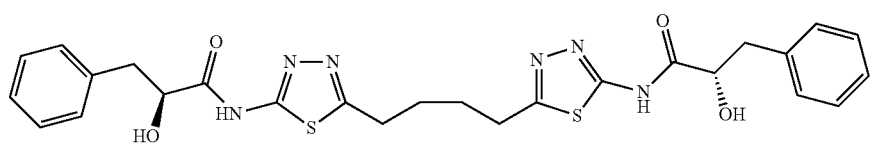

146

A flask was charged with 1001 (200 mg, 0.78 mmol), L-(−)-3-phenyllactic acid (285 mg, 1.716 mmol), and HOBt (464 mg, 3.43 mmol) in DMF (3 ml) was added EDC (822 mg, 4.28 mmol) followed by triethylamine (0.718 ml, 5.15 mmol). The resulting mixture was stirred at room temperature overnight before it was quenched by addition of water (~5 mL). The mixture was partitioned between water and EtOAc. The organic extract was washed with more water, dried over sodium sulfate, filtered and evaporated. The crude material was purified by silica gel chromatography eluting with 0-6% MeOH in $CH_2Cl_2$ to afford 146. $^1$H NMR (300 MHz, DMSO-$d_6$) δ 12.27 (s, 2H), 7.31 (m, 10H), 5.78 (m, 2H), 4.44 (m, 2H), 3.05 (m, 6H), 2.87 (m, 2H), 1.79 (bs, 4H).

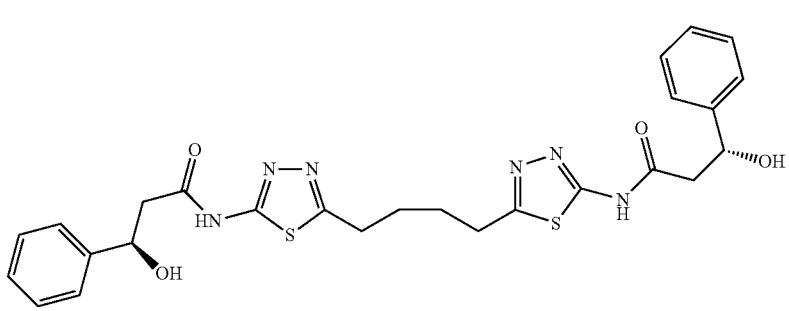

127

To a suspension of (R)-(+)-3-hydroxy-3-phenylpropionic acid (285 mg, 1.72 mmol) and HATU (719 mg, 1.89 mmol) in DMF (3 mL) was added DIEA (0.329 ml, 1.89 mmol) followed by 1001 (200 mg, 0.78 mmol). The resulting mixture was stirred at room temperature overnight before it was quenched by addition of water (~10 mL). The white precipitate was collected by suction filtration, rinsed with more water and dried. The crude material was purified by recrystallization with DMSO and MeOH to afford 127. $^1$H NMR (300 MHz, DMSO-$d_6$) δ 12.38 (s, 2H), 7.34 (m, 10H), 5.56 (m, 2H), 5.10 (m, 2H), 3.04 (bs, 4H), 2.80 (m, 4H), 1.80 (bs, 4H).

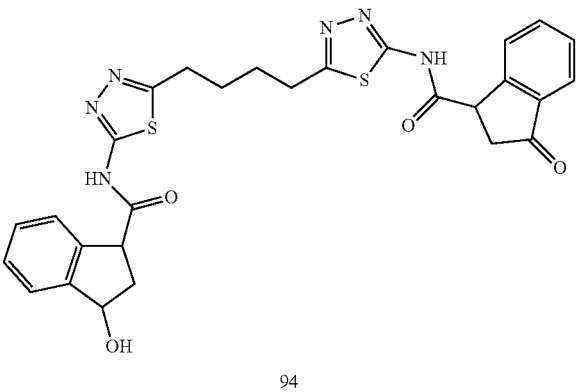

94

To a suspension of 3-Oxo-1-indancarboxylic acid (604 mg, 3.43 mmol) and HATU (1.47 g, 3.86 mmol) in DMF (5 mL) was added DIEA (0.672 ml, 3.86 mmol) followed by 1001 (400 mg, 1.56 mmol). The resulting mixture was stirred at room temperature overnight before it was quenched by addition of water (~10 mL). The light brown precipitate was collected by suction filtration, rinsed with water and dried. The crude material was purified by recrystallization with a mixture of DMSO and MeOH to afford 64.

To a suspension of 64 (100 mg, 0.175 mmol) in EtOH (20 ml) at 0° C. was added NaBH$_4$ (15 mg, 0.384 mmol) and the resulting mixture was stirred for 1 h before it was quenched by 1N HCl. The mixture was partitioned between 1N HCl and EtOAc, the organic extract was dried over sodium sulfate, filtered and evaporated. The crude material was purified by silica gel chromatography eluting with 0-6% MeOH in CH$_2$Cl$_2$ and further purified by recrystallization with a mixture of DMSO and MeOH to afford 94. $^1$H NMR (300 MHz, DMSO-$d_6$) δ 12.81 (s, 2H), 7.34 (m, 8H), 5.56 (m, 2H), 5.11 (t, 2H), 4.15 (t, 2H), 3.05 (bs, 4H), 2.70 (m, 2H), 2.15 (m, 2H), 1.80 (bs, 4H).

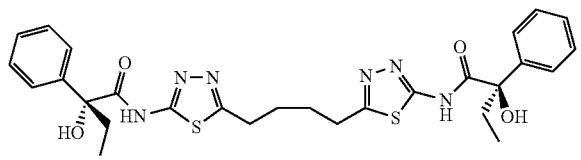

143

To a suspension of (R)-2-hydroxy-2-phenylbutyric acid (310 mg, 1.72 mmol) and HATU (719 mg, 1.89 mmol) in DMF (3 mL) was added DIEA (0.329 ml, 1.89 mmol) followed by 1001 (200 mg, 0.78 mmol). The resulting mixture was stirred at room temperature overnight before it was quenched by addition of water (~10 mL). The crude material was purified by HPLC to afford 143. $^1$H NMR (300 MHz, DMSO-$d_6$) δ 7.61 (d, J=7.65 Hz, 4H), 7.34 (m, 6H), 2.99 (bs, 4H), 2.26 (m, 2H), 2.10 (m, 2H) 1.74 (bs, 4H), 0.80 (t, 6H).

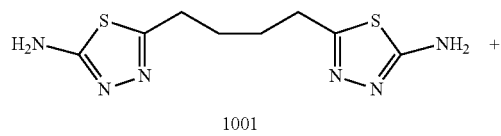

1001

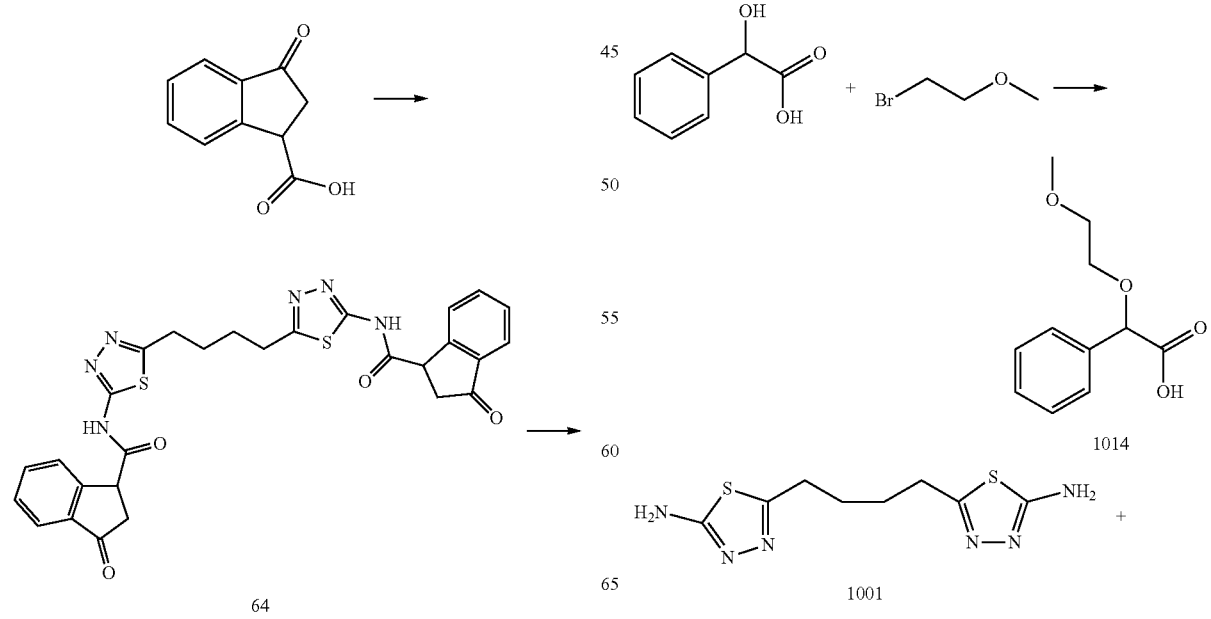

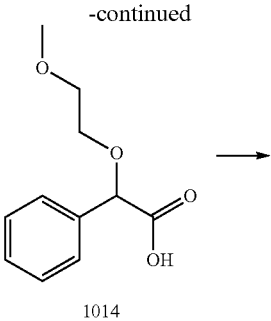

1014

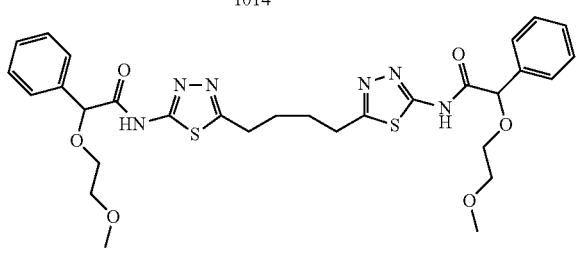

203

To a solution of DL-mandelic acid (1 g, 6.57 mmol) in DMF (10 ml) at 0° C. was added NaH (700 mg, 19.7 mmol) and allowed the mixture to stir for 20 minutes before 2-bromoethyl methyl ether (1.24 ml, 13.1 mmol) was added dropwise. The resulting mixture was stirred at 0° C. and slowly warmed up to room temperature overnight before it was quenched by 1N HCl. The mixture was partitioned between 1N HCl and EtOAc, the organic extract was washed with water, dried over sodium sulfate, filtered and evaporated to afford 1014.

To a suspension of 1014 (500 mg, 2.37 mmol) and HATU (995 mg, 2.62 mmol) in DMF (3 mL) was added DIEA (0.456 ml, 2.62 mmol) followed by 1001 (277 mg, 1.08 mmol). The resulting mixture was stirred at room temperature overnight before it was quenched by addition of water (~6 mL). The mixture was partitioned between water and EtOAc. The organic extract was washed with water, dried over sodium sulfate, filtered and evaporated. The crude material was purified by HPLC to afford 203. $^1$H NMR (300 MHz, DMSO-d$_6$) δ 12.58 (s, 2H), 7.49-7.37 (m, 10H), 5.22 (s, 2H), 3.66-3.54 (m, 8H), 3.27 (s, 6H), 3.01 (bs, 4H), 1.75 (bs, 4H).

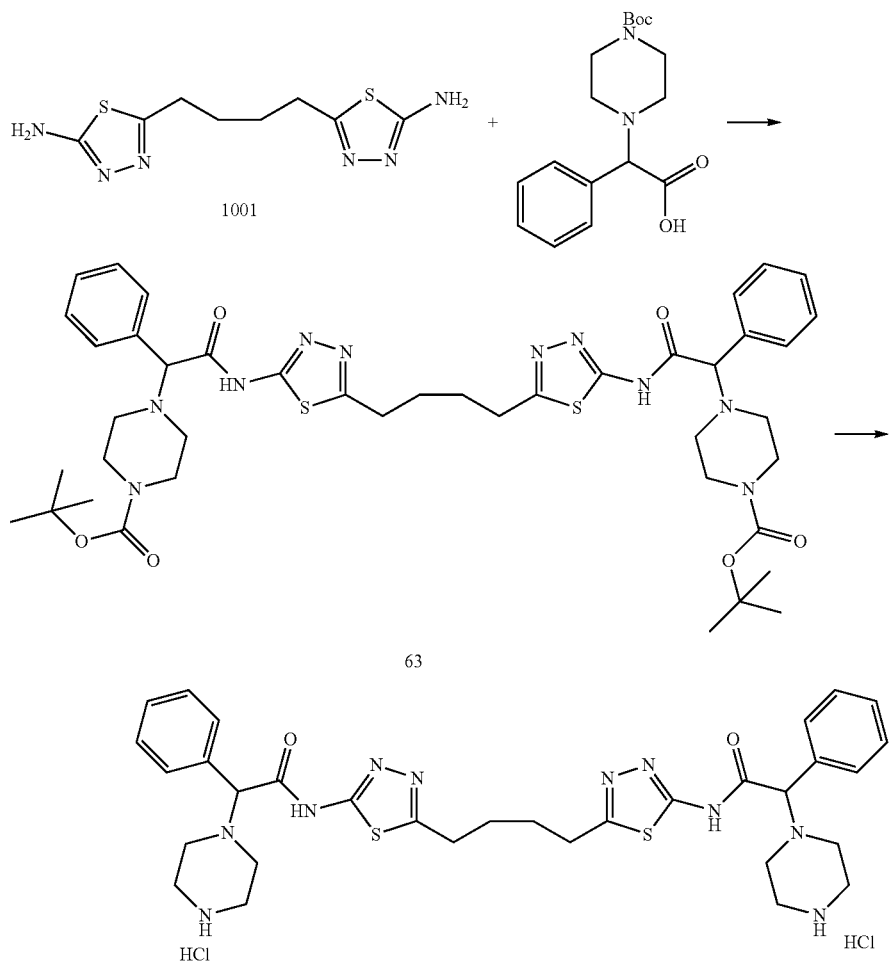

To a suspension of 2-(4-Boc-piperazinyl)-2-phenylacetic acid (1.1 g, 3.43 mmol) and HATU (1.47 g, 3.86 mmol) in DMF (5 mL) was added DIEA (0.672 ml, 3.86 mmol) followed by 1001 (400 mg, 1.56 mmol). The resulting mixture was stirred at room temperature overnight before it was quenched by addition of water (~10 mL). The white precipitate was collected by suction filtration, rinsed with water and dried. The crude material was purified by recrystallization with DMSO and MeOH to afford 63.

A flask was charged with 63 and 4N HCl in 1,4-dioxane (6 ml) and the resulting mixture was stirred at room temperature for 3 h. The precipitation was collected by filtration, rinse with EtOAc/CH$_2$Cl$_2$ and dried to afford 77. $^1$H NMR (300 MHz, DMSO-d$_6$) δ 9.10 (bs, 4H), 7.51-7.41 (m, 10H), 4.90 (bs, 2H), 4.62 (s, 2H), 3.15 (bs, 8H), 3.03 (bs, 4H), 2.73 (bs, 8H), 1.76 (bs, 4H).

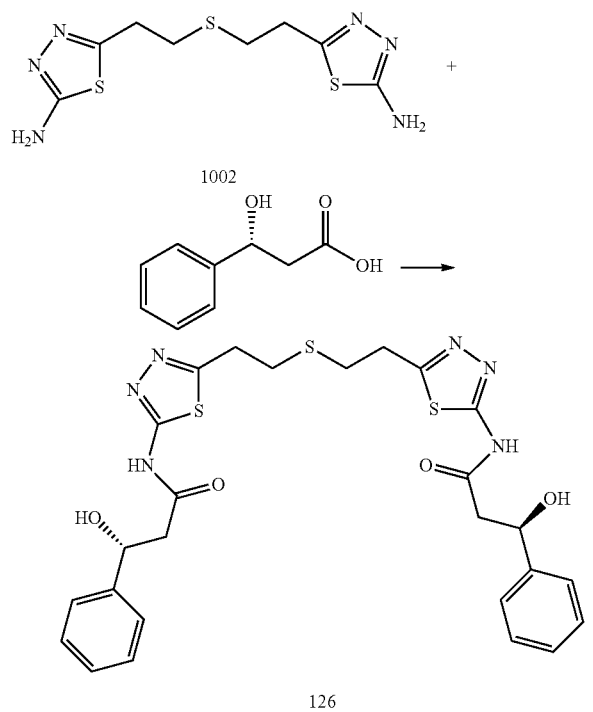

To a suspension of (R)-(+)-3-hydroxy-3-phenylpropionic acid (254 mg, 1.53 mmol) and HATU (640 mg, 1.68 mmol) in DMF (3 mL) was added DIEA (0.292 ml, 1.68 mmol) followed by 1002 (200 mg, 0.693 mmol). The resulting mixture was stirred at room temperature overnight before it was quenched by addition of water (~10 mL). The white precipitate was collected by suction filtration, rinsed with water and dried. The crude material was purified by recrystallization with a mixture of DMSO and MeOH to afford 126. $^1$H NMR (300 MHz, DMSO-d$_6$) δ 12.40 (s, 2H), 7.38 (m, 10H), 5.55 (m, 2H), 5.09 (m, 2H), 3.27 (t, 4H), 2.95 (t, 4H), 2.82 (m, 4H).

A flask was charged with 1002 (200 mg, 0.693 mmol), 2-(4-Boc-piperazinyl)-2-phenylacetic acid (244 mg, 0.763 mmol), and HOBt (187 mg, 1.39 mmol) in DMF (3 ml) was added EDC (332 mg, 1.73 mmol) followed by triethylamine (0.290 ml, 2.08 mmol). The resulting mixture was stirred at room temperature overnight before phenylacetyl chloride (0.037 ml, 0.277 mmol) was added dropwise at 0° C. and stirred for 1 h before it was quenched by addition of water (~10 mL). The white precipitate was collected by suction filtration, rinsed with water and dried. The crude material was purified by HPLC to afford 70 and 76.

A flask was charged with 70 and 4N HCl in 1,4-dioxane (6 ml) and the resulting mixture was stirred at room temperature for 3 h. The precipitation was collected by filtration, rinse with EtOAc/CH₂Cl₂ and dried to afford 78. ¹H NMR (300 MHz, DMSO-d₆) δ 12.70 (s, 2H), 8.97 (bs, 2H), 7.50-7.29 (m, 10H), 4.72 (bs, 1H), 4.59 (s, 1H), 3.82 (s, 2H), 3.27 (t, 4H), 3.15 (bs, 4H), 2.92 (t, 4H), 2.70 (bs, 4H).

79

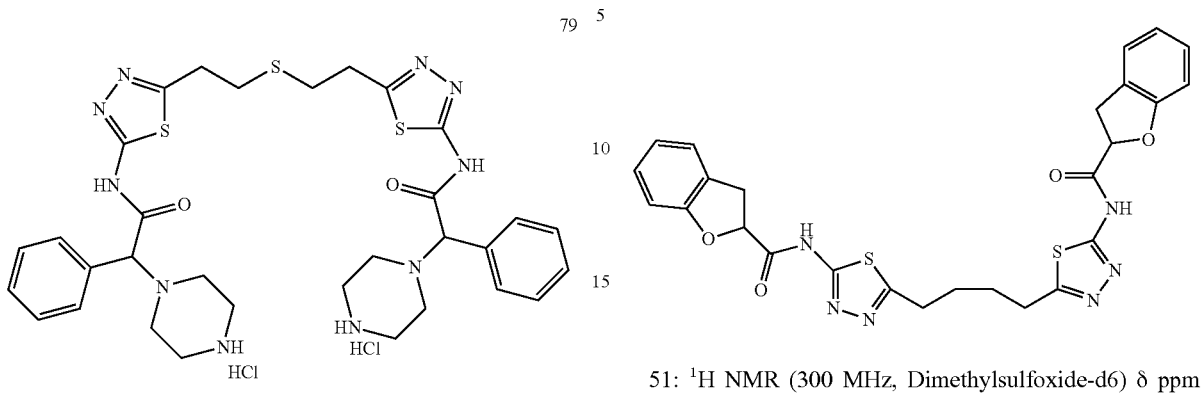

A flask was charged with 76 and 4N HCl in 1,4-dioxane (6 ml) and the resulting mixture was stirred at room temperature for 3 h. The precipitation was collected by filtration, rinse with EtOAc/CH₂Cl₂ and dried to afford 79. ¹H NMR (300 MHz, DMSO-d₆) δ 12.87 (s, 2H), 9.03 (bs, 4H), 7.50-7.40 (m, 10H), 4.67 (bs, 2H), 4.59 (s, 2H), 3.28 (t, 4H), 3.14 (bs, 8H), 2.97 (t, 4H), 2.71 (bs, 8H).

Amide Coupling General Procedure (Used for Following Examples):

To a 0.2 molar concentration suspension of carboxylic acid (2 equivalents) in DMF was added HATU (2 equivalents) and stirred till reaction mixture is clear followed by the addition of an amine (1 equivalent) and DIPEA (4 equivalents). The resulting mixture was stirred at room temperature overnight before it was quenched by the addition of water. The solid separated was filtered, washed with water and dried.

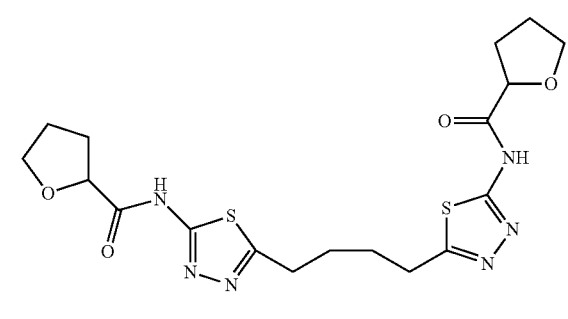 [SMILES: O=C(Nc1nnc(CCCCc2nnc(NC(=O)C3CCCO3)s2)s1)C1CCCO1]

39: ¹H NMR (300 MHz, Dimethylsulfoxide-d6) δ ppm 1.89-2.01 (m, 6H) 2.18-2.29 (m, 2H) 2.95-3 (m, 4H) 3.79-3.86 (m, 2H) 3.94-4.02 (m, 2H) 4.55-4.6 (m, 2H) 12.29 (brs, 2H).

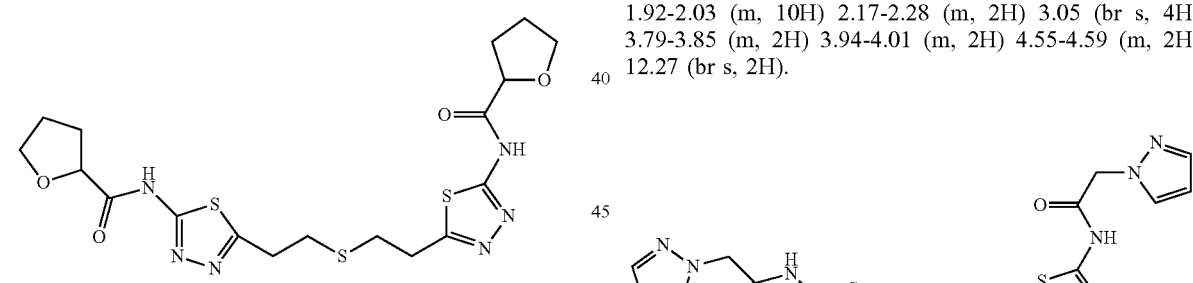

41: ¹H NMR (300 MHz, Dimethylsulfoxide-d6) δ ppm 2.93-2.98 (m, 4H) 3.27-3.32 (m, 4H), 4.46 (s, 4H), 5.18-5.2 (br s, 2H) 6.88-7.03 (m, 8H) 12.87-12.92 (br s, 2H).

51: ¹H NMR (300 MHz, Dimethylsulfoxide-d6) δ ppm 1.78 (br s, 4H) 3.05-3.06 (br s, 4H), 3.38-3.40 (m, 2H) 3.54-3.63 (m, 2H) 5.44-5.50 (m, 2H) 6.92-7.26 (m, 8H) 12.78 (br s, 2H).

54: ¹H NMR (300 MHz, Dimethylsulfoxide-d6) δ ppm 1.92-2.03 (m, 10H) 2.17-2.28 (m, 2H) 3.05 (br s, 4H) 3.79-3.85 (m, 2H) 3.94-4.01 (m, 2H) 4.55-4.59 (m, 2H) 12.27 (br s, 2H).

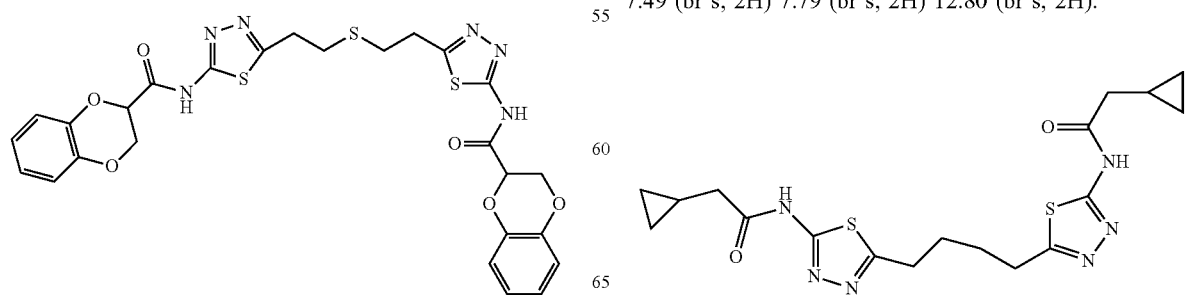

60: ¹H NMR (300 MHz, Dimethylsulfoxide-d6) δ ppm 1.77 (br s, 4H) 3.04 (br s, 4H) 5.20 (s, 4H) 6.31 (br s, 2H) 7.49 (br s, 2H) 7.79 (br s, 2H) 12.80 (br s, 2H).

85: ¹H NMR (300 MHz, Dimethylsulfoxide-d6) δ ppm 0.20-0.21 (br s, 4H) 0.48-0.50 (br s, 4H) 1.79 (br s, 4H) 2.35-2.38 (br s, 4H) 3.04 (br s, 4H) 12.32 (br s, 2H).

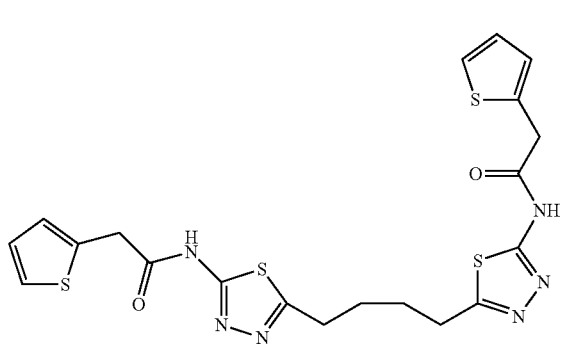 [SMILES: O=C(Cc1cccs1)Nc1nnc(CCCCc2nnc(NC(=O)Cc3cccs3)s2)s1]

87: ¹H NMR (300 MHz, Dimethylsulfoxide-d6) δ ppm 1.78 (br s, 4H) 3.03 (br s, 4H) 4.05 (s, 4H) 6.99 (br s, 4H) 7.42-7.44 (m, 2H) 12.68 (br s, 2H).

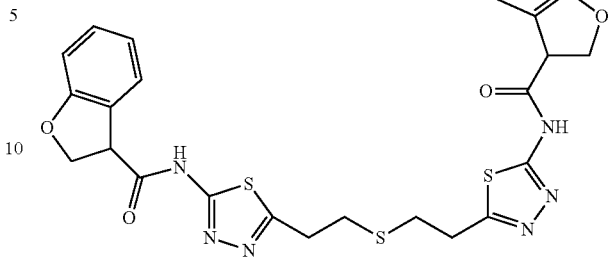

133: ¹H NMR (300 MHz, Dimethylsulfoxide-d6) δ ppm 2.92-2.97 (m, 4H) 3.26-3.30 (m, 4H) 4.61-4.87 (m, 6H) 6.83-6.89 (m, 4H) 7.16-7.21 (m, 2H) 7.36-7.38 (m, 2H) 12.95 (br s, 2H).

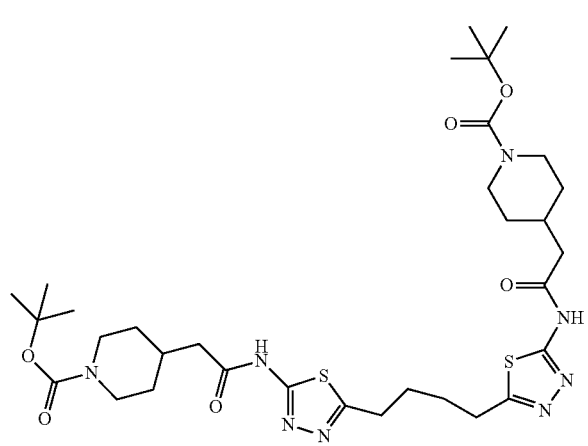 [SMILES: CC(C)(C)OC(=O)N1CCC(CC(=O)Nc2nnc(CCCCc3nnc(NC(=O)CC4CCN(C(=O)OC(C)(C)C)CC4)s3)s2)CC1]

114: ¹H NMR (300 MHz, Dimethylsulfoxide-d6) δ ppm 1.01-1.12 (m, 4H) 1.40 (s, 18H) 1.61-1.65 (m, 4H) 1.78 (br s, 4H) 1.95 (br s, 2H) 3.84 (m, 4H) 2.65-2.75 (m, 4H) 3.03 (br s, 4H) 3.89-3.93 (m, 4H) 12.39 (br s, 2H).

135: ¹H NMR (300 MHz, Dimethylsulfoxide-d6) δ ppm 1.77 (br s, 4H) 3.03 (br s, 4H) 4.60-4.87 (m, 6H) 6.83-6.89 (m, 4H) 7.16-7.22 (m, 2H) 7.36-7.38 (m, 2H) 12.92 (br s, 2H).

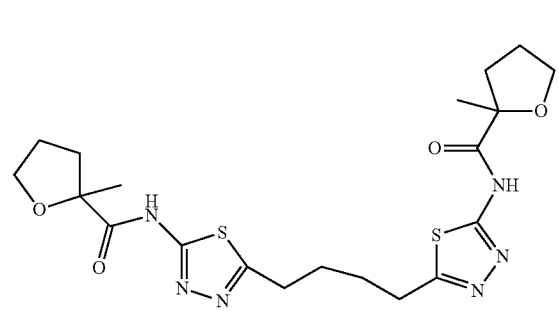 [SMILES: CC1(C(=O)Nc2nnc(CCCCc3nnc(NC(=O)C4(C)CCCO4)s3)s2)CCCO1]

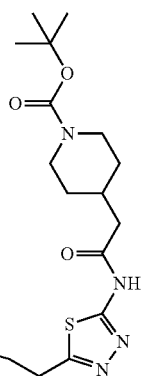

123: ¹H NMR (300 MHz, Dimethylsulfoxide-d6) δ ppm 1.43 (s, 6H) 1.79-1.94 (m, 10H) 2.22-2.31 (m, 2H) 3.05 (br s, 4H) 3.85-4.01 (m, 4H) 11.85 (br s, 2H).

114: ¹H NMR (300 MHz, Dimethylsulfoxide-d6) δ ppm 1.01-1.12 (m, 4H) 1.40 (s, 18H) 1.61-1.65 (m, 4H) 1.78 (br s, 4H) 1.95 (br s, 2H) 3.84 (m, 4H) 2.65-2.75 (m, 4H) 3.03 (br s, 4H) 3.89-3.93 (m, 4H) 12.39 (br s, 2H).

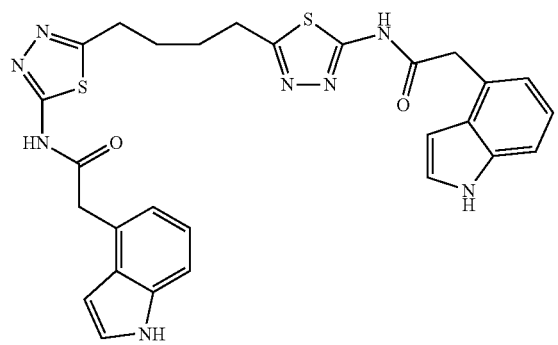 [SMILES: O=C(Cc1cccc2[nH]ccc12)Nc1nnc(CCCCc2nnc(NC(=O)Cc3cccc4[nH]ccc34)s2)s1]
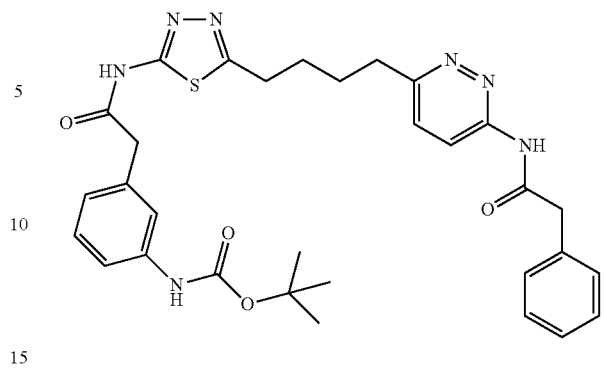
323: ¹H NMR (300 MHz, Dimethylsulfoxide-d6) δ ppm 1.76 (brs, 4H) 3.01 (brs, 4H) 4.02 (s, 4H) 6.56 (s, 2H) 6.94-7.05 (m, 4H) 7.31-7.33 (m, 4H) 11.12 (brs, 2H) 12.69 (s, 2H).
399: ¹H NMR (300 MHz, Dimethylsulfoxide-d6) δ ppm 1.48 (s, 9H) 1.75 (brs, 4H) 2.90 (brs, 2H) 3.02 (brs, 2H) 3.74-3.78 (m, 4H) 6.92-6.94 (m, 1H) 7.20-7.36 (m, 7H) 7.51-7.58 (m, 2H) 8.18-8.21 (d, 1H) 9.34 (s, 1H) 11.26 (s, 1H) 12.65 (brs, 1H).
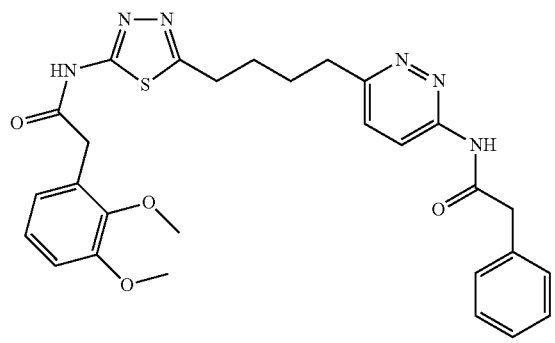 [SMILES: COc1cccc(CC(=O)Nc2nnc(CCCCc3ccc(NC(=O)Cc4ccccc4)nn3)s2)c1OC]
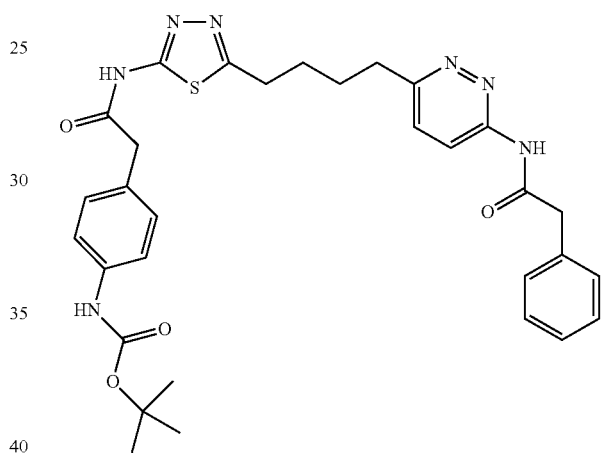
397: ¹H NMR (300 MHz, Dimethylsulfoxide-d6) δ ppm 1.75 (brs, 4H) 2.90 (brs, 2H) 3.02 (brs, 2H) 3.67-3.82 (m, 10H) 6.85-7.03 (m, 4H) 7.26-7.36 (m, 5H) 7.55-7.58 (d, 1H) 8.18-8.21 (d, 1H) 11.26 (s, 1H) 12.65 (brs, 1H).
400: ¹H NMR (300 MHz, Dimethylsulfoxide-d6) δ ppm 1.48 (s, 9H) 1.75 (brs, 4H) 2.90 (brs, 2H) 3.02 (brs, 2H) 3.71-3.78 (m, 4H) 7.18-7.42 (m, 9H) 7.54-7.58 (m, 2H) 8.18-8.21 (d, 1H) 9.34 (s, 1H) 11.26 (s, 1H) 12.65 (brs, 1H).
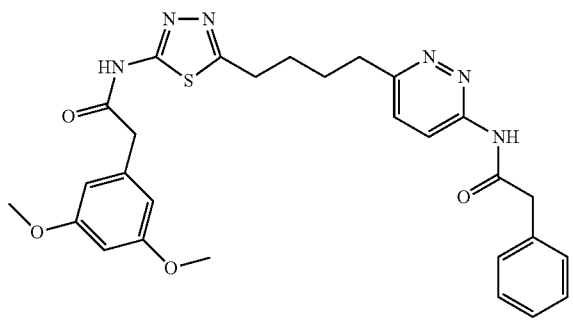 [SMILES: COc1cc(CC(=O)Nc2nnc(CCCCc3ccc(NC(=O)Cc4ccccc4)nn3)s2)cc(OC)c1]
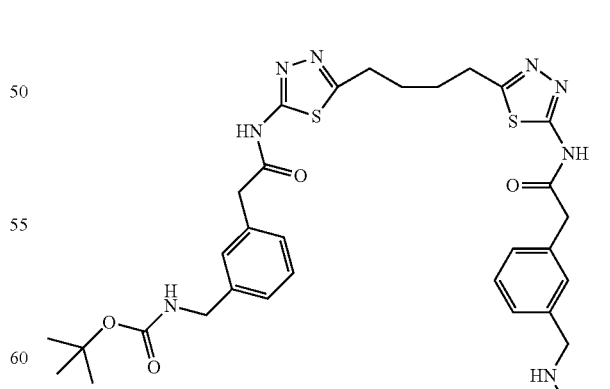
398: ¹H NMR (300 MHz, Dimethylsulfoxide-d6) δ ppm 1.75 (brs, 4H) 2.90 (brs, 2H) 3.02 (brs, 2H) 3.72-3.78 (m, 10H) 6.42-6.51 (m, 4H) 7.36 (m, 5H) 7.54-7.58 (d, 1H) 8.18-8.21 (d, 1H) 11.26 (s, 1H) 12.65 (brs, 1H).

324: ¹H NMR (300 MHz, Dimethylsulfoxide-d6) δ ppm 1.39 (s, 18H) 1.76 (brs, 4H) 3.01 (brs, 4H) 3.79 (s, 4H) 4.11-4.13 (brs, 4H) 7.13-7.38 (m, 8H) 12.65 (s, 2H).

Method C: Via Aluminum Amide Coupling with Esters/Lactones

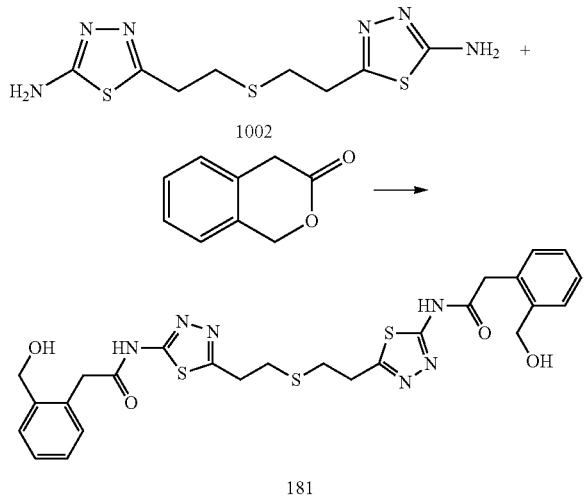

To a suspension of 1002 (288 mg, 1.00 mmol) in toluene (9 mL) was added 3-isochromanone (311 mg, 2.10 mmol) followed by trimethyl aluminum (2M in toluene, 1.0 mL, 2.00 mmol). The resulting mixture was stirred at 75° C. for 15 h, cooled to room temperature and diluted with ethyl acetate (50 mL). The organic layer was washed with water (3×20 mL), 10% sodium chloride solution (10 mL), dried (magnesium sulfate) and concentrated under reduced pressure. The crude product was purified by HPLC to afford N,N'-(5,5'-(thiobis(ethane-2,1-diyl))bis(1,3,4-thiadiazole-5,2-diyl))bis(2-(2-(hydroxymethyl)phenyl)acetamide) (181, 78 mg). ¹H NMR (300 MHz, DMSO-d₆) δ 7.42 (d, J=6.84 Hz, 2H), 7.26 (bs, 6H), 4.57 (s, 4H), 3.90 (s, 4H), 3.27 (t, J=6.62 Hz, 4H), 2.94 (t, J=6.44 Hz, 4H)

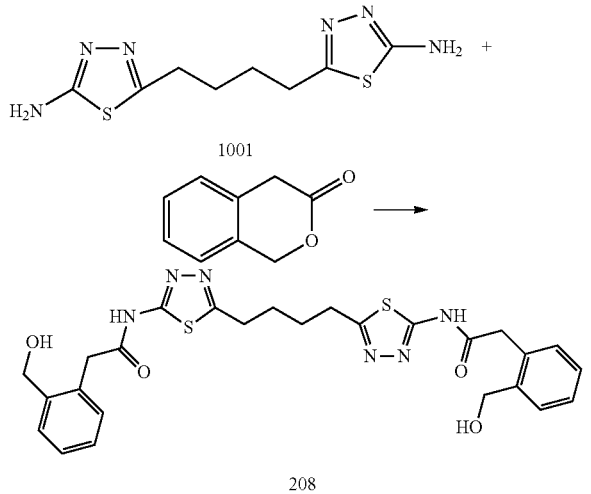

To a suspension of 1001 (256 mg, 1.00 mmol) in toluene (8 mL) was added 3-isochromanone (311 mg, 2.10 mmol) followed by trimethyl aluminum (2M in toluene, 1.0 mL, 2.00 mmol). The resulting mixture was stirred at 75° C. 15 h, cooled to room temperature and diluted with ethyl acetate (50 mL). The organic layer was washed with water (3×20 mL), 10% sodium chloride solution (10 mL), dried (magnesium sulfate) and concentrated under reduced pressure. The crude product was purified by HPLC to afford N,N'-(5,5'-(thiobis(ethane-2,1-diyl))bis(1,3,4-thiadiazole-5,2-diyl))bis(2-(2-(hydroxymethyl)phenyl)acetamide) (208, 62 mg). ¹H NMR (300 MHz, DMSO-d₆) δ 7.41 (s, 2H), 7.26 (s, 6H), 4.56 (s, 4H), 3.01 (bs, 4H), 1.76 (bs, 4H)

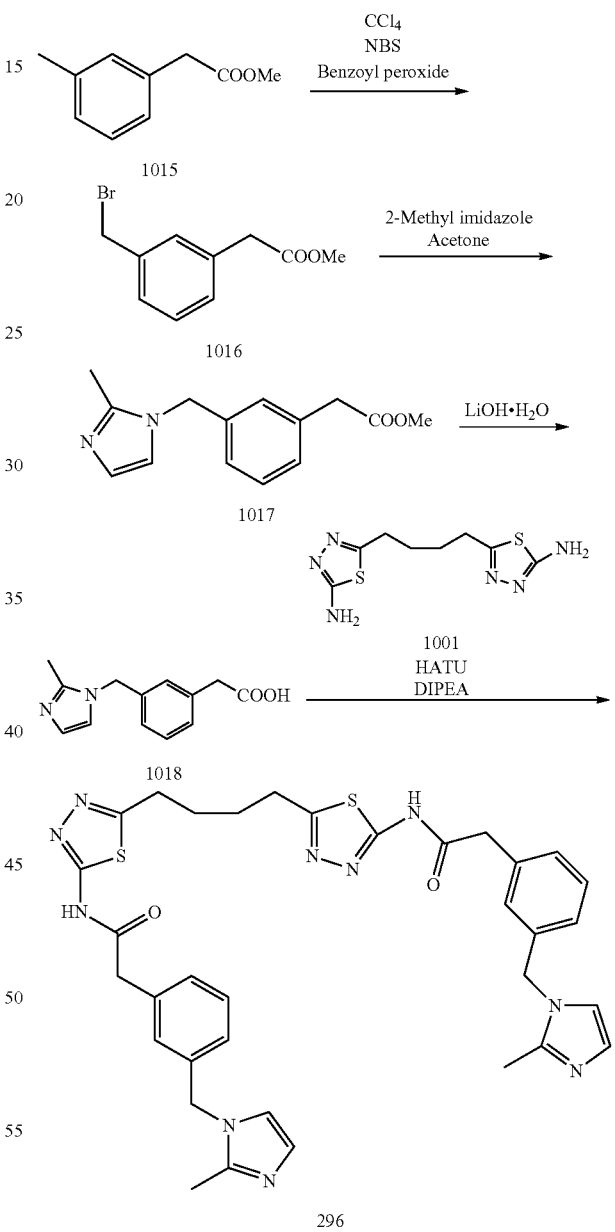

To a solution of 1015 (3.2 g, 19.5 mmol) in carbon tetrachloride (150 mL) was added N-bromosuccinimide (3.47 g, 19.6 mmol) and benzoyl peroxide (10 mg, catalytic). The resulting mixture was refluxed overnight before it was filtered hot. The filtrate was concentrated under reduced pressure and the residue obtained was purified by silica gel chromatography eluting with 20% ethylacetate/hexane to afford 1016 (2 g, 42% yield) as an oil. ¹H NMR (300 MHz, Chloroform-d) δ ppm 3.66 (s, 2H) 3.74 (s, 3H) 4.51 (s, 2H) 7.35 (m, 4H).

To a solution of 1016 (0.243 g, 1 mmol) in acetone (10 mL) was added 2-methyl imidazole (0.41 g, 5 mmol). The resulting mixture was refluxed overnight before it was concentrated under reduced pressure and the residue obtained was diluted with water (~100 mL). The resulting solution was partitioned between water and ethyl acetate. The organic extract was washed with more water, separated, dried over sodium sulfate, filtered and evaporated. The residue obtained was purified by silica gel chromatography eluting with MeOH/dichloromethane to afford 1017 (0.17 g, 69% yield) as an oil. ¹H NMR (300 MHz, Chloroform-d) δ ppm 2.37 (s, 3H) 3.63 (s, 2H) 3.72 (s, 3H) 5.07 (s, 2H) 6.87 (s, 1H) 6.96-7.02 9 m, 2H) 7.23-7.33 (m, 3H)

To a solution of 1017 (0.17 g, 0.69 mmol) in THF/MeOH/Water (10 mL, 2 mL, 2 mL) was added lithium hydroxide monohydrate (0.06 g, 1.42 mmol). The resulting mixture was stirred at room temperature overnight before it was concentrated under reduced pressure. The residue obtained was diluted with water (~20 mL) and the resulting solution was acidified with acetic acid. The aqueous layer was concentrated and the product was isolated by prep HPLC. The residue obtained was dissolved in water (5 mL) and concentrated hydrochloric acid (83 μL) was added to it before it was concentrated and dried to afford 1018 (0.15 gm) as a hydrochloride salt.

To a suspension of carboxylic acid 1018 (105 mg, 0.39 mmol) in DMF (3 mL) was added HATU (150 mg, 0.39 mmol) and stirred till reaction mixture is clear followed by the addition of an amine 1001 (50.5 mg, 0.197 mmol) and DIPEA (0.14 mL, 0.8 mmol). The resulting mixture was stirred at room temperature overnight before it was quenched by the addition of water. The solid separated was filtered, washed with water and dried to afford 296 (112 mg, 83%). ¹H NMR (300 MHz, Dimethylsulfoxide-d6) δ ppm 1.76 (brs, 4H) 2.38 (s, 6H) 3.01 (brs, 4H) 3.82 (s, 4H) 5.25 (s, 4H) 7.09-7.38 (m, 12H) 12.64-12.67 (brs, 2H).

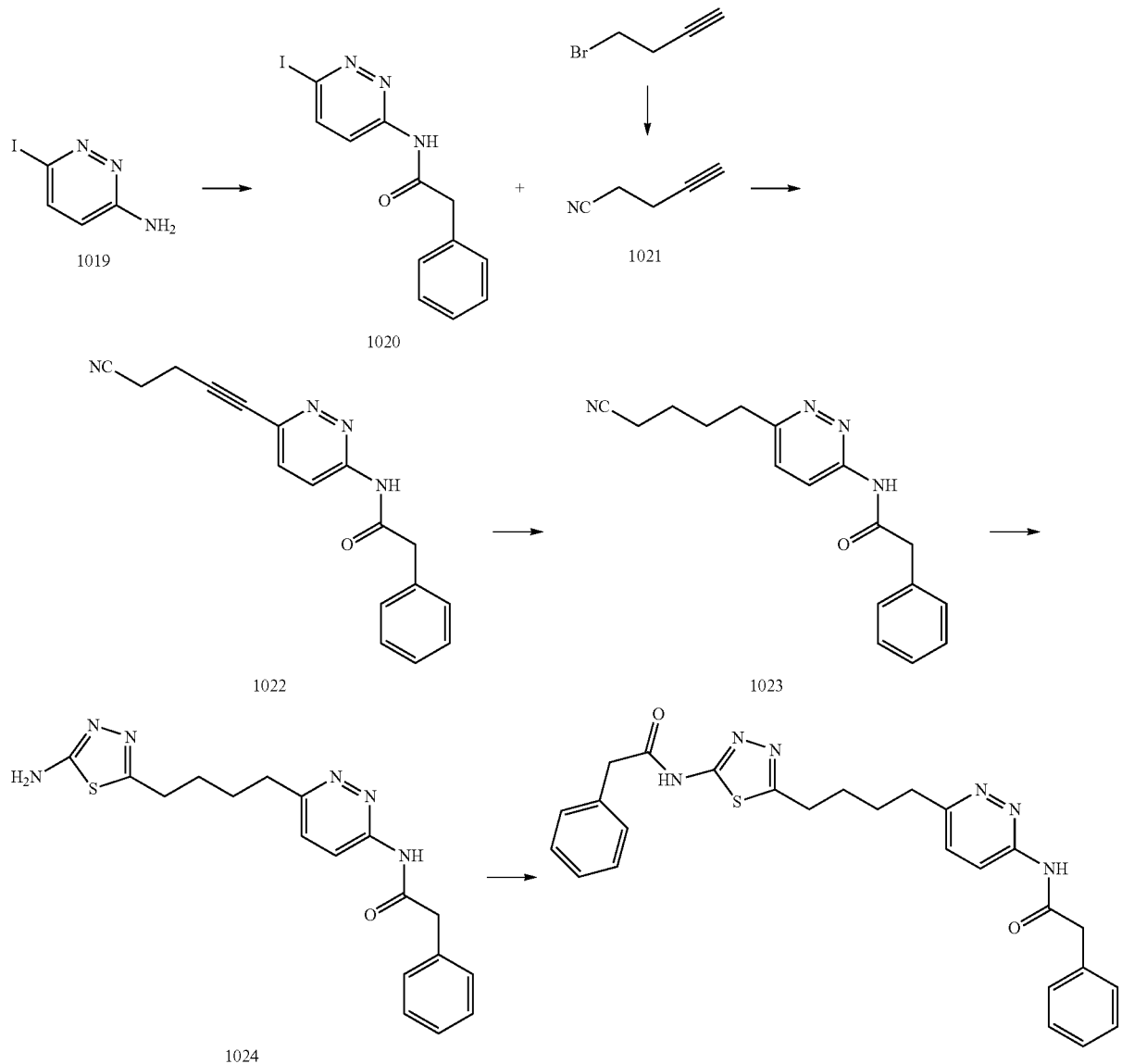

To a suspension of 1019 (1.5 g, 6.8 mmol) in CH$_2$Cl$_2$ (15 mL) at 0° C. was added Et$_3$N (1.9 ml, 13.6 mmol) dropwise followed by phenyl acetyl chloride (1.07 ml, 8.1 mmol) dropwise. The resulting mixture was stirred at 0° C. and then slowly warmed up to room temperature for 2 days. The crude material was purified by silica gel chromatography eluting with 0-25% EtOAc in hexane to afford 1020.

To a solution of 4-bromo-1-butyne (7 g, 53 mmol) in DMSO (30 ml) at 0° C. was added NaI (7.94 g, 53 mmol). The mixture was stirred at room temperature for 2 h before it was cooled to 0° C. and followed by addition of NaCN (5.2 g, 106 mmol). The resulting mixture was heated at 80° C. for 2.5 h and then stirred at room temperature overnight. The mixture was partitioned between water and EtOAc. The organic extract was washed with water, dried over sodium sulfate, filtered and evaporated to afford 1021.

To a mixture of 1020 (400 mg, 1.18 mmol), PdCl$_2$(PPh$_3$)$_2$ (41 mg, 0.059 mmol) and CuI (11 mg, 0.059 mmol) in Et$_3$N (3 ml) and THF (6 ml) under argon atmosphere was added 1021 (187 mg, 2.36 mmol), then heated at 60° C. overnight. After removal of the solvent, the residue was purified by silica gel chromatography eluting with 0-60% EtOAc in Hexane to afford 1022.

To a solution of 1022 (118 mg, 0.406 mmol) in the mixture of EtOAc (60 ml) and EtOH (15 ml) was added Pd(OH)$_2$/C (50 mg, 0.356 mmol). Hydrogen was bubbled through the resulting mixture and stirred for 1 h. The Pd catalyst was filtered off and the filtrate was concentrated to afford 1023.

A mixture of 1023 (127 mg, 0.431 mmol) and thiosemicarbazide (51 mg, 0.561 mmol) in TFA (3 mL) was heated at 85° C. for 5 h. The reaction was cooled to room temperature and poured onto a mixture of ice-water. The mixture was basified with NaOH pellets (pH 10). The crude material was purified by silica gel chromatography eluting with 0-6% MeOH in CH$_2$Cl$_2$ to afford 1024.

To a solution of 1024 (38.4 mg, 0.104 mmol) in NMP (1 mL) at 0° C. was added phenyl acetyl chloride (0.017 mL, 0.125 mmol) dropwise. The resulting mixture was stirred at 0° C. for 1.5 h before it was quenched by addition of water (~10 mL). The mixture was partitioned between water and EtOAc. The organic extract was washed with water, dried over sodium sulfate, filtered and evaporated. The crude material was purified by silica gel chromatography eluting with 0-6% MeOH in CH$_2$Cl$_2$ to afford 295. $^1$H NMR (300 MHz, DMSO-d$_6$) δ 12.65 (s, 1H), 11.26 (s, 1H), 8.22-8.19 (d, J=8.82 Hz, 1H), 7.58-7.54 (d, J=9.72 Hz, 1H), 7.36-7.28 (m, 10H), 3.81-3.78 (d, J=8.43 Hz, 4H), 3.01 (bs, 2H), 2.90 (bs, 2H), 1.73 (bs, 4H).

Compound 1024 can also be prepared according to the following procedure:

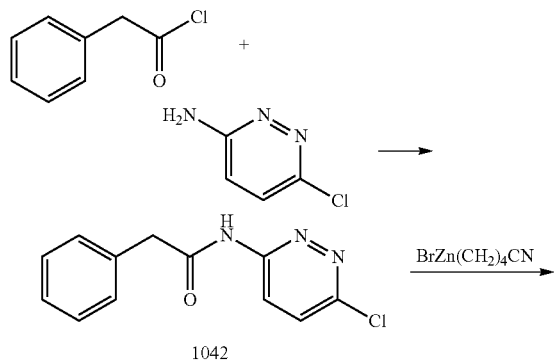

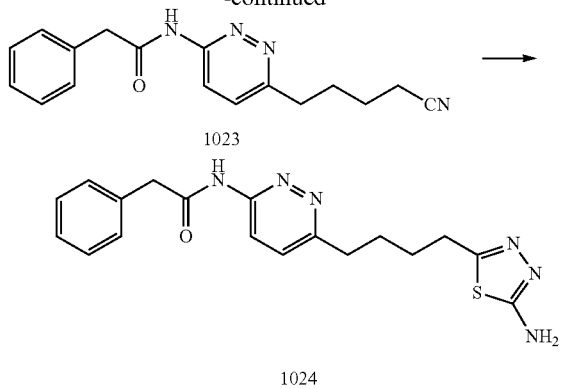

To a solution of 3-amino-6-chloropyridazine (11.14 g, 86.0 mmol) in NMP (279 mL) at 19° C. was added phenylacetyl chloride (18.2 mL, 137.6 mmol) dropwise over 5 minutes with the internal temperature of the solution maintained T$_1$≤28° C. The resulting mixture was stirred at 19° C. for 90 minutes and poured into ice water (557 mL). The white precipitate was collected by suction filtration, rinsed with water (2×110 mL) and diethyl ether (110 mL). The product was dried overnight under high vacuum to afford N-(6-chloropyridazin-3-yl)-2-phenylacetamide (xxx, 18.8 g). $^1$H NMR (300 MHz, DMSO-d$_6$) δ 11.57 (s, 1H), 8.40 (d, J=9.636 Hz, 1H), 7.90 (d, J=9.516 Hz, 1H), 7.36 (m, 5H) 3.82 (s, 2H)

A 1000 mL three-neck flask fitted with internal temperature probe and addition funnel was flushed with Ar$_{(g)}$. Under positive Argon pressure 4-cyanobutylzinc bromide (0.5M in THF, 500 mL, 250 mmol) was charged into the addition funnel then added to the reaction vessel at room temperature. Solid N-(6-chloropyridazin-3-yl)-2-phenylacetamide (20.6 g, 83.3 mmol) was added to the stirred solution at RT under Ar$_{(g)}$ flow, followed by the addition of NiCl$_2$ (dppp) (4.52 g, 8.33 mmol). The resulting mixture was stirred at 19° C. for 240 minutes and then quenched with ethanol (120 mL). Water (380 mL) added to the stirred red solution, giving a thick precipitate. Ethyl acetate (760 mL) added and stirred well for 30 minutes. The solids were removed by filtration through a pad of celite. The mother liquor was then transferred to a separatory funnel and the organic layer was washed with H$_2$O (380 mL), 0.5% ethylenediaminetetraacetic acid solution (380 mL) and again with H$_2$O (380 mL). The organic layer was concentrated by rotoevaporation. Resulting red oil was redissolved in EtOAc (200 mL) and 1M HCl (380 mL) was added to the well stirred flask. After 30 minutes the mixture was transferred to separatory funnel and the aqueous layer collected. The organic layer was extracted with 1M HCl (2×380 mL). The aqueous layer's pH was then adjusted to ~7 using 7.5% sodium bicarbonate solution and the pale yellow precipitate was collected by suction filtration, rinsed with water (200 mL) and diethyl ether (2×200 mL). The solid was dried overnight under high vacuum to afford N-(6-(4-cyanobutyl)pyridazin-3-yl)-2-phenylacetamide (1023, 14.76 g). $^1$H NMR (300 MHz, DMSO-d$_6$) δ 11.29 (s, 1H), 8.23 (d, J=9.036 Hz, 1H), 7.59 (d, J=9.246 Hz, 1H), 7.32 (m, 5H), 3.79 (s, 2H), 2.90 (t, J=7.357 Hz, 2H), 2.56 (t, J=7.038 Hz, 2H), 1.79 (t, J=7.311 Hz, 2H), 1.63 (t, J=7.01 Hz, 2H)

N-(6-(4-cyanobutyl)pyridazin-3-yl)-2-phenylacetamide (14.7 g, 50.2 mmol) was charged into a 250 mL round bottom flask fitted with an open top reflux condenser. To the flask was added thiosemicarbazide (5.03 g, 55.2 mmol) and trifluoroacetic acid (88 mL). The reaction slurry was heated in a 65° C. bath for 2 h. After cooling to RT, H$_2$O (150 mL) was added and stirred for 30 minutes. The mixture was then slowly transferred to a stirred 7.5% sodium bicarbonate solution (1400 mL) cooled in a 0° C. bath. The precipitate was collected by suction filtration, rinsed with water (2×200 mL), diethyl ether (2×200 mL) and dried under high vacuum overnight. The off-white solid was slurried in DMSO (200 mL) and heated in an 80° C. bath until the internal temperature reached 65° C. DMSO (105 mL) was used to rinse sides of flask. H$_2$O (120 mL) was slowly added until the solution became slightly cloudy and then the mixture was removed from heat bath and allowed to cool to ambient temperature while stirring. The pale green precipitate was collected by suction filtration, rinsed with water (200 mL) and diethyl ether (2×200 mL). The solid was dried overnight under high vacuum to provide N-(6-(4-(5-amino-1,3,4-thiadiazol-2-yl)butyl)pyridazin-3-yl)-2-phenylacetamide (1024, 15.01 g). $^1$H NMR (300 MHz, DMSO-d$_6$) δ 11.28 (s, 1H), 8.23 (d, J=8.916 Hz, 1H), 7.59 (d, J=8.826 Hz, 1H), 7.36 (m, 5H), 7.07 (s, 2H), 3.78 (s, 2H), 2.87 (t, J=6.799 Hz, 4H), 1.69 (bm, 4H)

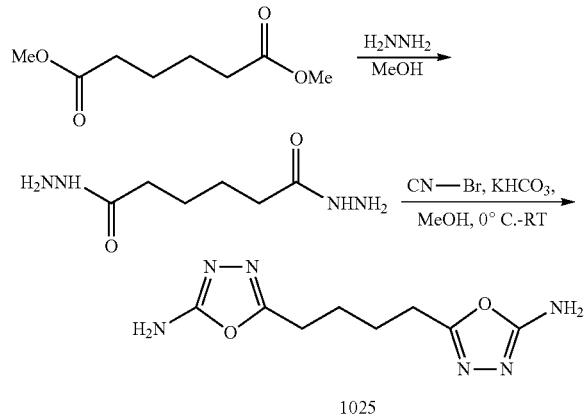

1025

To a solution of dimethyl adipate (28.7 mmol, 5.0 g, 4.7 mL, 1.0 equiv.) in 20 mL of MeOH was added anhydrous hydrazine (229.6 mmol, 7.36 g, 7.51 mL, 8.0 equiv.) and the mixture heated to 50° C., giving a white precipitate. The mixture was heated for one hour and then allowed to cool to room temperature. The white solid was collected by filtration and washed with additional MeOH then dried under high vacuum giving 4.6 g of adipohydrizide. $^1$HNMR (300 MHz, DMSO-d$_6$) δ 8.91 (s, 2H), 4.14 (s, 4H), 2.00 (br s, 4H), 1.46 (br s, 4H).

To a 0° C. cooled slurry of adipohydrizide (12.49 mmol, 4.0 g, 1.0 equiv.), potassium bicarbonate (15.61 mmol, 1.56 g, 1.25 equiv.) in 25 mL of MeOH was added solid cyanogen bromide (13.74 mmol, 1.44 g, 1.1 equiv.) in one portion. This mixture was stirred at 0° C. and allowed to warm to RT over one hour and then stirred overnight. The volatiles were removed under reduced pressure and the solids diluted with water. The pH was adjusted to 12 with 2.5 N NaOH and the solids collected by filtration. The white solid was washed with water and dried under high vacuum to give 1.73 g of oxadiazole 1025. $^1$HNMR (300 MHz, DMSO-d$_6$) δ 6.85 (s, 4H), 2.68 (s, 4H), 1.68 (s, 4H).

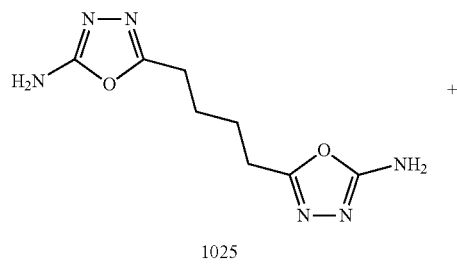

1025

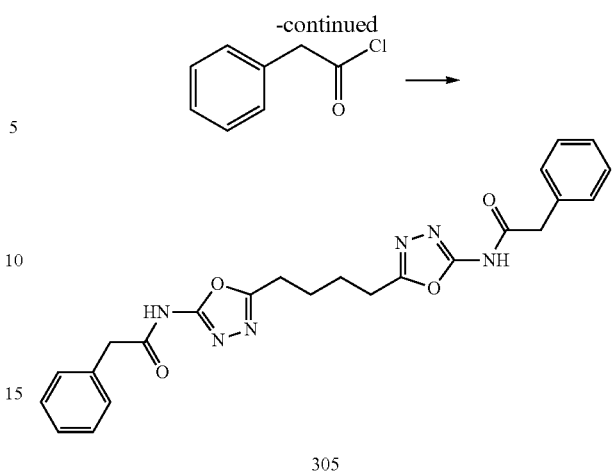

305

To a suspension of oxadiazole 1025 (181 mg, 0.81 mmol) in NMP (9 mL) was added triethylamine (0.564 mL, 4.05 mmol) and the mixture warmed to 70° C. The mixture was allowed to stir for 30 minutes followed by the addition of phenylacetyl chloride (0.234 mL, 1.77 mmol). The reaction temperature was held at 70° C. for 15 hours then allowed to cool to room temperature. The crude reaction mixture was purified by reverse phase HPLC giving 305 (0.015 g). $^1$HNMR (300 MHz, DMSO-d$_6$) δ 11.74 (s, 2H), 7.33 (s, 10H), 3.74 (s, 4H), 2.85 (s, 4H), 1.76 (s, 4H).

Functionalization of Diacylated Cores:

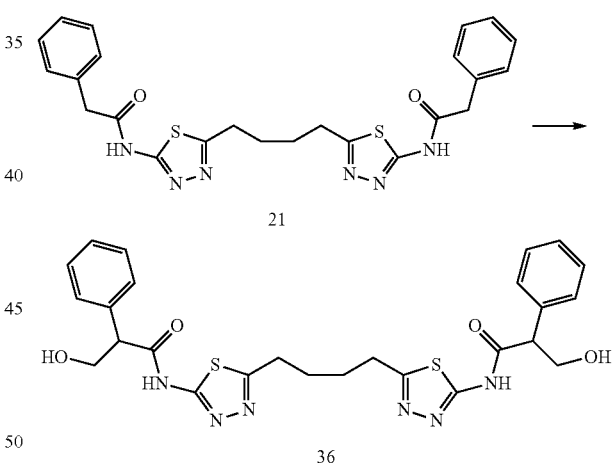

To a suspension of 21 (2.25 g, 4.57 mmol) in a mixture of THF (250 mL) and H$_2$O (20 mL) at room temperature was added NaOH (1.83 g, 45.67 mmol) and formaldehyde solution (37% in water, 14.83 mL, 182.70 mmol). The resulting mixture was heated at 60° C. for 7 h before it was cooled to 0° C. and acidified to pH 7 with aq. HCl solution. The white precipitate was collected by suction filtration, rinsed with water and dried to provide N,N'-[5,5'-(butane-1,4-diyl)-bis(1,3,4-thiadiazole-5,2-diyl)]-bis(3-hydroxy-2-phenylpropanamide) (36, 624 mg). The 2$^{nd}$ precipitation from the filtrate provided additional product (1.29 g). $^1$H NMR (300 MHz, DMSO-d$_6$) δ 12.65 (bs, 2H), 7.35-7.30 (m, 10H), 5.09 (bs, 2H), 4.10-4.02 (m, 4H), 3.61 (d, J=8.1 Hz, 2H), 3.02 (bs, 4H), 1.76 (bs, 4H).

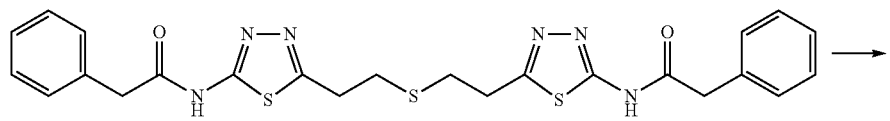

199

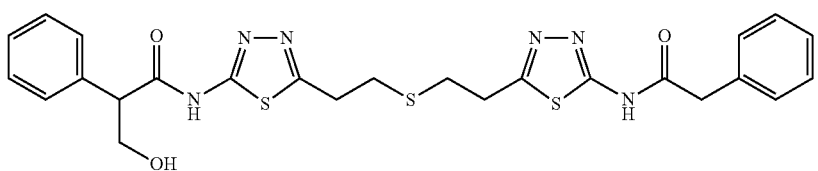

29

To a suspension of 199 (300 mg, 0.572 mmol) in a mixture of THF (50 mL) and MeOH (5 ml) was added potassium carbonate (158 mg, 1.144 mmol) and formaldehyde solution (37% in water, 2 mL). The resulting mixture was stirred at room temperature for 48 h before it was cooled to 0° C. and acidified to pH 7 with aq. HCl solution. The white precipitate was collected by suction filtration, rinsed with water and dried. The crude material was purified by HPLC to afford 29. $^1$H NMR (300 MHz, DMSO-$d_6$) δ 7.34-7.26 (m, 10H), 4.13-4.02 (m, 2H), 3.81 (s, 2H), 3.62 (m, 2H), 3.24 (t, 4H), 2.93 (t, 4H).

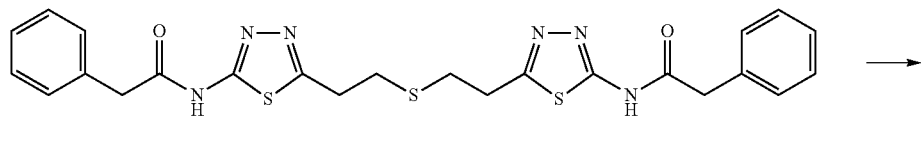

199

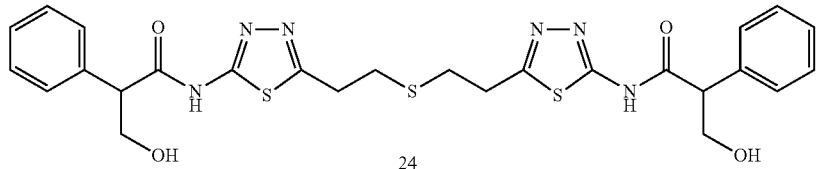

24

To a suspension of 199 (2.0 g, 3.81 mmol) in a mixture of THF (250 mL) and MeOH (20 ml) H$_2$O (20 mL) at room temperature was added 1N NaOH (20 ml) and formaldehyde solution (37% in water, 15 mL). The resulting mixture was heated at 50° C. overnight before it was cooled to 0° C. and acidified to pH 7 with aq. HCl solution. The white precipitate was collected by suction filtration, rinsed with water and dried. The crude material was purified by HPLC to afford 24. $^1$H NMR (300 MHz, DMSO-$d_6$) δ 12.67 (bs, 2H), 7.36-7.30 (m, 10H), 5.10 (bs, 2H), 4.10-4.02 (m, 4H), 3.61 (d, 2H), 3.27 (t, 4H), 2.95 (t, 4H).

Prodrugs:

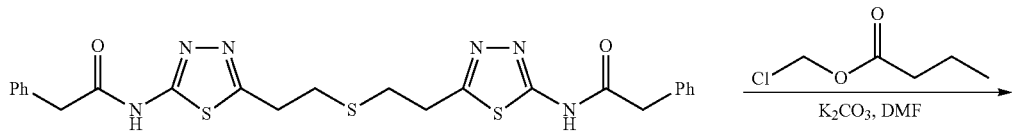

1

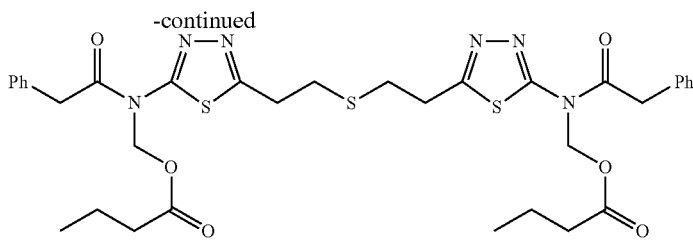

8

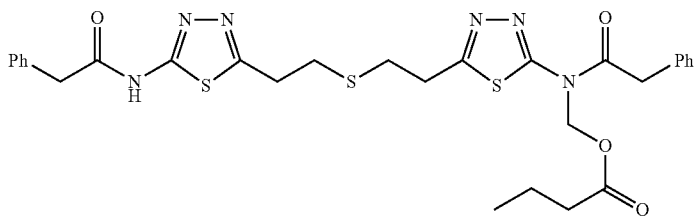

7

To a flask containing N,N'-(5,5'-(thiobis(ethane-2,1-diyl))bis(1,3,4-thiadiazole-5,2-diyl))bis(2-phenylacetamide) (1) (9.4 mmol, 5.0 g, 1.0 equiv.) was added 100 mL DMF, $K_2CO_3$ (20.98 mmol, 2.89 g, 2.2 equiv.), and chloromethyl butyrate (20.98 mmol, 2.86 g, 2.62 mL, 2.2 equiv.). The mixture stirred at room temperature for 15 hours then diluted with 200 mL water and 200 mL EtOAc. The layers were separated and the aqueous layer extracted with EtOAc (2×100 mL) and the organic layers combined, washed with water, brine and dried over $Na_2SO_4$. The $Na_2SO_4$ was removed by filtration and the volatiles removed under reduced pressure. The compounds were purified by reverse phase chromatography (MeCN, $H_2O$) giving 0.235 g of compound 8 and 0.126 g of compound 7.

$^1$HNMR (300 MHz, DMSO, $d_6$) Compound 8: δ 7.31 (m, 10H), 6.18 (s, 4H), 3.82 (s, 4H), 3.17 (dd, 2H, J=6.8 Hz), 2.92 (dd, 2H, J=6.8 Hz), 2.93 (m, 4H), 2.32 (dd, 2H, J=7.2 Hz), 1.54 (dt, 2H, J=7.2, 7.4 Hz), 0.87 (t, 3H, J=7.4 Hz).

$^1$HNMR (300 MHz, DMSO, $d_6$) Compound 7: δ 12.68 (s, 1H), 7.32 (m, 10H), 6.18 (s, 2H), 3.82 (s, 4H), 3.26 (dd, 2H, J=7.0 Hz), 3.17 (dd, 2H, J=6.8 Hz), 2.93 (m, 4H), 2.32 (dd, 2H, J=7.2 Hz), 1.54 (dt, 2H, J=7.2, 7.4 Hz), 0.87 (t, 3H, J=7.4 Hz).

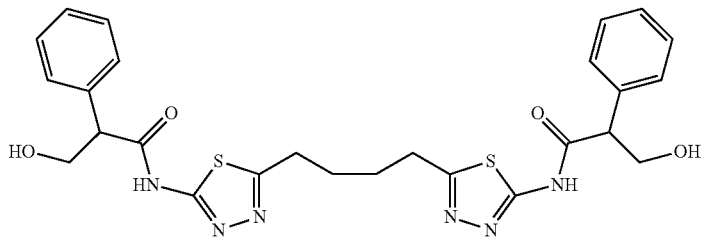

36

+

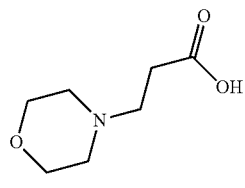

·HCl

→

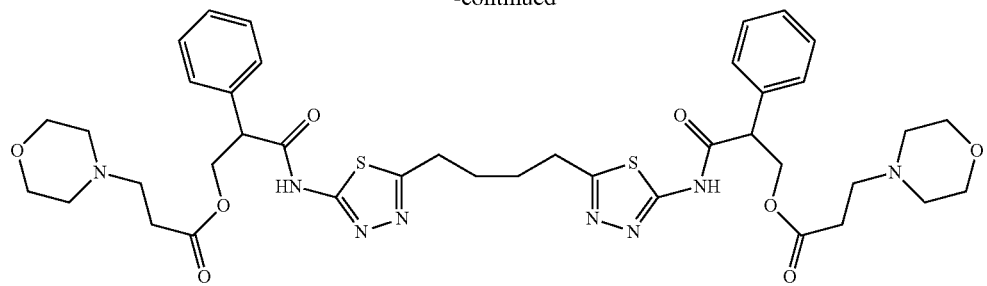

188

+

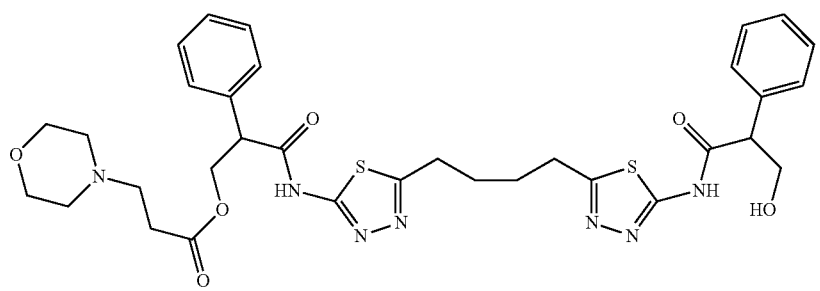

228

To a suspension of 3-morpholin-4-yl-propionic acid hydrochloride (500 mg, 2.56 mmol) in DMF (20 mL) at 0° C. was added N-(3-dimethylaminopropyl)-N'-ethylcarbodiimide hydrochloride (534 mg, 2.79 mmol). The resulting mixture was stirred at 0° C. for 40 min and followed by addition of diol 36 (642 mg, 1.16 mmol) and 4-DMAP (454 mg, 3.72 mmol). The resulting mixture was stirred from 0° C. to room temperature over a period of 3.5 h before it was diluted with EtOAc and cold water. The organic layer was separated and washed with water (3×50 mL), brine, dried (MgSO$_4$) and concentrated. The crude product was purified by silica gel chromatography eluting with 10-25% MeOH in EtOAc to provide {[5,5'-(butane-1,4-diyl)-bis(1,3,4-thiadiazole-5,2-diyl)]-bis(azanediyl)}-bis(3-oxo-2-phenylpropane-3,1-diyl)-bis(3-morpholinopropanoate) (188, 340 mg) and a less polar product, 3-((5-{4-[5-(3-hydroxy-2-phenyl-propanamido)-1,3,4-thiadiazol-2-yl]butyl}-1,3,4-thiadiazol-2-yl)amino)-3-oxo-2-phenylpropyl 3-morpholinopropanoate (228, 103 mg). 188: $^1$H NMR (300 MHz, DMSO-d$_6$) δ 12.80 (s, 2H), 7.39 (m, 10H), 4.62 (t, J=9.6 Hz, 2H), 4.33-4.27 (m, 4H), 3.48 (bs, 8H), 3.02 (bs, 4H), 2.45 (bs, 8H), 2.25 (bs, 8H), 1.76 (bs, 4H).

228: $^1$H NMR (300 MHz, MeOD-d$_4$) δ 7.43-7.37 (m, 10H), 4.71 (t, J=10.5 Hz, 1H), 4.41 (m, 1H), 4.30-4.24 (m, 2H), 4.06-4.03 (m, 1H), 3.80-3.76 (m, 1H), 3.62 (bs, 4H), 3.11 (bs, 4H), 2.63-2.52 (m, 4H), 2.40 (bs, 4H), 1.90 (bs, 4H).

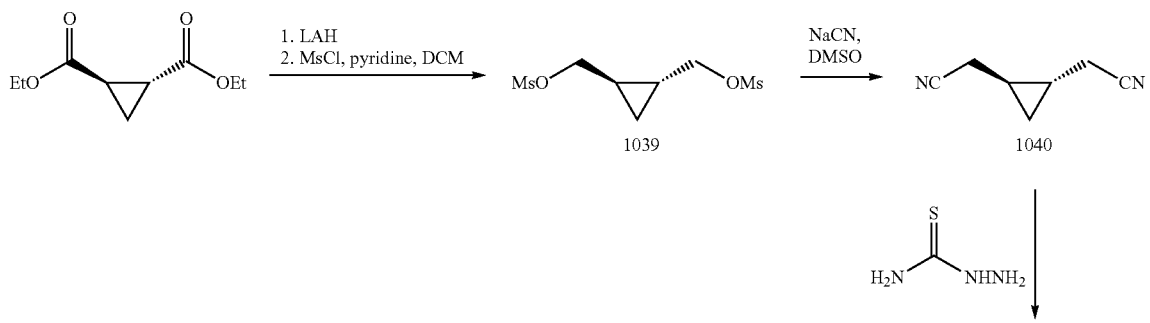

-continued

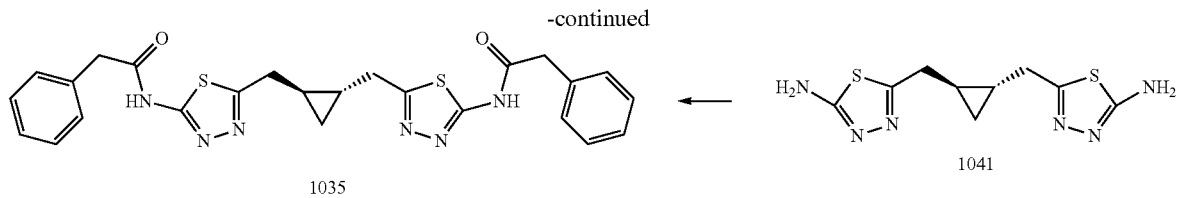

1035   1041

To a solution of diethyl trans-1,2-cyclopropanedicarboxylate (5.00 g, 26.85 mmol) in THF (20 mL) at 0° C. was added a solution of LAH (67.13 mL, 1.0 M in THF, 67.13 mmol) dropwise. The resulting mixture was stirred at 0° C. for 1.5 h before it was quenched with H$_2$O (20 mL), 2N aq. NaOH (20 mL) and H$_2$O (20 mL). The mixture was stirred vigorously for 1 h at room temperature before it was filtered through a plug of celite. The filtrate was dried (MgSO$_4$) and concentrated to provide the desired diol (2.73 g) as a colorless oil.

A mixture of the diol (2.00 g, 19.58 mmol) in CH$_2$Cl$_2$ (75 mL) at 0° C. was added pyridine (6.34 mL, 78.33 mmol) and followed by MsCl (3.33 mL, 43.08 mmol) dropwise. The resulting mixture was stirred 0° C. for 1 h before it was warmed up to room temperature. The reaction was quenched with H$_2$O and diluted with ether. The organic layer was washed with brine, dried (MgSO$_4$) and concentrated to provide 1039. This crude product was dissolved in DMSO (75 mL), and added NaCN (2.88 g, 58.75 mmol) and NaI (294 mg, 1.96 mmol). The resulting mixture was heated at 45° C. for 8 h before it was allowed to cool to room temperature and diluted with EtOAc and H$_2$O. The organic layer was separated, washed with brine, dried (MgSO$_4$) and concentrated to provide the crude product 1040 which was used in the following step without purification.

A mixture of 1040 and thiosemicarbazide (3.75 g, 41.12 mmol) in trifluoroacetic acid (TFA) (20 mL) was heated at 80° C. for 5 h. The reaction was cooled to room temperature and poured into a mixture of ice and water. Sodium hydroxide pellets were added to the mixture until it was basic (pH 14). The white precipitate was collected by suction filtration, rinsed with water, ether and dried to provide 1041 (472 mg).

To a suspension of 1041 (70 mg, 0.26 mmol) in 1-Methyl-2-pyrrolidinone (NMP) (5 mL) at 0° C. was added phenylacetyl chloride (72 μL, 0.55 mmol) dropwise. The resulting mixture was stirred at 0° C. for 1 h before it was quenched by addition of water (~3 mL). The white precipitate was collected by suction filtration, rinsed with water and dried to provide 1035 (37 mg). $^1$H NMR (300 MHz, DMSO-d$_6$) δ 12.65 (s, 2H), 7.34-7.27 (m, 10H), 3.82 (s, 4H), 3.04-2.75 (m, 4H), 1.14-1.12 (m, 2H), 0.63-0.59 (m, 2H).

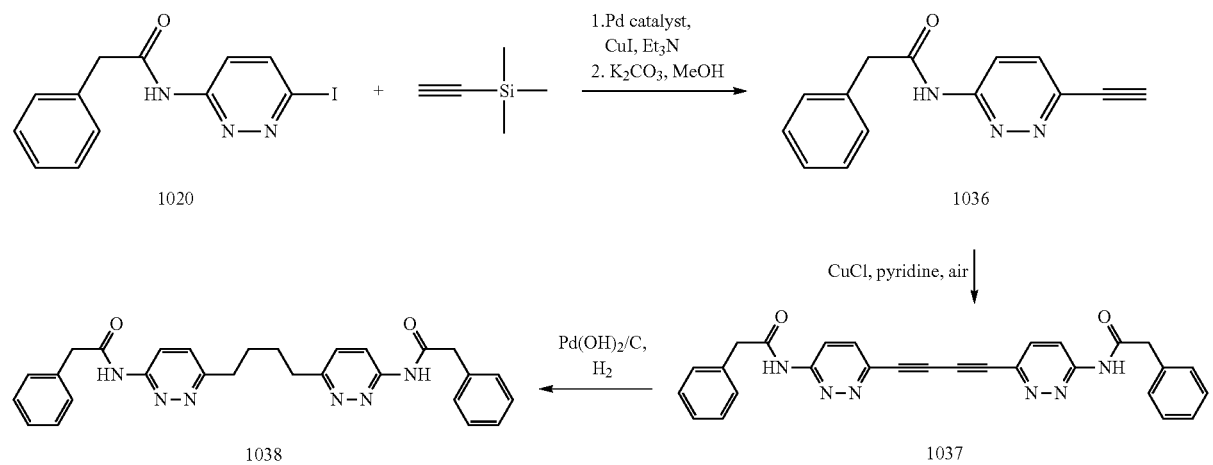

1020   1036

1038   1037

To a solution of 1020 (1.50 g, 4.42 mmol), ethynyltrimethylsilane (813 uL, 5.75 mmol), PdCl$_2$(PPh$_3$)$_2$ (310 mg, 0.44 mmol) and CuI (59 mg, 0.31 mmol) in THF (20 mL) under argon atmosphere at room temperature was added Et$_3$N (6.16 mL, 44.23 mmol). The resulting mixture was heated at 50° C. for 5 h before it was allowed to cool to room temperature and filtered through a plug of celite. The filtrate was concentrated and the crude residue was purified by flash column chromatography over silica gel eluting with 10-50% EtOAc in hexanes to provide the desired product (1.21 g) as a solid.

A mixture of the foregoing intermediate (1.07 g, 3.48 mmol) and K$_2$CO$_3$ (0.40 g, 2.90 mmol) in MeOH (100 mL) was stirred at room temperature for 5 h before it was concentrated under reduced pressure. The residue was re-dissolved in a mixture of EtOAc and H$_2$O, and was neutralized with 1N aq. HCl solution to pH 7. The organic layer was separated, washed with brine, dried (MgSO$_4$) and concentrated. The crude residue was purified by flash column chromatography over silica gel eluting with 10-50% EtOAc in hexanes to provide the desired alkyne 1036 (0.48 g) as a white solid.

To a solution of alkyne 1036 (52 mg, 0.22 mmol) in pyridine (5 mL) at room temperature was added CuCl (4.3 mg, 0.04 mmol). The resulting mixture was stirred under a stream of air for 40 min as all of the starting material was consumed. The reaction mixture was diluted with saturated aq. NH$_4$Cl solution (~2 mL). The off-white precipitate was collected by suction filtration, washed with H$_2$O and dried. This crude bis-acetylene product 1037 (52 mg) was used in the following step without further purification.

A mixture of 1037 (52 mg) and Pd(OH)$_2$/C (100 mg) in a mixture of DMF (5 mL) and THF (10 mL) was stirred at room temperature under 1 atmosphere of H$_2$ for 3 h as all of the starting material was consumed. The palladium catalyst was filtered off and the filtrate was concentrated. The crude residue was purified by column chromatography over silica gel eluting with 1-10% MeOH in CH$_2$Cl$_2$ to provide the desired product 1038 (18 mg) as a solid. $^1$H NMR (300 MHz, DMSO-d$_6$) δ 11.26 (s, 2H), 8.20 (d, J=8.97 Hz, 2H), 7.56 (d, J=8.77 Hz, 2H), 7.36-7.24 (m, 10H), 3.78 (s, 4H), 2.90 (bs, 4H), 1.73 (bs, 4H).

To a solution of 1081 (0.625 g, 2.87 mmol) in NMP (12.5 mL) was added phenylacetyl chloride (0.487 g, 0.42 mL, 3.15 mmol) dropwise and the mixture stirred at room temperature for one hour under an atmosphere of Argon. The mixture was poured into water (100 mL) and the solids collected by filtration. The solids were washed with water and dried under high vacuum to give 0.805 g of 1082. $^1$HNMR (DMSO, d$_6$): δ 12.65 (s, 1H) 7.31 (m, 5H), 3.80 (s, 2H), 3.00 (t, 2H, J=7.3 Hz), 2.53 (t, 2H, J=7.1 Hz), 1.78 (dq, 2H, J=7.3, 7.1 Hz), 1.61 (dq, 2H, J=7.3, 7.1 Hz).

To a solution of 1082 (0.49 g, 1.33 mmol) in TFA (10 mL) was added thiosemicarbazide (0.23 g, 1.46 mmol) and the mixture heated at 70° C. overnight under an atmosphere of Argon. The mixture was allowed to cool to room tempera-

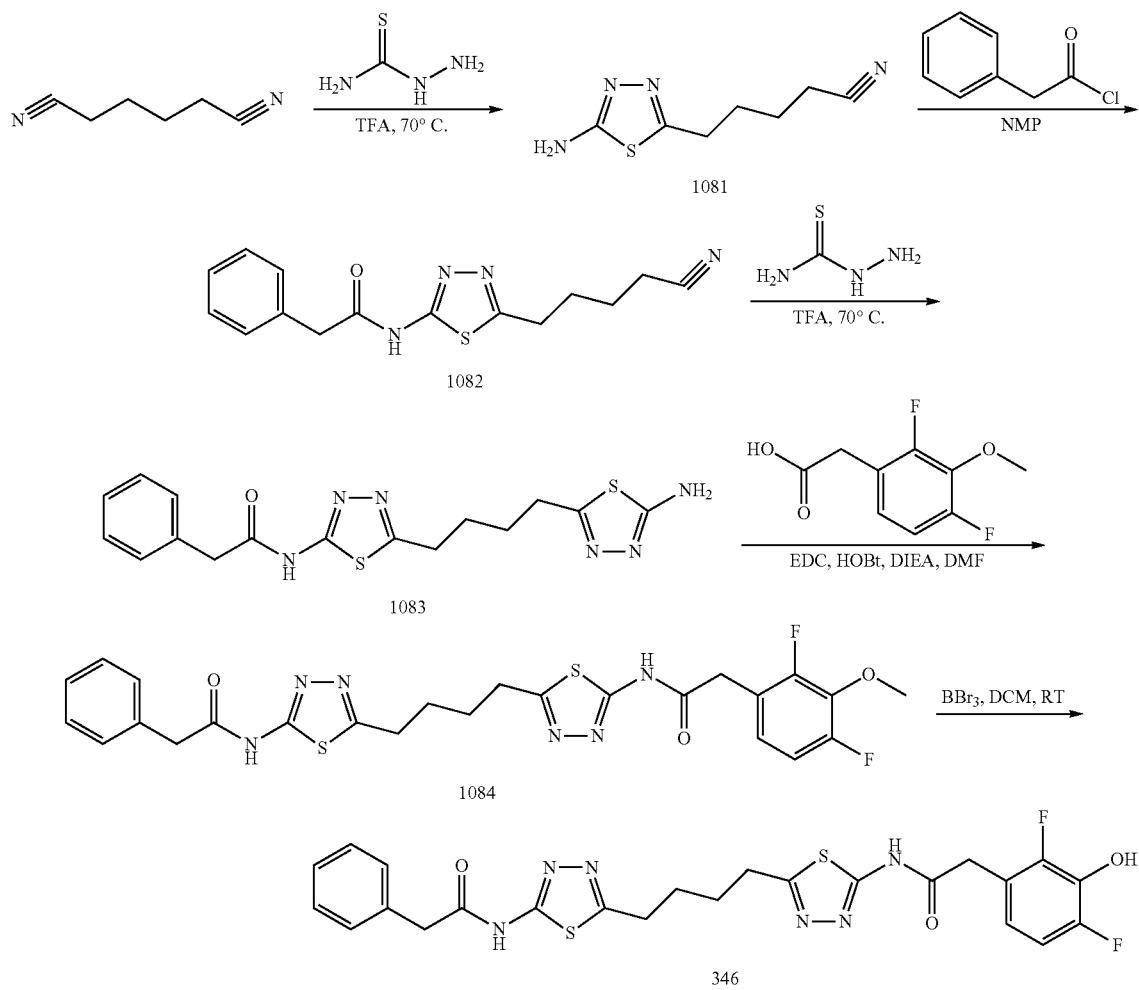

To a solution of adiponitrile (19.02 g, 175.8 mmol) in TFA (50 mL) was added thiosemicarbazide (16.02 g, 175.8 mmol) and the mixture heated to 70° C. for 4 hours under an atmosphere of Argon. The mixture was allowed to cool to room temperature and the volatiles removed under reduced pressure. The residue was diluted with water (200 mL) and the pH adjusted to 7 with solid NaOH giving a white precipitate that was collected by filtration and washed with water. The solids were dried under high vacuum giving 9.22 g of 1081. $^1$HNMR (DMSO, d$_6$): δ 7.02 (br s, 2H) 2.84 (m, 2H), 2.55 (m, 2H), 1.67 (m, 4H).

ture and the volatiles removed under reduced pressure. The residue was diluted with water (50 mL) and the pH adjusted to 7 with solid NaOH giving a white precipitate that was collected by filtration and washed with water. The solids were dried under high vacuum giving 0.367 g of 1083. $^1$HNMR (DMSO, d$_6$): δ 12.70 (s, 1H) 7.34 (br s, 5H), 7.16 (s, 2H), 3.82 (s, 2H), 3.01 (s, 2H), 2.84 (S, 2H), 1.71 (br s, 4H).

To a solution of 1083 (0.10 g, 0.267 mmol), 2,4-difluoro-3-methoxyphenylacetic acid (0.058 g, 0.267 mmol), EDC (0.127 g, 0.667 mmol), HOBt (0.090 g, 0.667 mmol) in DMF (4 mL) was added DIEA (0.171 g, 0.231 mL, 1.335 mmol) and the mixture stirred overnight under an atmosphere of Argon. The mixture was poured into water (20 mL) and the solids formed were collected by filtration, washed with water and dried under high vacuum. The crude 1084 was used in the following step without purification. To a solution of 1084 (0.050 g, 0.091 mmol) in dichloromethane (1 mL) was added BBr₃ (1.0 mL, 1 mmol, 1.0 M in dichloromethane) and the mixture stirred for 4 hours at room temperature under an atmosphere of Argon. The volatiles were removed under reduced pressure and the residue diluted with dichloromethane (5 mL). The volatiles were removed under reduced pressure and the residue diluted with water (15 mL) and the pH adjusted to 12. The aqueous layer was washed with dichloromethane (4×5 mL) and the pH adjusted to 4. The solids were collected by filtration, washed with water and dried under high vacuum giving 0.029 g of 346. $^1$HNMR (DMSO, d₆): δ 12.66 (s, 2H), 10.12 (s, 1H), 7.33 (s, 5H), 7.00 (m, 1H), 6.80 (m, 1H), 3.84 (s, 2H), 3.81 (s, 2H), 3.02 (br s, 4H), 1.76 (br s, 4H).

A flask was charged with 1024 (100 mg, 0.27 mmol), tropic acid (54 mg, 0.326 mmol) in DMF (2 ml) at 0° C. was added HOBT (88 mg, 0.652 mmol) followed by EDCI (156 mg, 0.815 mmol). The resulting mixture was slowly warmed up to room temperature and stirred for 3 h before it was quenched by addition of water (~10 mL). The white precipitate was collected by suction filtration, rinsed with more water and dried to afford 314. $^1$H NMR (300 MHz, DMSO-d₆) δ 12.65 (s, 1H), 11.26 (s, 1H), 8.22-8.19 (d, J=8.82 Hz, 1H), 7.58-7.54 (d, J=9.72 Hz, 1H), 7.36-7.28 (m, 10H), 4.10-4.05 (m, 2H), 3.78 (s, 3H), 3.65 (s, 1H), 3.01 (bs, 2H), 2.90 (bs, 2H), 1.73 (bs, 4H).

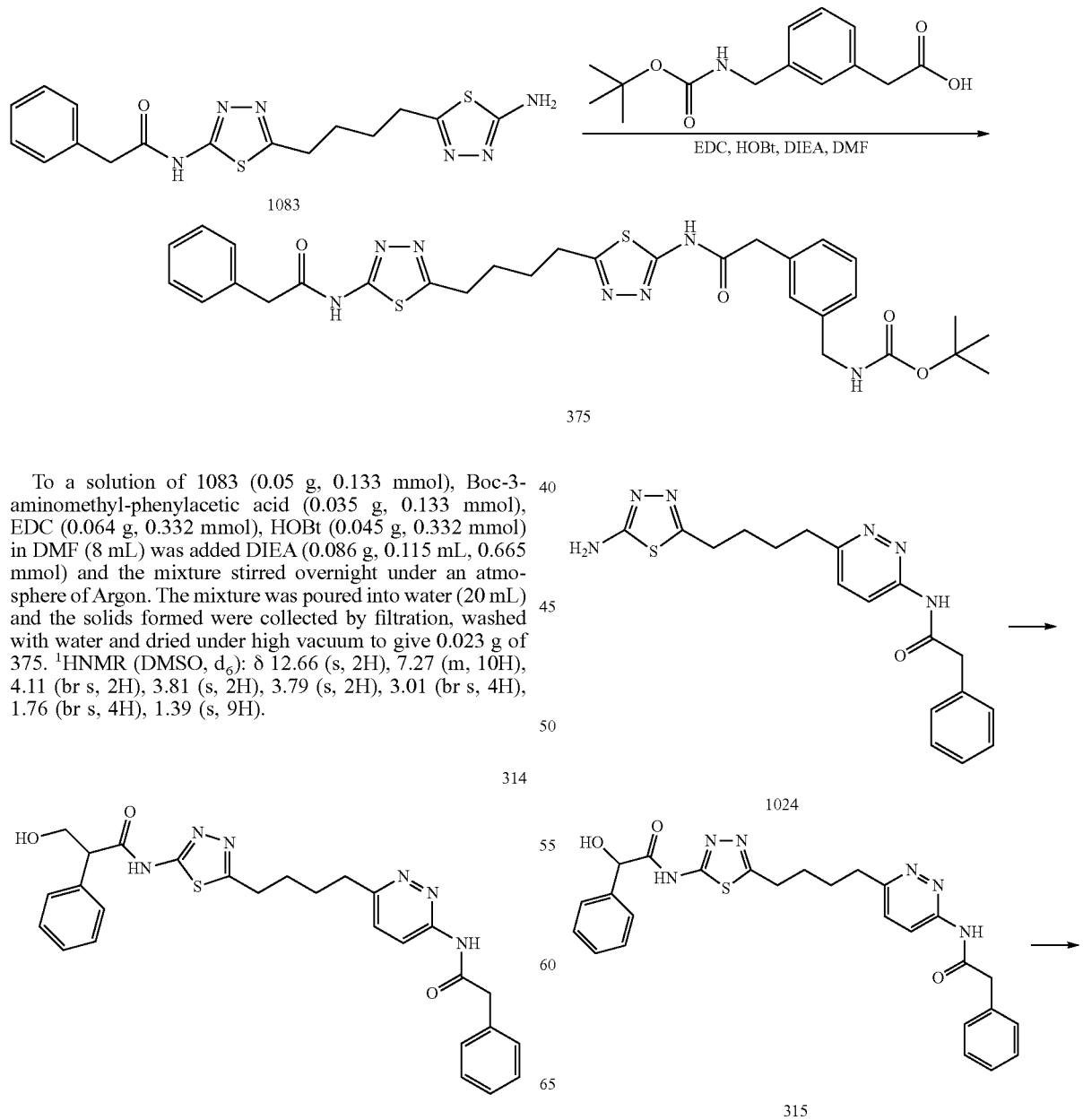

To a solution of 1083 (0.05 g, 0.133 mmol), Boc-3-aminomethyl-phenylacetic acid (0.035 g, 0.133 mmol), EDC (0.064 g, 0.332 mmol), HOBt (0.045 g, 0.332 mmol) in DMF (8 mL) was added DIEA (0.086 g, 0.115 mL, 0.665 mmol) and the mixture stirred overnight under an atmosphere of Argon. The mixture was poured into water (20 mL) and the solids formed were collected by filtration, washed with water and dried under high vacuum to give 0.023 g of 375. $^1$HNMR (DMSO, d₆): δ 12.66 (s, 2H), 7.27 (m, 10H), 4.11 (br s, 2H), 3.81 (s, 2H), 3.79 (s, 2H), 3.01 (br s, 4H), 1.76 (br s, 4H), 1.39 (s, 9H).

-continued

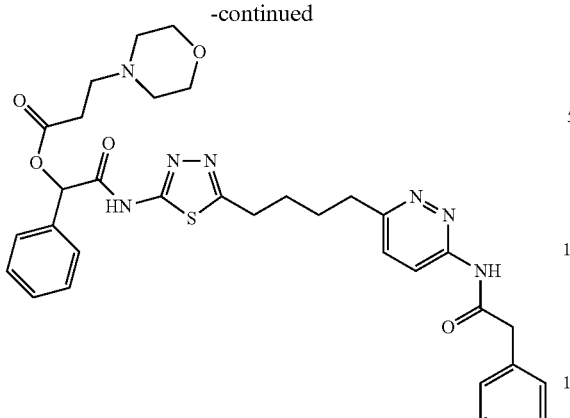

334

A flask was charged with 1024 (500 mg, 1.36 mmol), DL-mandelic acid (248 mg, 1.63 mmol) in DMF (10 ml) at 0° C. was added HOBT (441 mg, 3.26 mmol) followed by EDCI (781 mg, 4.08 mmol). The resulting mixture was stirred at 0° C. for 10 minutes then warmed up to room temperature and stirred for 10 minutes before it was quenched by addition of water (~50 mL) at 0° C. The white precipitate was collected by suction filtration, rinsed with more water and dried to afford 315. $^1$H NMR (300 MHz, DMSO-d$_6$) δ 12.65 (s, 1H), 11.26 (s, 1H), 8.22-8.19 (d, J=8.82 Hz, 1H), 7.58-7.50 (m, 3H), 7.36-7.28 (m, 8H), 6.35 (s, 1H), 5.32 (s, 1H), 3.78 (s, 2H), 3.01 (bs, 2H), 2.90 (bs, 2H), 1.73 (bs, 4H).

To a suspension of 3-morpholin-4-yl-propionic acid hydrochloride (209 mg, 1.07 mmol) in DMF (10 ml) was added EDCI (308 mg, 1.61 mmol). The resulting mixture was stirred at 0° C. for 1 hour and followed by addition of 315 (447 mg, 0.889 mmol) and 4-DMAP (261 mg, 2.14 mmol). The resulting mixture was stirred from 0° C. to room temperature over a period of 6 h before it was quenched by addition of ice water (~50 mL). The white precipitate was collected by suction filtration, rinsed with more water. The crude material was purified by silica gel chromatography eluting with 0-6% MeOH in EtOAc to afford 334. $^1$H NMR (300 MHz, DMSO-d$_6$) δ 12.95 (s, 1H), 11.26 (s, 1H), 8.22-8.19 (d, J=9.45 Hz, 1H), 7.58-7.26 (m, 11H), 6.14 (s, 1H), 3.78 (s, 2H), 3.54 (bs, 4H), 3.01 (bs, 2H), 2.90 (bs, 2H), 2.63 (bs, 4H), 2.38 (bs, 4H), 1.73 (bs, 4H).

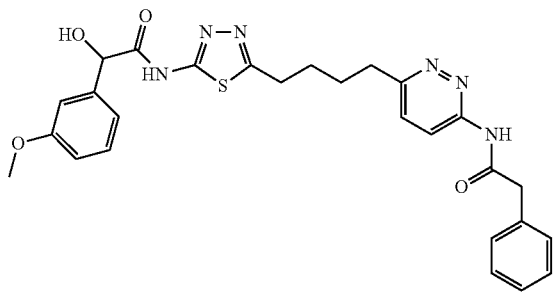

317

Compound 317 was prepared according to the procedure above for compound 315. $^1$H NMR (300 MHz, DMSO-d$_6$) δ 12.40 (s, 1H), 11.26 (s, 1H), 8.22-8.19 (d, J=9.03 Hz, 1H), 7.58-7.54 (d, J=9.72 Hz, 1H), 7.36-6.87 (m, 9H), 6.35 (bs, 1H), 5.30 (s, 1H), 3.78 (m, 5H), 3.01 (bs, 2H), 2.90 (bs, 2H), 1.73 (bs, 4H).

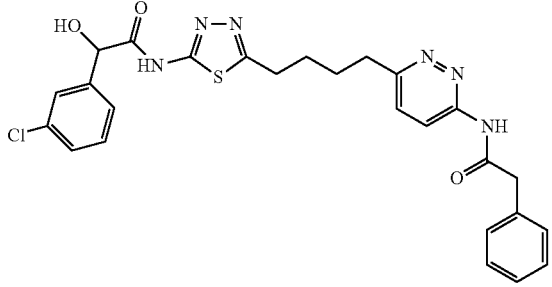

318

Compound 318 was prepared according to the procedure above for compound 315. $^1$H NMR (300 MHz, DMSO-d$_6$) δ 12.50 (s, 1H), 11.26 (s, 1H), 8.22-8.19 (d, J=9.43 Hz, 1H), 7.60-7.27 (m, 10H), 6.51 (bs, 1H), 5.35 (s, 1H), 3.78 (s, 2H), 3.01 (bs, 2H), 2.90 (bs, 2H), 1.73 (bs, 4H).

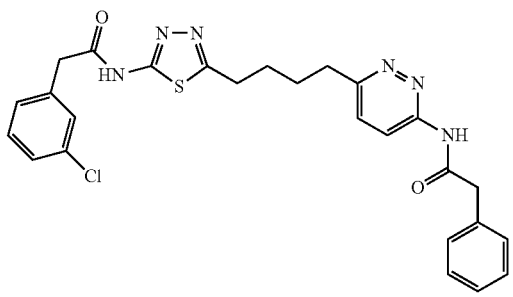

335

A flask was charged with 1024 (50 mg, 0.135 mmol), 3-chlorophenylacetic acid (28 mg, 0.163 mmol) in DMF (1 ml) at 0° C. was added HOBT (44 mg, 0.326 mmol) followed by EDCI (78 mg, 0.408 mmol). The resulting mixture was slowly warmed up to room temperature and stirred for 1 h before it was quenched by addition of water (~5 mL). The white precipitate was collected by suction filtration, rinsed with more water and ether then dried to afford 335. $^1$H NMR (300 MHz, DMSO-d$_6$) δ 12.65 (s, 1H), 11.26 (s, 1H), 8.22-8.19 (d, J=8.82 Hz, 1H), 7.58-7.54 (d, J=9.72 Hz, 1H), 7.36-7.28 (m, 9H), 3.84 (s, 2H), 3.78 (s, 2H), 3.01 (bs, 2H), 2.90 (bs, 2H), 1.73 (bs, 4H).

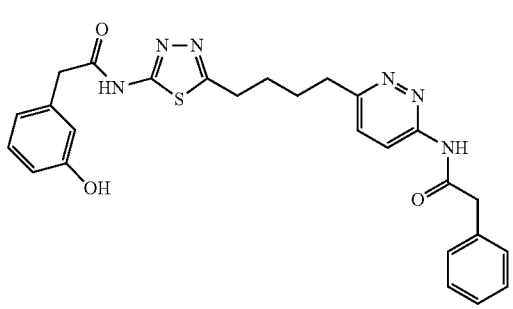

337

Compound 337 was prepared according to the procedure above for compound 335. ¹H NMR (300 MHz, DMSO-d₆) δ 12.65 (s, 1H), 11.26 (s, 1H), 9.38 (s, 1H), 8.22-8.19 (d, J=8.37 Hz, 1H), 7.58-7.54 (d, J=9.63 Hz, 1H), 7.36-7.09 (m, 6H), 6.75-6.65 (m, 3H), 3.78 (s, 2H), 3.70 (s, 2H), 3.01 (bs, 2H), 2.90 (bs, 2H), 1.73 (bs, 4H).

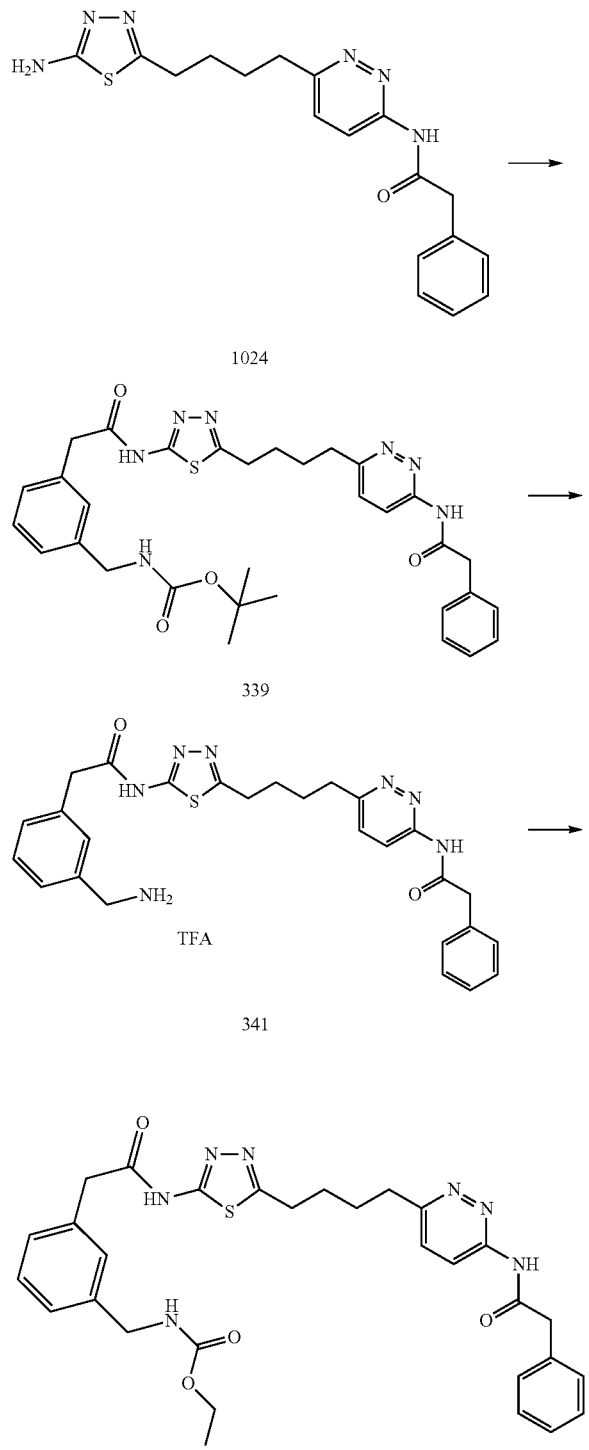

339, 341, 382: A flask was charged with 1024 (100 mg, 0.27 mmol), Boc-3-aminomethyl-phenylacetic acid (86 mg, 0.325 mmol) in DMF (2 ml) at 0° C. was added HOBT (88 mg, 0.65 mmol) followed by EDCI (156 mg, 0.812 mmol). The resulting mixture was stirred at 0° C. for 5 minutes then warmed up to room temperature and stirred for 1.5 h before it was quenched by addition of water (~10 mL) at 0° C. The white precipitate was collected by suction filtration, rinsed with more water and ether then dried to afford 339. ¹H NMR (300 MHz, DMSO-d₆) δ 12.65 (s, 1H), 11.26 (s, 1H), 8.22-8.19 (d, J=8.82 Hz, 1H), 7.58-7.54 (d, J=9.42 Hz, 1H), 7.36-7.13 (m, 9H), 4.13-4.11 (d, J=10.62, 2H), 3.78 (s, 4H), 3.01 (bs, 2H), 2.90 (bs, 2H), 1.73 (bs, 4H), 1.38 (s, 9H).

To a suspension of 339 (50 mg, 0.081 mmol) in dichloromethane (2 ml) was added TFA (2 ml) at 0° C. The resulting mixture was stirred at room temperature for 20 minutes before it was evaporated under vacuo to dryness. Ether was added and the white precipitate was collected by suction filtration, rinsed with more ether and dichloromethane then dried to afford 341. ¹H NMR (300 MHz, DMSO-d₆) δ 12.65 (s, 1H), 11.26 (s, 1H), 8.22-8.19 (d, J=8.82 Hz, 1H), 8.14-8.11 (bs, 2H), 7.58-7.54 (d, J=9.42 Hz, 1H), 7.36-7.13 (m, 9H), 4.06-4.03 (m, 2H), 3.84 (s, 2H), 3.78 (s, 2H), 3.01 (bs, 2H), 2.90 (bs, 2H), 1.73 (bs, 4H).

To a solution of 341 (10 mg, 0.0159 mmol) in DMF (1 ml) at 0° C. was added triethylamine (4.4 ul, 0.0317 mmol) drop wise followed by ethyl chloroformate (1.8 ul, 0.0191 mmol) drop wise. The resulting mixture was slowly warmed up to room temperature and stirred for 30 minutes before it was quenched by addition of water (~1 mL) at 0° C. The mixture was partitioned between water and EtOAc. The organic extract was washed with water, dried over sodium sulfate, filtered and evaporated. The crude material was purified by silica gel chromatography eluting with 0-6% MeOH in CH₂Cl₂ to afford 382. ¹H NMR (300 MHz, DMSO-d₆) δ 12.65 (s, 1H), 11.26 (s, 1H), 8.22-8.19 (d, J=8.82 Hz, 1H), 7.67-7.58 (bs, 1H), 7.58-7.54 (d, J=9.42 Hz, 1H), 7.36-7.13 (m, 9H), 4.18-4.16 (m, 2H), 4.06-4.0 (q, 2H), 3.78 (s, 4H), 3.01 (bs, 2H), 2.90 (bs, 2H), 1.73 (bs, 4H), 1.19-1.13 (t, 3H).

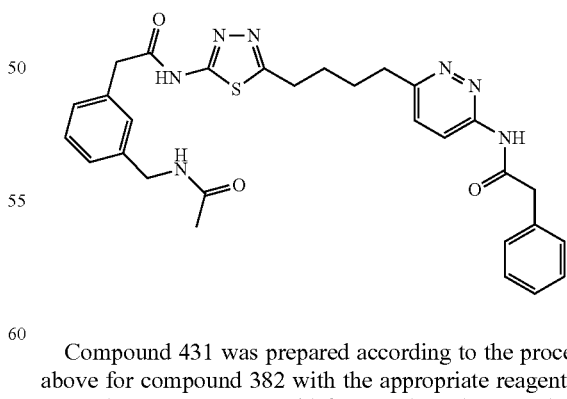

Compound 431 was prepared according to the procedure above for compound 382 with the appropriate reagents. ¹H NMR (300 MHz, DMSO-d₆) δ 12.65 (s, 1H), 11.26 (s, 1H), 8.35 (s, 1H), 8.22-8.19 (d, J=8.88 Hz, 1H), 7.57-7.54 (d, J=9.51 Hz, 1H), 7.38-7.15 (m, 9H), 4.25-4.24 (d, J=5.64 Hz, 2H), 3.76 (s, 4H), 3.01 (bs, 2H), 2.90 (bs, 2H), 1.87 (s, 3H), 1.73 (bs, 4H).

432

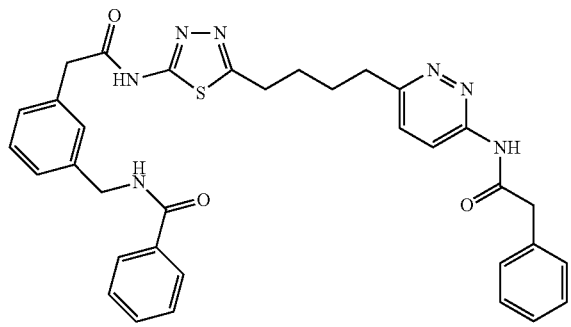

Compound 432 was prepared according to the procedure above for compound 382 with the appropriate reagents. $^1$H NMR (300 MHz, DMSO-d$_6$) δ 12.63 (s, 1H), 11.26 (s, 1H), 9.04-9.01 (m, 1H), 8.22-8.19 (d, J=8.91 Hz, 1H), 7.93-7.89 (d, J=9.51 Hz, 2H), 7.58-7.25 (m, 13H), 4.50-4.48 (d, J=5.91 Hz, 2H), 3.78 (s, 4H), 3.01 (bs, 2H), 2.90 (bs, 2H), 1.73 (bs, 4H).

433

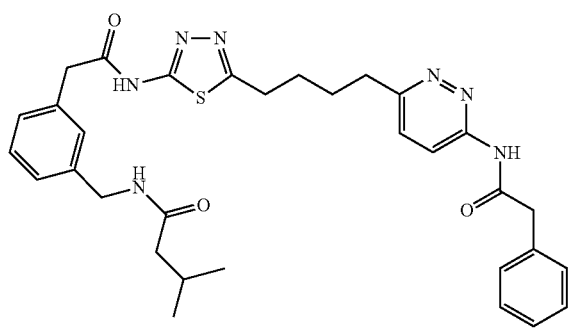

Compound 433 was prepared according to the procedure above for compound 382 with the appropriate reagents. $^1$H NMR (300 MHz, DMSO-d$_6$) δ 12.63 (s, 1H), 11.26 (s, 1H), 8.31-8.21 (m, 1H), 8.20-8.19 (d, J=9.57 Hz, 1H), 7.57-7.54 (d, J=8.73 Hz, 1H), 7.35-7.13 (m, 9H), 4.26-4.24 (d, J=5.52 Hz, 2H), 3.78 (s, 4H), 3.01 (bs, 2H), 2.90 (bs, 2H), 2.0 (s, 3H), 1.73 (bs, 4H), 0.86-0.85 (d, J=3.99 Hz, 6H).

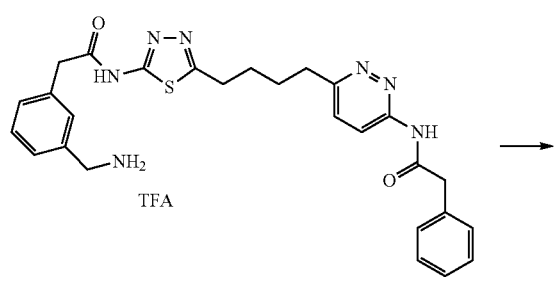

341
TFA

→

476

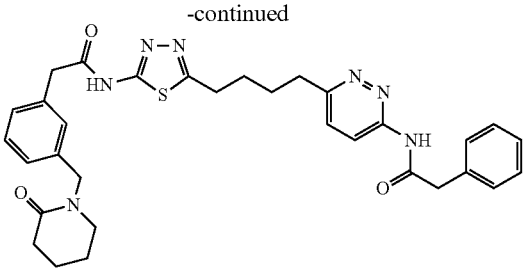

To a solution of 341 (70 mg, 0.111 mmol) in DMF (1 ml) at 0° C. was added triethylamine (31 ul, 0.22 mmol) drop wise followed by 5-bromovaleryl chloride (12 ul, 0.122 mmol) drop wise. The resulting mixture was slowly warmed up to room temperature and stirred for 1 h. Potassium tert-butoxide (50 mg, 0.445 mmol) was then added to the reaction mixture at 0° C. The resulting mixture was slowly warmed up to room temperature and stirred for overnight before it was quenched by addition of water (~2 mL) at 0° C. The mixture was partitioned between water and EtOAc. The organic extract was washed with water, dried over sodium sulfate, filtered and evaporated. The crude material was purified by silica gel chromatography eluting with 0-6% MeOH in CH$_2$Cl$_2$ to afford 476. $^1$H NMR (300 MHz, DMSO-d$_6$) δ 12.65 (s, 1H), 11.26 (s, 1H), 8.22-8.19 (d, J=8.82 Hz, 1H), 7.58-7.54 (d, J=9.42 Hz, 1H), 7.36-7.13 (m, 9H), 4.50 (s, 2H), 3.78 (s, 4H), 3.35 (bs, 2H), 3.20 (bs, 2H), 3.01 (bs, 2H), 2.90 (bs, 2H), 2.30 (bs, 2H), 1.68-1.80 (d, 6H).

340

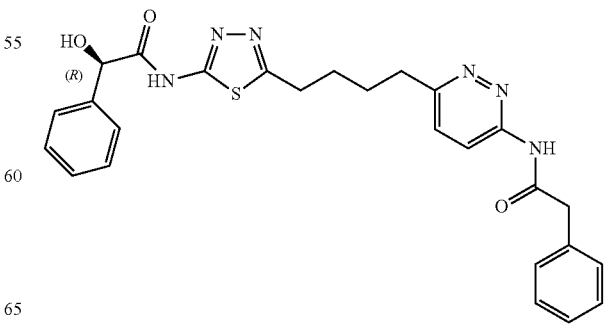

Compound 340 was prepared according to the procedure above for compound 315 with the appropriate reagents. $^1$H NMR (300 MHz, DMSO-d$_6$) δ 12.50 (s, 1H), 11.26 (s, 1H), 8.22-8.19 (d, J=9.24 Hz, 1H), 7.60-7.27 (m, 10H), 6.51 (bs, 1H), 5.35 (s, 1H), 3.78 (s, 2H), 3.01 (bs, 2H), 2.90 (bs, 2H), 1.73 (bs, 4H).

349

Compound 349 was prepared according to the procedure above for compound 315 with the appropriate reagents. ¹H NMR (300 MHz, DMSO-d₆) δ 12.41 (s, 1H), 11.26 (s, 1H), 8.22-8.19 (d, J=8.76 Hz, 1H), 7.58-7.27 (m, 11H), 6.36 (s, 1H), 5.34 (s, 1H), 3.78 (s, 2H), 3.01 (bs, 2H), 2.90 (bs, 2H), 1.73 (bs, 4H).

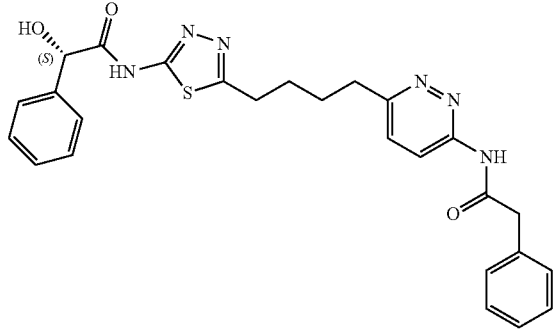

350

Compound 350 was prepared according to the procedure above for compound 315 with the appropriate reagents. ¹H NMR (300 MHz, DMSO-d₆) δ 12.41 (s, 1H), 11.26 (s, 1H), 8.22-8.19 (d, J=8.67 Hz, 1H), 7.58-7.27 (m, 11H), 6.34 (s, 1H), 5.34 (s, 1H), 3.78 (s, 2H), 3.01 (bs, 2H), 2.90 (bs, 2H), 1.73 (bs, 4H).

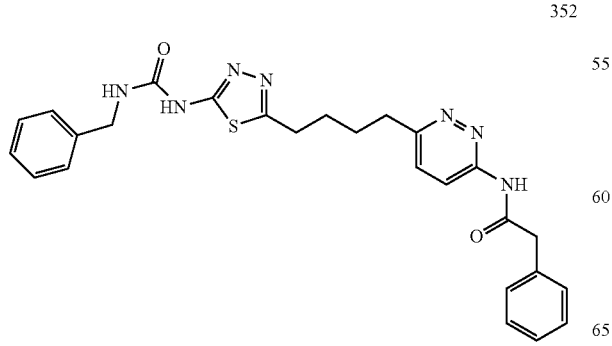

351

Compound 351 was prepared according to the procedure above for compound 315 with the appropriate reagents. ¹H NMR (300 MHz, DMSO-d₆) δ 12.50 (s, 1H), 11.26 (s, 1H), 8.21-8.18 (d, J=8.67 Hz, 1H), 7.58-7.54 (d, J=9.72 Hz, 1H), 7.36-7.23 (m, 8H), 6.67 (s, 1H), 5.40 (s, 1H), 3.78 (s, 2H), 3.01 (bs, 2H), 2.90 (bs, 2H), 1.73 (bs, 4H).

352

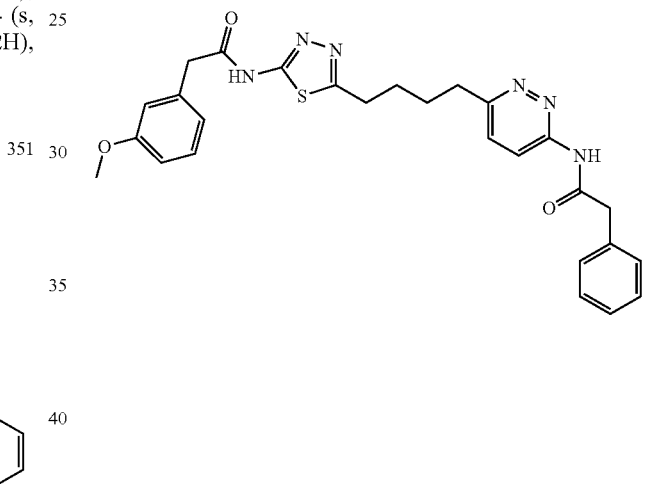

To a solution of 1024 (50 mg, 0.136 mmol) in DMF (1 ml) at 0° C. was added triethylamine (38 ul, 0.271 mmol) drop wise followed by benzyl isocyanate (20 ul, 0.163 mmol) drop wise. The resulting mixture was slowly warmed up to room temperature and stirred for 40 minutes before it was quenched by addition of water (~5 mL) at 0° C. The white precipitate was collected by suction filtration, rinsed with more water. The crude material was purified by silica gel chromatography eluting with 0-6% MeOH in CH₂Cl₂ to afford 352. ¹H NMR (300 MHz, DMSO-d₆) δ 11.26 (s, 1H), 10.82 (s, 1H), 8.22-8.19 (d, J=9.42 Hz, 1H), 7.58-7.54 (d, J=8.79 Hz, 1H), 7.36-7.31 (m, 10H), 7.06 (bs, 1H), 4.37-4.35 (d, J=5.22 Hz, 2H), 3.78 (s, 2H), 2.99-2.90 (m, 4H), 1.73 (bs, 4H).

353

Compound 353 was prepared according to the procedure above for the preparation of compound 335. ¹H NMR (300 MHz, DMSO-d₆) δ 12.57 (s, 1H), 11.26 (s, 1H), 8.22-8.19 (d, J=9.45 Hz, 1H), 7.57-7.54 (d, J=9.48 Hz, 1H), 7.36-7.25 (m, 6H), 6.91-6.84 (m, 3H), 3.76 (m, 7H), 3.01 (bs, 2H), 2.90 (bs, 2H), 1.73 (bs, 4H).

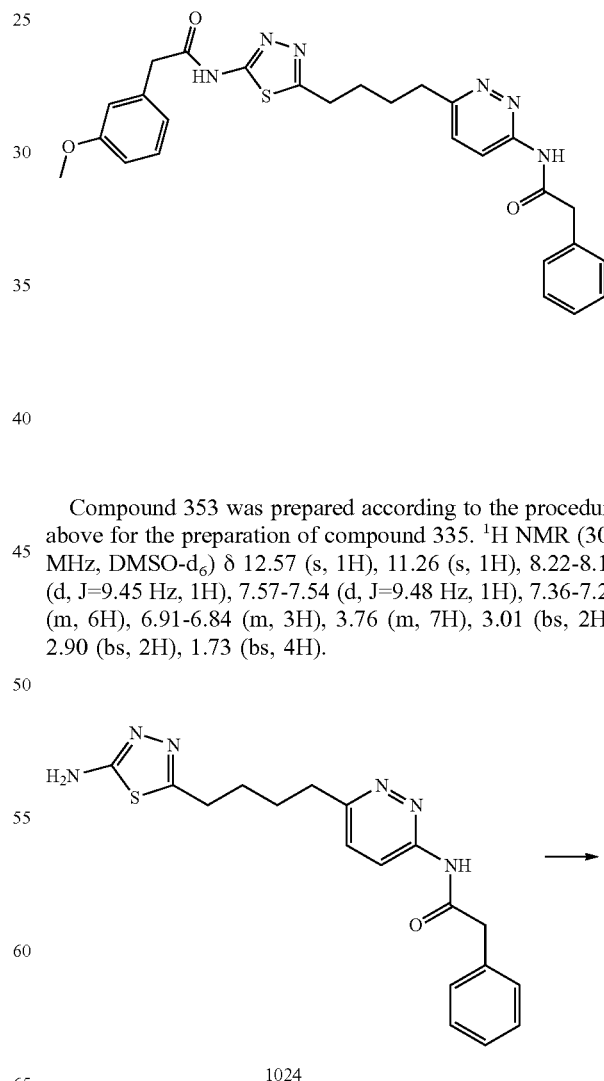

1024

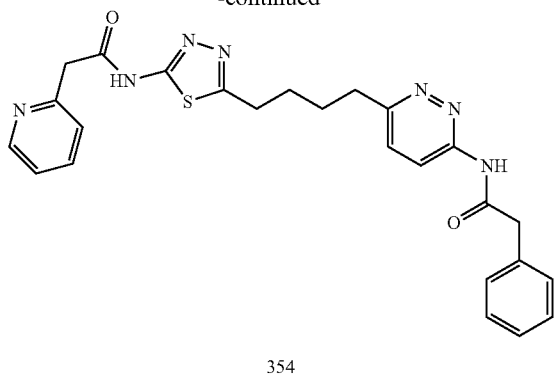

354

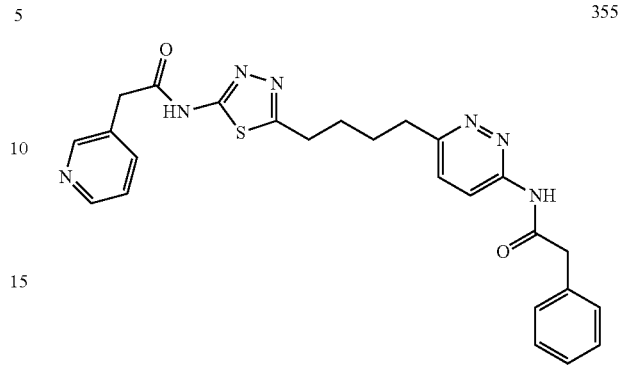

355

A flask was charged with 1024 (50 mg, 0.135 mmol), 2-pyridine acetic acid hydrochloride (27 mg, 0.156 mmol) in DMF (1 ml) at 0° C. was added propylphosphonic anhydride solution (91 ul) followed by triethylamine (54 ul, 0.39 mmol). The resulting mixture was slowly warmed up to room temperature and stirred for 1 h before it was quenched by addition of water (~5 mL). The white precipitate was collected by suction filtration, rinsed with more water and ether then dried to afford 354. $^1$H NMR (300 MHz, DMSO-$d_6$) δ 12.65 (s, 1H), 11.26 (s, 1H), 8.51 (s, 1H), 8.22-8.19 (d, J=8.97 Hz, 1H), 7.81-7.76 (m, 1H), 7.58-7.54 (d, J=9.06 Hz, 1H), 7.42-7.26 (m, 7H), 4.02 (s, 2H), 3.78 (s, 2H), 3.01 (bs, 2H), 2.90 (bs, 2H), 1.73 (bs, 4H).

Compound 355 was prepared according to the procedure above for the preparation of compound 354. $^1$H NMR (300 MHz, DMSO-$d_6$) δ 12.70 (s, 1H), 11.26 (s, 1H), 8.53-8.49 (m, 1H), 8.22-8.19 (d, J=9.0 Hz, 1H), 7.77-7.73 (d, J=8.46 Hz, 1H), 7.58-7.54 (d, J=9.48 Hz, 1H), 7.38-7.26 (m, 7H), 3.88 (s, 2H), 3.78 (s, 2H), 3.01 (bs, 2H), 2.90 (bs, 2H), 1.73 (bs, 4H).

Compounds 309 and 310 were prepared according to the procedure above for the preparation of compound 354.

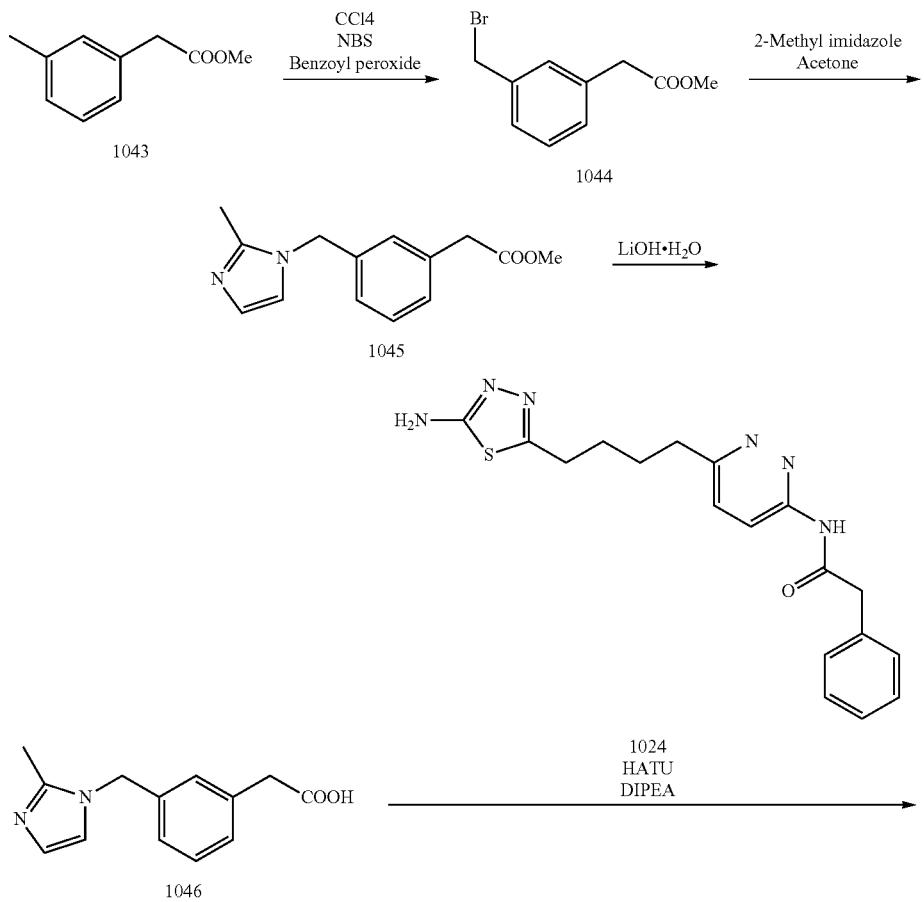

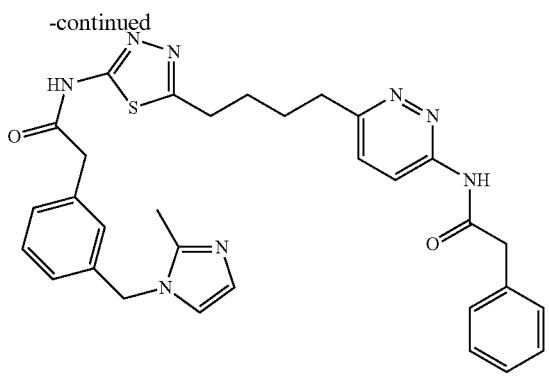

380

To a solution of 1043 (3.2 g, 19.5 mmol) in carbon tetrachloride (150 mL) was added N-bromosuccinimide (3.47 g, 19.6 mmol) and benzoyl peroxide (10 mg, catalytic). The resulting mixture was refluxed overnight before it was filtered hot. The filtrate was concentrated under reduced pressure and the residue obtained was purified by silica gel chromatography eluting with 20% ethylacetate/hexane to afford 1044 (2 g, 42% yield) as an oil. $^1$H NMR (300 MHz, Chloroform-d) δ ppm 3.66 (s, 2H) 3.74 (s, 3H) 4.51 (s, 2H) 7.35 (m, 4H)

To a solution of 1044 (0.243 g, 1 mmol) in acetone (10 mL) was added 2-methyl imidazole (0.41 g, 5 mmol). The resulting mixture was refluxed overnight before it was concentrated under reduced pressure and the residue obtained was diluted with water (~100 mL). The resulting solution was partitioned between water and ethyl acetate. The organic extract was washed with more water, separated, dried over sodium sulfate, filtered and evaporated. The residue obtained was purified by silica gel chromatography eluting with MeOH/dichloromethane to afford 1045 (0.17 g, 69% yield) as an oil. $^1$H NMR (300 MHz, Chloroform-d) δ ppm 2.37 (s, 3H) 3.63 (s, 2H) 3.72 (s, 3H) 5.07 (s, 2H) 6.87 (s, 1H) 6.96-7.02 9 m, 2H) 7.23-7.33 (m, 3H)

To a solution of 1045 (0.17 g, 0.69 mmol) in THF/MeOH/Water (10 mL, 2 mL, 2 mL) was added lithium hydroxide monohydrate (0.06 g, 1.42 mmol). The resulting mixture was stirred at room temperature overnight before it was concentrated under reduced pressure. The residue obtained was diluted with water (~20 mL) and the resulting solution was acidified with acetic acid. The aqueous layer was concentrated and the product was isolated by prep HPLC. The residue obtained was dissolved in water (mL) and concentrated hydrochloric acid (mL) was added to it before it was concentrated and dried to afford 1046 (0.15 gm) as a hydrochloride salt.

To a suspension of carboxylic acid 1046 (41.8 mg, 0.157 mmol) in DMF (3 mL) was added HATU (61.3 mg, 0.161 mmol) and stirred till reaction mixture is clear followed by the addition of an amine 1024 (52.5 mg, 0.142 mmol) and DIPEA (50 ul, 0.29 mmol). The resulting mixture was stirred at room temperature overnight before it was quenched by the addition of water. The resulting solution was partitioned between water and ethyl acetate. The organic extract was washed with more water, separated, dried over sodium sulfate, filtered and evaporated. The residue obtained was triturated with ether. The solid separated was filtered, washed with ether and dried to afford 380 (40 mg, 48%). $^1$H NMR (300 MHz, Dimethylsulfoxide-d6) δ ppm 1.74 (brs, 4H) 2.91-3.02 (brs, 4H) 3.78-3.83 (m, 4H) 5.34 (s, 2H) 7.16-7.57 (m, 12H) 8.19-8.22 (d, 1H) 11.26 (s, 1H) 12.65 (brs, 1H)

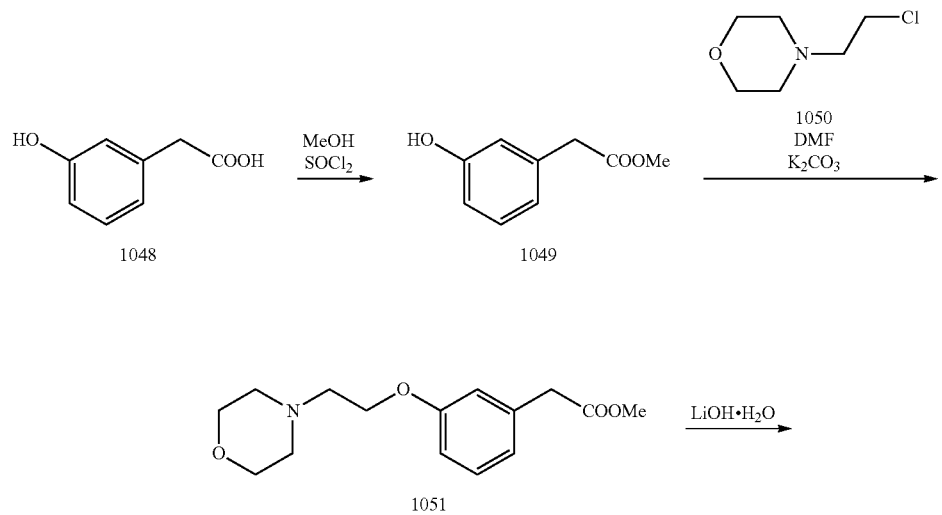

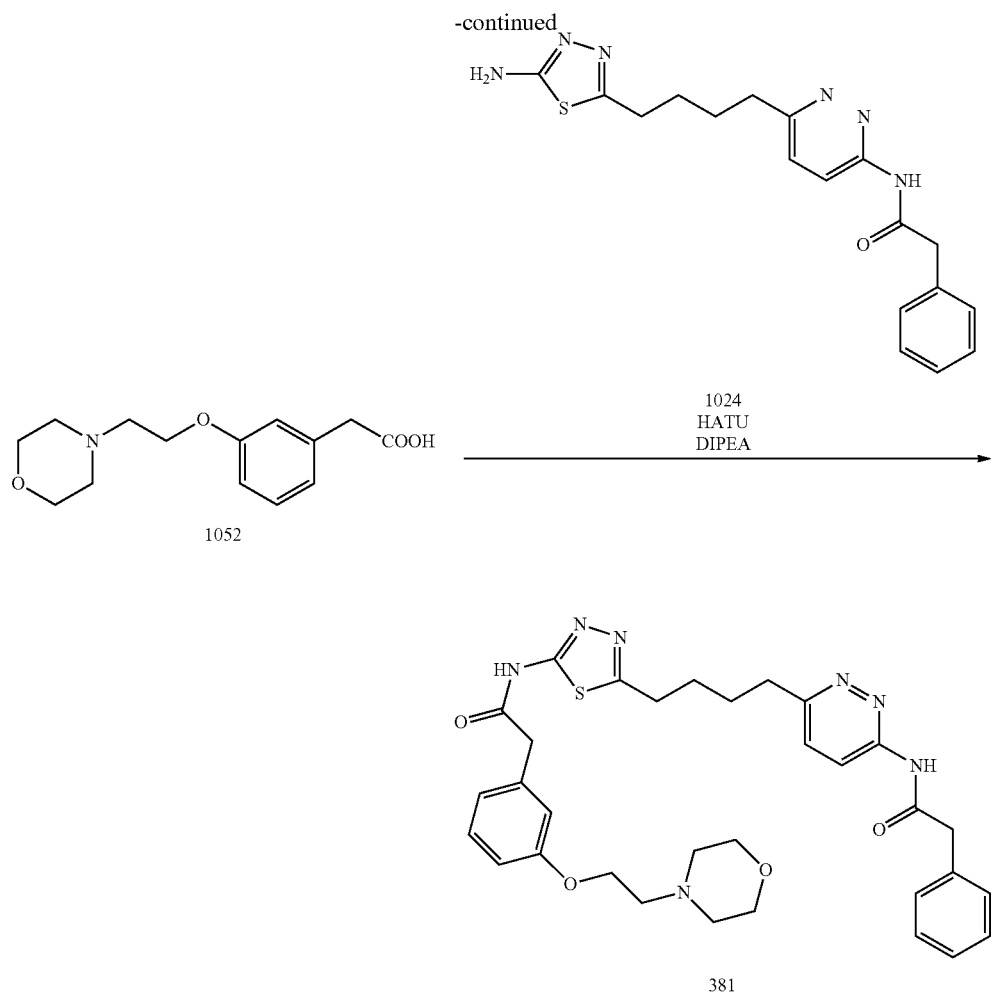

To an ice cold solution of 1048 (5 g, 0.033 mol) in methanol (50 mL) was added thionyl chloride (0.2 mL) and the resulting mixture was stirred at room temperature overnight before it was concentrated under reduced pressure. The residue obtained was dried at high vacuum overnight to afford 1049 (5 gm) as an oil and was used as such for the next step. $^1$H NMR (300 MHz, Chloroform-d) δ ppm 3.62 (s, 2H) 3.74 (s, 3H) 6.76-6.87 (m, 3H) 7.18-7.21 (m, 1H).

To a solution of 1049 (1 g, 6 mmol) in DMF (20 mL) was added potassium carbonate (2.08 g, 15 mmol), 1050 (1.225 g, 6.62 mmol) and sodium iodide (10 mg). The resulting mixture was stirred at 80° C. overnight before it was diluted with water (~100 mL). The resulting solution was partitioned between water and ethyl acetate. The organic extract was washed with more water, separated, dried over sodium sulfate, filtered and evaporated. The residue obtained was purified by silica gel chromatography eluting with MeOH/dichloromethane to afford 1051 (1 g, 60% yield) as an oil. $^1$H NMR (300 MHz, Chloroform-d) δ ppm 2.61 (s, 4H) 2.83 (t, 2H) 3.62 (s, 2H) 3.63 (s, 3H) 3.73-3.77 (m, 4H) 4.14 (t, 2H) 6.88-6.91 (m, 3H) 7.26-7.29 (m, 1H)

To a solution of 1051 (1 g, 3.57 mmol) in THF/MeOH/Water (30 mL, 5 mL, 5 mL) was added lithium hydroxide monohydrate (0.3 g, 7.14 mmol). The resulting mixture was stirred at room temperature overnight before it was concentrated under reduced pressure. The residue obtained was diluted with water (~50 mL) and the resulting solution was acidified with 1N hydrochloric acid. The aqueous layer was concentrated and the product was isolated by prep HPLC. The residue obtained was dissolved in water (mL) and concentrated hydrochloric acid (mL) was added to it before it was concentrated and dried to afford 1052 as a hydrochloride salt.

To a suspension of carboxylic acid 1052 (47.4 mg, 0.157 mmol) in DMF (3 mL) was added HATU (61.3 mg, 0.161 mmol) and stirred till reaction mixture is clear followed by the addition of an amine 1024 (52.5 mg, 0.142 mmol) and DIPEA (50 ul, 0.29 mmol). The resulting mixture was stirred at room temperature overnight before it was quenched by the addition of water. The resulting solution was partitioned between water and ethyl acetate. The organic extract was washed with more water, separated, dried over sodium sulfate, filtered and evaporated. The residue obtained was purified by silica gel chromatography eluting with MeOH/dichloromethane to afford 381 (40 mg, 46% yield). $^1$H NMR (300 MHz, Dimethylsulfoxide-d6) δ ppm 1.74 (brs, 4H) 2.72 (t, 2H) 2.89-2.9 (m, 4H) 3.02 (brs, 4H) 3.336 (m, 2H) 3.76-3.78 (m, 2H) 4.09 (m, 2H) 6.88-6.93 (m, 3H) 7.24-7.36 (m, 6H) 7.54-7.58 (d, 1H) 8.18-8.21 (d, 1H) 11.26 (s, 1H) 12.65 (brs, 1H).

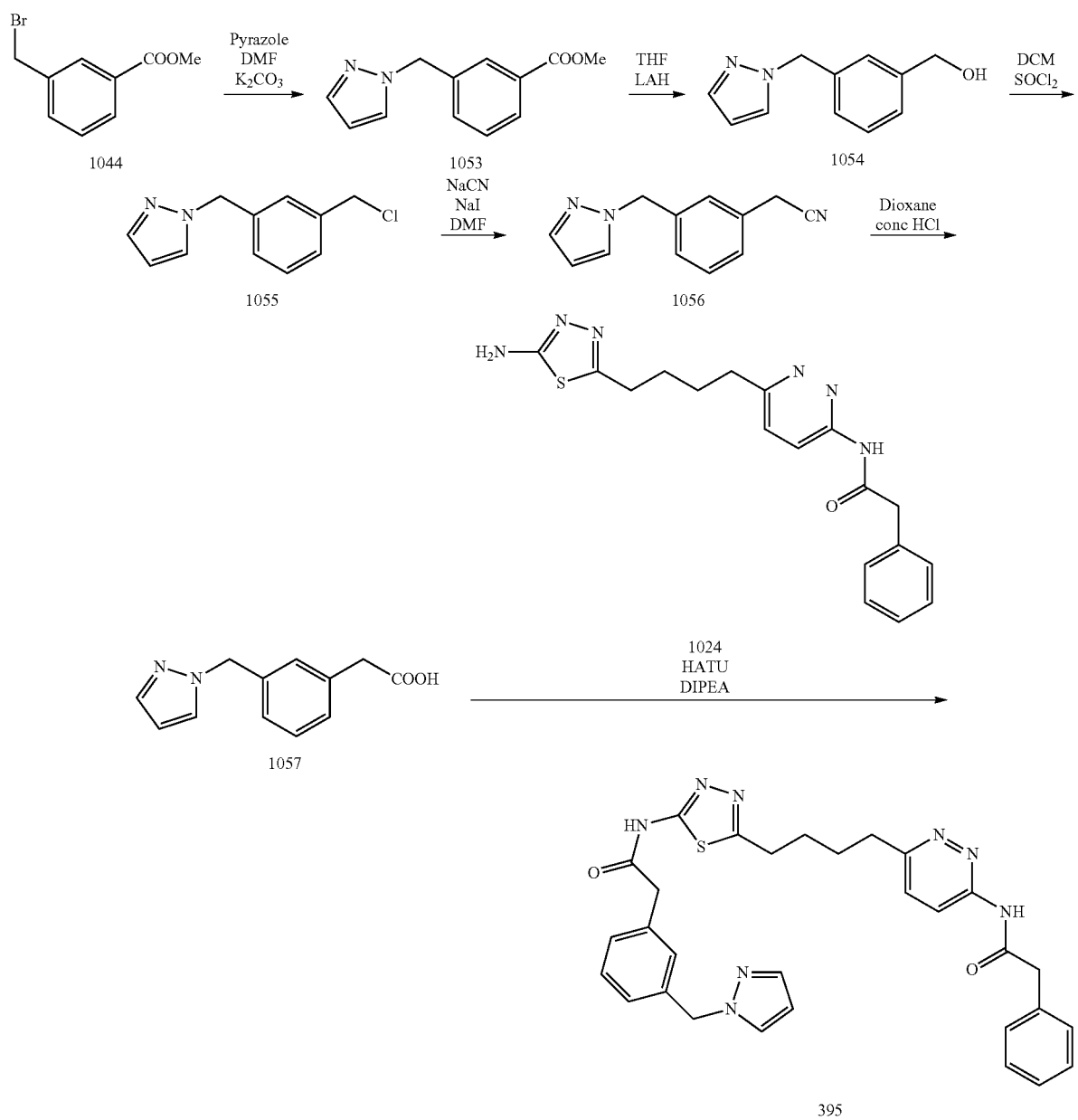

To a solution of 1044 (2.29 g, 0.01 mol) in DMF (100 mL) was added potassium carbonate (1.38 g, 0.01 mmol) and pyrazole (0.68 g, 0.01 mol). The resulting mixture was stirred at 70° C. for 5 hr before it was diluted with water (~100 mL). The resulting solution was partitioned between water and ethyl acetate. The organic extract was washed with more water, separated, dried over sodium sulfate, filtered and evaporated. The residue obtained was purified by silica gel chromatography eluting with EtOAc/Hexane to afford 1053 (1 g, 50% yield). $^1$H NMR (300 MHz, Chloroform-d) δ ppm 3.94 (s, 3H) 5.40 (s, 2H) 6.33 (s, 1H) 7.42-7.48 (m, 3H) 7.58 (s, 1H) 7.95 (s, 1H) 8.00-8.02 (m, 1H)

To an ice cold solution of 1053 (1 g, 4.62 mmol) in THF (20 mL) was added lithium aluminum hydride (2.5 mL, 2M/THF) drop wise and the resulting reaction mixture was stirred at 0° C. for 5 hr before it was quenched with saturated Rochelle salt solution. The resulting solution was partitioned between water and ethyl acetate. The organic extract was washed with more water, separated, dried over sodium sulfate, filtered and evaporated to afford 1054 (0.8 g, 92% yield). $^1$H NMR (300 MHz, Chloroform-d) δ ppm 4.71 (s, 2H) 5.35 (s, 2H) 6.30 (s, 1H) 7.15-7.43 (m, 5H) 7.58 (s, 1H)

To a solution of 1054 (0.8 g, 4.2 mmol) in dichloromethane (20 mL) was added thionyl chloride and the resulting mixture was stirred at room temperature for 5 hr before it was concentrated under the reduced pressure. The residue obtained was dried at high vacuum overnight to afford 1055 (1 g, 97% yield) as a HCl salt. $^1$H NMR (300 MHz, Dimethylsulfoxide-d6) δ ppm 4.75 (s, 2H) 5.38 (s, 2H) 6.30 (s, 1H) 7.19-7.50 (m, 5H) 7.86 (s, 1H) 11.49-11.60 (brs, 1H)

To a solution of 1055 (1 g, 4.1 mmol) in DMF (20 mL) was added sodium cyanide (0.625 g, 12.7 mmol) and sodium iodide (20 mg) and the resulting reaction mixture was stirred at 70° C. for 2 hr before it was diluted with water. The resulting solution was partitioned between water and ethyl acetate. The organic extract was washed with more water, separated, dried over sodium sulfate, filtered and evaporated. The residue obtained was purified by silica gel chromatography eluting with EtOAc/Hexane to afford 1056 (0.664 g, 83% yield). ¹H NMR (300 MHz, Chloroform-d) δ ppm 3.76 (s, 2H) 5.38 (s, 2H) 6.35 (s, 1H) 7.19-7.46 (m, 5H) 7.61 (s, 1H)

To a solution of 1056 (0.664 g, 3.3 mmol) in dioxane (5 mL) was added concentrated hydrochloric acid (5 mL) and the resulting reaction mixture was stirred at 90° C. overnight before it was concentrated under the reduced pressure. The residue obtained was purified through prep HPLC and was converted to HCl salt to afford 1057 (0.5 g, 40% yield). ¹H NMR (300 MHz, Dimethylsulfoxide-d6) δ ppm 3.55 (s, 2H) 5.33 (s, 2H) 6.29 (s, 1H) 7.14-7.20 (m, 4H) 7.48 (s, 1H) 7.84 (s, 1H) 11.97-11.99 (brs, 1H)

To a suspension of carboxylic acid 1057 (19.8 mg, 0.0785 mmol) in DMF (2 mL) was added HATU (30.6 mg, 0.08 mmol) and stirred till reaction mixture is clear followed by the addition of an amine 1024 (26.25 mg, 0.07 mmol) and DIPEA (25 ul, 0.15 mmol). The resulting mixture was stirred at room temperature overnight before it was quenched by the addition of water. The solid separated was filtered, washed with water and dried to afford 395 (18 mg, 45% yield). ¹H NMR (300 MHz, Dimethylsulfoxide-d6) δ ppm 1.74 (brs, 4H) 2.89-3.04 (m, 4H) 3.78 (s, 4H) 5.33 (s, 2H) 6.27-6.28 (s, 1H) 7.09-7.58 (m, 11H) 7.82 (s, 1H) 8.19-8.21 (d, 1H) 11.26 (s, 1H) 12.65 (brs, 1H)

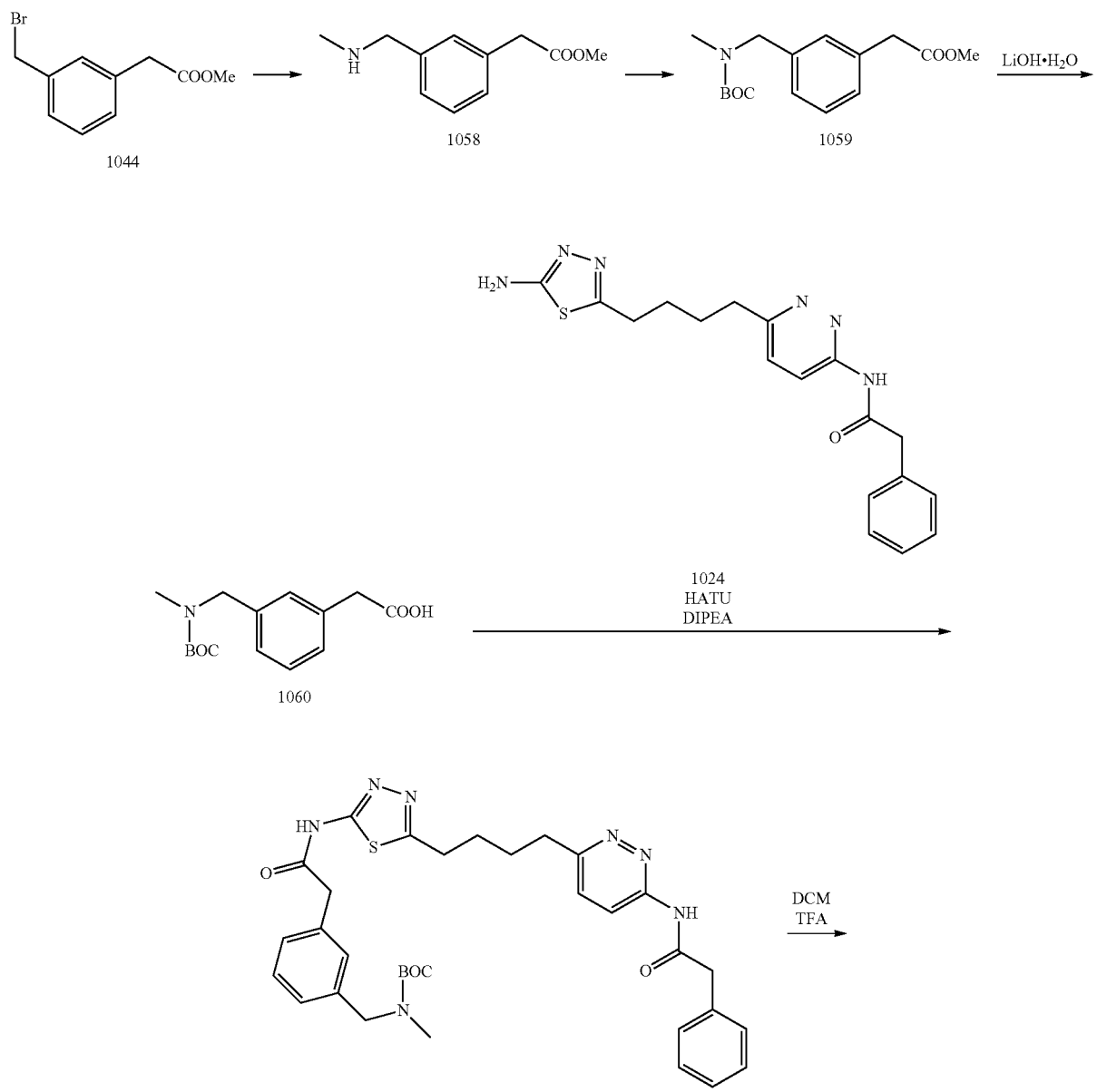

107

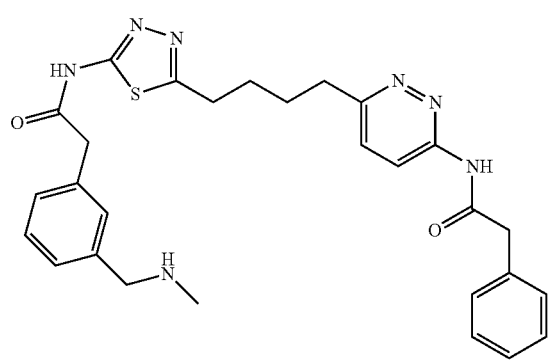

408

108

-continued

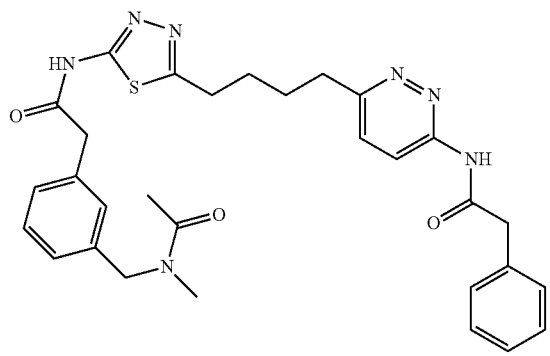 [SMILES: CC(=O)N(C)Cc1cccc(CC(=O)Nc2nnc(CCCCc3ccc(NC(=O)Cc4ccccc4)nn3)s2)c1]

445

To a solution of 1044 (1 g, 4.1 mmol) in THF (5 mL) was added 2M/THF methyl amine solution (2 mL) and the resulting reaction mixture was stirred at room temperature overnight before it was concentrated under the reduced pressure. The residue obtained was partitioned between water and ethyl acetate. The organic extract was washed with more water, separated, dried over sodium sulfate, filtered and evaporated. The residue obtained was purified by silica gel chromatography eluting with MeOH/dichloromethane to afford 1058 (0.26 g, 33% yield). $^1$H NMR (300 MHz, Chloroform-d) δ ppm 2.49 (s, 3H) 3.66 (s, 2H) 3.73 (s, 3H) 3.79 (s, 2H) 7.2-7.33 (m, 4H).

To a solution of 1058 (0.26 g, 1.35 mmol) in dichloromethane (5 mL) was added boc anhydride (0.293 g, 1.35 mmol) and the resulting reaction mixture was stirred at room temperature for 4 hr before it was purified by silica gel chromatography eluting with EtOAc/Hexane to afford 1059 (0.3 g, 77% yield). $^1$H NMR (300 MHz, Chloroform-d) δ ppm 1.5 (s, 9H) 2.84 (s, 3H) 3.66 (s, 2H) 3.73 (s, 3H) 4.44 (s, 2H) 7.17-7.32 (m, 4H).

To an ice cold solution of 1059 (0.3 g, 1.02 mmol) in dioxane (3 mL) and water (2 mL) was added lithium hydroxide monohydrate (0.086 g, 2.04 mmol) and the resulting reaction mixture was stirred at 0° C. for 3 hr before it was acidified with 1N HCl. The resulting solution was partitioned between water and ethyl acetate. The organic extract was washed with more water, separated, dried over sodium sulfate, filtered and evaporated. The residue obtained was dried at high vacuum overnight to afford 1060 (0.2 g, 70% yield). $^1$H NMR (300 MHz, Chloroform-d) δ ppm 1.5 (s, 9H) 2.84 (s, 3H) 3.66 (s, 2H) 4.43 (s, 2H) 7.17-7.32 (m, 4H)

To a suspension of carboxylic acid 1060 (51.1 mg, 0.183 mmol) in DMF (3 mL) was added HATU (69.7 mg, 0.183 mmol) and stirred till reaction mixture is clear followed by the addition of an amine 1024 (61.3 mg, 0.166 mmol) and DIPEA (58 ul, 0.33 mmol). The resulting mixture was stirred at room temperature overnight before it was quenched by the addition of water. The resulting solution was partitioned between water and ethyl acetate. The organic extract was washed with more water, separated, dried over sodium sulfate, filtered and evaporated. The residue obtained was purified by silica gel chromatography eluting with MeOH/dichloromethane to afford 445 (0.06 g, 57% yield). $^1$H NMR (300 MHz, Dimethylsulfoxide-d6) δ ppm 1.37-1.38 (s, 9H) 1.74 (brs, 4H) 2.76 (s, 3H) 2.89 (brs, 2H) 3.02 (brs, 2H) 3.78-3.80 (m, 4H) 4.36 (s, 2H) 7.11-7.36 (m, 9H) 7.54-7.57 (d, 1H) 8.18-8.21 (d, 1H) 11.26 (s, 1H) 12.65 (brs, 1H).

Prep of 445 Via 396 Deprotection to 408 and Re-Acylation:

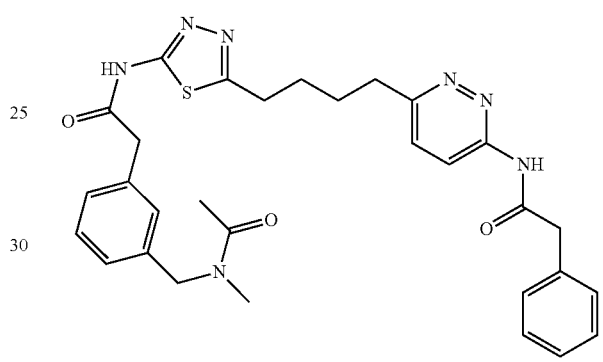

To an ice cold solution of 408 (26 mg, 0.04 mmol) in DMF (1 mL) was added triethylamine (12.3 uL, 0.088 mmol) and acetyl chloride (3.16 uL, 0.044 mmol). The resulting mixture was stirred at room temperature for 2 hr before it was diluted with water. The solid separated was filtered, washed with water and dried at high vacuum overnight to afford 445 (10 mg, 48% yield). $^1$H NMR (300 MHz, Dimethylsulfoxide-d6) δ ppm 1.74 (brs, 4H) 2.05 (m, 3H) 2.91-3.02 (m, 7H) 3.78-3.82 (m, 4H) 4.49-4.56 (m, 2H) 7.18-7.36 (m, 9H) 7.55-7.58 (d, 1H) 8.18-8.21 (d, 1H) 8.75-8.7 (brs, 2H) 11.26 (s, 1H) 12.65 (brs, 1H).

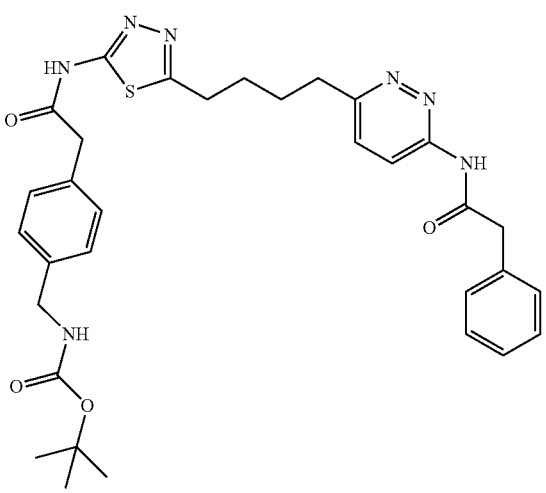 [SMILES: CC(C)(C)OC(=O)NCc1ccc(CC(=O)Nc2nnc(CCCCc3ccc(NC(=O)Cc4ccccc4)nn3)s2)cc1]

Compound 401 was prepared according to the procedure above for the preparation of compound 339. ¹H NMR (300 MHz, Dimethylsulfoxide-d6) δ ppm 1.40 (s, 9H) 1.75 (brs, 4H) 2.87 (brs, 2H) 2.89 (brs, 2H) 3.78 (s, 4H) 4.09-4.11 (brs, 2H) 7.18-7.36 (m, 9H) 7.54-7.58 (d, 1H) 8.18-8.21 (d, 1H) 11.26 (s, 1H) 12.65 (brs, 1H)

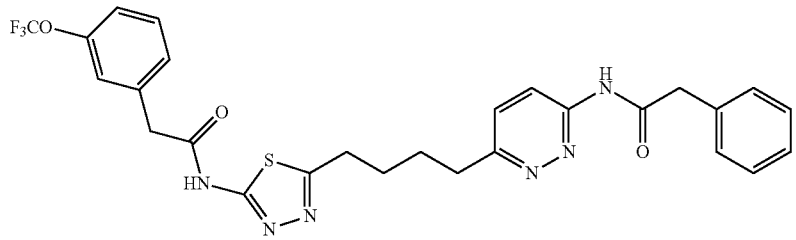

413

Compound 413 was prepared according to the procedure above for the preparation of compound 315. ¹H NMR (300 MHz, DMSO-$d_6$) δ 12.68 (bs, 1H), 11.26 (s, 1H), 8.20 (d, J=9.46 Hz, 1H), 7.58-7.26 (m, 10H), 3.90 (s, 2H), 3.78 (s, 2H), 3.02 (bs, 2H), 2.90 (bs, 2H), 1.74 (bs, 4H).

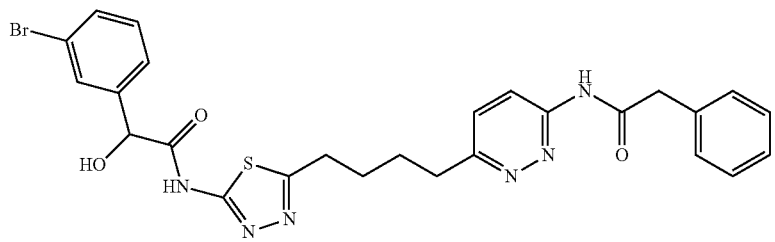 [SMILES: O=C(Cc1ccccc1)Nc1ccc(CCCCc2nnc(NC(=O)C(O)c3cccc(Br)c3)s2)nn1]

Compound 415 was prepared according to the procedure above for the preparation of compound 315: ¹H NMR (300 MHz, DMSO-$d_6$) δ 12.48 (s, 1H), 11.26 (s, 1H), 8.20 (d, J=8.95 Hz, 1H), 7.75 (s, 1H), 7.58-7.26 (m, 9H), 6.52 (m, 1H), 5.35 (m, 1H), 3.78 (s, 2H), 3.02 (m, 2H), 2.90 (m, 2H), 1.74 (bs, 4H).

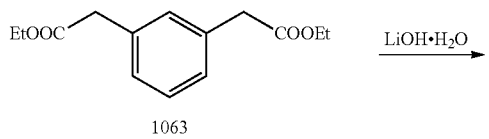

1063

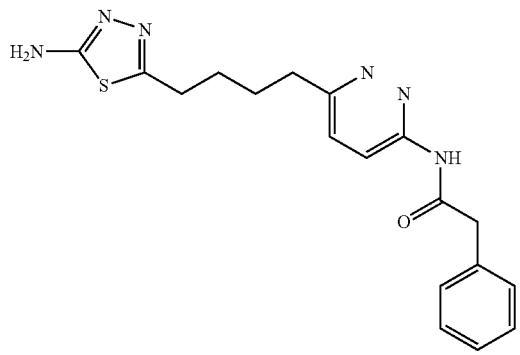

1064

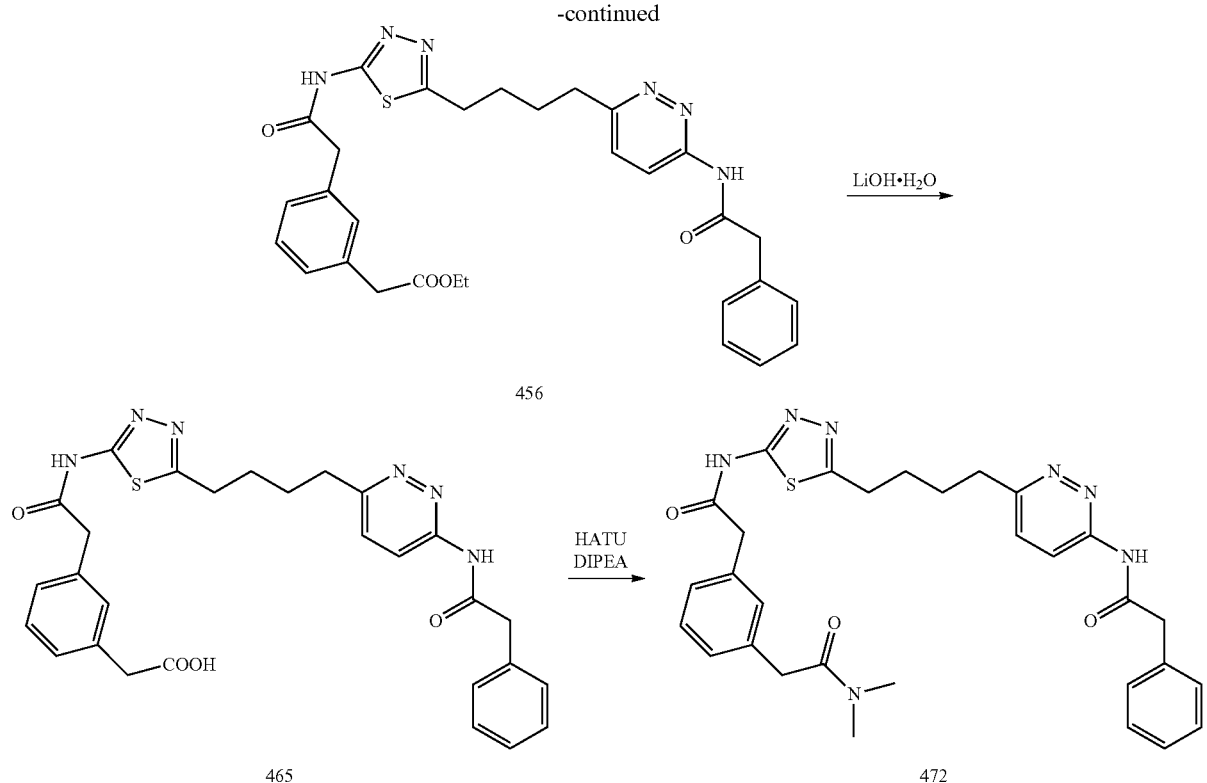

456

465

472

To a solution of 1063 (6.31 g, 24.9 mmol) in ethanol was added lithium hydroxide monohydrate (1.048 g, 24.9 mmol) and the resulting reaction mixture was stirred at room temperature for 3 hr before it was concentrated under the reduced pressure. The residue obtained was diluted with water and was acidified with 6N HCl. The solution was extracted with ethyl acetate. The organic extract was washed with more water, separated, dried over sodium sulfate, filtered and evaporated. The residue obtained was purified by silica gel chromatography eluting with EtOAc/hexane to afford 1064 (3 g, 53% yield).

To a suspension of carboxylic acid 1064 (0.1 g, 0.44 mmol) in DMF (2 mL) was added HATU (0.17 g, 0.44 mmol) and stirred till reaction mixture is clear followed by the addition of an amine 1024 (0.15 g, 0.4 mmol) and DIPEA (0.14 mL, 0.8 mmol). The resulting mixture was stirred at room temperature overnight before it was quenched by the addition of water. The solid separated was filtered, washed with water and dried to afford 456 (0.2, 86% yield). $^1$H NMR (300 MHz, Dimethylsulfoxide-d6) δ ppm 1.18 (t, 3H) 1.74 (brs, 4H) 2.88-2.90 (m, 2H) 3.01-3.04 (m, 2H) 3.66 (s, 2H) 3.78 (s, 4H) 4.05-4.12 (q, 2H) 7.19-7.36 (m, 9H) 7.55-7.58 (m, 1H) 8.18-8.21 (d, 1H) 11.26 (s, 1H) 12.65 (brs, 1H).

To a solution of 456 (0.205 g, 0.358 mmol) in Dioxane/Water (20 mL/6 mL) was added lithium hydroxide monohydrate (0.06 g, 1.42 mmol). The resulting mixture was stirred at room temperature for 3 hr before it was acidified with acetic acid. The solution was concentrated under reduced pressure and the residue obtained was diluted with water. The solid separated was filtered, washed with water and dried at high vacuum overnight. The residue obtained was purified by silica gel chromatography eluting with MeOH/dichloromethane to afford 465 (0.15 g, 77% yield). $^1$H NMR (300 MHz, Dimethylsulfoxide-d6) δ ppm 1.74 (brs, 4H) 2.90 (brs, 2H) 3.01 (brs, 2H) 3.5 (s, 2H) 3.78 (s, 4H) 7.19-7.36 (m, 9H) 7.55-7.58 (m, 1H) 8.18-8.21 (d, 1H) 11.26 (s, 1H) 12.32 (brs, 1H) 12.65 (s, 1H).

To a suspension of carboxylic acid 465 (25 mg, 0.046 mmol) in DMF (1 mL) was added HATU (19.2 mg, 0.05 mmol) and stirred till reaction mixture is clear followed by the addition of an N,N-dimethylamine (2M/THF, 30 uL, 0.05 mmol) and DIPEA (16 uL, 0.092 mmol). The resulting mixture was stirred at room temperature for 3 hr before it was quenched by the addition of water. The solid separated was filtered, washed with water and dried to afford 472 (19 mg, 73% yield). $^1$H NMR (300 MHz, Dimethylsulfoxide-d6) δ ppm 1.74 (brs, 4H) 2.83-2.90 (brs, 6H) 3.01 (brs, 4H) 3.68 (s, 2H) 3.78 (s, 4H) 7.14-7.36 (m, 9H) 7.55-7.58 (d, 1H) 8.18-8.21 (d, 1H) 11.26 (s, 1H) 12.65 (brs, 1H).

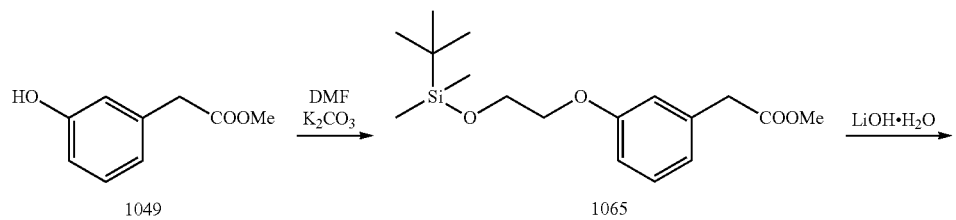

1049

1065

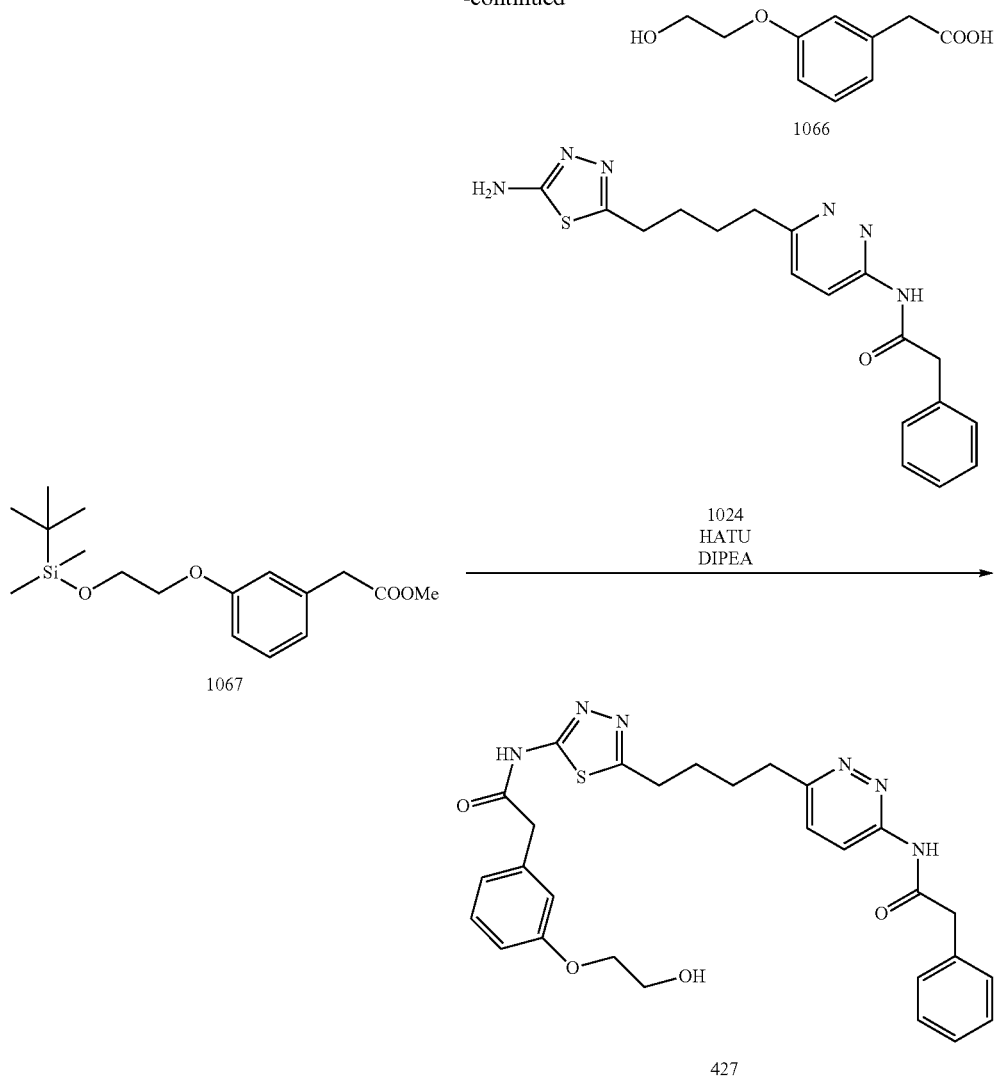

To a solution of 1049 (1 g, 6 mmol) in DMF (20 mL) was added potassium carbonate (1.662 g, 12 mmol) and (2.16 g, 9 mmol). The resulting mixture was stirred at 70° C. overnight before it was diluted with water (~100 mL). The resulting solution was partitioned between water and ethyl acetate. The organic extract was washed with more water, separated, dried over sodium sulfate, filtered and evaporated. The residue obtained was purified by silica gel chromatography eluting with EtOAc/Hexane to afford 1065 (1.78 g, 91% yield) as an oil. $^1$H NMR (300 MHz, Chloroform-d) δ ppm 0.13 (s, 6H) 0.95 (s, 9H) 3.63 (s, 2H) 3.73 (s, 2H) 3.99-4.06 (m, 4H) 6.87 (m, 3H) 7.3 (m, 1H).

To a solution of 1065 (1.78 g, 5.5 mmol) in THF/MeOH/Water (30 mL, 3 mL, 3 mL) was added lithium hydroxide monohydrate (0.46 g, 10.9 mmol). The resulting mixture was stirred at room temperature overnight before it was concentrated under reduced pressure. The residue obtained was diluted with water (~20 mL) and the resulting solution was acidified with 6N hydrochloric acid. The solution was partitioned between water and ethyl acetate. The organic extract was washed with more water, separated, dried over sodium sulfate, filtered and evaporated. The residue obtained was purified by silica gel chromatography eluting with EtOAc/Hexane to afford 1065 and 1066. $^1$H NMR (300 MHz, Dimethylsulfoxide-d6) δ ppm 3.54 (s, 2H) 3.72 (brs, 2H) 3.96-3.98 (brs, 2H) 4.85 (brs, 1H) 6.82-6.85 (m, 3H) 7.0-7.22 (m, 1H) 12.3 (brs, 1H).

To a suspension of carboxylic acid 1065 (27 mg, 0.137 mmol) in DMF (2 mL) was added HATU (52.2 mg, 0.137 mmol) and stirred till reaction mixture is clear followed by the addition of an amine 1024 (46 mg, 0.125 mmol) and DIPEA (44 ul, 0.25 mmol). The resulting mixture was stirred at room temperature overnight before it was quenched by the addition of water. The solid separated was filtered, washed with water and dried. The solid obtained was purified by prep HPLC to afford 427 (16 mg, 23% yield). $^1$H NMR (300 MHz, Dimethylsulfoxide-d6) δ ppm 1.75 (brs, 4H) 2.90 (brs, 2H) 3.02 (brs, 2H) 3.71-3.78 (m, 6H) 3.98-3.99 (brs, 2H) 4.84-4.87 (brs, 1H) 6.83-6.92 (m, 3H) 7.21-7.36 (m, 6H) 7.54-7.58 (d, 1H) 8.2-8.23 (d, 1H) 11.26 (s, 1H) 12.65 (brs, 1H).

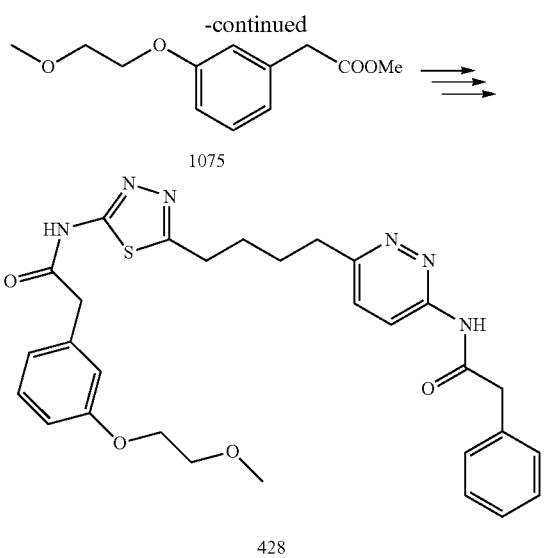

To a solution of 1049 (1 g, 6 mmol) in acetone (50 mL) was added cesium carbonate (2.545 g, 7.83 mmol), 2-bromoethyl methyl ether (0.92 g, 6.62 mmol) and sodium iodide (10 mg). The resulting mixture was stirred at 50° C. overnight before it was filtered. The filtrate was evaporated and the residue obtained was purified by silica gel chromatography eluting with EtOAc/Hexane to afford 1075 (0.97 g, 72% yield) as oil. $^1$H NMR (300 MHz, Chloroform-d) δ ppm 3.48 (s, 3H) 3.63 (s, 2H) 3.72 (brs, 2H) 4.14-4.15 (t, 2H) 6.86-6.9 (m, 3H) 7.26-7.29 (m, 1H).

The remainder of the preparation for compound 428 followed the procedure above for compound 427. 428: $^1$H NMR (300 MHz, Dimethylsulfoxide-d6) δ ppm 1.75 (brs, 4H) 2.90 (brs, 2H) 3.02 (brs, 2H) 3.32 (s, 3H) 3.66 (brs, 2H) 3.78 (brs, 4H) 4.08 (brs, 2H) 6.88-6.92 (m, 3H) 7.25-7.27 (m, 6H) 7.54-7.58 (d, 1H) 8.2-8.23 (d, 1H) 11.26 (s, 1H) 12.65 (brs, 1H).

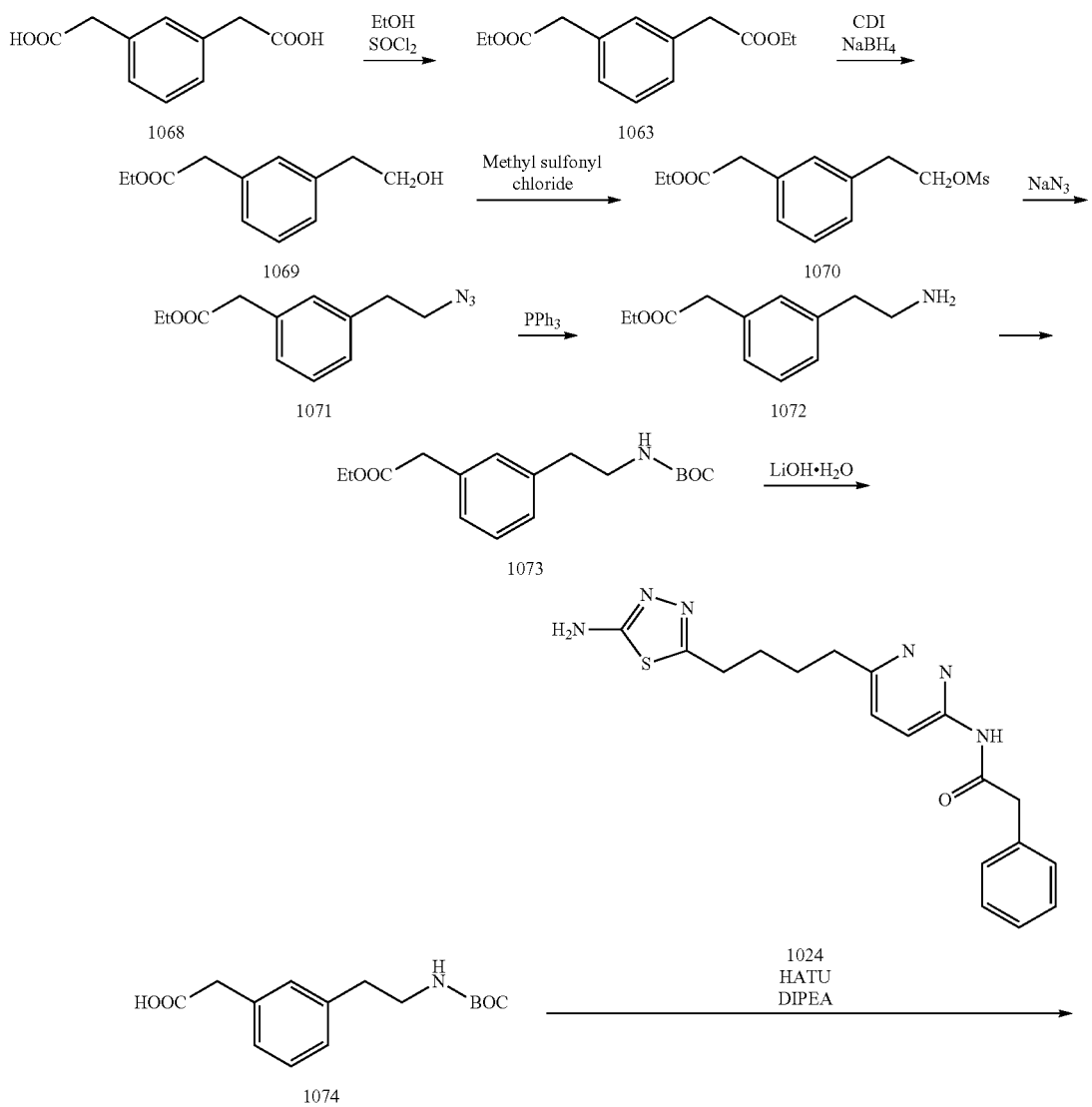

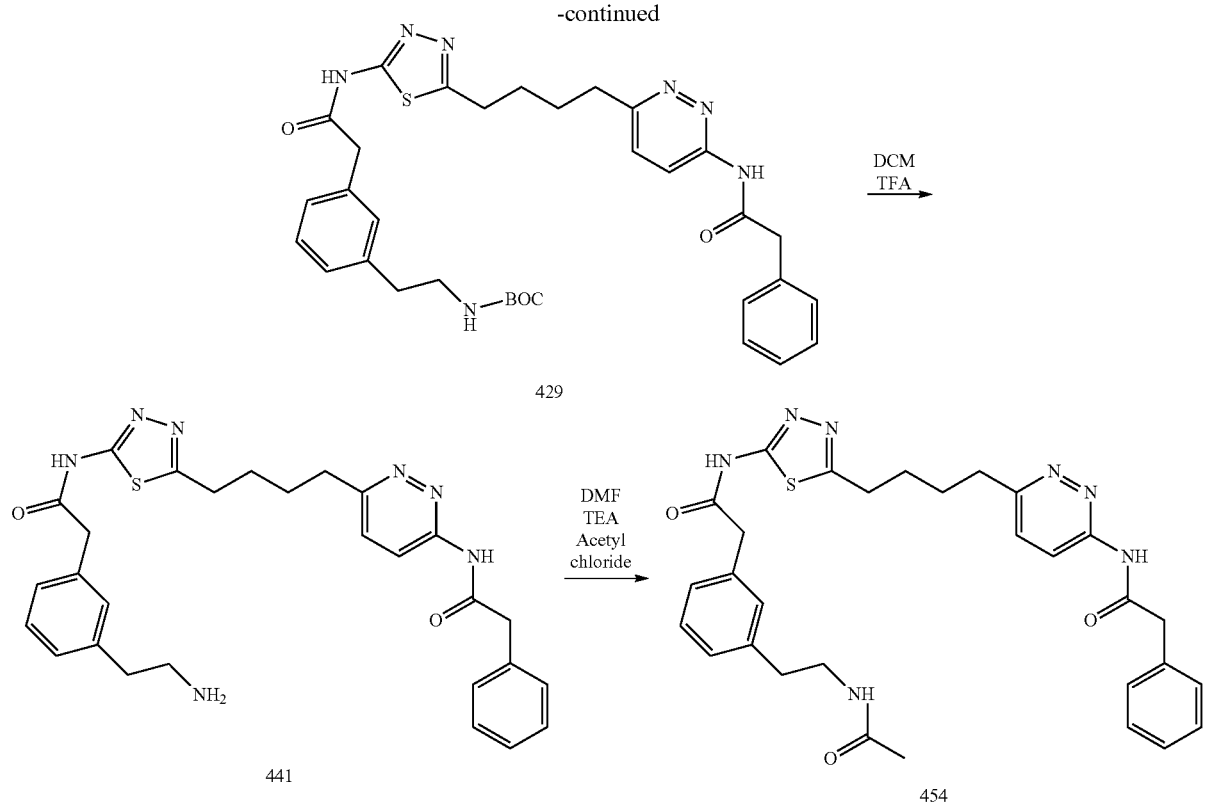

429

441

454

To an ice cold solution of 1068 (6 g, 30.9 mmoL) in ethanol (50 mL) was added thionyl chloride (2 mL) and the resulting reaction mixture was stirred at room temperature overnight before it was concentrated under the reduced pressure. The residue obtained was partitioned between water and ethyl acetate. The organic extract was washed with more water, separated, dried over sodium sulfate, filtered and evaporated to afford 1063 (6 gm).

To a stirred solution of 1063 (3.35 g, 13.4 mmol) in THF (50 mL) was added CDI (2.44 g, 15 mmol) and the resulting mixture was stirred for 2 hr followed by the addition of water (13 mL). The reaction mixture was cooled to 0° C. and sodium borohydride (2.87 g, 76 mmol) was added portionwise. The stirring was continued at room temperature for 3 hr before it was diluted with ethyl acetate and acidified with 6N HCl. The organic layer was separated, dried over sodium sulfate, filtered and evaporated. The residue obtained was purified by silica gel chromatography eluting with EtOAc/Hexane to afford 1069 (0.563 g, 20% yield) as an oil. $^1$H NMR (300 MHz, Chloroform-d) δ ppm 1.27-1.31 (q, 3H) 2.87-2.92 (d, 2H) 3.63 (s, 2H) 3.87-3.92 (t, 2H) 4.18-4.2 (q, 2H) 7.19-7.31 (m, 4H).

To an ice cold solution of 1069 (0.563 g, 2.7 mmol) in dichloromethane (40 mL) and triethylamine (0.47 mL, 3.3 mmol) was added methane sulfonylchloride (0.23 mL, 3.3 mmol) and the resulting mixture was stirred at 0° C. for 2 hr and at room temperature for 1 hr before it was diluted with saturated aqueous sodium bicarbonate solution. The solution was extracted with ethyl acetate. The organic extract was washed with more water, separated, dried over sodium sulfate, filtered and evaporated to afford 1070 (0.78 g, 100% yield). $^1$H NMR (300 MHz, Chloroform-d) δ ppm 1.27-1.31 (q, 3H) 2.87 (s, 3H) 3.08 (t, 2H) 3.63 (s, 2H) 4.18-4.2 (t, 2H) 4.45 (q, 2H) 7.19-7.31 (m, 4H).

To a solution of 1070 (0.787 g, 2.7 mmol) in DMF (6 mL) was added sodium azide (0.358 g, 5.5 mmol) and the resulting reaction mixture was stirred at 60° C. for 3 hr before it was partitioned between water and ethyl acetate. The organic extract was washed with more water, separated, dried over sodium sulfate, filtered and evaporated. The residue obtained was purified by silica gel chromatography eluting with EtOAc/Hexane to afford 1071 (0.5 g, 78% yield) as an oil. $^1$H NMR (300 MHz, Chloroform-d) δ ppm 1.27-1.31 (q, 3H) 2.92 (t, 2H) 3.54 (t, 2H) 3.63 (s, 2H) 4.18-4.2 (q, 2H) 7.19-7.29 (m, 4H).

To a solution of 1071 (0.5 g, 2.1 mmol) in THF (25 mL) was added triphenylphosphine (0.787 g, 3 mmol) and the reaction mixture was stirred at room temperature under argon for overnight before it was diluted with 1 mL of water. The reaction was continued at 50° C. for 1 hr before it was concentrated under the reduced pressure. The residue was partitioned between saturated sodium bicarbonate solution and dichloromethane. The organic layer was separated, dried over sodium sulfate, filtered and evaporated. The residue obtained was purified by silica gel chromatography eluting with MeOH/dichloromethane to afford 1072 (0.43 g, 100% yield) as an oil. $^1$H NMR (300 MHz, Chloroform-d) δ ppm 1.27-1.31 (q, 3H) 2.75-2.79 (t, 2H) 2.98-3.02 (t, 2H) 3.63 (s, 2H) 4.18-4.2 (q, 2H) 7.13-7.29 (m, 4H).

To a solution of 1072 (0.427 g, 2 mmol) in dichloromethane (30 mL) was added di-tert-butyl dicarbonate (0.447 g, 2 mmol) and the reaction mixture was stirred at room temperature for 5 hr before it was purified by silica gel chromatography eluting with EtOAc/Hexane to afford 1073 (0.577 g, 91% yield) as an oil. $^1$H NMR (300 MHz, Chloroform-d) δ ppm 1.27-1.31 (q, 3H) 1.59 (s, 9H) 2.82 (t, 2H) 3.4 (m, 2H) 3.63 (s, 2H) 4.18 (q, 2H) 7.13-7.29 (m, 4H).

To a solution of 1073 (0.577 g, 1.8 mmol) in Dioxane/Water (10 mL/3 mL) was added lithium hydroxide monohydrate (0.158 g, 3.6 mmol). The resulting mixture was stirred at room temperature overnight before it was concentrated under reduced pressure. The residue obtained was diluted with water (~20 mL) and the resulting solution was acidified with 1N hydrochloric acid. The solution was partitioned between water and ethyl acetate. The organic extract was washed with more water, separated, dried over sodium sulfate, filtered and evaporated to afford 1074 (0.35 g, 67% yield). $^1$H NMR (300 MHz, Chloroform-d) δ ppm 2.82 (m, 2H) 3.4 (m, 2H) 3.63 (s, 2H) 4.6 (brs, 1H) 7.13-7.29 (m, 4H).

To a suspension of carboxylic acid 1074 (43.8 mg, 0.157 mmol) in DMF (2 mL) was added HATU (61.3 mg, 0.161 mmol) and stirred till reaction mixture is clear followed by the addition of an amine 1024 (52.5 mg, 0.142 mmol) and DIPEA (50 ul, 0.287 mmol). The resulting mixture was stirred at room temperature overnight before it was quenched by the addition of water. The solid separated was filtered, washed with water and dried to afford 429 (60 mg, 67% yield). $^1$H NMR (300 MHz, Dimethylsulfoxide-d6) δ ppm 1.37-1.38 (s, 9H) 1.74 (brs, 4H) 2.69-2.71 (m, 2H) 2.87-2.88 (m, 2H) 2.9-3.15 (m, 4H) 3.78 (s, 4H) 7.09 (brs, 1H) 7.12-7.36 (m, 9H) 7.54-7.57 (d, 1H) 8.18-8.21 (d, 1H) 11.26 (s, 1H) 12.65 (brs, 1H).

To a suspension of 429 (50 mg, 79.5 mmol) in dichloromethane (5 mL) was added TFA (1 mL) and the reaction mixture was stirred at room temperature for overnight before it was concentrated under the reduced pressure. The residue obtained was triturated with ether. The solid separated was filtered, washed with ether and dried at high vacuum overnight to afford 441 (45 mg, 88% yield) as a TFA salt. $^1$H NMR (300 MHz, Dimethylsulfoxide-d6) δ ppm 1.74 (brs, 4H) 2.86-3.02 (m, 8H) 3.78-3.80 (s, 4H) 7.12-7.36 (m, 8H) 7.58 (d, 1H) 7.78 (brs, 3H) 8.18-8.21 (d, 1H) 11.26 (s, 1H) 12.65 (brs, 1H).

To an ice cold solution of 441 (23 mg, 0.035 mmol) in DMF (1 mL) was added triethylamine (11 uL, 0.079 mmol) and acetyl chloride (2.8 uL, 0.038 mmol). The resulting mixture was stirred at room temperature for 2 hr before it was diluted with water. The solid separated was filtered, washed with water and dried at high vacuum overnight to afford 454 (10 mg, 50% yield). $^1$H NMR (300 MHz, Dimethylsulfoxide-d6) δ ppm 1.75-1.79 (m, 7H) 2.67-2.70 (m, 2H) 2.9 (brs, 2H) 3.00-3.02 (m, 2H) 3.21-3.26 (m, 2H) 3.78 (s, 4H) 7.12-7.36 (m, 9H) 7.58 (d, 1H) 7.9 (brs, 1H) 8.18-8.21 (d, 1H) 11.26 (s, 1H) 12.65 (brs, 1H).

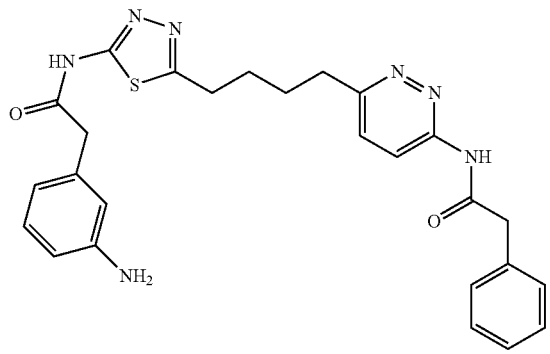 [SMILES: Nc1cccc(CC(=O)Nc2nnc(CCCCc3ccc(NC(=O)Cc4ccccc4)nn3)s2)c1]

Compound 409 was prepared via TFA deprotection of compound 399 according to the procedure above for the preparation of compound 441. $^1$H NMR (300 MHz, Dimethylsulfoxide-d6) δ ppm 1.75 (brs, 4H) 2.90 (brs, 2H) 3.02 (brs, 2H) 3.78 (brs, 4H) 6.89-6.98 (m, 4H) 7.25-7.36 (m, 7H) 7.51-7.58 (d, 1H) 8.2-8.23 (d, 1H) 9.34 (s, 1H) 11.26 (s, 1H) 12.65 (brs, 1H).

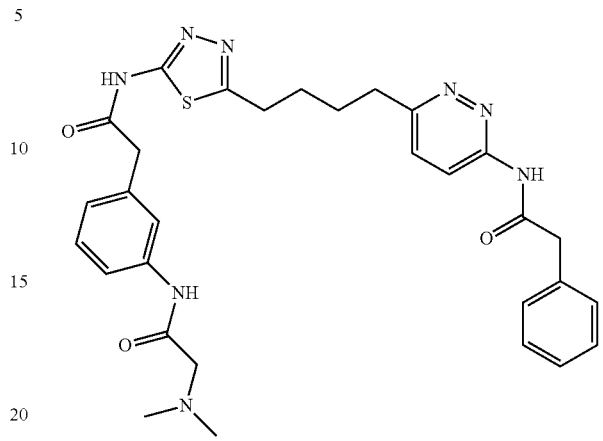

Compound 457 was prepared by acylation of 409 according to the amide coupling procedure above for the preparation of compound 39. $^1$H NMR (300 MHz, Dimethylsulfoxide-d6) δ ppm 1.74 (brs, 4H) 2.32 (s, 6H) 2.89 (m, 2H) 3.02 (m, 2H) 3.13 (s, 2H) 3.78 (s, 4H) 7.01-7.04 (m, 1H) 7.25-7.38 (m, 6H) 7.54-7.58 (m, 3H) 8.18-8.21 (d, 1H) 9.77 (s, 1H) 11.26 (s, 1H) 12.65 (brs, 1H)

348

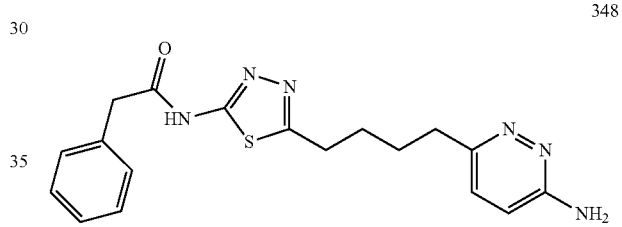

To a suspension of 295 (30 mg, 0.0617 mmol) in MeOH (2 ml) at 0° C. was added 2N NaOH (2 ml) solution. The resulting mixture was stirred at room temperature overnight. The solvent was evaporated under vacuo and the mixture was acidified with 1N HCl to pH 6. The white precipitate was collected by suction filtration, rinsed with more water and dried to afford 348. $^1$H NMR (300 MHz, DMSO-d$_6$) δ 7.32-7.24 (m, 5H), 7.15-7.12 (d, J=9.57 Hz, 1H), 6.72-6.69 (d, J=9.15 Hz, 1H), 6.09 (s, 2H), 3.77 (s, 2H), 2.99-2.96 (bs, 2H), 2.76-2.70 (bs, 2H), 1.70 (bs, 4H).

366

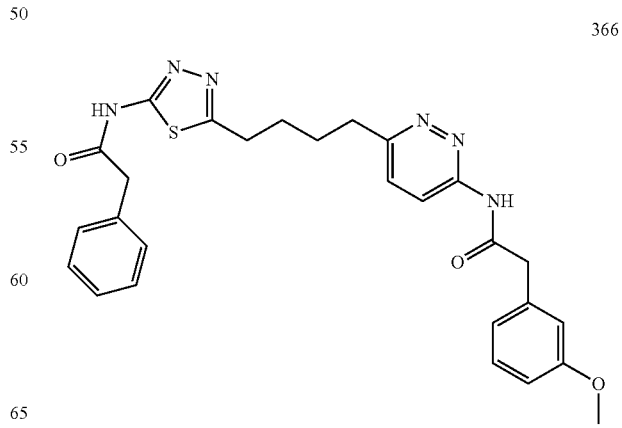

366: ¹H NMR (300 MHz, DMSO-d₆) δ 12.65 (s, 1H), 11.26 (s, 1H), 8.22-8.19 (d, J=8.82 Hz, 1H), 7.58-7.54 (d, J=9.32 Hz, 1H), 7.33-7.25 (m, 6H), 6.95-6.82 (m, 3H), 3.81 (s. 3H), 3.75 (s, 4H), 3.01 (bs, 2H), 2.90 (bs, 2H), 1.73 (bs, 4H).

367

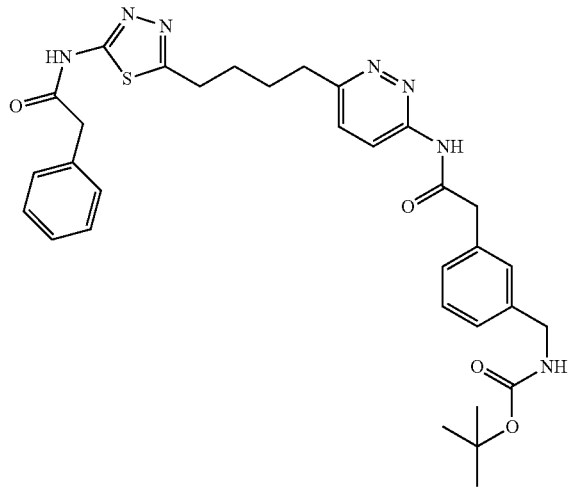

367: A flask was charged with 348 (100 mg, 0.27 mmol), Boc-3-aminomethyl-phenylacetic acid (86 mg, 0.325 mmol) in DMF (2 ml) at 0° C. was added HOBT (88 mg, 0.65 mmol) followed by EDCI (156 mg, 0.812 mmol). The resulting mixture was stirred at 0° C. for 5 minutes then warmed up to room temperature overnight before it was quenched by addition of water (~10 mL) at 0° C. The white precipitate was collected by suction filtration, rinsed with more water. The crude material was purified by silica gel chromatography eluting with 0-6% MeOH in CH₂Cl₂ to afford 367.

368

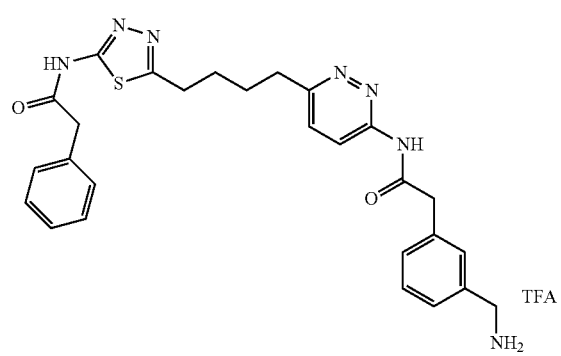

Compound 368 was prepared via the deprotection of compound 367 according to the procedure above for compound 341. ¹H NMR (300 MHz, DMSO-d₆) δ 12.65 (s, 1H), 11.26 (s, 1H), 8.22-8.16 (m, 3H), 7.58-7.54 (d, J=9.27 Hz, 1H), 7.40-7.28 (m, 9H), 4.04 (s, 2H), 3.81 (s. 4H), 3.01 (bs, 2H), 2.90 (bs, 2H), 1.73 (bs, 4H).

383

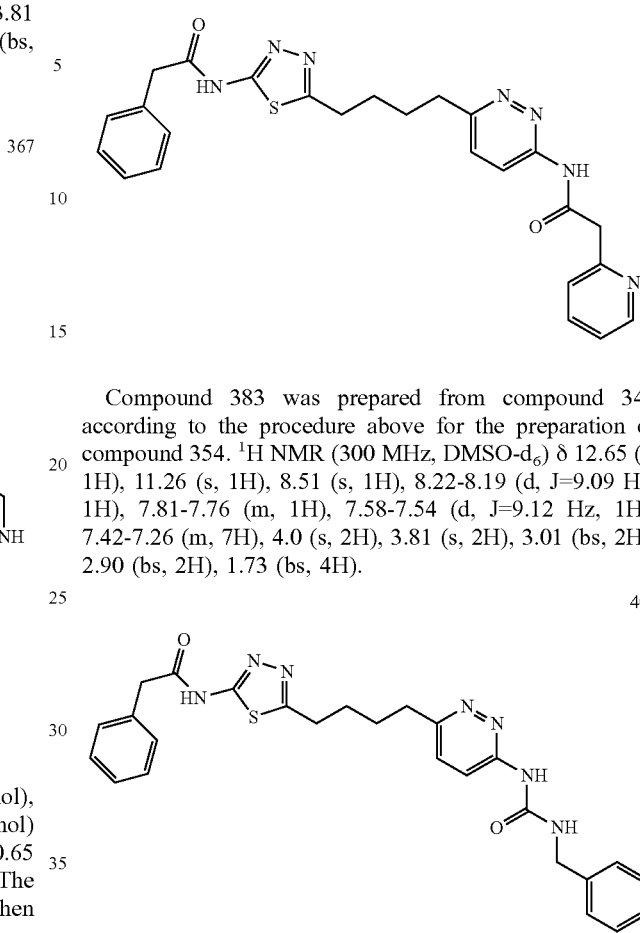

Compound 383 was prepared from compound 348 according to the procedure above for the preparation of compound 354. ¹H NMR (300 MHz, DMSO-d₆) δ 12.65 (s, 1H), 11.26 (s, 1H), 8.51 (s, 1H), 8.22-8.19 (d, J=9.09 Hz, 1H), 7.81-7.76 (m, 1H), 7.58-7.54 (d, J=9.12 Hz, 1H), 7.42-7.26 (m, 7H), 4.0 (s, 2H), 3.81 (s, 2H), 3.01 (bs, 2H), 2.90 (bs, 2H), 1.73 (bs, 4H).

405

To a solution of 348 (56.5 mg, 0.153 mmol) in DMF (1 ml) at 0° C. was added triethylamine (43 ul, 0.306 mmol) drop wise followed by benzyl isocyanate (23 ul, 0.184 mmol) drop wise. The resulting mixture was slowly warmed up to room temperature and stirred for 6 h before it was quenched by addition of water (~5 mL) at 0° C. The white precipitate was collected by suction filtration, rinsed with more water and ether and dichloromethane then dried to afford 405. ¹H NMR (300 MHz, DMSO-d₆) δ 12.65 (s, 1H), 9.57 (s, 1H), 8.25 (bs, 1H), 7.74-7.71 (d, J=8.61 Hz, 1H), 7.50-7.47 (d, J=9.42 Hz, 1H), 7.34-7.27 (m, 10H), 4.42-4.40 (d, J=5.46 Hz, 2H), 3.80 (s, 2H), 3.01 (bs, 2H), 2.90 (bs, 2H), 1.73 (bs, 4H).

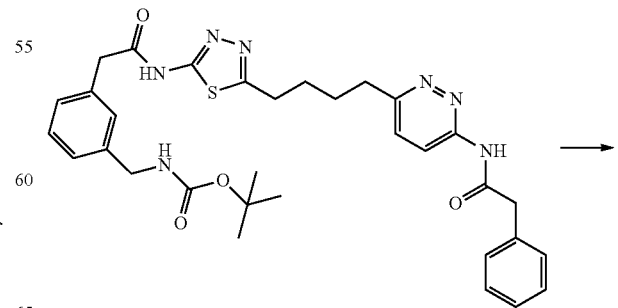

339

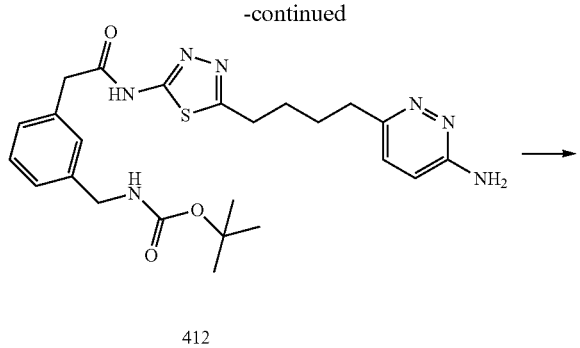

412

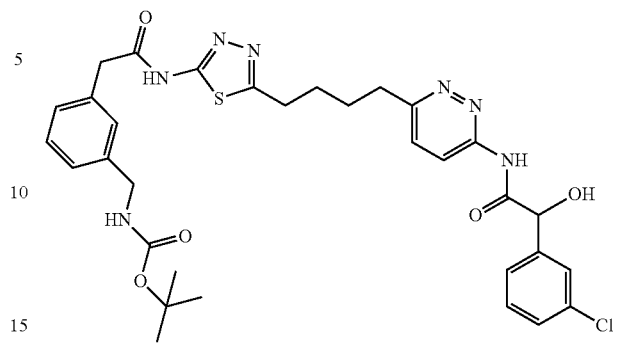

422

422: $^1$H NMR (300 MHz, DMSO-$d_6$) δ 12.65 (s, 1H), 10.74 (s, 1H), 8.18-8.15 (d, J=9.51 Hz, 1H), 7.61-7.12 (m, 9H), 6.62 (s, 1H), 5.33 (s, 1H), 4.13-4.11 (d, J=5.58 Hz, 2H), 3.78 (s, 2H), 3.01 (bs, 2H), 2.90 (bs, 2H), 1.73 (bs, 4H), 1.38 (s, 9H).

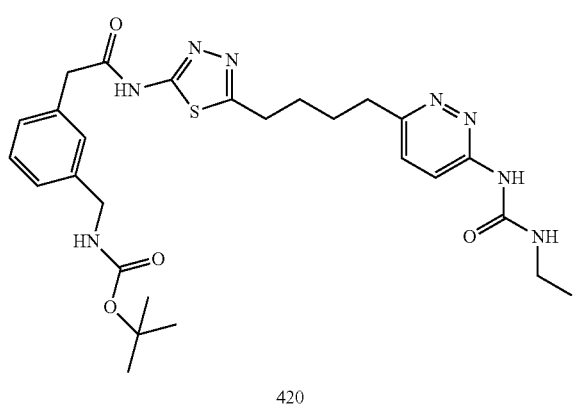

420

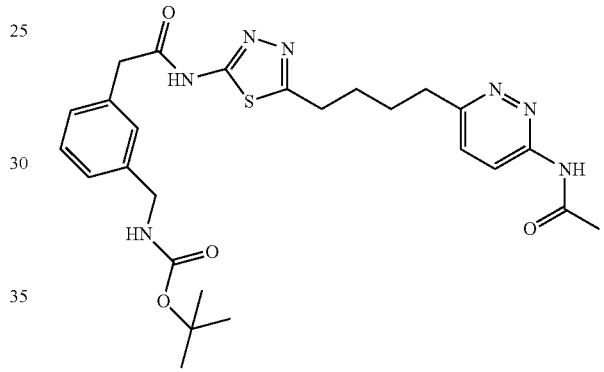

424

To a suspension of 339 (1 g, 1.62 mmol) in MeOH (10 ml) at 0° C. was added 2N NaOH (10 ml) solution. The resulting mixture was stirred at room temperature overnight. The solvent was evaporated under vacuo and the mixture was acidified with 6N HCl to pH 6 at 0° C. The mixture was triturated with EtOAc and the white precipitate was collected by suction filtration, rinsed with more EtOAc and dried to afford 412. $^1$H NMR (300 MHz, DMSO-$d_6$) δ 12.66 (s, 1H), 7.29-7.22 (m, 2H), 7.19-7.13 (m, 4H), 6.72 (d, J=8.86 Hz, 1H), 6.12 (bs, 2H), 4.12 (d, J=6.09 Hz, 2H), 3.79 (s, 2H), 3.01 (m, 2H), 2.71 (m, 2H), 1.70 (bs, 4H), 1.39 (s, 9H).

To a solution of 412 (60 mg, 0.121 mmol) in DMF (1 ml) at 0° C. was added triethylamine (34 ul, 0.242 mmol) drop wise followed by ethyl isocyanate (11 ul, 0.145 mmol) drop wise. The resulting mixture was slowly warmed up to room temperature and stirred for 6 h before it was quenched by addition of water (~5 mL) at 0° C. The white precipitate was collected by suction filtration. The crude material was purified by silica gel chromatography eluting with 0-6% MeOH in CH$_2$Cl$_2$ to afford 420. $^1$H NMR (300 MHz, DMSO-$d_6$) 12.65 (s, 1H), 11.27 (s, 1H), 9.42 (s, 1H), 8.22-8.19 (d, J=8.61 Hz, 1H), 7.77-7.13 (m, 5H), 6.56-6.53 (bs, 1H), 4.12-4.11 (d, 2H), 3.78 (s, 2H), 3.23-3.16 (m, 2H), 3.01 (bs, 2H), 2.90 (bs, 2H), 1.73 (bs, 4H), 1.38 (s, 9H), 1.10-1.07 (t, 3H).

To a solution of 412 (40 mg, 0.0804 mmol) in DMF (1 ml) at 0° C. was added triethylamine (17 ul, 0.121 mmol) drop wise followed by acetic anhydride (8 ul, 0.0844 mmol) drop wise. The resulting mixture was slowly warmed up to room temperature and stirred overnight before it was quenched by addition of water (~5 mL) at 0° C. The mixture was partitioned between water and EtOAc. The organic extract was washed with water, dried over sodium sulfate, filtered and evaporated. The crude material was purified by silica gel chromatography eluting with 0-6% MeOH in CH$_2$Cl$_2$ to afford 424. $^1$H NMR (300 MHz, DMSO-$d_6$) δ 12.65 (s, 1H), 11.01 (s, 1H), 8.23-8.20 (d, J=8.61 Hz, 1H), 7.57-7.55 (d, J=8.16 Hz, 1H), 7.38-7.12 (m, 4H), 4.13-4.11 (d, J=5.76 Hz, 2H), 3.78 (s, 2H), 3.01 (bs, 2H), 2.90 (bs, 2H), 2.14 (s, 3H), 1.75 (bs, 4H), 1.39 (s, 9H).

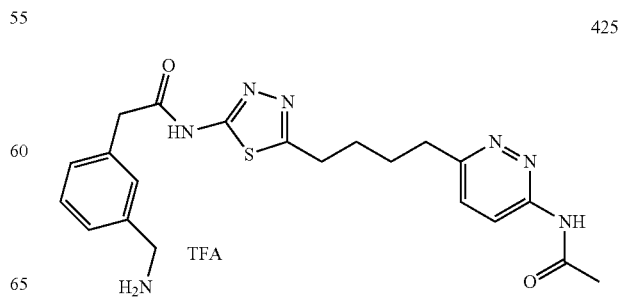

425

To a suspension of 424 (10 mg, 0.018 mmol) in dichloromethane (1 ml) was added TFA (1 ml) at 0° C. The resulting mixture was stirred at room temperature for 1 h before it was evaporated under vacuo to dryness. Ether was added and the white precipitate was collected by suction filtration, rinsed with more ether and dried to afford 425. $^1$H NMR (300 MHz, DMSO-$d_6$) δ 12.70 (s, 1H), 11.0 (s, 1H), 8.22-8.19 (d, J=8.82 Hz, 1H), 8.16-8.08 (bs, 2H), 7.58-7.54 (d, J=9.42 Hz, 1H), 7.39-7.30 (m, 4H), 4.06-4.03 (m, 2H), 3.84 (s, 2H), 3.01 (bs, 2H), 2.90 (bs, 2H), 2.14 (s, 3H), 1.75 (bs, 4H).

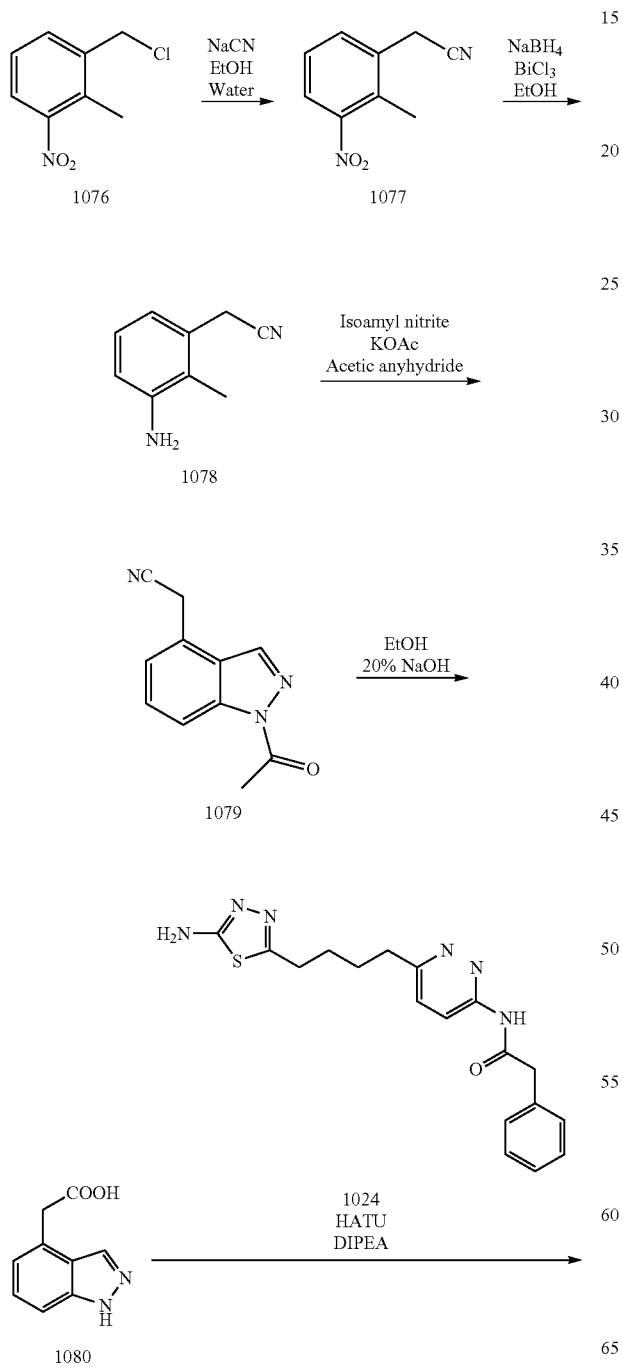

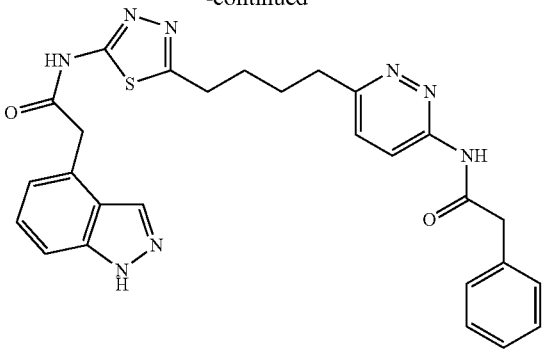

512

To a solution of 1076 (1.8 g, 10 mmol) in ethanol/water (40 mL/20 mL) was added sodium cyanide (0.98 g, 20 mmol). The resulting mixture was stirred at 90° C. for 4 hr before it was cooled to 0° C. Solid separated was filtered, washed with water and dried at high vacuum overnight to afford 1077 (1.5 g, 85% yield).

To an ice cold solution of 1077 (1 g, 5.68 mmol) in ethanol (50 mL) was added sodium borohydride (0.86 g, 22.72 mmol) followed by the addition of bismuth chloride (2 g, 6.248 mmol) portionwise. The resulting mixture was stirred at room temperature for 3 hr before it was filtered through the celite pad. Filtrate was concentrated and the residue obtained was partitioned between aq sodium bicarbonate solution and ethyl acetate. The organic extract was separated, dried over sodium sulfate, filtered and evaporated to afford 1078 (0.82 g, 100% yield). $^1$H NMR (300 MHz, Chloroform-d) δ ppm 2.17 (s, 3H) 3.69-3.71 (brs, 4H) 6.71-6.74 (d, 1H) 6.80-6.83 (d, 1H) 7.04-7.09 (m, 1H).

To a solution of 1078 (0.3 g, 2 mmol) in toluene (10 mL) was added potassium acetate (0.2 g, 2.04 mmol) and acetic anhydride (0.55 mL, 5.83 mmol). The resulting mixture was stirred at 80° C. for 1 hr followed by the addition of isoamyl nitrite (0.4 mL, 3 mmol). Stirring was continued at 80° C. overnight before it was cooled to room temperature. The solution was partitioned between water and ethyl acetate. The organic extract was washed with more water, separated, dried over sodium sulfate, filtered and evaporated. The residue obtained was purified by silica gel chromatography eluting with EtOAc/Hexane to afford 1079 (0.22 g, 54% yield). $^1$H NMR (300 MHz, Chloroform-d) δ ppm 2.85 (s, 3H) 4.09 (s, 2H) 7.39-7.41 (d, 1H) 7.58-7.63 (m, 1H) 8.28 (s, 1H) 8.48-8.51 (d, 1H)

To a solution of 1079 (0.44 g, 2.21 mmol) in ethanol (5 mL) was added 20% aqueous sodium hydroxide (5 mL). The resulting mixture was stirred at 90° overnight before it was concentrated. The residue obtained was diluted with water, acidified with acetic acid and extracted with ethyl acetate. The organic extract was separated, dried over sodium sulfate, filtered and evaporated to afford 1080 (0.1 g, 51% yield). $^1$H NMR (300 MHz, Dimethylsulfoxide-d6) δ ppm 3.89 (s, 2H) 6.98-7.0 (d, 1H) 7.27-7.32 (m, 1H) 7.43-7.46 (d, 1H) 8.10 (s, 1H) 12.3-13.2 (broad doublet, 2H)

To a suspension of carboxylic acid 1080 (60 mg, 0.34 mmol) in DMF (2 mL) was added HATU (130 mg, 0.34 mmol) and stirred till reaction mixture is clear followed by the addition of an amine 1024 (114 mg, 0.31 mmol) and DIPEA (108 uL, 0.62 mmol). The resulting mixture was stirred at room temperature for 3 hr before it was quenched by the addition of water. The solid separated was filtered, washed with water and dried. The residue obtained was purified by silica gel chromatography eluting with MeOH/dichloromethane to afford 512 (14 mg, 9% yield). ¹H NMR (300 MHz, Dimethylsulfoxide-d6) δ ppm 1.74 (brs, 4H) 2.89 (brs, 2H) 2.91 (brs, 2H) 3.78 (s, 2H) 4.13 (s, 2H) 7.05-7.08 (m, 1H) 7.27-7.57 (m, 8H) 8.19 (d, 2H) 11.26 (s, 1H) 12.76-12.80 (brs, 1H) 13.11 (s, 1H).

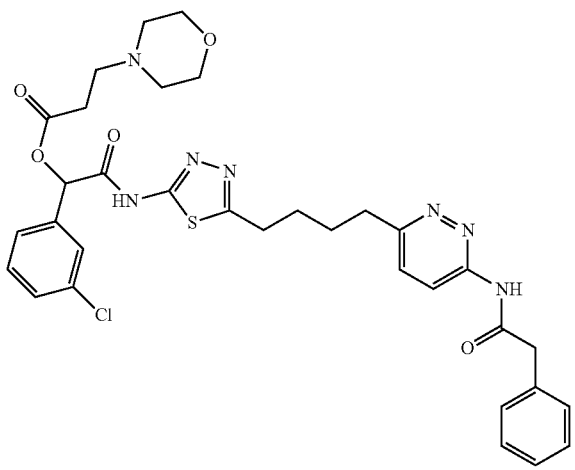

389

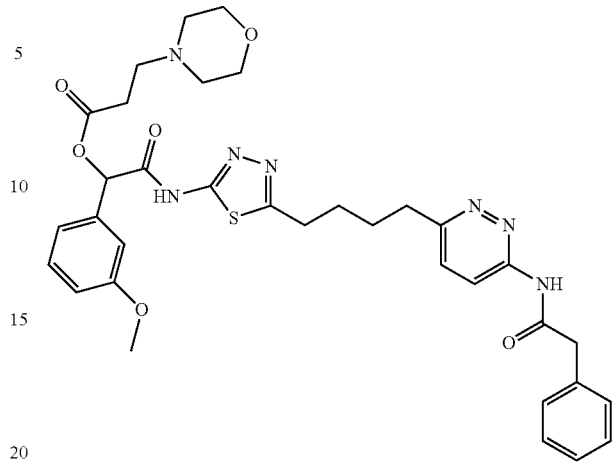

404

Compound 404 was prepared according to the procedure above for the preparation of compound 334. ¹H NMR (300 MHz, DMSO-d₆) δ 12.95 (s, 1H), 11.26 (s, 1H), 8.22-8.19 (d, J=9.60 Hz, 1H), 7.58-7.54 (d, J=9.03 Hz, 1H), 7.39-7.26 (m, 6H), 7.12 (s, 2H), 7.01-6.98 (m, 1H), 6.10 (s, 1H), 3.78 (s, 5H), 3.54 (bs, 4H), 3.01 (bs, 2H), 2.90 (bs, 2H), 2.64 (bs, 4H), 2.38 (bs, 4H), 1.74 (bs, 4H).

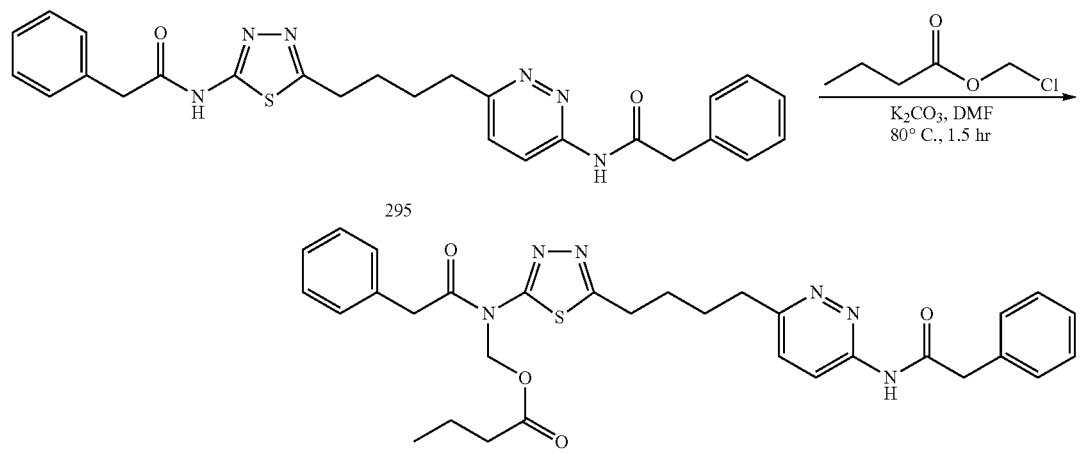

Compound 389 was prepared according to the procedure above for the preparation of compound 334. ¹H NMR (300 MHz, DMSO-d₆) δ 12.95 (s, 1H), 11.26 (s, 1H), 8.22-8.19 (d, J=8.91 Hz, 1H), 7.61-7.26 (m, 10H), 6.17 (s, 1H), 3.78 (s, 2H), 3.54 (bs, 4H), 3.01 (bs, 2H), 2.90 (bs, 2H), 2.67-2.62 (m, 4H), 2.38 (bs, 4H), 1.73 (bs, 4H).

To a flask was added K₂CO₃ (0.28 g, 2.06 mmol), compound 295 (0.5 g, 1.03 mmol) followed by 25 mL of DMF. The mixture was stirred for 15 minutes and chloromethyl butyrate (0.17 g, 1.23 mmol) was added and the reaction placed under an atmosphere of argon. The mixture was heated to 80° C. for 1.5 hours, allowed to cool to room temperature and poured into 200 ml water. The mixture was transferred to a separatory funnel, extracted with EtOAc (3×100 mL), the organic layers separated and washed with water (3×50 mL), brine (2×50 ml) and dried over Na₂SO₄. The Na₂SO₄ was removed by filtration and the volatiles removed under reduced pressure. The crude material was purified by reverse-phase chromatography giving 0.15 g of compound 402.

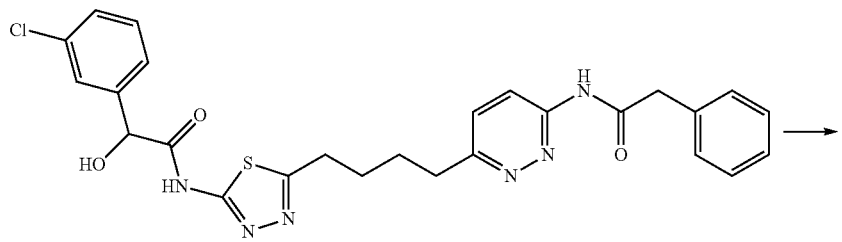

318

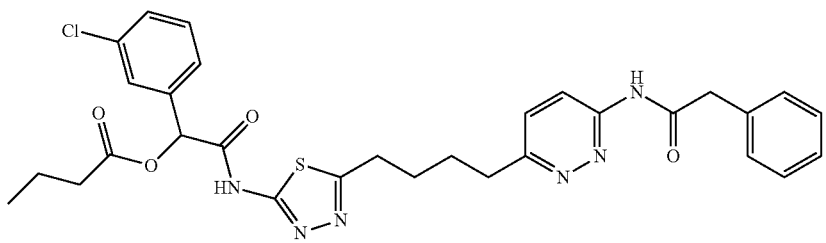

439

To a solution of 318 (100 mg, 0.19 mmol) in CH₂Cl₂ (5 mL) at 0° C. was added pyridine (300 μL) and followed by addition of a solution of butyryl chloride (43 mL, 0.41 mmol) in CH₂Cl₂ (5 mL) dropwise. The resulting mixture was stirred at 0° C. for 1 h before it was partitioned between EtOAc and H₂O. The organic layer was separated, dried (MgSO₄) and concentrated. The residue was purified by flash column chromatography over silica gel eluting with 1-10% MeOH in CH₂Cl₂ to provide the desired product 439 (117 mg). ¹H NMR (300 MHz, CDCl₃) δ 13.01 (bs, 1H), 10.12 (s, 1H), 8.49 (d, J=9.64 Hz, 1H), 7.77 (s, 1H), 7.57 (d, J=7.11 Hz, 1H), 7.40-7.30 (m, 8H), 6.57 (s, 1H), 3.97 (s, 2H), 3.09 (bs, 2H), 3.00 (bs, 2H), 2.48 (m, 2H), 1.91 (bs, 4H), 1.85-1.62 (m, 2H), 0.98 (t, J=7.07 Hz, 3H).

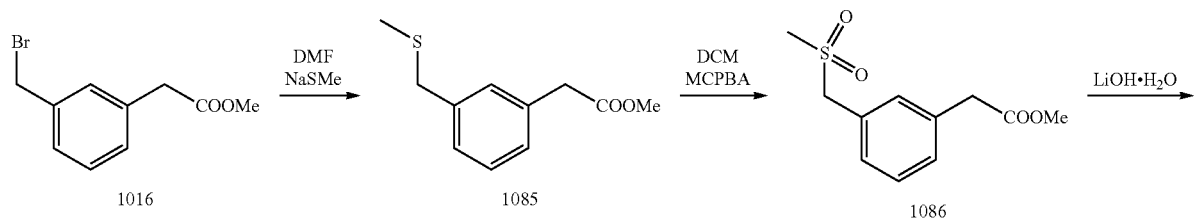

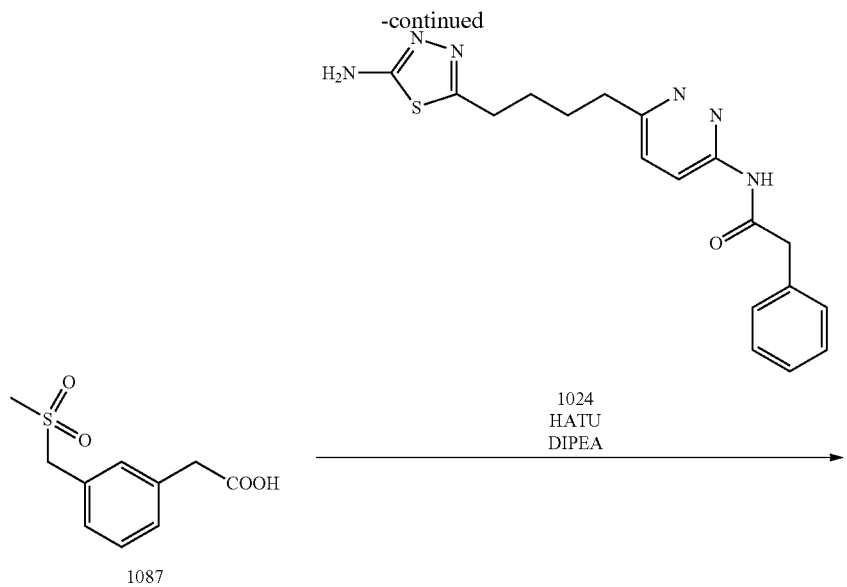

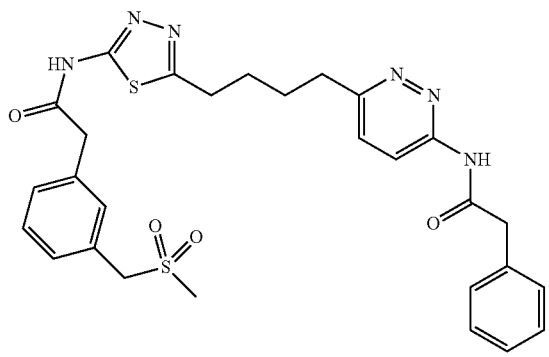

634

To a solution of sodium thiomethoxide (0.266 g, 3.8 mmol) in DMF (10 mL) was added a solution of 1016 (0.657 g, 2.7 mmol) in DMF and the resulting mixture was stirred at room temperature for overnight. The solution was partitioned between water and ethyl acetate. The organic extract was washed with more water, separated, dried over sodium sulfate, filtered and evaporated. The residue obtained was purified by silica gel chromatography eluting with EtOAc/Hexane to afford 1085 (0.41 g, 72% yield). $^1$H NMR (300 MHz, Chloroform-d) δ ppm 2.03-2.04 (s, 3H) 3.66-3.73 (m, 7H) 7.21-7.32 (m, 4H).

To a solution of 1085 (0.503 g, 2.39 mmol) in dichloromethane was added MCPBA (1.338 g, 7.78 mmol) and the resulting mixture was stirred at room temperature for 4 hr before it was diluted with aq. Sodium thiosulfate solution. Organic layer was separated, washed with saturated aq. Sodium bicarbonate solution and water, dried over sodium sulfate, filtered and concentrated. The residue obtained was purified by silica gel chromatography eluting with EtOAc/Hexane to afford 1086 (0.5 g, 86% yield). $^1$H NMR (300 MHz, Chloroform-d) δ ppm 2.8 (s, 3H) 3.7-3.74 (m, 5H) 4.27 (s, 2H) 7.30-7.4 (m, 4H).

To an ice cold solution of 1086 (0.5 g, 2.06 mmol) in dioxane (10 mL) and water (10 mL) was added lithium hydroxide monohydrate (0.26 g, 6.19 mmol) and the resulting reaction mixture was stirred at room temperature for overnight before it was concentrated. The residue obtained was diluted with water and was acidified with acetic acid. The resulting solution was partitioned between water and ethyl acetate. The organic extract was washed with more water, separated, dried over sodium sulfate, filtered and evaporated. The residue obtained was triturated with ether. The solid separated was filtered, washed with ether and dried at high vacuum overnight to afford 1087 (0.3 g, 64% yield). $^1$H NMR (300 MHz, Dimethylsulfoxide-d6) δ ppm 2.92 (s, 3H) 3.61 (s, 2H) 4.48 (s, 2H) 7.31-7.35 (m, 4H) 12.37 (s, 1H).

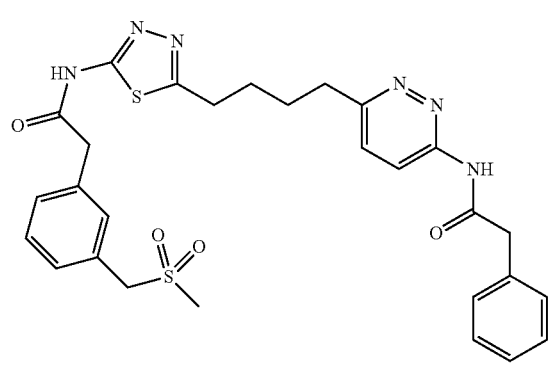
634
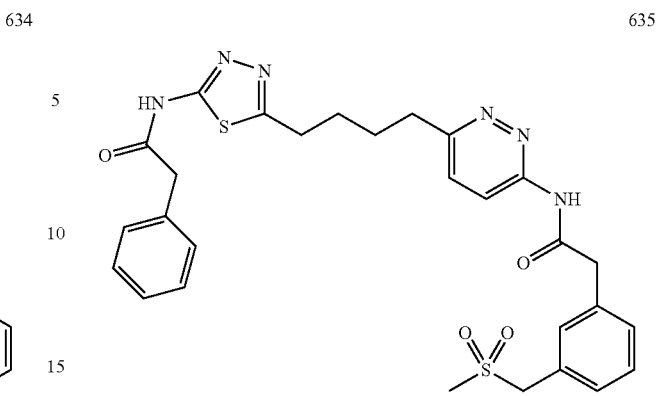
635
Compound 634 was prepared using procedures analogous to those above. ¹H NMR (300 MHz, Dimethylsulfoxide-d6) δ ppm 1.74 (brs, 4H) 2.91 (brs, 5H) 3.03 (brs, 2H) 3.78 (s, 2H) 3.85 (s, 2H) 4.49 (s, 2H) 7.32-7.40 (m, 9H) 7.55-7.58 (d, 1H) 8.19 (d, 1H) 11.26 (s, 1H) 12.69 (s, 1H).
Compound 635 was prepared using procedures analogous to those above. ¹H NMR (300 MHz, Dimethylsulfoxide-d6) δ ppm 1.75 (brs, 4H) 2.91 (brs, 5H) 3.03 (brs, 2H) 3.82 (s, 4H) 4.49 (s, 2H) 7.32-7.40 (m, 9H) 7.55-7.58 (d, 1H) 8.19 (d, 1H) 11.26 (s, 1H) 12.69 (s, 1H).
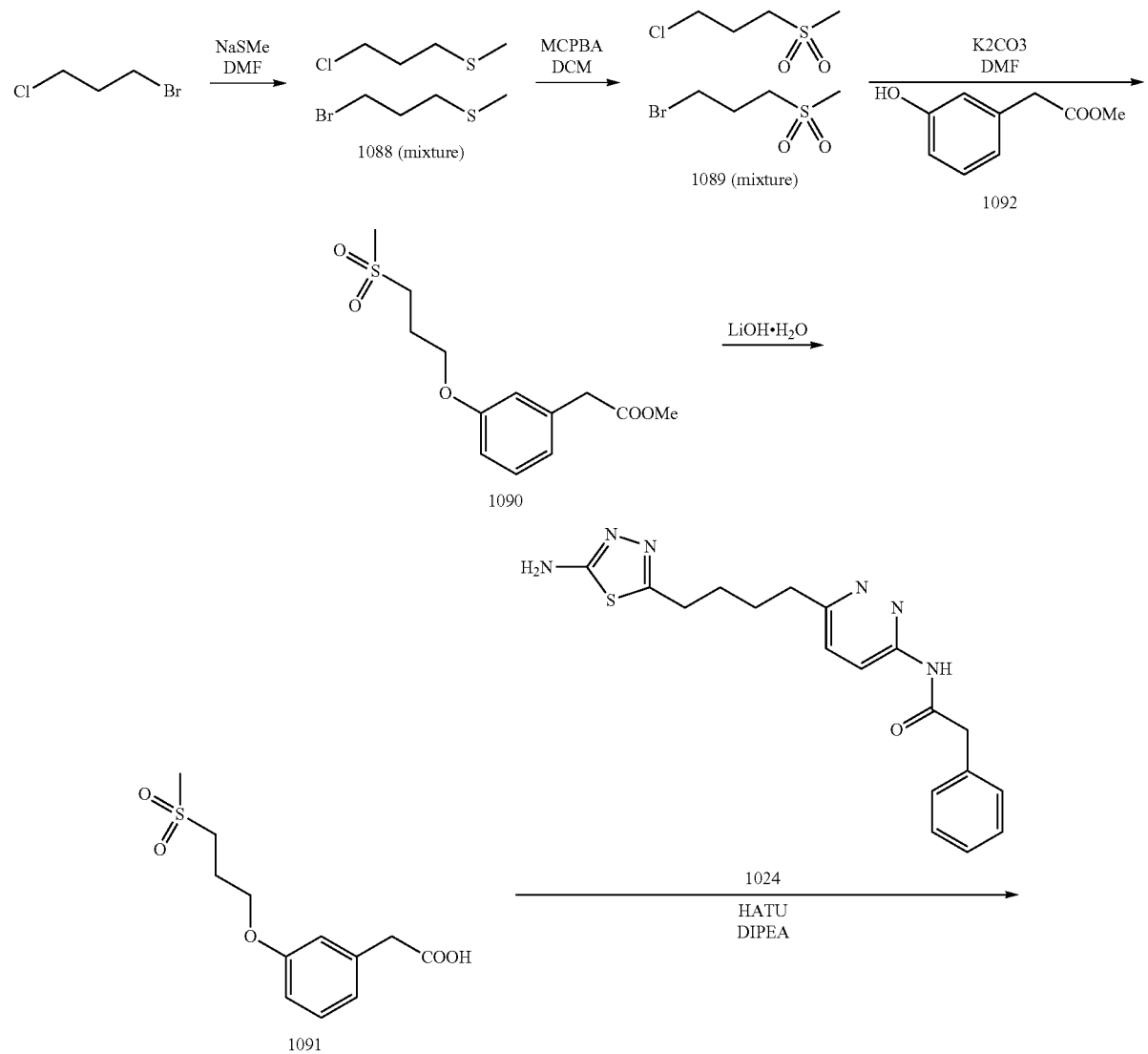

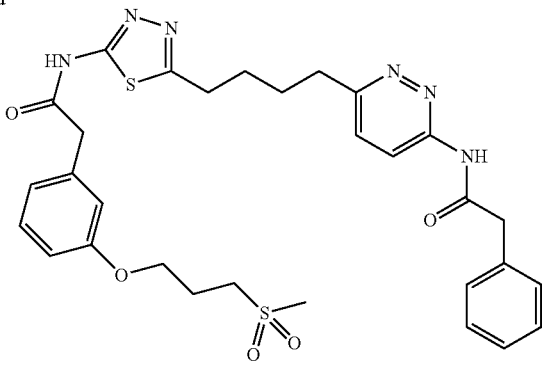

583

To a solution of 1,3-bromo chloropropane (1.57 g, 10 mmol) in DMF (10 mL) was added sodium thiomethoxide (0.63 g, 9 mmol) and the resulting reaction mixture was stirred at room temperature overnight and at 70° C. for another day. The solution was partitioned between water and ethyl acetate. The organic extract was washed with more water, separated, dried over sodium sulfate, filtered and evaporated to afford 1088 (1.3 gm) which is used for the next step without purification.

To a solution of 1088 (1.3 g, 7.7 mmol) in dichloromethane (100 mL) was added MCPBA (5.15 g, 23.34 mmol) and the resulting mixture was stirred at room temperature for overnight before it was diluted with aq. Sodium thiosulfate solution. Organic layer was separated, washed with saturated aq. Sodium bicarbonate solution and water, dried over sodium sulfate, filtered and concentrated. The residue obtained was purified by silica gel chromatography eluting with EtOAc/Hexane to afford 1089 (0.3 gm). $^1$H NMR (300 MHz, Chloroform-d) δ ppm 2.38-2.49 (m, 2H) 2.99 (s, 3H) 3.22-3.27 (m, 2H) 3.57-3.77 (m, 2H).

To a solution of 1092 (0.525 g, 3.16 mmol) in DMF (15 mL) was added potassium carbonate (0.873 g, 6.32 mmol), 1089 (0.74 g, 4.74 mmol) and sodium iodide (10 mg). The resulting mixture was stirred at 70° C. overnight before it was diluted with water (~100 mL). The resulting solution was partitioned between water and ethyl acetate.

The organic extract was washed with more water, separated, dried over sodium sulfate, filtered and evaporated. The residue obtained was purified by silica gel chromatography eluting with EtOAc/Hexane to afford 1090 (0.53 g, 59% yield). $^1$H NMR (300 MHz, Chloroform-d) δ ppm 2.35-2.40 (m, 2H) 2.99 (s, 3H) 3.26-3.31 (m, 2H) 3.63 (s, 2H) 3.73 (s, 3H) 4.16 (t, 2H) 6.81-6.93 (m, 3H) 7.25 (m, 1H).

To a solution of 1090 (0.53 g, 1.85 mmol) in dioxane (8 mL) and water (4 mL) was added lithium hydroxide monohydrate (0.156 g, 3.71 mmol) and the resulting reaction mixture was stirred at room temperature for 5 hr before it was acidified with acetic acid. The resulting solution was partitioned between water and ethyl acetate. The organic extract was washed with more water, separated, dried over sodium sulfate, filtered and evaporated. The residue obtained was triturated with ether. The solid separated was filtered, washed with ether and dried at high vacuum overnight to afford 1091 (0.2 g, 40% yield). $^1$H NMR (300 MHz, Chloroform-d) δ ppm 2.32-2.42 (m, 2H) 2.99 (s, 3H) 3.26-3.31 (m, 2H) 3.66 (s, 2H) 4.12-4.16 (t, 2H) 6.83-6.94 (m, 3H) 7.26-7.31 (m, 1H).

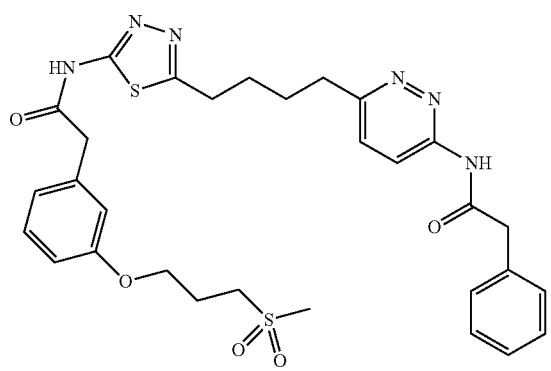

583

Compound 583 was prepared by coupling of 1091 with 1024 using procedure described for Amide Coupling General Procedure. $^1$H NMR (300 MHz, Dimethylsulfoxide-d6) δ ppm 1.74 (brs, 4H) 2.15-2.19 (m, 2H) 2.90-3.03 (m, 7H) 3.27-3.39 (m, 2H) 3.78 (s, 4H) 4.07-4.11 (t, 2H) 6.90-6.93 (m, 3H) 7.24-7.37 (m, 6H) 7.55-7.58 (d, 1H) 8.19 (d, 1H) 11.26 (s, 1H) 12.69 (s, 1H).

623

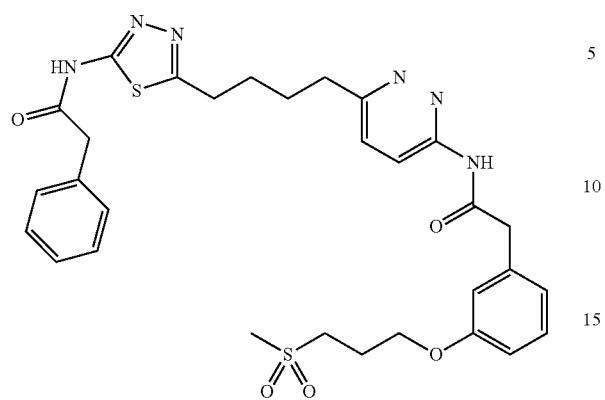

Compound 623 was prepared by coupling of 11 with 348 using procedure described for Amide Coupling General Procedure. ¹H NMR (300 MHz, Dimethylsulfoxide-d6) δ ppm 1.74 (brs, 4H) 2.15-2.19 (m, 2H) 2.90-3.03 (m, 7H) 3.27-3.39 (m, 2H) 3.75-3.78 (m, 4H) 4.07-4.11 (t, 2H) 6.90-6.97 (m, 3H) 7.26-7.34 (m, 6H) 7.58 (d, 1H) 8.19 (d, 1H) 11.26 (s, 1H) 12.69 (s, 1H).

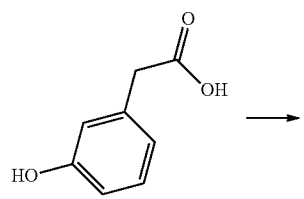

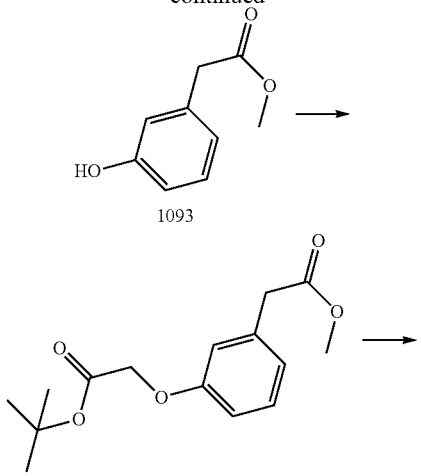

To a solution of 3-hydroxyphenylacetic acid (1 g, 0.00657 mol) in MeOH (10 ml) at 0° C. was added (Trimethylsilyl)diazomethane solution (2 M in hexanes, 20 ml) dropwise. The resulting mixture was stirred at room temperature for 30 minutes before it was evaporated to dryness. The crude material was purified by silica gel chromatography eluting with 0-25% EtOAc in Hexanes to afford 1093.

1094 was made using procedure described for compound 1119.

1095 was made using procedure described for compound 1102.

646

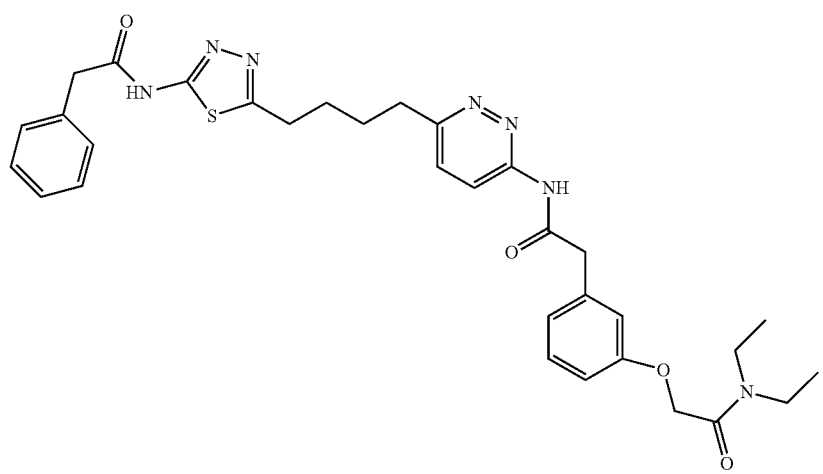

646 was made using procedure described for compound 666. ¹H NMR (300 MHz, CDCl₃) δ 10.32 (s, 1H), 8.50-8.47 (d, J=8.52 Hz, 1H), 7.90-7.70 (m, 1H), 7.40-7.36 (m, 6H), 7.03-6.86 (m, 3H), 4.72 (s, 2H), 4.02 (s, 2H), 3.90 (s, 2H), 3.44-3.39 (m, 4H), 3.09-2.96 (d, 4H), 1.87 (bs, 4H), 1.24-1.16 (m, 6H).

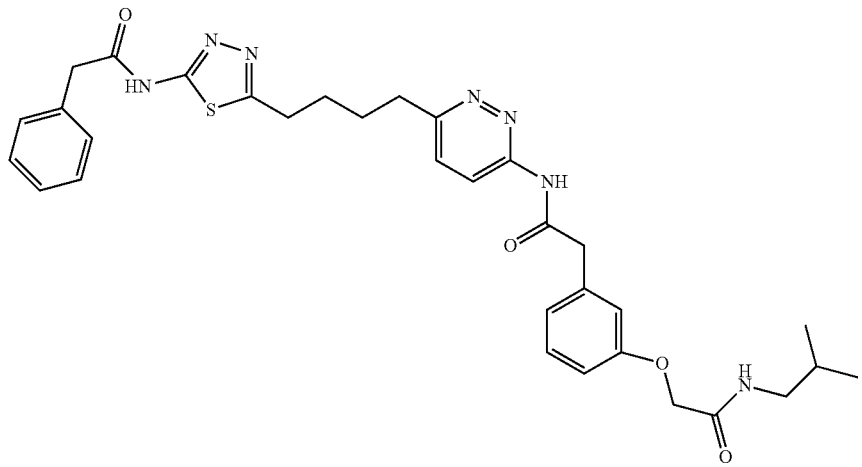

647

647 was made using procedure described for compound 666. ¹H NMR (300 MHz, DMSO-d₆) δ 12.61 (s, 1H), 11.22 (s, 1H), 8.22-8.19 (d, J=9.18 Hz, 1H), 8.02-8.10 (t, 1H), 7.58-7.55 (d, J=9.12 Hz, 1H), 7.36-7.24 (m, 5H), 6.99-6.84 (m, 3H), 4.48 (s, 2H), 3.82 (s, 2H), 3.75 (s, 2H), 3.50 (s, 2H), 3.01-2.90 (m, 5H), 1.73 (bs, 4H), 0.82-0.80 (d, J=6.69 Hz, 6H).

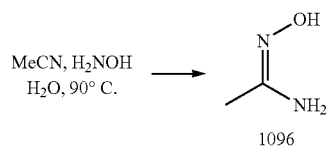

1096

A solution of hydroxylamine (50% in water, 7.4 mL) was added to acetonitrile (60 mL) and the mixture heated to 90° C. for 16 hours. The mixture was cooled to room temperature then cooled in a wet-ice bath giving a precipitate. The solids were collected by filtration and rinsed with cold acetonitrile (10 mL) and dried under high vacuum giving 4.47 g of N'-hydroxyacetimidamide 1096. See Zemolka, S. et al PCT Int Appl 2009118174. ¹H NMR 300 MHz CDCl₃: δ 4.57 (br s, 2H), 1.89 (s, 3H).

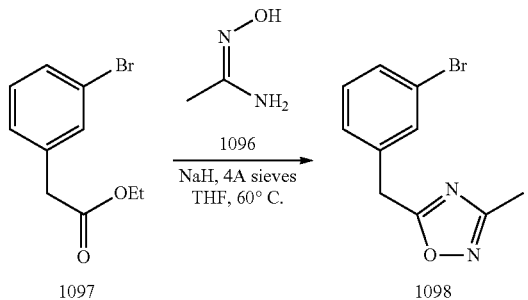

A flask was charged with N'-hydroxyacetimidamide 1096 (0.45 g, 6.17 mmol) followed by THF (25 mL), NaH (60% in oil, 0.246 g, 6.17 mmol), 4 A molecular sieves (4.5 g) and the mixture heated to 60° C. under an atmosphere of argon for 1 hour. A solution of ethyl 2-(3-bromophenyl)acetate 1097 (1.5 g, 6.17 mmol) in THF (12.5 mL) was added to the N'-hydroxyacetimidamide mixture and heated at 60° C. for 16 hours. The mixture was diluted with water (100 mL) and extracted with EtOAc (2×25 mL). The organic layers were combined, washed with water (25 mL), brine (2×25 mL) and dried over Na₂SO₄. The Na₂SO₄ was removed by filtration and the volatiles removed under reduced pressure. The crude material was purified by normal phase chromatography 0-30% EtOAc/hexanes giving 0.56 g of 5-(3-bromobenzyl)-3-methyl-1,2,4-oxadiazole 1098. ¹H NMR 300 MHz CDCl₃: δ 7.48-7.42 (m, 2H), 7.26-7.24 (m, 2H), 4.15 (s, 2H), 2.38 (s, 3H).

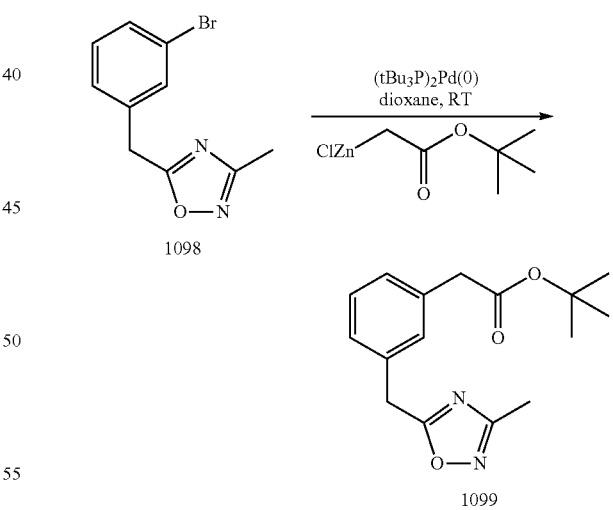

To a solution of 5-(3-bromobenzyl)-3-methyl-1,2,4-oxadiazole 1098 (0.50 g, 1.97 mmol) in dioxane (1 mL), under an atmosphere of Argon, was added Bis(tri-t-butylphosphine)palladium(0) (0.15 g, 0.295 mmol) followed by the addition of 2-tert-butoxy-2-oxoethylzinc chloride (0.5 M in diethyl ether, 4.92 mmol, 9.84 mL). The mixture was allowed to stir under argon for 20 hours and the volatiles were removed under reduced pressure. The residue was taken up in EtOAc (10 mL) and washed with water (2×5 mL), brine (2×5 mL) and dried over Na$_2$SO$_4$. The Na$_2$SO$_4$ was removed by filtration and the volatiles removed under reduced pressure. The crude material was purified by normal phase chromatography 0-50% EtOAc/Hexanes to give 0.300 g tert-butyl 2-(3-((3-methyl-1,2,4-oxadiazol-5-yl)methyl)phenyl)acetate 1099. $^1$H NMR 300 MHz CDCl$_3$: δ 7.40-7.18 (m, 4H), 4.17 (s, 2H), 3.51 (s, 2H), 2.36 (s, 3H), 1.43 (s, 9H).

The mixture was extracted with EtOAc (3×2 mL) and the organic layers combined, washed with brine and dried over Na$_2$SO$_4$. The Na$_2$SO$_4$ was removed by filtration and the volatiles removed under reduced pressure to give 0.041 g of 2-(3-((3-methyl-1,2,4-oxadiazol-5-yl)methyl)phenyl)acetic acid 1100. $^1$H NMR 300 MHz CDCl$_3$: δ 7.40-7.18 (m, 4H), 4.18 (s, 2H), 3.63 (s, 2H), 2.36 (s, 3H).

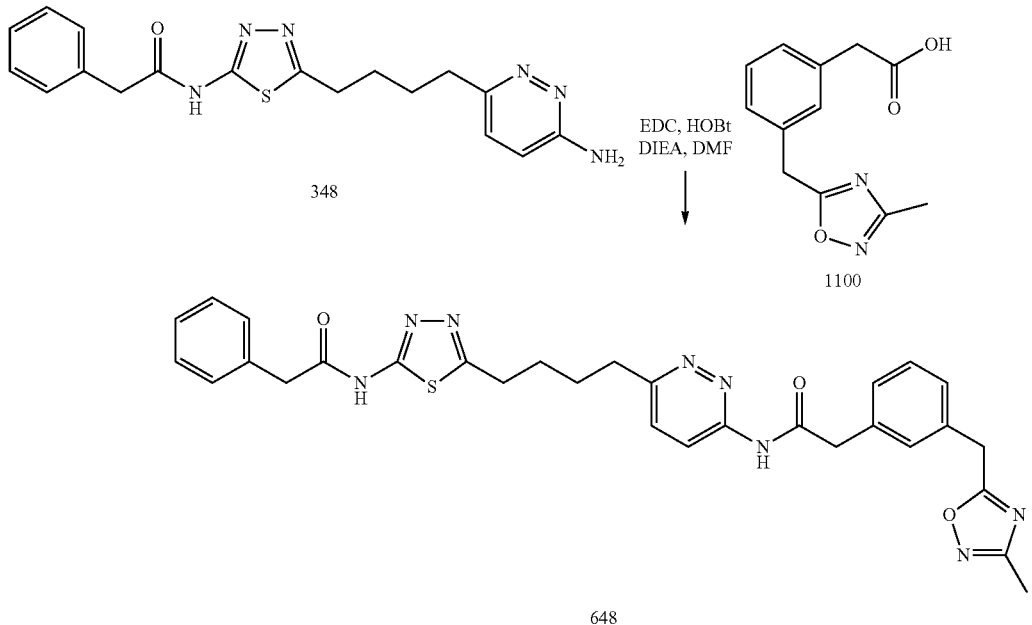

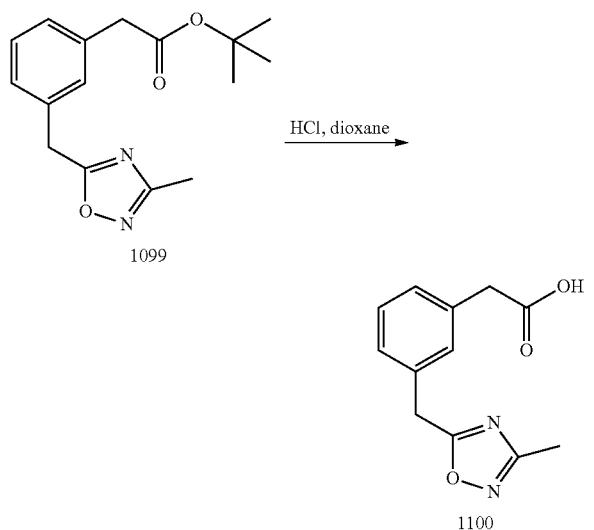

To a mixture of tert-butyl 2-(3-((3-methyl-1,2,4-oxadiazol-5-yl)methyl)phenyl)acetate 1099 (0.127 g, 0.44 mmol) in dioxane (3 mL) was added 4N HCl in dioxane (1 mL) and stirred under an atmosphere of argon for 2 hours. The volatiles were removed under reduced pressure and the residue diluted with water (5 mL) and the pH adjusted to 12 with 2.5 N NaOH. The mixture was washed with dichloromethane (4×2 mL) and the pH adjusted to 6 with 1 N HCl.

To a solution of N-(5-(4-(6-aminopyridazin-3-yl)butyl)-1,3,4-thiadiazol-2-yl)-2-phenylacetamide 348 (0.061 g, 0.0165 mmol), 2-(3-((3-methyl-1,2,4-oxadiazol-5-yl)methyl)phenyl)acetic acid 1100 (0.040 g, 0.18 mmol), 1-ethyl-3-(3-dimethylaminopropyl) carbodiimide (0.078 g, 0.41 mmol), 1-hydroxybenzotriazole (0.055 g, 0.41 mmol) in DMF (3 mL) was added DIEA (0.085 g, 0.115 mL, 0.66 mmol) and the mixture stirred for 16 hours. The mixture was diluted with water (20 mL) and extracted with EtOAc (3×20 mL). The organic layers were combined, washed with water (3×20 mL), brine (2×20 mL) and dried over Na$_2$SO$_4$. The Na$_2$SO$_4$ was removed by filtration and the volatiles removed under reduced pressure. The crude material was purified by normal phase chromatography 0-5% MeOH/dichloromethane giving 0.003 g of 2-(3-((3-methyl-1,2,4-oxadiazol-5-yl)methyl)phenyl)-N-(6-(4-(5-(2-phenylacetamido)-1,3,4-thiadiazol-2-yl)butyl)pyridazin-3-yl)acetamide 648. $^1$H NMR 300 MHz CDCl$_3$: δ 12.59 (s, 1H), 10.53 (s, 1H), 8.45 (d, 1H, J=12.2 Hz), 7.4-7.1 (m, 10H), 4.15 (s, 2H), 4.03 (s, 2H), 3.94 (s, 2H), 3.02 (m, 2H), 2.94 (m, 2H), 2.33 (s, 3H), 1.85 (m, 4H).

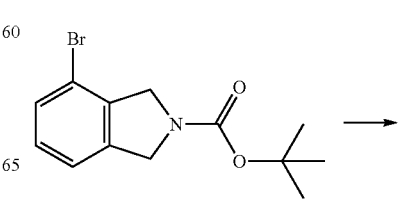

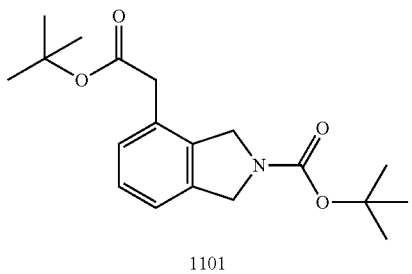

1101

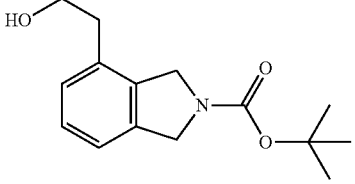

1102

1101 was made using procedure described for compound 1119.

To a solution of 1101 (470 mg, 1.41 mmol) in MeOH (5 ml) and $H_2O$ (5 ml) at 0° C. was added lithium hydroxide monohydrate (296 mg, 7.05 mmol). The resulting mixture was stirred at room temperature for 3 days before it was evaporated to dryness. The mixture was then acidified with 1N HCl (pH 4), and it was partitioned between water and EtOAc. The organic extract was washed with water, dried over sodium sulfate, filtered and evaporated to afford 1102.

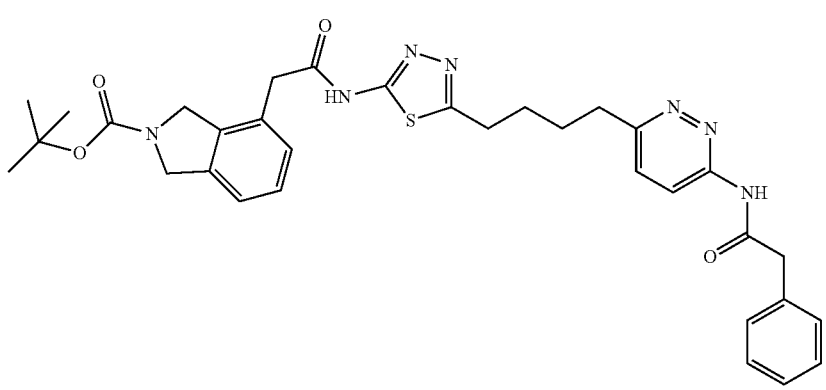

608

608 was made using procedure described for compound 664. $^1$H NMR (300 MHz, DMSO-$d_6$) δ 12.71 (s, 1H), 11.32 (s, 1H), 8.22-8.19 (d, J=9.15 Hz, 1H), 7.58-7.54 (d, J=9.27 Hz, 1H), 7.38-7.28 (m, 8H), 4.63 (bs, 4H), 3.82 (s, 2H), 3.78 (s, 2H), 3.01 (bs, 2H), 2.90 (bs, 2H), 1.73 (bs, 4H), 1.48-1.44 (d, J=5.93 Hz, 9H).

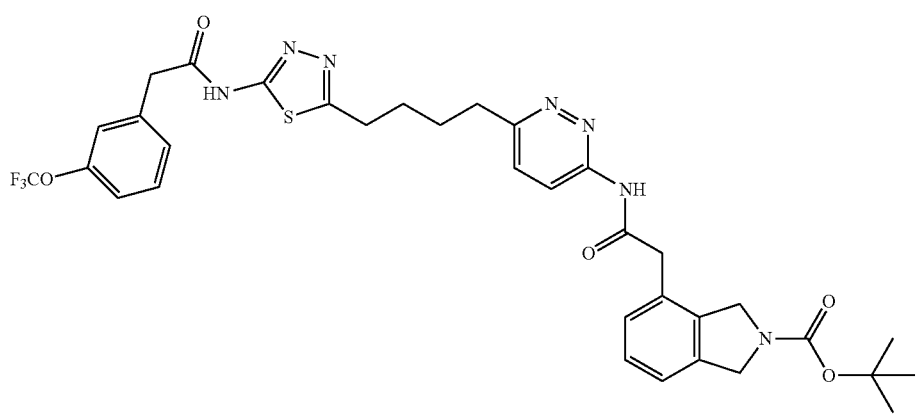

612

612 was made using procedure described for compound 666. ¹H NMR (300 MHz, DMSO-d₆) δ 11.32 (s, 1H), 8.22-8.19 (d, J=9.78 Hz, 1H), 7.58-7.54 (d, J=9.72 Hz, 1H), 7.48-7.28 (m, 7H), 4.67-4.61 (m, 4H), 3.88 (s, 2H), 3.80 (s, 2H), 3.01 (bs, 2H), 2.90 (bs, 2H), 1.73 (bs, 4H), 1.48-1.44 (d, J=9.93 Hz, 9H).

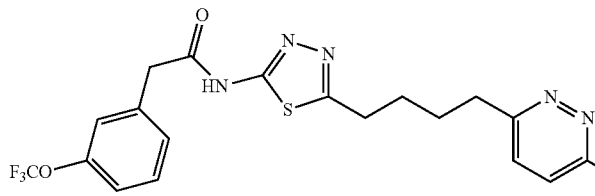

649

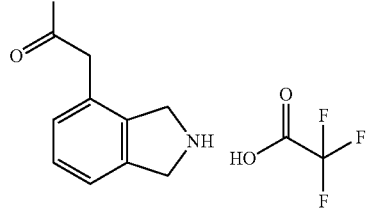

649 was made using procedure described for compound 695. ¹H NMR (300 MHz, DMSO-d₆) δ 11.36 (s, 1H), 8.20-8.17 (d, J=9.78 Hz, 1H), 7.60-7.57 (d, J=8.92 Hz, 1H), 7.52-7.32 (m, 7H), 4.61-4.56 (d, J=16.99 Hz, 4H), 3.91 (s, 2H), 3.87 (s, 2H), 3.01 (bs, 2H), 2.90 (bs, 2H), 1.73 (bs, 4H).

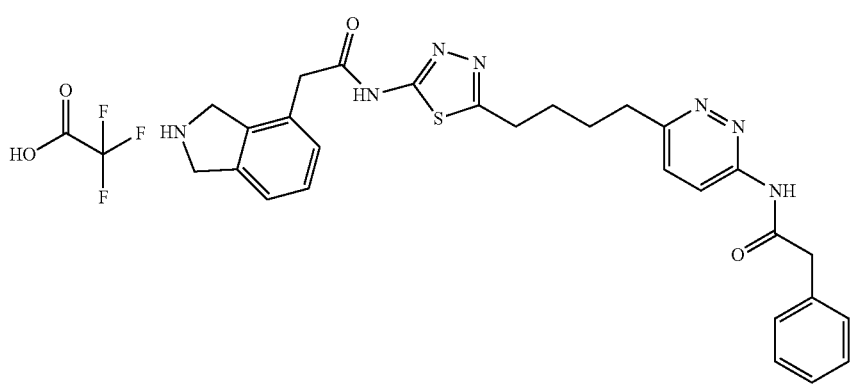

650

650 was made using procedure described for compound 695. ¹H NMR (300 MHz, DMSO-d₆) δ 12.71 (s, 1H), 11.32 (s, 1H), 9.40 (bs, 1H), 8.22-8.19 (d, J=9.09 Hz, 1H), 7.58-7.54 (d, J=9.36 Hz, 1H), 7.38-7.28 (m, 8H), 4.63 (bs, 4H), 3.82 (s, 2H), 3.78 (s, 2H), 3.01 (bs, 2H), 2.90 (bs, 2H), 1.73 (bs, 4H).

651

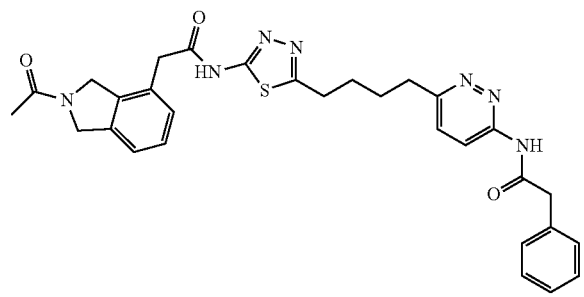

To a solution of 650 (30 mg, 0.0468 mmol) in DMF (1 ml) at 0° C. was added triethylamine (13 ul, 0.0936 mmol) dropwise followed by acetic anhydride (4.64 ul, 0.0491 mmol) dropwise. The resulting mixture was stirred at 0° C. for 20 minutes before it was quenched by addition of ice water (~5 mL). The white precipitate was collected by suction filtration, rinsed with more water. The crude material was purified by silica gel chromatography eluting with 0-6% MeOH in CH₂Cl₂ to afford 651. ¹H NMR (300 MHz, DMSO-d₆) δ 12.71 (s, 1H), 11.32 (s, 1H), 8.22-8.19 (d, J=9.27 Hz, 1H), 7.58-7.54 (d, J=9.00 Hz, 1H), 7.38-7.28 (m, 8H), 4.88 (bs, 2H), 4.67 (bs, 2H), 3.82 (s, 2H), 3.78 (s, 2H), 3.01 (bs, 2H), 2.90 (bs, 2H), 2.11 (s, 3H), 1.73 (bs, 4H).

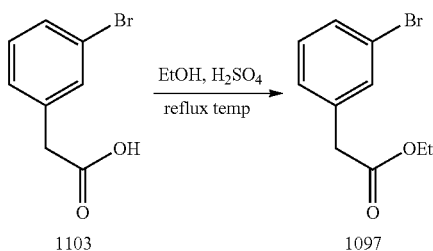 [SMILES: O=C(O)Cc1cccc(Br)c1 ; CCOC(=O)Cc1cccc(Br)c1]

1103      1097

To a solution of 2-(3-bromophenyl)acetic acid 1103 (10.0 g, 46.5 mmol) in 100 mL EtOH was added conc. H₂SO₄ (10 drops) and the mixture heated to relux temperature for 3 hours. The mixture was allowed to cool to room temperature and the volatiles were removed under reduced pressure. The residue was taken up in EtOAc (100 mL) and washed with water (2×50 mL), saturated NaHCO₃ (1×25 mL), brine (2×25 mL) and dried over Na$_2$SO$_4$. The Na$_2$SO$_4$ was removed by filtration and the volatiles removed under reduced pressure to give ethyl 2-(3-bromophenyl)acetate 1097 (11.1 grams) as a liquid). $^1$H NMR 300 MHz CDCl$_3$: δ 7.41 (m, 2H), 7.20 (m, 2H), 4.14 (q, 2H, J=9.5 Hz), 3.57 (s, 2H), 1.25 (t, 3H, J=9.5 Hz).

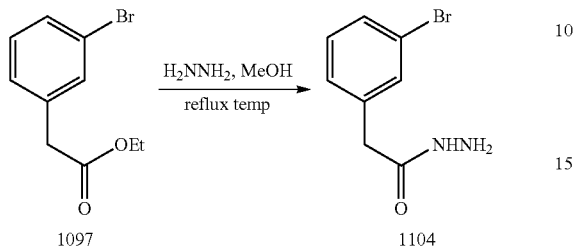

To a solution of ethyl 2-(3-bromophenyl)acetate 1097 (1.5 g, 6.17 mmol) in MeOH (20 mL) was added hydrazine (0.79 g, 24.7 mmol) and the mixture heated to reflux temperature for 4 hours. The mixture was allowed to cool to room temperature giving rise to a white precipitate which was collected by filtration and rinsed with MeOH (10 mL). After drying under reduced pressure 1.4 grams of 2-(3-bromophenyl)acetohydrazide 1104 was isolated. $^1$H NMR 300 MHz CDCl$_3$: δ 7.42 (s, 2H), 7.20 (s, 2H), 6.73 (br s, 1H), 3.51 (s, 2H), 1.81 (br s, 2H).

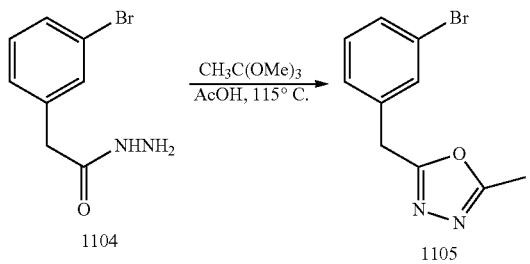

To a solution of 2-(3-bromophenyl)acetohydrazide 1104 (1.0 g, 4.37 mmol) in AcOH (10 mL) was added trimethylorthoacetate (2.62 g, 21.83 mmol) and the mixture heated to 115° C. for 18 hours. The volatiles were removed under reduced pressure and the residue purified by reverse phase chromatography to give 0.59 g of 2-(3-bromobenzyl)-5-methyl-1,3,4-oxadiazole 1105. $^1$H NMR 300 MHz CDCl$_3$: δ 7.45 (m, 2H), 7.23 (m, 2H), 4.12 (s, 2H), 2.49 (s, 3H).

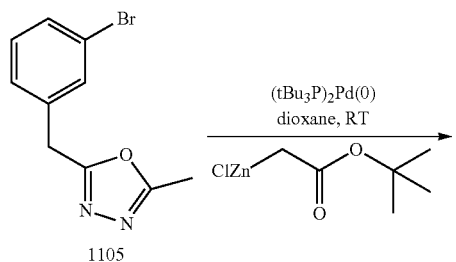

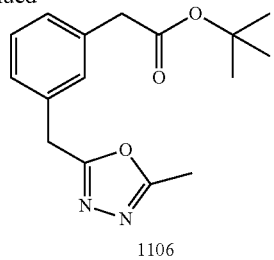

To a solution of 2-(3-bromobenzyl)-5-methyl-1,3,4-oxadiazole 1105 (0.50 g, 1.97 mmol) in dioxane (1 mL), under an atmosphere of Argon, was added Bis(tri-t-butylphosphine)palladium(0) (0.15 g, 0.295 mmol) followed by the addition of 2-tert-butoxy-2-oxoethylzinc chloride (0.5 M in diethyl ether, 4.92 mmol, 9.84 mL). The mixture was allowed to stir under Argon for 20 hours and the volatiles were removed under reduced pressure. The residue was taken up in EtOAc (10 mL) and washed with water (2×5 mL), brine (2×5 mL) and dried over Na$_2$SO$_4$. The Na$_2$SO$_4$ was removed by filtration and the volatiles removed under reduced pressure. The crude material was purified by normal phase chromatography 0-50% EtOAc/Hexanes to give 0.338 g of tert-butyl 2-(3-((5-methyl-1,3,4-oxadiazol-2-yl)methyl)phenyl)acetate 1106. $^1$H NMR 300 MHz CDCl$_3$: δ 7.24 (m, 4H), 4.12 (s, 2H), 3.51 (s, 2H), 2.46 (s, 3H), 1.43 (s, 9H).

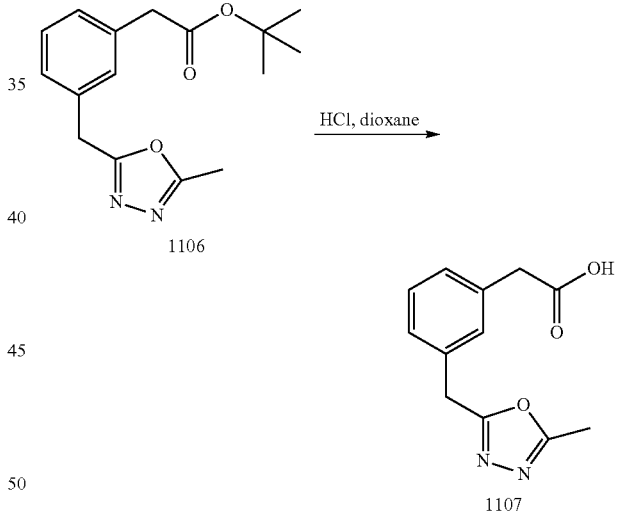

To a mixture of tert-butyl 2-(3-((5-methyl-1,3,4-oxadiazol-2-yl)methyl)phenyl)acetate 1106 (0.127 g, 0.44 mmol) in dioxane (3 mL) was added 4N HCl in dioxane (1 mL) and stirred under an atmosphere of Argon for 2 hours. The volatiles were removed under reduced pressure and the residue diluted with water (5 mL) and the pH adjusted to 12 with 2.5 N NaOH. The mixture was washed with dichloromethane (4×2 mL) and the pH adjusted to 6 with 1 N HCl. The mixture was extracted with EtOAc (3×2 mL) and the organic layers combined, washed with brine and dried over Na$_2$SO$_4$. The Na$_2$SO$_4$ was removed by filtration and the volatiles removed under reduced pressure to give 0.023 g of 2-(3-((5-methyl-1,3,4-oxadiazol-2-yl)methyl)phenyl)acetic acid 1107.

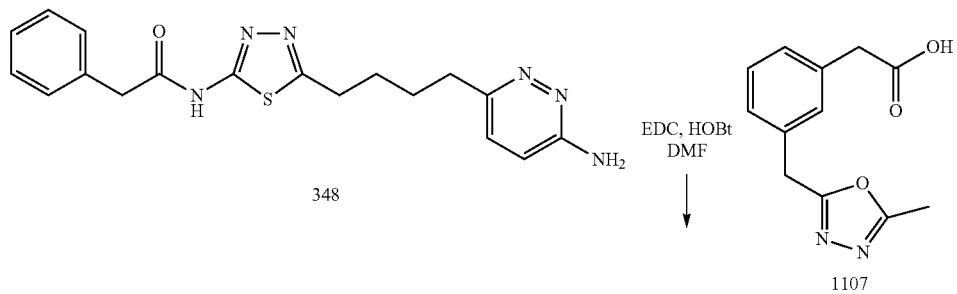

348

1107

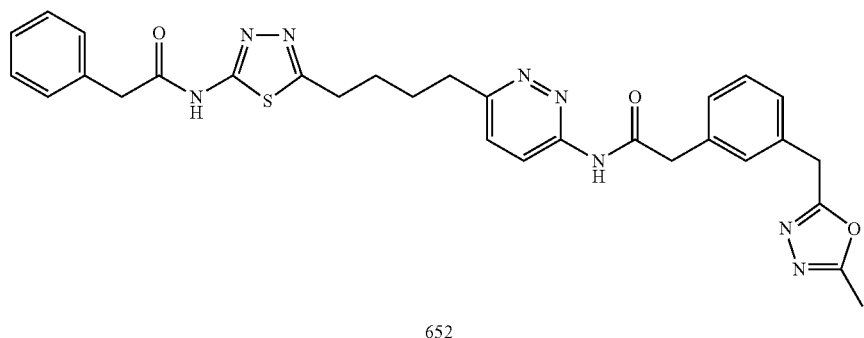

652

A solution of N-(5-(4-(6-aminopyridazin-3-yl)butyl)-1,3,4-thiadiazol-2-yl)-2-phenylacetamide 348 (0.035 g, 0.094 mmol), 2-(3-((5-methyl-1,3,4-oxadiazol-2-yl)methyl)phenyl)acetic acid 1107 (0.023 g, 0.094 mmol), 1-ethyl-3-(3-dimethylaminopropyl) carbodiimide (0.045 g, 0.235 mmol), 1-hydroxybenzotriazole (0.032 g, 0.235 mmol) in DMF (1.75 mL) was stirred for 16 hours and diluted with water (20 mL). The mixture was extracted with EtOAc (3×20 mL) the organic layers combined, washed with water (3×20 mL), brine (2×20 mL) and dried over Na$_2$SO$_4$. The Na$_2$SO$_4$ was removed by filtration and the volatiles removed under reduced pressure. The crude material was purified by reverse phase chromatography giving 0.004 g of 2-(3-((5-methyl-1,3,4-oxadiazol-2-yl)methyl)phenyl)-N-(6-(4-(5-(2-phenylacetamido)-1,3,4-thiadiazol-2-yl)butyl)pyridazin-3-yl)acetamide 652. $^1$H NMR 300 MHz DMSO-d6: δ 12.62 (s, 1H), 11.24 (s, 1H), 8.16 (d, 1H, J=12.2 Hz), 7.54 (d, 1H, J=12.2 Hz), 7.3-7.1 (m, 9H), 4.20 (s, 2H), 3.78 (s, 2H), 3.74 (s, 2H), 2.99 (m, 2H), 2.87 (m, 2H), 2.41 (s, 3H), 1.72 (m, 4H).

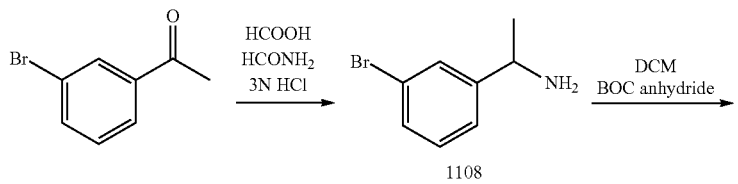

1108

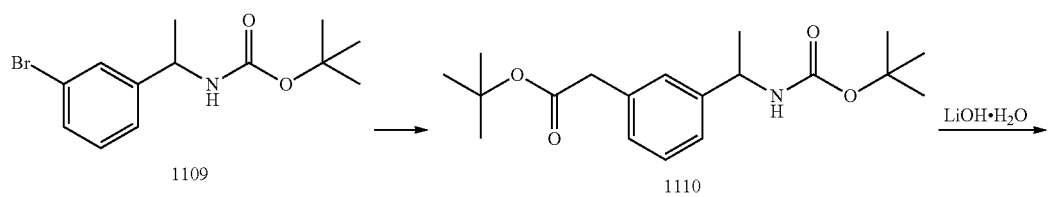

1109

1110

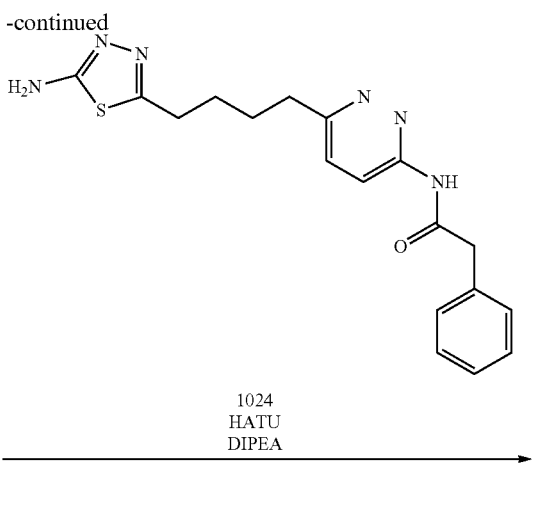

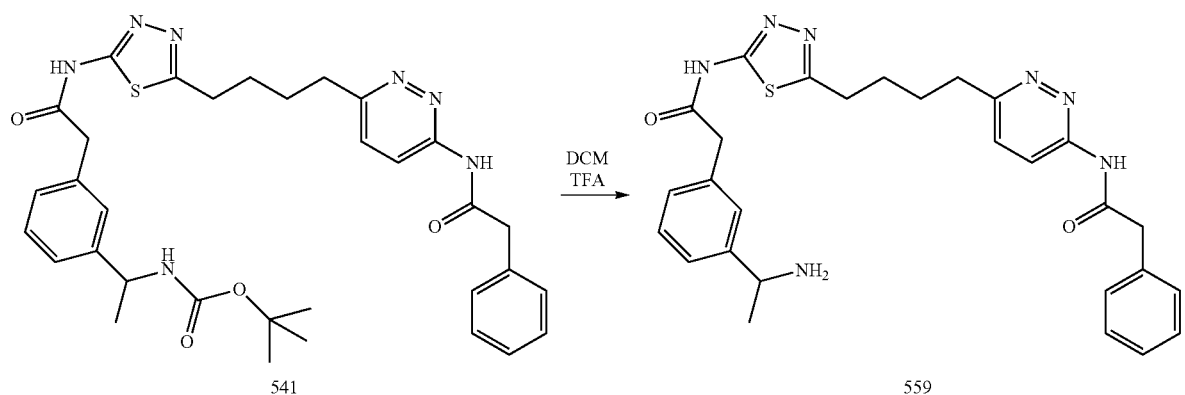

A mixture of 3-bromoacetophenone (5 g, 25.1 mmol) in formic acid (6 gm) and formamide (25 mL) was heated to 170° C. for overnight before it was extracted with toluene. Organic layer was separated and concentrated. The residue obtained was diluted with 3N HCl and the resulting mixture was refluxed overnight before it was cooled to room temperature. The solution was extracted with ether. Aqueous layer was separated, basified with aq. Sodium hydroxide solution and extracted with ether. Organic layer was separated, dried over sodium sulfate, filtered and concentrated to afford 1108 (3 g, 60% yield). $^1$H NMR (300 MHz, Chloroform-d) δ ppm 1.22-1.25 (d, 3H) 3.97-3.99 (q, 1H) 7.23-7.4 (m, 3H) 7.6 (s, 1H).

To a solution of 1108 (2.945 g, 14.7 mmol) in dichloromethane (100 mL) was added boc anhydride (3.21 g, 14.7 mmol) and the reaction mixture was stirred at room temperature overnight before it was concentrated and purified by silica gel chromatography eluting with EtOAc/Hexane to afford 1109 (3 g, 68% yield). $^1$H NMR (300 MHz, Dimethylsulfoxide-d6) δ ppm 1.29-1.31 (d, 3H) 1.38 (s, 9H) 4.61-4.63 (q, 1H) 7.3 (brs, 2H) 7.41-7.5 (m, 3H).

To a degassed solution of 1109 (0.5 g, 1.66 mmol) and bis(tri-tert-butylphosphine)palladium(0) (0.085 g, 0.166 mmol) in dioxane (3 mL) was added 2-tert-Butoxy-2-oxo-ethylzinc chloride (8.5 mL, 4.15 mmol) under Argon and the resulting reaction mixture was stirred at room temperature for 4 hr before it was quenched with saturated aqueous ammonium chloride solution. The resulting solution was partitioned between water and ethyl acetate. The organic extract was washed with more water, separated, dried over sodium sulfate, filtered and evaporated. The residue obtained was purified by silica gel chromatography eluting with EtOAc/Hexane to afford 1110 (0.35 g, 62% yield). $^1$H NMR (300 MHz, Dimethylsulfoxide-d6) δ ppm 1.29-1.31 (d, 3H) 1.388-1.42 (brs, 18H) 3.53 (s, 2H) 4.59-4.63 (q, 1H) 7.09 (brs, 1H) 7.12-7.20 (brs, 2H) 7.25-7.27 (m, 1H) 7.27-7.30 (m, 1H).

To a solution of 1110 (0.44 g, 1.3 mmol) in methanol (40 mL) and water (10 mL) was added lithium hydroxide monohydrate (0.4 gm) and the resulting reaction mixture was stirred at room temperature for 2 days before it was concentrated. The residue obtained was diluted with ice cold water and acidified with acetic acid. The resulting solution was partitioned between water and ethyl acetate. The organic extract was washed with more water, separated, dried over sodium sulfate, filtered and evaporated. The residue obtained was purified by silica gel chromatography eluting with EtOAc/Hexane to afford 1111 (0.316 g, 86% yield). $^1$H NMR (300 MHz, Dimethylsulfoxide-d6) δ ppm 1.22-1.39 (m, 12H) 3.55 (s, 2H) 4.58-4.63 (q, 1H) 7.11-7.38 (m, 5H) 12.29 (s, 1H).

541

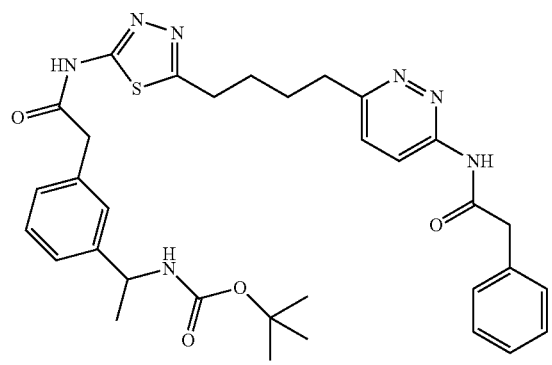

$^1$H NMR (300 MHz, Dimethylsulfoxide-d6) δ ppm 1.43 (m, 12H) 1.89 (brs, 4H) 2.97-3.08 (m, 4H) 3.95-4.03 (m, 4H) 4.71-4.77 (q, 1H) 7.24-7.43 (m, 11H) 8.45-8.48 (d, 1H) 10.99 (s, 1H) 12.4 (brs, 1H).

543

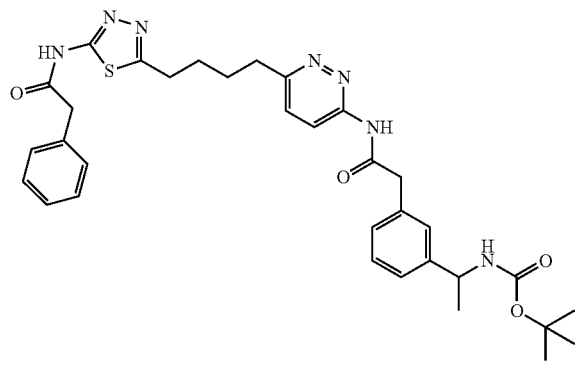

$^1$H NMR (300 MHz, Dimethylsulfoxide-d6) δ ppm 1.43 (m, 12H) 1.89 (brs, 4H) 2.97-3.08 (m, 4H) 3.95-4.03 (m, 4H) 4.71-4.77 (q, 1H) 7.24-7.43 (m, 11H) 8.45-8.48 (d, 1H) 10.22 (brs, 1H) 12.4 (brs, 1H).

559

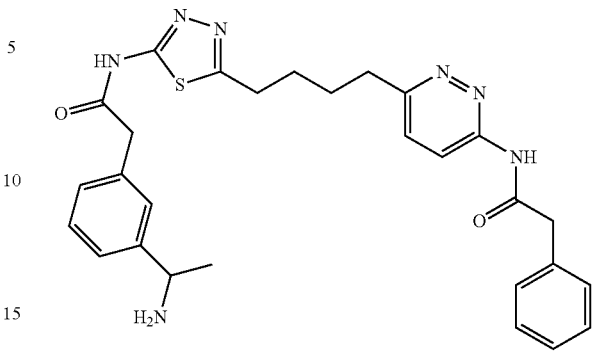

$^1$H NMR (300 MHz, Dimethylsulfoxide-d6) δ ppm 1.5-1.52 (d, 3H) 1.75 (brs, 4H) 2.88-2.93 (m, 2H) 3.03-3.05 (m, 2H) 3.79 (s, 2H) 3.86 (s, 2H) 4.38-4.44 (q, 1H) 7.27-7.59 (m, 10H) 8.20-8.23 (m, 4H) 11.27 (s, 1H) 12.71 (s, 1H).

560

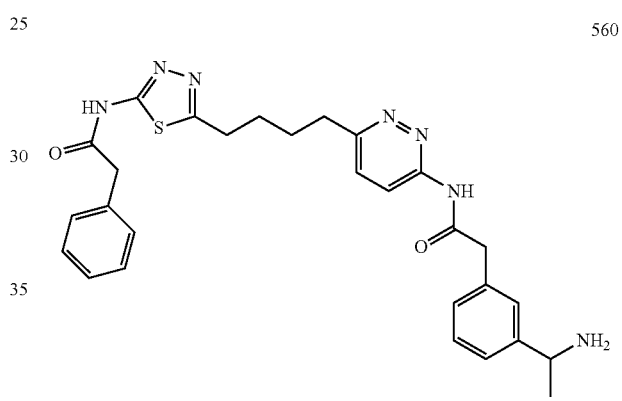

$^1$H NMR (300 MHz, Dimethylsulfoxide-d6) δ ppm 1.5-1.52 (d, 3H) 1.75 (brs, 4H) 2.88-2.93 (m, 2H) 3.03-3.05 (m, 2H) 3.86 (s, 4H) 4.38-4.44 (q, 1H) 7.27-7.59 (m, 10H) 8.20-8.23 (m, 4H) 11.27 (s, 1H) 12.71 (s, 1H).

624

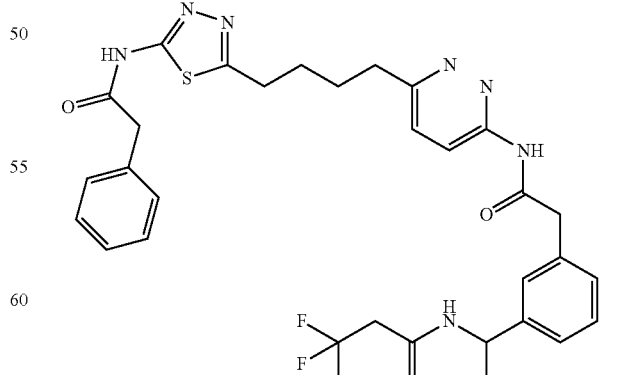

$^1$H NMR (300 MHz, Dimethylsulfoxide-d6) δ ppm 1.5-1.52 (d, 3H) 1.75 (brs, 4H) 2.88-2.93 (m, 2H) 3.03-3.05 (m, 2H) 3.78 (s, 2H) 3.82 (s, 2H) 4.91-4.96 (q, 1H) 7.20-7.35 (m, 9H) 7.55-7.58 (d, 1H) 8.20-8.23 (d, 1H) 8.68-8.71 (m, 1H) 11.27 (s, 1H) 12.71 (s, 1H).

yield). $^1$H NMR (300 MHz, Dimethylsulfoxide-d6) δ ppm 1.24-1.26 (d, 3H) 4.22-4.24 (q, 1H) 7.1-7.16 (t, 1H) 7.41-7.46 (m, 1H) 7.76 (m, 1H).

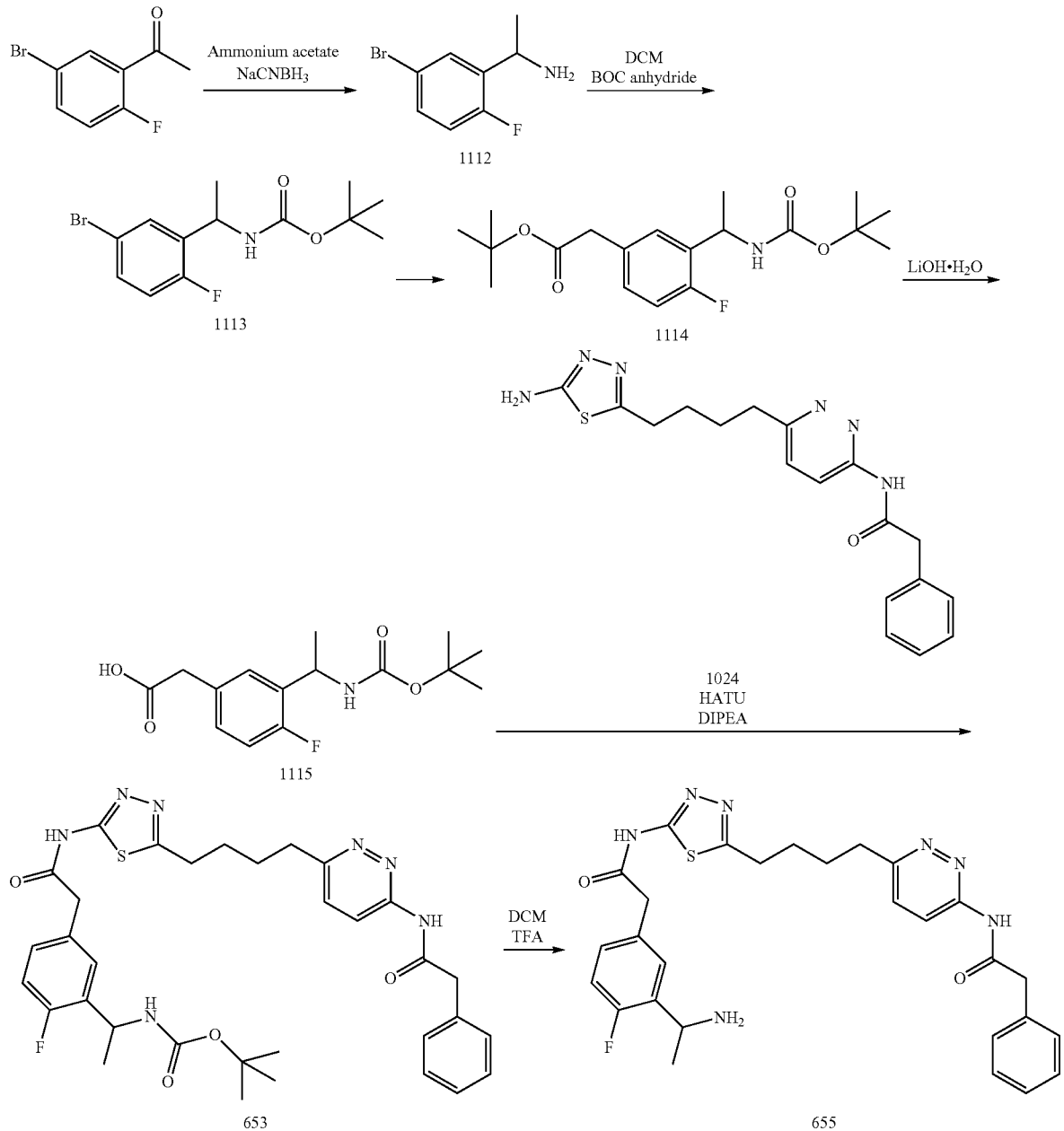

To an ice cold solution of 1-(5-bromo-2-fluorophenyl) ethanone (4.5 g, 20.7 mmol) in methanol (100 mL) was added ammonium acetate (32 g, 414.7 mmol) and sodium cyanoborohydride (6.15 g, 28.98 mmol). The reaction mixture was stirred at room temperature over the weekend before it was concentrated. The residue obtained was diluted with water, basified to pH-13 with 1N NaOH and extracted with dichloromethane. The organic extract was separated, dried over sodium sulfate, filtered and evaporated. The residue obtained was purified by silica gel chromatography eluting with EtOAc/Hexane to afford 1112 (1.8 g, 40%

To a solution of 1112 (1.97 g, 9 mmol) in dichloromethane (100 mL) was added boc anhydride (1.97 g, 9 mmol) and the reaction mixture was stirred at room temperature overnight before it was concentrated and purified by silica gel chromatography eluting with EtOAc/Hexane to afford 1113 (2.4 g, 83% yield). $^1$H NMR (300 MHz, Dimethylsulfoxide-d6) δ ppm 1.29-1.32 (d, 3H) 1.39 (s, 9H) 4.87 (q, 1H) 7.14-7.21 (t, 1H) 7.46-7.58 (m, 3H).

To a degassed solution of 1113 (2.4 g, 7.54 mmol) and bis(tri-tert-butylphosphine)palladium(0) (0.77 g, 1.508 mmol) in dioxane (12 mL) was added 2-tert-Butoxy-2-oxoethylzinc chloride (38 mL, 18.85 mmol) under Argon and the resulting reaction mixture was stirred at room temperature for 4 hr before it was quenched with saturated aqueous ammonium chloride solution. The resulting solution was partitioned between water and ethyl acetate. The organic extract was washed with more water, separated, dried over sodium sulfate, filtered and evaporated. The residue obtained was purified by silica gel chromatography eluting with EtOAc/Hexane to afford 1114 (2 g, 75% yield). ¹H NMR (300 MHz, Dimethylsulfoxide-d6) δ ppm 1.29-1.32 (d, 3H) 1.38-1.41 (m, 18H) 3.53 (s, 2H) 4.87 (q, 1H) 7.05-7.16 (m, 2H) 7.26-7.29 (m, 1H) 7.48 (m, 1H).

To a solution of 1114 (2 g, 5.66 mmol) in methanol (100 mL) and water (25 mL) was added lithium hydroxide monohydrate (2 gm) and the resulting reaction mixture was stirred at room temperature for 2 days before it was concentrated. The residue obtained was diluted with ice cold water and acidified with acetic acid. The resulting solution was partitioned between water and ethyl acetate. The organic extract was washed with more water, separated, dried over sodium sulfate, filtered and evaporated. The residue obtained was purified by silica gel chromatography eluting with EtOAc/Hexane to afford 1115 (1.5 g, 89% yield). ¹H NMR (300 MHz, Dimethylsulfoxide-d6) δ ppm 1.29-1.31 (d, 3H) 1.38 (s, 9H) 3.53 (s, 2H) 4.87 (q, 1H) 7.05-7.19 (m, 2H) 7.26-7.29 (m, 1H) 7.45-7.48 (m, 1H) 12.32 (s, 1H).

653

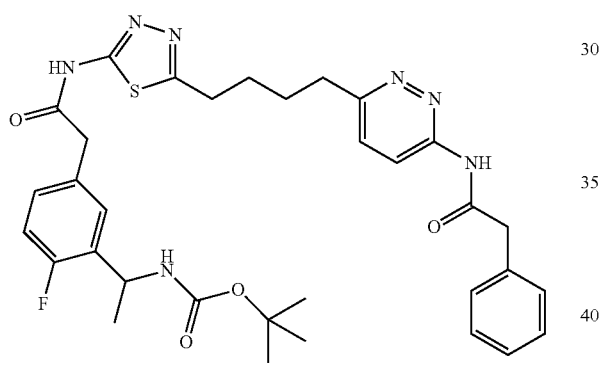

¹H NMR (300 MHz, Dimethylsulfoxide-d6) δ ppm 1.30-1.33 (m, 12H) 1.74 (brs, 4H) 2.89 (m, 2H) 3.02 (m, 2H) 3.78 (s, 4H) 4.85 (q, 1H) 7.10-7.57 (m, 11H) 8.19-8.22 (d, 1H) 11.26 (s, 1H) 12.64 (s, 1H).

654

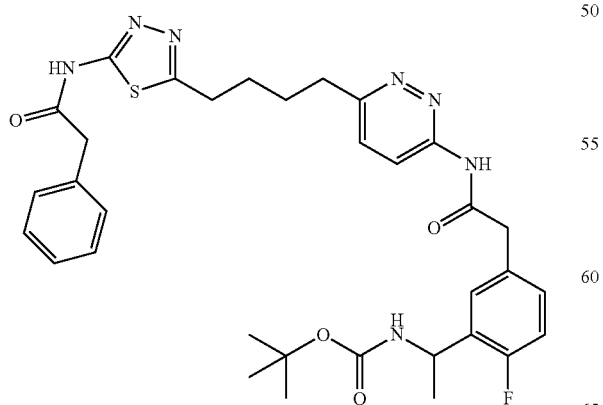

¹H NMR (300 MHz, Dimethylsulfoxide-d6) δ ppm 1.28-1.32 (m, 12H) 1.73-1.75 (brs, 4H) 2.87 (m, 2H) 2.89 (m, 2H) 3.75 (s, 2H) 3.81 (s, 2H) 4.85 (q, 1H) 7.06-7.57 (m, 11H) 8.18-8.21 (d, 1H) 11.26 (s, 1H) 12.64 (s, 1H).

655

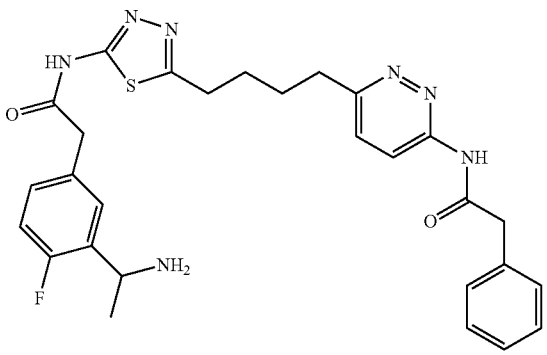

¹H NMR (300 MHz, Dimethylsulfoxide-d6) δ ppm 1.51-1.53 (m, 3H) 1.75 (brs, 4H) 2.90 (m, 2H) 3.02 (m, 2H) 3.78 (s, 2H) 3.85 (s, 2H) 4.65 (q, 1H) 7.25-7.61 (m, 10H) 8.21-8.25 (d, 1H) 8.33-8.35 (brs, 3H) 11.29 (s, 1H) 12.68 (s, 1H).

656

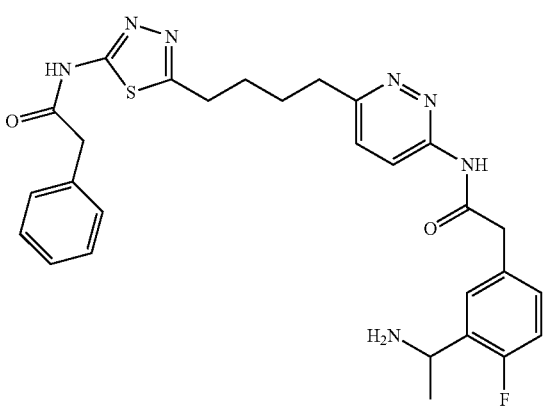

¹H NMR (300 MHz, Dimethylsulfoxide-d6) δ ppm 1.54 (d, 3H) 1.75-1.76 (brs, 4H) 2.91 (m, 2H) 3.02 (m, 2H) 3.81-3.83 (m, 4H) 4.65 (q, 1H) 7.24-7.63 (m, 10H) 8.22-8.25 (d, 1H) 8.36 (brs, 3H) 11.35 (s, 1H) 12.66 (s, 1H).

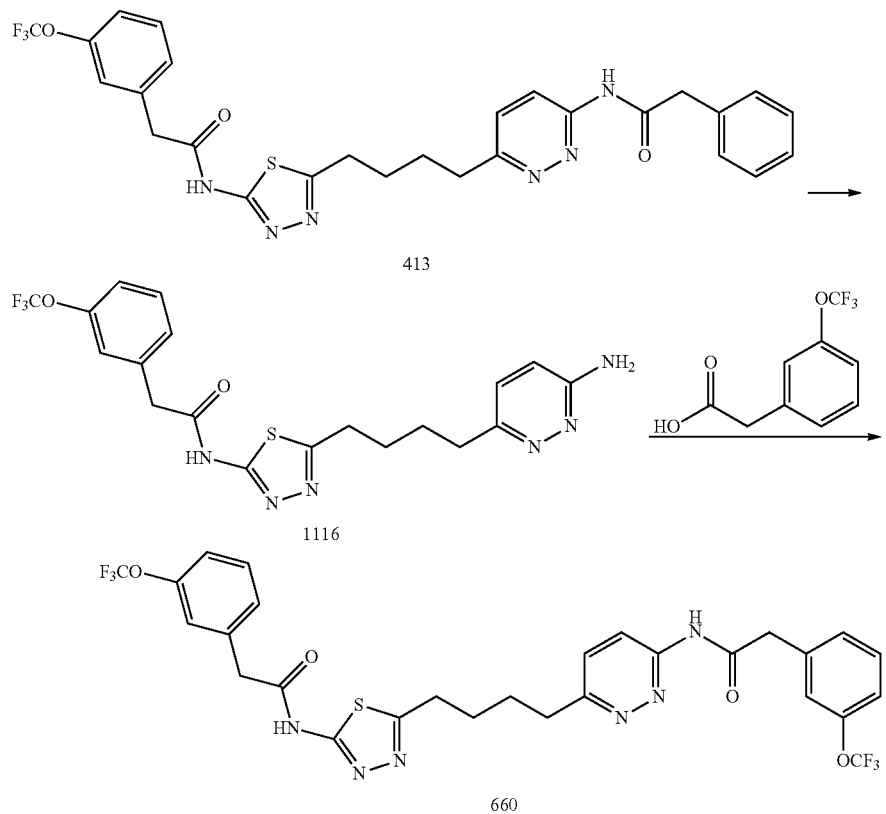

To a mixture of 413 (1.62 g) in MeOH (25 mL), THF (10 mL) and H₂O (10 mL) at room temperature was added 1N aq. NaOH (8 mL). This mixture was stirred for 24 h before the organic volatile was removed under reduced pressure. The residue was neutralized to pH 7 with 1N aq. HCl solution and extracted with EtOAc (2×20 mL). The combined extract was dried (MgSO₄) and concentrated. The crude was purified by silica gel chromatography eluting with 1-15% MeOH in dichloromethane to afford amine 1116. The resulting amine 1116 was converted to 660 as described for 335. ¹H NMR (300 MHz, DMSO-d₆) δ 12.68 (bs, 1H), 11.31 (s, 1H), 8.20 (d, J=9.2 Hz, 1H), 7.57 (d, J=8.8 Hz, 1H), 7.52-7.21 (m, 8H), 3.90 (s, 2H), 3.87 (s, 2H), 3.06-2.86 (m, 4H), 1.77-1.72 (m, 4H).

3-Amino-6-chloropyridazine (55.5 g, 0.428 mol) and 3-(Trifluoromethoxy)phenylacetic acid (1.1 equiv., 0.471 mol, 104 g) were dissolved in DMF (30.0 vol., 1.66 L) in a 3000 mL three neck round-bottom flask. Addition of DIEA (1.1 equiv., 0.471 mol, 82 mL) via addition funnel was done over 5 minutes. Propylphosphonic anhydride solution (300 mL of a 50% solution in DMF, 1.1 equiv., 0.471 mol,) was charged into a 500 mL addition funnel and added dropwise to reaction solution (keeping reaction temperature ≤+30° C.). The reaction usually goes to completion after 3 hours (TLC: 6:4 hexanes-ethyl acetate). Reaction mixture was then poured into 7.5% sodium bicarbonate (80.0 vol., 4.4 L) which was chilled in an ice bath. Off-white crystalline powder was filtered through a Büchner funnel, rinsed with water (20.0 vol., 1.1 L). Dried in a 50° C. vacuum to a constant weight to afford N-(6-chloropyridazin-3-yl)-2-(3-(trifluoromethoxy)phenyl)acetamide 1117: yield of 119.6 g (77%). ¹H NMR (300 MHz, DMSO-d₆) δ 11.63 (s, 1H), 8.38 (d, J=9.4 Hz, 1H), 7.88 (d, J=9.4 Hz, 1H), 7.52-7.27 (m, 4H), 3.90 (s, 2H).

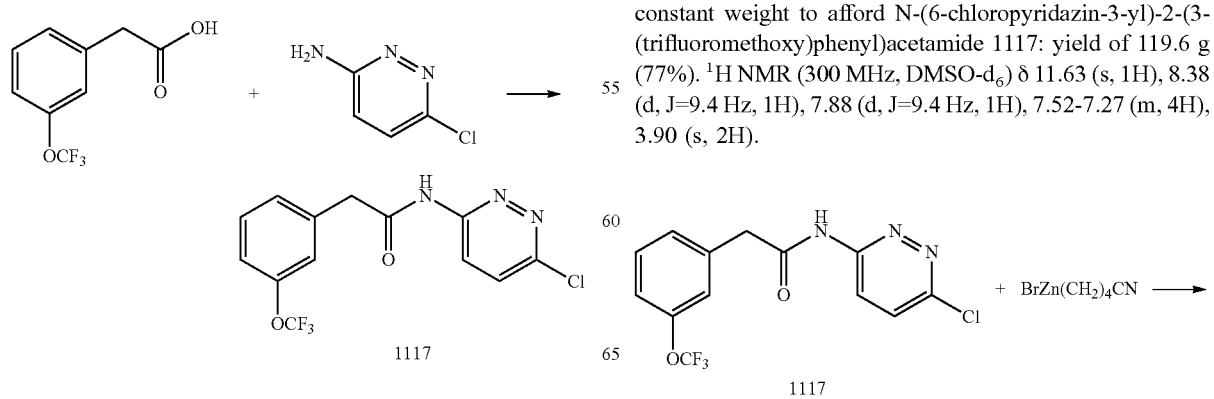

161

-continued

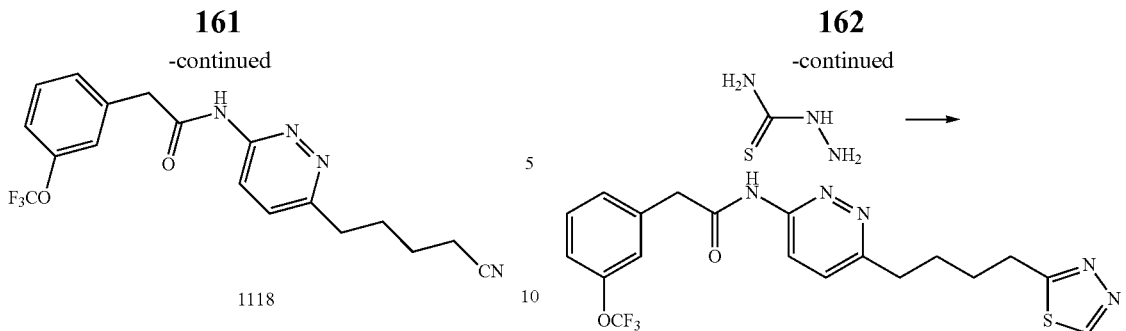

1118

4-Cyanobutylzinc bromide solution (3.0 equiv., 0.50 mol, 1.0 L) was charged into an argon gas purged 5000 mL 3 neck round bottom flask. Argon₍g₎ purge for 5 minutes followed by the addition of 1117 (1.0 equiv., 0.167 mol, 55.3 g) and NiCl₂(dppp) (0.15 equiv., 0.0251 mol, 13.6 g) under a blanket of argon₍g₎. The reaction usually goes to completion after 4 hours (TLC: 1:1 hexanes-ethyl acetate). EtOAc (15 vol., 832 mL) added to deep red solution. Water (15 vol., 832 mL) was added, thick slurry formed. 1N HCl added until slurry breaks to pale blue layer (~6 vol., 333 mL). Transferred to separatory funnel and organic layer was washed with 1N HCl (2×500 mL), dried (MgSO₄) and concentrated by rotary evaporation (bath ≤30° C.) to a solid reddish oil. Oil dissolved in dichloromethane (15 vol., 832 mL), silica gel (100 g) was slurried into red solution, this was concentrated by rotary evaporation (bath ≤30° C.) to a solid reddish powder. Loaded onto a bed of silica gel (5 cm×11 cm), flushed with 25% hexanes in ethyl acetate (3 L), combined organics concentrated by rotary evaporation (bath ≤30° C.). Dried under high vacuum to a constant weight to afford N-(6-(4-cyanobutyl)pyridazin-3-yl)-2-(3-(trifluoromethoxy)phenyl)acetamide 1118: yield of 58.2 g (92%). $^1$H NMR (300 MHz, DMSO-d₆) δ 11.41 (s, 1H), 8.28 (d, J=9.2 Hz, 1H), 7.65 (d, J=9.2 Hz, 1H), 7.52-7.27 (m, 4H), 3.89 (s, 2H), 2.92 (t, J=7.5 Hz, 2H), 2.56 (t, J=7.0 Hz, 2H), 1.80 (m, 2H), 1.61 (m, 2H).

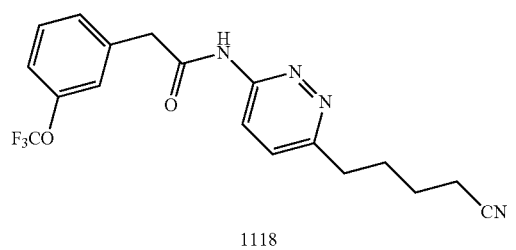

1118

162

-continued

657

1118 (1.0 equiv., 0.154 mol, 58.2 g) was charged into a 500 mL round bottom flask along with thiosemicarbazide (1.2 equiv., 0.184 mol, 16.8 g). TFA (5 vol., 291 mL) slowly added to reaction vessel while stirring. The reaction slurry was heated in a 65° C. bath with an open top reflux condenser. The reaction usually goes to completion after 5 hours (determined by LC/MS). Toluene (10 vol., 582 mL) added to deep red solution, azeotroped by rotary evaporation (bath ≤30° C.) to a red oil. Slowly transferred oil to a well stirred 6000 mL Erlenmeyer flask containing 7.5% sodium bicarbonate solution (69 vol., 4.0 L) cooled in a 0° C. bath. The crystals were filtered through a Büchner funnel and rinsed twice with diethyl ether (5 vol., 2×250 mL). Dried under high vacuum to a constant weight to afford N-(6-(4-(5-amino-1,3,4-thiadiazol-2-yl)butyl)pyridazin-3-yl)-2-(3-(trifluoromethoxy)phenyl)acetamide 657; yield of 55.7 g (80%). $^1$H NMR (300 MHz, DMSO-d₆) δ 11.33 (s, 1H), 8.21 (d, J=9.2 Hz, 1H), 7.58 (d, J=9.2 Hz, 1H), 7.51-7.26 (m, 4H), 6.99 (s, 2H), 3.88 (s, 2H), 2.87 (m, 4H), 1.71 (m, 4H).

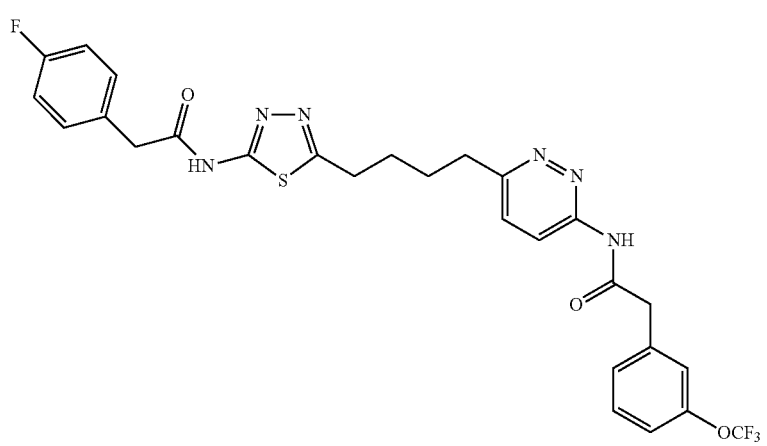

661

To a solution of 657 (50 mg, 0.11 mmol) in DMF (3 mL) at 0° C. was added 4-fluorophenyl acetic acid (22 mg, 0.14 mmol), HOBt (30 mg, 0.22 mmol) and EDCI (42 mg, 0.22 mmol). The resulting mixture was stirred at room temperature for 1.5 h before it was cooled to 0° C. and quenched with H$_2$O. The precipitate was collected by suction filtration and further purified by silica gel chromatography eluting with 1-10% MeOH in dichloromethane to afford 661. $^1$H NMR (300 MHz, DMSO-d$_6$) δ 12.65 (bs, 1H), 11.31 (s, 1H), 8.20 (d, J=9.1 Hz, 1H), 7.57 (d, J=9.4 Hz, 1H), 7.49-7.14 (m, 8H), 3.87 (s, 2H), 3.81 (s, 2H), 3.06-2.86 (m, 4H), 1.77-1.72 (m, 4H).

663 was prepared by the procedure as described for compound 661. $^1$H NMR (300 MHz, DMSO-d$_6$) δ 12.74 (bs, 1H), 11.31 (s, 1H), 8.20 (d, J=9.2 Hz, 1H), 7.57 (d, J=9.2 Hz, 1H), 7.51-7.19 (m, 7H), 3.97 (s, 2H), 3.87 (s, 2H), 3.06-2.86 (m, 4H), 1.77-1.72 (m, 4H).

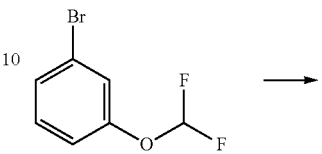

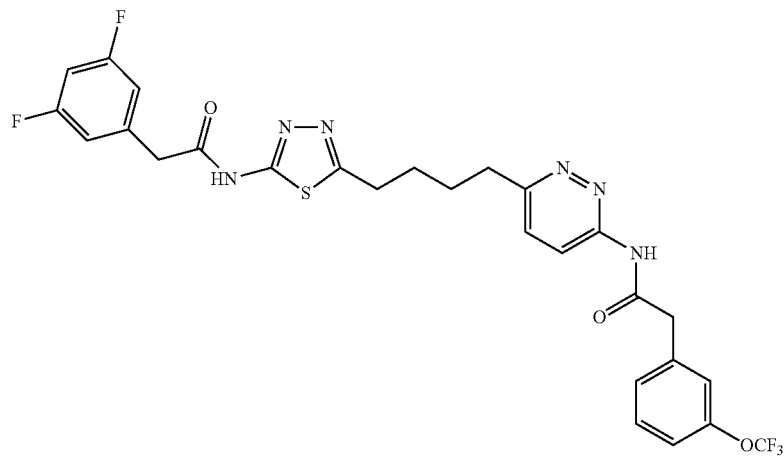

662

662 was prepared by the procedure as described for compound 661. $^1$H NMR (300 MHz, DMSO-d$_6$) δ 12.67 (bs, 1H), 11.31 (s, 1H), 8.20 (d, J=9.1 Hz, 1H), 7.57 (d, J=9.1 Hz, 1H), 7.51-7.07 (m, 7H), 3.89 (s, 2H), 3.87 (s, 2H), 3.06-2.86 (m, 4H), 1.77-1.72 (m, 4H).

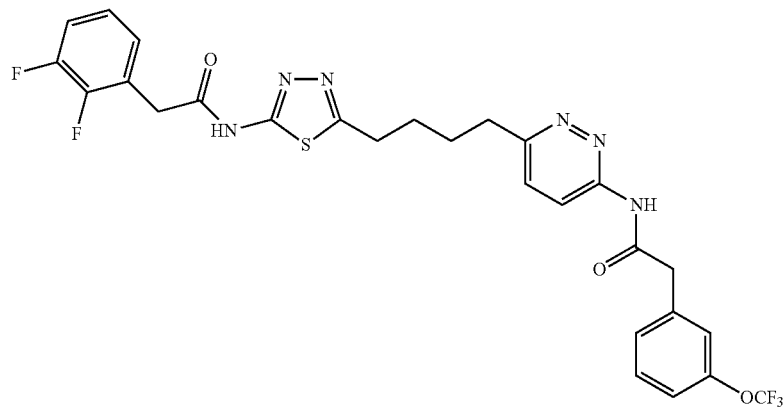

663

-continued

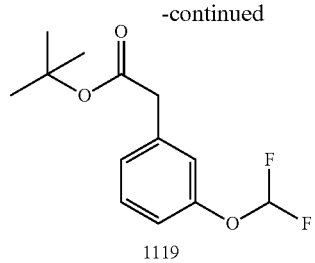
1119

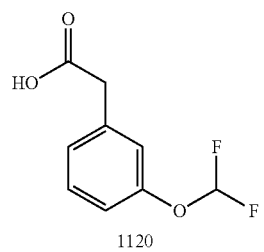
1120

To a mixture of 1-bromo-3-(difluoromethoxy) benzene (1 g, 4.5 mmol), bis(tri-tert-butylphosphine) palladium(0) (460 mg, 0.9 mmol) in 1,4-dioxane (30 ml) under argon atmosphere was added 0.5 M of 2-tert-butoxy-2-oxoethyl zinc chloride in ether (22.5 ml). The resulting mixture was stirred at room temperature overnight. The mixture was partitioned between saturated NH₄Cl and EtOAc. The organic extract was washed with brine, dried over sodium sulfate, filtered and evaporated. The crude material was purified by silica gel chromatography eluting with 0-10% EtOAc in Hexane to afford 1119.

To a solution of 1119 (300 mg, 1.16 mmol) in dichloromethane (5 ml) at 0° C. was added TFA (3 ml) dropwise. The resulting mixture was stirred at room temperature overnight before it was evaporated to dryness then triturated the residue with ether to afford 1120.

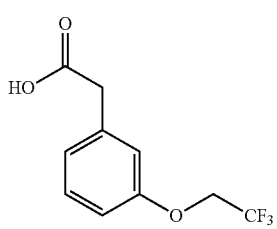
1121

1121 was made using procedure described for compound 1120 from 1-Bromo-3-(2,2,2-trifluoroethoxy)benzene.

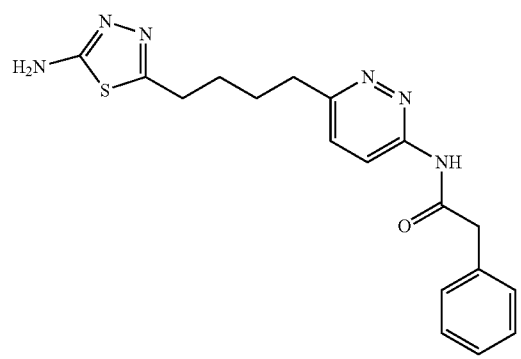
1024

-continued

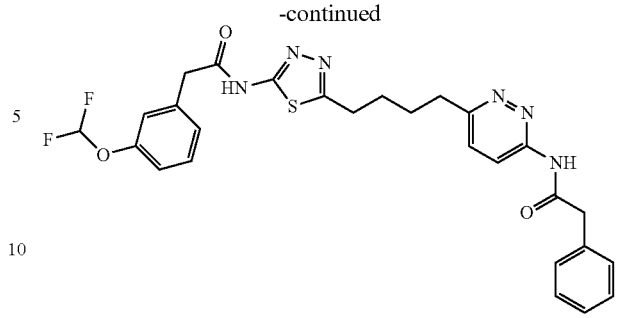
664

A flask was charged with 1024 (50 mg, 0.135 mmol), 1120 (28 mg, 0.142 mmol) in DMF (1 ml) at 0° C. was added HOBT (39 mg, 0.285 mmol) followed by EDCI (68 mg, 0.356 mmol). The resulting mixture was slowly warmed up to room temperature and stirred for 2 h before it was quenched by addition of ice water (~5 mL). The white precipitate was collected by suction filtration, rinsed with more water to afford 664. $^1$H NMR (300 MHz, DMSO-d₆) δ 12.71 (s, 1H), 11.32 (s, 1H), 8.22-8.19 (d, J=9.12 Hz, 1H), 7.58-7.54 (d, J=9.03 Hz, 1H), 7.48-6.99 (m, 10H), 3.85 (s, 2H), 3.78 (s, 2H), 3.01 (bs, 2H), 2.90 (bs, 2H), 1.73 (bs, 4H).

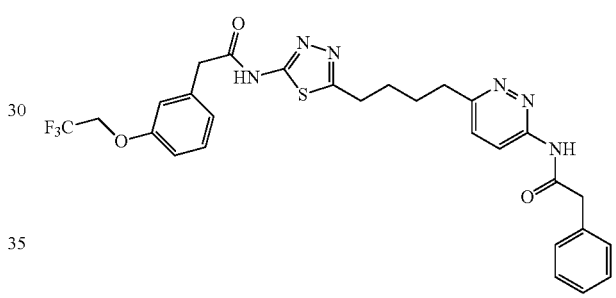
665

665 was made using procedure described for compound 664. $^1$H NMR (300 MHz, DMSO-d₆) δ 12.71 (s, 1H), 11.32 (s, 1H), 8.22-8.19 (d, J=9.12 Hz, 1H), 7.58-7.54 (d, J=9.03 Hz, 1H), 7.38-7.28 (m, 6H), 7.03-6.97 (m, 3H), 4.77-4.74 (q, 2H), 3.80-3.78 (d, J=5.82 Hz, 4H), 3.01 (bs, 2H), 2.90 (bs, 2H), 1.73 (bs, 4H).

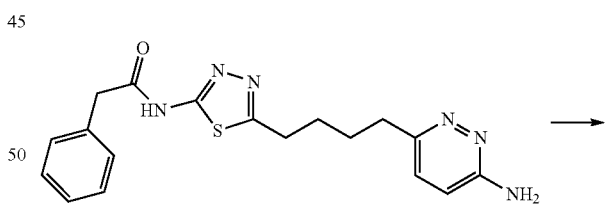
348

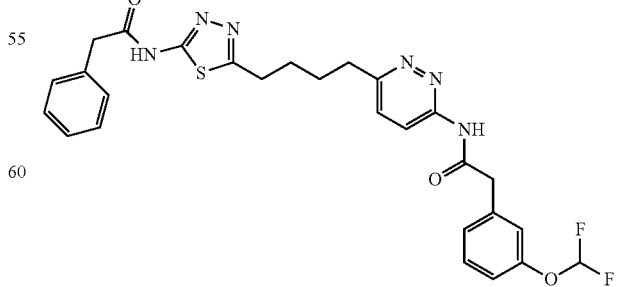
666

A flask was charged with 348 (50 mg, 0.135 mmol), 1120 (28 mg, 0.142 mmol) in DMF (1 ml) at 0° C. was added HOBT (39 mg, 0.285 mmol) followed by EDCI (68 mg, 0.356 mmol). The resulting mixture was slowly warmed up to room temperature and stirred overnight before it was quenched by addition of ice water (~5 mL). The white precipitate was collected by suction filtration, rinsed with more water. The crude material was purified by silica gel chromatography eluting with 0-6% MeOH in dichloromethane to afford 666. $^1$H NMR (300 MHz, DMSO-d$_6$) δ 12.71 (s, 1H), 11.32 (s, 1H), 8.22-8.19 (d, J=9.12 Hz, 1H), 7.58-7.54 (d, J=9.03 Hz, 1H), 7.48-6.98 (m, 10H), 3.81 (bs, 4H), 3.01 (bs, 2H), 2.90 (bs, 2H), 1.73 (bs, 4H).

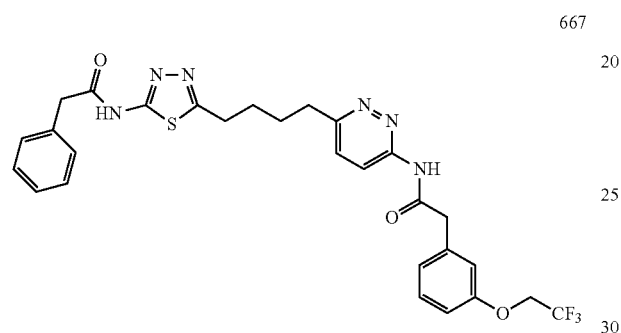

667

667 was made using procedure described for compound 666. $^1$H NMR (300 MHz, DMSO-d$_6$) δ 12.71 (s, 1H), 11.32 (s, 1H), 8.22-8.19 (d, J=9.12 Hz, 1H), 7.58-7.54 (d, J=8.97 Hz, 1H), 7.35-7.28 (m, 6H), 7.03-6.97 (m, 3H), 4.77-4.74 (q, 2H), 3.87 (s, 2H), 3.78 (s, 2H), 3.01 (bs, 2H), 2.90 (bs, 2H), 1.73 (bs, 4H).

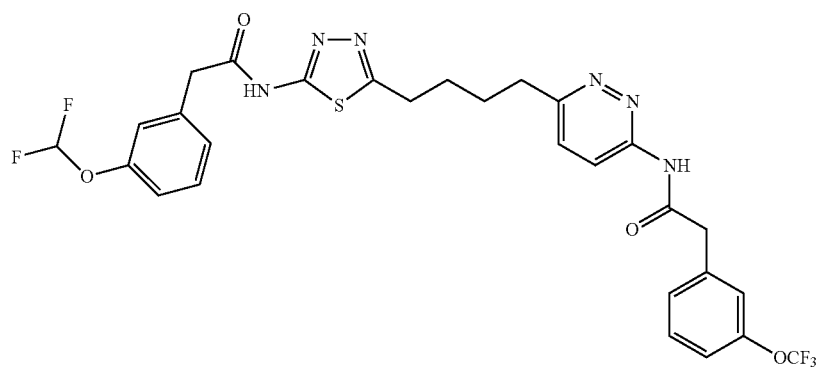

668

668 was made using procedure described for compound 675. $^1$H NMR (300 MHz, DMSO-d$_6$) δ 12.71 (s, 1H), 11.32 (s, 1H), 8.22-8.19 (d, J=9.15 Hz, 1H), 7.58-6.99 (m, 10H), 3.87-3.84 (d, 4H), 3.01 (bs, 2H), 2.90 (bs, 2H), 1.73 (bs, 4H).

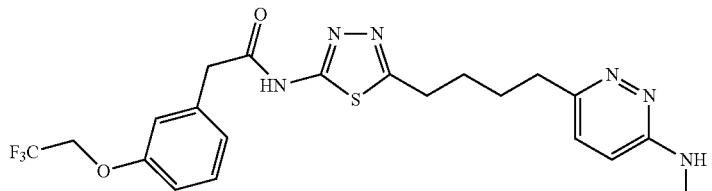

669

669 was made using procedure described for compound 675. $^1$H NMR (300 MHz, DMSO-d$_6$) δ 12.71 (s, 1H), 11.32 (s, 1H), 8.22-8.19 (d, J=9.09 Hz, 1H), 7.58-7.54 (d, J=9.37 Hz, 1H), 7.48-7.28 (m, 6H), 7.03-6.97 (m, 2H), 4.77-4.74 (q, 2H), 3.87 (s, 2H), 3.78 (s, 2H), 3.01 (bs, 2H), 2.90 (bs, 2H), 1.73 (bs, 4H).

657

670

A flask was charged with 657 (50 mg, 0.111 mmol), 2-pyridine acetic acid hydrochloride (20 mg, 0.116 mmol) in DMF (1 ml) at 0° C. was treated with propylphosphonic anhydride solution (91 ul) followed by triethylamine (40 ul, 0.29 mmol). The resulting mixture was slowly warmed up to room temperature and stirred for 1 h before it was quenched by addition of ice water (~5 mL). The yellow precipitate was collected by suction filtration, rinsed with more water. The crude material was purified by silica gel chromatography eluting with 0-6% MeOH in dichloromethane to afford 670. $^1$H NMR (300 MHz, DMSO-d$_6$) δ 12.67 (s, 1H), 11.32 (s, 1H), 8.53-8.49 (m, 1H), 8.22-8.19 (d, J=9.12 Hz, 1H), 7.78-7.76 (t, 1H), 7.58-7.26 (m, 7H), 4.01 (s, 2H), 3.87 (s, 2H), 3.01 (bs, 2H), 2.90 (bs, 2H), 1.73 (bs, 4H).

671

671 was made using procedure described for compound 670. $^1$H NMR (300 MHz, DMSO-d$_6$) δ 12.70 (s, 1H), 11.32 (s, 1H), 8.53-8.48 (m, 2H), 8.22-8.19 (d, J=9.12 Hz, 1H), 7.76-7.26 (m, 7H), 3.87 (s, 4H), 3.01 (bs, 2H), 2.90 (bs, 2H), 1.73 (bs, 4H).

672

672 was made using procedure described for compound 670. $^1$H NMR (300 MHz, DMSO-d$_6$) δ 11.32 (s, 1H), 8.53-8.52 (bs, 2H), 8.22-8.19 (d, J=9.12 Hz, 1H), 7.58-7.26 (m, 7H), 3.87 (s, 4H), 3.01 (bs, 2H), 2.90 (bs, 2H), 1.73 (bs, 4H).

673

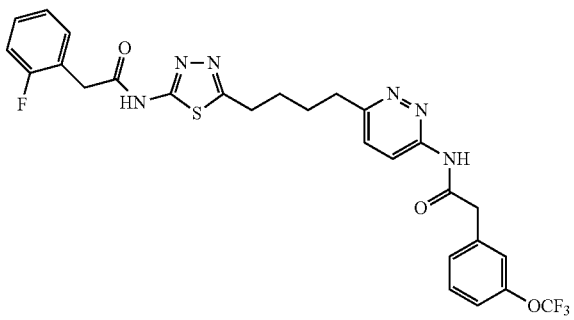

673 was prepared by the procedure as described for compound 661. ¹H NMR (300 MHz, DMSO-d₆) δ 12.69 (bs, 1H), 11.31 (s, 1H), 8.20 (d, J=9.1 Hz, 1H), 7.57 (d, J=9.1 Hz, 1H), 7.51-7.21 (m, 8H), 3.90 (s, 2H), 3.87 (s, 2H), 3.06-2.86 (m, 4H), 1.77-1.72 (m, 4H).

A flask was charged with 657 (70 mg, 0.155 mmol), 5-pyrimidineacetic acid (22 mg, 0.162 mmol) in DMF (1 ml) at 0° C. was added HOBT (44 mg, 0.326 mmol) followed by EDCI (78 mg, 0.408 mmol). The resulting mixture was slowly warmed up to room temperature and stirred for overnight before it was quenched by addition of ice water (~5 mL). The white precipitate was collected by suction filtration, rinsed with more water. The crude material was purified by silica gel chromatography eluting with 0-6% MeOH in dichloromethane to afford 675. ¹H NMR (300 MHz, DMSO-d₆) δ 12.75 (s, 1H), 11.32 (s, 1H), 9.11 (s, 1H), 8.76 (s, 1H), 8.22-8.19 (d, J=9.12 Hz, 1H), 7.59-7.26 (m, 6H), 3.94 (s, 2H), 3.87 (s, 2H), 3.01 (bs, 2H), 2.90 (bs, 2H), 1.73 (bs, 4H).

674

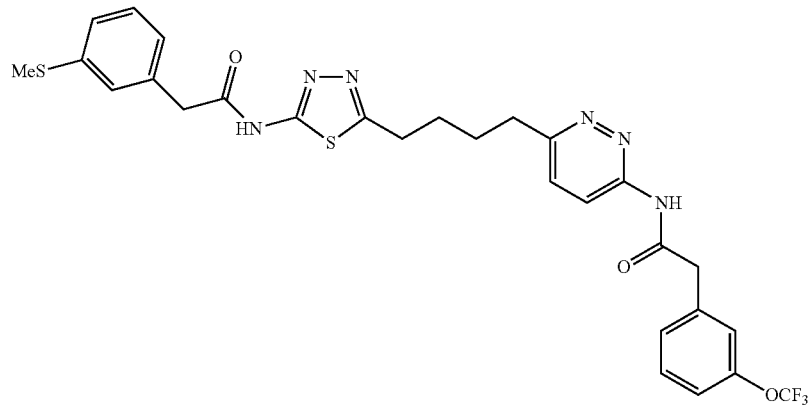

674 was prepared by the procedure as described for compound 661. ¹H NMR (300 MHz, DMSO-d₆) δ 12.63 (bs, 1H), 11.32 (s, 1H), 8.20 (d, J=9.2 Hz, 1H), 7.57 (d, J=9.2 Hz, 1H), 7.51-7.38 (m, 3H), 7.33-7.09 (m, 5H), 3.87 (s, 2H), 3.79 (s, 2H), 3.06-2.86 (m, 4H), 2.48 (s, 3H), 1.77-1.72 (m, 4H).

675

676

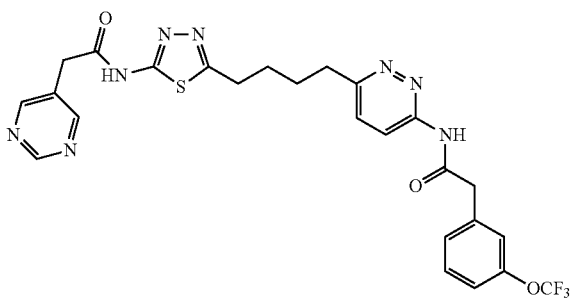

676 was made using procedure described for compound 675. ¹H NMR (300 MHz, DMSO-d₆) δ 12.75 (s, 1H), 11.32 (s, 1H), 8.70 (s, 1H), 8.61-8.57 (m, 2H), 8.22-8.19 (d, J=9.36 Hz, 1H), 7.59-7.26 (m, 5H), 4.11 (s, 2H), 3.87 (s, 2H), 3.01 (bs, 2H), 2.90 (bs, 2H), 1.73 (bs, 4H).

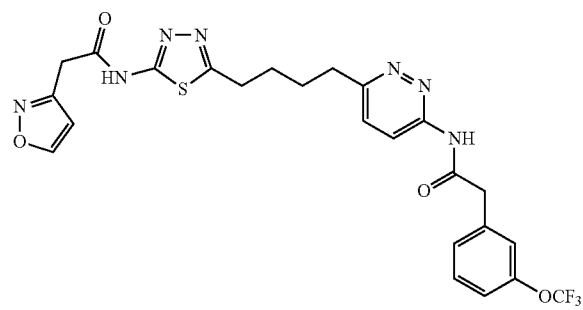
677
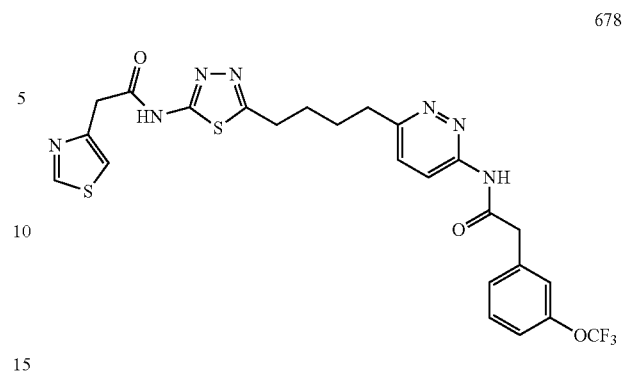
678
677 was made using procedure described for compound 675. $^1$H NMR (300 MHz, DMSO-d$_6$) δ 12.75 (s, 1H), 11.32 (s, 1H), 8.89 (s, 1H), 8.22-8.19 (d, J=9.15 Hz, 1H), 7.59-7.26 (m, 5H), 6.62 (s, 1H), 3.99 (s, 2H), 3.87 (s, 2H), 3.01 (bs, 2H), 2.90 (bs, 2H), 1.73 (bs, 4H).
678 was made using procedure described for compound 675. $^1$H NMR (300 MHz, DMSO-d$_6$) δ 12.75 (s, 1H), 11.32 (s, 1H), 9.06 (s, 1H), 8.22-8.19 (d, J=9.21 Hz, 1H), 7.59-7.26 (m, 6H), 4.03 (s, 2H), 3.87 (s, 2H), 3.01 (bs, 2H), 2.90 (bs, 2H), 1.73 (bs, 4H).
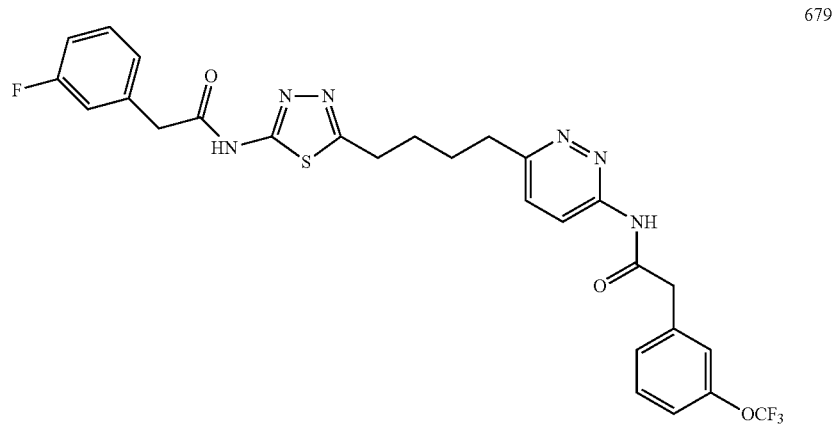 [SMILES: O=C(Cc1cccc(OC(F)(F)F)c1)Nc1ccc(CCCCc2nnc(NC(=O)Cc3cccc(F)c3)s2)nn1]
679
679 was prepared by the procedure as described for compound 661. $^1$H NMR (300 MHz, DMSO-d$_6$) δ 12.67 (bs, 1H), 11.31 (s, 1H), 8.20 (d, J=9.2 Hz, 1H), 7.57 (d, J=9.2 Hz, 1H), 7.51-7.36 (m, 4H), 7.29-7.12 (m, 4H), 3.87 (s, 2H), 3.85 (s, 2H), 3.06-2.86 (m, 4H), 1.77-1.72 (m, 4H).
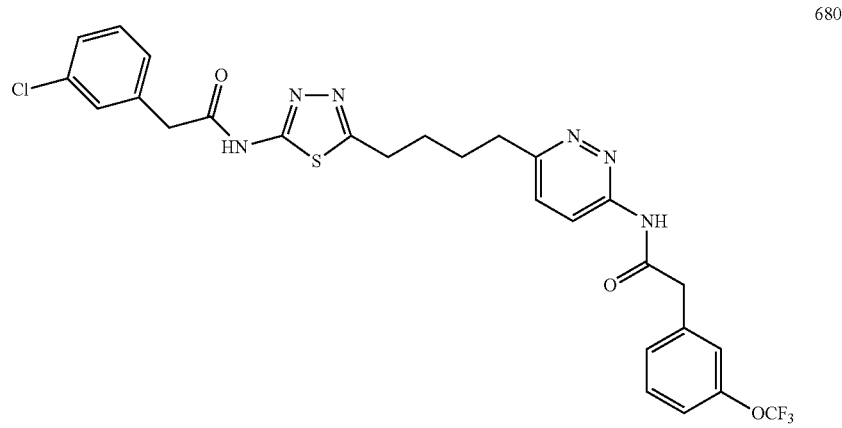 [SMILES: O=C(Cc1cccc(OC(F)(F)F)c1)Nc1ccc(CCCCc2nnc(NC(=O)Cc3cccc(Cl)c3)s2)nn1]
680

680 was prepared by the procedure as described for compound 661. $^1$H NMR (300 MHz, DMSO-$d_6$) δ 12.67 (bs, 1H), 11.31 (s, 1H), 8.20 (d, J=9.3 Hz, 1H), 7.57 (d, J=9.0 Hz, 1H), 7.51-7.28 (m, 8H), 3.87 (s, 2H), 3.84 (s, 2H), 3.06-2.86 (m, 4H), 1.77-1.72 (m, 4H).

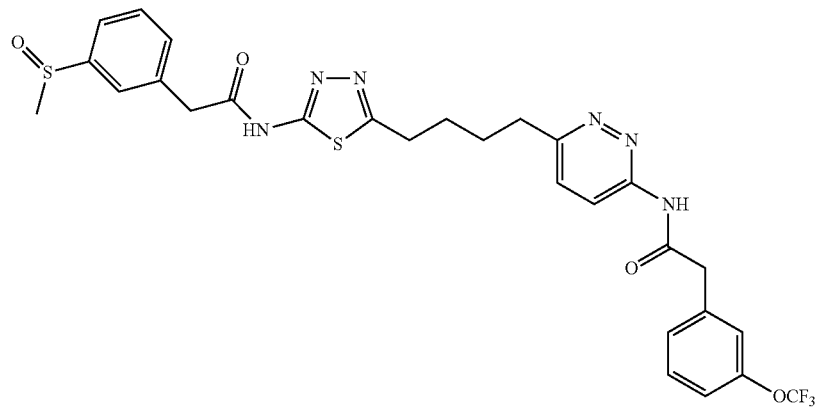

682

To a solution of 674 (100 mg, 0.16 mmol) in dichloromethane at −78° C. was added m-CPBA (60 mg, 0.24 mmol) in 4 portions. The resulting mixture was stirred at that temperature for 1 h before it was slowly warmed up to −10° C. and quenched with 25% aq. Na$_2$S$_2$O$_3$ solution. The reaction was diluted with EtOAc, washed with saturated aq. NaHCO$_3$ (3×10 mL). The combined organic layer was separated, washed with brine, dried (MgSO$_4$) and concentrated. The crude was purified by HPLC to afford 682. $^1$H NMR (300 MHz, DMSO-$d_6$) δ 12.72 (bs, 1H), 11.31 (s, 1H), 8.20 (d, J=9.0 Hz, 1H), 7.68 (m, 1H), 7.60-7.26 (m, 8H), 3.91 (s, 2H), 3.87 (s, 2H), 3.06-2.86 (m, 4H), 2.76 (s, 3H), 1.77-1.72 (m, 4H).

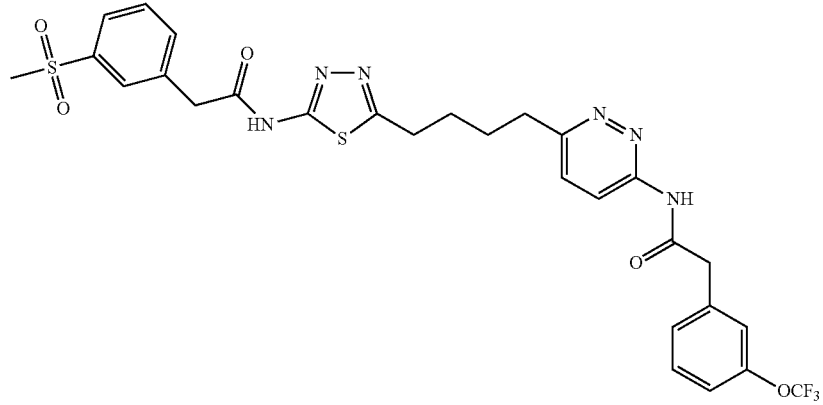

681

681 was prepared from 657 and 3-methylsulphonylphenyl acetic acid by the procedure as described for compound 661. $^1$H NMR (300 MHz, DMSO-$d_6$) δ 12.72 (bs, 1H), 11.31 (s, 1H), 8.20 (d, J=9.0 Hz, 1H), 7.92-7.83 (m, 2H), 7.70-7.26 (m, 7H), 3.93 (s, 2H), 3.87 (s, 2H), 3.23 (s, 3H), 3.06-2.86 (m, 4H), 1.77-1.72 (m, 4H).

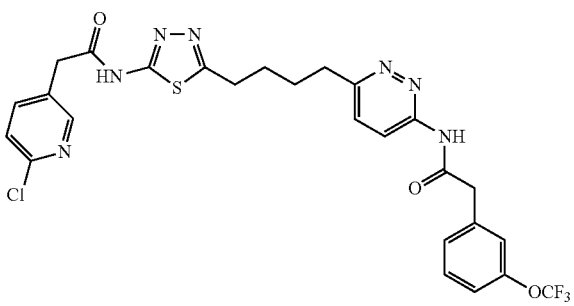

683

683 was made using procedure described for compound 675. ¹H NMR (300 MHz, DMSO-d₆) δ 12.75 (s, 1H), 11.32 (s, 1H), 8.36 (s, 1H), 8.21-8.18 (d, J=9.18 Hz, 1H), 7.84-7.80 (d, J=9.36 Hz, 1H), 7.59-7.26 (m, 6H), 3.90-3.87 (d, 4H), 3.01 (bs, 2H), 2.90 (bs, 2H), 1.73 (bs, 4H).

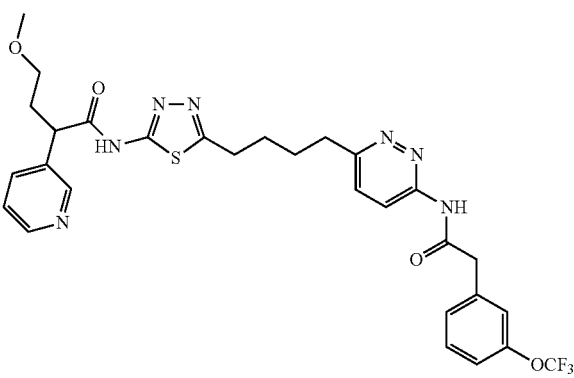

684

684 was made using procedure described for compound 675. ¹H NMR (300 MHz, DMSO-d₆) δ 12.75 (s, 1H), 11.32 (s, 1H), 8.57 (s, 1H), 8.51-8.49 (d, J=9.18 Hz, 1H), 8.21-8.18 (d, J=9.06 Hz, 1H), 7.79-7.75 (d, J=9.36 Hz, 1H), 7.59-7.26 (m, 6H), 4.07 (t, 2H), 3.87 (s, 2H), 3.30-3.28 (m, 1H), 3.19 (s, 3H), 3.01 (bs, 2H), 2.90 (bs, 2H), 2.3-2.5 (m, 1H), 1.99-1.96 (m, 1H), 1.73 (bs, 4H).

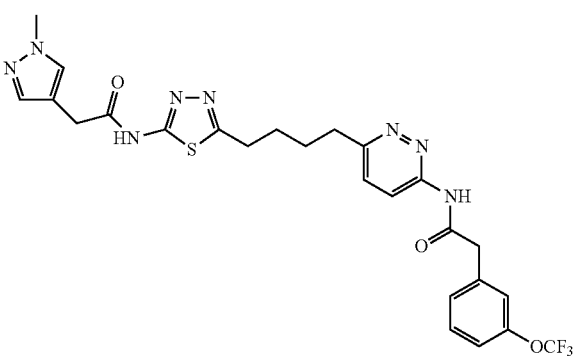

685

685 was prepared by the procedure as described for compound 661. ¹H NMR (300 MHz, DMSO-d₆) δ 12.52 (bs, 1H), 11.31 (s, 1H), 8.20 (d, J=9.1 Hz, 1H), 7.61-7.25 (m, 7H), 3.87 (s, 2H), 3.80 (s, 3H), 3.62 (s, 2H), 3.06-2.86 (m, 4H), 1.77-1.72 (m, 4H).

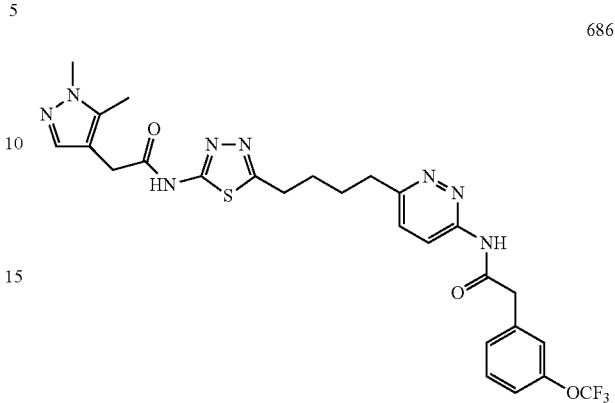

686

686 was prepared by the procedure as described for compound 661. ¹H NMR (300 MHz, DMSO-d₆) δ 12.53 (bs, 1H), 11.32 (s, 1H), 8.20 (d, J=9.1 Hz, 1H), 7.58 (d, J=9.2 Hz, 1H), 7.52-7.26 (m, 4H), 5.96 (s, 1H), 3.87 (s, 2H), 3.67 (s, 2H), 3.64 (s, 3H), 3.06-2.86 (m, 4H), 2.21 (s, 3H), 1.77-1.72 (m, 4H).

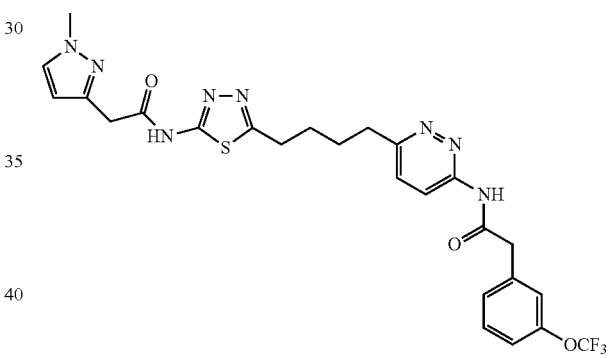

687

687 was prepared by the procedure as described for compound 661. ¹H NMR (300 MHz, DMSO-d₆) δ 12.56 (bs, 1H), 11.32 (s, 1H), 8.20 (d, J=9.3 Hz, 1H), 7.61-7.38 (m, 6H), 6.17 (d, J=2.2 Hz, 1H), 3.87 (s, 2H), 3.79 (s, 3H), 3.75 (s, 2H), 3.03-2.90 (m, 4H), 1.7-1.72 (m, 4H).

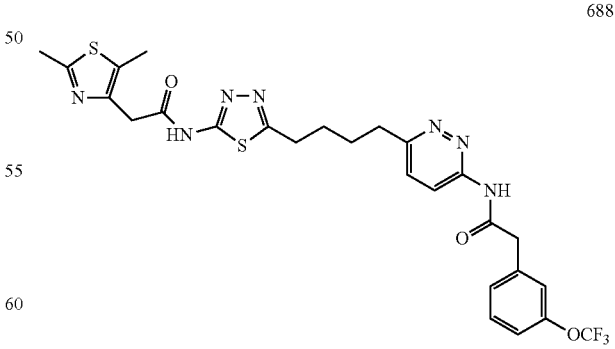

688

688 was prepared by the procedure as described for compound 661. ¹H NMR (300 MHz, DMSO-d₆) δ 12.61 (bs, 1H), 11.32 (s, 1H), 8.20 (d, J=9.3 Hz, 1H), 7.58 (d, J=9.3 Hz, 1H), 7.51-7.26 (m, 4H), 3.87 (s, 2H), 3.84 (s, 2H), 3.07-2.86 (m, 4H), 1.77-1.72 (m, 4H).

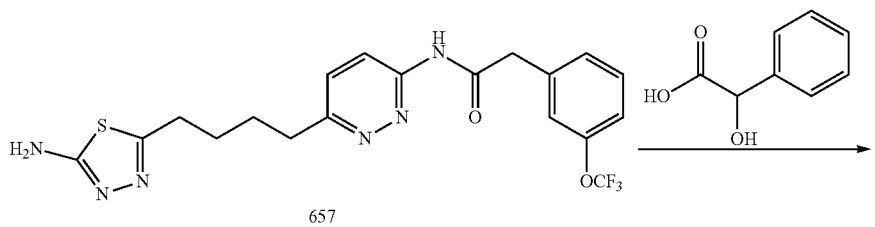

657

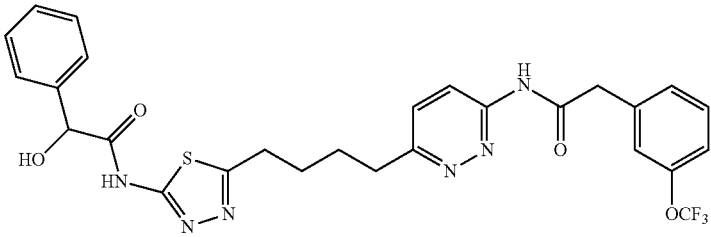

689

+

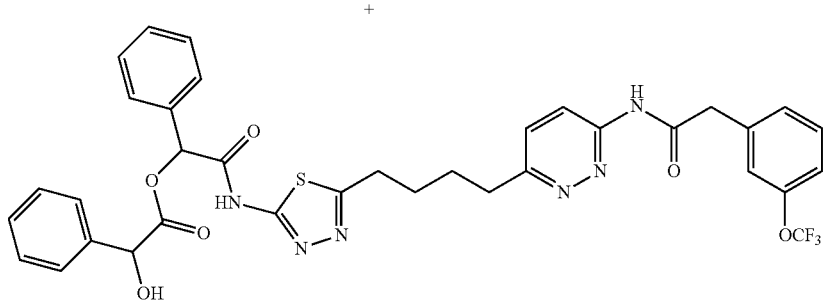

690

To a solution of 657 (200 mg, 0.44 mmol) in DMF (4 mL) at 0° C. was added mandelic acid (124 mg, 0.66 mmol), HOBt (119 mg, 0.88 mmol) and EDCI (170 mg, 0.88 mmol). The resulting mixture was stirred at room temperature for 1.5 h before it was cooled to 0° C. and quenched with H₂O. The precipitate was collected by suction filtration and further purified by silica gel chromatography eluting with 1-10% MeOH in dichloromethane to afford 690 and a more polar 689. 689: ¹H NMR (300 MHz, DMSO-d₆) δ 12.42 (bs, 1H), 11.31 (s, 1H), 8.20 (d, J=9.2 Hz, 1H), 7.58-7.27 (m, 10H), 6.35 (d, J=4.4 Hz, 1H), 5.34 (d, J=4.3 Hz, 1H), 3.87 (s, 2H), 3.03-2.89 (m, 4H), 1.77-1.73 (m, 4H). 690: ¹H NMR (300 MHz, DMSO-d₆) δ 13.05 (bs, 1H), 11.31 (s, 1H), 8.20 (d, J=9.0 Hz, 1H), 7.59-7.26 (m, 15H), 6.26 (d, J=5.5 Hz, 1H), 6.11 (s, 1H), 5.38 (d, J=5.3 Hz, 1H), 3.87 (s, 2H), 3.03-2.88 (m, 4H), 1.76-1.73 (m, 4H).

447

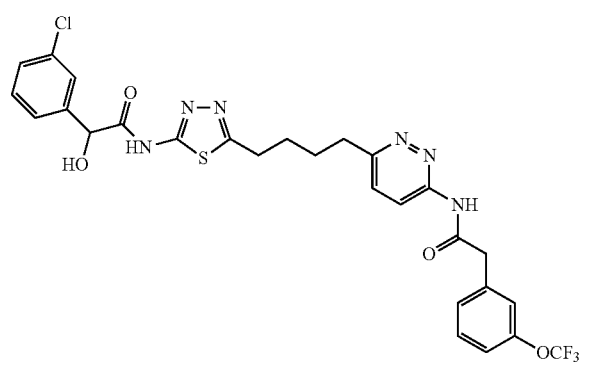

447 was prepared from 657 and 3-chloromandelic acid by the procedure as described for compound 689. ¹H NMR (300 MHz, DMSO-d₆) δ 12.48 (bs, 1H), 11.31 (s, 1H), 8.20 (d, J=9.2 Hz, 1H), 7.59-7.26 (m, 9H), 6.53 (m, 1H), 5.36 (t, J=0.7 Hz, 1H), 3.87 (s, 2H), 3.03-2.90 (m, 4H), 1.75-1.71 (m, 4H).

692

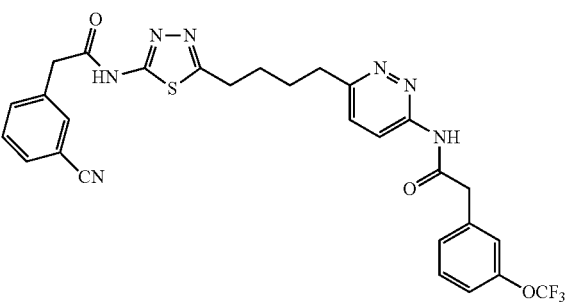

692 was made using procedure described for compound 675. ¹H NMR (300 MHz, DMSO-d₆) δ 12.75 (s, 1H), 11.32 (s, 1H), 8.21-8.18 (d, J=9.18 Hz, 1H), 7.80-7.26 (m, 9H), 3.92 (s, 2H), 3.87 (s, 2H), 3.01 (bs, 2H), 2.90 (bs, 2H), 1.73 (bs, 4H).

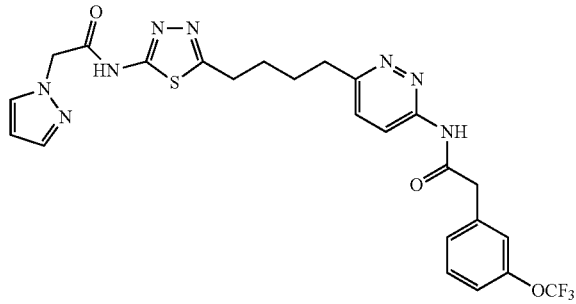

693

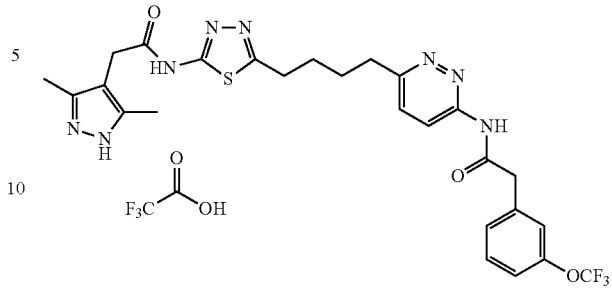

695

693 was made using procedure described for compound 675. ¹H NMR (300 MHz, DMSO-d₆) δ 12.75 (s, 1H), 11.32 (s, 1H), 8.22-8.19 (d, J=9.06 Hz, 1H), 7.79 (s, 1H), 7.59-7.26 (m, 6H), 6.31 (s, 1H), 5.20 (s, 2H), 3.87 (s, 2H), 3.01 (bs, 2H), 2.90 (bs, 2H), 1.73 (bs, 4H).

To a solution of 694 (50 mg, 0.081 mmol) in dichloromethane (2 ml) was added TFA (2 ml) at 0° C. The resulting mixture was stirred at room temperature for 1 h before it was evaporated under vacuo to dryness. Ether was added and the white precipitate was collected by suction filtration, rinsed with more ether to afford 695. ¹H NMR (300 MHz, DMSO-d₆) δ 12.71 (s, 1H), 11.32 (s, 1H), 8.22-8.19 (d, J=9.36 Hz, 1H), 7.60-7.57 (d, J=9.27 Hz, 1H), 7.51-7.28 (m, 4H), 3.88 (s, 2H), 3.57 (s, 2H), 3.01 (bs, 2H), 2.90 (bs, 2H), 2.45 (s, 3H), 2.15 (s, 3H), 1.73 (bs, 4H).

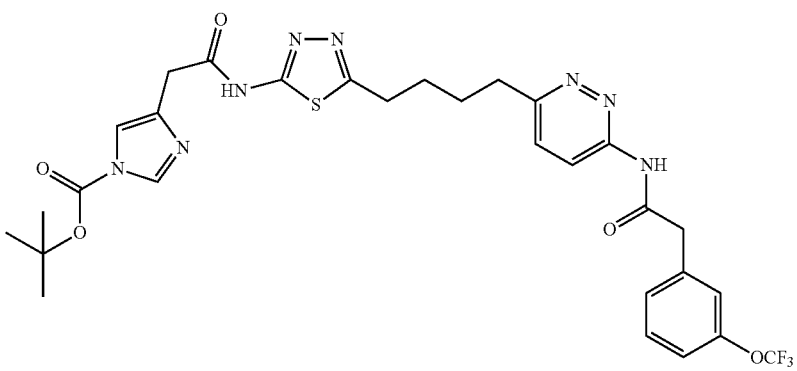

696

696 was made using procedure described for compound 695. ¹H NMR (300 MHz, DMSO-d₆) δ 12.71 (s, 1H), 11.32 (s, 1H), 8.22-8.19 (d, J=9.30 Hz, 1H), 8.15 (s, 1H), 7.58-7.54 (d, J=9.30 Hz, 1H), 7.48-7.28 (m, 5H), 3.87 (s, 2H), 3.76 (s, 2H), 3.01 (bs, 2H), 2.90 (bs, 2H), 1.73 (bs, 4H), 1.59 (s, 9H).

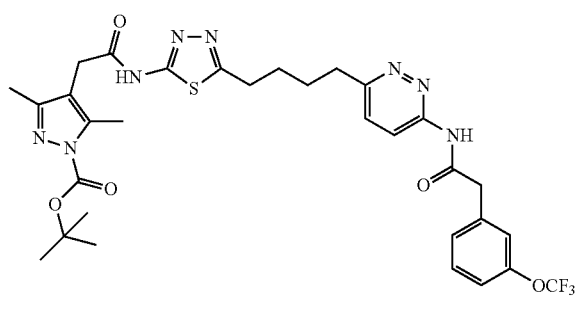

694

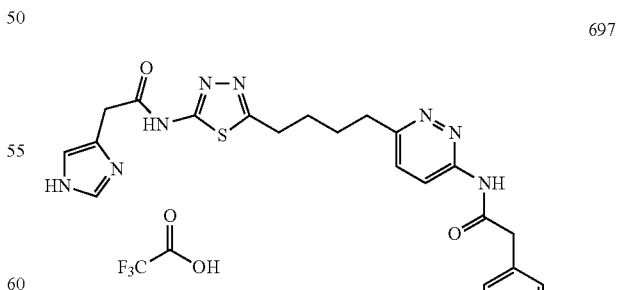

697

694 was made using procedure described for compound 675. ¹H NMR (300 MHz, DMSO-d₆) δ 12.71 (s, 1H), 11.32 (s, 1H), 8.22-8.18 (d, J=9.15 Hz, 1H), 7.58-7.54 (d, J=9.18 Hz, 1H), 7.48-7.26 (m, 4H), 3.87 (s, 2H), 3.63 (s, 2H), 3.01 (bs, 2H), 2.90 (bs, 2H), 2.39 (s, 3H), 2.13 (s, 3H), 1.73 (bs, 4H), 1.57 (s, 9H).

697 was made using procedure described for compound 695. ¹H NMR (300 MHz, DMSO-d₆) δ 14.22 (s, 1H), 12.71 (s, 1H), 11.32 (s, 1H), 9.01 (s, 1H), 8.22-8.19 (d, J=9.15 Hz, 1H), 7.59-7.26 (m, 6H), 4.04 (s, 2H), 3.87 (s, 2H), 3.01 (bs, 2H), 2.90 (bs, 2H), 1.73 (bs, 4H).

Preparative HPLC Purification

All reverse phase preparative HPLC purifications were performed using a Shimadzu Prominence Preparative Liquid Chromatograph with the column at ambient temperature. Mobile phases A and B consisted of 0.1% formic acid in water and 0.1% formic acid in acetonitrile, respectively. Crude product mixtures were dissolved in DMF, DMSO or mixtures thereof at concentrations of approximately 100 mg/mL and chromatographed according to the methods described in Table 2. Appropriate chromatographic fractions were then evaporated under high vacuum at 45° C. using a Savant Speed Vac Plus Model SC210A to yield purified products.

TABLE 2

Preparative HPLC Method Descriptions

| Compound ID | Column | Time (min) | % MPB | Flow Rate (mL/min) | Product Retention Time (min) |
|---|---|---|---|---|---|
| 7 | 1 | 0 | 20 | 2 | 7.4 |
|   |   | 1 | 20 | 2 |   |
|   |   | 2 | 20 | 5 |   |
|   |   | 3 | 70 | 5 |   |
|   |   | 14 | 100 | 5 |   |
| 8 | 1 | 0 | 20 | 2 | 11.5 |
|   |   | 1 | 20 | 2 |   |
|   |   | 2 | 20 | 5 |   |
|   |   | 3 | 70 | 5 |   |
|   |   | 14 | 100 | 5 |   |
| 26 | 1 | 0 | 40 | 1 | 6 |
|   |   | 1 | 40 | 2 |   |
|   |   | 3.5 | 40 | 4 |   |
|   |   | 4 | 40 | 4.73 |   |
|   |   | 10 | 90 | 4.73 |   |
| 29 | 2 | 0 | 40 | 2 | 7.7 |
|   |   | 1 | 40 | 3 |   |
|   |   | 2 | 40 | 18.9 |   |
|   |   | 13 | 50 | 18.9 |   |
| 36 | 2 | 0 | 32 | 3 | 12.1 |
|   |   | 0.5 | 32 | 5 |   |
|   |   | 1 | 32 | 18.9 |   |
|   |   | 13 | 35 | 18.9 |   |
| 143 | 2 | 0 | 50 | 3 | 9.1 |
|   |   | 1 | 50 | 3 |   |
|   |   | 2 | 50 | 18.9 |   |
|   |   | 5 | 50 | 18.9 |   |
|   |   | 15 | 80 | 18.9 |   |
| 153 | 2 | 0 | 35 | 3 | 6.2 |
|   |   | 1 | 35 | 3 |   |
|   |   | 2 | 35 | 18.9 |   |
|   |   | 4 | 35 | 18.9 |   |
|   |   | 14 | 75 | 18.9 |   |
| 199 | 2 | 0 | 45 | 3 | 8.3 |
|   |   | 1 | 45 | 3 |   |
|   |   | 2 | 45 | 18.9 |   |
|   |   | 3 | 45 | 18.9 |   |
|   |   | 13 | 65 | 18.9 |   |
| 203 | 2 | 0 | 50 | 3 | 9.6 |
|   |   | 1 | 50 | 3 |   |
|   |   | 2 | 50 | 18.9 |   |
|   |   | 5 | 50 | 18.9 |   |
|   |   | 15 | 60 | 18.9 |   |
| 208 | 2 | 0 | 35 | 3 | 7.6 |
|   |   | 1 | 35 | 3 |   |
|   |   | 2 | 35 | 18.9 |   |
|   |   | 4 | 35 | 18.9 |   |
|   |   | 14 | 50 | 18.9 |   |

The following representative synthetic protocols may also be used for producing compounds of the invention.

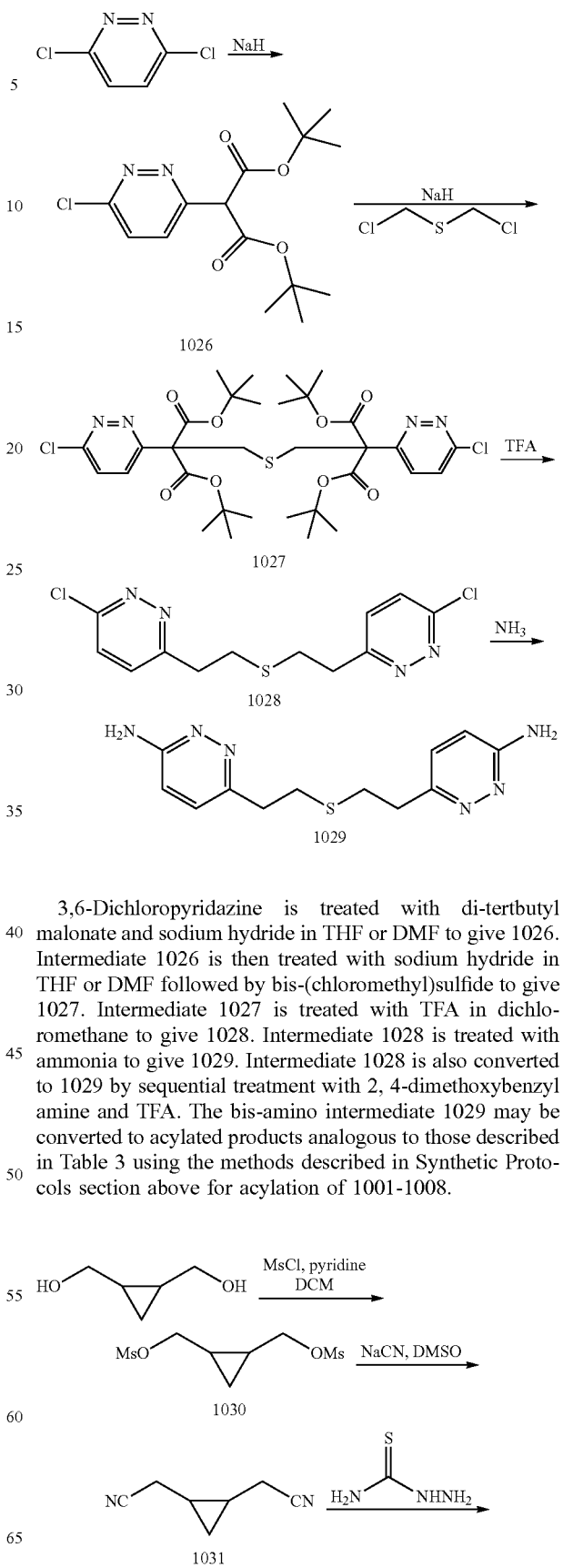

3,6-Dichloropyridazine is treated with di-tertbutyl malonate and sodium hydride in THF or DMF to give 1026. Intermediate 1026 is then treated with sodium hydride in THF or DMF followed by bis-(chloromethyl)sulfide to give 1027. Intermediate 1027 is treated with TFA in dichloromethane to give 1028. Intermediate 1028 is treated with ammonia to give 1029. Intermediate 1028 is also converted to 1029 by sequential treatment with 2,4-dimethoxybenzyl amine and TFA. The bis-amino intermediate 1029 may be converted to acylated products analogous to those described in Table 3 using the methods described in Synthetic Protocols section above for acylation of 1001-1008.

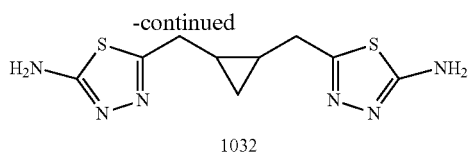

1032

Both trans- and cis-cyclopropane-1,2-diyldimethanols are converted into the corresponding bis-nitrile 1031 via bis-mesylated intermediate 1030. The bismesylate intermediate 1030 is prepared by treating the diol with methanesulfonyl chloride in the presence of pyridine or triethylamine in dichloromethane. The bisnitrile 1031 is prepared by treating 1030 with sodium cyanide in DMSO or ethanol/water. Using a procedure similar to that described for the preparation 1001, bis-nitrile 1031 undergoes cyclization with thiosemicarbazide in TFA to provide bis-amino intermediate 1032. The bis-amino intermediate 1032 may be converted to acylated products analogous to those described in Table 3 using the methods described in Synthetic Protocols section above for acylation of 1001-1008.

2 mM NAD$^+$, and 10 ppm antifoam) and 50 μL added to a 96-well half area clear plate (Corning #3695). Compound (2 μL) was added to give a final DMSO concentration of 2% at 2× the desired concentration of compound. Enzymatic reaction was started with the addition of 50 μL of enzyme solution (50 mM Tris-HCl pH 8.0, 0.2 mM EDTA, 150 mM K$_2$HPO$_4$, 0.1 mg/ml BSA, 1 mM DTT, 10 ppm antifoam, 4 units/ml GDH, 4 mM adenosine diphosphate, and 4 nM GAC) and read in a Molecular Devices M5 plate reader at 20° C. The plate reader was configured to read absorbance (λ=340 nm) in kinetic mode for 15 minutes. Data was recorded as milli-absorbance units per minute and slopes were compared to a control compound and a DMSO-only control on the same plate. Compounds with slopes less than the DMSO control were considered inhibitors and plate variability was assessed using the control compound.

Results from this assay for several compounds of the invention are shown in Table 3, expressed as IC50, or half maximal inhibitory concentration, wherein IC50 is a quantitative measure indicating how much compound is needed to inhibit a given biological activity by half.

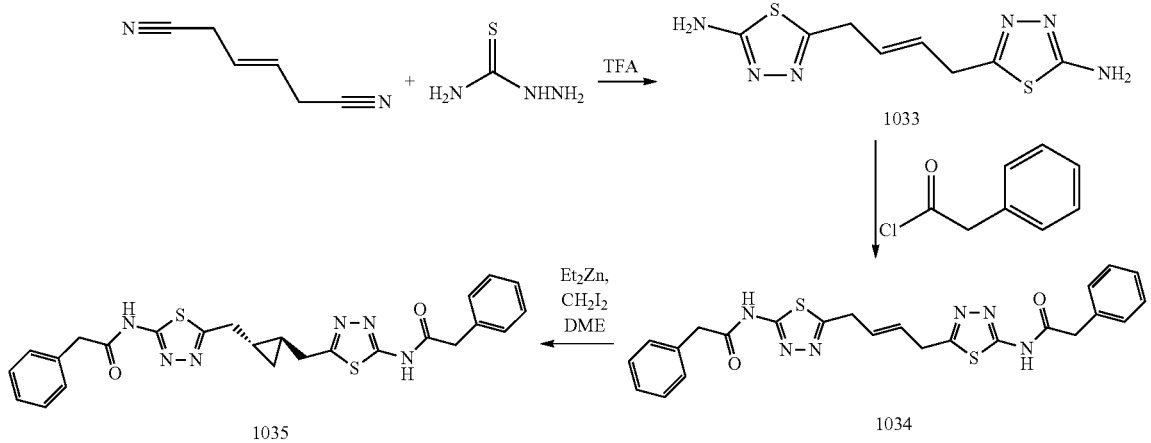

The alkene analog 1033 is prepared from trans-3-hexenedinitrile using a procedure similar to that described for the preparation 1001. The bis-amino intermediate 1033 may be converted to acylated products analogous to those described in Table 3 (for example, 1034) using the methods described in Synthetic Protocols section above for acylation of 1001-1008. The products may be further converted to cyclopropyl analogs (exemplified by 1035) under the Simmons-Smith conditions (Et$_2$Zn, CH$_2$I$_2$,1,2-dimethoxyethane).

Example 2: Compound Assays

Compounds were assayed in both an in vitro biochemical assay and a cell proliferation assay as follows. The IC50 results are provided in Table 3.

Recombinant Enzyme Assay

Compounds were assessed for their ability to inhibit the enzymatic activity of a recombinant form of Glutaminase 1 (GAC) using a biochemical assay that couples the production of glutamate (liberated by GAC) to glutamate dehydrogenase (GDH) and measuring the change in absorbance for the reduction of NAD$^+$ to NADH. Substrate solution was prepared (50 mM Tris-HCl pH 8.0, 0.2 mM EDTA, 150 mM K$_2$HPO$_4$, 0.1 mg/ml BSA, 1 mM DTT, 20 mM L-glutamine, Recombinant Enzyme Assay—Time Dependence Compounds were assessed for their ability to inhibit the enzymatic activity of a recombinant form of Glutaminase 1 (GAC) using a biochemical assay that couples the production of glutamate (liberated by GAC) to glutamate dehydrogenase (GDH) and measuring the change in absorbance for the reduction of NAD$^+$ to NADH. Enzyme solution was prepared (50 mM Tris-HCl pH 8.0, 0.2 mM EDTA, 150 mM K$_2$HPO$_4$, 0.1 mg/ml BSA, 1 mM DTT, 10 ppm antifoam, 4 units/ml GDH, 4 mM adenosine diphosphate, and 4 nM GAC) and 50 μL added to a 96-well half area clear plate (Corning #3695). Compound (2 μL) was added to give a final DMSO concentration of 2% at 2× the desired concentration of compound. The enzyme/compound mix was sealed with sealing foil (USA Scientific) and allowed to incubate, with mild agitation, for 60 minutes at 20° C. Enzymatic reaction was started with the addition of 50 μL of substrate solution (50 mM Tris-HCl pH 8.0, 0.2 mM EDTA, 150 mM K$_2$HPO$_4$, 0.1 mg/ml BSA, 1 mM DTT, 20 mM L-glutamine, 2 mM NAD$^+$, and 10 ppm antifoam) and read in a Molecular Devices M5 plate reader at 20° C. The plate reader was configured to read absorbance (λ=340 nm) in kinetic mode for 15 minutes. Data was recorded as milli-absorbance units per minute and slopes were compared to a control compound and a DMSO-only control on the same plate. Compounds with slopes less than the DMSO control were considered inhibitors and plate variability was assessed using the control compound.

Results from this assay for several compounds of the invention are shown in Table 3, expressed as IC50, or half maximal inhibitory concentration, wherein IC50 is a quantitative measure indicating how much compound is needed to inhibit a given biological activity by half.

Cell Proliferation Assay

P493-6 (myc "on") cells were maintained in growth media (RPMI-1640, 10% FBS, 2 mM glutamine, 100 units/ml Penicillin and 100 µg/ml streptomycin) at 37° C. with 5% $CO_2$. For compound assay, P493-6 cells were plated in 96-well V-bottom plates on the day of compound addition in 50 µl of growth media at a cell density of 200,000 cells/ml (10,000 cells/well). Compounds were serially diluted in 100% DMSO at 200-times the final concentration. Compounds were diluted 100-fold into growth media and then 50 µl of this mixture was added to cell plates making the final concentration of DMSO 0.5%. Cells were incubated with compound for 72 hrs at 37° C. with 5% $CO_2$ and analyzed for antiproliferative effects either by Cell Titer Glo (Promega) or FACS analysis using the Viacount (Millipore) kit on the Guava instrument.

Results from this assay for several compounds of the invention are shown in Table 3, expressed as IC50, or half maximal inhibitory concentration, wherein IC50 is a quantitative measure indicating how much compound is needed to inhibit a given biological activity by half.

TABLE 3

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 1 | 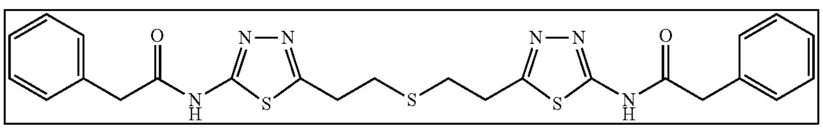 [SMILES: O=C(Cc1ccccc1)Nc1nnc(CCSCCc2nnc(NC(=O)Cc3ccccc3)s2)s1] | 0.10 | 0.20 | 0.47 |
| 2 | 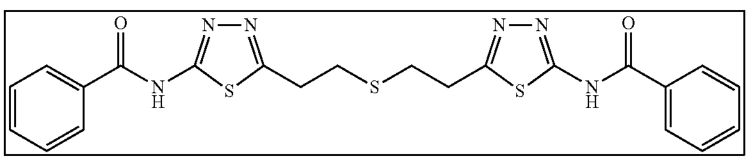 [SMILES: O=C(Nc1nnc(CCSCCc2nnc(NC(=O)c3ccccc3)s2)s1)c1ccccc1] | | 4.1 | 0.63 |
| 3 | 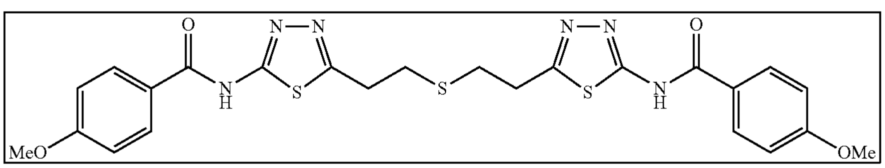 [SMILES: COc1ccc(C(=O)Nc2nnc(CCSCCc3nnc(NC(=O)c4ccc(OC)cc4)s3)s2)cc1] | >50 | | >50 |
| 4 | 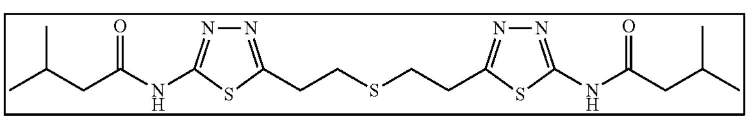 | 13 | | >50 |
| 5 | 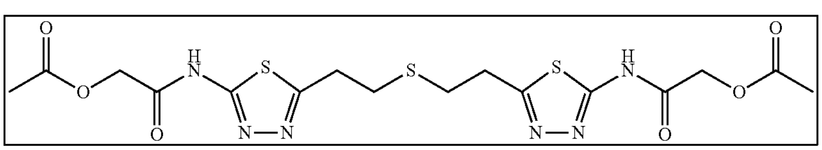 [SMILES: CC(=O)OCC(=O)Nc1nnc(CCSCCc2nnc(NC(=O)COC(C)=O)s2)s1] | >50 | | >50 |
| 6 | 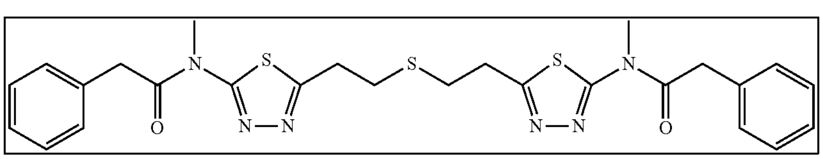 [SMILES: CN(C(=O)Cc1ccccc1)c1nnc(CCSCCc2nnc(N(C)C(=O)Cc3ccccc3)s2)s1] | >50 | | 2.7 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 7 | 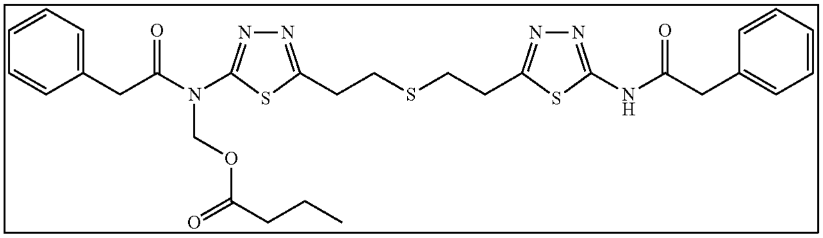 [SMILES: CCCC(=O)OCN(C(=O)Cc1ccccc1)c1nnc(CCSCCc2nnc(NC(=O)Cc3ccccc3)s2)s1] | | >50 | 1.0 |
| 8 | 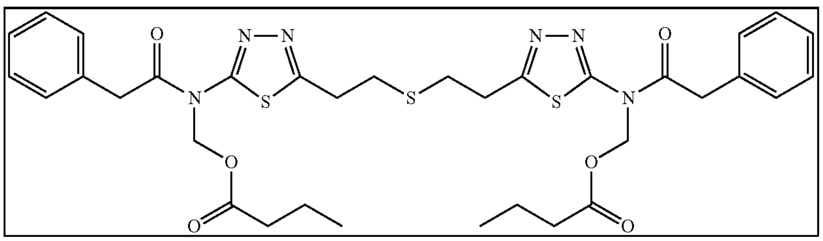 [SMILES: CCCC(=O)OCN(C(=O)Cc1ccccc1)c1nnc(CCSCCc2nnc(N(COC(=O)CCC)C(=O)Cc3ccccc3)s2)s1] | | >50 | 1.6 |
| 9 | 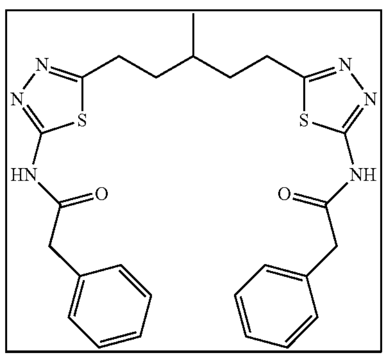 [SMILES: CC(CCc1nnc(NC(=O)Cc2ccccc2)s1)CCc1nnc(NC(=O)Cc2ccccc2)s1] | | >50 | >50 |
| 10 | 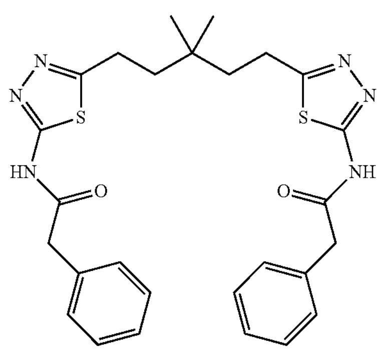 [SMILES: CC(C)(CCc1nnc(NC(=O)Cc2ccccc2)s1)CCc1nnc(NC(=O)Cc2ccccc2)s1] | | >50 | >50 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 11 | 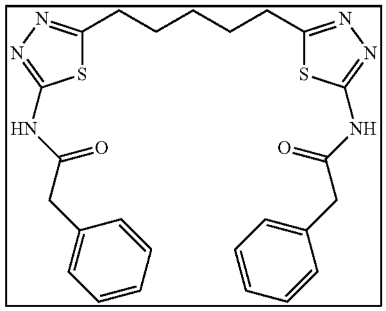 [SMILES: O=C(Cc1ccccc1)Nc1nnc(CCCCCc2nnc(NC(=O)Cc3ccccc3)s2)s1] | | 1.4 | 0.89 |
| 12 | 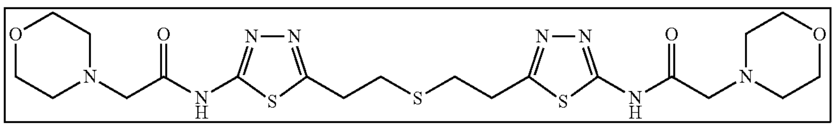 [SMILES: O=C(CN1CCOCC1)Nc1nnc(CCSCCc2nnc(NC(=O)CN3CCOCC3)s2)s1] | | >50 | 36 |
| 13 | 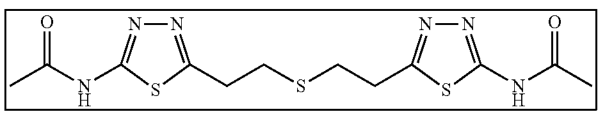 [SMILES: CC(=O)Nc1nnc(CCSCCc2nnc(NC(C)=O)s2)s1] | | 7.7 | 12 |
| 14 | 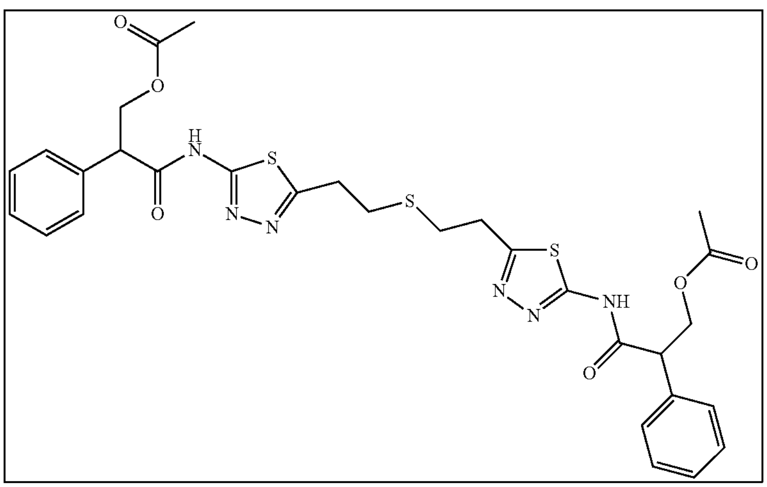 [SMILES: CC(=O)OCC(C(=O)Nc1nnc(CCSCCc2nnc(NC(=O)C(COC(C)=O)c3ccccc3)s2)s1)c1ccccc1] | | 2.8 | 1.8 |
| 15 | 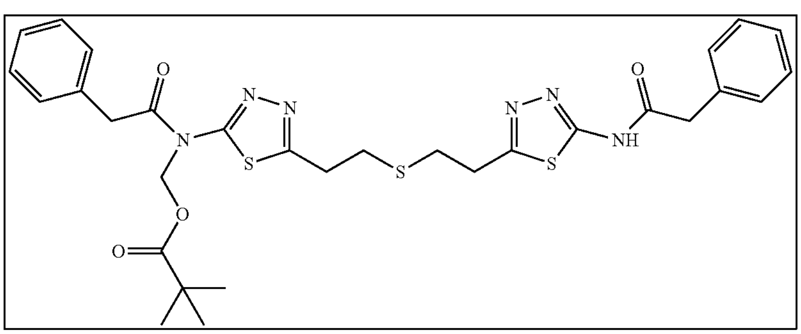 [SMILES: CC(C)(C)C(=O)OCN(C(=O)Cc1ccccc1)c1nnc(CCSCCc2nnc(NC(=O)Cc3ccccc3)s2)s1] | | >50 | 1.2 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 16 | 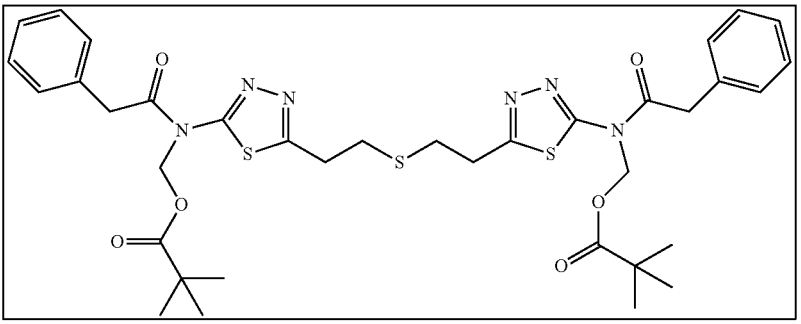 [SMILES: CC(C)(C)C(=O)OCN(C(=O)Cc1ccccc1)c1nnc(CCSCCc2nnc(N(COC(=O)C(C)(C)C)C(=O)Cc3ccccc3)s2)s1] | | >50 | 0.80 |
| 17 | 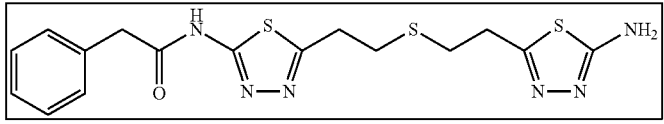 [SMILES: Nc1nnc(CCSCCc2nnc(NC(=O)Cc3ccccc3)s2)s1] | | 15 | 4.2 |
| 18 | 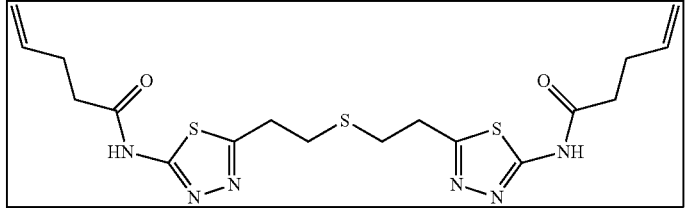 [SMILES: C=CCCC(=O)Nc1nnc(CCSCCc2nnc(NC(=O)CCC=C)s2)s1] | | 4.5 | 8.2 |
| 19 | 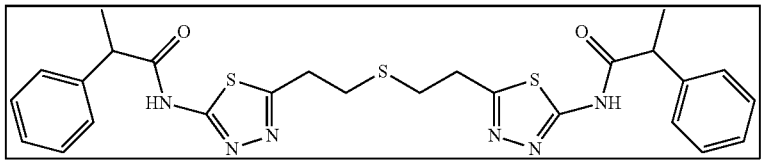 [SMILES: CC(C(=O)Nc1nnc(CCSCCc2nnc(NC(=O)C(C)c3ccccc3)s2)s1)c1ccccc1] | | 11 | 1.7 |
| 20 | 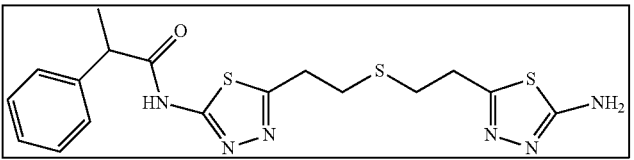 [SMILES: CC(C(=O)Nc1nnc(CCSCCc2nnc(N)s2)s1)c1ccccc1] | | 6.6 | 2.6 |
| 21 | 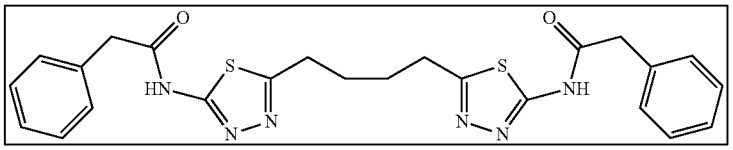 [SMILES: O=C(Cc1ccccc1)Nc1nnc(CCCCc2nnc(NC(=O)Cc3ccccc3)s2)s1] | | 0.16 | 0.02 |
| 22 | 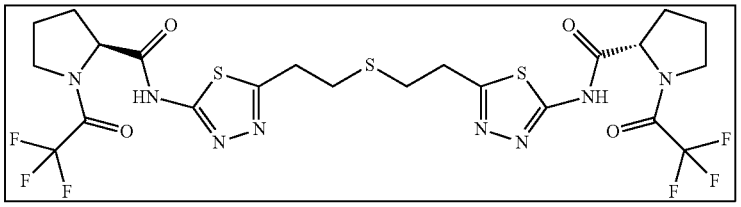 [SMILES: O=C(Nc1nnc(CCSCCc2nnc(NC(=O)[C@@H]3CCCN3C(=O)C(F)(F)F)s2)s1)[C@@H]1CCCN1C(=O)C(F)(F)F] | | >50 | >50 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 23 | 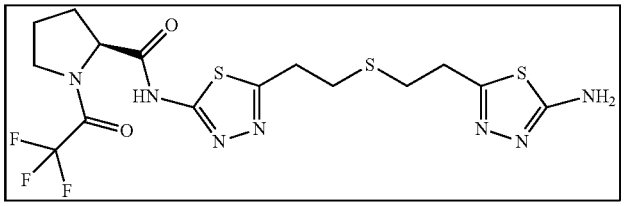 [SMILES: Nc1nnc(CCSCCc2nnc(NC(=O)[C@@H]3CCCN3C(=O)C(F)(F)F)s2)s1] | | >50 | >50 |
| 24 | 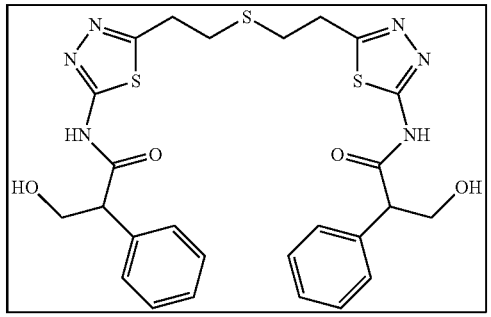 [SMILES: O=C(Nc1nnc(CCSCCc2nnc(NC(=O)C(CO)c3ccccc3)s2)s1)C(CO)c1ccccc1] | | 0.51 | 2.3 |
| 25 | 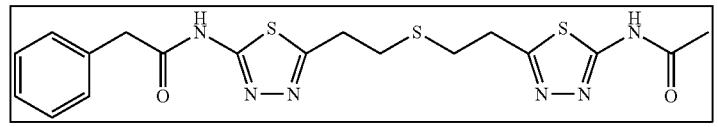 [SMILES: CC(=O)Nc1nnc(CCSCCc2nnc(NC(=O)Cc3ccccc3)s2)s1] | | 1.2 | 1.5 |
| 26 | 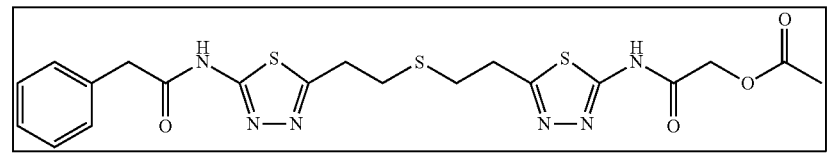 [SMILES: CC(=O)OCC(=O)Nc1nnc(CCSCCc2nnc(NC(=O)Cc3ccccc3)s2)s1] | | 5.6 | 0.70 |
| 27 | 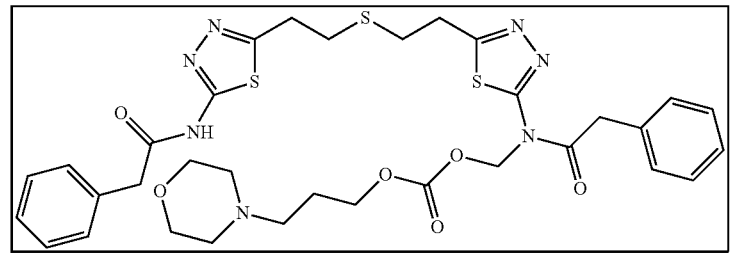 [SMILES: O=C(Cc1ccccc1)Nc1nnc(CCSCCc2nnc(N(COC(=O)OCCCN3CCOCC3)C(=O)Cc3ccccc3)s2)s1] | | >50 | 0.47 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 28 | 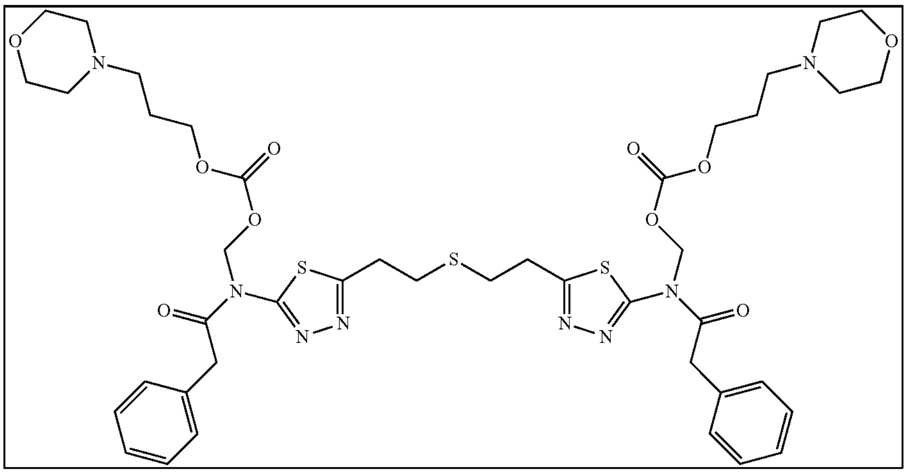 [SMILES: O=C(OCCCN1CCOCC1)OCN(C(=O)Cc1ccccc1)c1nnc(CCSCCc2nnc(N(COC(=O)OCCCN3CCOCC3)C(=O)Cc3ccccc3)s2)s1] | | >50 | 1.0 |
| 29 | 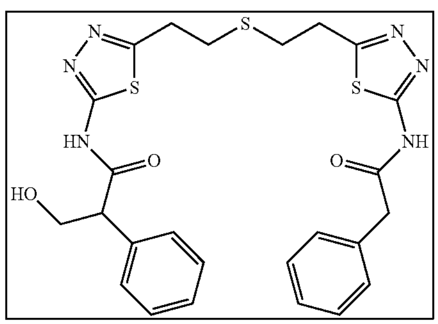 [SMILES: O=C(Cc1ccccc1)Nc1nnc(CCSCCc2nnc(NC(=O)C(CO)c3ccccc3)s2)s1] | 0.56 | | 4.1 |
| 30 | 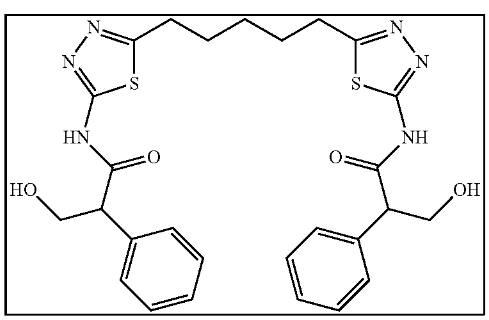 [SMILES: O=C(Nc1nnc(CCCCCc2nnc(NC(=O)C(CO)c3ccccc3)s2)s1)C(CO)c1ccccc1] | 1.2 | | 2.5 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 31 | 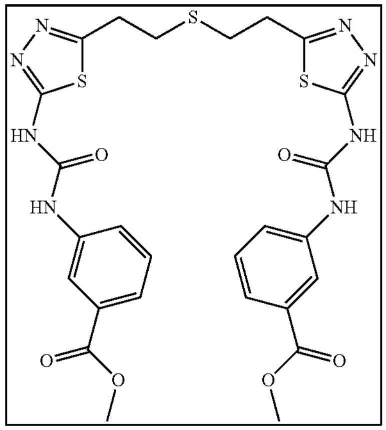 [SMILES: COC(=O)c1cccc(NC(=O)Nc2nnc(CCSCCc3nnc(NC(=O)Nc4cccc(C(=O)OC)c4)s3)s2)c1] | | >50 | 4.3 |
| 32 | 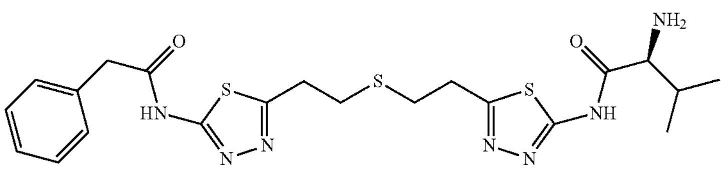 [SMILES: CC(C)[C@H](N)C(=O)Nc1nnc(CCSCCc2nnc(NC(=O)Cc3ccccc3)s2)s1] | | 7.0 | 11 |
| 33 | 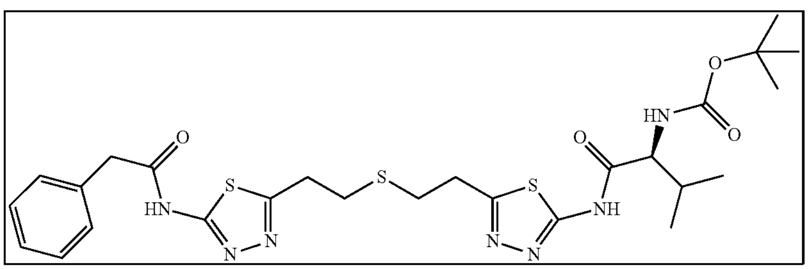 [SMILES: CC(C)[C@H](NC(=O)OC(C)(C)C)C(=O)Nc1nnc(CCSCCc2nnc(NC(=O)Cc3ccccc3)s2)s1] | | 13 | 5.3 |
| 34 | 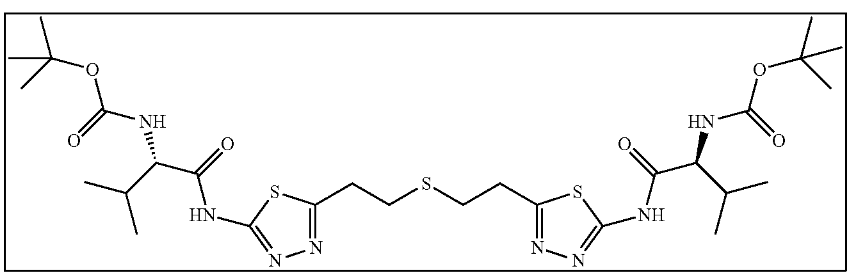 [SMILES: CC(C)[C@H](NC(=O)OC(C)(C)C)C(=O)Nc1nnc(CCSCCc2nnc(NC(=O)[C@@H](NC(=O)OC(C)(C)C)C(C)C)s2)s1] | | >50 | >50 |
| 35 | 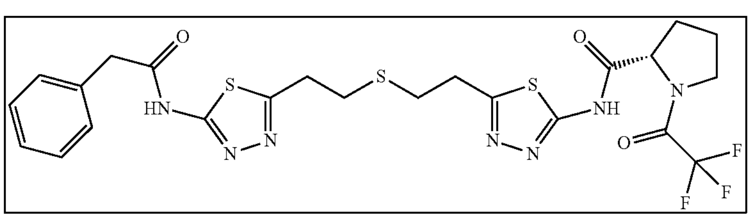 [SMILES: O=C(Cc1ccccc1)Nc1nnc(CCSCCc2nnc(NC(=O)[C@@H]3CCCN3C(=O)C(F)(F)F)s2)s1] | | 18 | 3.8 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 36 | 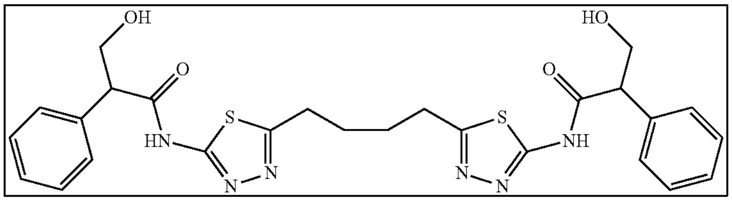 [SMILES: O=C(Nc1nnc(CCCCc2nnc(NC(=O)C(CO)c3ccccc3)s2)s1)C(CO)c1ccccc1] | 0.04 | 0.22 | 0.16 |
| 37 | 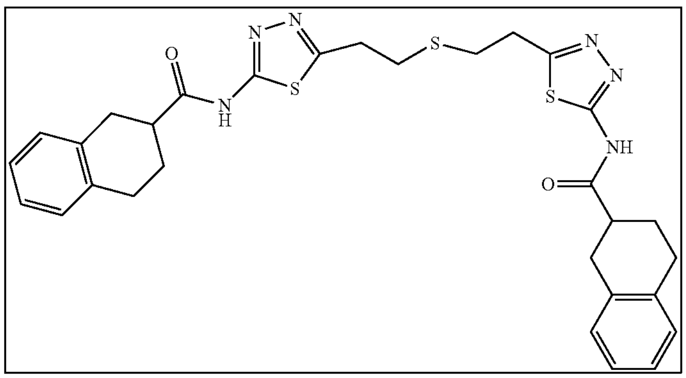 [SMILES: O=C(Nc1nnc(CCSCCc2nnc(NC(=O)C3CCc4ccccc4C3)s2)s1)C1CCc2ccccc2C1] | | >50 | >50 |
| 38 | 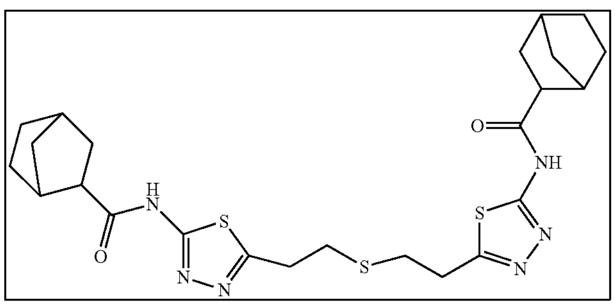 [SMILES: O=C(Nc1nnc(CCSCCc2nnc(NC(=O)C3CC4CCC3C4)s2)s1)C1CC2CCC1C2] | | >50 | 3.2 |
| 39 | 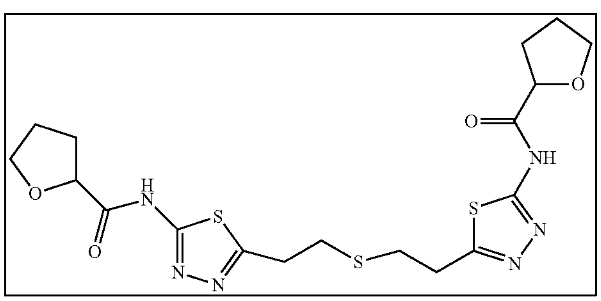 [SMILES: O=C(Nc1nnc(CCSCCc2nnc(NC(=O)C3CCCO3)s2)s1)C1CCCO1] | | 26 | 4.5 |
| 40 | 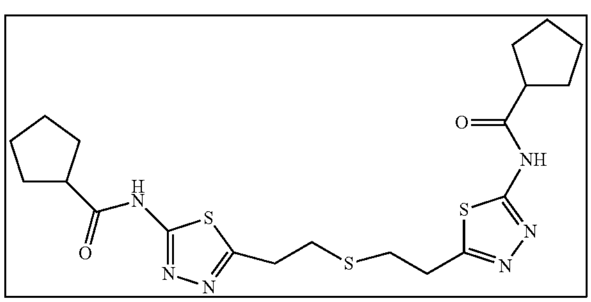 [SMILES: O=C(Nc1nnc(CCSCCc2nnc(NC(=O)C3CCCC3)s2)s1)C1CCCC1] | | 3.7 | 0.56 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 41 | 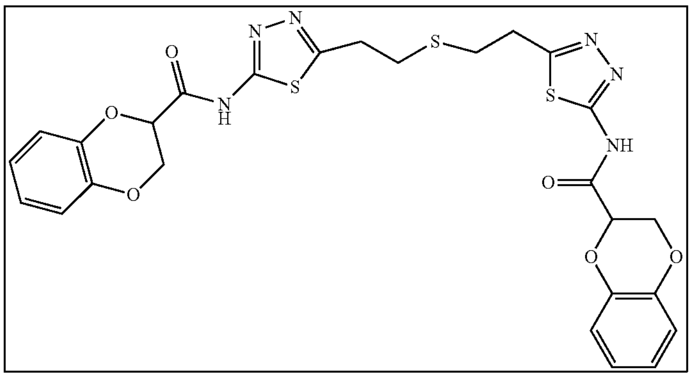 [SMILES: O=C(Nc1nnc(CCSCCc2nnc(NC(=O)C3COc4ccccc4O3)s2)s1)C1COc2ccccc2O1] | | 7.9 | 33 |
| 42 | 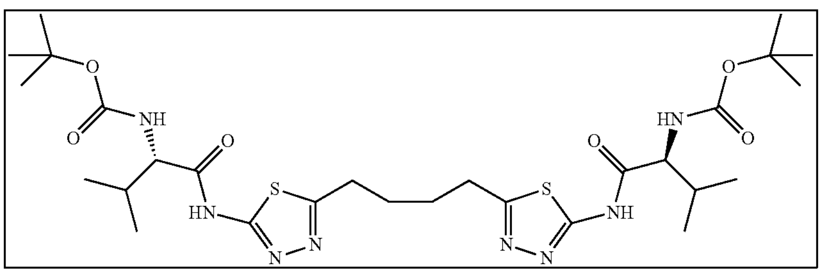 [SMILES: CC(C)[C@H](NC(=O)OC(C)(C)C)C(=O)Nc1nnc(CCCCc2nnc(NC(=O)[C@@H](NC(=O)OC(C)(C)C)C(C)C)s2)s1] | | >50 | >50 |
| 43 | 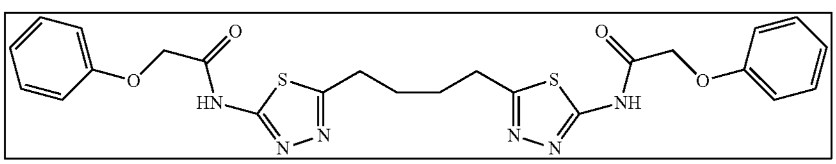 [SMILES: O=C(COc1ccccc1)Nc1nnc(CCCCc2nnc(NC(=O)COc3ccccc3)s2)s1] | | 2.3 | >50 |
| 44 | 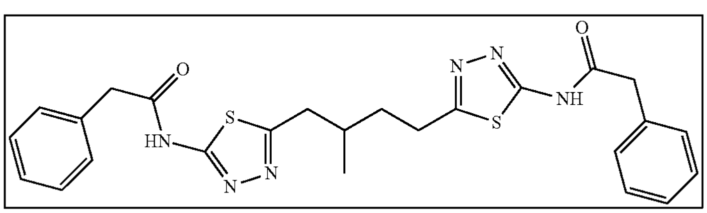 [SMILES: CC(CCc1nnc(NC(=O)Cc2ccccc2)s1)Cc1nnc(NC(=O)Cc2ccccc2)s1] | | 4.9 | 2.6 |
| 45 | 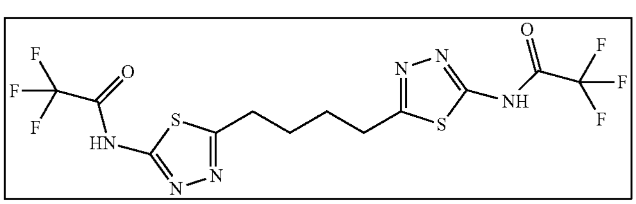 [SMILES: O=C(Nc1nnc(CCCCc2nnc(NC(=O)C(F)(F)F)s2)s1)C(F)(F)F] | | >50 | >50 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 46 | 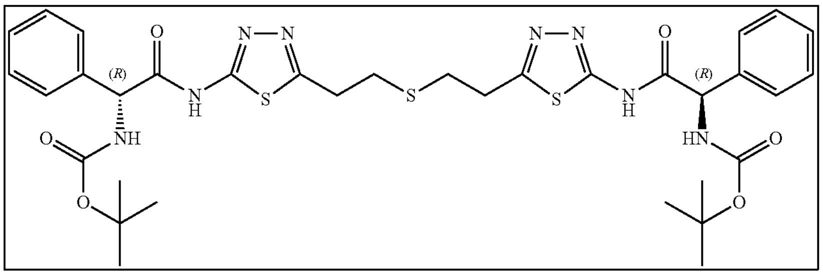 | | >50 | 16 |
| 47 | 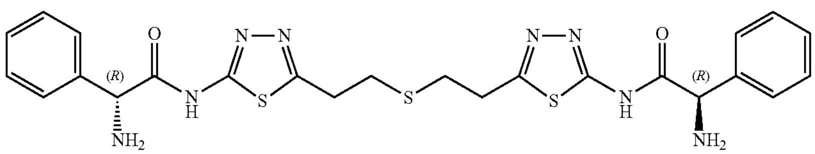 | | 8.3 | 35 |
| 48 | 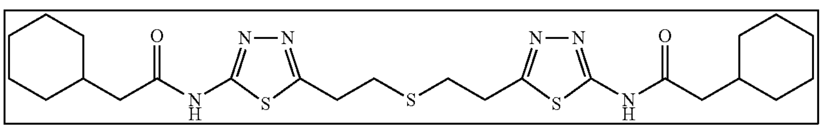 [SMILES: O=C(CC1CCCCC1)Nc1nnc(CCSCCc2nnc(NC(=O)CC3CCCCC3)s2)s1] | | >50 | 0.42 |
| 49 | 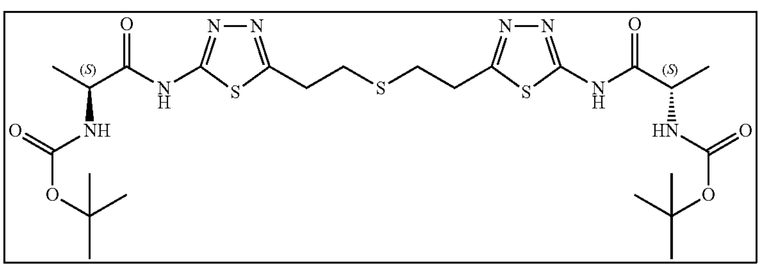 | | 36 | 17 |
| 50 | 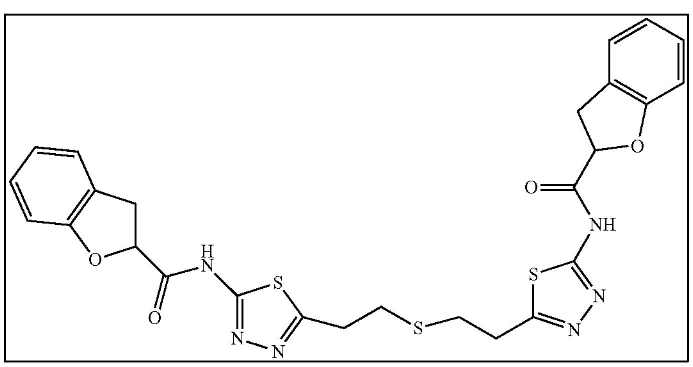 [SMILES: O=C(Nc1nnc(CCSCCc2nnc(NC(=O)C3Cc4ccccc4O3)s2)s1)C1Cc2ccccc2O1] | | 2.5 | 8.2 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 51 | 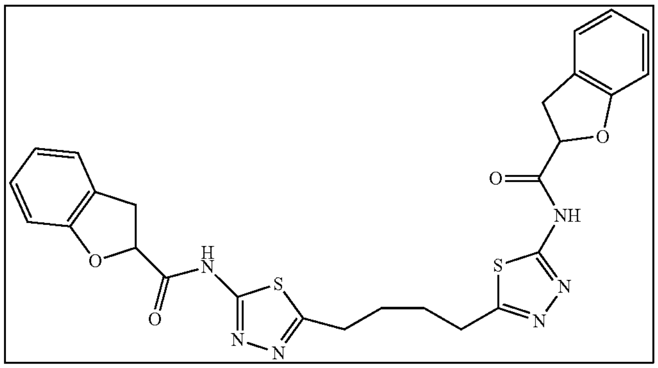 [SMILES: O=C(Nc1nnc(CCCCc2nnc(NC(=O)C3Cc4ccccc4O3)s2)s1)C1Cc2ccccc2O1] | | 1.2 | 1.3 |
| 52 | 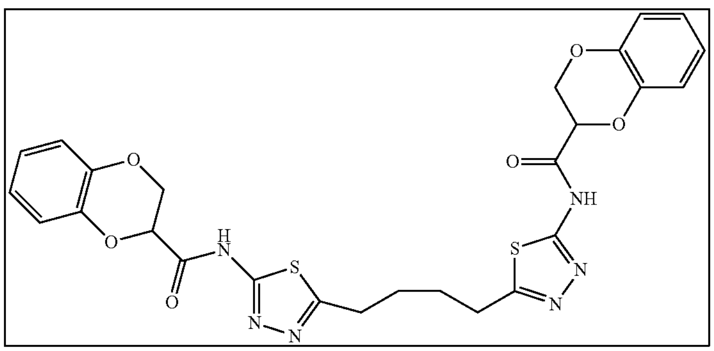 [SMILES: O=C(Nc1nnc(CCCCc2nnc(NC(=O)C3COc4ccccc4O3)s2)s1)C1COc2ccccc2O1] | | 8.3 | 30 |
| 53 | 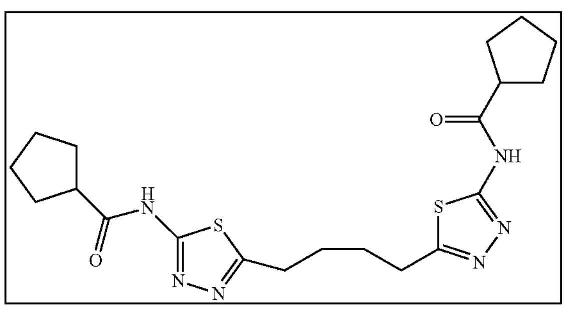 | | >50 | 34 |
| 54 | 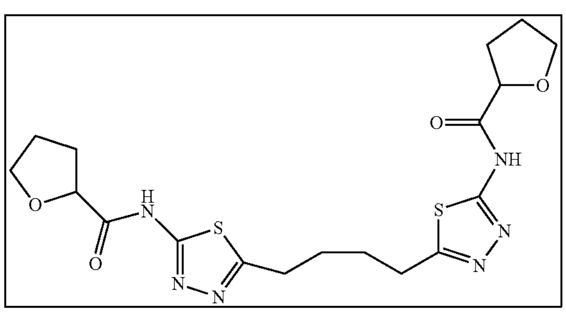 [SMILES: O=C(Nc1nnc(CCCCc2nnc(NC(=O)C3CCCO3)s2)s1)C1CCCO1] | | 9.2 | 1.6 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 55 | 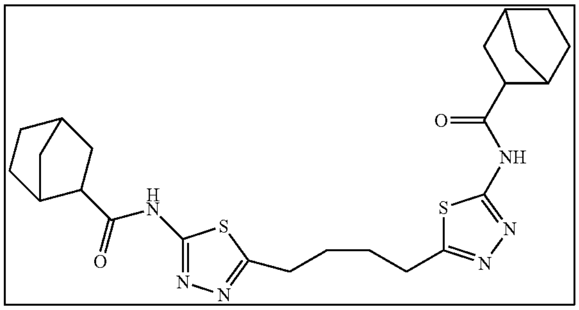 [SMILES: O=C(Nc1nnc(CCCCc2nnc(NC(=O)C3CC4CCC3C4)s2)s1)C1CC2CCC1C2] | | >50 | 3.9 |
| 56 | 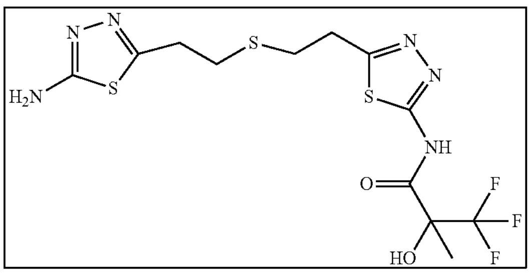 [SMILES: CC(O)(C(=O)Nc1nnc(CCSCCc2nnc(N)s2)s1)C(F)(F)F] | | >50 | |
| 57 | 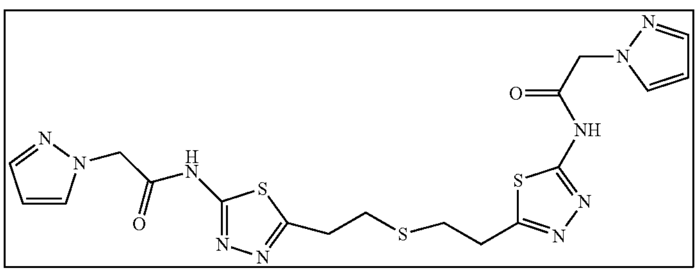 [SMILES: O=C(Cn1cccn1)Nc1nnc(CCSCCc2nnc(NC(=O)Cn3cccn3)s2)s1] | | 40 | |
| 58 | 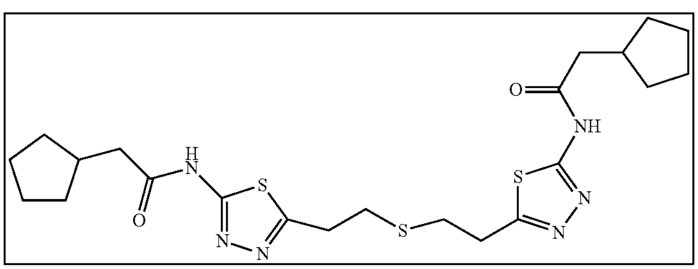 [SMILES: O=C(CC1CCCC1)Nc1nnc(CCSCCc2nnc(NC(=O)CC3CCCC3)s2)s1] | | >50 | 3.7 |
| 59 | 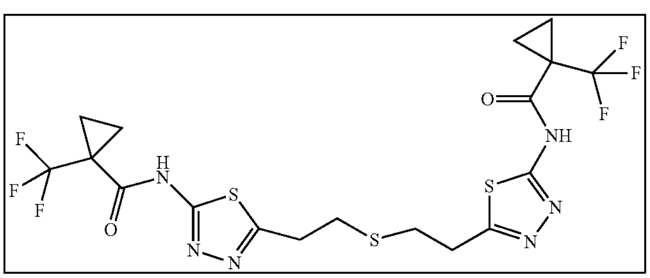 [SMILES: O=C(Nc1nnc(CCSCCc2nnc(NC(=O)C3(C(F)(F)F)CC3)s2)s1)C1(C(F)(F)F)CC1] | | >50 | |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 60 | 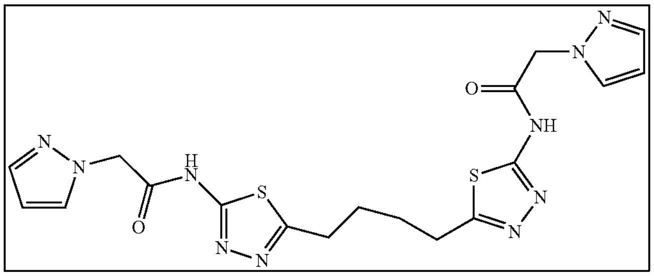 [SMILES: O=C(Cn1cccn1)Nc1nnc(CCCCc2nnc(NC(=O)Cn3cccn3)s2)s1] | | 24 | 14 |
| 61 | 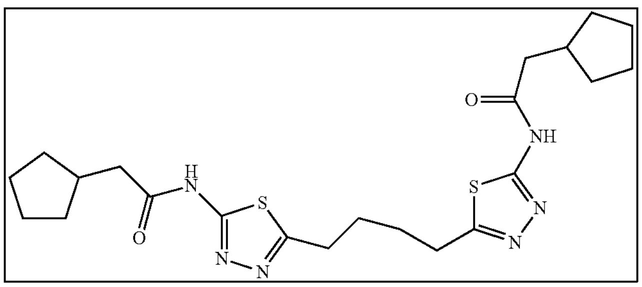 [SMILES: O=C(CC1CCCC1)Nc1nnc(CCCCc2nnc(NC(=O)CC3CCCC3)s2)s1] | | >50 | |
| 62 | 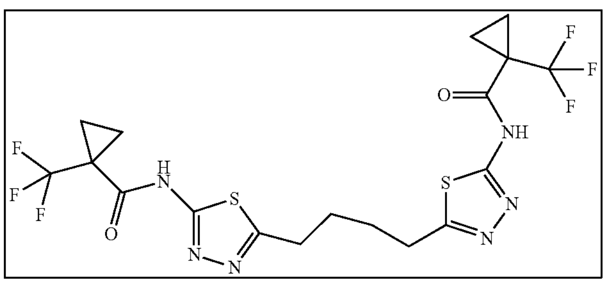 [SMILES: O=C(Nc1nnc(CCCCc2nnc(NC(=O)C3(C(F)(F)F)CC3)s2)s1)C1(C(F)(F)F)CC1] | | >50 | 19 |
| 63 | 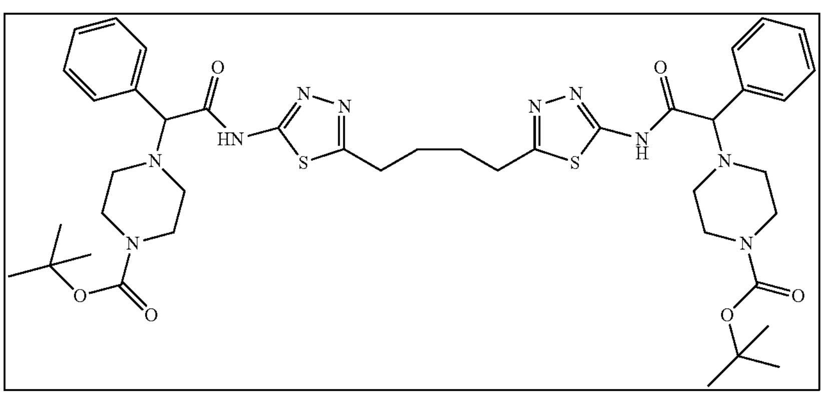 [SMILES: CC(C)(C)OC(=O)N1CCN(C(C(=O)Nc2nnc(CCCCc3nnc(NC(=O)C(c4ccccc4)N4CCN(C(=O)OC(C)(C)C)CC4)s3)s2)c2ccccc2)CC1] | | 25 | 2.6 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 64 | 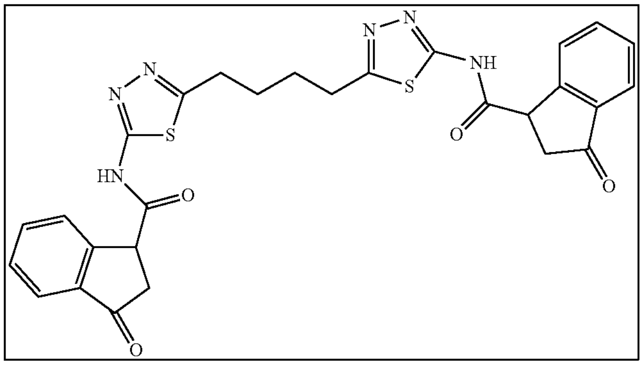 [SMILES: O=C1CC(C(=O)Nc2nnc(CCCCc3nnc(NC(=O)C4CC(=O)c5ccccc54)s3)s2)c2ccccc21] | | 1.3 | 0.23 |
| 65 | 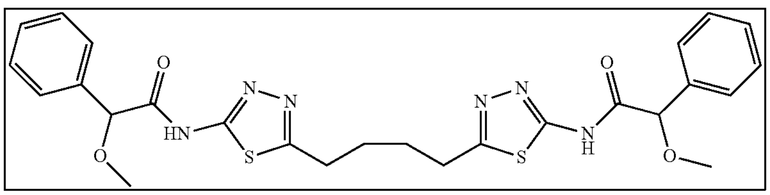 [SMILES: COC(C(=O)Nc1nnc(CCCCc2nnc(NC(=O)C(OC)c3ccccc3)s2)s1)c1ccccc1] | | 1.3 | 0.52 |
| 66 | 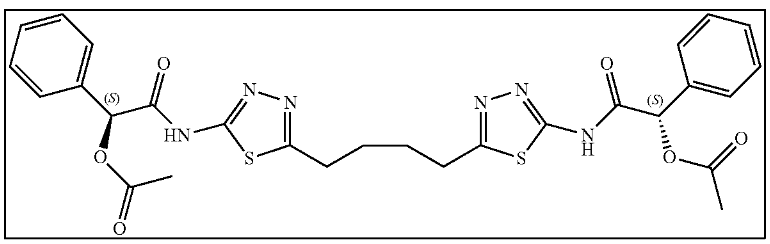 | | 20 | |
| 67 | 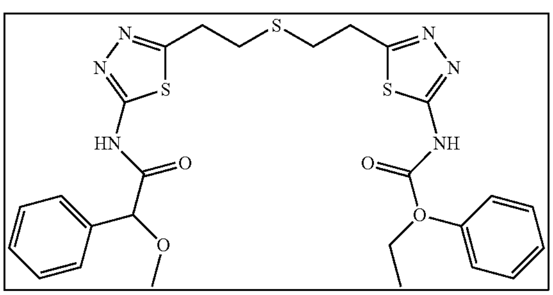 | | 3.0 | 1.8 |
| 68 | 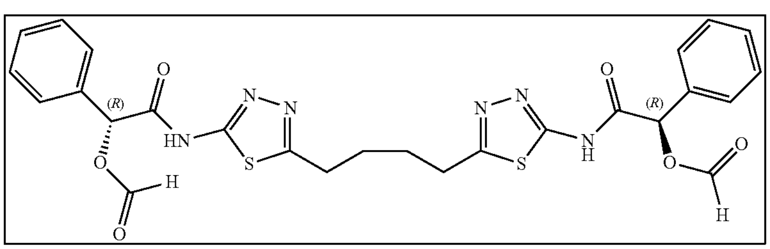 | | 4.9 | 0.34 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 69 | 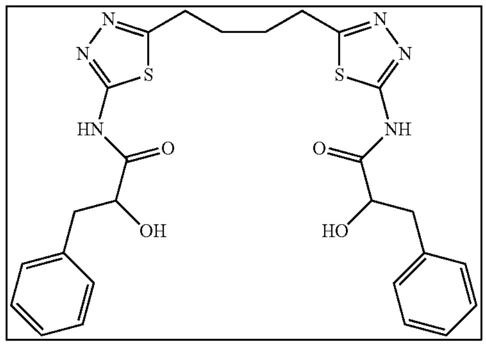 [SMILES: O=C(Nc1nnc(CCCCc2nnc(NC(=O)C(O)Cc3ccccc3)s2)s1)C(O)Cc1ccccc1] | | 0.69 | 0.33 |
| 70 | 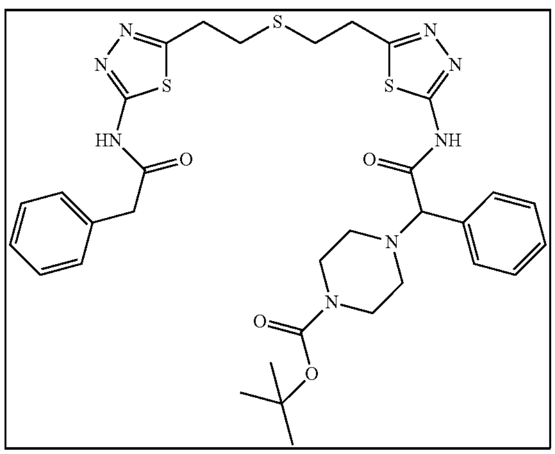 [SMILES: CC(C)(C)OC(=O)N1CCN(C(C(=O)Nc2nnc(CCSCCc3nnc(NC(=O)Cc4ccccc4)s3)s2)c2ccccc2)CC1] | | 3.4 | 3.4 |
| 71 | 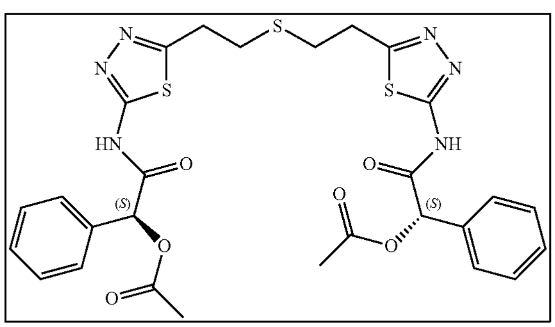 | | >50 | 6.9 |
| 72 | 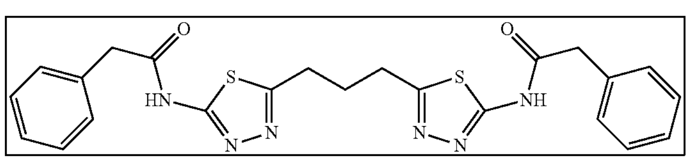 [SMILES: O=C(Cc1ccccc1)Nc1nnc(CCCc2nnc(NC(=O)Cc3ccccc3)s2)s1] | | 0.59 | 0.47 |

TABLE 3-continued
| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 73 | 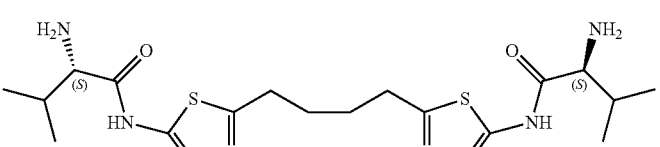 2 TFA | | | >50 |
| 74 | 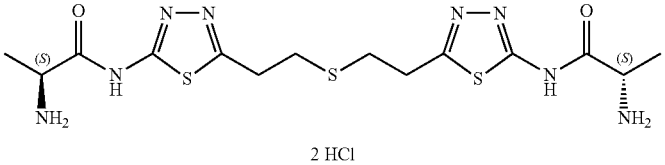 2 HCl | | | >50 |
| 75 | 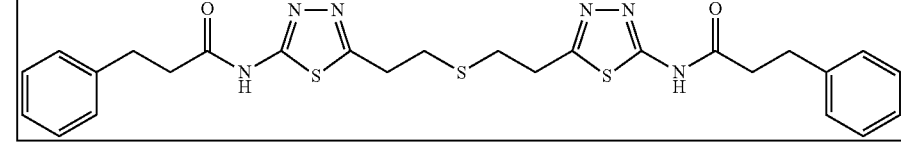 | | | >50 |
| 76 | 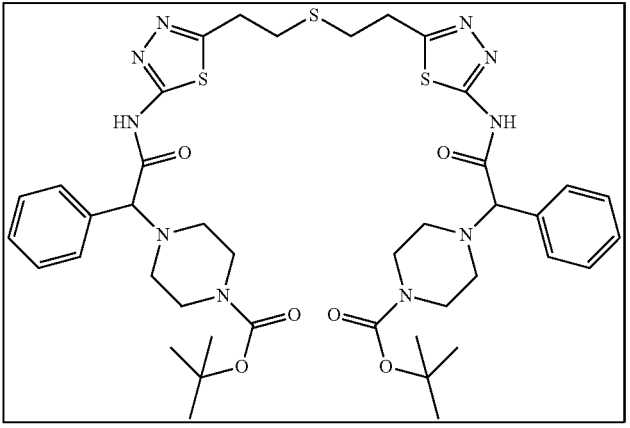 [SMILES: CC(C)(C)OC(=O)N1CCN(C(C(=O)Nc2nnc(CCSCCc3nnc(NC(=O)C(c4ccccc4)N4CCN(C(=O)OC(C)(C)C)CC4)s3)s2)c2ccccc2)CC1] | | | >50 |
| 77 | 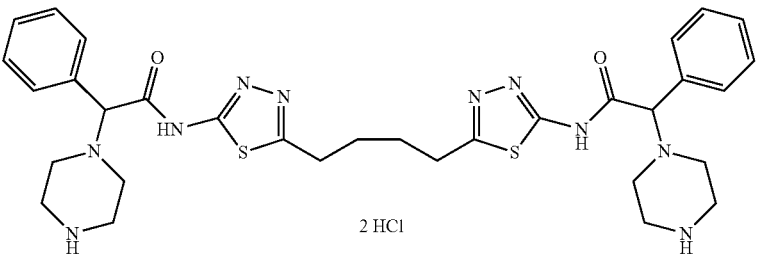 [SMILES: O=C(Nc1nnc(CCCCc2nnc(NC(=O)C(c3ccccc3)N3CCNCC3)s2)s1)C(c1ccccc1)N1CCNCC1] 2 HCl | | 6.1 | 34 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 78 | 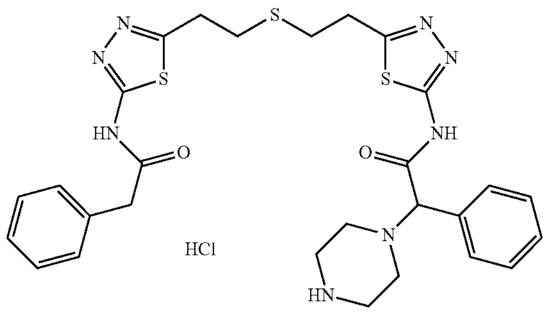 [SMILES: O=C(Cc1ccccc1)Nc1nnc(CCSCCc2nnc(NC(=O)C(c3ccccc3)N3CCNCC3)s2)s1 ; Cl] | | 0.84 | 10 |
| 79 | 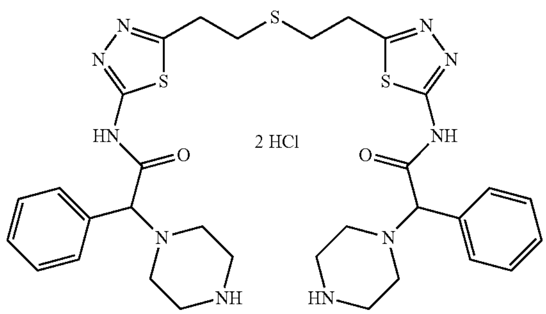 [SMILES: O=C(Nc1nnc(CCSCCc2nnc(NC(=O)C(c3ccccc3)N3CCNCC3)s2)s1)C(c1ccccc1)N1CCNCC1] | | 2.0 | 20 |
| 80 | 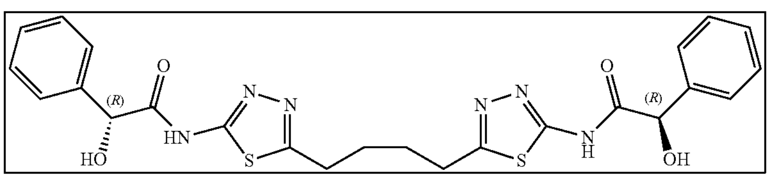 | | 1.8 | 1.3 |
| 81 | 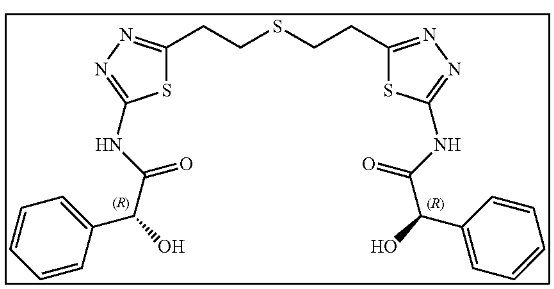 | | 10 | 7.6 |
| 82 | 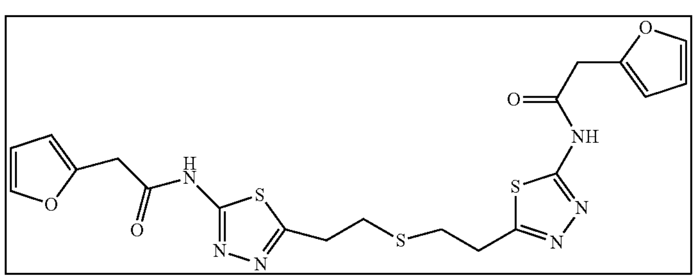 [SMILES: O=C(Cc1ccco1)Nc1nnc(CCSCCc2nnc(NC(=O)Cc3ccco3)s2)s1] | | 0.80 | 1.3 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 83 | 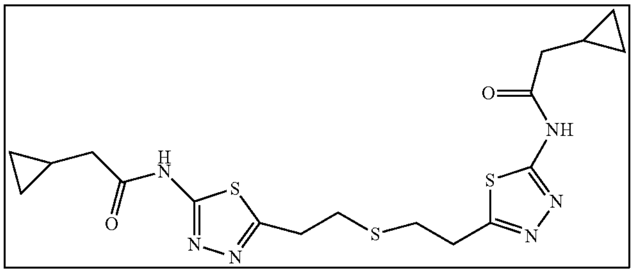 [SMILES: O=C(CC1CC1)Nc1nnc(CCSCCc2nnc(NC(=O)CC3CC3)s2)s1] | | 3.9 | 1.4 |
| 84 | 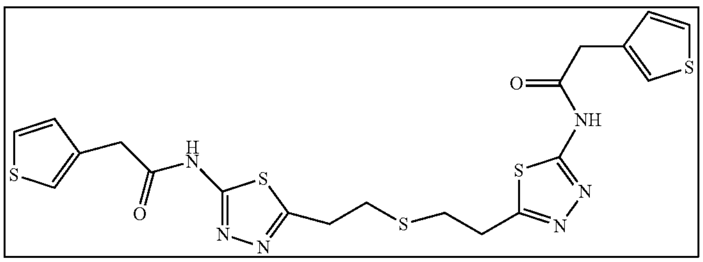 [SMILES: O=C(Cc1ccsc1)Nc1nnc(CCSCCc2nnc(NC(=O)Cc3ccsc3)s2)s1] | | 0.23 | 0.89 |
| 85 | 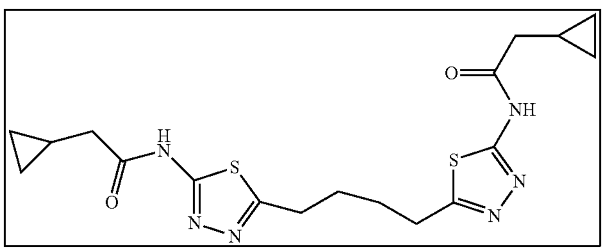 [SMILES: O=C(CC1CC1)Nc1nnc(CCCCc2nnc(NC(=O)CC3CC3)s2)s1] | | 1.5 | 1.8 |
| 86 | 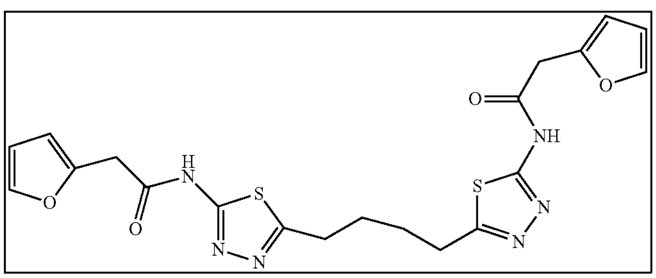 [SMILES: O=C(Cc1ccco1)Nc1nnc(CCCCc2nnc(NC(=O)Cc3ccco3)s2)s1] | | 0.32 | 0.52 |
| 87 | 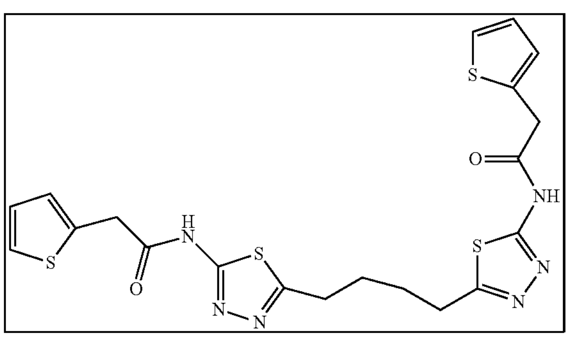 [SMILES: O=C(Cc1cccs1)Nc1nnc(CCCCc2nnc(NC(=O)Cc3cccs3)s2)s1] | | 0.18 | 0.06 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 88 | 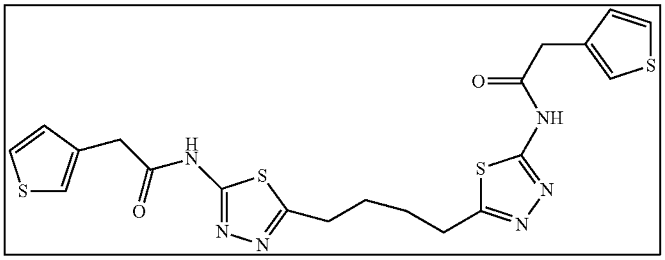 [SMILES: O=C(Cc1ccsc1)Nc1nnc(CCCCc2nnc(NC(=O)Cc3ccsc3)s2)s1] | | 0.20 | 0.12 |
| 89 | 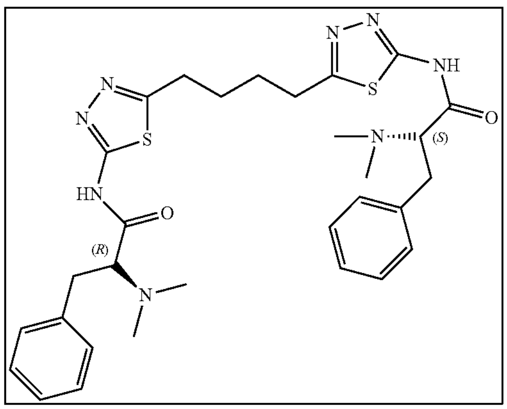 | | | >20 |
| 90 | 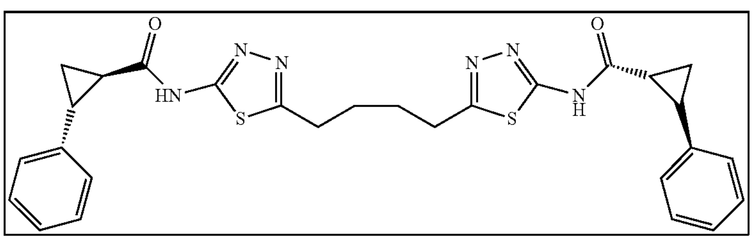 | | | >20 |
| 91 | 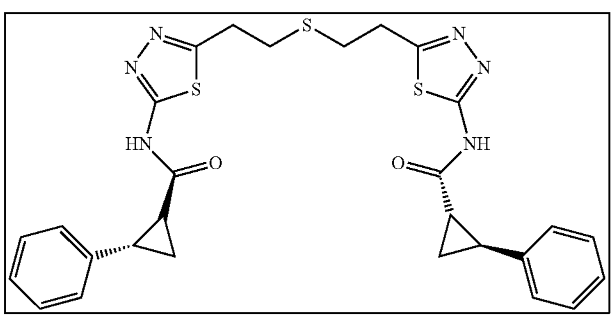 | | | >20 |
| 92 | 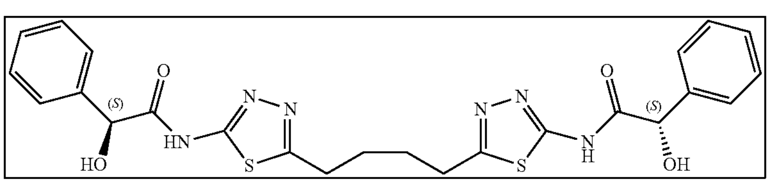 | 0.14 | 0.38 | 0.47 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 93 | 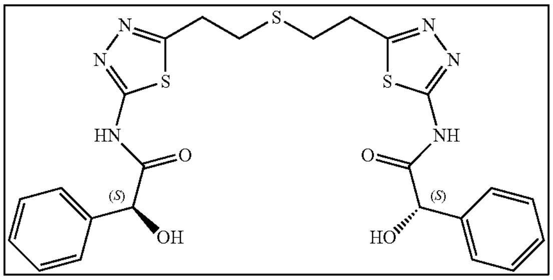 | | 0.90 | 2.0 |
| 94 | 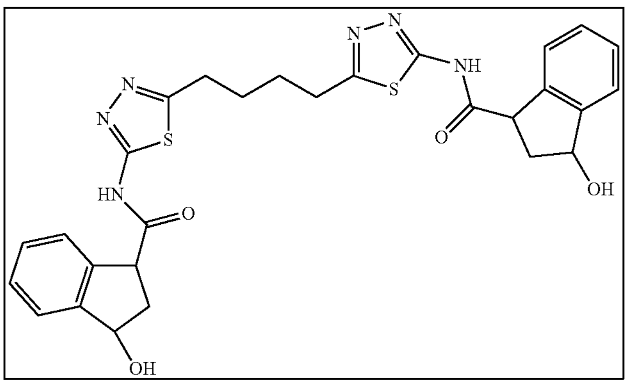 [SMILES: O=C(Nc1nnc(CCCCc2nnc(NC(=O)C3CC(O)c4ccccc43)s2)s1)C1CC(O)c2ccccc21] | | 0.28 | 0.47 |
| 95 | 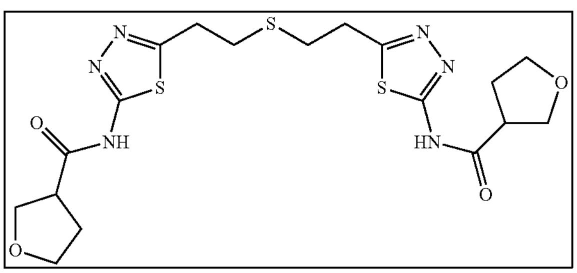 [SMILES: O=C(Nc1nnc(CCSCCc2nnc(NC(=O)C3CCOC3)s2)s1)C1CCOC1] | | 2.9 | 45 |
| 96 | 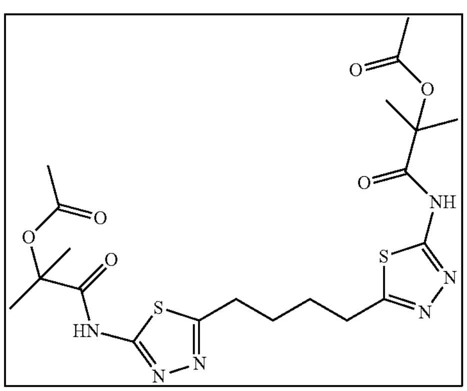 [SMILES: CC(=O)OC(C)(C)C(=O)Nc1nnc(CCCCc2nnc(NC(=O)C(C)(C)OC(C)=O)s2)s1] | | | >20 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 97 | 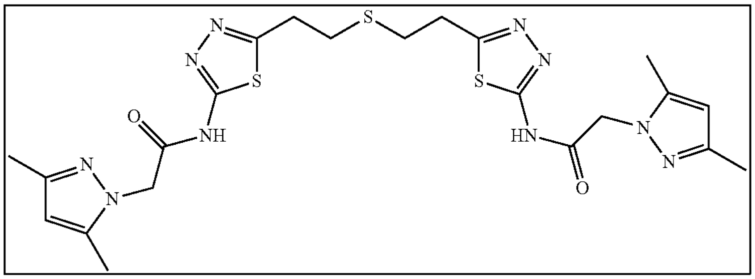 | | 0.56 | 17 |
| 98 | 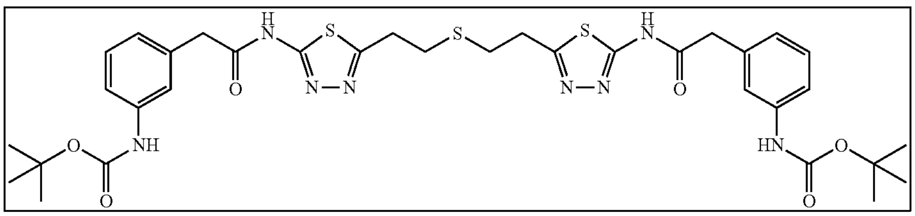 [SMILES: CC(C)(C)OC(=O)Nc1cccc(CC(=O)Nc2nnc(CCSCCc3nnc(NC(=O)Cc4cccc(NC(=O)OC(C)(C)C)c4)s3)s2)c1] | | >20 | 3.9 |
| 99 | 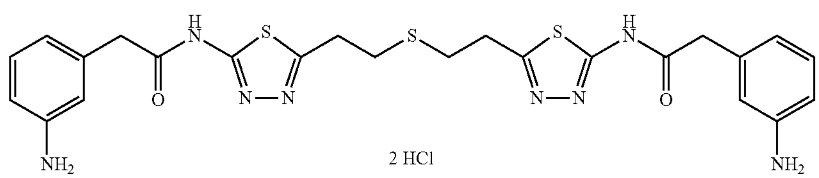 [SMILES: Nc1cccc(CC(=O)Nc2nnc(CCSCCc3nnc(NC(=O)Cc4cccc(N)c4)s3)s2)c1] | | 2.7 | 1.0 |
| 100 | 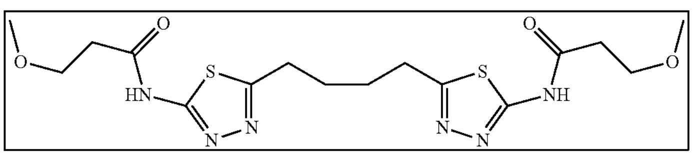 | | 8.1 | 9.0 |
| 101 | 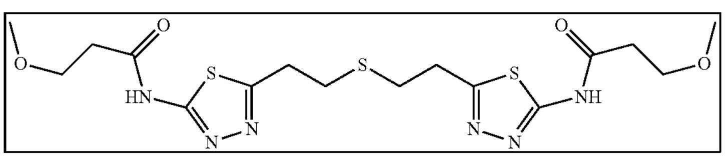 | | 24 | 17 |
| 102 | 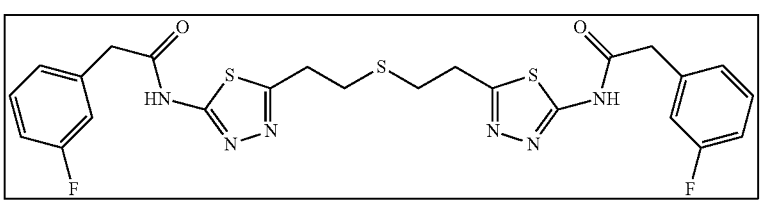 [SMILES: O=C(Cc1cccc(F)c1)Nc1nnc(CCSCCc2nnc(NC(=O)Cc3cccc(F)c3)s2)s1] | | 0.24 | 1.4 |
| 103 | 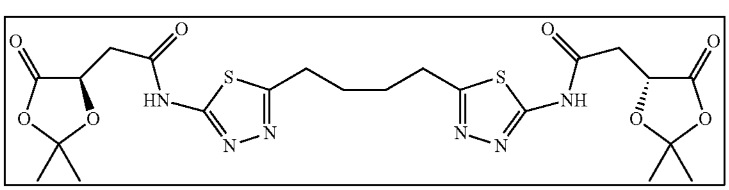 [SMILES: CC1(C)OC(=O)[C@@H](CC(=O)Nc2nnc(CCCCc3nnc(NC(=O)C[C@H]4OC(C)(C)OC4=O)s3)s2)O1] | | 19 | >50 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 104 | 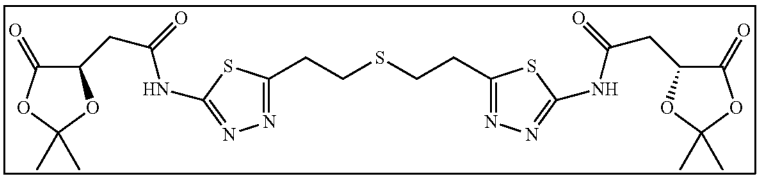 [SMILES: CC1(C)OC(=O)[C@@H](CC(=O)Nc2nnc(CCSCCc3nnc(NC(=O)C[C@H]4OC(C)(C)OC4=O)s3)s2)O1] | | | >20 |
| 105 | 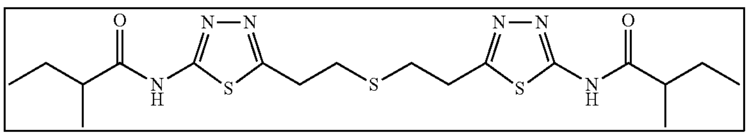 [SMILES: CCC(C)C(=O)Nc1nnc(CCSCCc2nnc(NC(=O)C(C)CC)s2)s1] | | 9.9 | 119 |
| 106 | 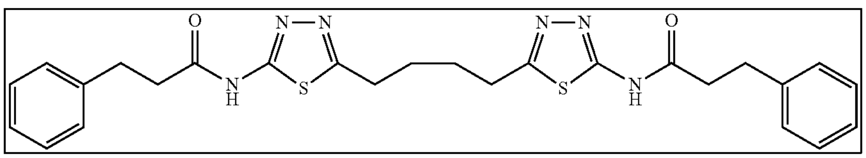 [SMILES: O=C(CCc1ccccc1)Nc1nnc(CCCCc2nnc(NC(=O)CCc3ccccc3)s2)s1] | | | >20 |
| 107 | 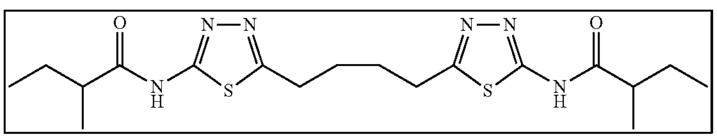 [SMILES: CCC(C)C(=O)Nc1nnc(CCCCc2nnc(NC(=O)C(C)CC)s2)s1] | | 4.3 | 1.2 |
| 108 | 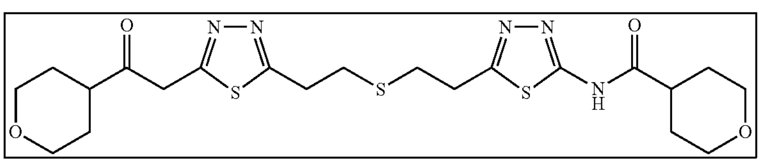 [SMILES: O=C(Cc1nnc(CCSCCc2nnc(NC(=O)C3CCOCC3)s2)s1)C1CCOCC1] | | | >20 |
| 109 | 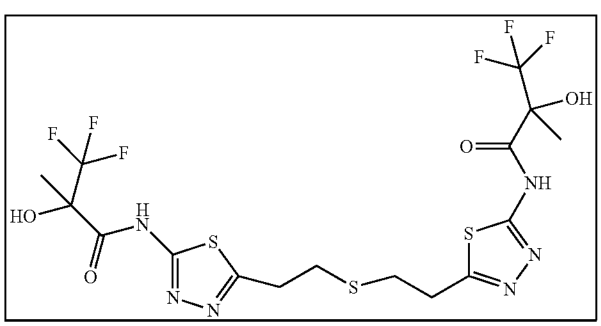 [SMILES: CC(O)(C(=O)Nc1nnc(CCSCCc2nnc(NC(=O)C(C)(O)C(F)(F)F)s2)s1)C(F)(F)F] | | | >20 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 110 | 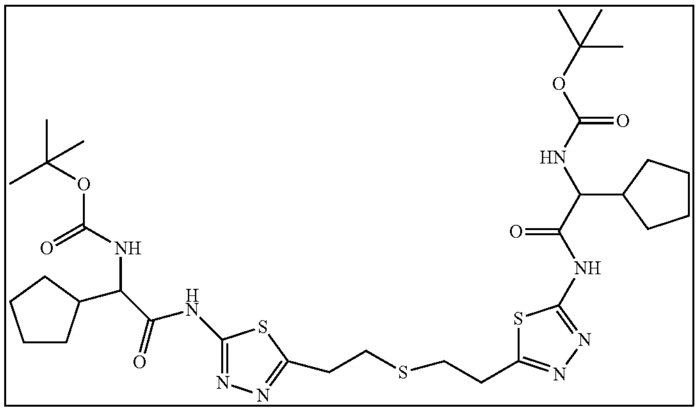 [SMILES: CC(C)(C)OC(=O)NC(C(=O)Nc1nnc(CCSCCc2nnc(NC(=O)C(NC(=O)OC(C)(C)C)C3CCCC3)s2)s1)C1CCCC1] | | | >20 |
| 111 | 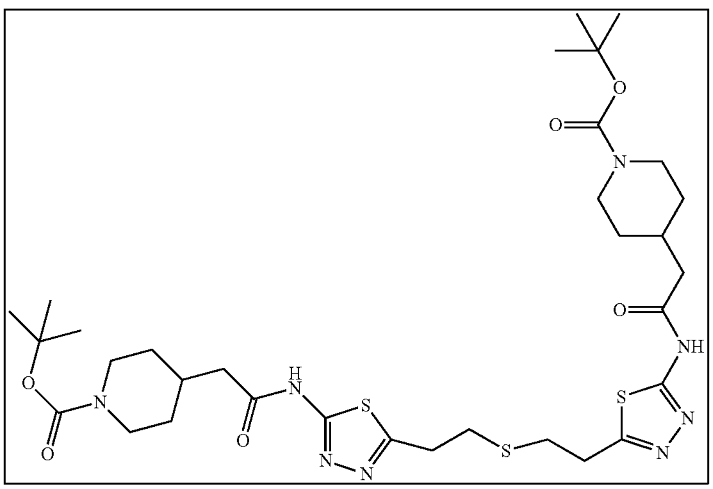 [SMILES: CC(C)(C)OC(=O)N1CCC(CC(=O)Nc2nnc(CCSCCc3nnc(NC(=O)CC4CCN(C(=O)OC(C)(C)C)CC4)s3)s2)CC1] | | 0.95 | 0.88 |
| 112 | 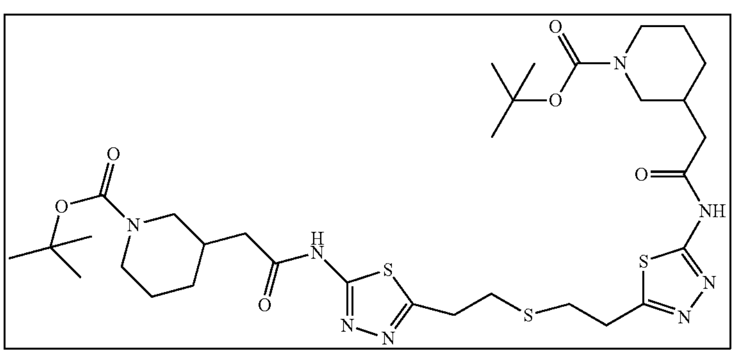 [SMILES: CC(C)(C)OC(=O)N1CCCC(CC(=O)Nc2nnc(CCSCCc3nnc(NC(=O)CC4CCCN(C(=O)OC(C)(C)C)C4)s3)s2)C1] | | 0.51 | 0.89 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 113 | 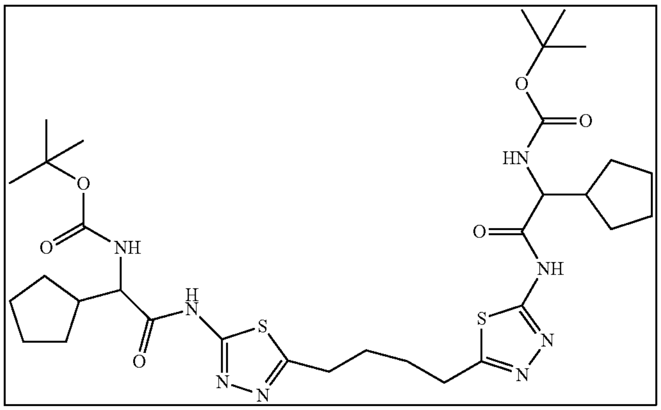 [SMILES: CC(C)(C)OC(=O)NC(C(=O)Nc1nnc(CCCCc2nnc(NC(=O)C(NC(=O)OC(C)(C)C)C3CCCC3)s2)s1)C1CCCC1] | | | >20 |
| 114 | 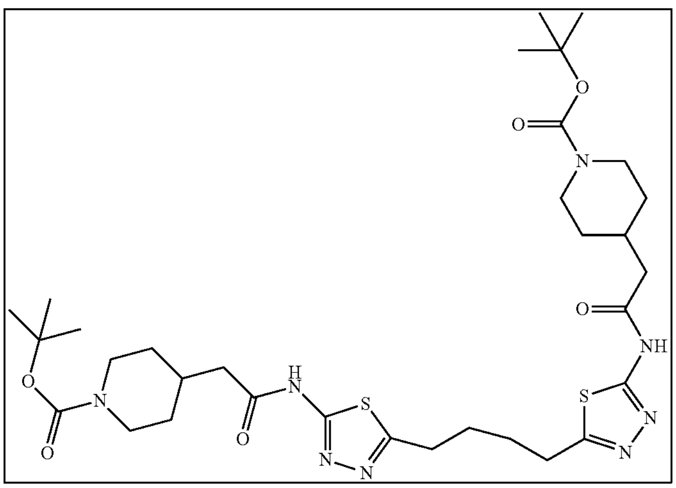 [SMILES: CC(C)(C)OC(=O)N1CCC(CC(=O)Nc2nnc(CCCCc3nnc(NC(=O)CC4CCN(C(=O)OC(C)(C)C)CC4)s3)s2)CC1] | | 0.60 | 0.56 |
| 115 | 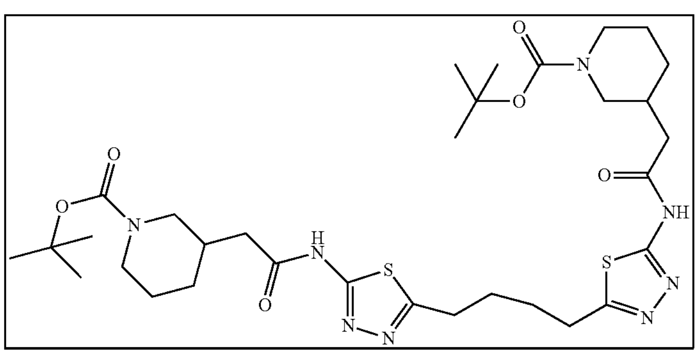 [SMILES: CC(C)(C)OC(=O)N1CCCC(CC(=O)Nc2nnc(CCCCc3nnc(NC(=O)CC4CCCN(C(=O)OC(C)(C)C)C4)s3)s2)C1] | | 0.62 | 1.1 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 116 | 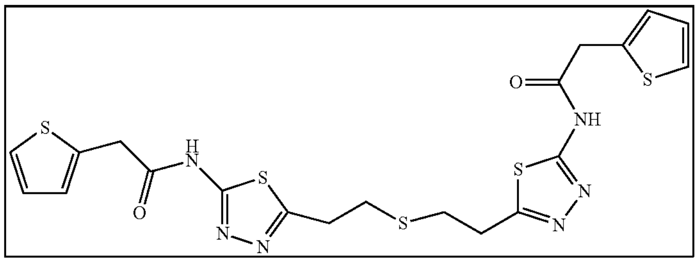 [SMILES: O=C(Cc1cccs1)Nc1nnc(CCSCCc2nnc(NC(=O)Cc3cccs3)s2)s1] | | 0.24 | 0.72 |
| 117 | 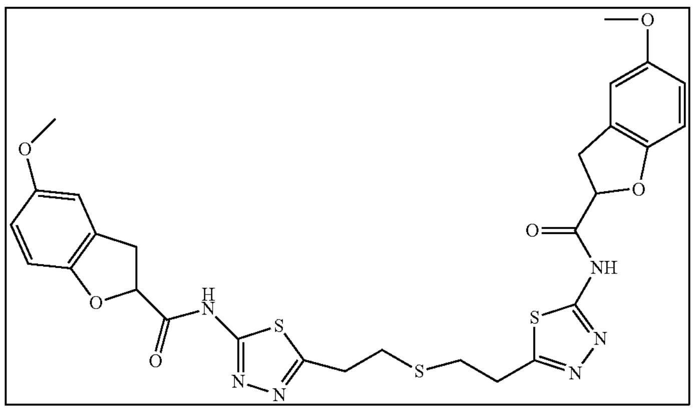 [SMILES: COc1ccc2c(c1)CC(C(=O)Nc1nnc(CCSCCc3nnc(NC(=O)C4Cc5cc(OC)ccc5O4)s3)s1)O2] | | 2.4 | 6.2 |
| 118 | 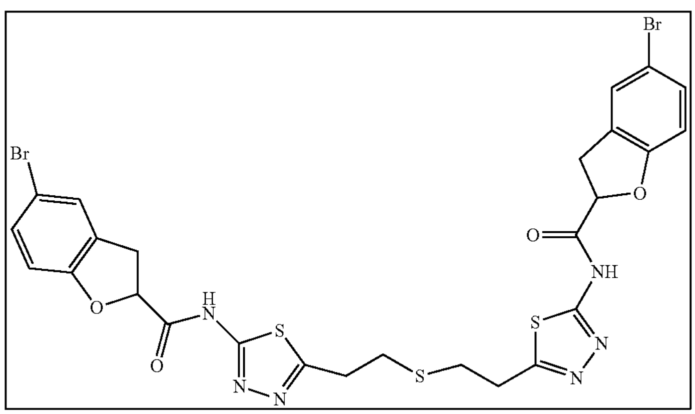 [SMILES: O=C(Nc1nnc(CCSCCc2nnc(NC(=O)C3Cc4cc(Br)ccc4O3)s2)s1)C1Cc2cc(Br)ccc2O1] | | 5.0 | 36 |
| 119 | 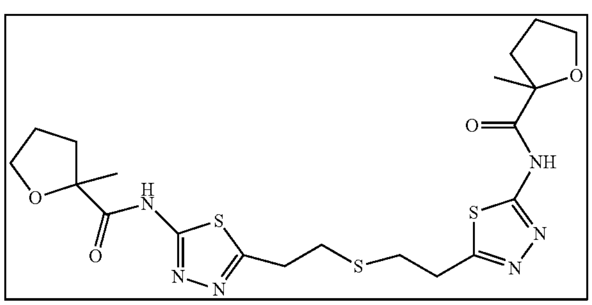 [SMILES: CC1(C(=O)Nc2nnc(CCSCCc3nnc(NC(=O)C4(C)CCCO4)s3)s2)CCCO1] | | >20 | 13 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 120 | 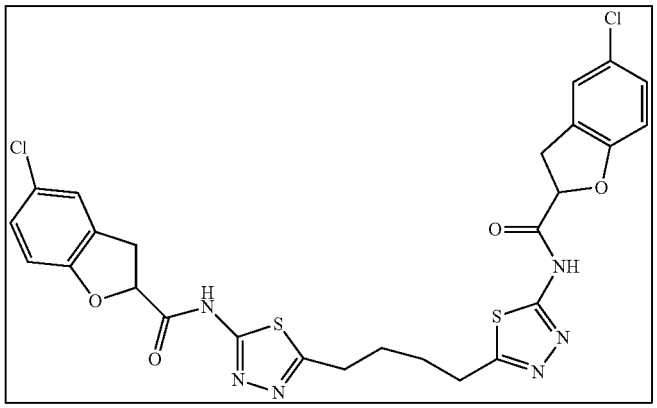 [SMILES: O=C(Nc1nnc(CCCCc2nnc(NC(=O)C3Cc4cc(Cl)ccc4O3)s2)s1)C1Cc2cc(Cl)ccc2O1] | | 1.8 | 38 |
| 121 | 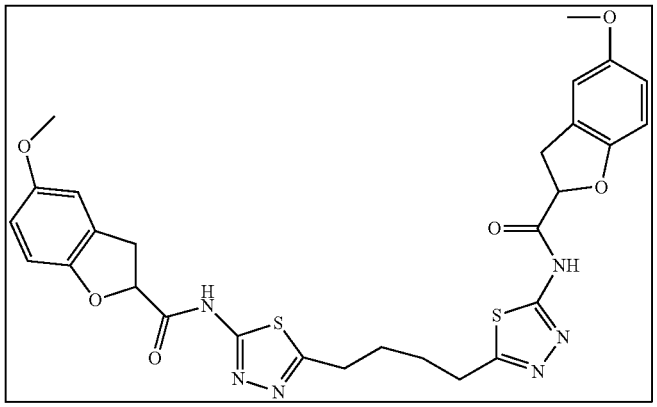 [SMILES: COc1ccc2c(c1)CC(C(=O)Nc1nnc(CCCCc3nnc(NC(=O)C4Cc5cc(OC)ccc5O4)s3)s1)O2] | | 1.7 | 3.5 |
| 122 | 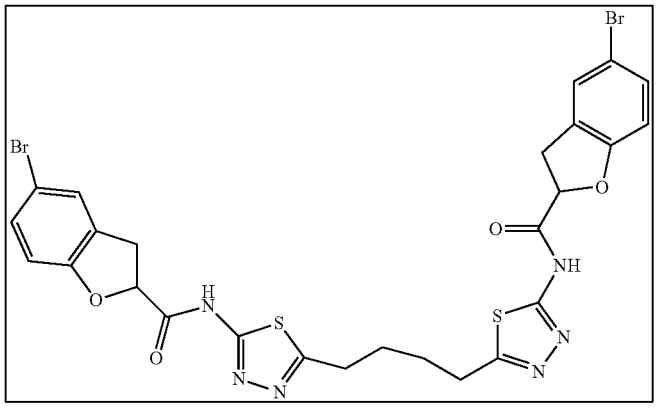 | | 3.5 | 43 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 123 | 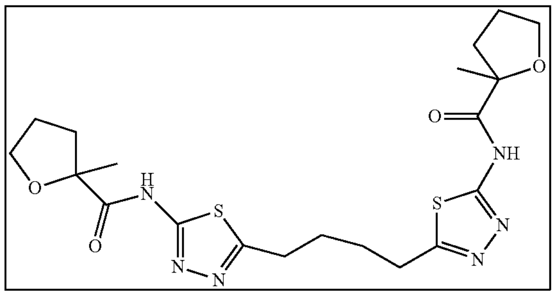 [SMILES: CC1(C(=O)Nc2nnc(CCCCc3nnc(NC(=O)C4(C)CCCO4)s3)s2)CCCO1] | | 12 | 6.6 |
| 124 | 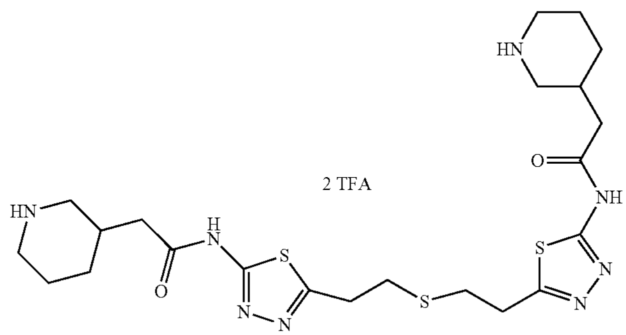 [SMILES: O=C(CC1CCCNC1)Nc1nnc(CCSCCc2nnc(NC(=O)CC3CCCNC3)s2)s1] | | | >20 |
| 125 | 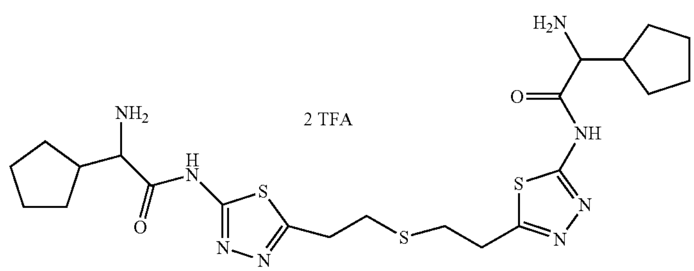 [SMILES: NC(C(=O)Nc1nnc(CCSCCc2nnc(NC(=O)C(N)C3CCCC3)s2)s1)C1CCCC1] | | | >20 |
| 126 | 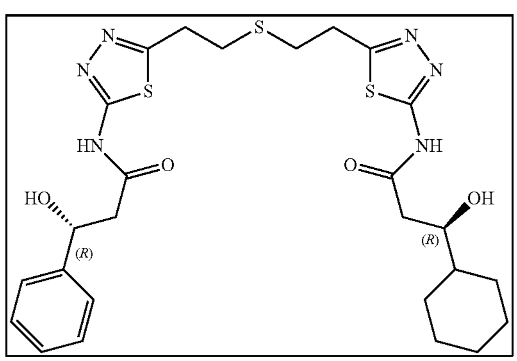 | 5.8 | 12 | |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 127 | 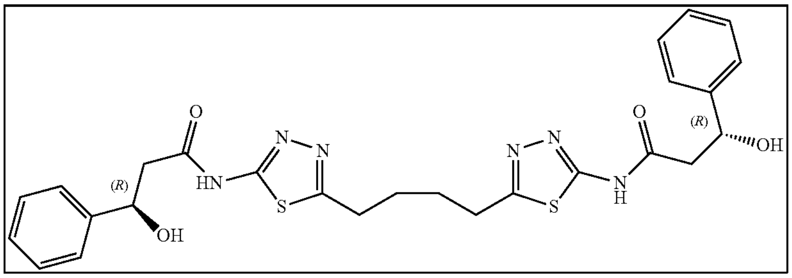 | | 1.8 | 0.45 |
| 128 | 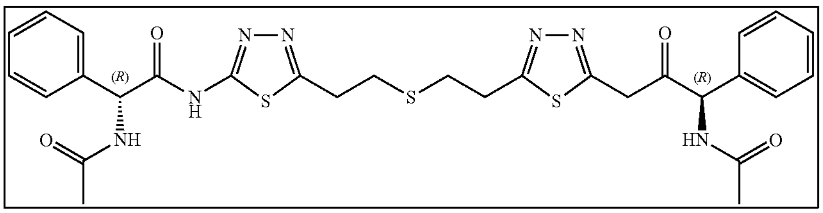 | | 32 | >50 |
| 129 | 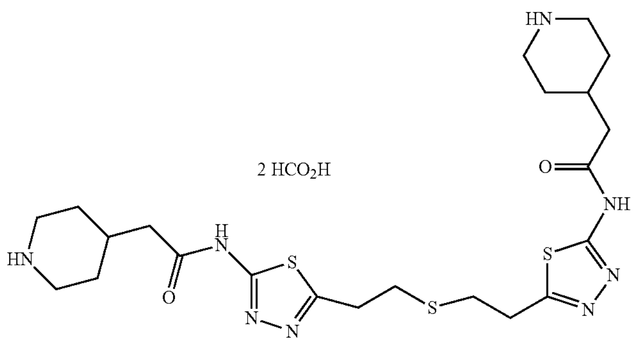 [SMILES: O=C(CC1CCNCC1)Nc1nnc(CCSCCc2nnc(NC(=O)CC3CCNCC3)s2)s1] | >20 | | >50 |
| 130 | 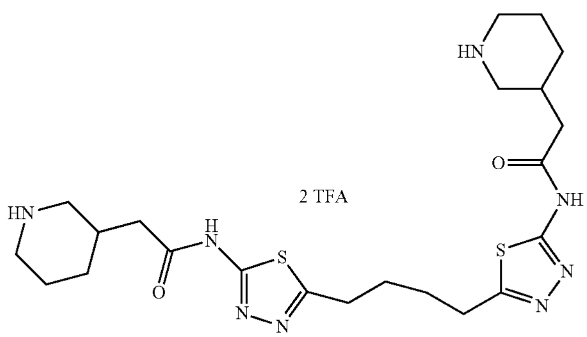 [SMILES: O=C(CC1CCCNC1)Nc1nnc(CCCCc2nnc(NC(=O)CC3CCCNC3)s2)s1] | >20 | | |
| 131 | 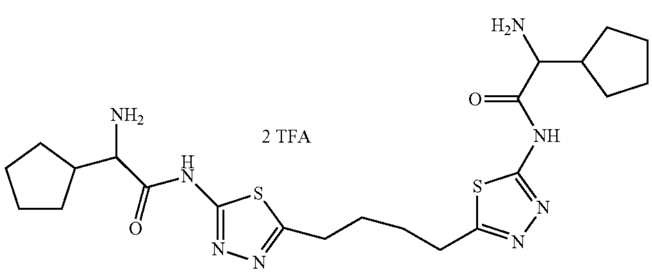 [SMILES: NC(C(=O)Nc1nnc(CCCCc2nnc(NC(=O)C(N)C3CCCC3)s2)s1)C1CCCC1] | 19 | | |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 132 | 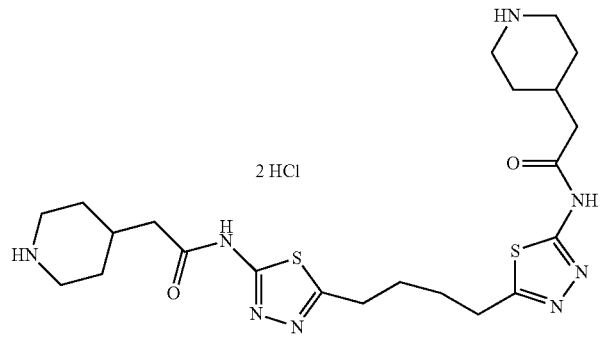 [SMILES: O=C(CC1CCNCC1)Nc1nnc(CCCCc2nnc(NC(=O)CC3CCNCC3)s2)s1] | | | >20 |
| 133 | 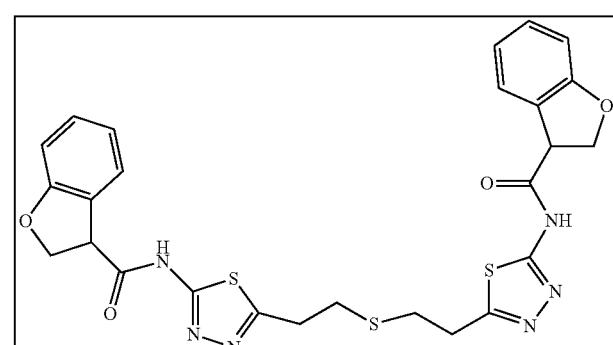 | | 0.51 | 0.15 |
| 134 | 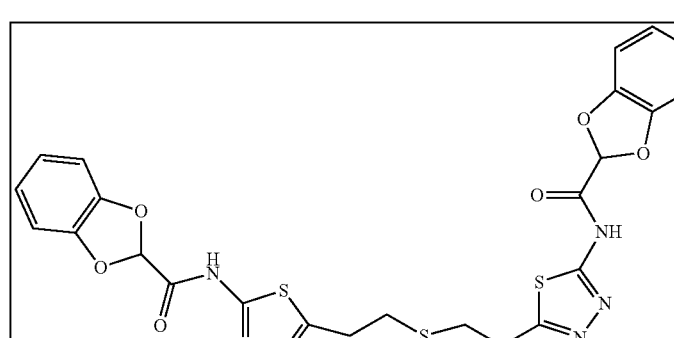 | | 14 | 28 |
| 135 | 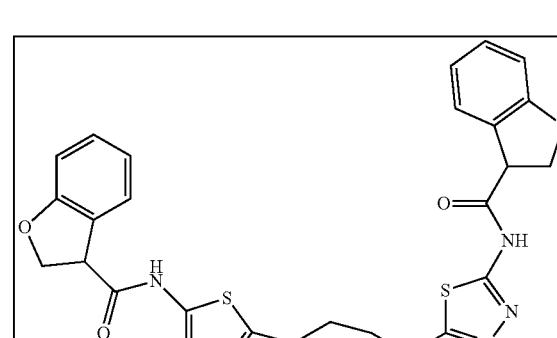 | | 0.30 | 0.49 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 136 | 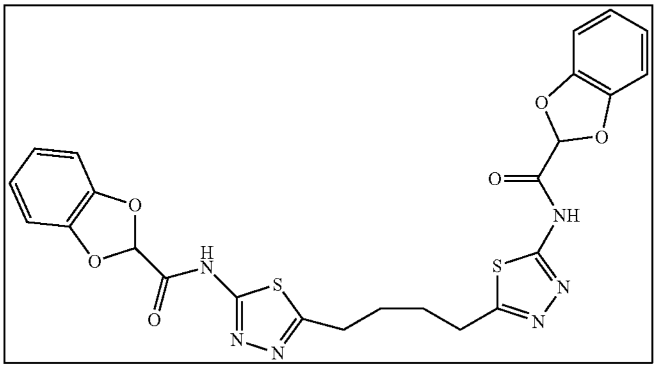 [SMILES: O=C(Nc1nnc(CCCCc2nnc(NC(=O)C3Oc4ccccc4O3)s2)s1)C1Oc2ccccc2O1] | | 7.0 | 4.7 |
| 137 | 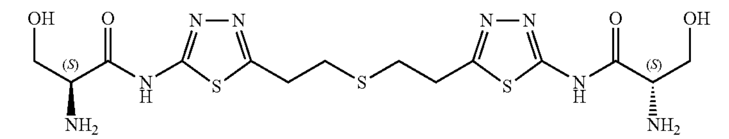 | | >20 | |
| 138 | 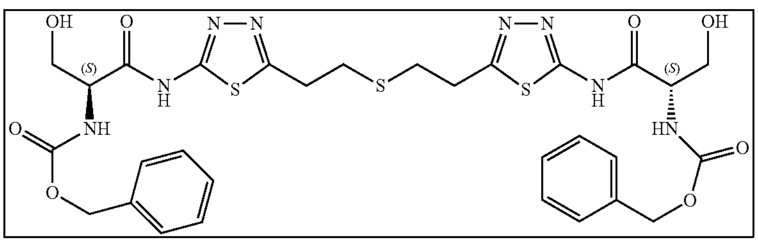 | 0.75 | | 2.7 |
| 139 | 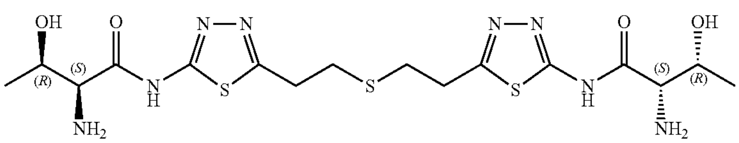 | | >20 | |
| 140 | 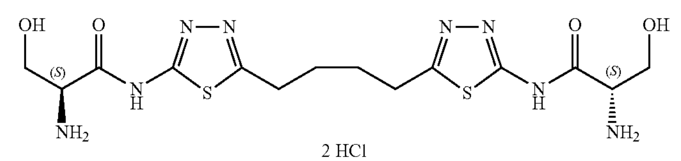 | 3.4 | | >50 |
| 141 | 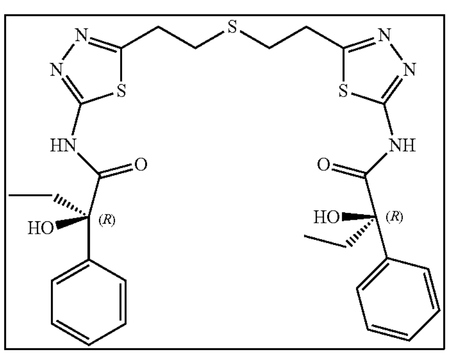 | 1.7 | | 4.3 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 142 | 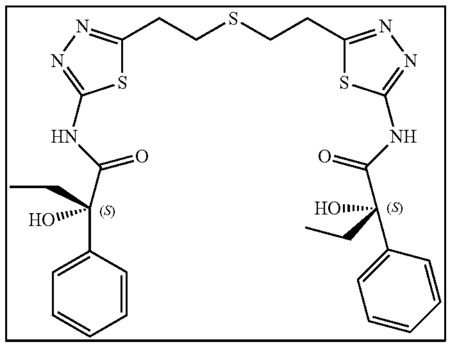 | | | >20 |
| 143 | 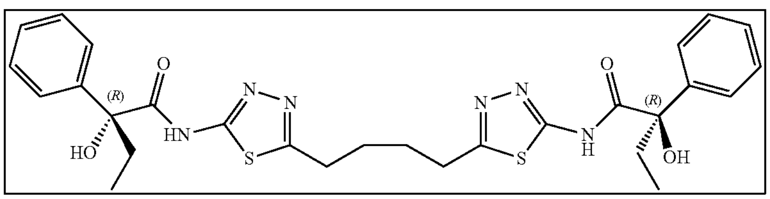 | | 0.57 | 2.2 |
| 144 | 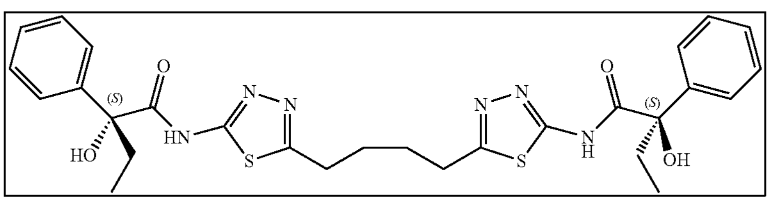 | | | >20 |
| 145 | 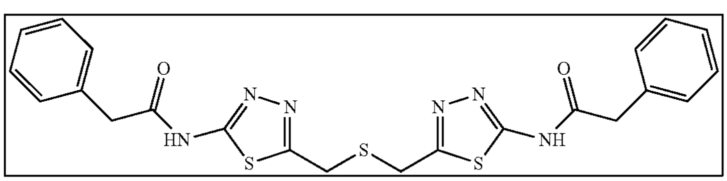 [SMILES: O=C(Cc1ccccc1)Nc1nnc(CSCc2nnc(NC(=O)Cc3ccccc3)s2)s1] | | | >20 |
| 146 | 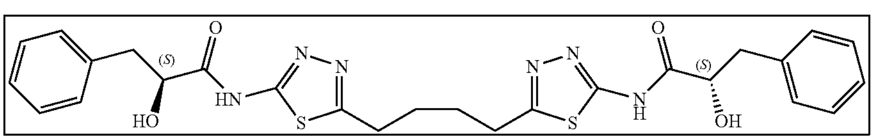 | | 0.43 | 0.46 |
| 147 | 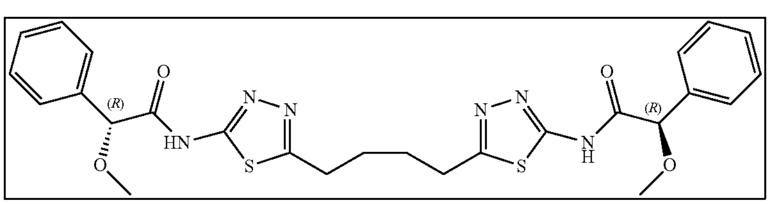 | | 0.62 | 0.37 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 148 | 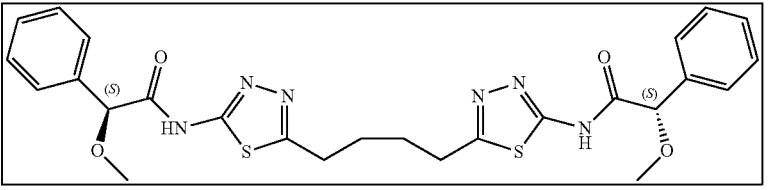 | | 0.59 | 0.39 |
| 149 | 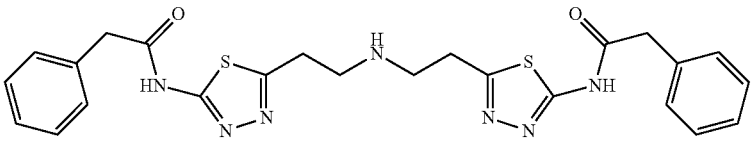 TFA | | 15 | |
| 150 | 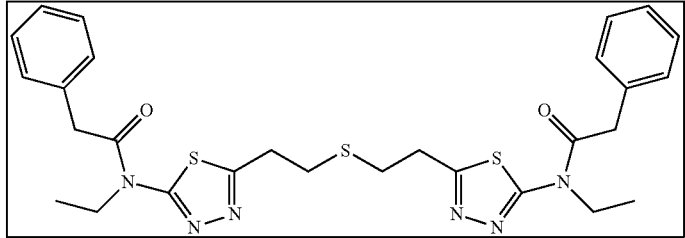 [SMILES: CCN(C(=O)Cc1ccccc1)c1nnc(CCSCCc2nnc(N(CC)C(=O)Cc3ccccc3)s2)s1] | | >20 | |
| 151 | 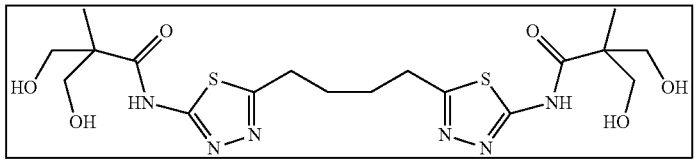 [SMILES: CC(CO)(CO)C(=O)Nc1nnc(CCCCc2nnc(NC(=O)C(C)(CO)CO)s2)s1] | | 14 | >50 |
| 152 | 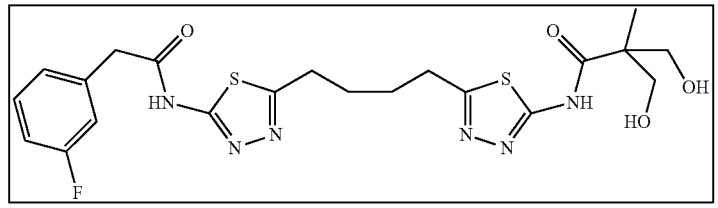 [SMILES: CC(CO)(CO)C(=O)Nc1nnc(CCCCc2nnc(NC(=O)Cc3cccc(F)c3)s2)s1] | | 0.73 | 1.1 |
| 153 | 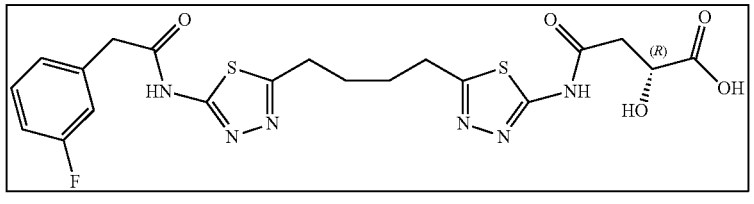 | | 1.0 | >50 |
| 154 | 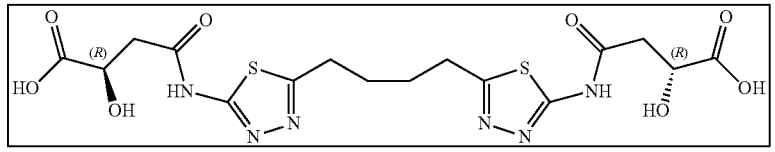 | | 19 | >50 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 155 | 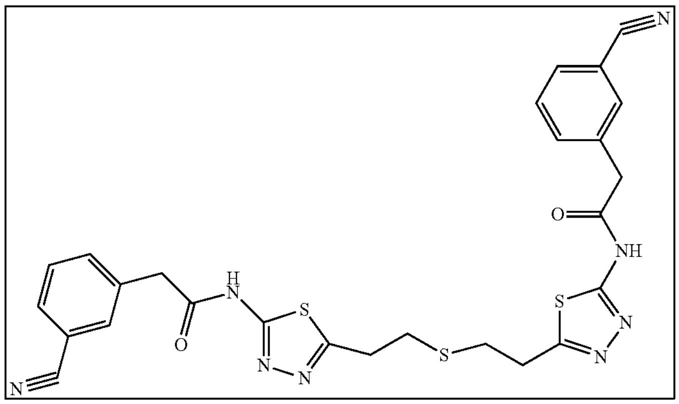 [SMILES: N#Cc1cccc(CC(=O)Nc2nnc(CCSCCc3nnc(NC(=O)Cc4cccc(C#N)c4)s3)s2)c1] | | 0.27 | 1.9 |
| 156 | 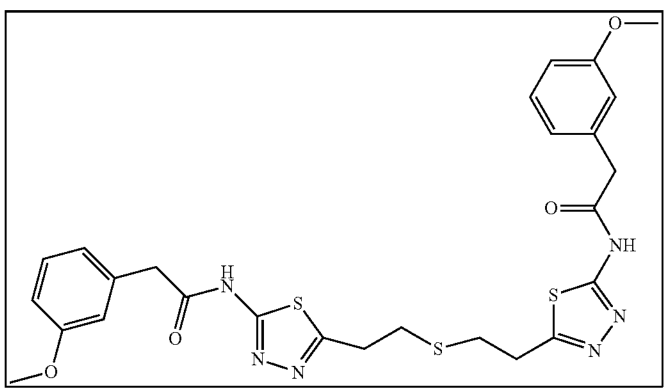 | | 0.12 | 0.63 |
| 157 | 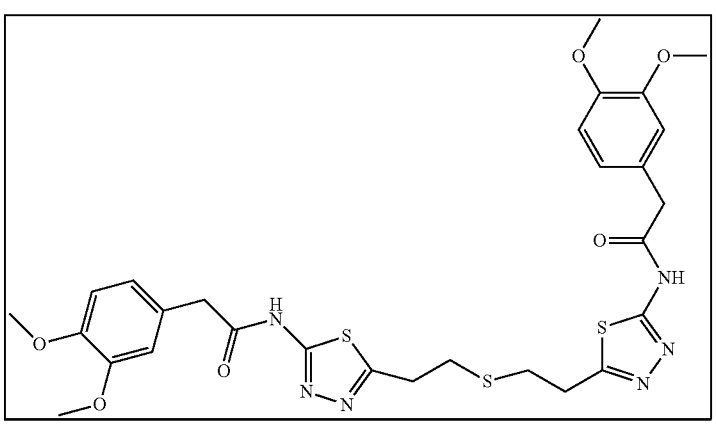 | | 0.34 | 0.18 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 158 | 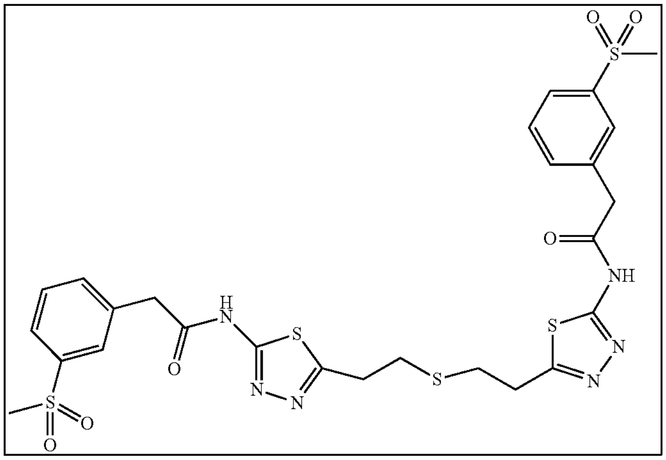 | | 0.22 | 8.1 |
| 159 | 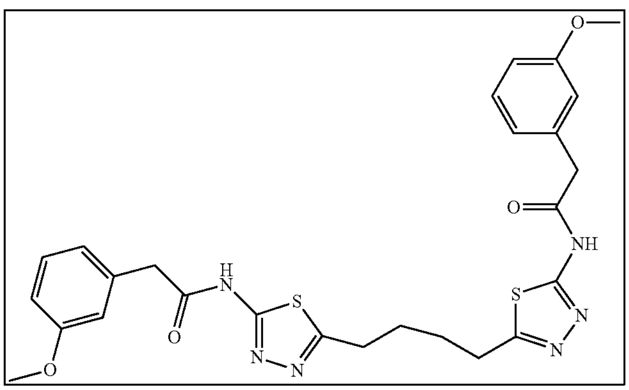 | | 0.11 | 0.05 |
| 160 | 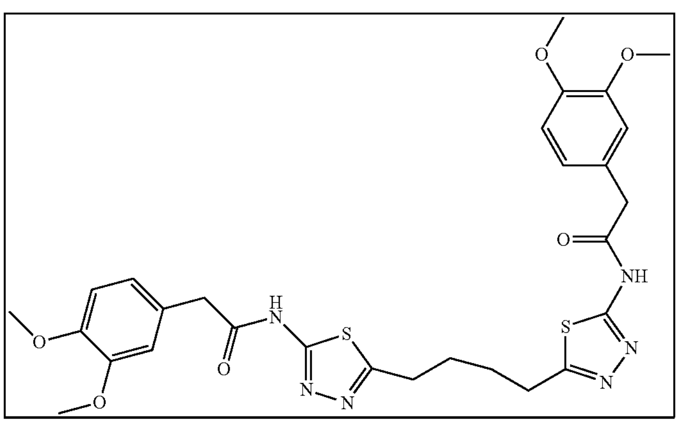 | | 0.16 | >50 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 161 | 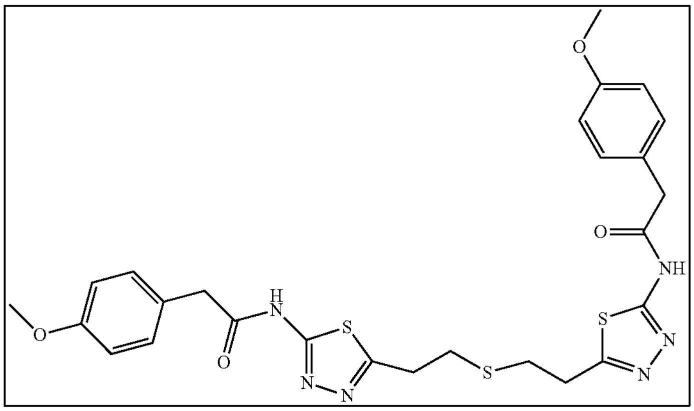 [SMILES: COc1ccc(CC(=O)Nc2nnc(CCSCCc3nnc(NC(=O)Cc4ccc(OC)cc4)s3)s2)cc1] | | 0.15 | 1.4 |
| 162 | 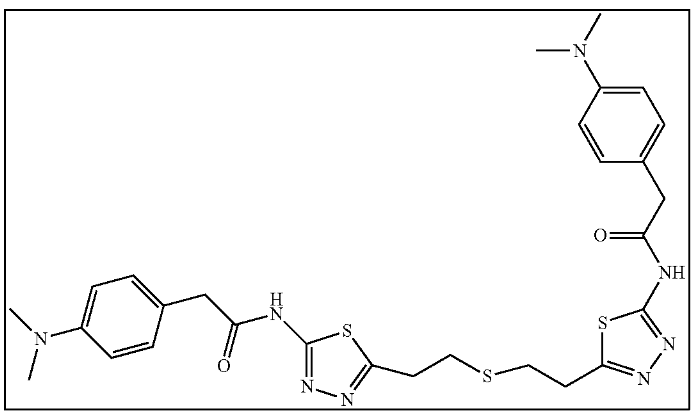 [SMILES: CN(C)c1ccc(CC(=O)Nc2nnc(CCSCCc3nnc(NC(=O)Cc4ccc(N(C)C)cc4)s3)s2)cc1] | | 0.23 | 0.15 |
| 163 | 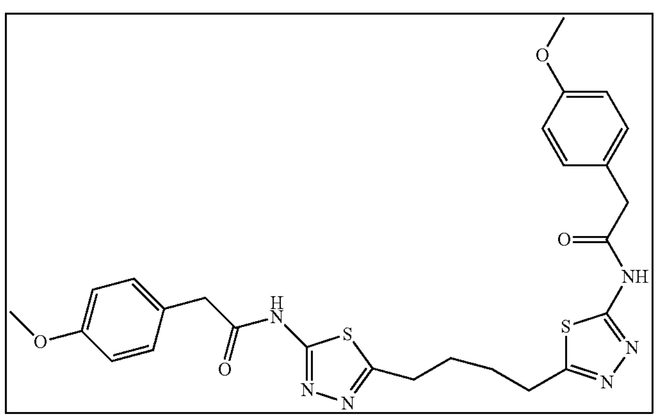 [SMILES: COc1ccc(CC(=O)Nc2nnc(CCCCc3nnc(NC(=O)Cc4ccc(OC)cc4)s3)s2)cc1] | | 0.13 | >50 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 164 | 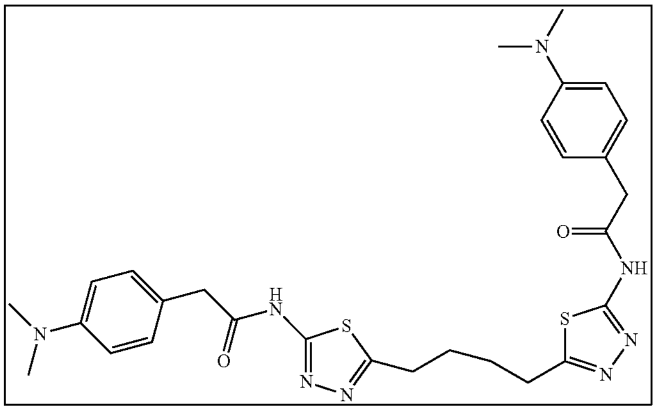 [SMILES: CN(C)c1ccc(CC(=O)Nc2nnc(CCCCc3nnc(NC(=O)Cc4ccc(N(C)C)cc4)s3)s2)cc1] | | 0.24 | 0.13 |
| 165 | 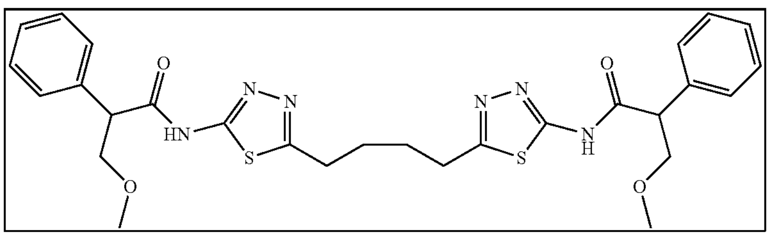 [SMILES: COCC(C(=O)Nc1nnc(CCCCc2nnc(NC(=O)C(COC)c3ccccc3)s2)s1)c1ccccc1] | | 0.51 | 33 |
| 166 | 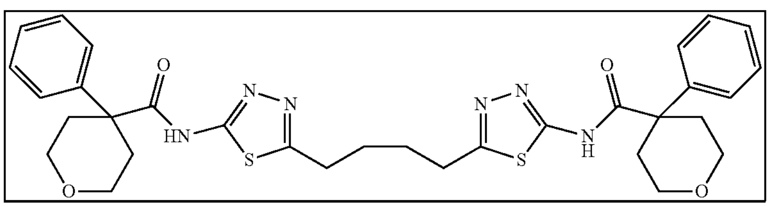 [SMILES: O=C(Nc1nnc(CCCCc2nnc(NC(=O)C3(c4ccccc4)CCOCC3)s2)s1)C1(c2ccccc2)CCOCC1] | | 7.4 | 6.8 |
| 167 | 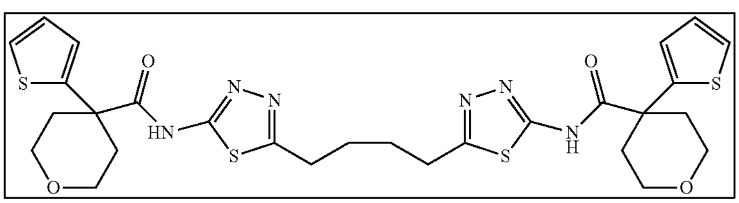 [SMILES: O=C(Nc1nnc(CCCCc2nnc(NC(=O)C3(c4cccs4)CCOCC3)s2)s1)C1(c2cccs2)CCOCC1] | | 11 | 34 |
| 168 | 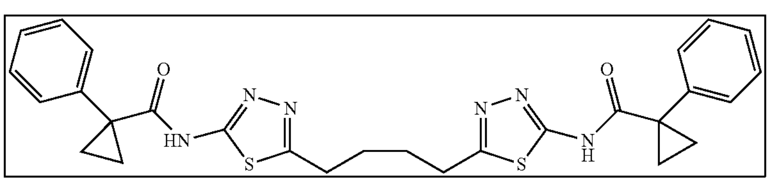 [SMILES: O=C(Nc1nnc(CCCCc2nnc(NC(=O)C3(c4ccccc4)CC3)s2)s1)C1(c2ccccc2)CC1] | | 1.3 | >50 |
| 169 | 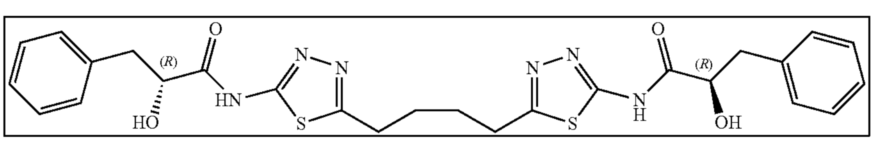 | | 0.71 | 3.4 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 170 | 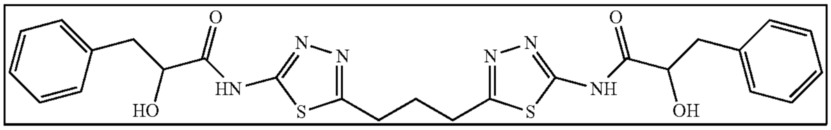 | 7.4 | 9.3 | |
| 171 | 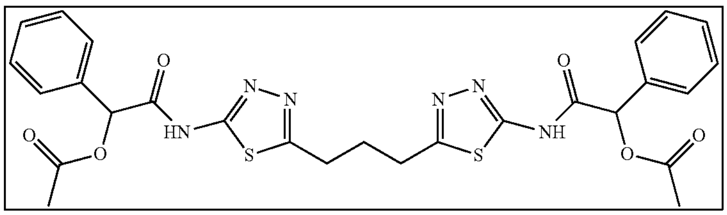 [SMILES: CC(=O)OC(C(=O)Nc1nnc(CCCc2nnc(NC(=O)C(OC(C)=O)c3ccccc3)s2)s1)c1ccccc1] | >20 | | |
| 172 | 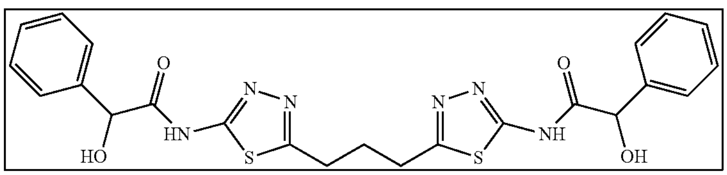 [SMILES: O=C(Nc1nnc(CCCc2nnc(NC(=O)C(O)c3ccccc3)s2)s1)C(O)c1ccccc1] | 1.7 | 3.7 | |
| 173 | 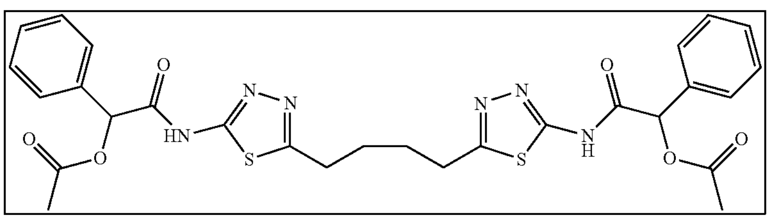 [SMILES: CC(=O)OC(C(=O)Nc1nnc(CCCCc2nnc(NC(=O)C(OC(C)=O)c3ccccc3)s2)s1)c1ccccc1] | 24 | 0.76 | |
| 174 | 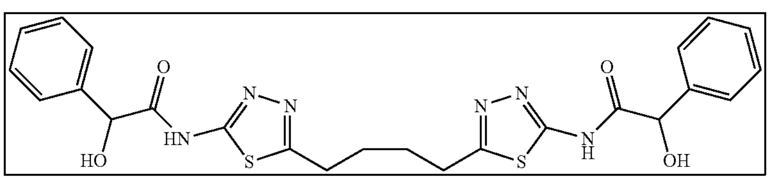 [SMILES: O=C(Nc1nnc(CCCCc2nnc(NC(=O)C(O)c3ccccc3)s2)s1)C(O)c1ccccc1] | 0.29 | 0.44 | |
| 175 | (2 HCl) | 6.3 | 23 | |
| 176 | 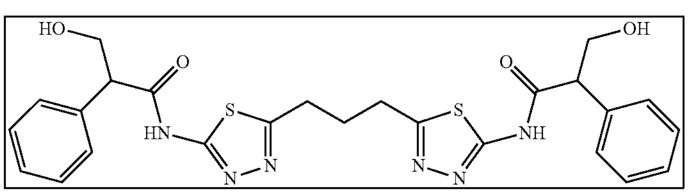 [SMILES: O=C(Nc1nnc(CCCc2nnc(NC(=O)C(CO)c3ccccc3)s2)s1)C(CO)c1ccccc1] | 0.57 | 1.5 | |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 177 | 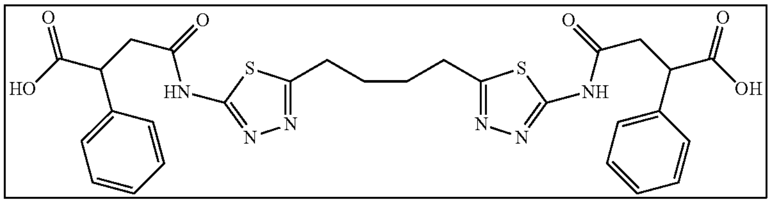 [SMILES: O=C(CC(C(=O)O)c1ccccc1)Nc1nnc(CCCCc2nnc(NC(=O)CC(C(=O)O)c3ccccc3)s2)s1] | | 1.1 | >50 |
| 178 | 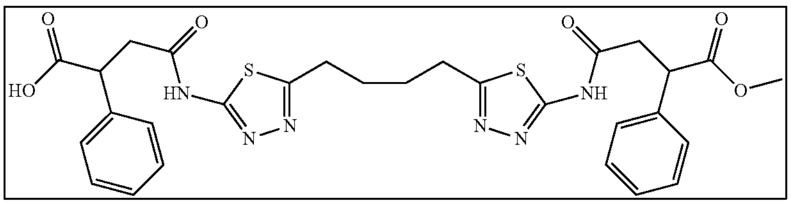 [SMILES: COC(=O)C(CC(=O)Nc1nnc(CCCCc2nnc(NC(=O)CC(C(=O)O)c3ccccc3)s2)s1)c1ccccc1] | | 1.5 | >50 |
| 179 | 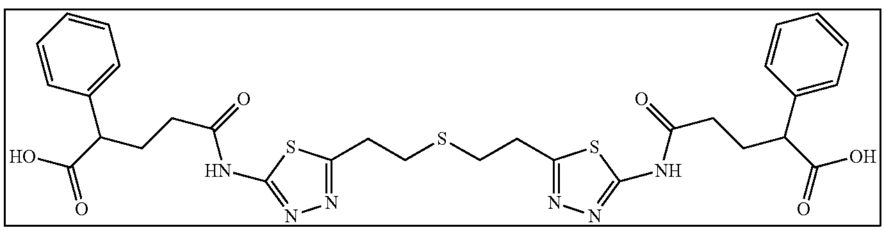 [SMILES: O=C(CCC(C(=O)O)c1ccccc1)Nc1nnc(CCSCCc2nnc(NC(=O)CCC(C(=O)O)c3ccccc3)s2)s1] | | 3.1 | >50 |
| 180 | 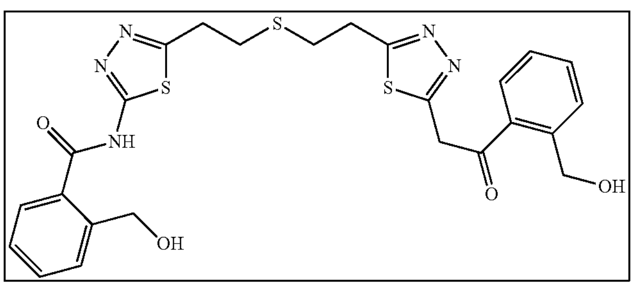 [SMILES: O=C(Cc1nnc(CCSCCc2nnc(NC(=O)c3ccccc3CO)s2)s1)c1ccccc1CO] | | 8.8 | >50 |
| 181 | 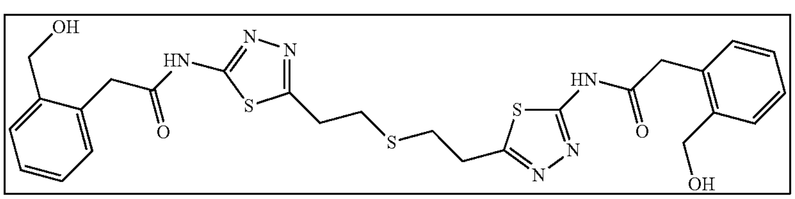 [SMILES: O=C(Cc1ccccc1CO)Nc1nnc(CCSCCc2nnc(NC(=O)Cc3ccccc3CO)s2)s1] | | 0.33 | 30 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 182 | 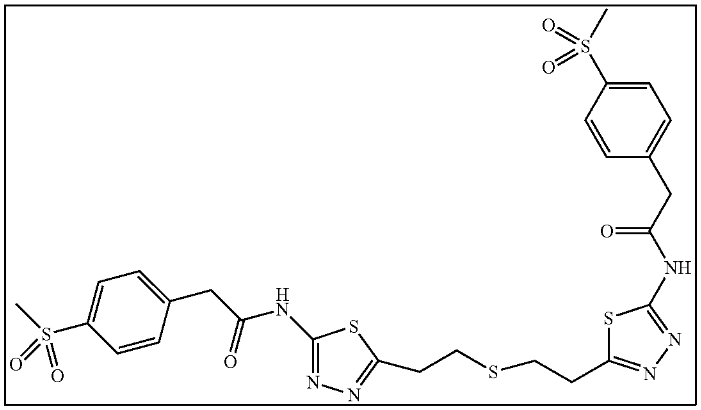 [SMILES: CS(=O)(=O)c1ccc(CC(=O)Nc2nnc(CCSCCc3nnc(NC(=O)Cc4ccc(S(C)(=O)=O)cc4)s3)s2)cc1] | | 0.58 | >50 |
| 183 | 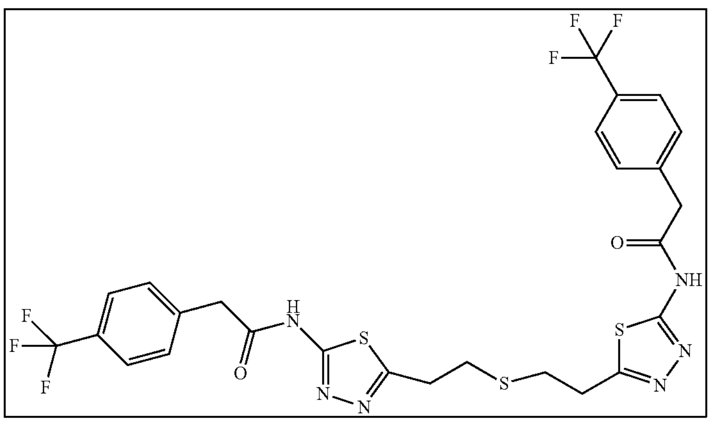 [SMILES: O=C(Cc1ccc(C(F)(F)F)cc1)Nc1nnc(CCSCCc2nnc(NC(=O)Cc3ccc(C(F)(F)F)cc3)s2)s1] | | | >20 |
| 184 | 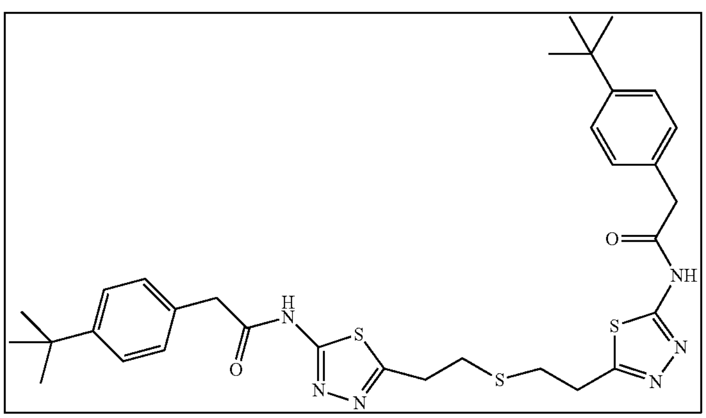 [SMILES: CC(C)(C)c1ccc(CC(=O)Nc2nnc(CCSCCc3nnc(NC(=O)Cc4ccc(C(C)(C)C)cc4)s3)s2)cc1] | | | >20 |

TABLE 3-continued
| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 185 | 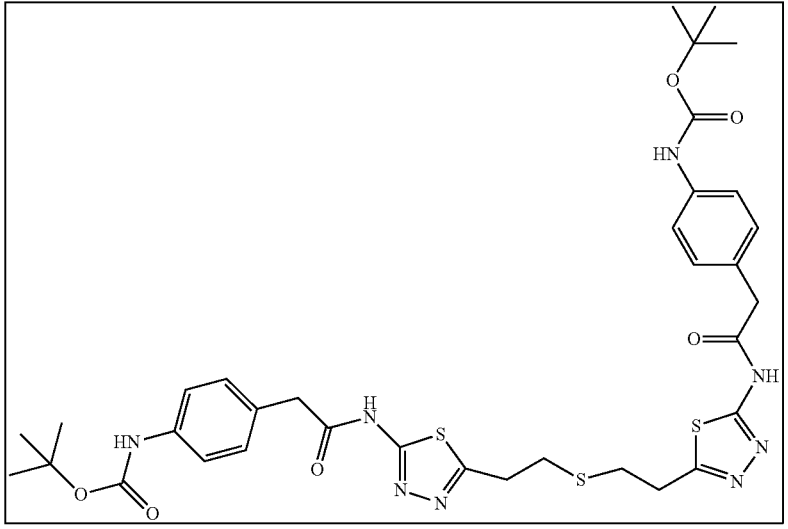 [SMILES: CC(C)(C)OC(=O)Nc1ccc(CC(=O)Nc2nnc(CCSCCc3nnc(NC(=O)Cc4ccc(NC(=O)OC(C)(C)C)cc4)s3)s2)cc1] | | >20 | 0.09 |
| 186 | 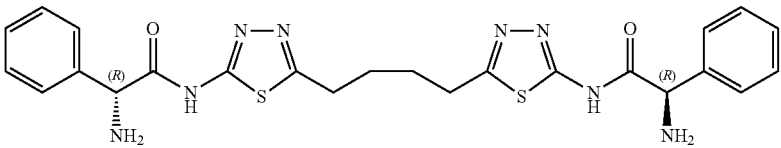 2 HCl | | 3.1 | 13 |
| 187 | 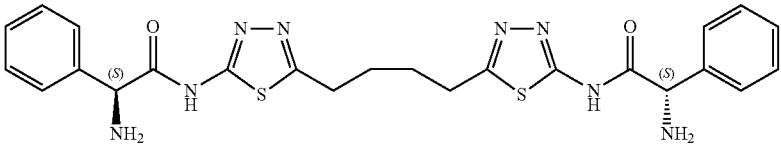 2 HCl | | 2.8 | 21 |
| 188 | 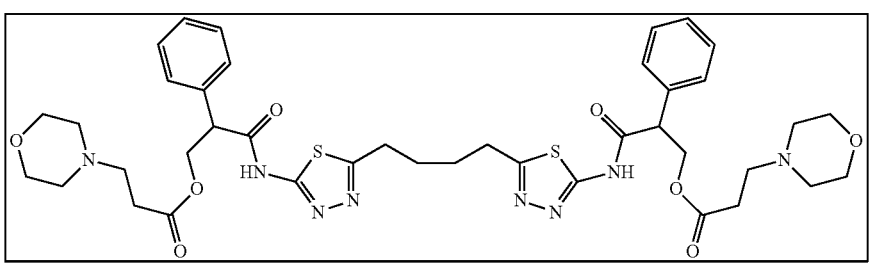 [SMILES: O=C(CCN1CCOCC1)OCC(C(=O)Nc1nnc(CCCCc2nnc(NC(=O)C(COC(=O)CCN3CCOCC3)c3ccccc3)s2)s1)c1ccccc1] | | 2.0 | 0.46 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 189 | 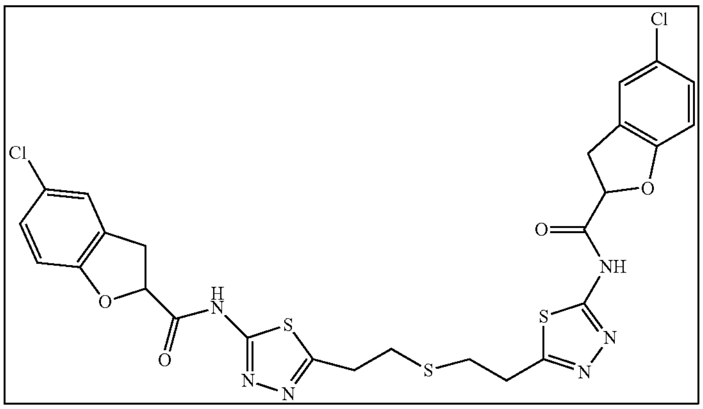 [SMILES: O=C(Nc1nnc(CCSCCc2nnc(NC(=O)C3Cc4cc(Cl)ccc4O3)s2)s1)C1Cc2cc(Cl)ccc2O1] | | | 4.4 |
| 190 | 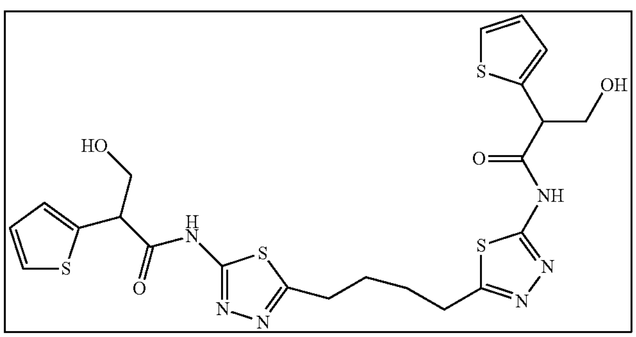 [SMILES: O=C(Nc1nnc(CCCCc2nnc(NC(=O)C(CO)c3cccs3)s2)s1)C(CO)c1cccs1] | | 0.25 | 0.49 |
| 191 | 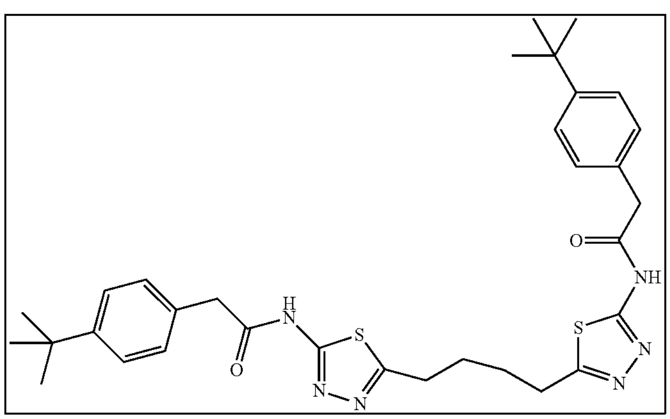 [SMILES: CC(C)(C)c1ccc(CC(=O)Nc2nnc(CCCCc3nnc(NC(=O)Cc4ccc(C(C)(C)C)cc4)s3)s2)cc1] | | | >20 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 192 | 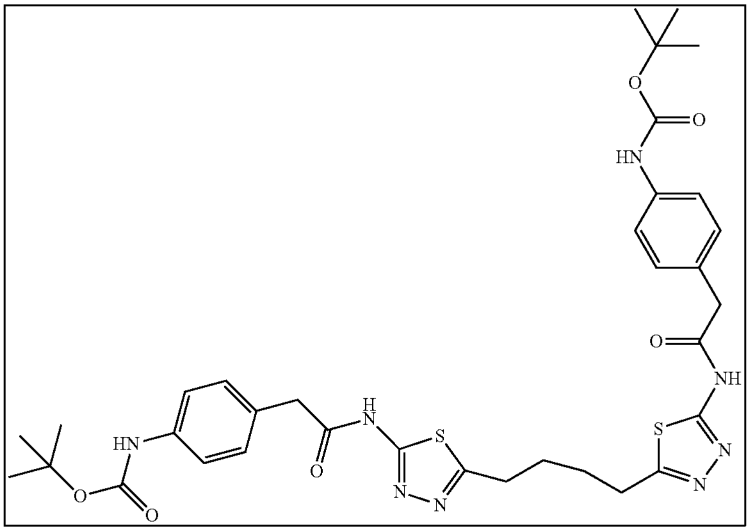 [SMILES: CC(C)(C)OC(=O)Nc1ccc(CC(=O)Nc2nnc(CCCCc3nnc(NC(=O)Cc4ccc(NC(=O)OC(C)(C)C)cc4)s3)s2)cc1] | | >20 | 0.03 |
| 193 | 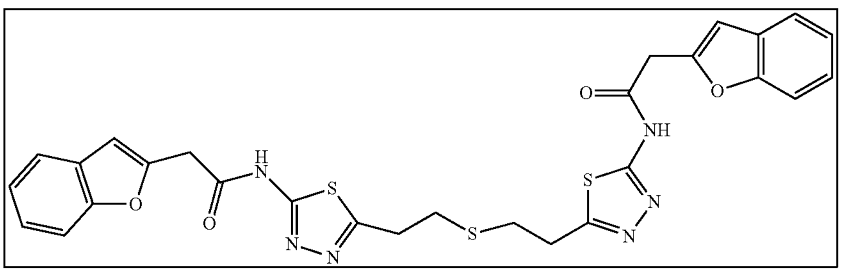 [SMILES: O=C(Cc1cc2ccccc2o1)Nc1nnc(CCSCCc2nnc(NC(=O)Cc3cc4ccccc4o3)s2)s1] | | | 3.4 |
| 194 | 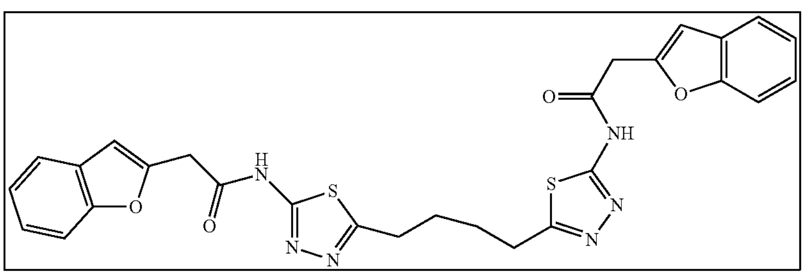 [SMILES: O=C(Cc1cc2ccccc2o1)Nc1nnc(CCCCc2nnc(NC(=O)Cc3cc4ccccc4o3)s2)s1] | | | 10 |
| 195 | 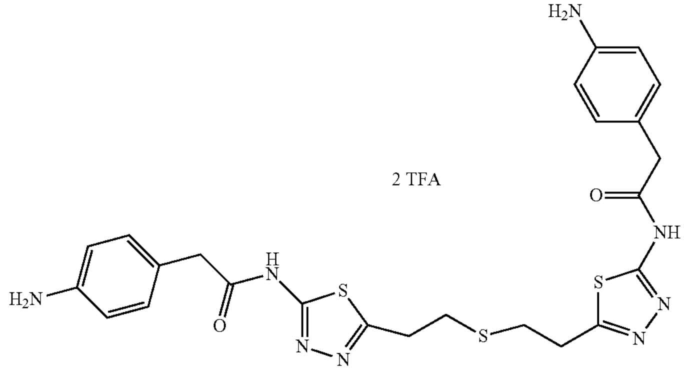 [SMILES: Nc1ccc(CC(=O)Nc2nnc(CCSCCc3nnc(NC(=O)Cc4ccc(N)cc4)s3)s2)cc1] | | 0.30 | 1.3 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 196 | 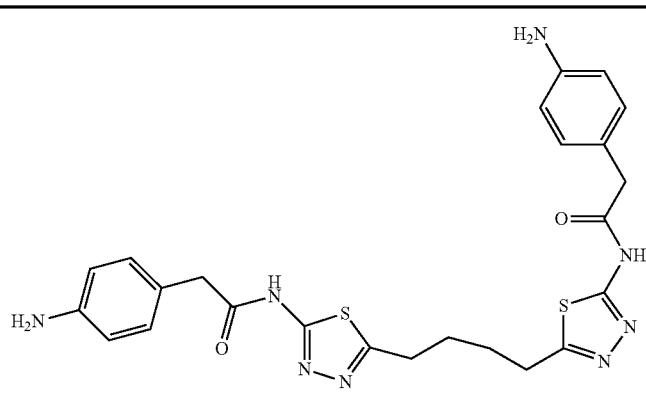 2 TFA | 0.19 | | 0.61 |
| 197 | 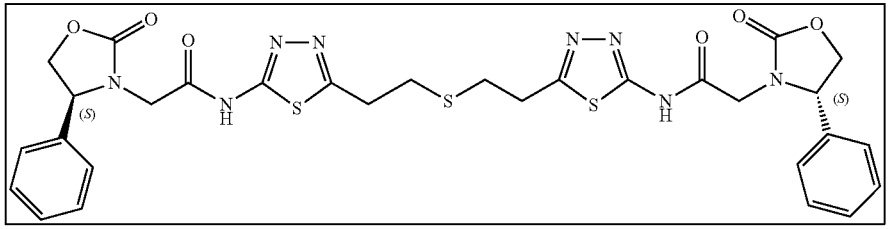 | | | 6.9 |
| 198 | 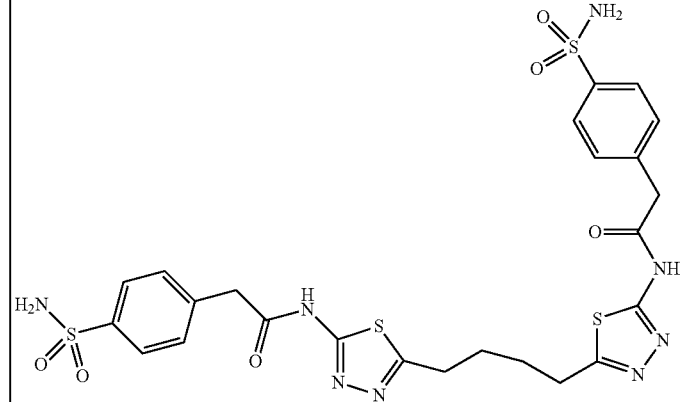 | 0.18 | | >50 |
| 199 | 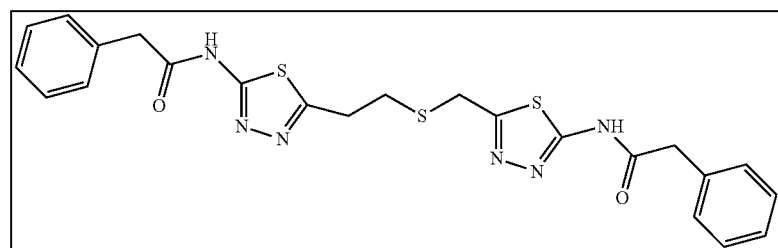 | 0.12 | | 0.17 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
| --- | --- | --- | --- | --- |
| 200 | 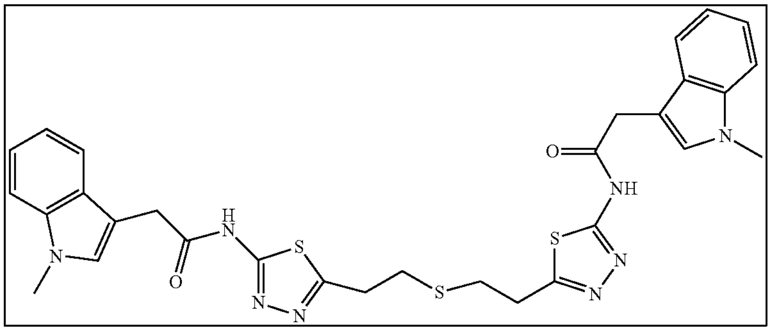 [SMILES: Cn1cc(CC(=O)Nc2nnc(CCSCCc3nnc(NC(=O)Cc4cn(C)c5ccccc45)s3)s2)c2ccccc21] | | | 0.61 |
| 201 | 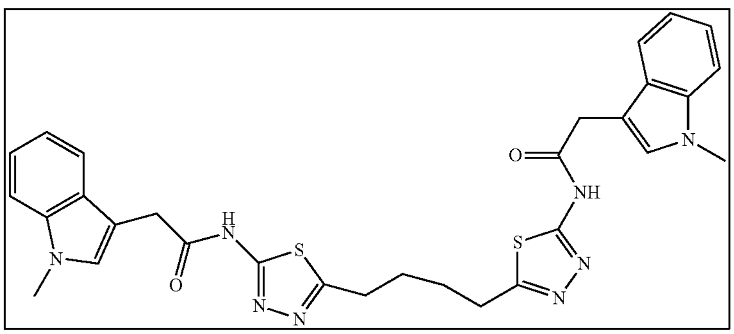 [SMILES: Cn1cc(CC(=O)Nc2nnc(CCCCc3nnc(NC(=O)Cc4cn(C)c5ccccc45)s3)s2)c2ccccc21] | | | 2.7 |
| 202 | 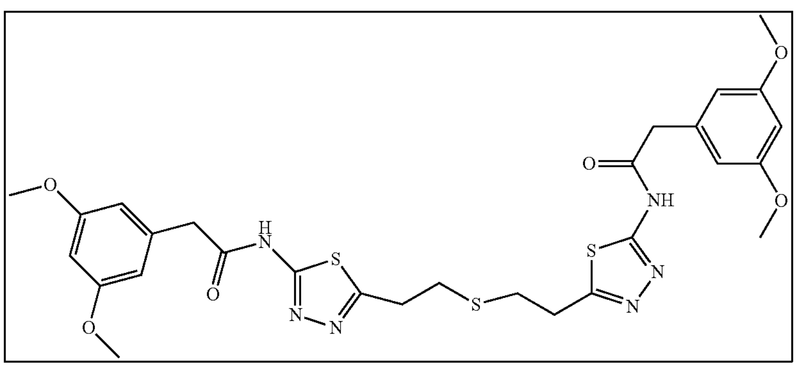 [SMILES: COc1cc(CC(=O)Nc2nnc(CCSCCc3nnc(NC(=O)Cc4cc(OC)cc(OC)c4)s3)s2)cc(OC)c1] | | 0.18 | 0.14 |
| 203 | 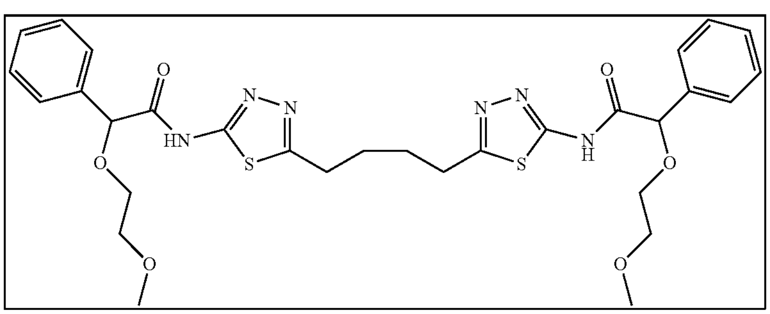 [SMILES: COCCOC(C(=O)Nc1nnc(CCCCc2nnc(NC(=O)C(OCCOC)c3ccccc3)s2)s1)c1ccccc1] | | 1.7 | 1.7 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 204 | 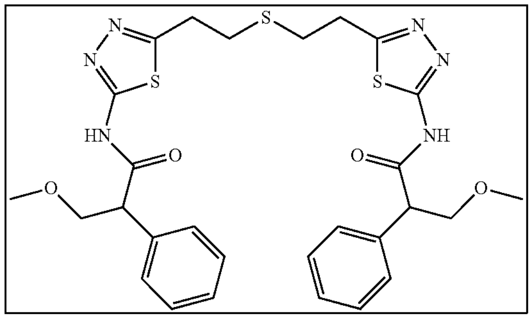 | | 0.92 | 2.4 |
| 205 | 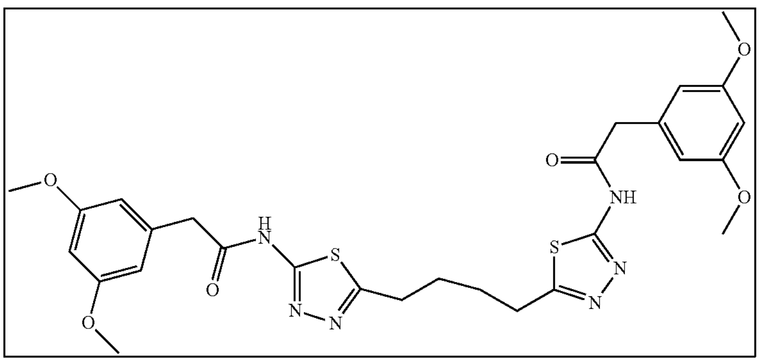 [SMILES: COc1cc(CC(=O)Nc2nnc(CCCCc3nnc(NC(=O)Cc4cc(OC)cc(OC)c4)s3)s2)cc(OC)c1] | | 0.38 | 4.1 |
| 206 | 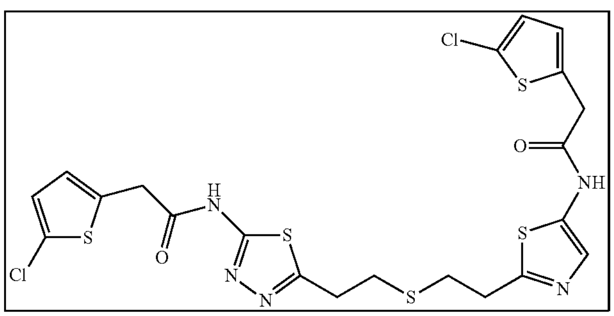 [SMILES: O=C(Cc1ccc(Cl)s1)Nc1cnc(CCSCCc2nnc(NC(=O)Cc3ccc(Cl)s3)s2)s1] | | | >20 |
| 207 | 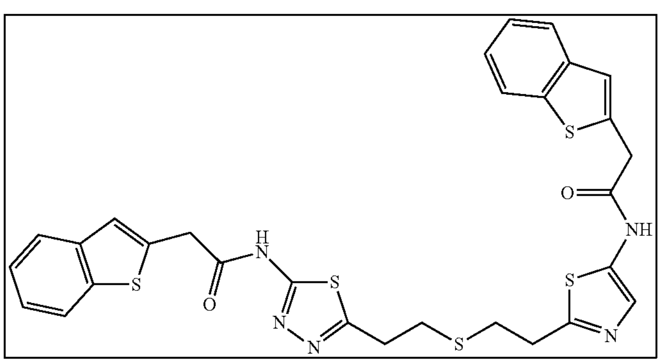 [SMILES: O=C(Cc1cc2ccccc2s1)Nc1cnc(CCSCCc2nnc(NC(=O)Cc3cc4ccccc4s3)s2)s1] | | | 13 |

TABLE 3-continued
| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 208 | 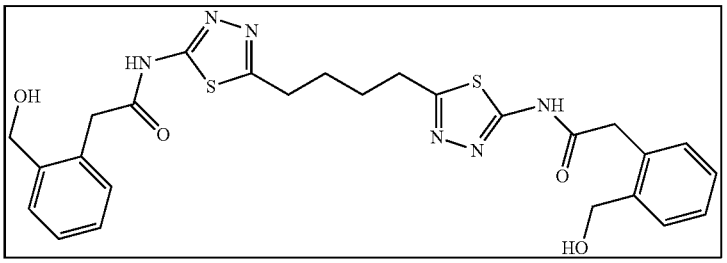 [SMILES: O=C(Cc1ccccc1CO)Nc1nnc(CCCCc2nnc(NC(=O)Cc3ccccc3CO)s2)s1] | | 0.17 | 9.0 |
| 209 | 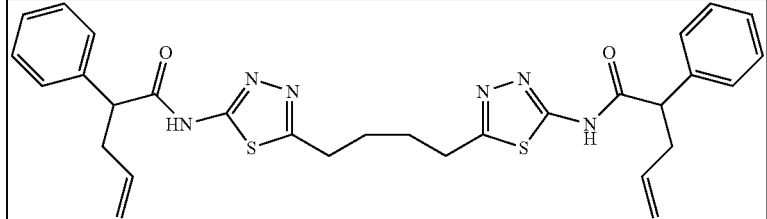 | | >20 | 22 |
| 210 | 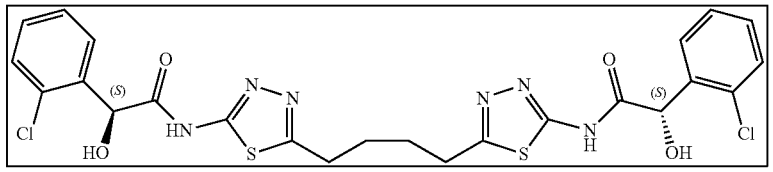 | | 0.38 | 0.42 |
| 211 | 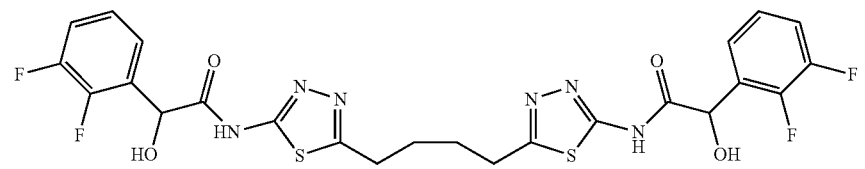 [SMILES: O=C(Nc1nnc(CCCCc2nnc(NC(=O)C(O)c3cccc(F)c3F)s2)s1)C(O)c1cccc(F)c1F] | | 1.2 | 1.0 |
| 212 | 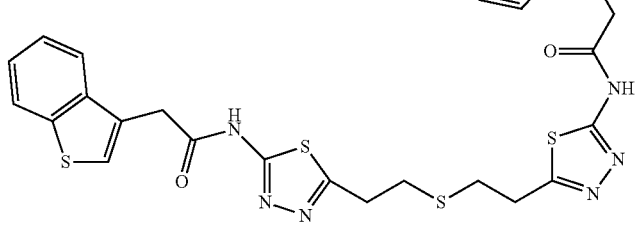 | | >20 | |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 213 | 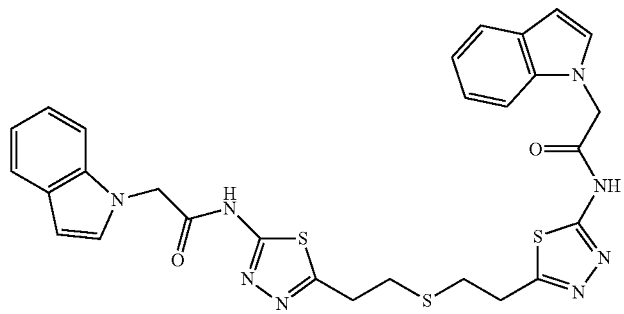 [SMILES: O=C(Cn1ccc2ccccc21)Nc1nnc(CCSCCc2nnc(NC(=O)Cn3ccc4ccccc43)s2)s1] | | 2.5 | 4.4 |
| 214 | 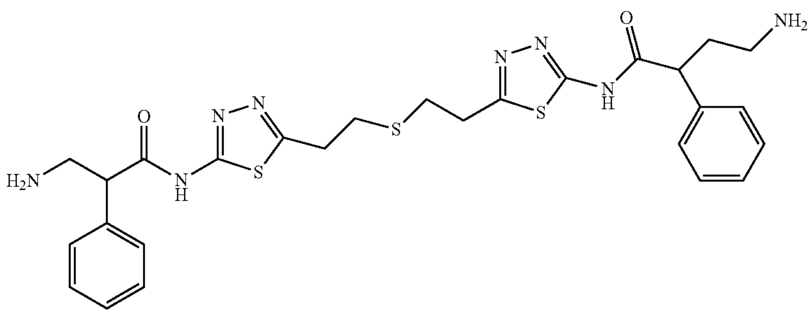 [SMILES: NCCC(C(=O)Nc1nnc(CCSCCc2nnc(NC(=O)C(CN)c3ccccc3)s2)s1)c1ccccc1] | | 0.82 | 1.2 |
| 215 | 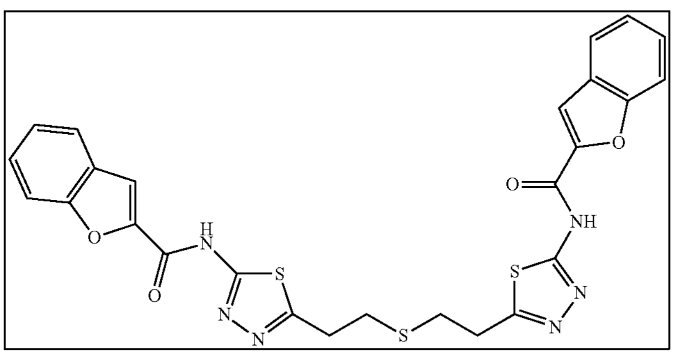 [SMILES: O=C(Nc1nnc(CCSCCc2nnc(NC(=O)c3cc4ccccc4o3)s2)s1)c1cc2ccccc2o1] | | | 16 |
| 216 | 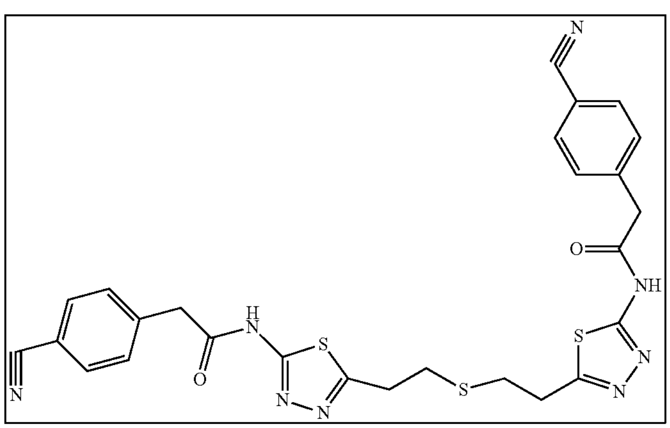 [SMILES: N#Cc1ccc(CC(=O)Nc2nnc(CCSCCc3nnc(NC(=O)Cc4ccc(C#N)cc4)s3)s2)cc1] | | 0.89 | >50 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 217 | 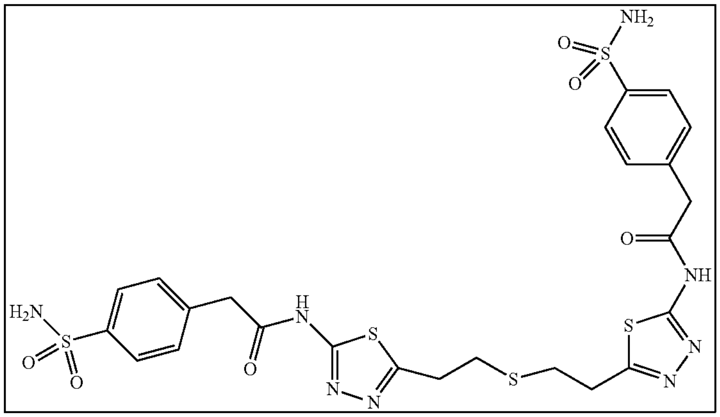 [SMILES: NS(=O)(=O)c1ccc(CC(=O)Nc2nnc(CCSCCc3nnc(NC(=O)Cc4ccc(S(N)(=O)=O)cc4)s3)s2)cc1] | | 0.24 | >50 |
| 218 | 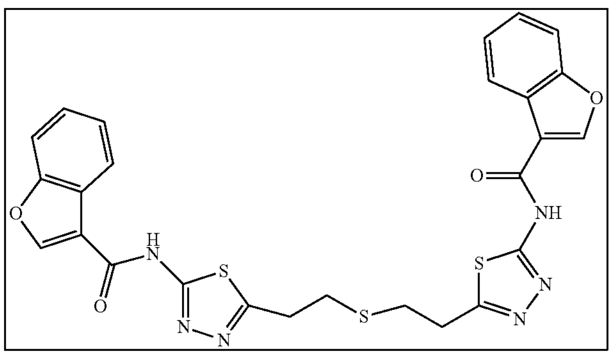 [SMILES: O=C(Nc1nnc(CCSCCc2nnc(NC(=O)c3coc4ccccc34)s2)s1)c1coc2ccccc12] | | | >20 |
| 219 | 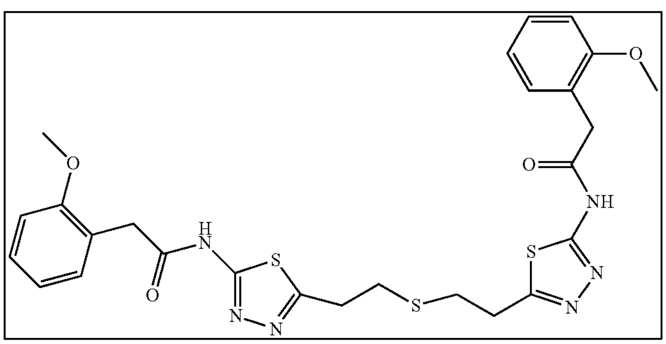 [SMILES: COc1ccccc1CC(=O)Nc1nnc(CCSCCc2nnc(NC(=O)Cc3ccccc3OC)s2)s1] | | 0.17 | 0.57 |
| 220 | 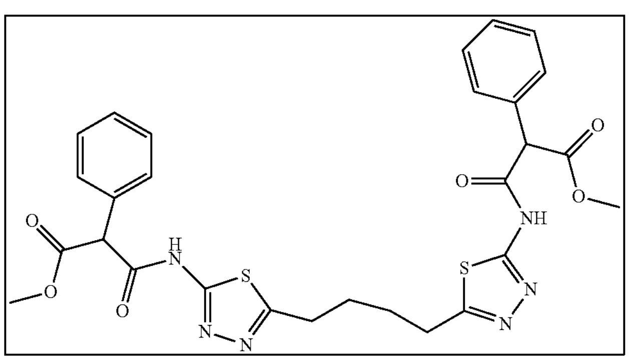 | | 1.6 | 0.31 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 221 | 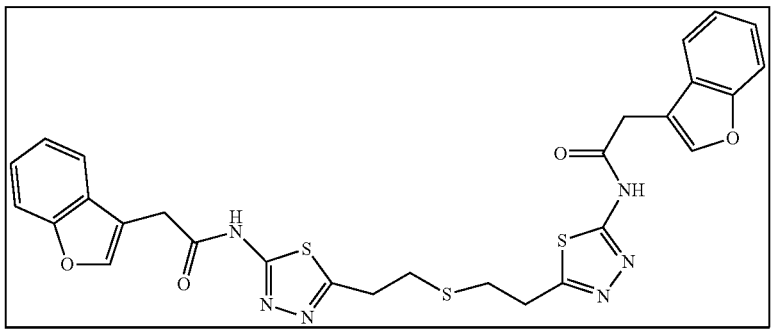 [SMILES: O=C(Cc1coc2ccccc12)Nc1nnc(CCSCCc2nnc(NC(=O)Cc3coc4ccccc34)s2)s1] | | | >20 |
| 222 | 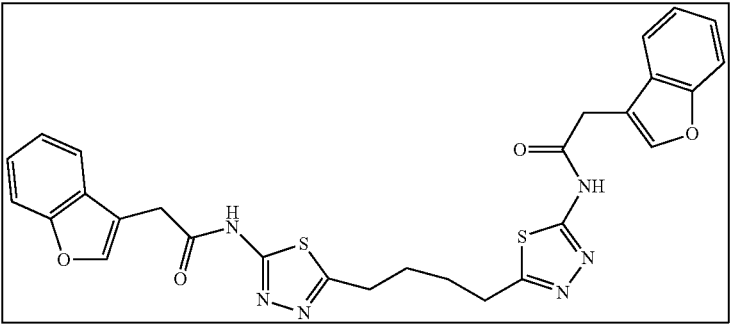 [SMILES: O=C(Cc1coc2ccccc12)Nc1nnc(CCCCc2nnc(NC(=O)Cc3coc4ccccc34)s2)s1] | | | >20 |
| 223 | 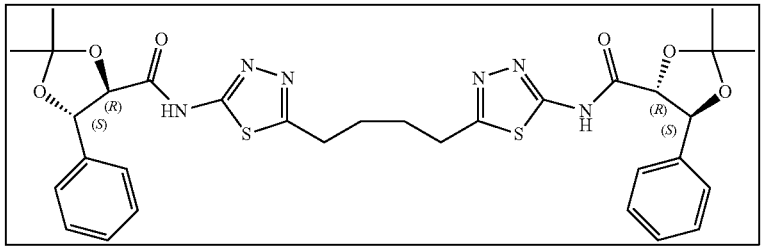 | | | >20 |
| 224 | 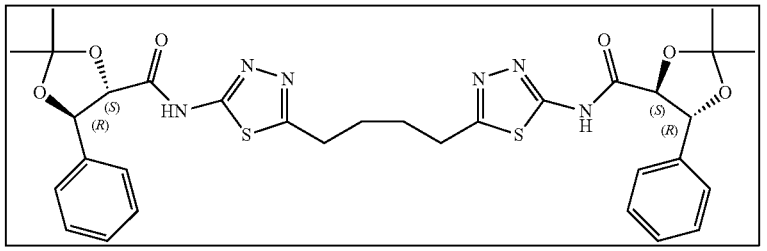 | | | >20 |
| 225 | 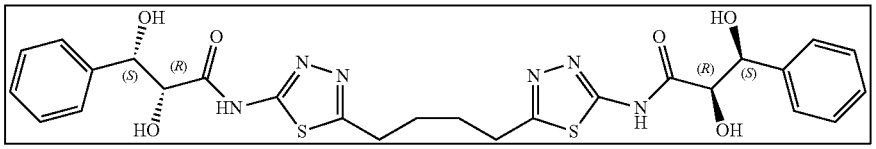 | | | >20 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 226 | 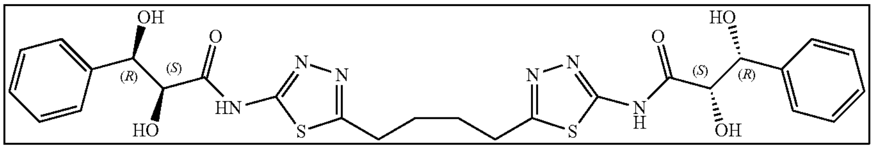 | | 2.3 | >50 |
| 227 | 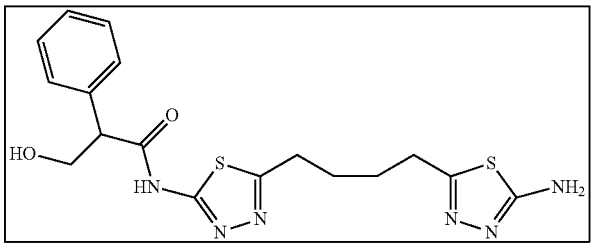 [SMILES: Nc1nnc(CCCCc2nnc(NC(=O)C(CO)c3ccccc3)s2)s1] | | 9.9 | 3.3 |
| 228 | 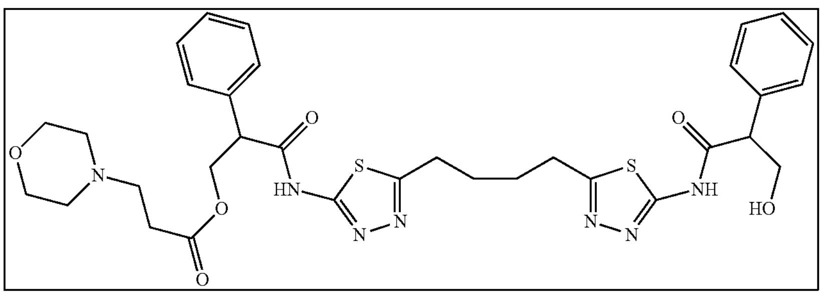 [SMILES: O=C(CCN1CCOCC1)OCC(C(=O)Nc1nnc(CCCCc2nnc(NC(=O)C(CO)c3ccccc3)s2)s1)c1ccccc1] | | 0.57 | 0.13 |
| 229 | 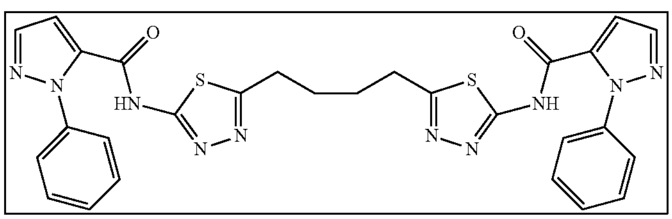 [SMILES: O=C(Nc1nnc(CCCCc2nnc(NC(=O)c3ccnn3-c3ccccc3)s2)s1)c1ccnn1-c1ccccc1] | | 3.9 | |
| 230 | 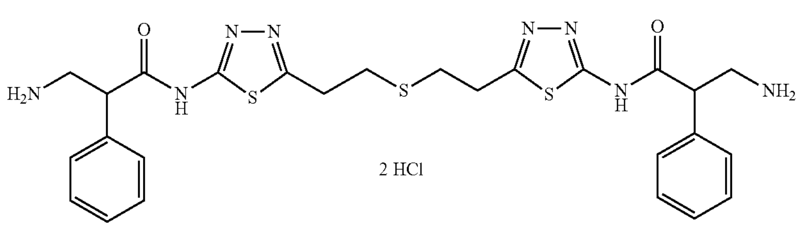 | | 12 | |
| 231 | 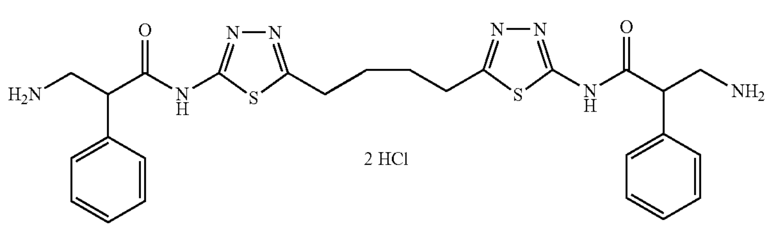 | | 7.4 | |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 232 | 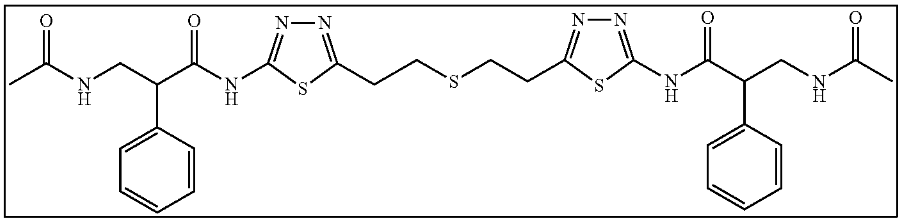 | | | 9.8 |
| 233 | 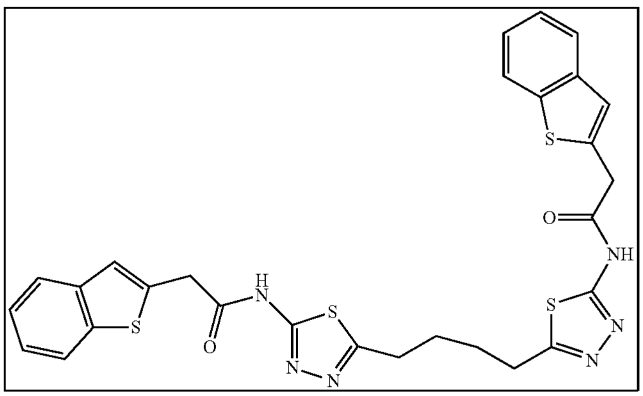 [SMILES: O=C(Cc1cc2ccccc2s1)Nc1nnc(CCCCc2nnc(NC(=O)Cc3cc4ccccc4s3)s2)s1] | | | 15 |
| 234 | 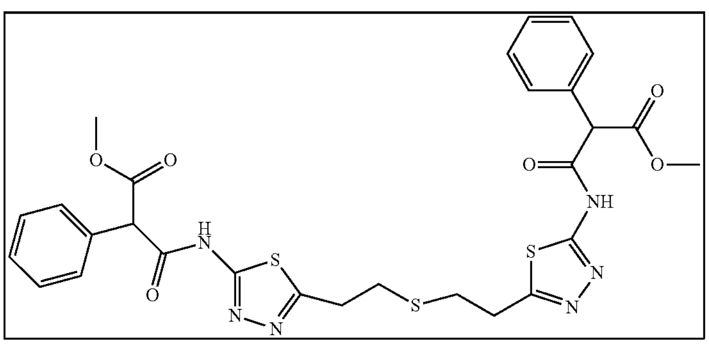 [SMILES: COC(=O)C(C(=O)Nc1nnc(CCSCCc2nnc(NC(=O)C(C(=O)OC)c3ccccc3)s2)s1)c1ccccc1] | | | 2.0 2.5 |
| 235 | 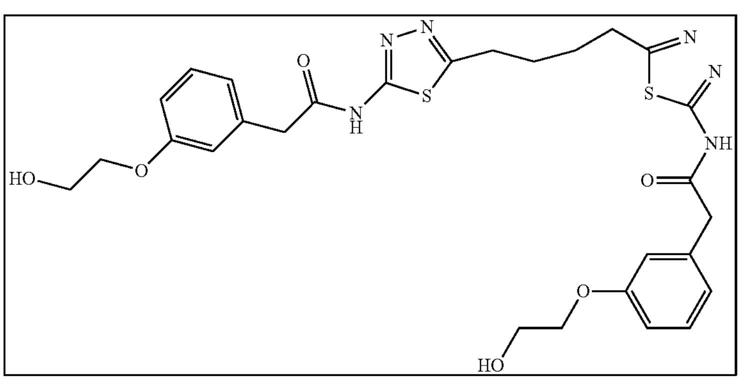 [SMILES: N=C(CCCCc1nnc(NC(=O)Cc2cccc(OCCO)c2)s1)SC(=N)NC(=O)Cc1cccc(OCCO)c1] | | | 0.11 0.21 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 236 | 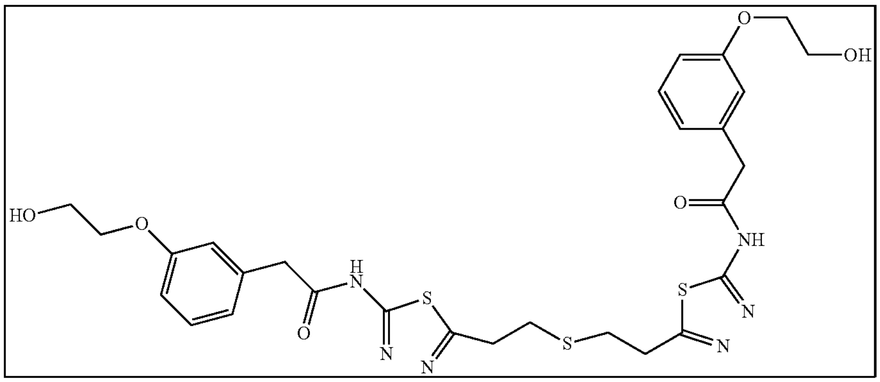 [SMILES: N=C(CCSCCC(=N)SC(=N)NC(=O)Cc1cccc(OCCO)c1)SC(=N)NC(=O)Cc1cccc(OCCO)c1] | | 0.20 | 1.4 |
| 237 | 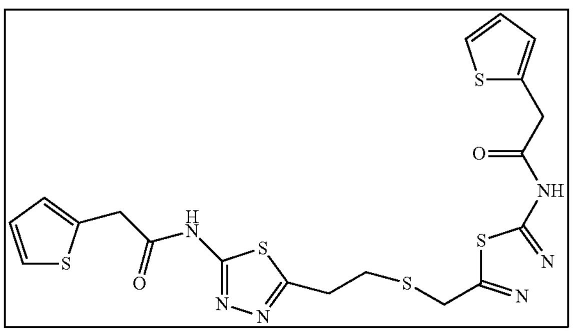 [SMILES: N=C(CSCCc1nnc(NC(=O)Cc2cccs2)s1)SC(=N)NC(=O)Cc1cccs1] | | 0.20 | 0.25 |
| 238 | 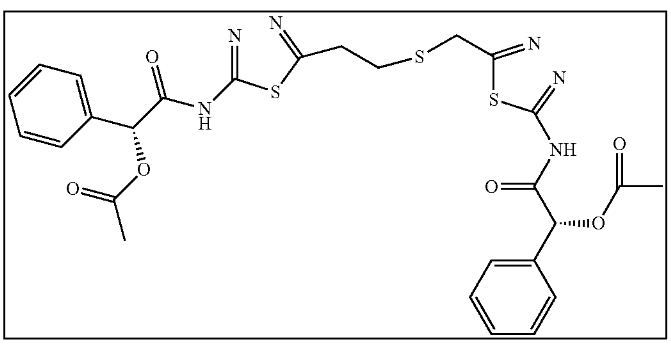 [SMILES: CC(=O)O[C@@H](C(=O)NC(=N)SC(=N)CCSCC(=N)SC(=N)NC(=O)[C@H](OC(C)=O)c1ccccc1)c1ccccc1] | | | 13 |
| 239 | 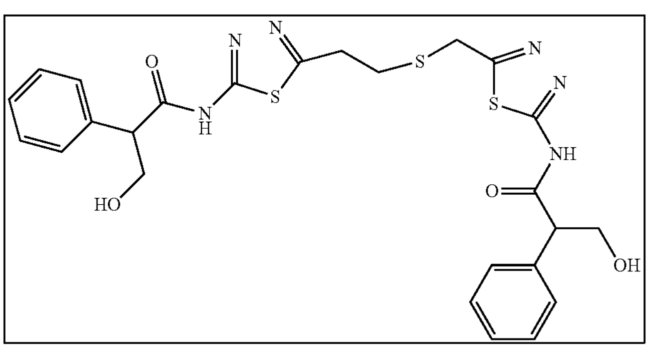 [SMILES: N=C(CCSCC(=N)SC(=N)NC(=O)C(CO)c1ccccc1)SC(=N)NC(=O)C(CO)c1ccccc1] | | 0.30 | 0.30 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 240 | 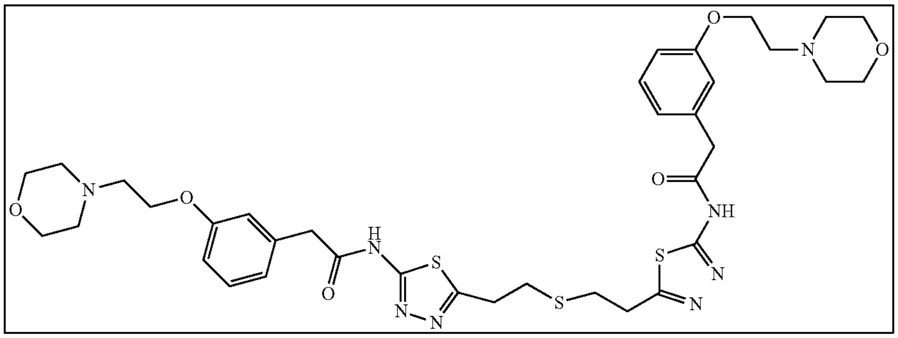 [SMILES: N=C(CCSCCc1nnc(NC(=O)Cc2cccc(OCCN3CCOCC3)c2)s1)SC(=N)NC(=O)Cc1cccc(OCCN2CCOCC2)c1] | 0.54 | | 1.3 |
| 241 | 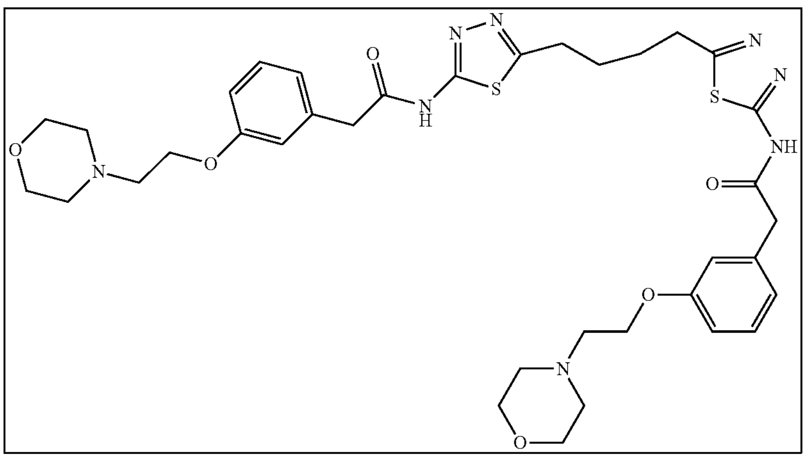 [SMILES: N=C(CCCCc1nnc(NC(=O)Cc2cccc(OCCN3CCOCC3)c2)s1)SC(=N)NC(=O)Cc1cccc(OCCN2CCOCC2)c1] | 0.38 | | 0.87 |
| 242 | 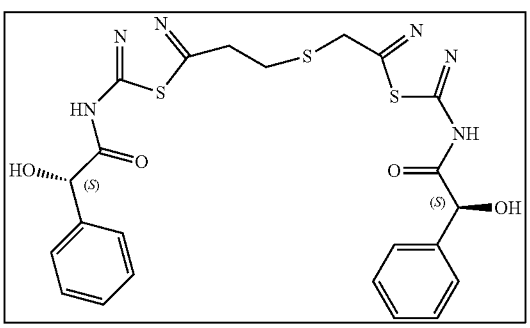 | 0.36 | | 0.22 |
| 243 | 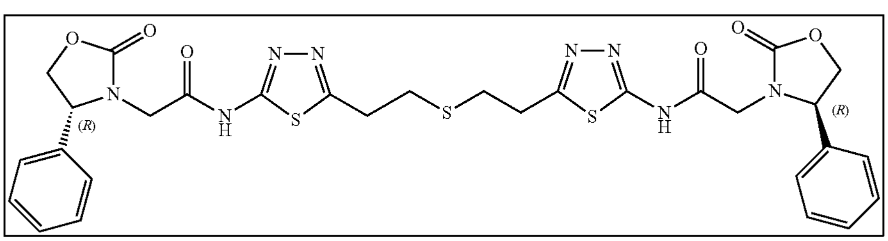 | 2.7 | | 33 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 244 | 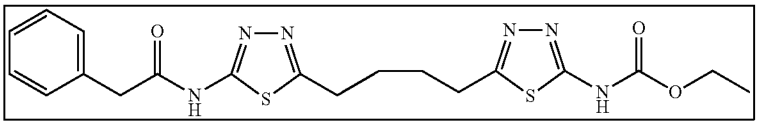 | | 0.84 | 1.7 |
| 245 | 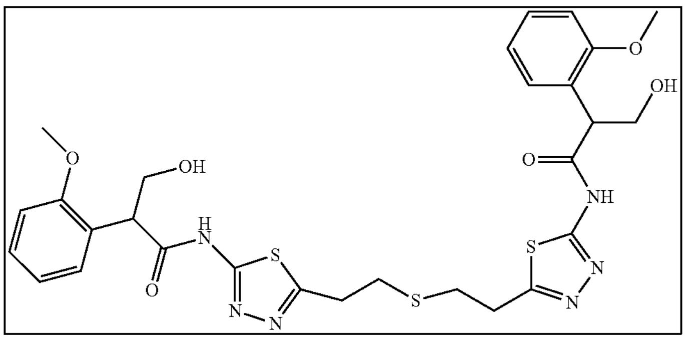 [SMILES: COc1ccccc1C(CO)C(=O)Nc1nnc(CCSCCc2nnc(NC(=O)C(CO)c3ccccc3OC)s2)s1] | | 0.52 | 2.5 |
| 246 | 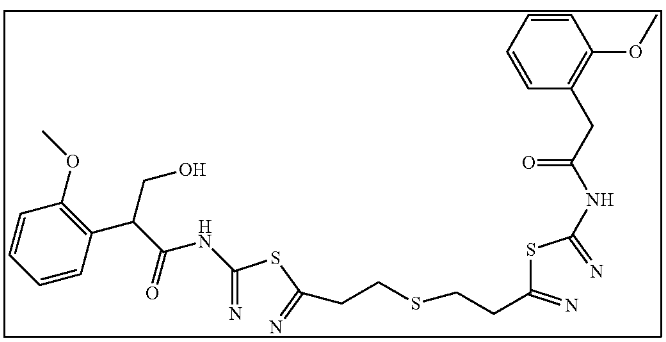 [SMILES: COc1ccccc1CC(=O)NC(=N)SC(=N)CCSCCC(=N)SC(=N)NC(=O)C(CO)c1ccccc1OC] | | 0.40 | 1.6 |
| 247 | 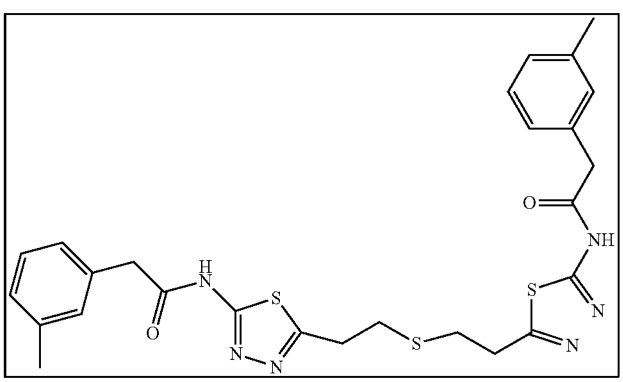 [SMILES: Cc1cccc(CC(=O)NC(=N)SC(=N)CCSCCc2nnc(NC(=O)Cc3cccc(C)c3)s2)c1] | | 0.19 | 0.83 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 248 | 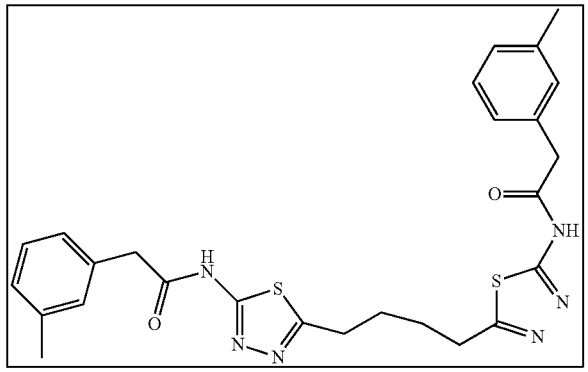 [SMILES: Cc1cccc(CC(=O)NC(=N)SC(=N)CCCCc2nnc(NC(=O)Cc3cccc(C)c3)s2)c1] | | | 2.3 |
| 249 | 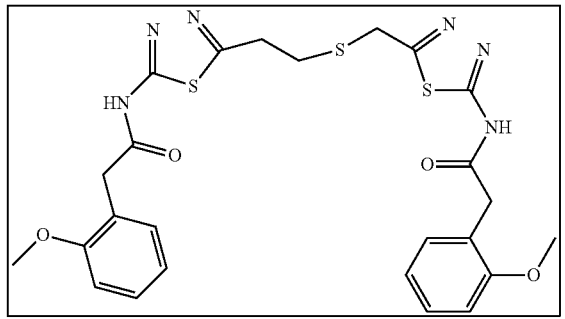 | | | 0.12 0.16 |
| 250 | 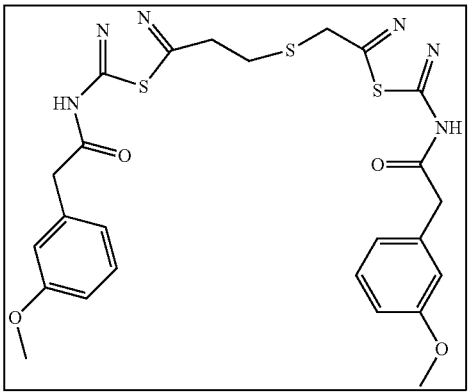 [SMILES: COc1cccc(CC(=O)NC(=N)SC(=N)CCSCC(=N)SC(=N)NC(=O)Cc2cccc(OC)c2)c1] | | | 0.12 0.14 |
| 251 | 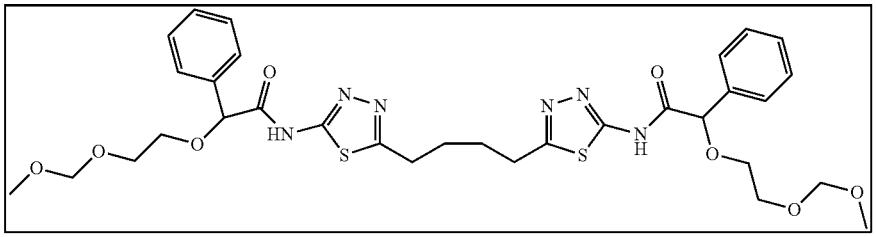 | | | 2.8 2.8 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 252 | 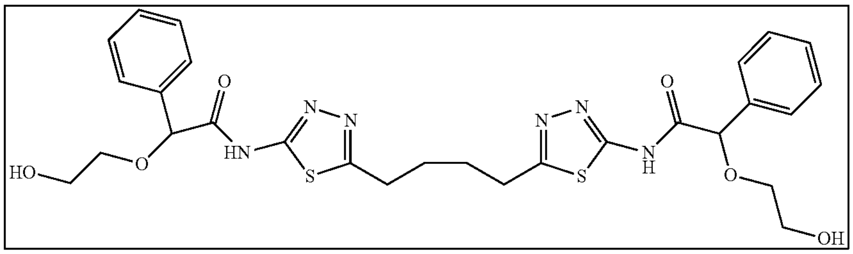 [SMILES: O=C(Nc1nnc(CCCCc2nnc(NC(=O)C(OCCO)c3ccccc3)s2)s1)C(OCCO)c1ccccc1] | | 1.2 | 6.3 |
| 253 | 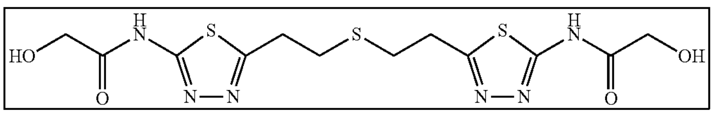 [SMILES: O=C(CO)Nc1nnc(CCSCCc2nnc(NC(=O)CO)s2)s1] | | | 21 |
| 254 | 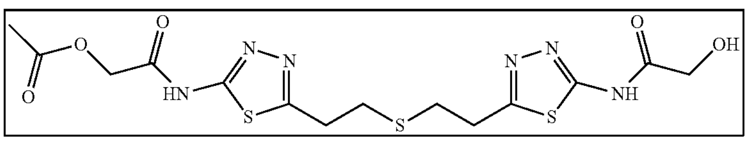 | | | >20 |
| 255 | 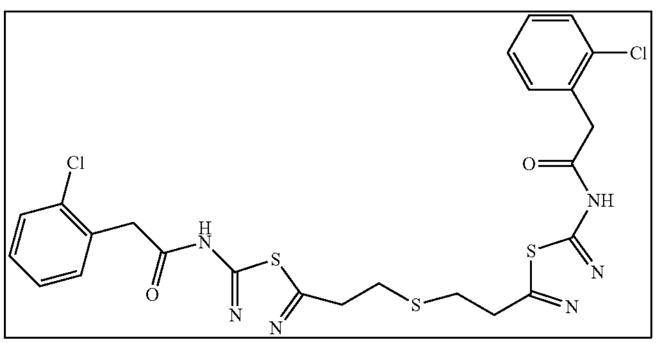 [SMILES: N=C(CCSCCC(=N)SC(=N)NC(=O)Cc1ccccc1Cl)SC(=N)NC(=O)Cc1ccccc1Cl] | | | 0.38 |
| 256 | 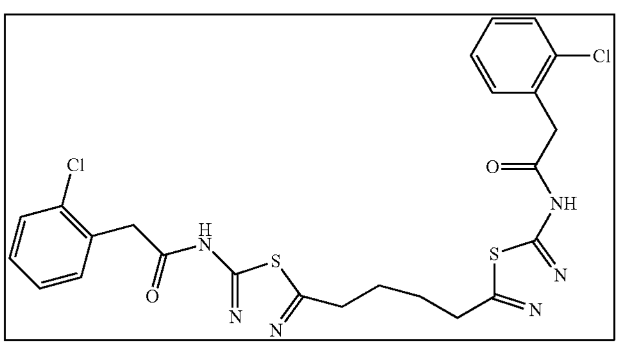 [SMILES: N=C(CCCCC(=N)SC(=N)NC(=O)Cc1ccccc1Cl)SC(=N)NC(=O)Cc1ccccc1Cl] | | | 0.11 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 257 | 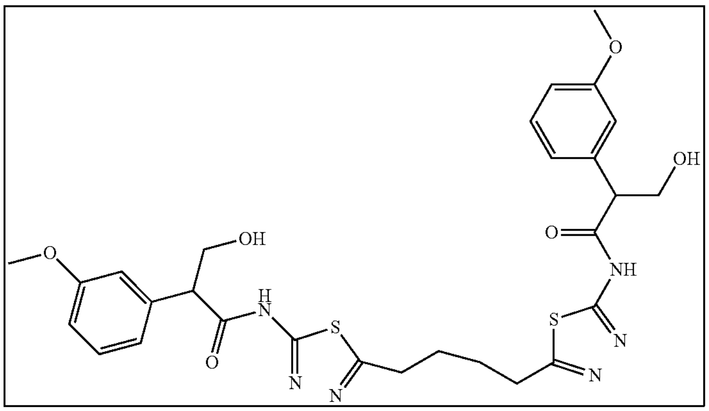 | | 0.12 | 0.073 |
| 258 | 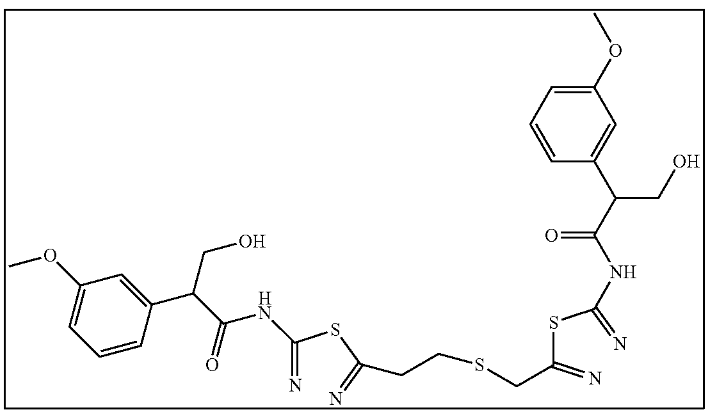 [SMILES: COc1cccc(C(CO)C(=O)NC(=N)SC(=N)CCCCC(=N)SC(=N)NC(=O)C(CO)c2cccc(OC)c2)c1] | | 0.19 | 0.18 |
| 259 | 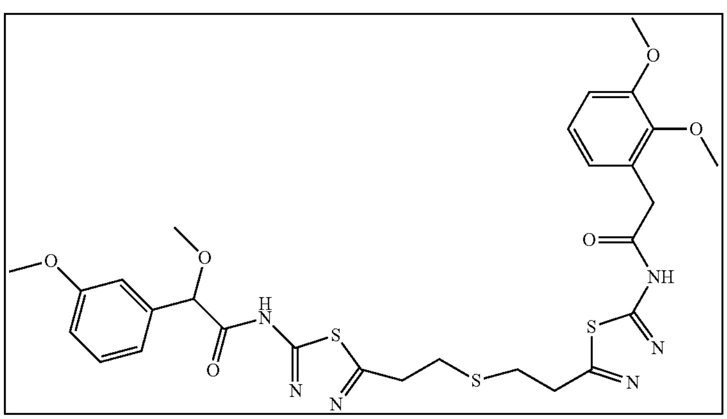 | | 0.23 | 0.57 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 260 | 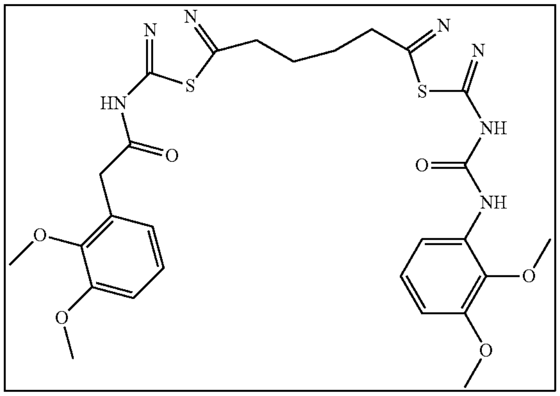 | | 0.15 | 0.084 |
| 261 | 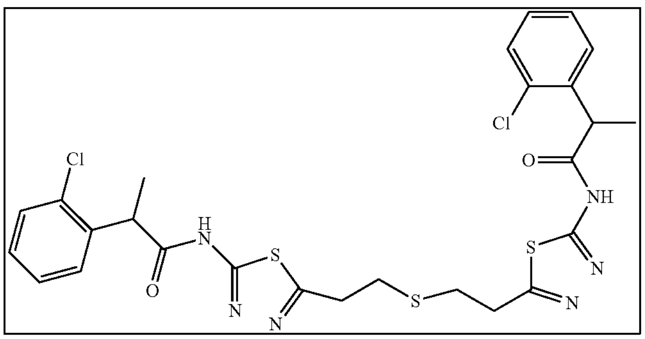 [SMILES: CC(C(=O)NC(=N)SC(=N)CCSCCC(=N)SC(=N)NC(=O)C(C)c1ccccc1Cl)c1ccccc1Cl] | | 0.70 | 2.6 |
| 262 | 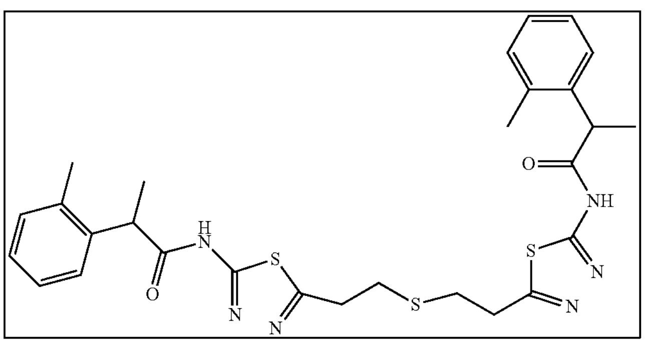 [SMILES: Cc1ccccc1C(C)C(=O)NC(=N)SC(=N)CCSCCC(=N)SC(=N)NC(=O)C(C)c1ccccc1C] | | 0.36 | 3.1 |
| 263 | 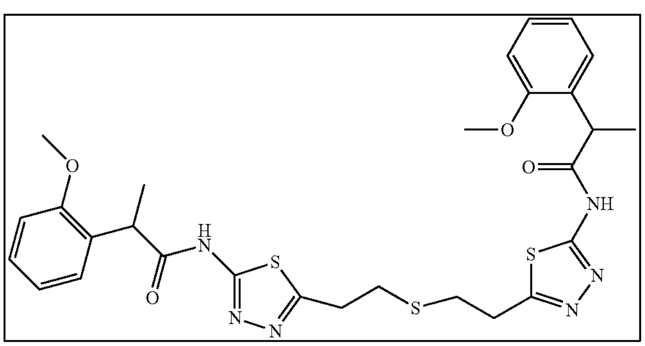 [SMILES: COc1ccccc1C(C)C(=O)Nc1nnc(CCSCCc2nnc(NC(=O)C(C)c3ccccc3OC)s2)s1] | | 0.32 | 3.9 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 264 | 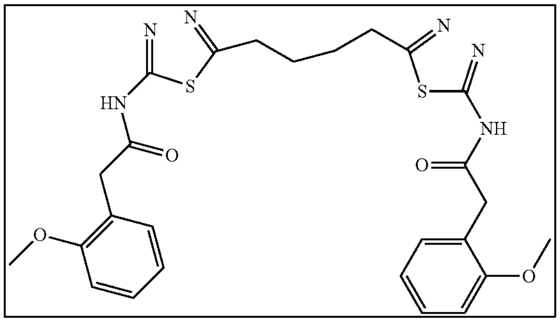 | | 0.072 | 0.01 |
| 265 | 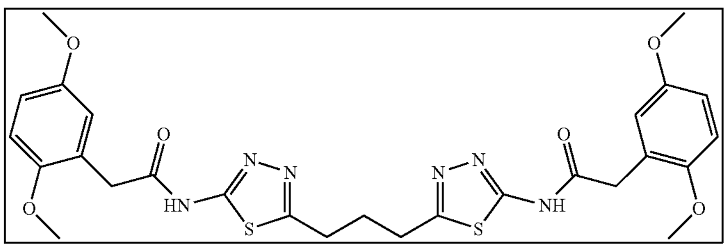 [SMILES: COc1ccc(OC)c(CC(=O)Nc2nnc(CCCc3nnc(NC(=O)Cc4cc(OC)ccc4OC)s3)s2)c1] | | 0.27 | 0.31 |
| 266 | 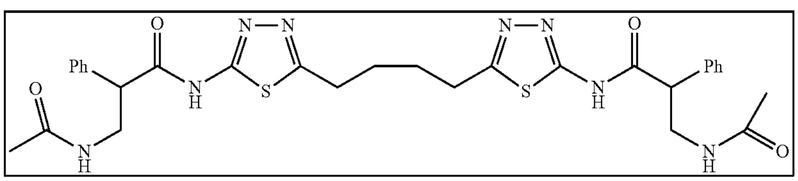 [SMILES: CC(=O)NCC(C(=O)Nc1nnc(CCCCc2nnc(NC(=O)C(CNC(C)=O)c3ccccc3)s2)s1)c1ccccc1] | | 2.2 | >50 |
| 267 | 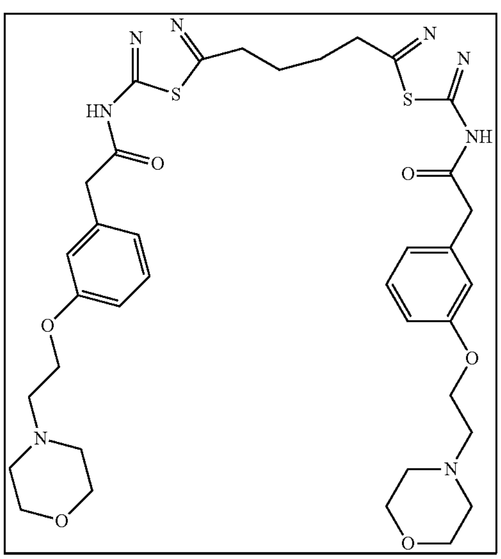 [SMILES: N=C(CCCCC(=N)SC(=N)NC(=O)Cc1cccc(OCCN2CCOCC2)c1)SC(=N)NC(=O)Cc1cccc(OCCN2CCOCC2)c1] | | 0.61 | 0.64 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 268 | 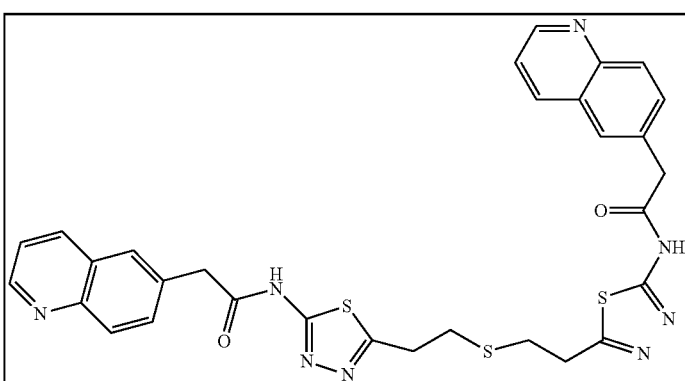 | | 0.60 | 5.4 |
| 269 | 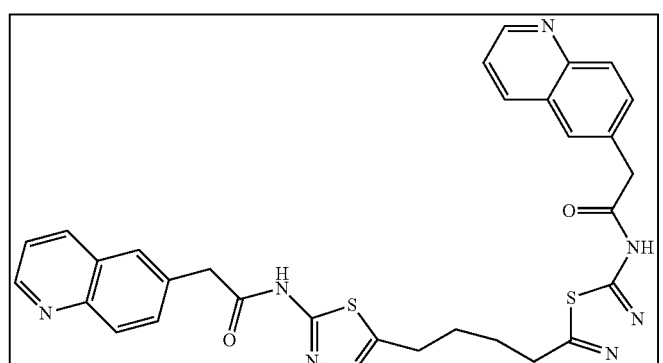 | | 0.26 | 0.52 |
| 270 | 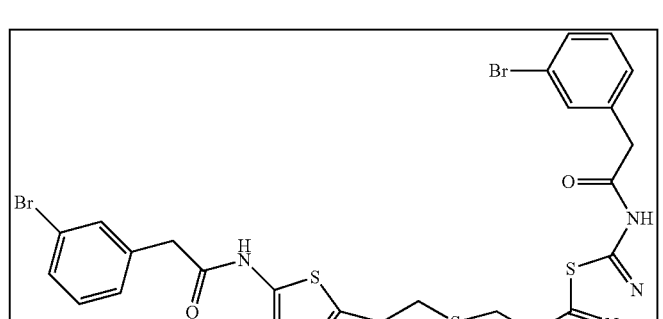 | >5 | 7.4 | 0.85 |
| 271 | 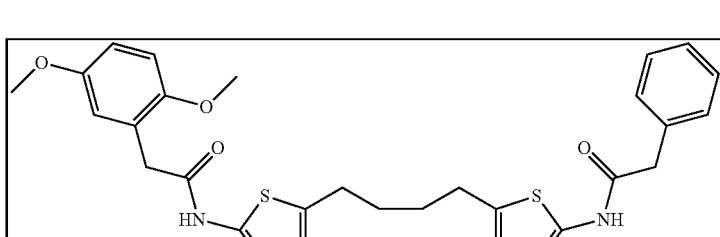 | | 0.10 | 0.63 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 272 | 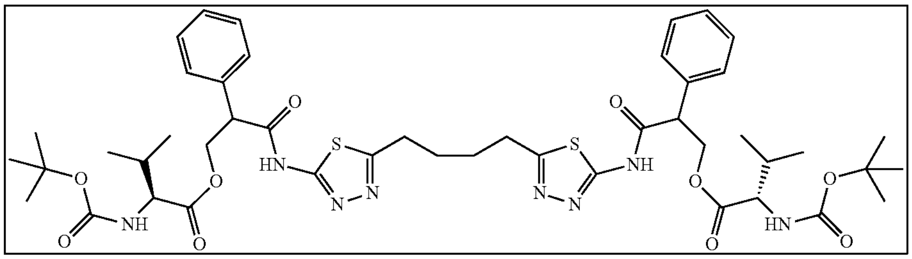 [SMILES: CC(C)[C@H](NC(=O)OC(C)(C)C)C(=O)OCC(C(=O)Nc1nnc(CCCCc2nnc(NC(=O)C(COC(=O)[C@@H](NC(=O)OC(C)(C)C)C(C)C)c3ccccc3)s2)s1)c1ccccc1] | | | >20 |
| 273 | 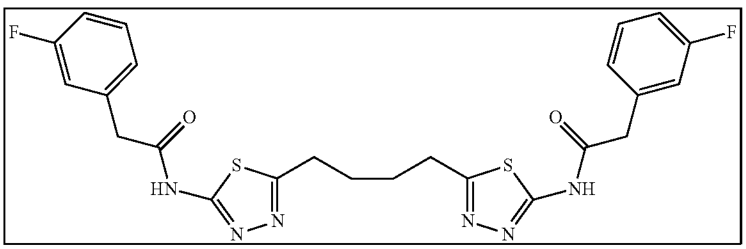 [SMILES: O=C(Cc1cccc(F)c1)Nc1nnc(CCCCc2nnc(NC(=O)Cc3cccc(F)c3)s2)s1] | | 0.14 | 0.07 |
| 274 | 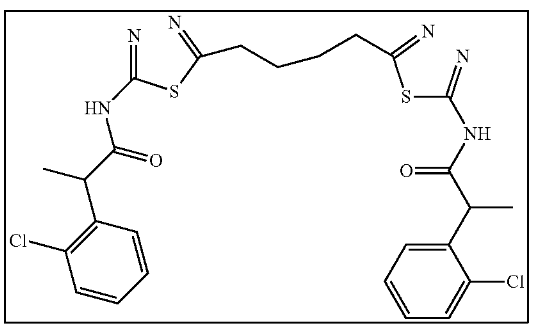 [SMILES: CC(C(=O)NC(=N)SC(=N)CCCCC(=N)SC(=N)NC(=O)C(C)c1ccccc1Cl)c1ccccc1Cl] | | 0.75 | 0.68 |
| 275 | 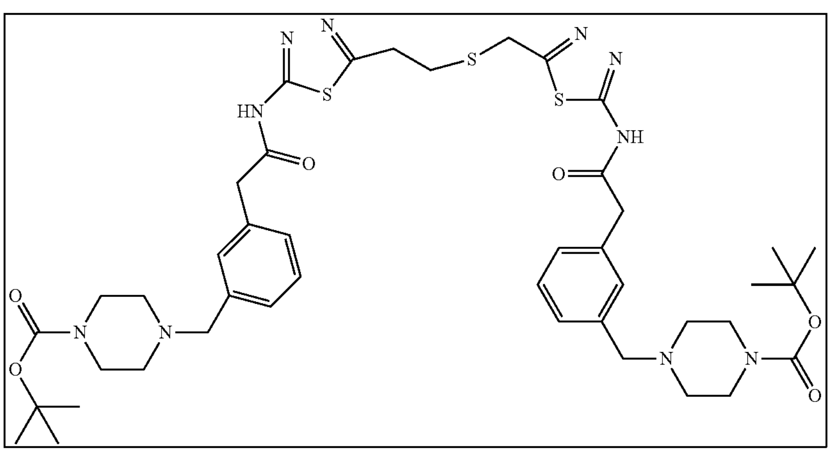 [SMILES: CC(C)(C)OC(=O)N1CCN(Cc2cccc(CC(=O)NC(=N)SC(=N)CCSCC(=N)SC(=N)NC(=O)Cc3cccc(CN4CCN(C(=O)OC(C)(C)C)CC4)c3)c2)CC1] | 0.15 | 2.2 | 0.34 |

TABLE 3-continued
| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 276 | 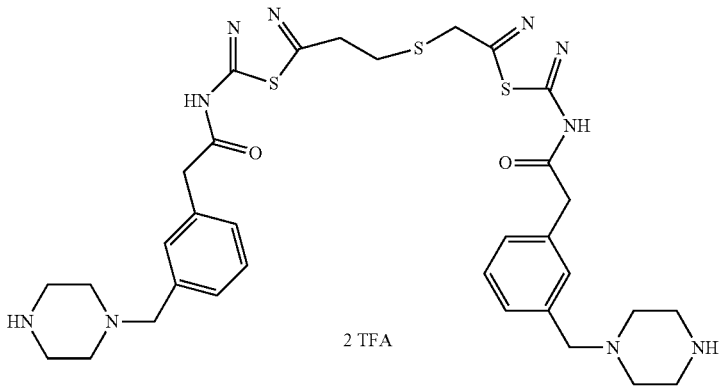 [SMILES: N=C(CCSCC(=N)SC(=N)NC(=O)Cc1cccc(CN2CCNCC2)c1)SC(=N)NC(=O)Cc1cccc(CN2CCNCC2)c1] 2 TFA | | 1.5 | 56 |
| 277 | 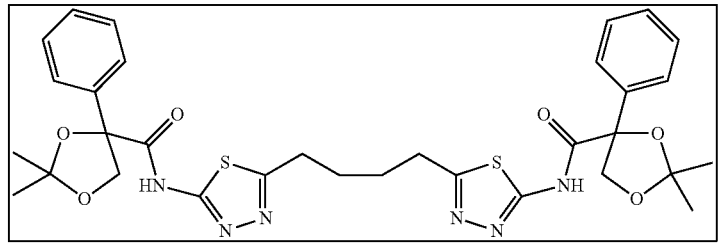 | | >20 | |
| 278 | 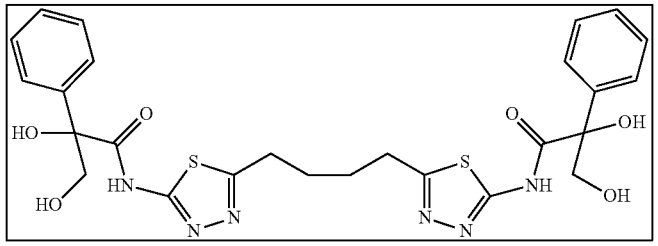 [SMILES: O=C(Nc1nnc(CCCCc2nnc(NC(=O)C(O)(CO)c3ccccc3)s2)s1)C(O)(CO)c1ccccc1] | | 0.38 | 0.16 |
| 279 | 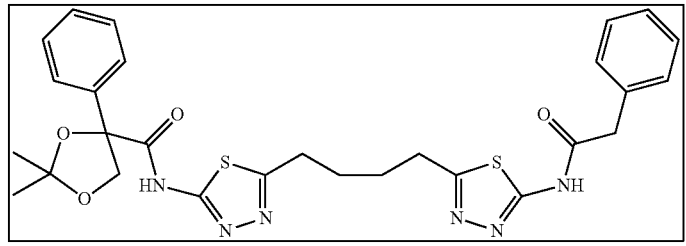 [SMILES: CC1(C)OCC(C(=O)Nc2nnc(CCCCc3nnc(NC(=O)Cc4ccccc4)s3)s2)(c2ccccc2)O1] | | 0.68 | 7.0 |
| 280 | 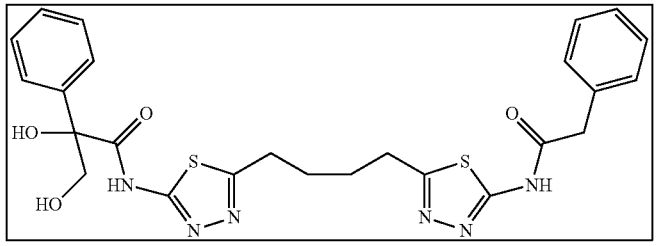 [SMILES: O=C(Cc1ccccc1)Nc1nnc(CCCCc2nnc(NC(=O)C(O)(CO)c3ccccc3)s2)s1] | | 0.29 | 0.23 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 281 | 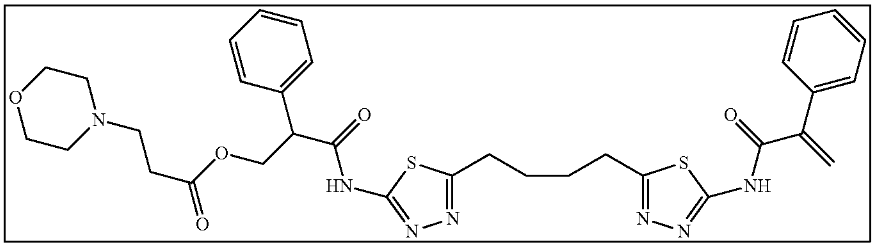 [SMILES: C=C(C(=O)Nc1nnc(CCCCc2nnc(NC(=O)C(COC(=O)CCN3CCOCC3)c3ccccc3)s2)s1)c1ccccc1] | | 0.74 | 0.66 |
| 282 | 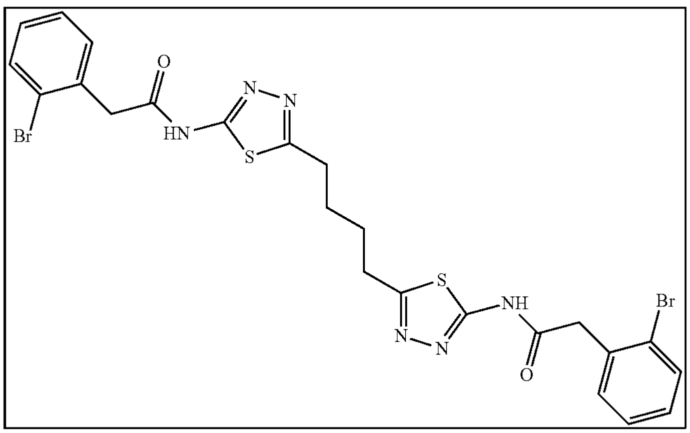 [SMILES: O=C(Cc1ccccc1Br)Nc1nnc(CCCCc2nnc(NC(=O)Cc3ccccc3Br)s2)s1] | | 0.082 | 0.37 |
| 283 | 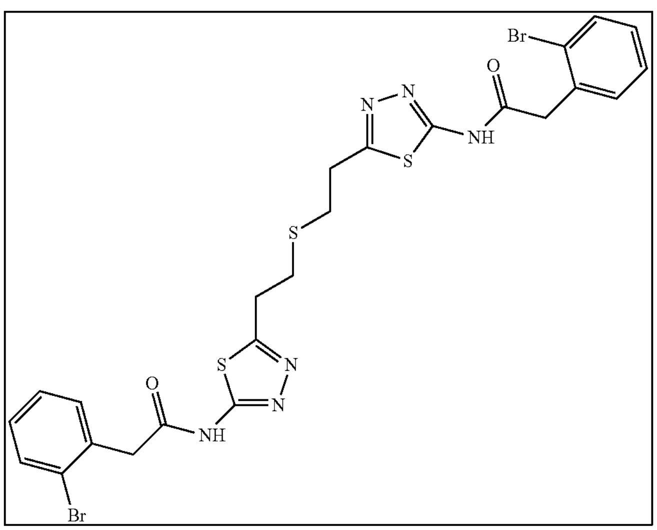 [SMILES: O=C(Cc1ccccc1Br)Nc1nnc(CCSCCc2nnc(NC(=O)Cc3ccccc3Br)s2)s1] | | 0.66 | 0.74 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 284 | 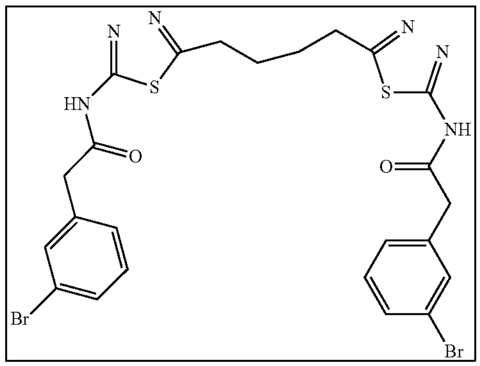 [SMILES: N=C(CCCCC(=N)SC(=N)NC(=O)Cc1cccc(Br)c1)SC(=N)NC(=O)Cc1cccc(Br)c1] | | 0.05 | >20 |
| 285 | 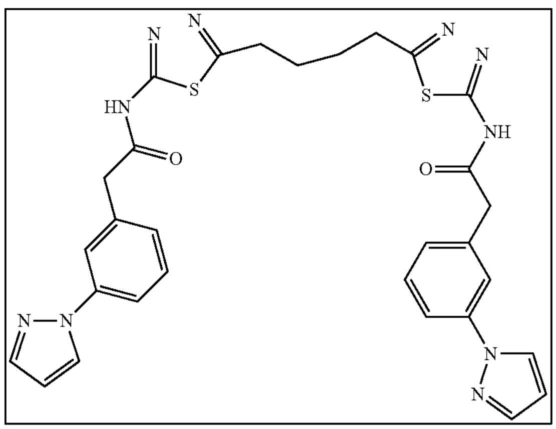 [SMILES: N=C(CCCCC(=N)SC(=N)NC(=O)Cc1cccc(-n2cccn2)c1)SC(=N)NC(=O)Cc1cccc(-n2cccn2)c1] | | 0.19 | 0.14 |
| 286 | (2 HCO2H) | | 0.54 | 6.4 |
| 287 | 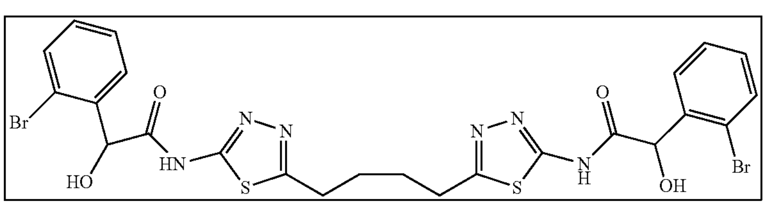 [SMILES: O=C(Nc1nnc(CCCCc2nnc(NC(=O)C(O)c3ccccc3Br)s2)s1)C(O)c1ccccc1Br] | | 0.57 | 1.3 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 288 | 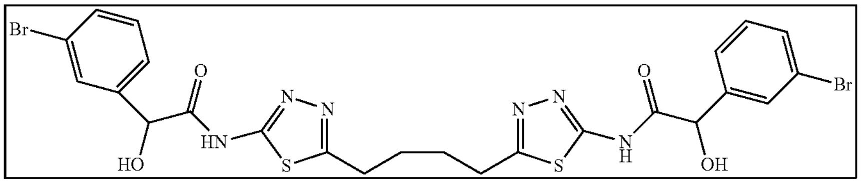 [SMILES: O=C(Nc1nnc(CCCCc2nnc(NC(=O)C(O)c3cccc(Br)c3)s2)s1)C(O)c1cccc(Br)c1] | 0.04 | 0.67 | 0.028 |
| 289 | 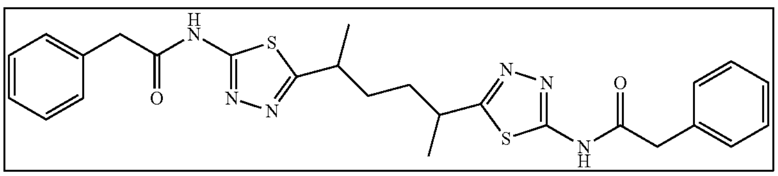 [SMILES: CC(CCC(C)c1nnc(NC(=O)Cc2ccccc2)s1)c1nnc(NC(=O)Cc2ccccc2)s1] | | 32 | |
| 290 | 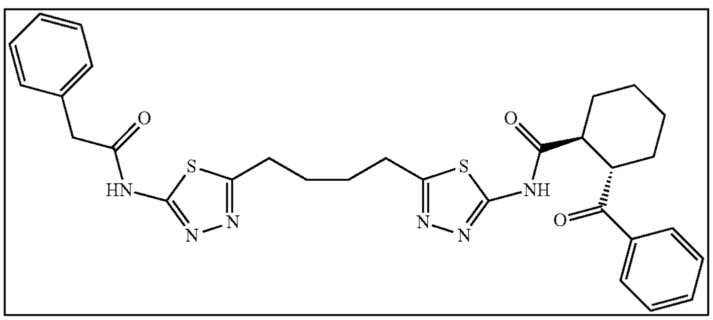 [SMILES: O=C(Cc1ccccc1)Nc1nnc(CCCCc2nnc(NC(=O)[C@H]3CCCC[C@@H]3C(=O)c3ccccc3)s2)s1] | | 0.80 | 0.79 |
| 291 | 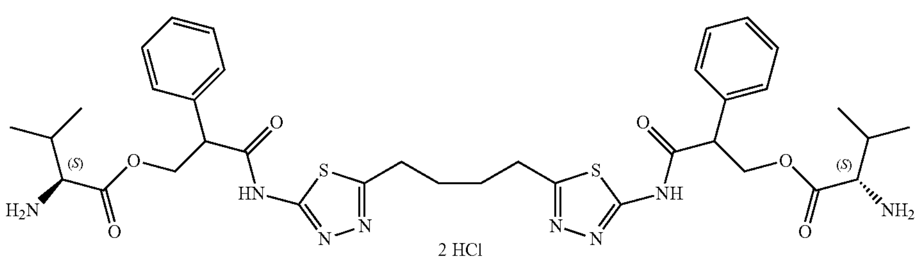 | | 1.5 | 1.8 |
| 292 | 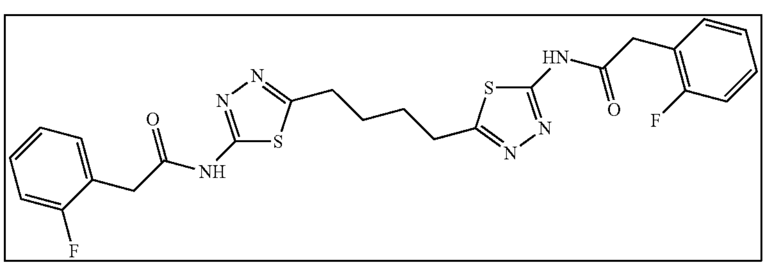 [SMILES: O=C(Cc1ccccc1F)Nc1nnc(CCCCc2nnc(NC(=O)Cc3ccccc3F)s2)s1] | | 0.12 | 0.012 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 293 | 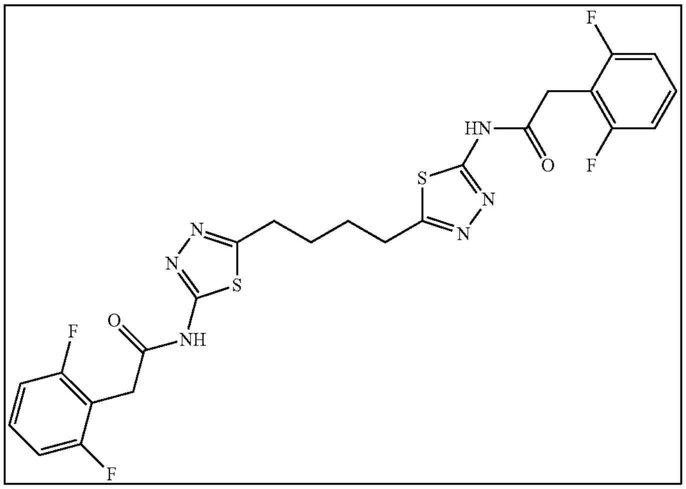 [SMILES: O=C(Cc1c(F)cccc1F)Nc1nnc(CCCCc2nnc(NC(=O)Cc3c(F)cccc3F)s2)s1] | | 0.24 | 0.04 |
| 294 | 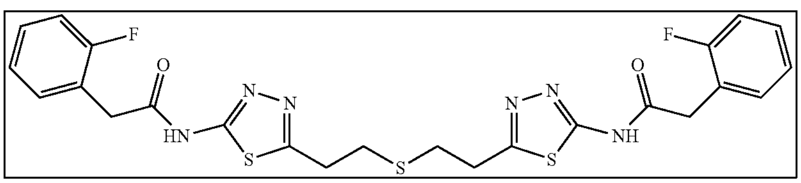 [SMILES: O=C(Cc1ccccc1F)Nc1nnc(CCSCCc2nnc(NC(=O)Cc3ccccc3F)s2)s1] | | 0.20 | 1.1 |
| 295 | 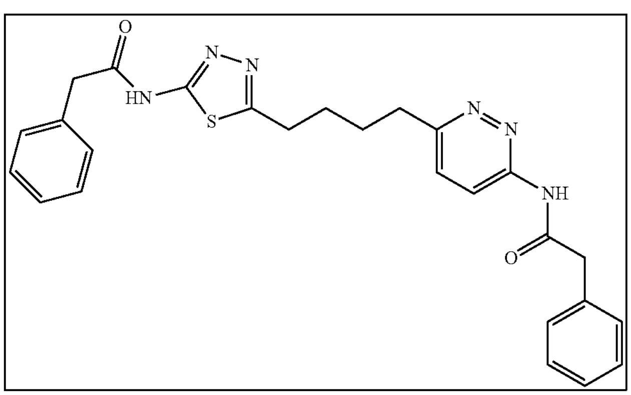 [SMILES: O=C(Cc1ccccc1)Nc1ccc(CCCCc2nnc(NC(=O)Cc3ccccc3)s2)nn1] | 0.01 | 0.057 | 0.039 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 296 | 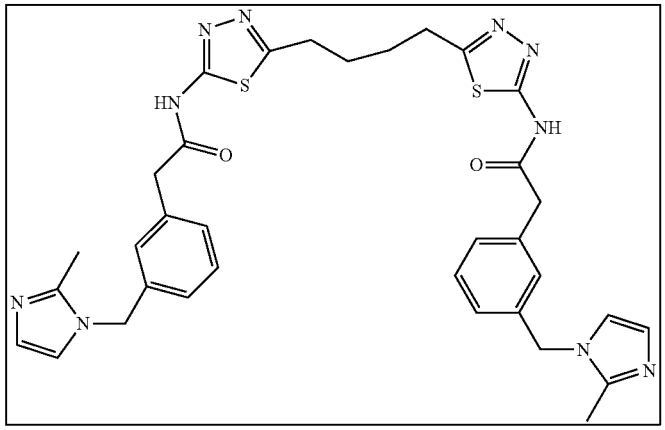 [SMILES: Cc1nccn1Cc1cccc(CC(=O)Nc2nnc(CCCCc3nnc(NC(=O)Cc4cccc(Cn5ccnc5C)c4)s3)s2)c1] | | 0.10 | 0.17 |
| 297 | 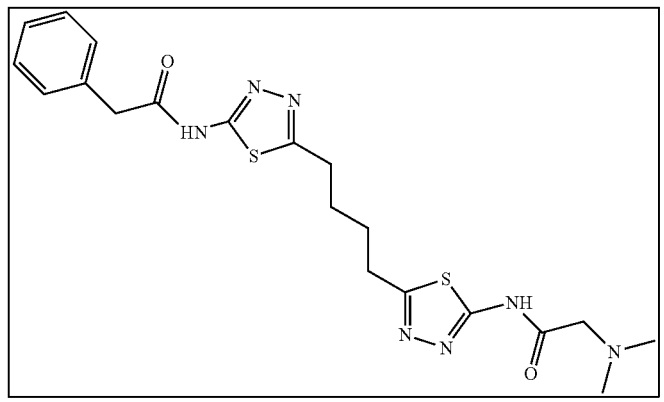 [SMILES: CN(C)CC(=O)Nc1nnc(CCCCc2nnc(NC(=O)Cc3ccccc3)s2)s1] | | 6.4 | |
| 298 | 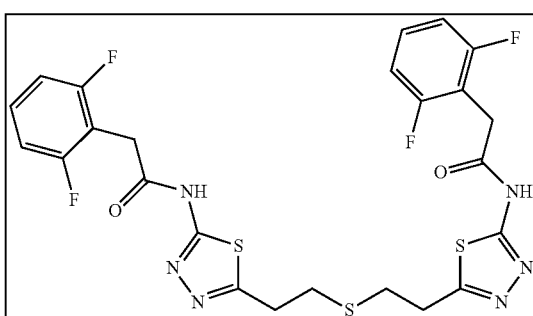 | | 0.73 | 5.1 |
| 299 | 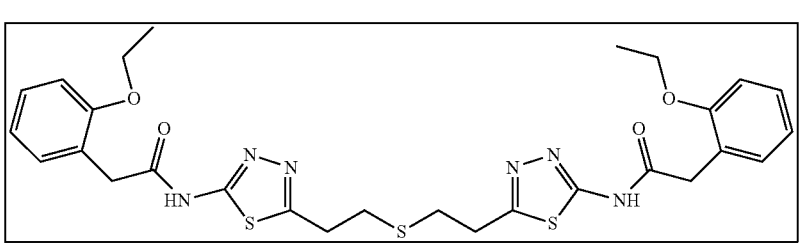 [SMILES: CCOc1ccccc1CC(=O)Nc1nnc(CCSCCc2nnc(NC(=O)Cc3ccccc3OCC)s2)s1] | | 0.33 | |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 300 | 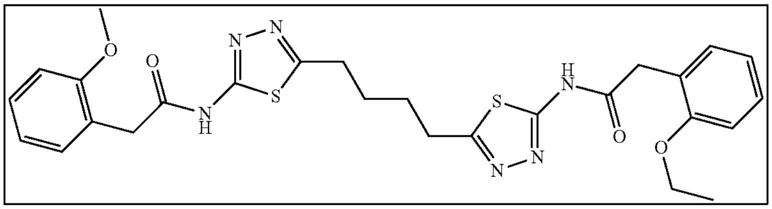 [SMILES: CCOc1ccccc1CC(=O)Nc1nnc(CCCCc2nnc(NC(=O)Cc3ccccc3OC)s2)s1] | | 0.16 | 0.16 |
| 301 | 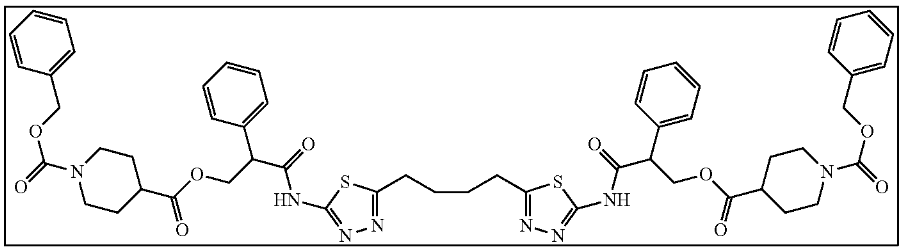 [SMILES: O=C(OCC(C(=O)Nc1nnc(CCCCc2nnc(NC(=O)C(COC(=O)C3CCN(C(=O)OCc4ccccc4)CC3)c3ccccc3)s2)s1)c1ccccc1)C1CCN(C(=O)OCc2ccccc2)CC1] | | >20 | 0.23 |
| 302 | 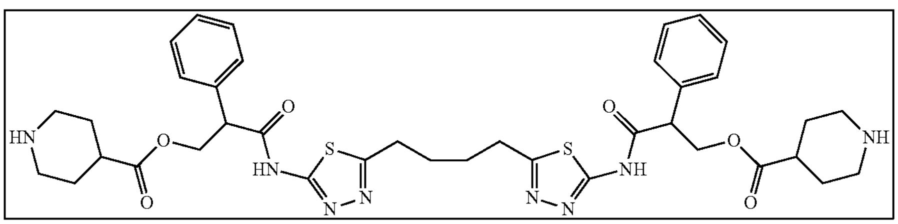 [SMILES: O=C(OCC(C(=O)Nc1nnc(CCCCc2nnc(NC(=O)C(COC(=O)C3CCNCC3)c3ccccc3)s2)s1)c1ccccc1)C1CCNCC1] | | 7.0 | 0.87 |
| 303 | 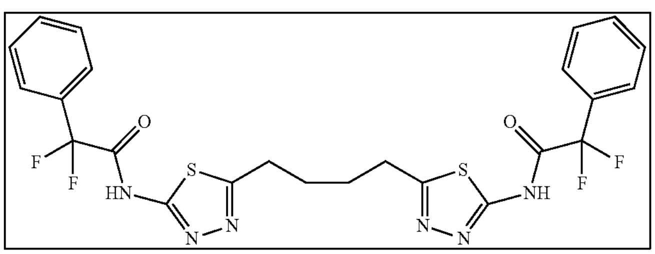 [SMILES: O=C(Nc1nnc(CCCCc2nnc(NC(=O)C(F)(F)c3ccccc3)s2)s1)C(F)(F)c1ccccc1] | | >20 | |
| 304 | 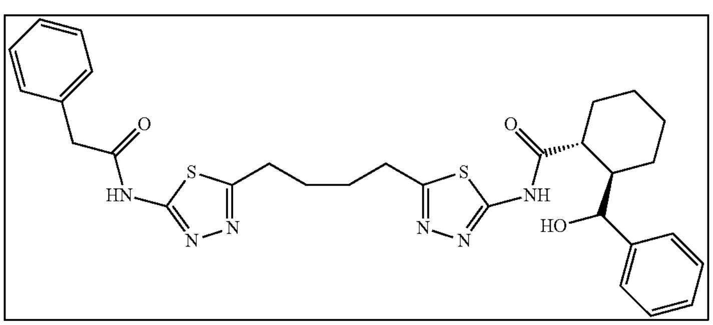 [SMILES: O=C(Cc1ccccc1)Nc1nnc(CCCCc2nnc(NC(=O)[C@@H]3CCCC[C@H]3C(O)c3ccccc3)s2)s1] | | 1.2 | 4.9 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 305 | 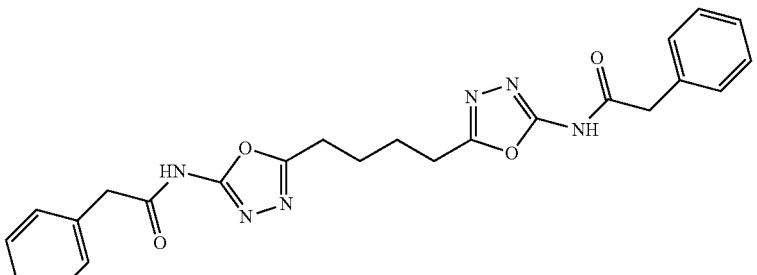 | | >20 | 102 |
| 1038 | 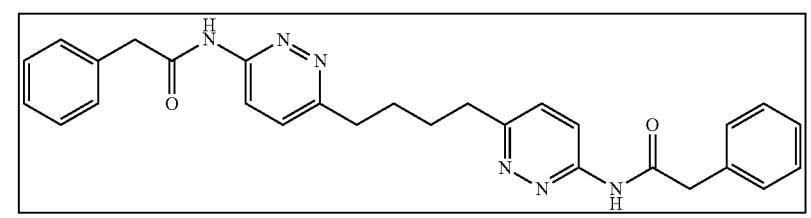 [SMILES: O=C(Cc1ccccc1)Nc1ccc(CCCCc2ccc(NC(=O)Cc3ccccc3)nn2)nn1] | | 0.080 | 1.5 |
| 306 | 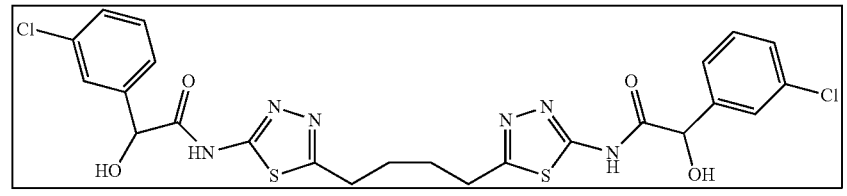 [SMILES: O=C(Nc1nnc(CCCCc2nnc(NC(=O)C(O)c3cccc(Cl)c3)s2)s1)C(O)c1cccc(Cl)c1] | 0.031 | 0.52 | 0.066 |
| 307 | 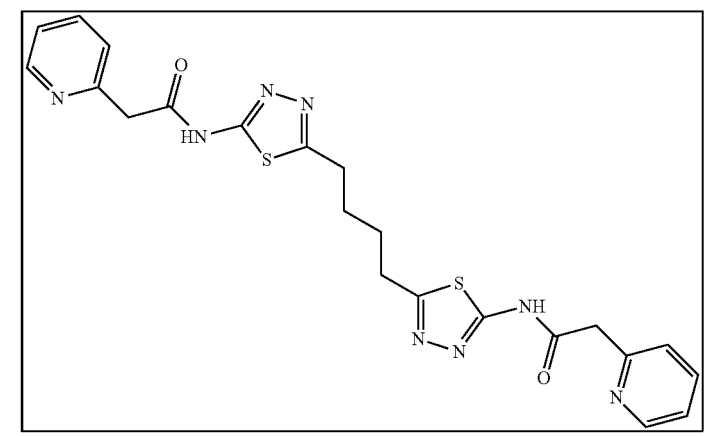 [SMILES: O=C(Cc1ccccn1)Nc1nnc(CCCCc2nnc(NC(=O)Cc3ccccn3)s2)s1] | | 6.4 | 9.3 |
| 308 | 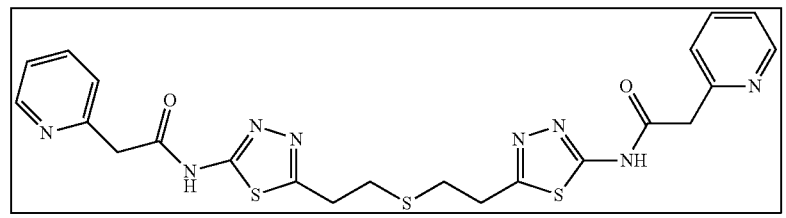 [SMILES: O=C(Cc1ccccn1)Nc1nnc(CCSCCc2nnc(NC(=O)Cc3ccccn3)s2)s1] | | 0.60 | 1.2 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 309 | (structure) | | 0.11 | 0.18 |
| 310 | (structure) | | 0.083 | 0.12 |
| 311 | (structure) | | 0.20 | 22. |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 312 | 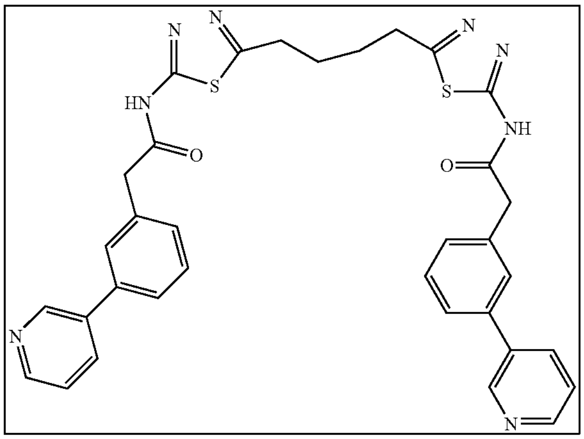 [SMILES: N=C(CCCCC(=N)SC(=N)NC(=O)Cc1cccc(-c2cccnc2)c1)SC(=N)NC(=O)Cc1cccc(-c2cccnc2)c1] | | >20 | N/D |
| 313 | 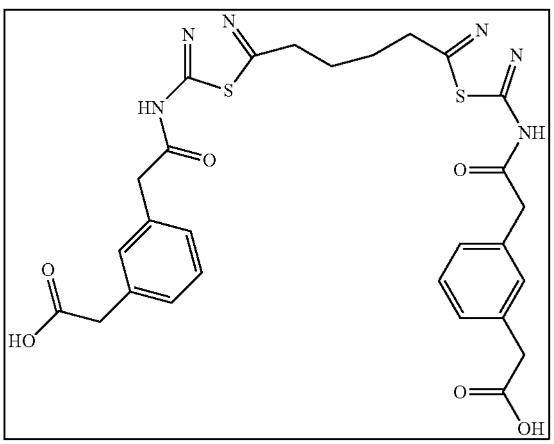 [SMILES: N=C(CCCCC(=N)SC(=N)NC(=O)Cc1cccc(CC(=O)O)c1)SC(=N)NC(=O)Cc1cccc(CC(=O)O)c1] | | 0.27 | 94 |
| 314 | 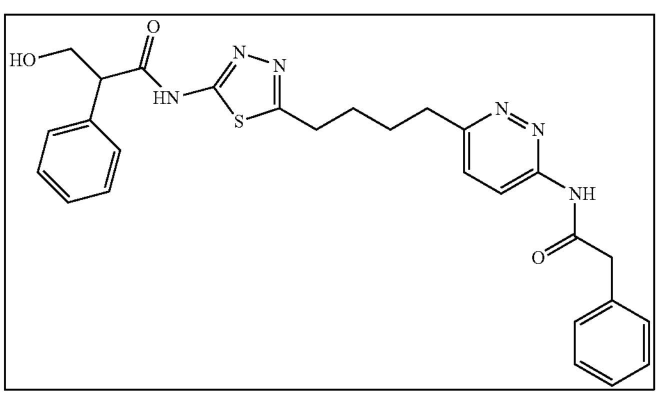 [SMILES: O=C(Cc1ccccc1)Nc1ccc(CCCCc2nnc(NC(=O)C(CO)c3ccccc3)s2)nn1] | | 0.14 | 0.048 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 315 | 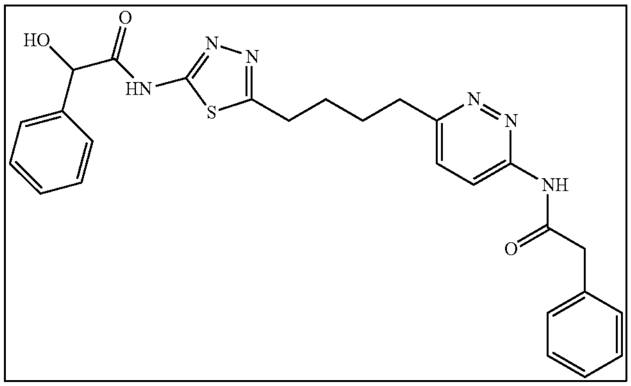 [SMILES: O=C(Cc1ccccc1)Nc1ccc(CCCCc2nnc(NC(=O)C(O)c3ccccc3)s2)nn1] | 0.017 | 0.12 | 0.035 |
| 316 | 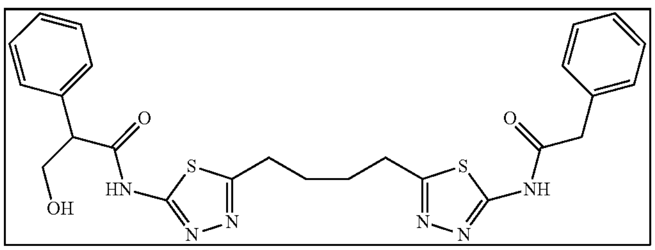 [SMILES: O=C(Cc1ccccc1)Nc1nnc(CCCCc2nnc(NC(=O)C(CO)c3ccccc3)s2)s1] | | 0.19 | 0.075 |
| 317 | 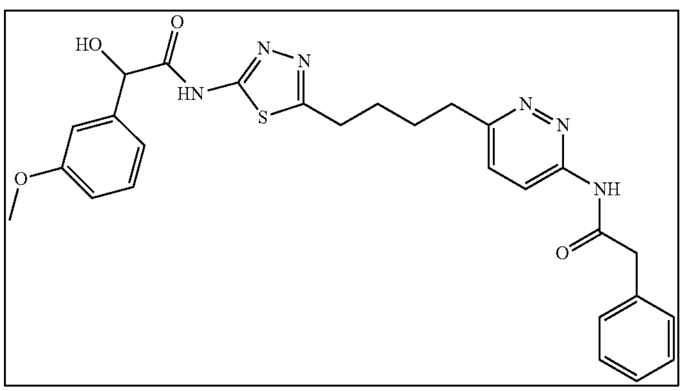 [SMILES: COc1cccc(C(O)C(=O)Nc2nnc(CCCCc3ccc(NC(=O)Cc4ccccc4)nn3)s2)c1] | 0.007 | 0.18 | 0.010 |
| 318 | 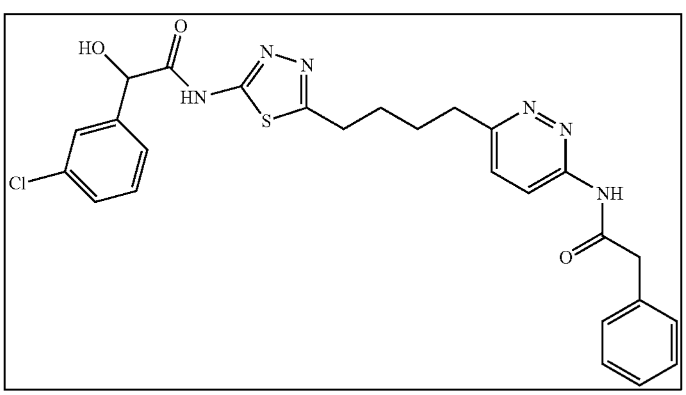 [SMILES: O=C(Cc1ccccc1)Nc1ccc(CCCCc2nnc(NC(=O)C(O)c3cccc(Cl)c3)s2)nn1] | 0.006 | 0.18 | 0.017 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 319 | 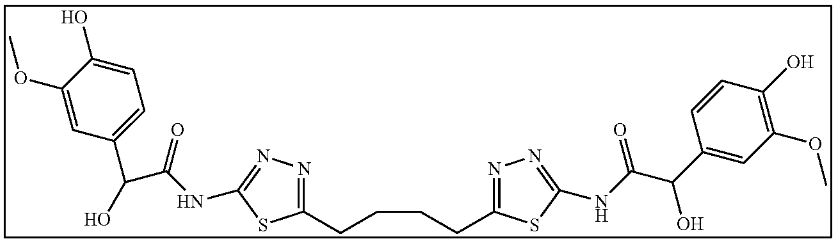 | | 0.64 | 10 |
| 320 | 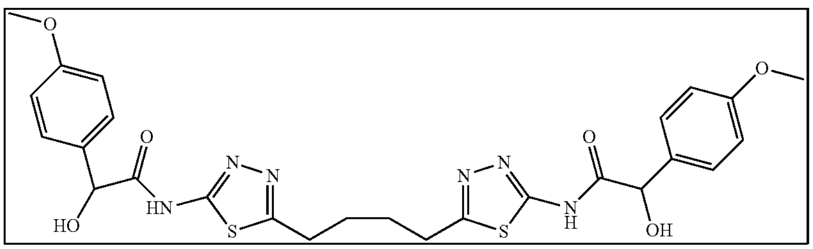 | | 0.40 | 0.19 |
| 321 | 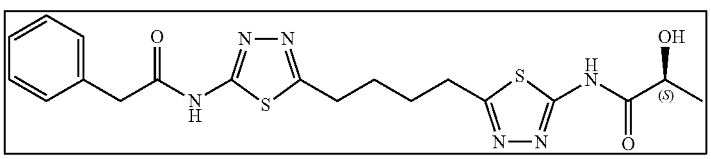 | | 2.5 | 2.6 |
| 322 | 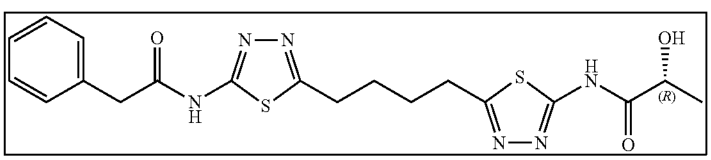 | | 2.8 | 3.0 |
| 323 | 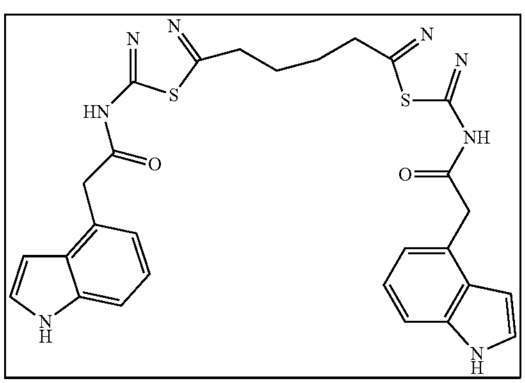 [SMILES: N=C(CCCCC(=N)SC(=N)NC(=O)Cc1cccc2[nH]ccc12)SC(=N)NC(=O)Cc1cccc2[nH]ccc12] | | 0.056 | 0.20 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 324 | 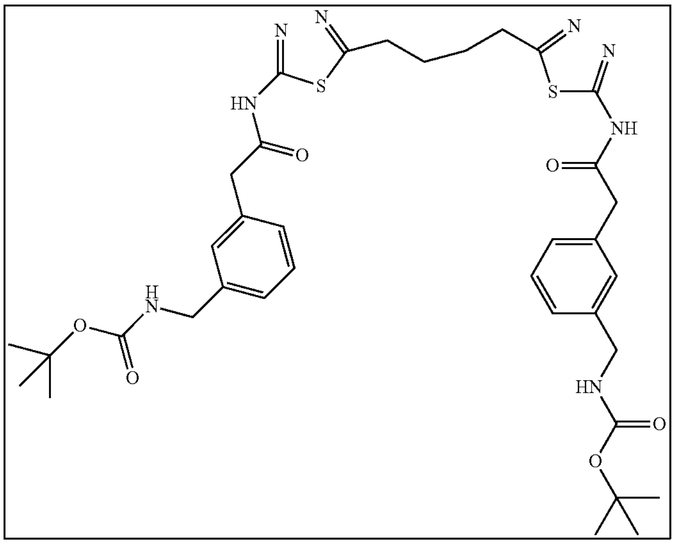 [SMILES: CC(C)(C)OC(=O)NCc1cccc(CC(=O)NC(=N)SC(=N)CCCCC(=N)SC(=N)NC(=O)Cc2cccc(CNC(=O)OC(C)(C)C)c2)c1] | 0.011 | 4.6 | 0.10 |
| 325 | 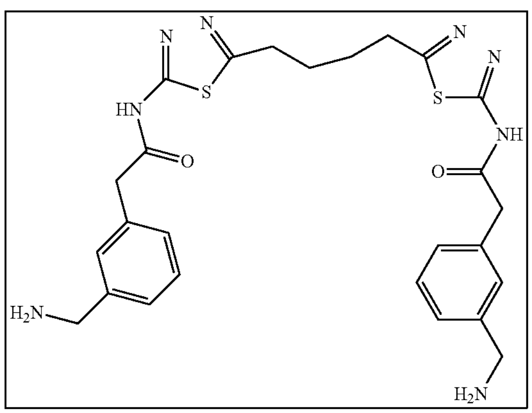 [SMILES: N=C(CCCCC(=N)SC(=N)NC(=O)Cc1cccc(CN)c1)SC(=N)NC(=O)Cc1cccc(CN)c1] | 0.17 | 0.66 | 0.030 |
| 326 | 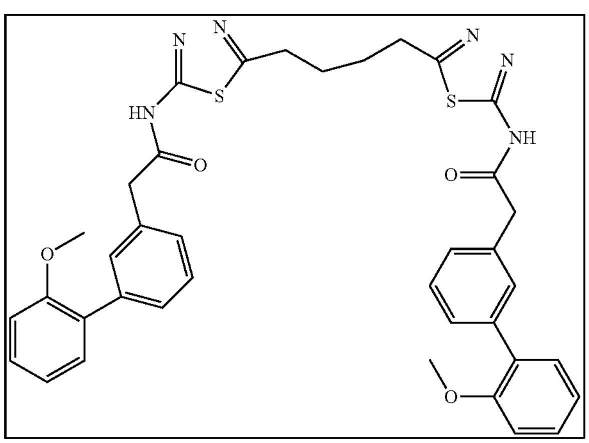 [SMILES: COc1ccccc1-c1cccc(CC(=O)NC(=N)SC(=N)CCCCC(=N)SC(=N)NC(=O)Cc2cccc(-c3ccccc3OC)c2)c1] | >20 | | N/D |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 327 | 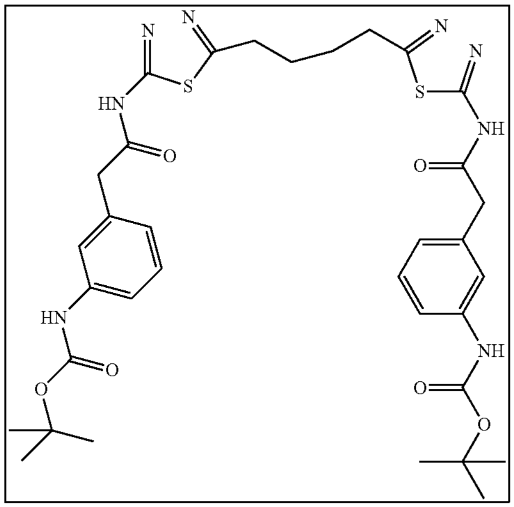 [SMILES: CC(C)(C)OC(=O)Nc1cccc(CC(=O)NC(=N)SC(=N)CCCCC(=N)SC(=N)NC(=O)Cc2cccc(NC(=O)OC(C)(C)C)c2)c1] | | >20 | 0.15 |
| 328 | 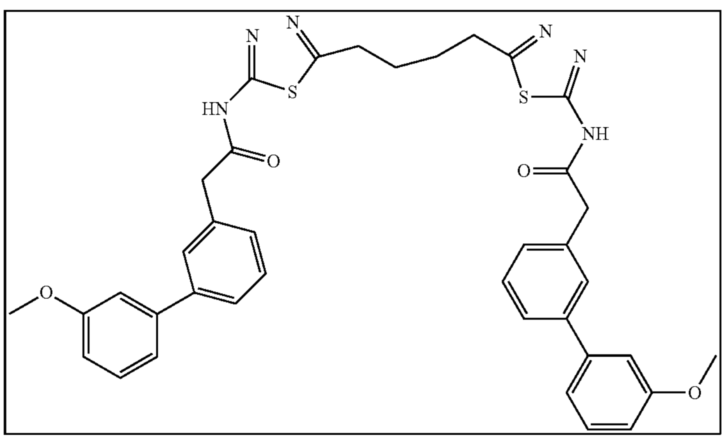 | | >20 | N/D |
| 329 | 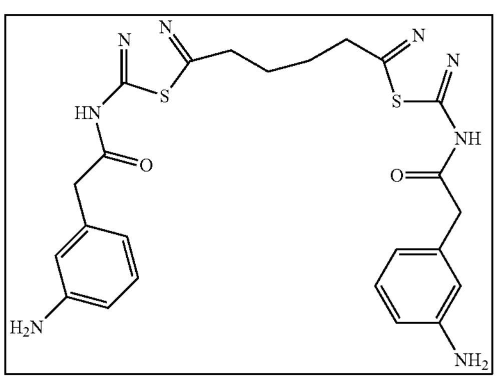 [SMILES: N=C(CCCCC(=N)SC(=N)NC(=O)Cc1cccc(N)c1)SC(=N)NC(=O)Cc1cccc(N)c1] | | 0.17 | 0.45 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 330 | 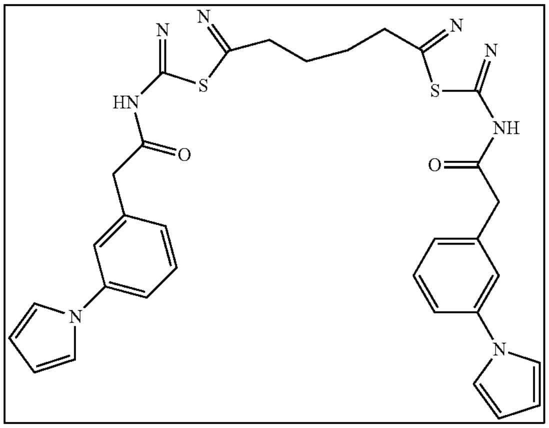 [SMILES: N=C(CCCCC(=N)SC(=N)NC(=O)Cc1cccc(-n2cccc2)c1)SC(=N)NC(=O)Cc1cccc(-n2cccc2)c1] | | >20 | N/D |
| 331 | 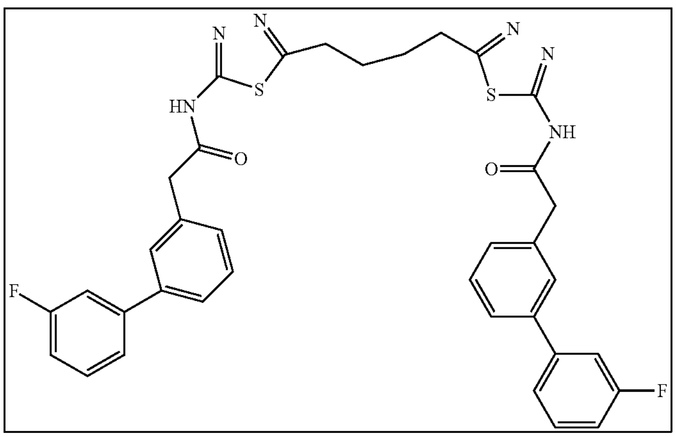 [SMILES: N=C(CCCCC(=N)SC(=N)NC(=O)Cc1cccc(-c2cccc(F)c2)c1)SC(=N)NC(=O)Cc1cccc(-c2cccc(F)c2)c1] | | >20 | N/D |
| 332 | 81% bis ester plus 19% mono ester | | 3.3 | 0.087 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 333 | 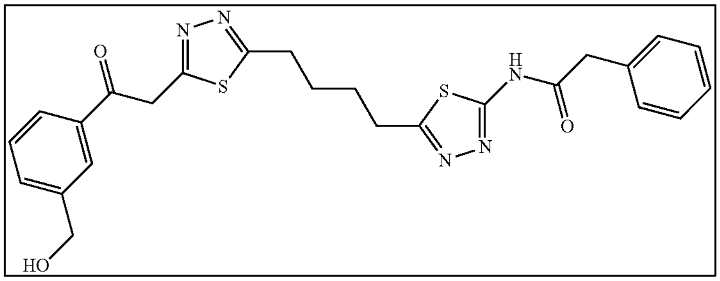 [SMILES: O=C(Cc1ccccc1)Nc1nnc(CCCCc2nnc(CC(=O)c3cccc(CO)c3)s2)s1] | | 0.10 | 1.6 |
| 334 | 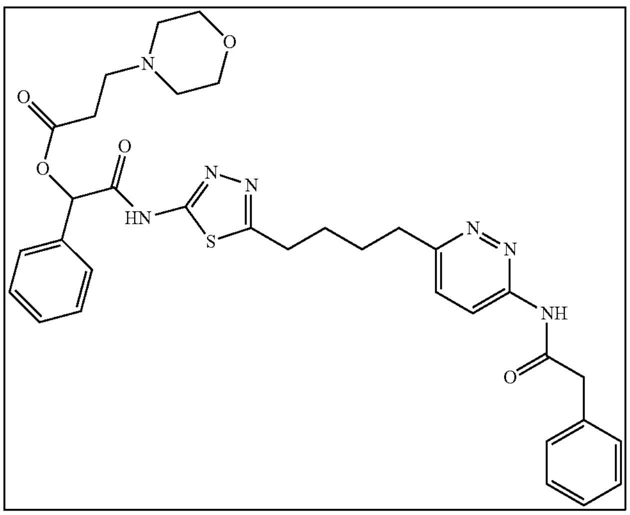 [SMILES: O=C(Cc1ccccc1)Nc1ccc(CCCCc2nnc(NC(=O)C(OC(=O)CCN3CCOCC3)c3ccccc3)s2)nn1] | | 0.64 | 0.030 |
| 335 | 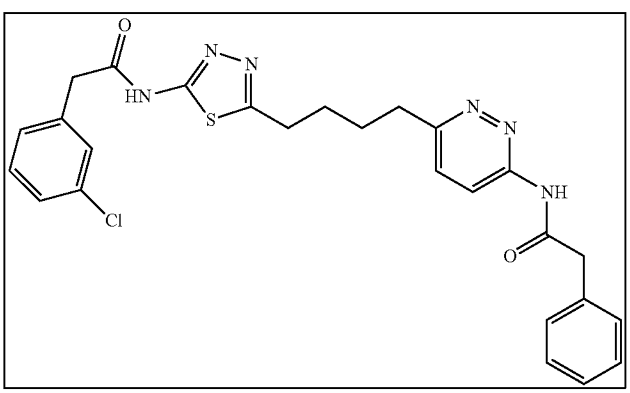 [SMILES: O=C(Cc1ccccc1)Nc1ccc(CCCCc2nnc(NC(=O)Cc3cccc(Cl)c3)s2)nn1] | | 0.062 | 0.050 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 336 | 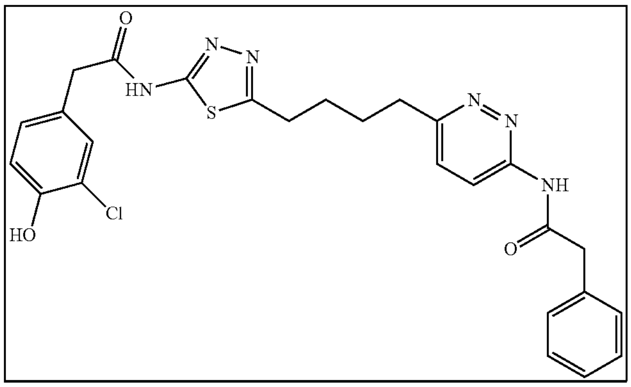 [SMILES: O=C(Cc1ccccc1)Nc1ccc(CCCCc2nnc(NC(=O)Cc3ccc(O)c(Cl)c3)s2)nn1] | | 0.068 | 0.052 |
| 337 | 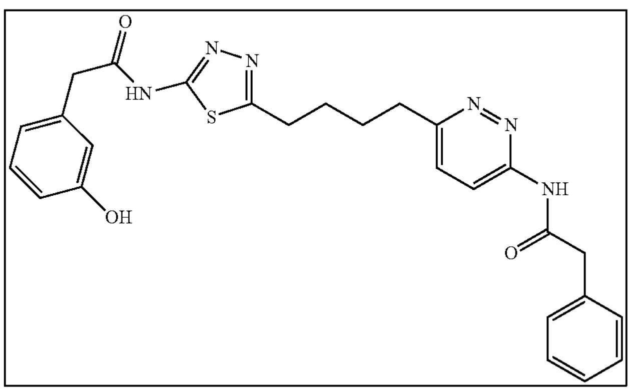 [SMILES: O=C(Cc1ccccc1)Nc1ccc(CCCCc2nnc(NC(=O)Cc3cccc(O)c3)s2)nn1] | | 0.076 | 0.021 |
| 338 | 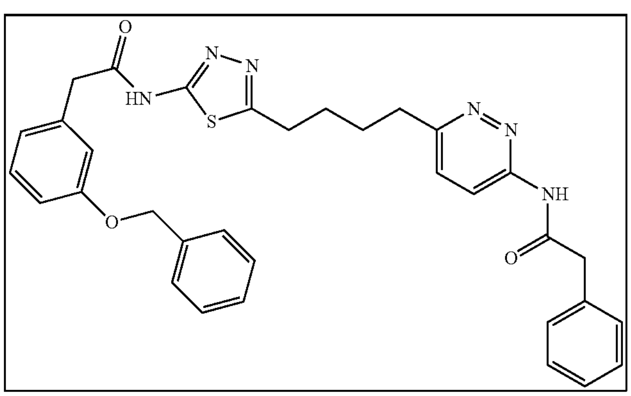 [SMILES: O=C(Cc1ccccc1)Nc1ccc(CCCCc2nnc(NC(=O)Cc3cccc(OCc4ccccc4)c3)s2)nn1] | | 0.15 | 0.043 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 339 | 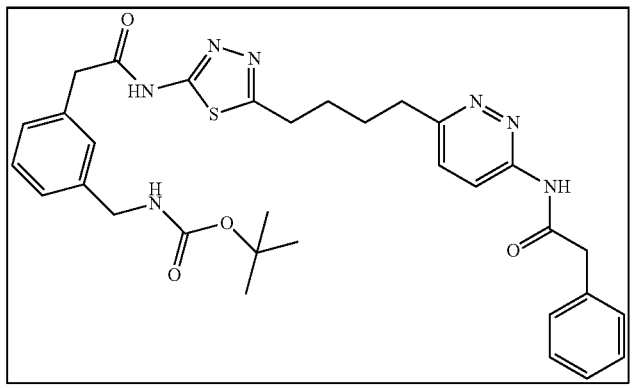 [SMILES: CC(C)(C)OC(=O)NCc1cccc(CC(=O)Nc2nnc(CCCCc3ccc(NC(=O)Cc4ccccc4)nn3)s2)c1] | 0.005 | 0.16 | 0.009 |
| 340 | 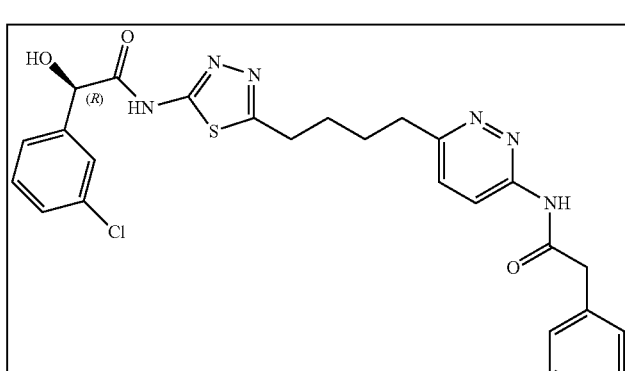 |  | 0.096 | 0.038 |
| 341 | 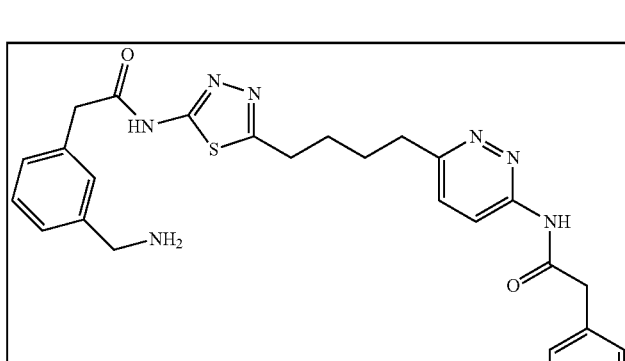 | 0.013 | 0.13 | 0.039 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 342 | 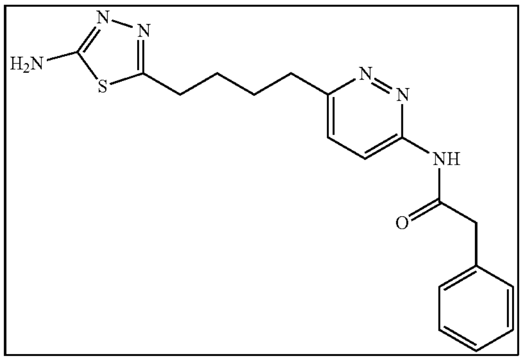 [SMILES: Nc1nnc(CCCCc2ccc(NC(=O)Cc3ccccc3)nn2)s1] | | 1.4 | 2.7 |
| 343 | 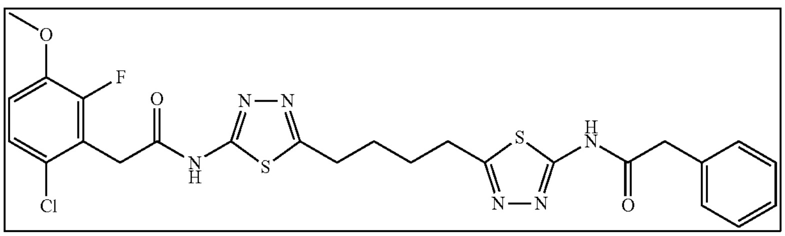 [SMILES: COc1ccc(Cl)c(CC(=O)Nc2nnc(CCCCc3nnc(NC(=O)Cc4ccccc4)s3)s2)c1F] | | 0.16 | 0.25 |
| 344 | 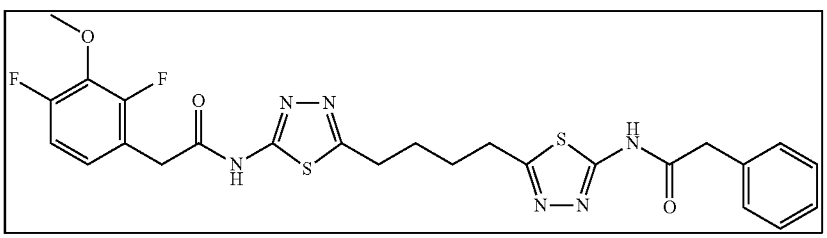 [SMILES: COc1c(F)ccc(CC(=O)Nc2nnc(CCCCc3nnc(NC(=O)Cc4ccccc4)s3)s2)c1F] | | | 0.088 |
| 345 | 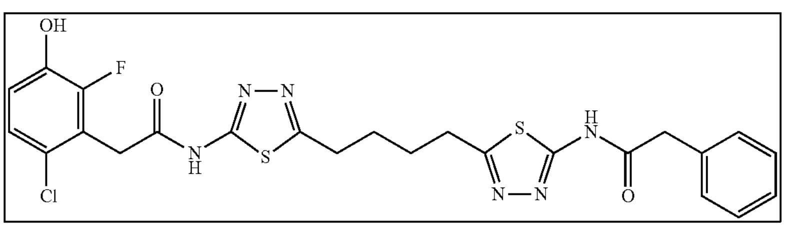 [SMILES: O=C(Cc1ccccc1)Nc1nnc(CCCCc2nnc(NC(=O)Cc3c(Cl)ccc(O)c3F)s2)s1] | | 0.16 | 0.24 |
| 346 | 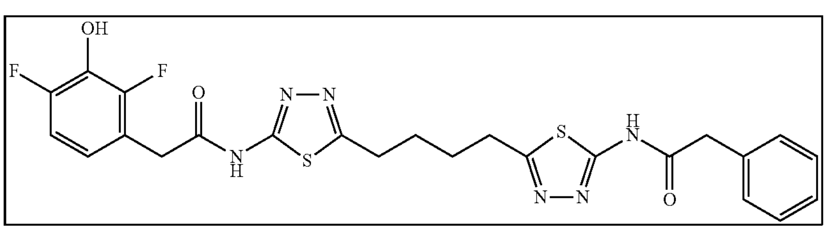 [SMILES: O=C(Cc1ccccc1)Nc1nnc(CCCCc2nnc(NC(=O)Cc3ccc(F)c(O)c3F)s2)s1] | | 0.12 | 0.087 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 527 | 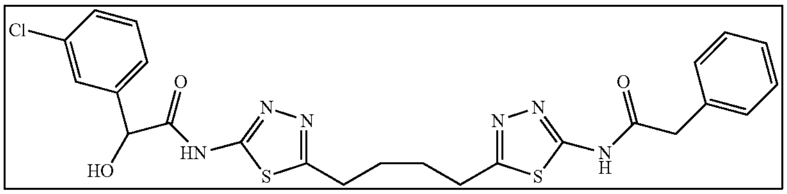 [SMILES: O=C(Cc1ccccc1)Nc1nnc(CCCCc2nnc(NC(=O)C(O)c3cccc(Cl)c3)s2)s1] | 0.024 | 0.13 | 0.098 |
| 347 | 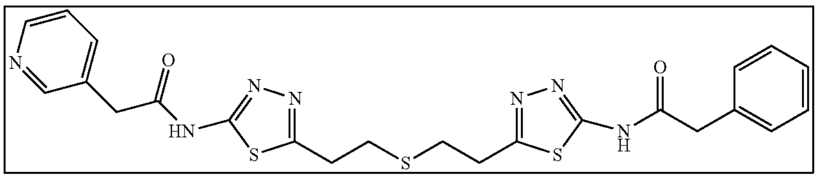 [SMILES: O=C(Cc1ccccc1)Nc1nnc(CCSCCc2nnc(NC(=O)Cc3cccnc3)s2)s1] | | 0.22 | 0.71 |
| 348 | 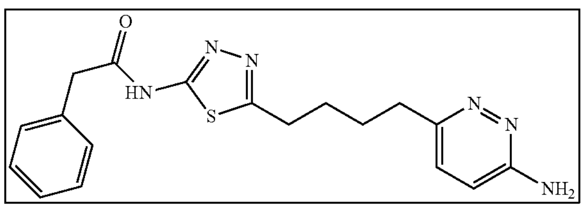 [SMILES: Nc1ccc(CCCCc2nnc(NC(=O)Cc3ccccc3)s2)nn1] | | 1.0 | 1.7 |
| 349 | 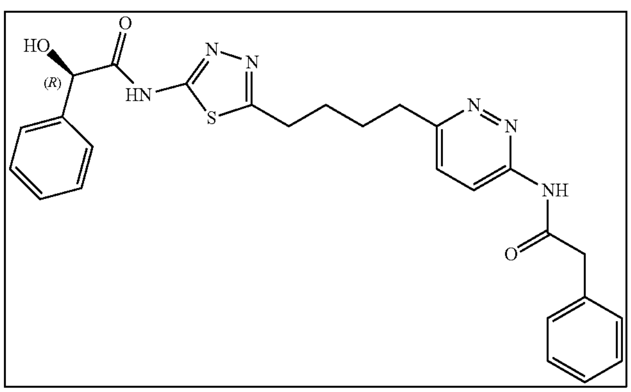 | | 0.12 | 0.12 |
| 350 | 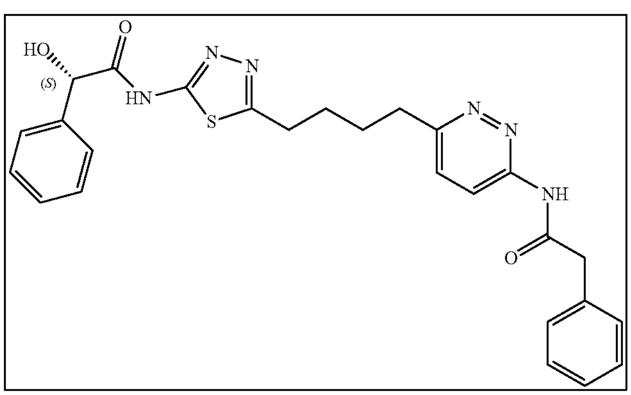 | | 0.079 | 0.029 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 351 | 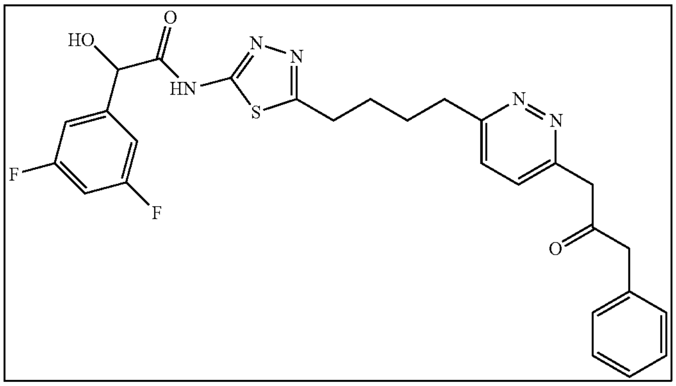 [SMILES: O=C(Cc1ccccc1)Cc1ccc(CCCCc2nnc(NC(=O)C(O)c3cc(F)cc(F)c3)s2)nn1] | | 0.11 | 0.049 |
| 352 | 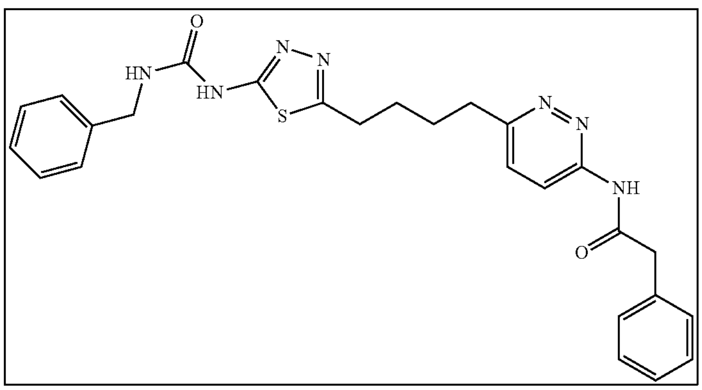 [SMILES: O=C(Cc1ccccc1)Nc1ccc(CCCCc2nnc(NC(=O)NCc3ccccc3)s2)nn1] | | 0.069 | 0.13 |
| 353 | 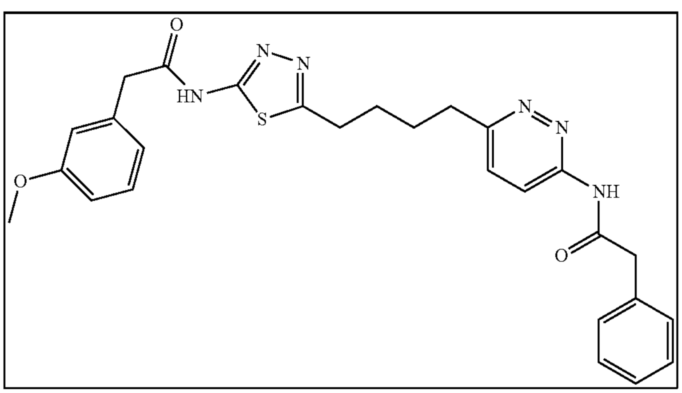 [SMILES: COc1cccc(CC(=O)Nc2nnc(CCCCc3ccc(NC(=O)Cc4ccccc4)nn3)s2)c1] | | 0.049 | 0.021 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 354 | 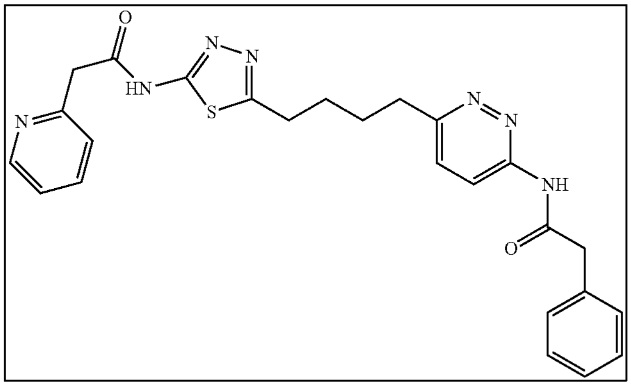 [SMILES: O=C(Cc1ccccc1)Nc1ccc(CCCCc2nnc(NC(=O)Cc3ccccn3)s2)nn1] | | 0.10 | 0.047 |
| 355 | 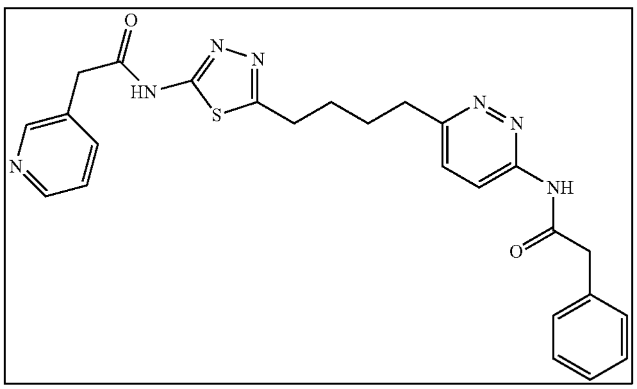 [SMILES: O=C(Cc1ccccc1)Nc1ccc(CCCCc2nnc(NC(=O)Cc3cccnc3)s2)nn1] | | 0.10 | 0.039 |
| 356 | 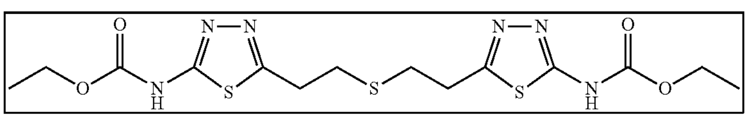 | | >20 | N/D |
| 357 | 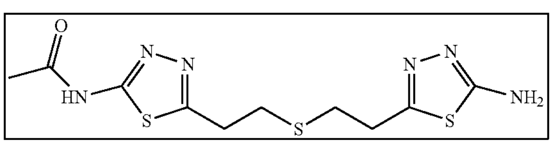 [SMILES: CC(=O)Nc1nnc(CCSCCc2nnc(N)s2)s1] | | >20 | N/D |
| 358 | 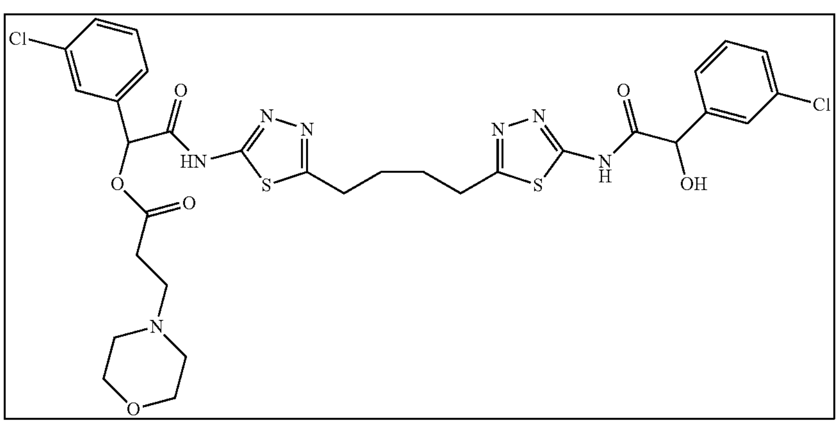 [SMILES: O=C(CCN1CCOCC1)OC(C(=O)Nc1nnc(CCCCc2nnc(NC(=O)C(O)c3cccc(Cl)c3)s2)s1)c1cccc(Cl)c1] | | 1.4 | 0.11 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 359 | 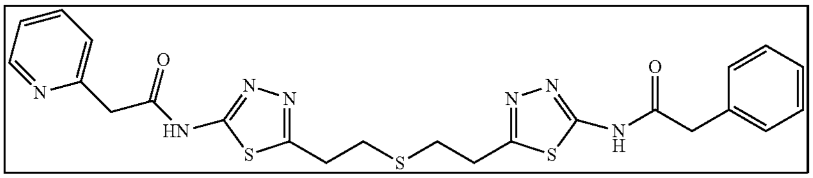 [SMILES: O=C(Cc1ccccc1)Nc1nnc(CCSCCc2nnc(NC(=O)Cc3ccccn3)s2)s1] | | 0.38 | 0.91 |
| 360 | 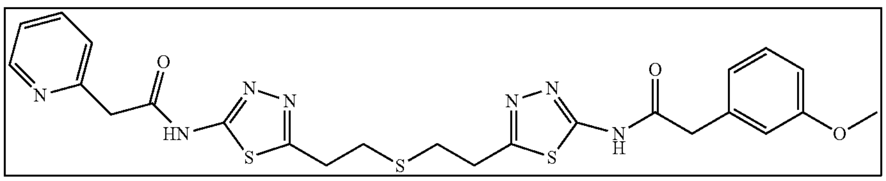 [SMILES: COc1cccc(CC(=O)Nc2nnc(CCSCCc3nnc(NC(=O)Cc4ccccn4)s3)s2)c1] | | 0.28 | 0.67 |
| 361 | 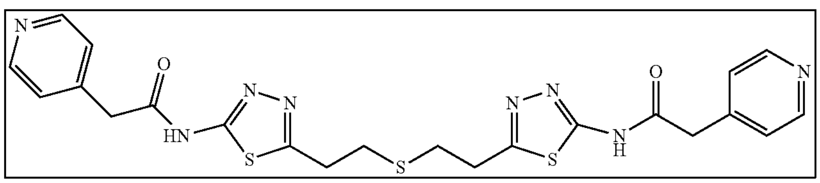 [SMILES: O=C(Cc1ccncc1)Nc1nnc(CCSCCc2nnc(NC(=O)Cc3ccncc3)s2)s1] | | 1.8 | >20 |
| 1035 | 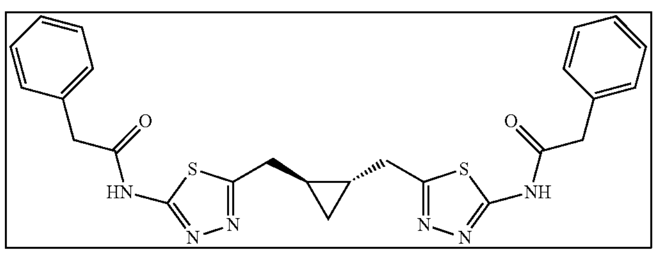 [SMILES: O=C(Cc1ccccc1)Nc1nnc(C[C@@H]2C[C@H]2Cc2nnc(NC(=O)Cc3ccccc3)s2)s1] | | >20 | N/D |
| 362 | 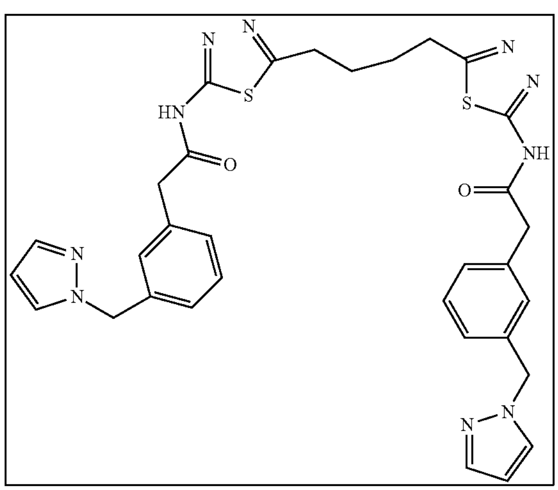 [SMILES: N=C(CCCCC(=N)SC(=N)NC(=O)Cc1cccc(Cn2cccn2)c1)SC(=N)NC(=O)Cc1cccc(Cn2cccn2)c1] | | 0.35 | 0.054 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 363 | 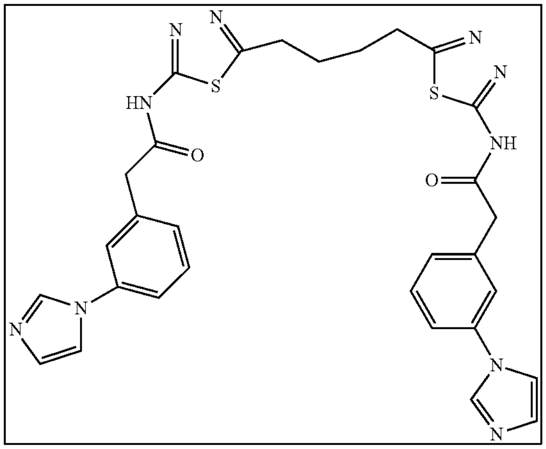 [SMILES: N=C(CCCCC(=N)SC(=N)NC(=O)Cc1cccc(-n2ccnc2)c1)SC(=N)NC(=O)Cc1cccc(-n2ccnc2)c1] | 0.065 | >20 | |
| 364 | 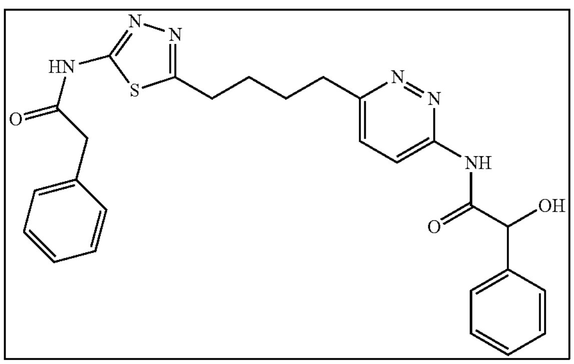 [SMILES: O=C(Cc1ccccc1)Nc1nnc(CCCCc2ccc(NC(=O)C(O)c3ccccc3)nn2)s1] | 0.030 | 0.15 | 0.26 |
| 365 | 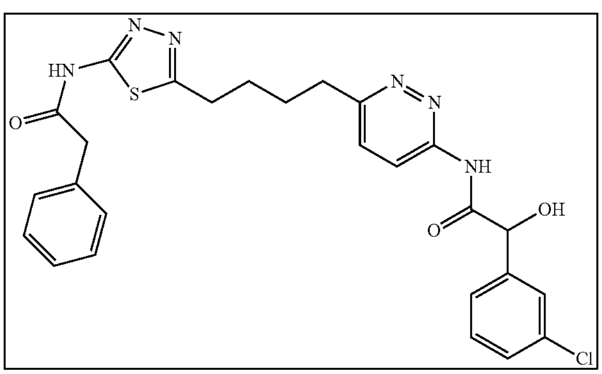 [SMILES: O=C(Cc1ccccc1)Nc1nnc(CCCCc2ccc(NC(=O)C(O)c3cccc(Cl)c3)nn2)s1] | 0.009 | 0.092 | 0.089 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 366 | 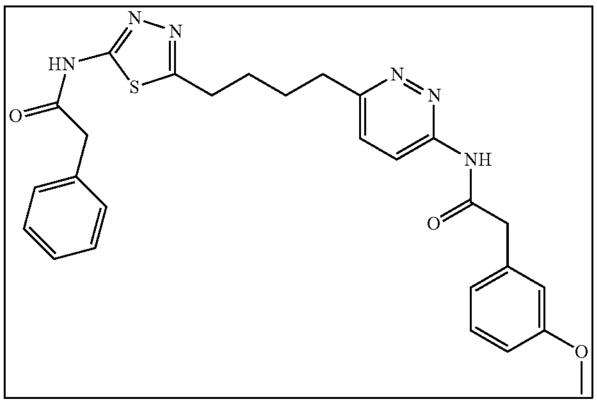 [SMILES: COc1cccc(CC(=O)Nc2ccc(CCCCc3nnc(NC(=O)Cc4ccccc4)s3)nn2)c1] | | 0.074 | 0.024 |
| 367 | 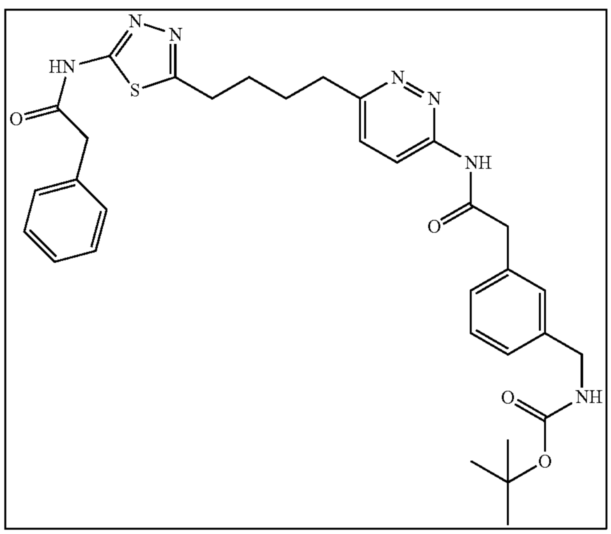 [SMILES: CC(C)(C)OC(=O)NCc1cccc(CC(=O)Nc2ccc(CCCCc3nnc(NC(=O)Cc4ccccc4)s3)nn2)c1] | 0.002 | 0.12 | 0.006 |
| 368 | 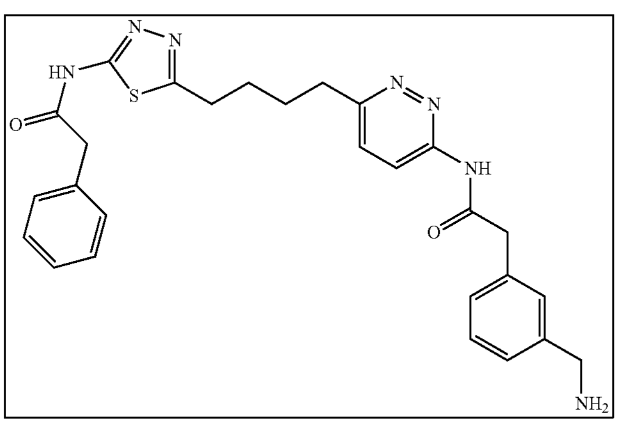 [SMILES: NCc1cccc(CC(=O)Nc2ccc(CCCCc3nnc(NC(=O)Cc4ccccc4)s3)nn2)c1] | 0.009 | 0.11 | 0.017 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 369 | 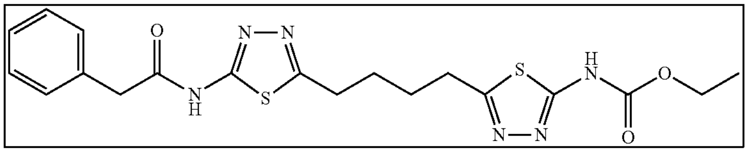 [SMILES: CCOC(=O)Nc1nnc(CCCCc2nnc(NC(=O)Cc3ccccc3)s2)s1] | | 0.81 | 1.9 |
| 370 | 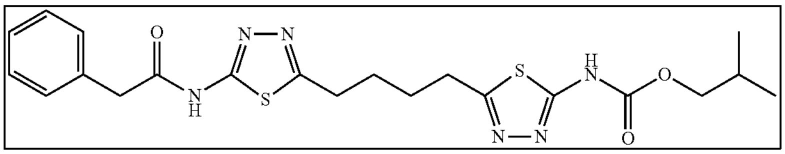 [SMILES: CC(C)COC(=O)Nc1nnc(CCCCc2nnc(NC(=O)Cc3ccccc3)s2)s1] | | 0.28 | 0.70 |
| 371 | 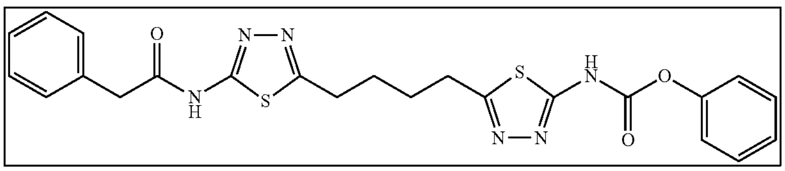 [SMILES: O=C(Cc1ccccc1)Nc1nnc(CCCCc2nnc(NC(=O)Oc3ccccc3)s2)s1] | | 0.43 | 5.2 |
| 372 | 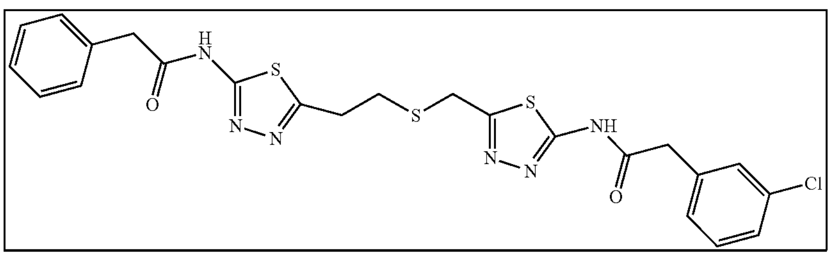 [SMILES: O=C(Cc1ccccc1)Nc1nnc(CCSCc2nnc(NC(=O)Cc3cccc(Cl)c3)s2)s1] | | 0.16 | 0.15 |
| 373 | 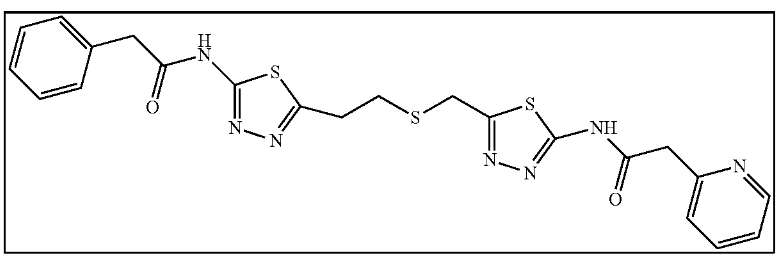 [SMILES: O=C(Cc1ccccc1)Nc1nnc(CCSCc2nnc(NC(=O)Cc3ccccn3)s2)s1] | | 0.17 | 0.28 |
| 374 | 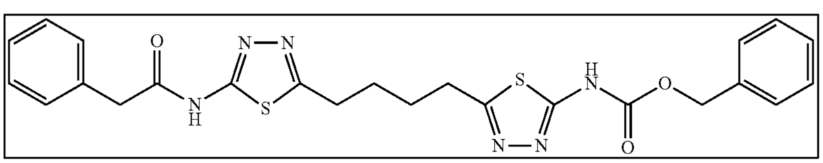 [SMILES: O=C(Cc1ccccc1)Nc1nnc(CCCCc2nnc(NC(=O)OCc3ccccc3)s2)s1] | | 0.26 | 0.47 |
| 375 | 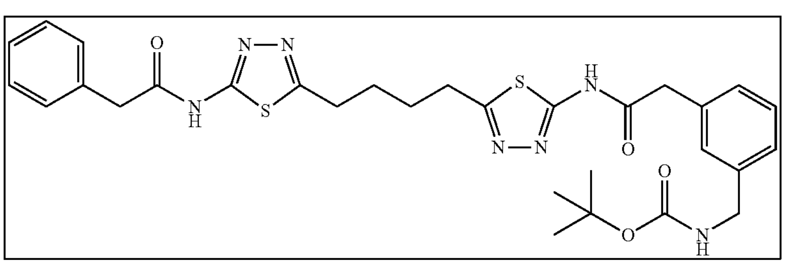 [SMILES: CC(C)(C)OC(=O)NCc1cccc(CC(=O)Nc2nnc(CCCCc3nnc(NC(=O)Cc4ccccc4)s3)s2)c1] | 0.005 | 0.38 | 0.041 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 376 | 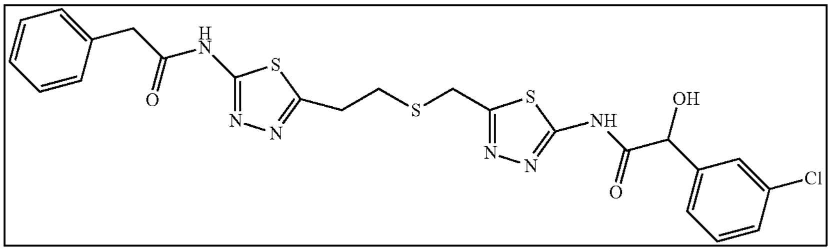 [SMILES: O=C(Cc1ccccc1)Nc1nnc(CCSCc2nnc(NC(=O)C(O)c3cccc(Cl)c3)s2)s1] | | 0.35 | 0.091 |
| 377 | 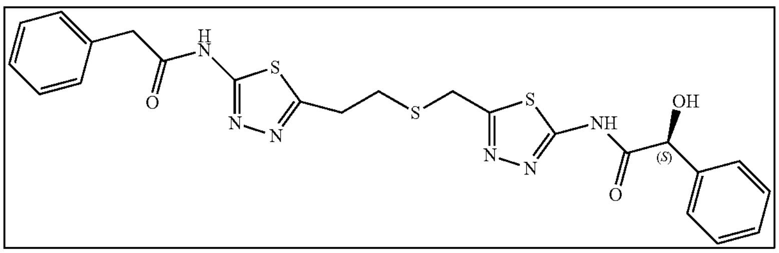 | | 0.28 | 0.10 |
| 378 | 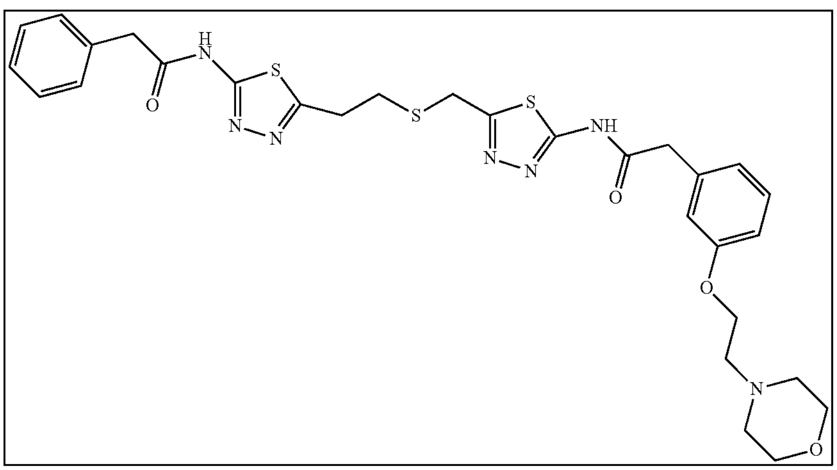 [SMILES: O=C(Cc1ccccc1)Nc1nnc(CCSCc2nnc(NC(=O)Cc3cccc(OCCN4CCOCC4)c3)s2)s1] | | 0.22 | 0.090 |
| 379 | 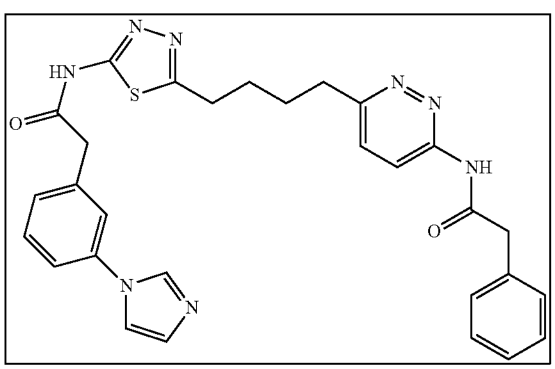 [SMILES: O=C(Cc1ccccc1)Nc1ccc(CCCCc2nnc(NC(=O)Cc3cccc(-n4ccnc4)c3)s2)nn1] | | 0.097 | 0.038 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 380 | 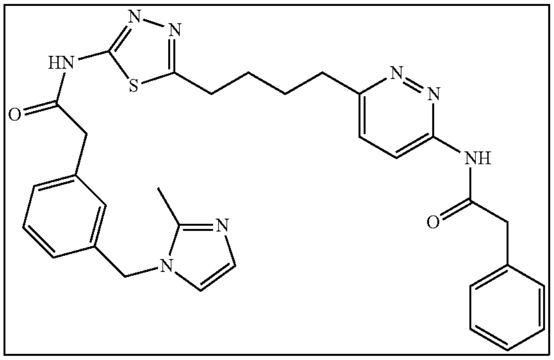 [SMILES: Cc1nccn1Cc1cccc(CC(=O)Nc2nnc(CCCCc3ccc(NC(=O)Cc4ccccc4)nn3)s2)c1] | | 0.12 | 0.019 |
| 381 | 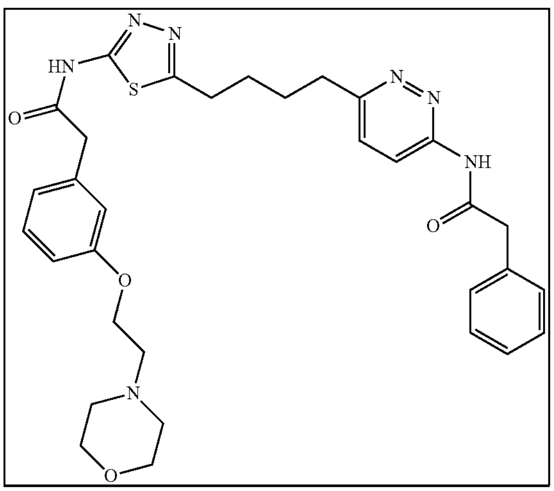 [SMILES: O=C(Cc1ccccc1)Nc1ccc(CCCCc2nnc(NC(=O)Cc3cccc(OCCN4CCOCC4)c3)s2)nn1] | | 0.16 | 0.018 |
| 382 | 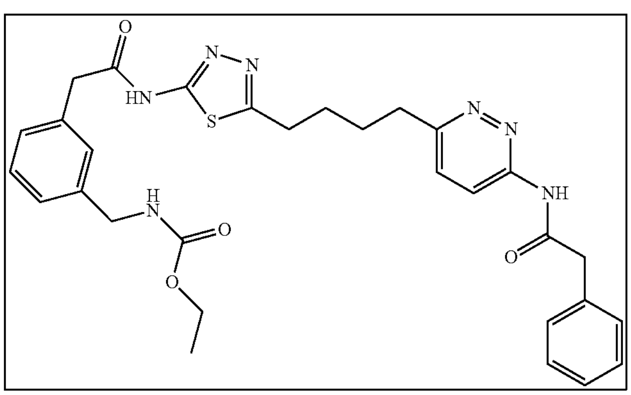 [SMILES: CCOC(=O)NCc1cccc(CC(=O)Nc2nnc(CCCCc3ccc(NC(=O)Cc4ccccc4)nn3)s2)c1] | 0.003 | 0.099 | 0.007 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 383 | 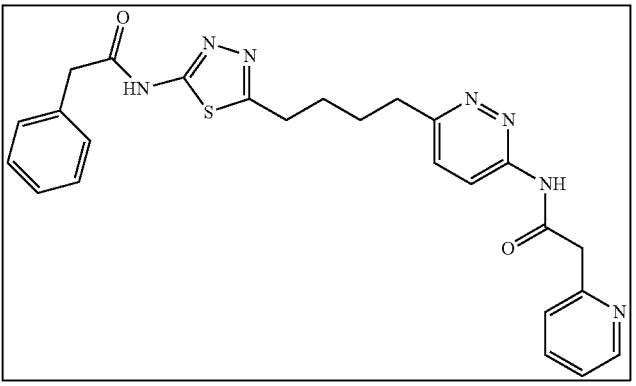 [SMILES: O=C(Cc1ccccn1)Nc1ccc(CCCCc2nnc(NC(=O)Cc3ccccc3)s2)nn1] | | 0.086 | 0.022 |
| 384 | 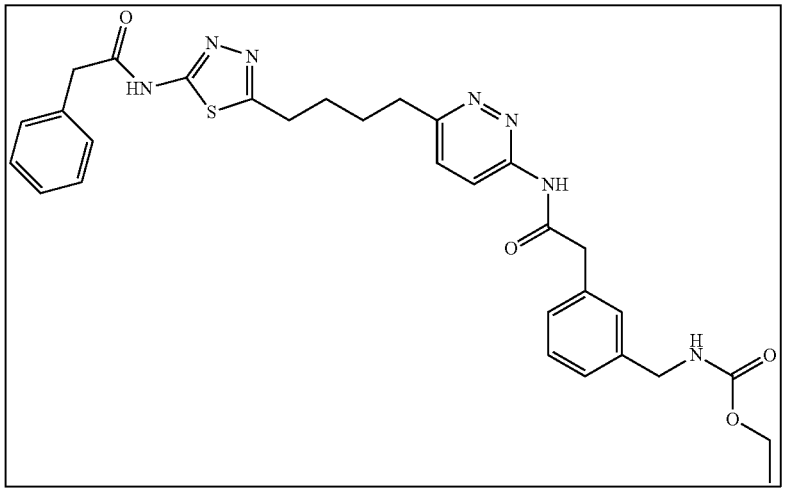 [SMILES: CCOC(=O)NCc1cccc(CC(=O)Nc2ccc(CCCCc3nnc(NC(=O)Cc4ccccc4)s3)nn2)c1] | 0.003 | 0.081 | 0.005 |
| 385 | 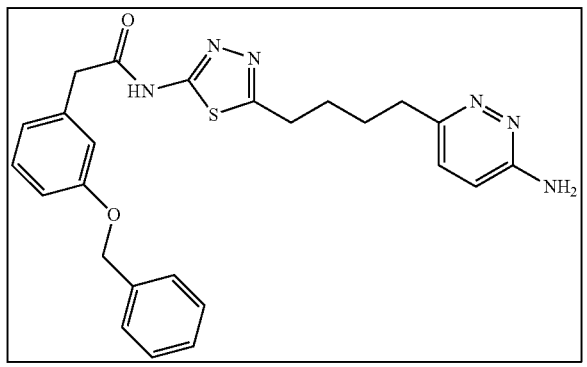 [SMILES: Nc1ccc(CCCCc2nnc(NC(=O)Cc3cccc(OCc4ccccc4)c3)s2)nn1] | | 0.26 | 0.72 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 386 | 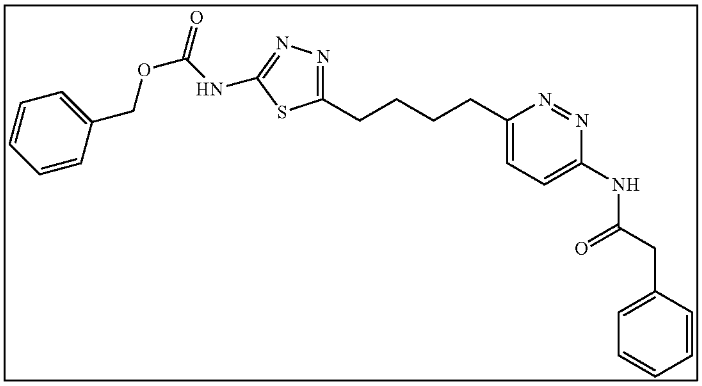 [SMILES: O=C(Cc1ccccc1)Nc1ccc(CCCCc2nnc(NC(=O)OCc3ccccc3)s2)nn1] | | 0.085 | 0.15 |
| 387 | 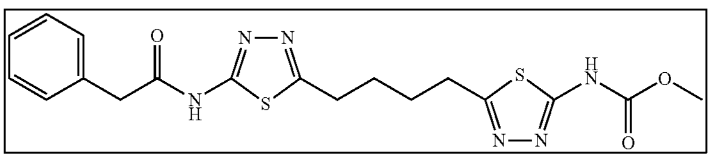 [SMILES: COC(=O)Nc1nnc(CCCCc2nnc(NC(=O)Cc3ccccc3)s2)s1] | | 1.2 | 2.3 |
| 388 | 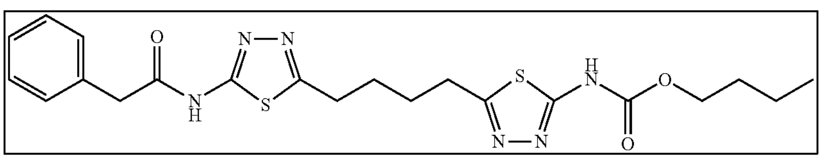 [SMILES: CCCCOC(=O)Nc1nnc(CCCCc2nnc(NC(=O)Cc3ccccc3)s2)s1] | | 0.21 | 0.75 |
| 389 | 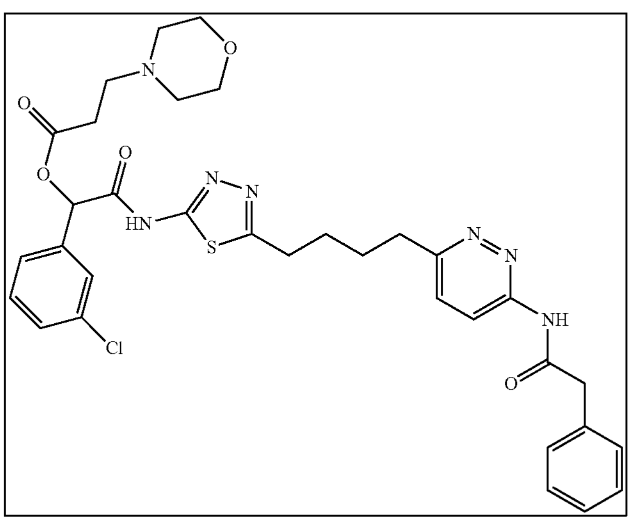 [SMILES: O=C(Cc1ccccc1)Nc1ccc(CCCCc2nnc(NC(=O)C(OC(=O)CCN3CCOCC3)c3cccc(Cl)c3)s2)nn1] | | 0.084 | 0.032 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 390 | 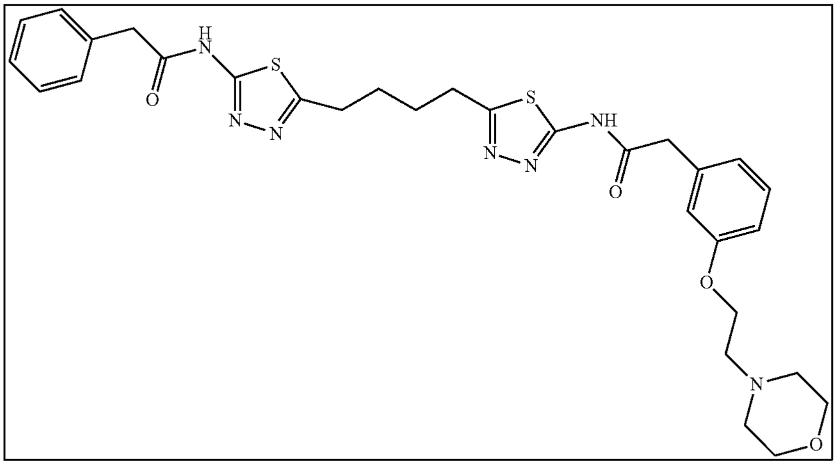 [SMILES: O=C(Cc1ccccc1)Nc1nnc(CCCCc2nnc(NC(=O)Cc3cccc(OCCN4CCOCC4)c3)s2)s1] | 0.042 | | 0.16 |
| 391 | 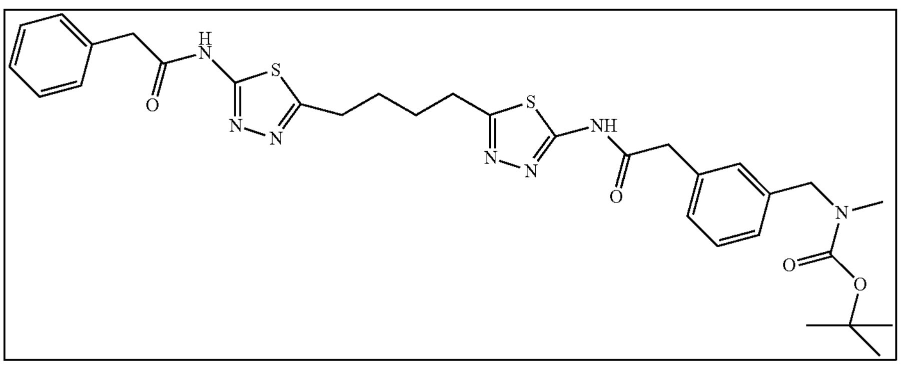 [SMILES: CN(Cc1cccc(CC(=O)Nc2nnc(CCCCc3nnc(NC(=O)Cc4ccccc4)s3)s2)c1)C(=O)OC(C)(C)C] | 0.007 | | 0.027 |
| 392 | 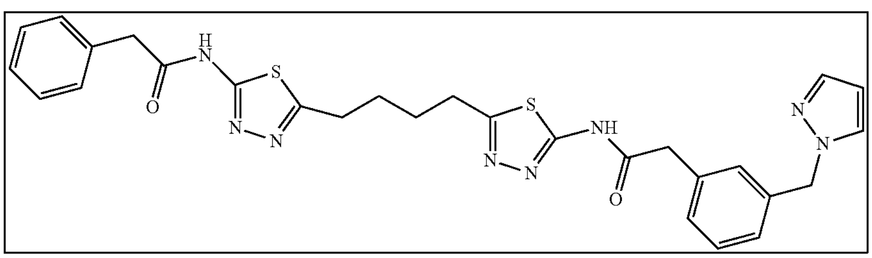 [SMILES: O=C(Cc1ccccc1)Nc1nnc(CCCCc2nnc(NC(=O)Cc3cccc(Cn4cccn4)c3)s2)s1] | 0.014 | | 0.072 |
| 393 | 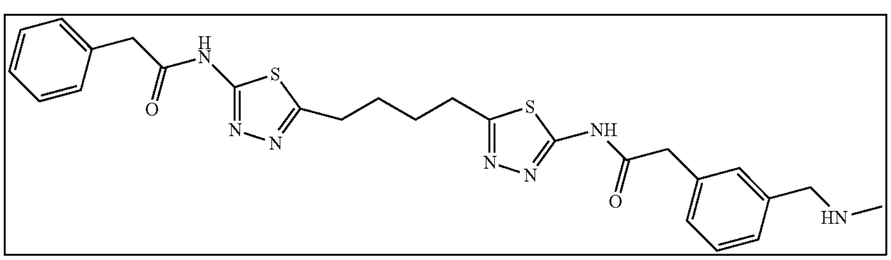 [SMILES: CNCc1cccc(CC(=O)Nc2nnc(CCCCc3nnc(NC(=O)Cc4ccccc4)s3)s2)c1] | 0.10 | | 0.90 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 394 | 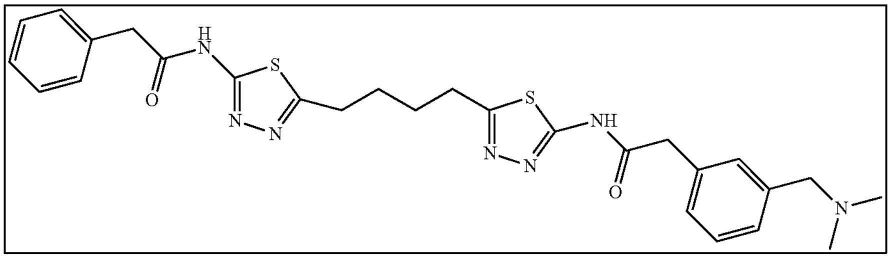 [SMILES: CN(C)Cc1cccc(CC(=O)Nc2nnc(CCCCc3nnc(NC(=O)Cc4ccccc4)s3)s2)c1] | | 0.088 | 1.2 |
| 395 | 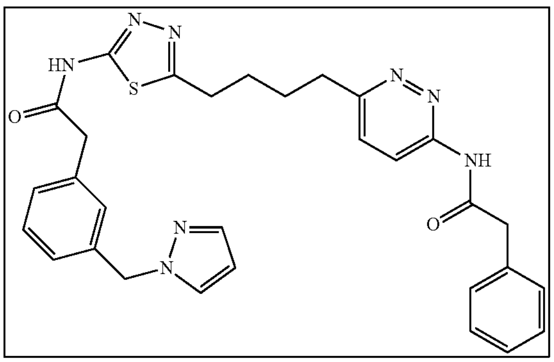 [SMILES: O=C(Cc1ccccc1)Nc1ccc(CCCCc2nnc(NC(=O)Cc3cccc(Cn4cccn4)c3)s2)nn1] | | 0.004 | 0.015 |
| 396 | 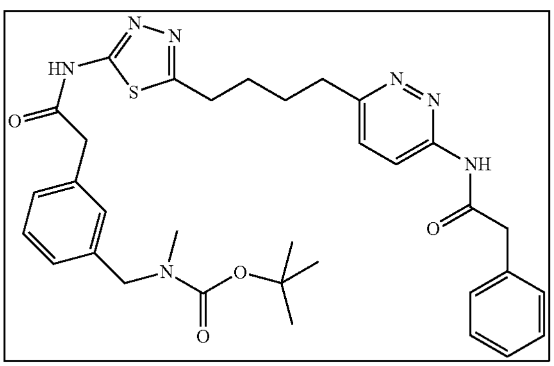 [SMILES: CN(Cc1cccc(CC(=O)Nc2nnc(CCCCc3ccc(NC(=O)Cc4ccccc4)nn3)s2)c1)C(=O)OC(C)(C)C] | | 0.004 | 0.005 |
| 397 | 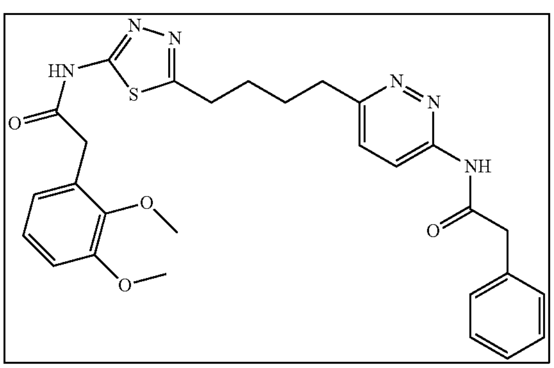 [SMILES: COc1cccc(CC(=O)Nc2nnc(CCCCc3ccc(NC(=O)Cc4ccccc4)nn3)s2)c1OC] | | 0.008 | 0.041 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 398 | 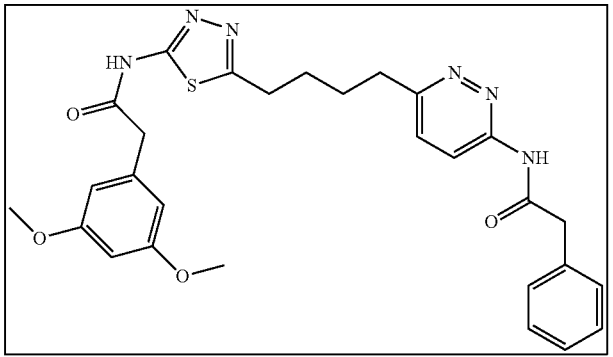 [SMILES: COc1cc(CC(=O)Nc2nnc(CCCCc3ccc(NC(=O)Cc4ccccc4)nn3)s2)cc(OC)c1] | 0.004 | | 0.023 |
| 399 | 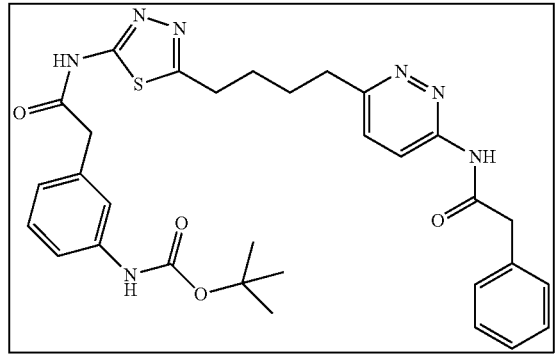 [SMILES: CC(C)(C)OC(=O)Nc1cccc(CC(=O)Nc2nnc(CCCCc3ccc(NC(=O)Cc4ccccc4)nn3)s2)c1] | 0.005 | | 0.026 |
| 400 | 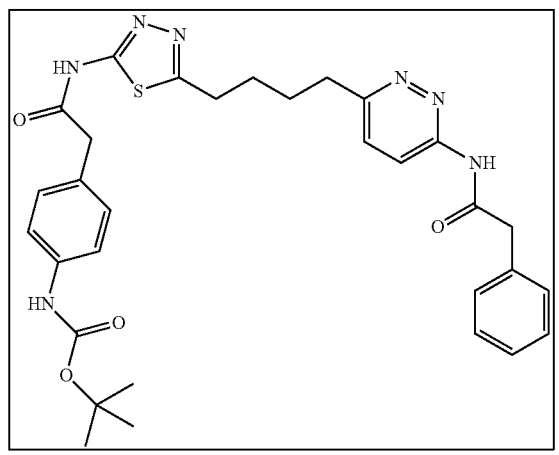 [SMILES: CC(C)(C)OC(=O)Nc1ccc(CC(=O)Nc2nnc(CCCCc3ccc(NC(=O)Cc4ccccc4)nn3)s2)cc1] | 0.015 | | 0.053 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 401 | 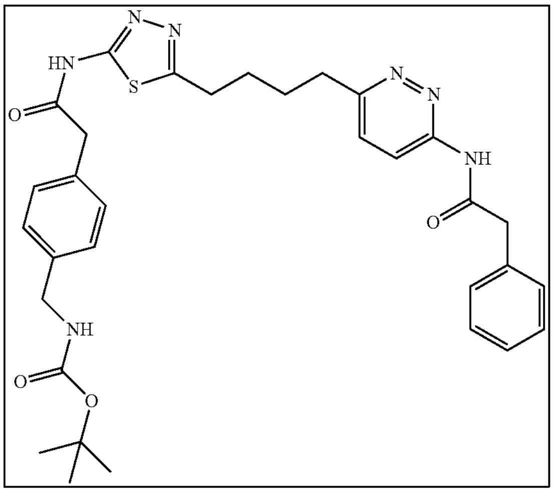 [SMILES: CC(C)(C)OC(=O)NCc1ccc(CC(=O)Nc2nnc(CCCCc3ccc(NC(=O)Cc4ccccc4)nn3)s2)cc1] | 0.005 | | 0.011 |
| 402 | 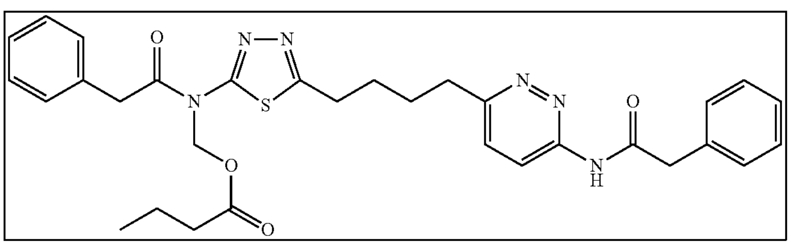 [SMILES: CCCC(=O)OCN(C(=O)Cc1ccccc1)c1nnc(CCCCc2ccc(NC(=O)Cc3ccccc3)nn2)s1] | 1.1 | | 0.054 |
| 403 | 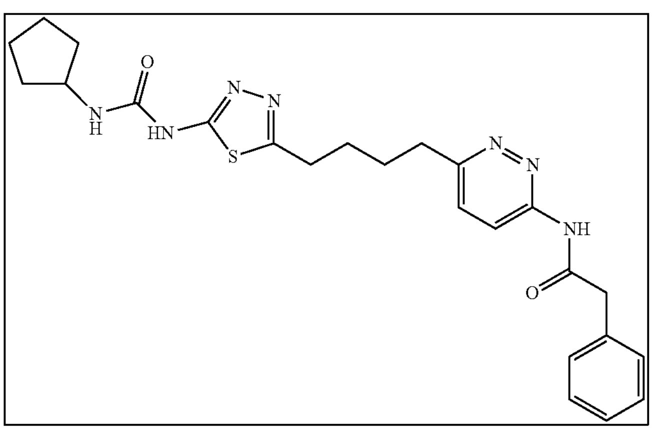 [SMILES: O=C(Cc1ccccc1)Nc1ccc(CCCCc2nnc(NC(=O)NC3CCCC3)s2)nn1] | 0.018 | | 0.12 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 404 | 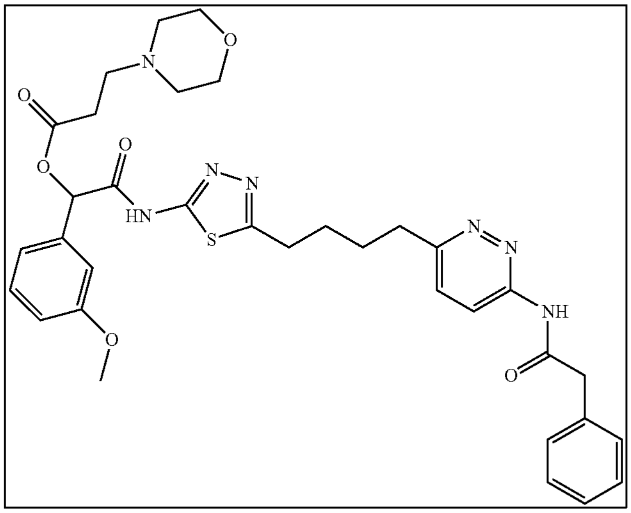 [SMILES: COc1cccc(C(OC(=O)CCN2CCOCC2)C(=O)Nc2nnc(CCCCc3ccc(NC(=O)Cc4ccccc4)nn3)s2)c1] | 0.060 | | 0.022 |
| 405 | 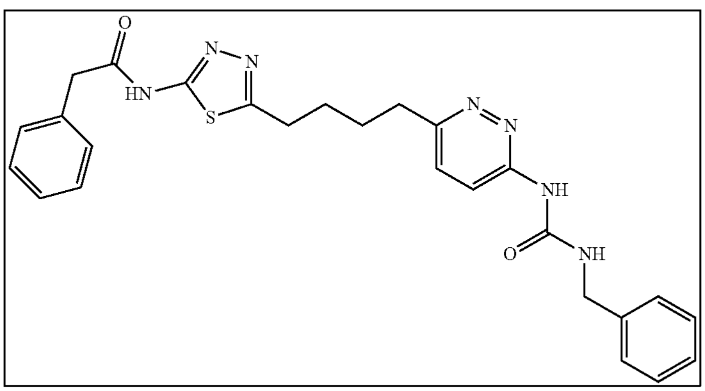 [SMILES: O=C(Cc1ccccc1)Nc1nnc(CCCCc2ccc(NC(=O)NCc3ccccc3)nn2)s1] | 0.081 | | 0.67 |
| 406 | 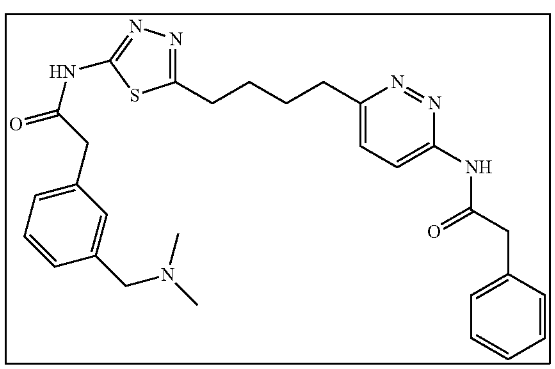 [SMILES: CN(C)Cc1cccc(CC(=O)Nc2nnc(CCCCc3ccc(NC(=O)Cc4ccccc4)nn3)s2)c1] | 0.016 | | 0.27 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 407 | 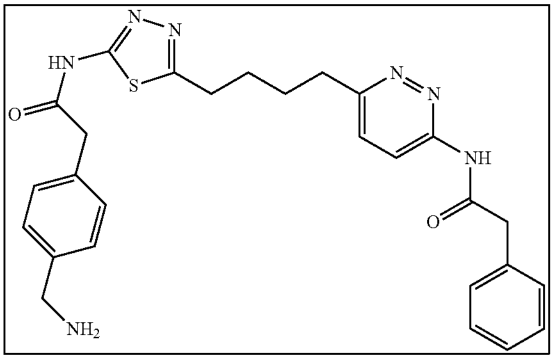 [SMILES: NCc1ccc(CC(=O)Nc2nnc(CCCCc3ccc(NC(=O)Cc4ccccc4)nn3)s2)cc1] | | 0.012 | 0.044 |
| 408 | 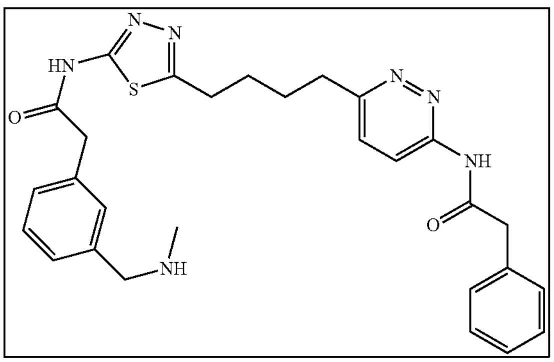 [SMILES: CNCc1cccc(CC(=O)Nc2nnc(CCCCc3ccc(NC(=O)Cc4ccccc4)nn3)s2)c1] | | 0.018 | 0.19 |
| 409 | 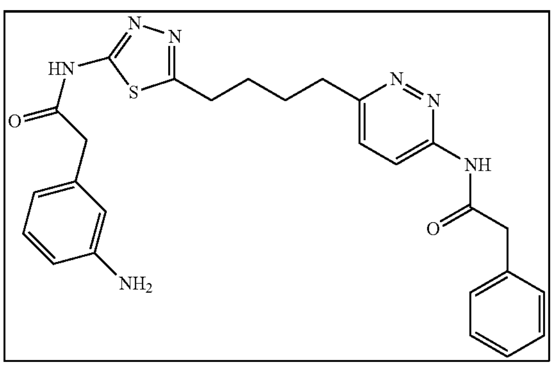 [SMILES: Nc1cccc(CC(=O)Nc2nnc(CCCCc3ccc(NC(=O)Cc4ccccc4)nn3)s2)c1] | | 0.008 | 0.037 |
| 410 | 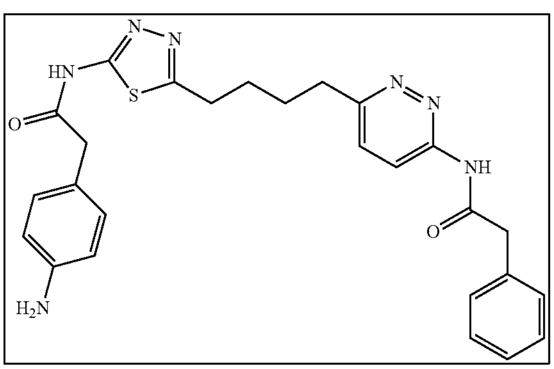 [SMILES: Nc1ccc(CC(=O)Nc2nnc(CCCCc3ccc(NC(=O)Cc4ccccc4)nn3)s2)cc1] | | 0.009 | 0.057 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 411 | 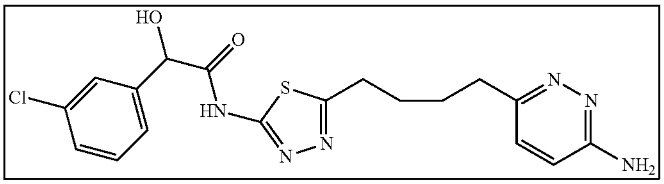 [SMILES: Nc1ccc(CCCCc2nnc(NC(=O)C(O)c3cccc(Cl)c3)s2)nn1] | 0.22 | | 0.74 |
| 412 | 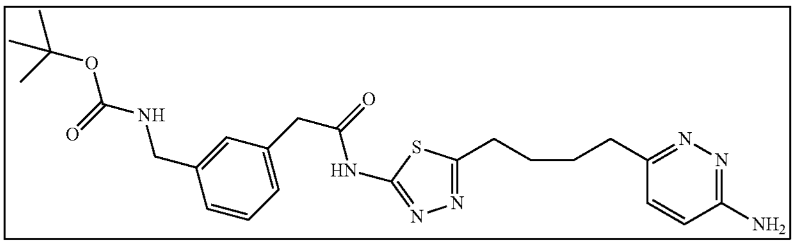 [SMILES: CC(C)(C)OC(=O)NCc1cccc(CC(=O)Nc2nnc(CCCCc3ccc(N)nn3)s2)c1] | 0.028 | | 0.11 |
| 413 | 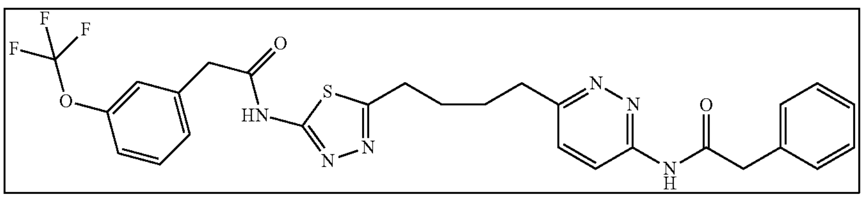 [SMILES: O=C(Cc1ccccc1)Nc1ccc(CCCCc2nnc(NC(=O)Cc3cccc(OC(F)(F)F)c3)s2)nn1] | 0.007 | | 0.045 |
| 414 | 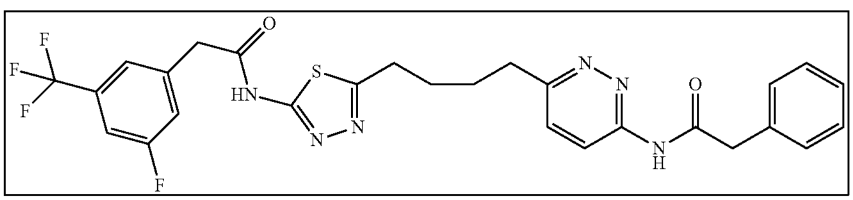 [SMILES: O=C(Cc1ccccc1)Nc1ccc(CCCCc2nnc(NC(=O)Cc3cc(F)cc(C(F)(F)F)c3)s2)nn1] | 0.010 | | 0.058 |
| 415 | 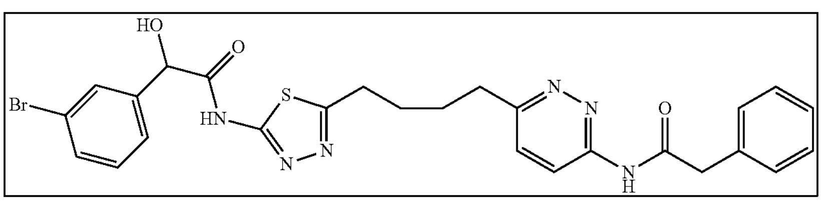 [SMILES: O=C(Cc1ccccc1)Nc1ccc(CCCCc2nnc(NC(=O)C(O)c3cccc(Br)c3)s2)nn1] | 0.006 | | 0.018 |
| 416 | 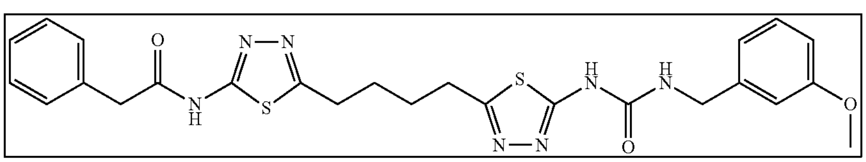 [SMILES: COc1cccc(CNC(=O)Nc2nnc(CCCCc3nnc(NC(=O)Cc4ccccc4)s3)s2)c1] | 0.055 | | 0.35 |
| 417 | 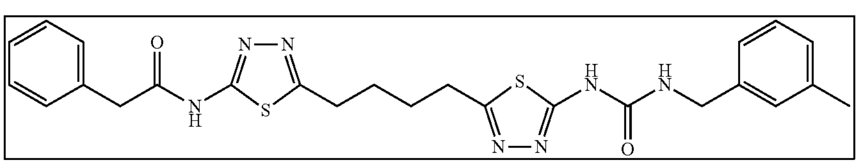 [SMILES: Cc1cccc(CNC(=O)Nc2nnc(CCCCc3nnc(NC(=O)Cc4ccccc4)s3)s2)c1] | 0.056 | | 0.32 |

TABLE 3-continued
| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 418 | 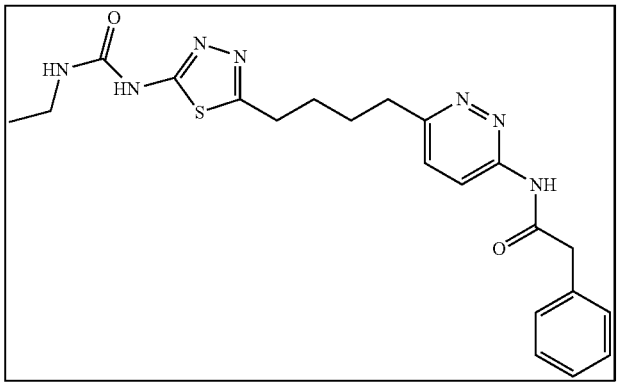 [SMILES: CCNC(=O)Nc1nnc(CCCCc2ccc(NC(=O)Cc3ccccc3)nn2)s1] | 0.14 | | 0.32 |
| 419 | 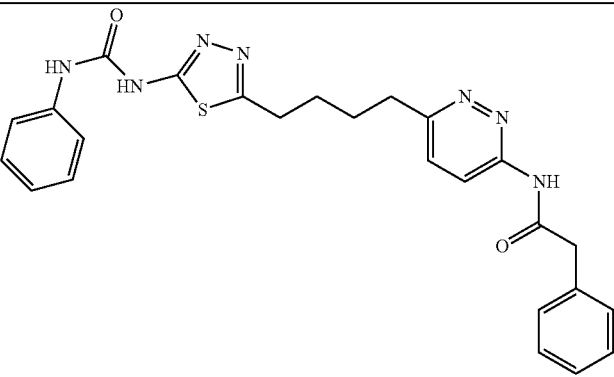 | 0.024 | | 0.064 |
| 420 | 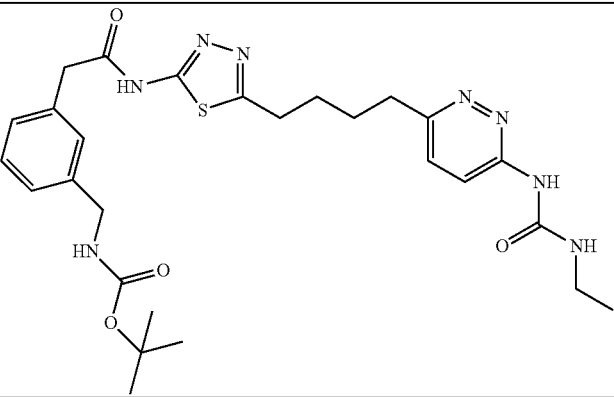 | 0.013 | | 0.070 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 421 | 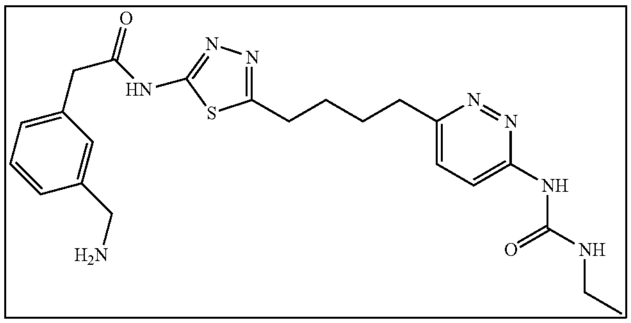 [SMILES: CCNC(=O)Nc1ccc(CCCCc2nnc(NC(=O)Cc3cccc(CN)c3)s2)nn1] | 0.29 | | 0.16 |
| 422 | 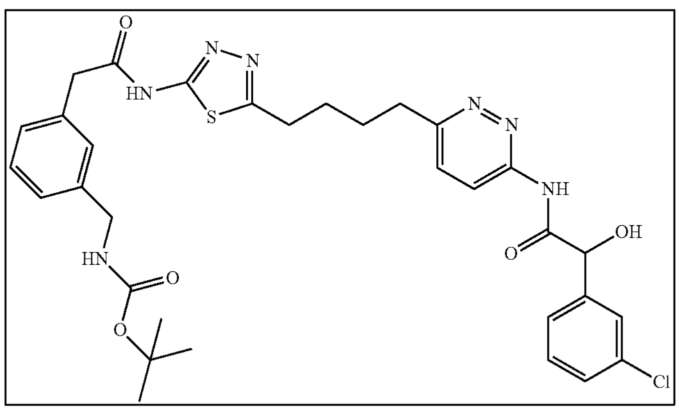 [SMILES: CC(C)(C)OC(=O)NCc1cccc(CC(=O)Nc2nnc(CCCCc3ccc(NC(=O)C(O)c4cccc(Cl)c4)nn3)s2)c1] | 0.007 | | 0.006 |
| 423 | 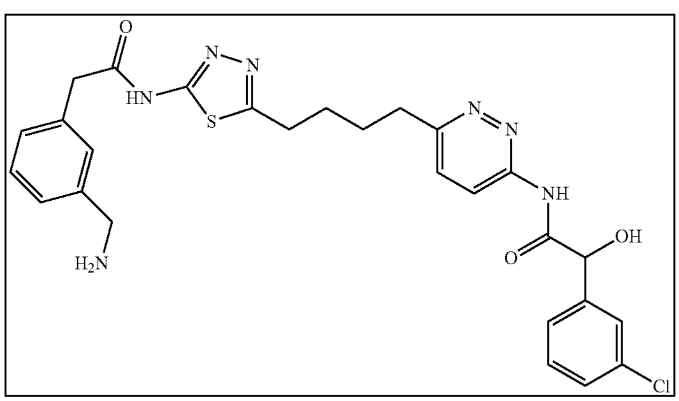 [SMILES: NCc1cccc(CC(=O)Nc2nnc(CCCCc3ccc(NC(=O)C(O)c4cccc(Cl)c4)nn3)s2)c1] | 0.022 | | 0.042 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 424 | 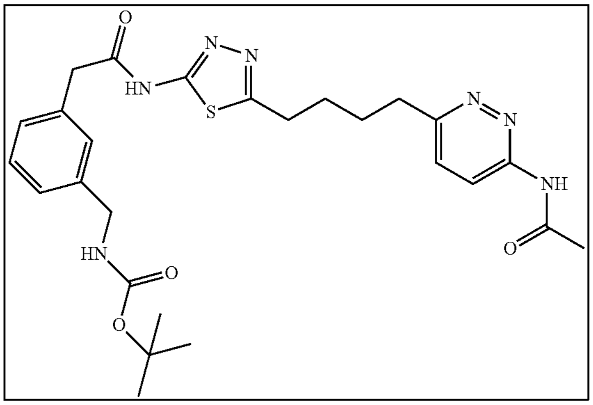 [SMILES: CC(=O)Nc1ccc(CCCCc2nnc(NC(=O)Cc3cccc(CNC(=O)OC(C)(C)C)c3)s2)nn1] | 0.006 | | 0.008 |
| 425 | 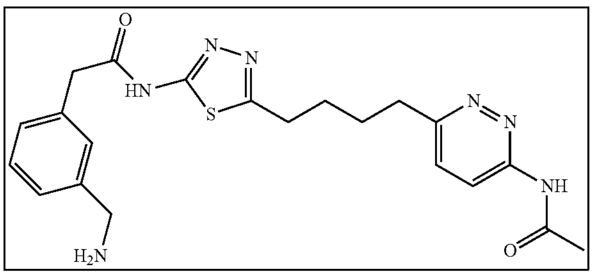 [SMILES: CC(=O)Nc1ccc(CCCCc2nnc(NC(=O)Cc3cccc(CN)c3)s2)nn1] | 0.086 | | 0.015 |
| 426 | 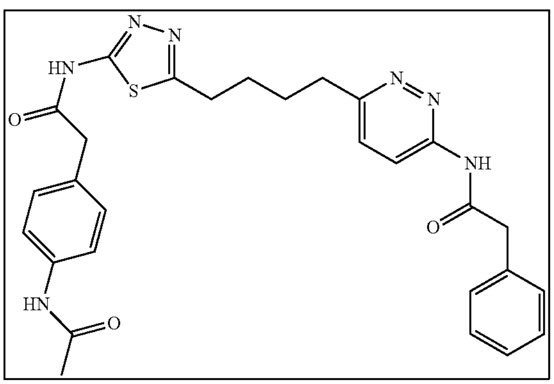 [SMILES: CC(=O)Nc1ccc(CC(=O)Nc2nnc(CCCCc3ccc(NC(=O)Cc4ccccc4)nn3)s2)cc1] | 0.011 | | 0.033 |
| 427 | 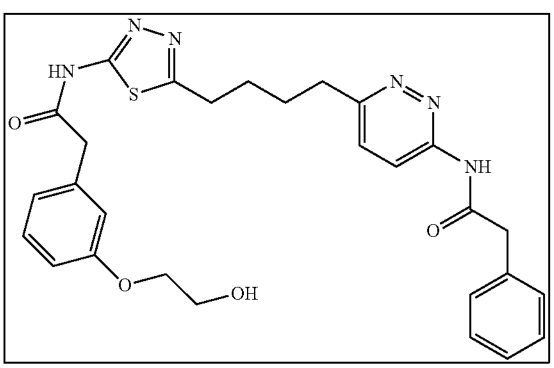 [SMILES: O=C(Cc1ccccc1)Nc1ccc(CCCCc2nnc(NC(=O)Cc3cccc(OCCO)c3)s2)nn1] | 0.007 | | 0.027 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 428 | 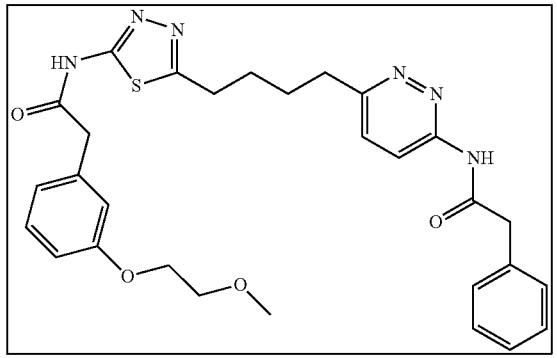 [SMILES: COCCOc1cccc(CC(=O)Nc2nnc(CCCCc3ccc(NC(=O)Cc4ccccc4)nn3)s2)c1] | 0.007 | | 0.019 |
| 429 | 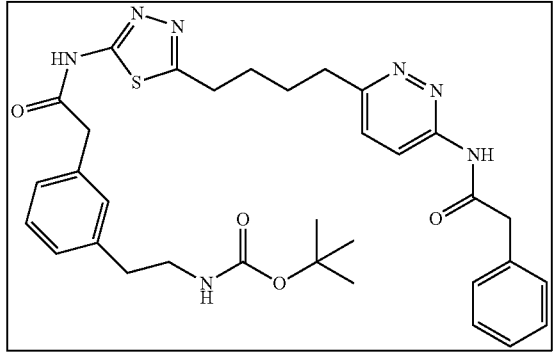 [SMILES: CC(C)(C)OC(=O)NCCc1cccc(CC(=O)Nc2nnc(CCCCc3ccc(NC(=O)Cc4ccccc4)nn3)s2)c1] | 0.004 | | 0.007 |
| 430 | 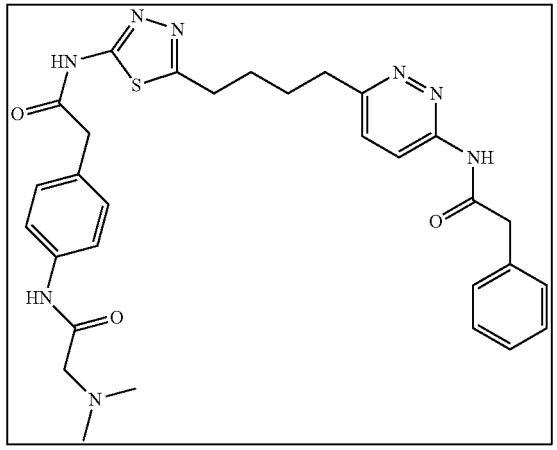 [SMILES: CN(C)CC(=O)Nc1ccc(CC(=O)Nc2nnc(CCCCc3ccc(NC(=O)Cc4ccccc4)nn3)s2)cc1] | 0.009 | | 0.027 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 431 | 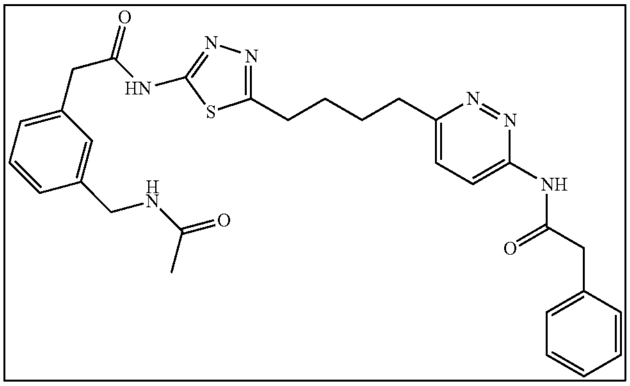 [SMILES: CC(=O)NCc1cccc(CC(=O)Nc2nnc(CCCCc3ccc(NC(=O)Cc4ccccc4)nn3)s2)c1] | 0.007 | | 0.026 |
| 432 | 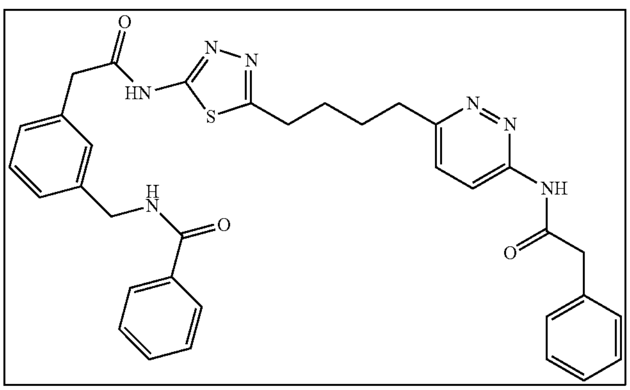 [SMILES: O=C(Cc1ccccc1)Nc1ccc(CCCCc2nnc(NC(=O)Cc3cccc(CNC(=O)c4ccccc4)c3)s2)nn1] | 0.002 | | 0.004 |
| 433 | 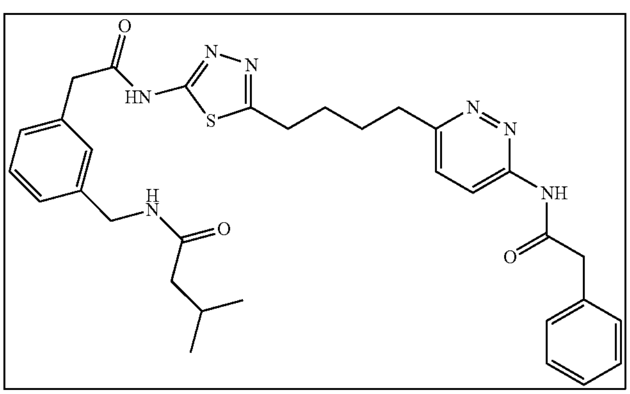 [SMILES: CC(C)CC(=O)NCc1cccc(CC(=O)Nc2nnc(CCCCc3ccc(NC(=O)Cc4ccccc4)nn3)s2)c1] | 0.002 | | 0.007 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 434 | 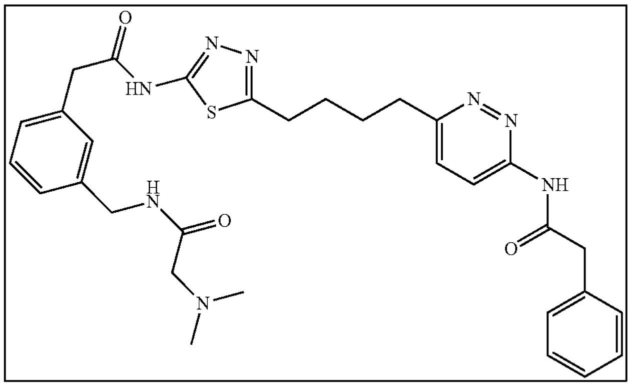 [SMILES: CN(C)CC(=O)NCc1cccc(CC(=O)Nc2nnc(CCCCc3ccc(NC(=O)Cc4ccccc4)nn3)s2)c1] | | 0.005 | 0.017 |
| 435 | 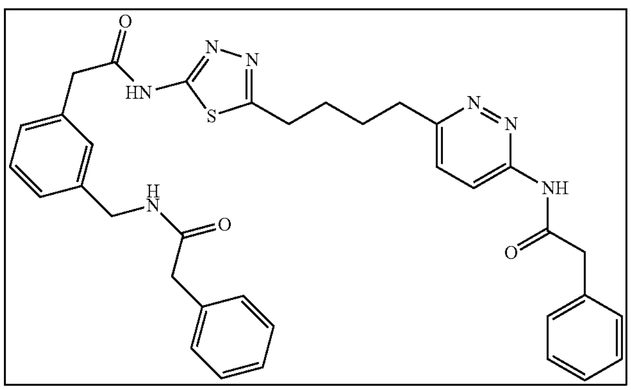 [SMILES: O=C(Cc1ccccc1)NCc1cccc(CC(=O)Nc2nnc(CCCCc3ccc(NC(=O)Cc4ccccc4)nn3)s2)c1] | | 0.002 | 0.006 |
| 436 | 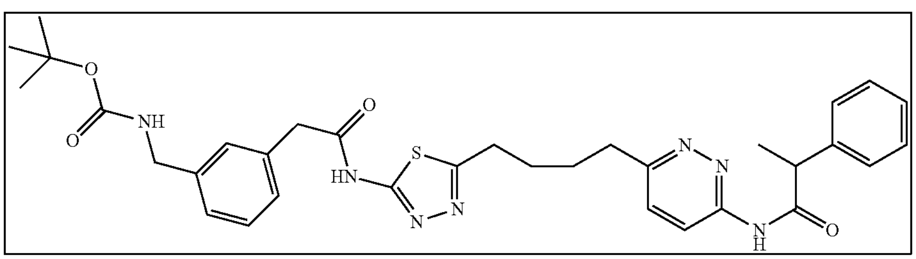 [SMILES: CC(C(=O)Nc1ccc(CCCCc2nnc(NC(=O)Cc3cccc(CNC(=O)OC(C)(C)C)c3)s2)nn1)c1ccccc1] | | 0.006 | 0.010 |
| 437 | 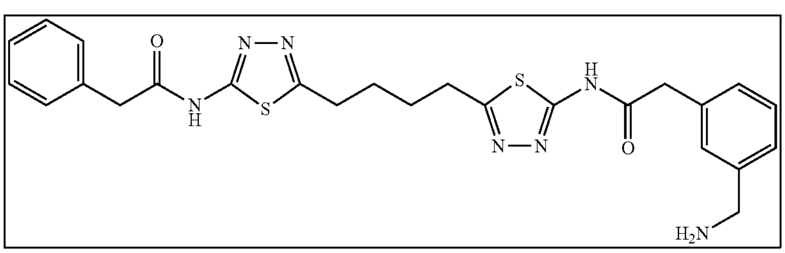 [SMILES: NCc1cccc(CC(=O)Nc2nnc(CCCCc3nnc(NC(=O)Cc4ccccc4)s3)s2)c1] | | 0.070 | 0.072 |
| 438 | 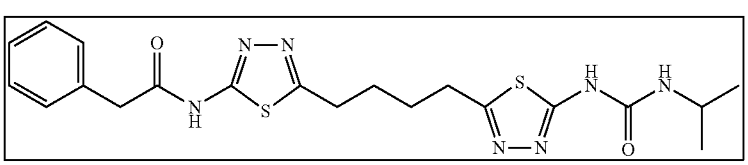 [SMILES: CC(C)NC(=O)Nc1nnc(CCCCc2nnc(NC(=O)Cc3ccccc3)s2)s1] | | 0.74 | 0.88 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 439 | 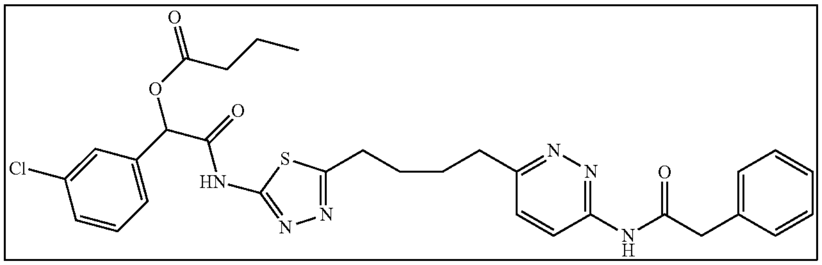 [SMILES: CCCC(=O)OC(C(=O)Nc1nnc(CCCCc2ccc(NC(=O)Cc3ccccc3)nn2)s1)c1cccc(Cl)c1] | | 0.25 | 0.056 |
| 440 | 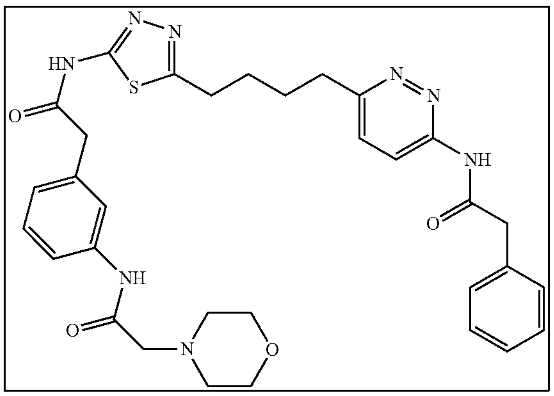 [SMILES: O=C(CN1CCOCC1)Nc1cccc(CC(=O)Nc2nnc(CCCCc3ccc(NC(=O)Cc4ccccc4)nn3)s2)c1] | | 0.008 | 0.031 |
| 441 | 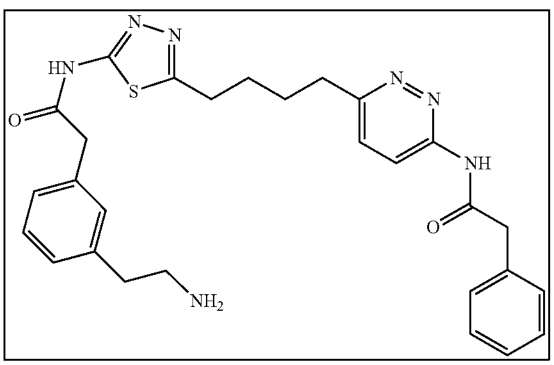 [SMILES: NCCc1cccc(CC(=O)Nc2nnc(CCCCc3ccc(NC(=O)Cc4ccccc4)nn3)s2)c1] | | 0.011 | 0.18 |
| 442 | 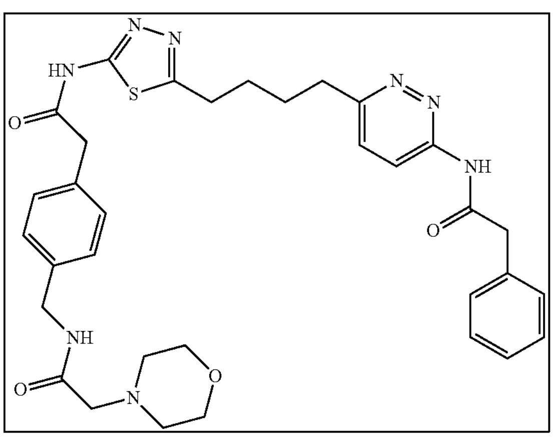 [SMILES: O=C(CN1CCOCC1)NCc1ccc(CC(=O)Nc2nnc(CCCCc3ccc(NC(=O)Cc4ccccc4)nn3)s2)cc1] | | 0.007 | 0.025 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 443 | 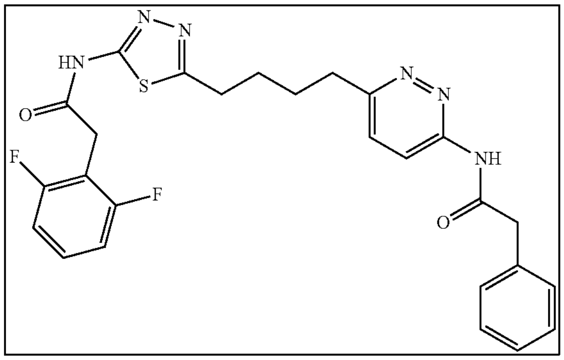 [SMILES: O=C(Cc1ccccc1)Nc1ccc(CCCCc2nnc(NC(=O)Cc3c(F)cccc3F)s2)nn1] | | 0.011 | 0.10 |
| 444 | 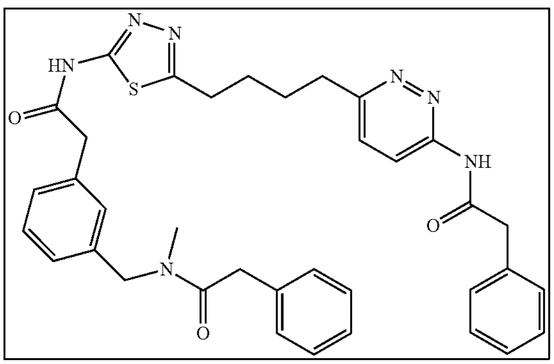 [SMILES: CN(Cc1cccc(CC(=O)Nc2nnc(CCCCc3ccc(NC(=O)Cc4ccccc4)nn3)s2)c1)C(=O)Cc1ccccc1] | | 0.003 | 0.008 |
| 445 | 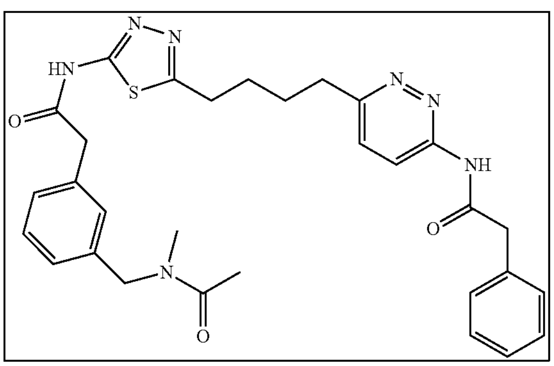 [SMILES: CC(=O)N(C)Cc1cccc(CC(=O)Nc2nnc(CCCCc3ccc(NC(=O)Cc4ccccc4)nn3)s2)c1] | | 0.004 | 0.022 |
| 446 | 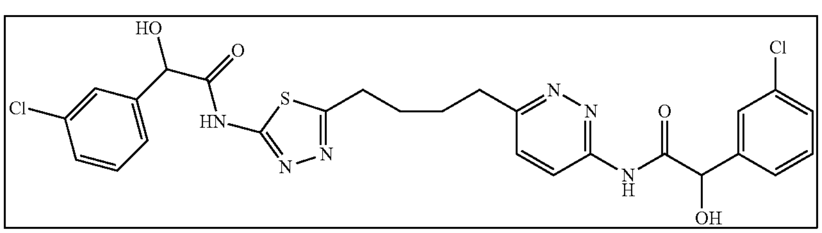 [SMILES: O=C(Nc1ccc(CCCCc2nnc(NC(=O)C(O)c3cccc(Cl)c3)s2)nn1)C(O)c1cccc(Cl)c1] | | 0.011 | 0.15 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 447 | 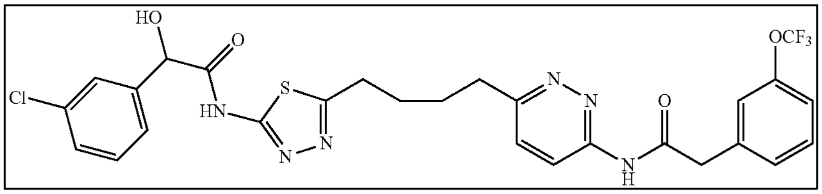 [SMILES: O=C(Cc1cccc(OC(F)(F)F)c1)Nc1ccc(CCCCc2nnc(NC(=O)C(O)c3cccc(Cl)c3)s2)nn1] | 0.005 | | 0.016 |
| 448 | 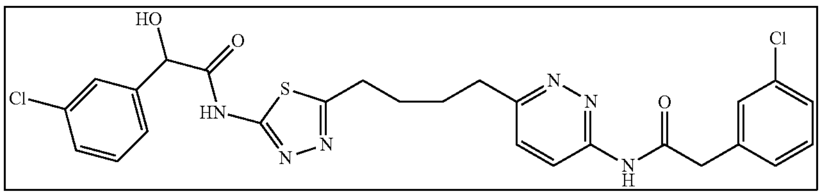 [SMILES: O=C(Cc1cccc(Cl)c1)Nc1ccc(CCCCc2nnc(NC(=O)C(O)c3cccc(Cl)c3)s2)nn1] | 0.005 | | 0.051 |
| 449 | 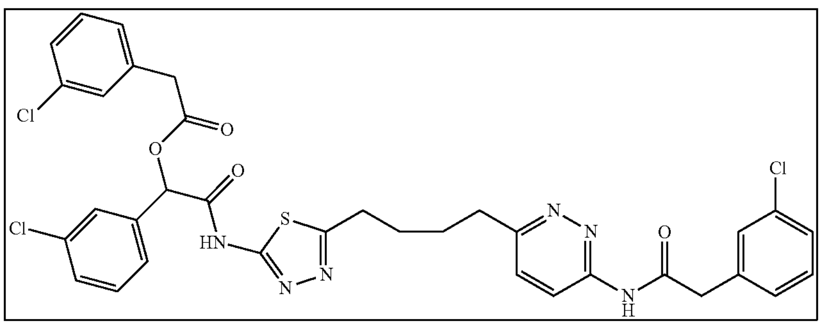 [SMILES: O=C(Cc1cccc(Cl)c1)Nc1ccc(CCCCc2nnc(NC(=O)C(OC(=O)Cc3cccc(Cl)c3)c3cccc(Cl)c3)s2)nn1] | 0.11 | | 0.12 |
| 450 | 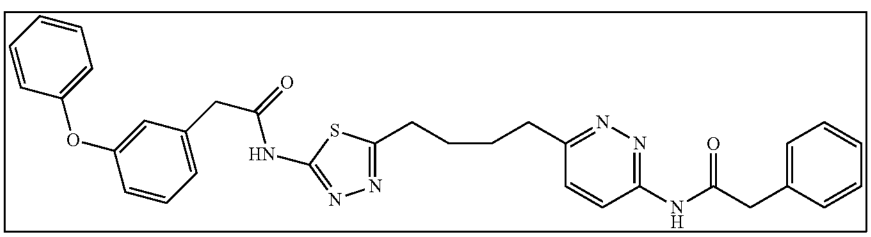 [SMILES: O=C(Cc1ccccc1)Nc1ccc(CCCCc2nnc(NC(=O)Cc3cccc(Oc4ccccc4)c3)s2)nn1] | 0.006 | | 0.042 |
| 451 | 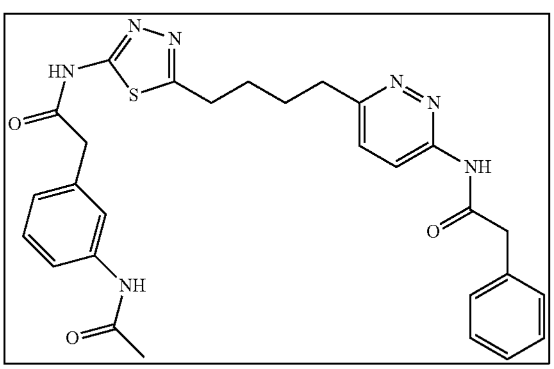 [SMILES: CC(=O)Nc1cccc(CC(=O)Nc2nnc(CCCCc3ccc(NC(=O)Cc4ccccc4)nn3)s2)c1] | 0.003 | | 0.056 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
| --- | --- | --- | --- | --- |
| 452 | 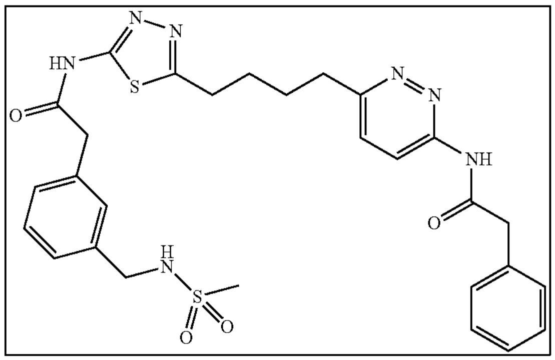 [SMILES: CS(=O)(=O)NCc1cccc(CC(=O)Nc2nnc(CCCCc3ccc(NC(=O)Cc4ccccc4)nn3)s2)c1] | 0.004 | | 0.049 |
| 453 | 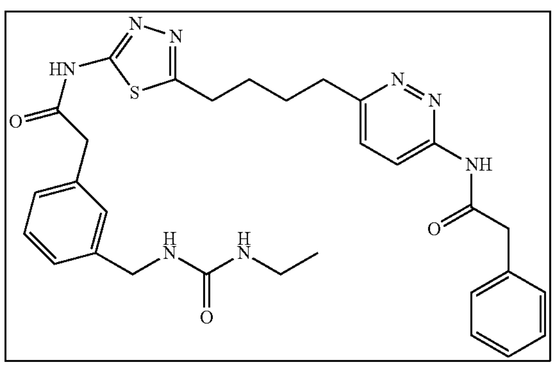 [SMILES: CCNC(=O)NCc1cccc(CC(=O)Nc2nnc(CCCCc3ccc(NC(=O)Cc4ccccc4)nn3)s2)c1] | 0.003 | | 0.015 |
| 454 | 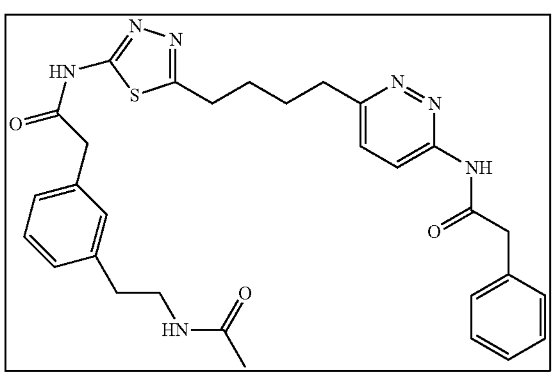 [SMILES: CC(=O)NCCc1cccc(CC(=O)Nc2nnc(CCCCc3ccc(NC(=O)Cc4ccccc4)nn3)s2)c1] | 0.006 | | 0.13 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 455 | 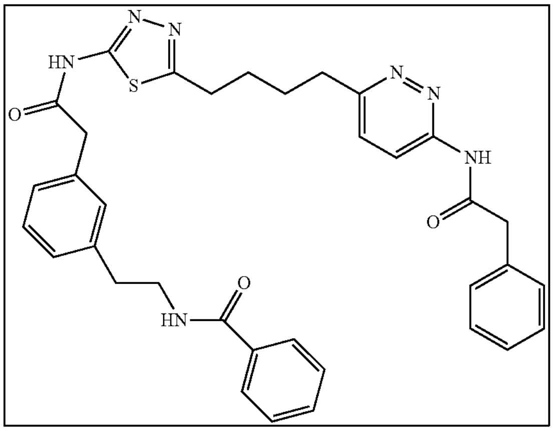 [SMILES: O=C(Cc1ccccc1)Nc1ccc(CCCCc2nnc(NC(=O)Cc3cccc(CCNC(=O)c4ccccc4)c3)s2)nn1] | 0.003 | | 0.012 |
| 456 | 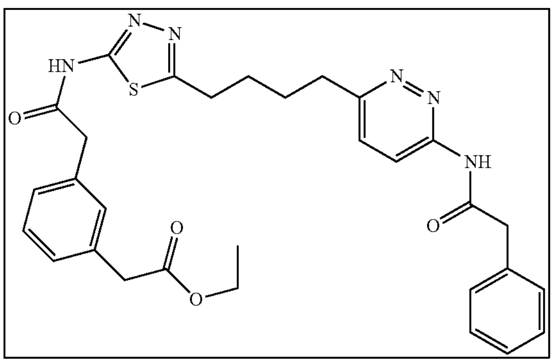 [SMILES: CCOC(=O)Cc1cccc(CC(=O)Nc2nnc(CCCCc3ccc(NC(=O)Cc4ccccc4)nn3)s2)c1] | 0.003 | | 0.024 |
| 457 | 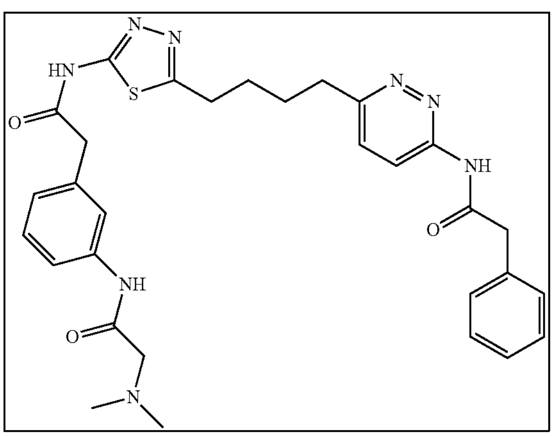 [SMILES: CN(C)CC(=O)Nc1cccc(CC(=O)Nc2nnc(CCCCc3ccc(NC(=O)Cc4ccccc4)nn3)s2)c1] | 0.009 | | 0.11 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 458 | 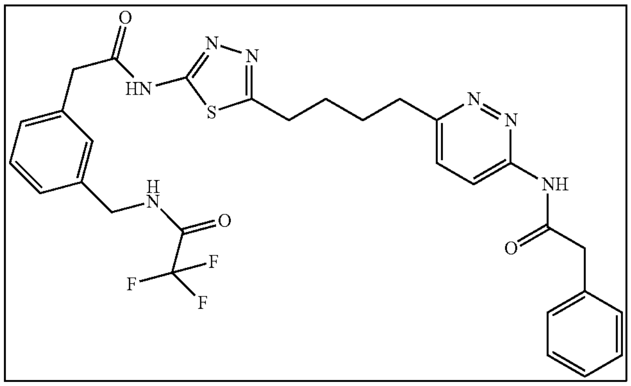 [SMILES: O=C(Cc1ccccc1)Nc1ccc(CCCCc2nnc(NC(=O)Cc3cccc(CNC(=O)C(F)(F)F)c3)s2)nn1] | 0.003 | | 0.013 |
| 459 | 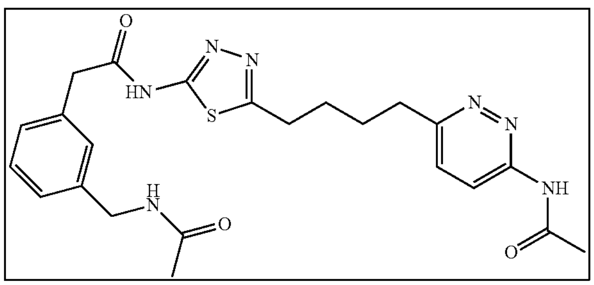 [SMILES: CC(=O)NCc1cccc(CC(=O)Nc2nnc(CCCCc3ccc(NC(C)=O)nn3)s2)c1] | 0.048 | | 0.57 |
| 460 | 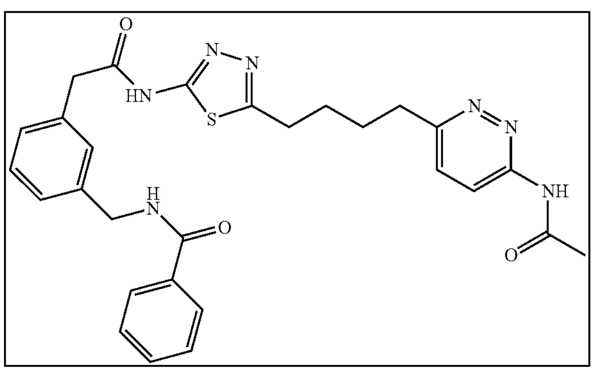 [SMILES: CC(=O)Nc1ccc(CCCCc2nnc(NC(=O)Cc3cccc(CNC(=O)c4ccccc4)c3)s2)nn1] | 0.005 | | 0.031 |
| 461 | 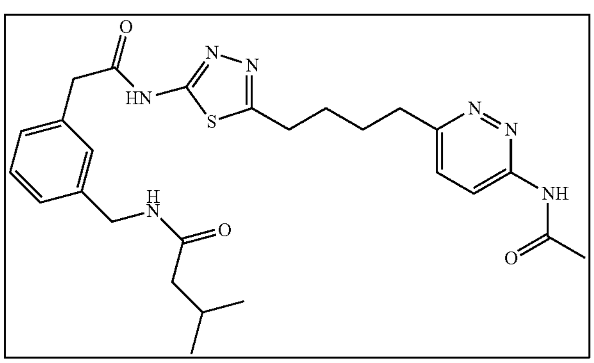 [SMILES: CC(=O)Nc1ccc(CCCCc2nnc(NC(=O)Cc3cccc(CNC(=O)CC(C)C)c3)s2)nn1] | 0.011 | | 0.062 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 462 | 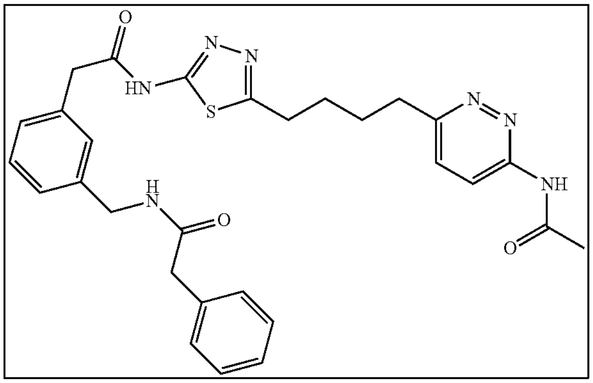 [SMILES: CC(=O)Nc1ccc(CCCCc2nnc(NC(=O)Cc3cccc(CNC(=O)Cc4ccccc4)c3)s2)nn1] | 0.006 | | 0.053 |
| 463 | 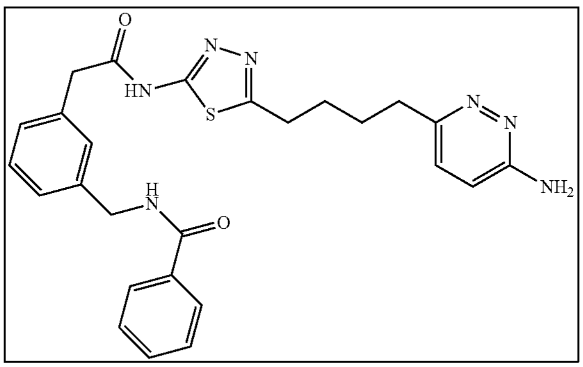 [SMILES: Nc1ccc(CCCCc2nnc(NC(=O)Cc3cccc(CNC(=O)c4ccccc4)c3)s2)nn1] | 0.052 | | 0.96 |
| 464 | 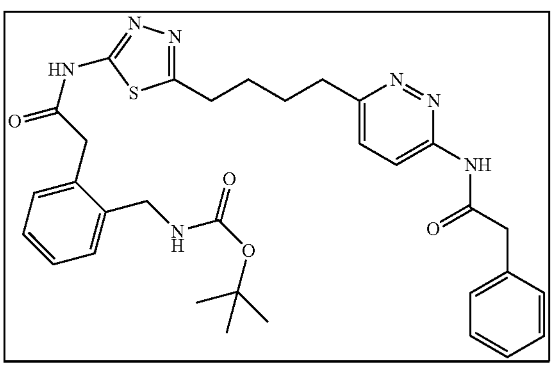 [SMILES: CC(C)(C)OC(=O)NCc1ccccc1CC(=O)Nc1nnc(CCCCc2ccc(NC(=O)Cc3ccccc3)nn2)s1] | 0.005 | | 0.059 |
| 465 | 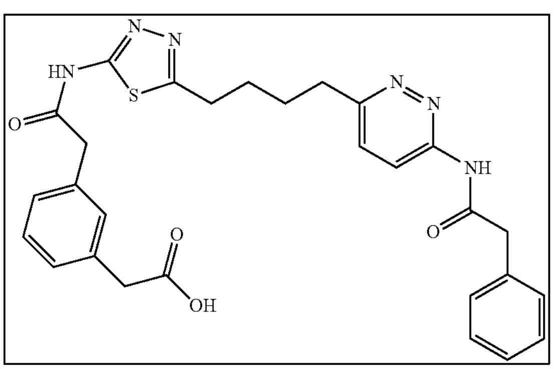 [SMILES: O=C(O)Cc1cccc(CC(=O)Nc2nnc(CCCCc3ccc(NC(=O)Cc4ccccc4)nn3)s2)c1] | 0.006 | | 0.92 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 466 | 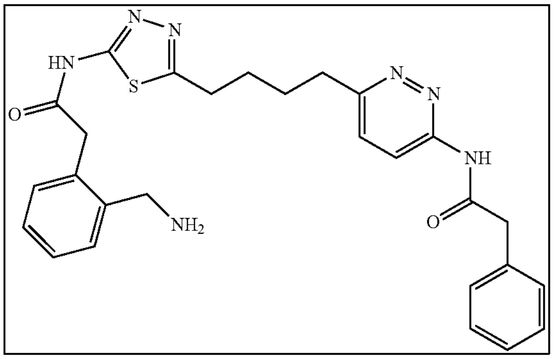 [SMILES: NCc1ccccc1CC(=O)Nc1nnc(CCCCc2ccc(NC(=O)Cc3ccccc3)nn2)s1] | | 0.051 | 1.3 |
| 467 | 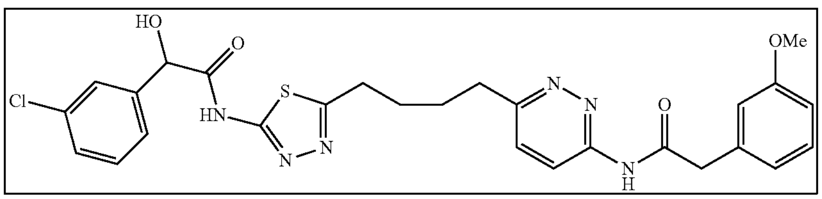 [SMILES: COc1cccc(CC(=O)Nc2ccc(CCCCc3nnc(NC(=O)C(O)c4cccc(Cl)c4)s3)nn2)c1] | | 0.005 | 0.047 |
| 468 | 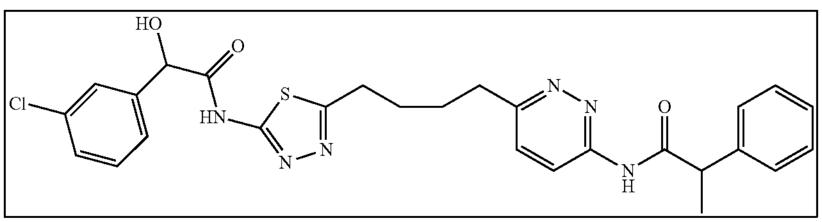 [SMILES: CC(C(=O)Nc1ccc(CCCCc2nnc(NC(=O)C(O)c3cccc(Cl)c3)s2)nn1)c1ccccc1] | | 0.016 | 0.27 |
| 469 | 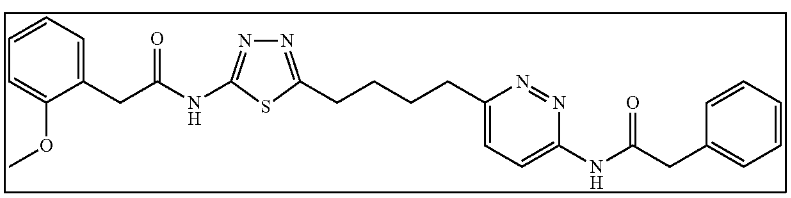 [SMILES: COc1ccccc1CC(=O)Nc1nnc(CCCCc2ccc(NC(=O)Cc3ccccc3)nn2)s1] | | 0.007 | 0.049 |
| 470 | 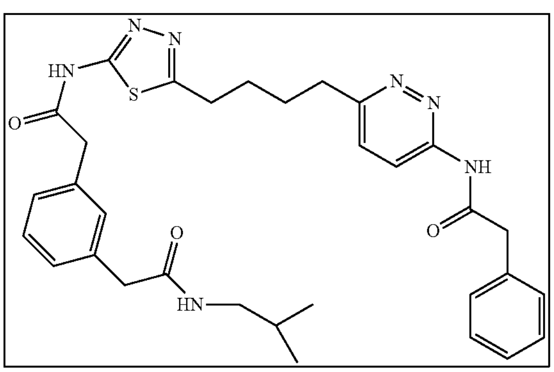 [SMILES: CC(C)CNC(=O)Cc1cccc(CC(=O)Nc2nnc(CCCCc3ccc(NC(=O)Cc4ccccc4)nn3)s2)c1] | | 0.003 | 0.009 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 471 | 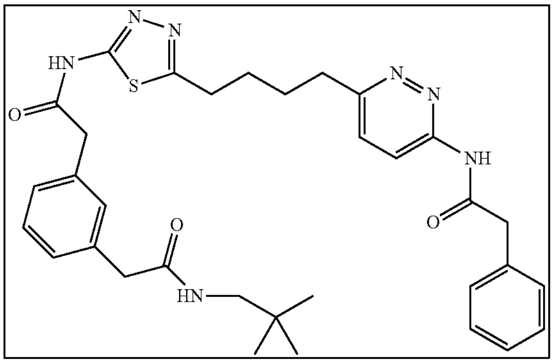 [SMILES: CC(C)(C)CNC(=O)Cc1cccc(CC(=O)Nc2nnc(CCCCc3ccc(NC(=O)Cc4ccccc4)nn3)s2)c1] | | 0.003 | 0.006 |
| 472 | 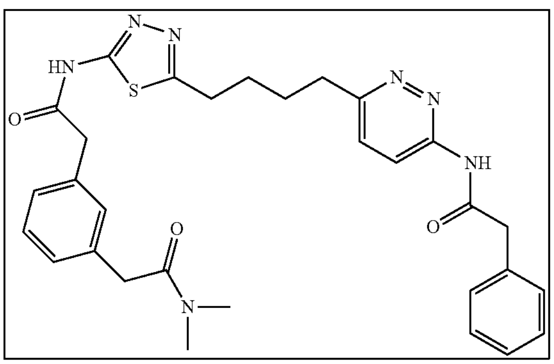 [SMILES: CN(C)C(=O)Cc1cccc(CC(=O)Nc2nnc(CCCCc3ccc(NC(=O)Cc4ccccc4)nn3)s2)c1] | | 0.006 | 0.024 |
| 473 | 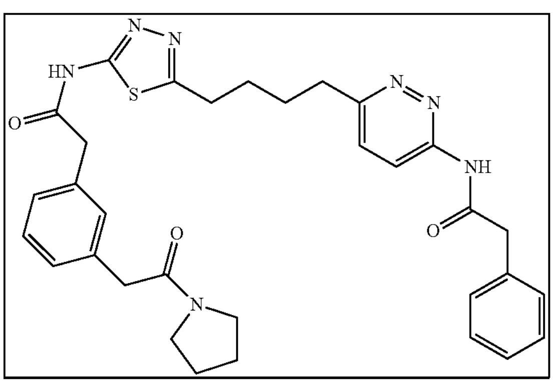 [SMILES: O=C(Cc1ccccc1)Nc1ccc(CCCCc2nnc(NC(=O)Cc3cccc(CC(=O)N4CCCC4)c3)s2)nn1] | | 0.002 | 0.006 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 474 | 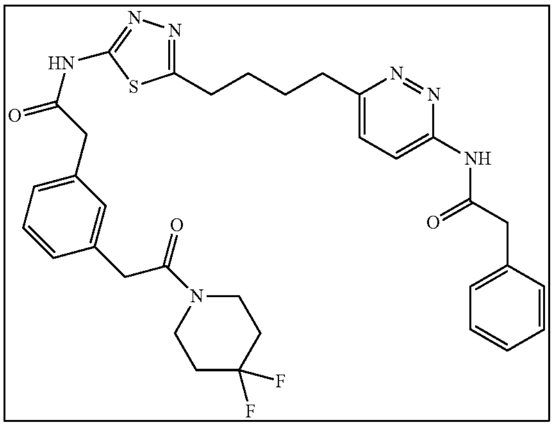 [SMILES: O=C(Cc1ccccc1)Nc1ccc(CCCCc2nnc(NC(=O)Cc3cccc(CC(=O)N4CCC(F)(F)CC4)c3)s2)nn1] | 0.003 | | 0.004 |
| 475 | 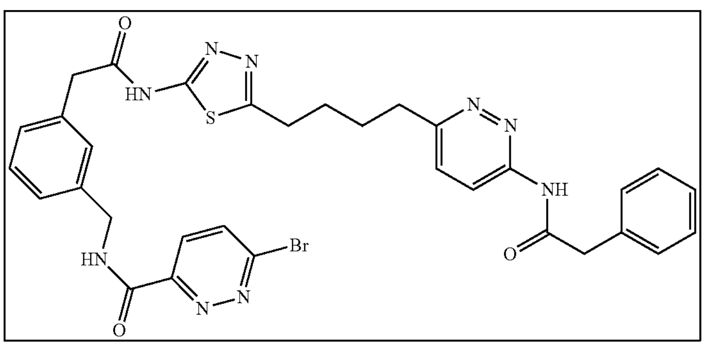 [SMILES: O=C(Cc1ccccc1)Nc1ccc(CCCCc2nnc(NC(=O)Cc3cccc(CNC(=O)c4ccc(Br)nn4)c3)s2)nn1] | 0.002 | | 0.003 |
| 476 | 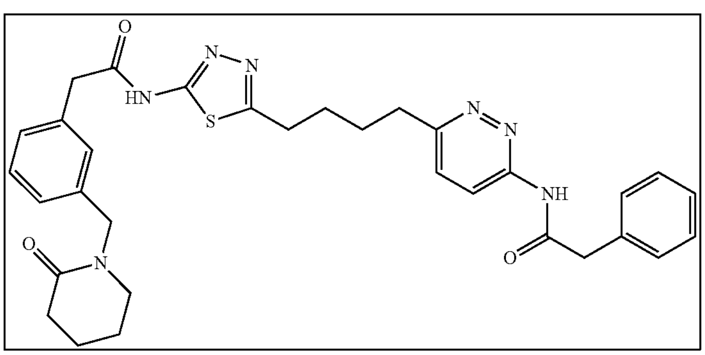 [SMILES: O=C(Cc1ccccc1)Nc1ccc(CCCCc2nnc(NC(=O)Cc3cccc(CN4CCCCC4=O)c3)s2)nn1] | 0.004 | | 0.012 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 477 | 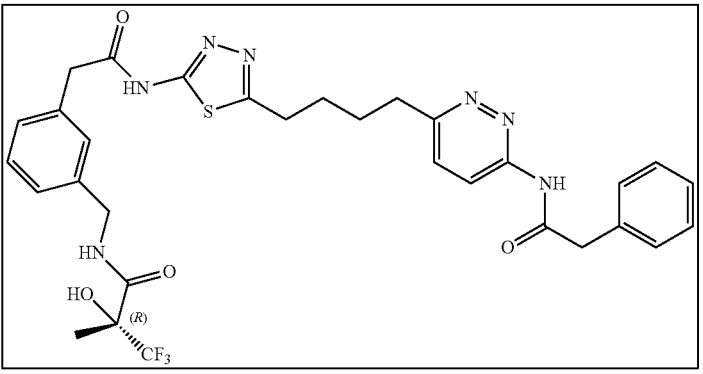 | 0.005 | | 0.015 |
| 478 | 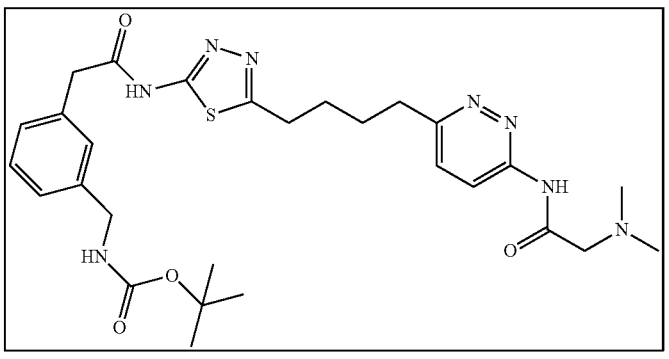 [SMILES: CN(C)CC(=O)Nc1ccc(CCCCc2nnc(NC(=O)Cc3cccc(CNC(=O)OC(C)(C)C)c3)s2)nn1] | 0.018 | | 0.046 |
| 479 | 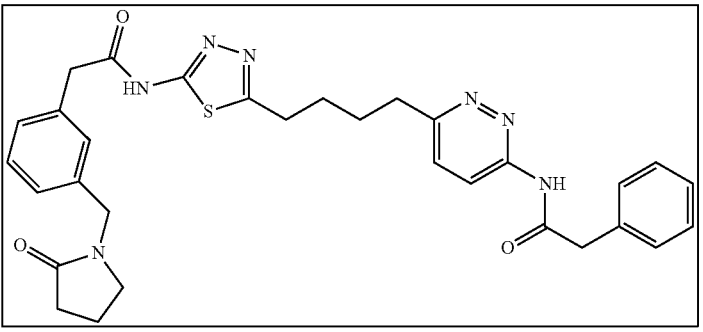 [SMILES: O=C(Cc1ccccc1)Nc1ccc(CCCCc2nnc(NC(=O)Cc3cccc(CN4CCCC4=O)c3)s2)nn1] | 0.005 | | 0.030 |
| 480 | 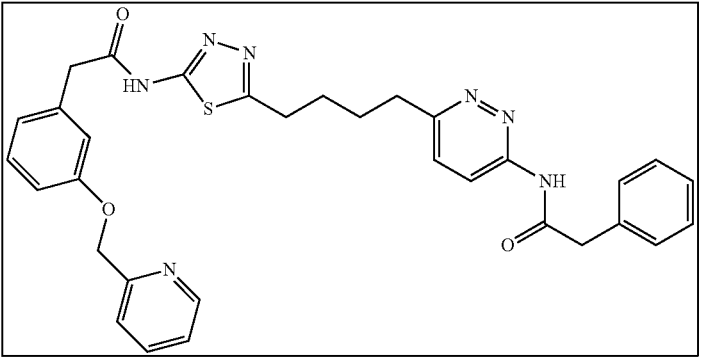 [SMILES: O=C(Cc1ccccc1)Nc1ccc(CCCCc2nnc(NC(=O)Cc3cccc(OCc4ccccn4)c3)s2)nn1] | >20 | | 6.3 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 481 | 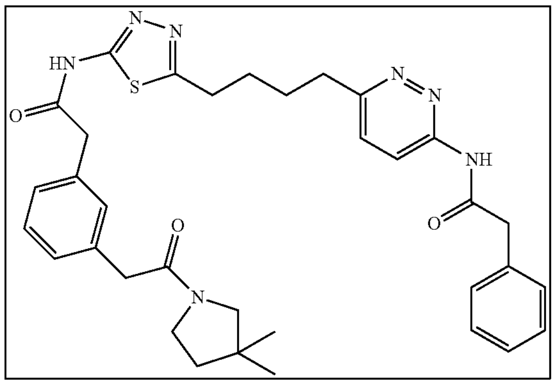 [SMILES: CC1(C)CCN(C(=O)Cc2cccc(CC(=O)Nc3nnc(CCCCc4ccc(NC(=O)Cc5ccccc5)nn4)s3)c2)C1] | 0.004 | | 0.012 |
| 482 | 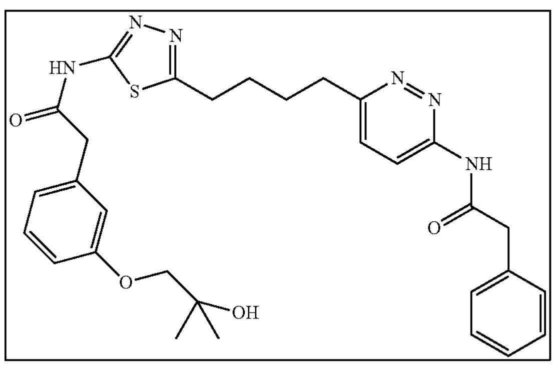 [SMILES: CC(C)(O)COc1cccc(CC(=O)Nc2nnc(CCCCc3ccc(NC(=O)Cc4ccccc4)nn3)s2)c1] | 0.007 | | 0.038 |
| 483 | 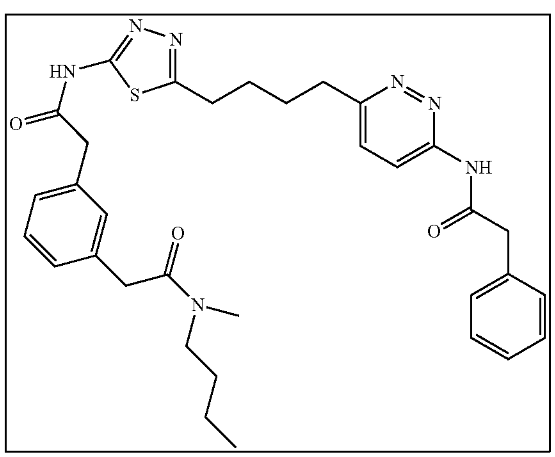 [SMILES: CCCCN(C)C(=O)Cc1cccc(CC(=O)Nc2nnc(CCCCc3ccc(NC(=O)Cc4ccccc4)nn3)s2)c1] | 0.004 | | 0.009 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 484 | 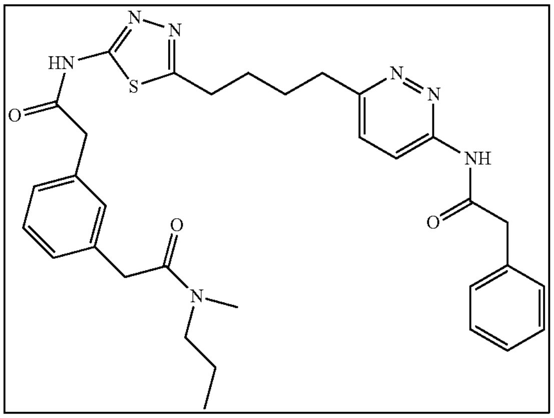 [SMILES: CCCN(C)C(=O)Cc1cccc(CC(=O)Nc2nnc(CCCCc3ccc(NC(=O)Cc4ccccc4)nn3)s2)c1] | 0.003 | | 0.011 |
| 485 | 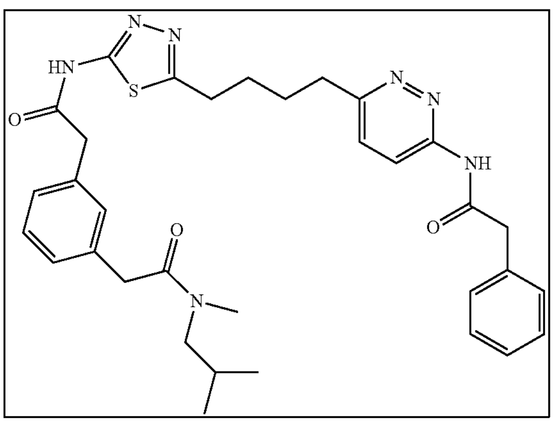 [SMILES: CC(C)CN(C)C(=O)Cc1cccc(CC(=O)Nc2nnc(CCCCc3ccc(NC(=O)Cc4ccccc4)nn3)s2)c1] | 0.004 | | 0.012 |
| 486 | 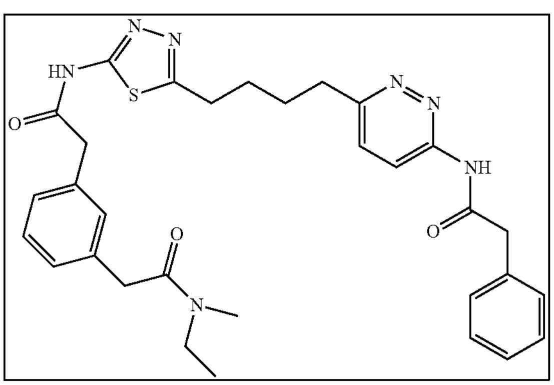 [SMILES: CCN(C)C(=O)Cc1cccc(CC(=O)Nc2nnc(CCCCc3ccc(NC(=O)Cc4ccccc4)nn3)s2)c1] | 0.004 | | 0.024 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 487 | 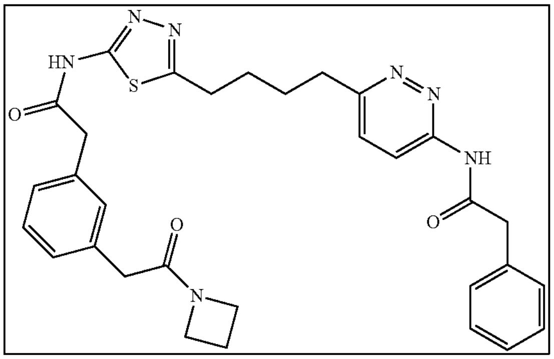 [SMILES: O=C(Cc1ccccc1)Nc1ccc(CCCCc2nnc(NC(=O)Cc3cccc(CC(=O)N4CCC4)c3)s2)nn1] | | 0.005 | 0.042 |
| 488 | 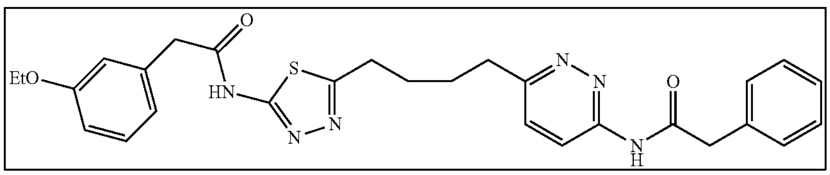 [SMILES: CCOc1cccc(CC(=O)Nc2nnc(CCCCc3ccc(NC(=O)Cc4ccccc4)nn3)s2)c1] | | 0.32 | 1.9 |
| 489 | 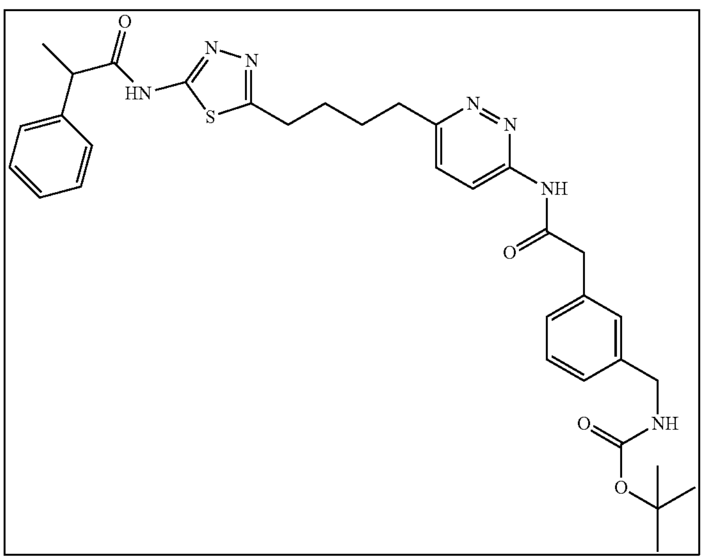 [SMILES: CC(C(=O)Nc1nnc(CCCCc2ccc(NC(=O)Cc3cccc(CNC(=O)OC(C)(C)C)c3)nn2)s1)c1ccccc1] | | 0.008 | 0.023 |
| 490 | 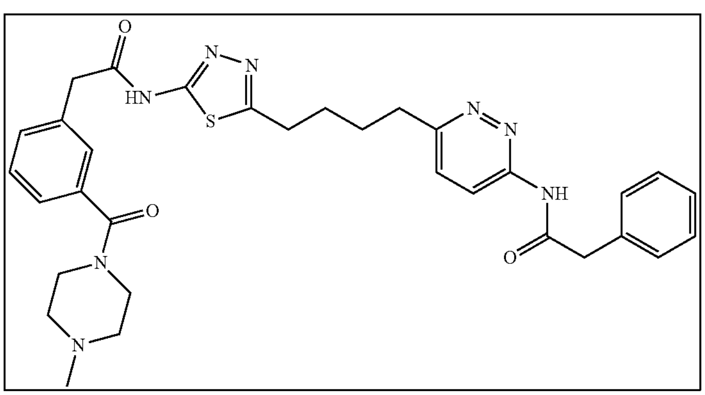 [SMILES: CN1CCN(C(=O)c2cccc(CC(=O)Nc3nnc(CCCCc4ccc(NC(=O)Cc5ccccc5)nn4)s3)c2)CC1] | | 0.011 | 0.25 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 491 | 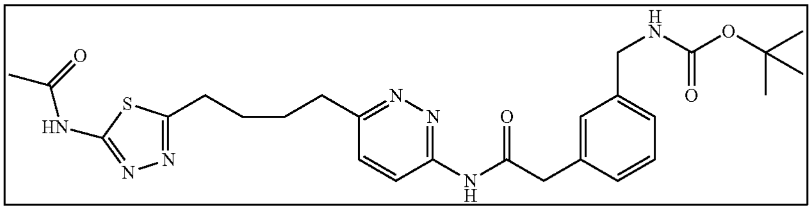 [SMILES: CC(=O)Nc1nnc(CCCCc2ccc(NC(=O)Cc3cccc(CNC(=O)OC(C)(C)C)c3)nn2)s1] | 0.008 | | 0.023 |
| 492 | 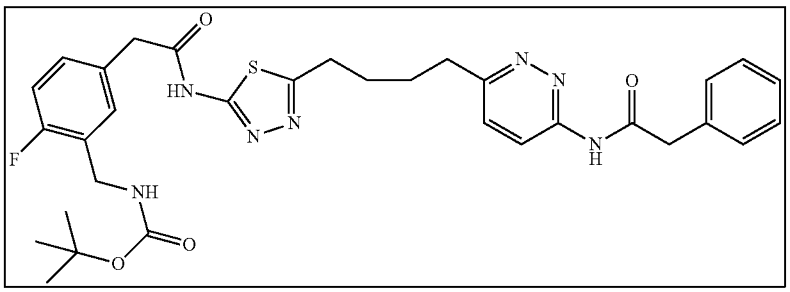 [SMILES: CC(C)(C)OC(=O)NCc1cc(CC(=O)Nc2nnc(CCCCc3ccc(NC(=O)Cc4ccccc4)nn3)s2)ccc1F] | 0.006 | | 0.014 |
| 493 | 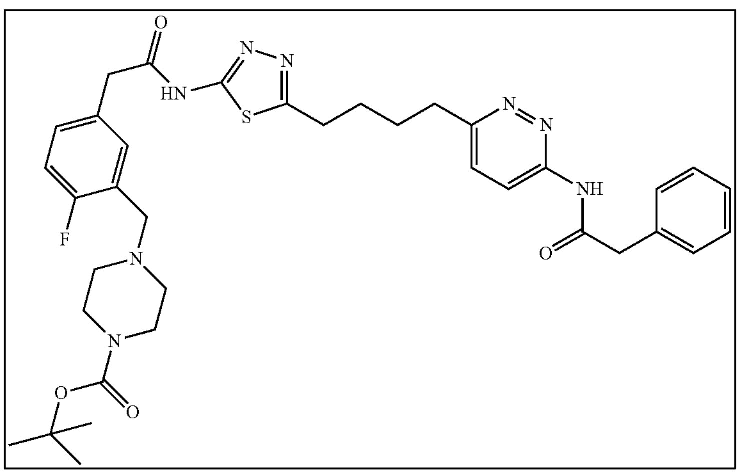 [SMILES: CC(C)(C)OC(=O)N1CCN(Cc2cc(CC(=O)Nc3nnc(CCCCc4ccc(NC(=O)Cc5ccccc5)nn4)s3)ccc2F)CC1] | 0.019 | | 0.057 |
| 494 | 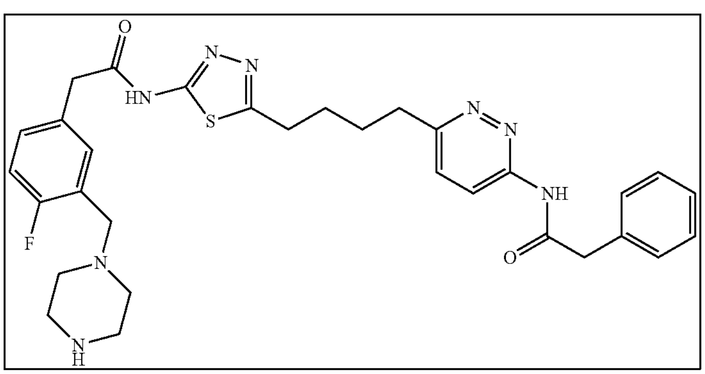 [SMILES: O=C(Cc1ccccc1)Nc1ccc(CCCCc2nnc(NC(=O)Cc3ccc(F)c(CN4CCNCC4)c3)s2)nn1] | 0.019 | | 0.58 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 495 | 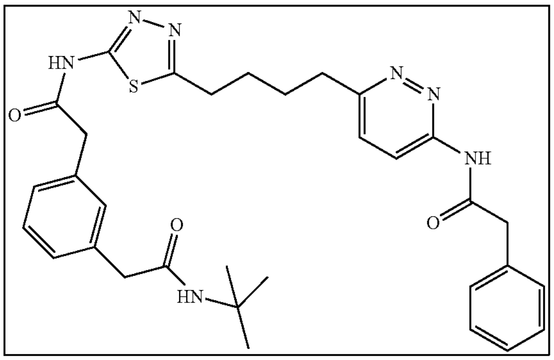 [SMILES: CC(C)(C)NC(=O)Cc1cccc(CC(=O)Nc2nnc(CCCCc3ccc(NC(=O)Cc4ccccc4)nn3)s2)c1] | | 0.005 | 0.014 |
| 496 | 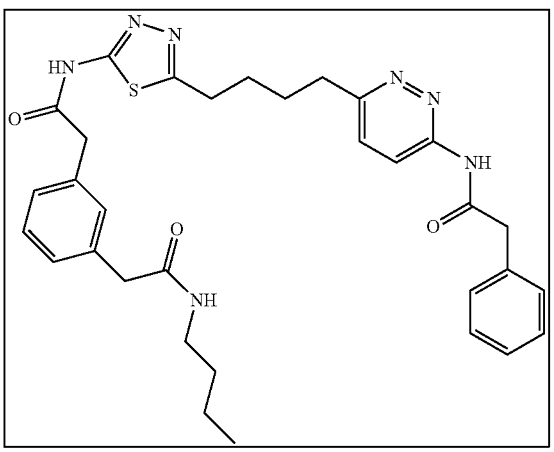 [SMILES: CCCCNC(=O)Cc1cccc(CC(=O)Nc2nnc(CCCCc3ccc(NC(=O)Cc4ccccc4)nn3)s2)c1] | | 0.003 | 0.017 |
| 497 | 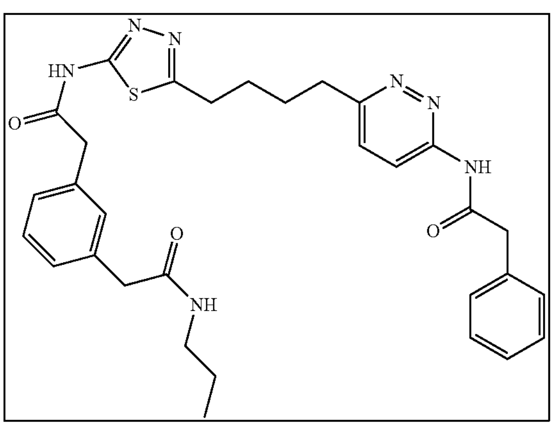 [SMILES: CCCNC(=O)Cc1cccc(CC(=O)Nc2nnc(CCCCc3ccc(NC(=O)Cc4ccccc4)nn3)s2)c1] | | 0.004 | 0.032 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 498 | 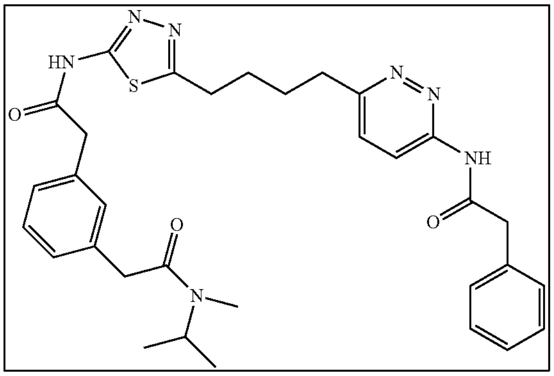 [SMILES: CC(C)N(C)C(=O)Cc1cccc(CC(=O)Nc2nnc(CCCCc3ccc(NC(=O)Cc4ccccc4)nn3)s2)c1] | 0.003 | | 0.017 |
| 499 | 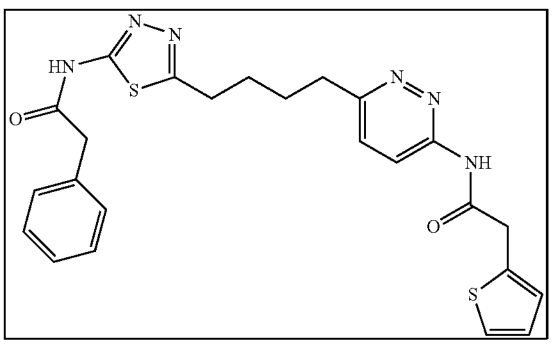 [SMILES: O=C(Cc1cccs1)Nc1ccc(CCCCc2nnc(NC(=O)Cc3ccccc3)s2)nn1] | 0.010 | | 0.19 |
| 500 | 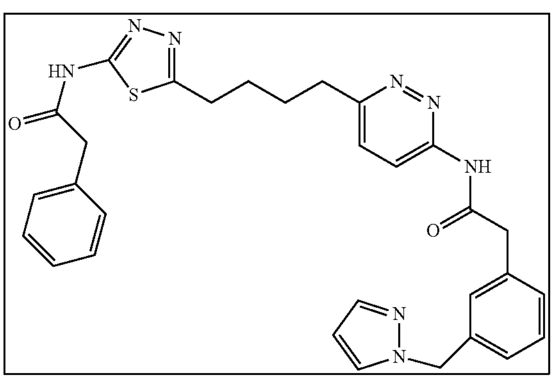 [SMILES: O=C(Cc1cccc(Cn2cccn2)c1)Nc1ccc(CCCCc2nnc(NC(=O)Cc3ccccc3)s2)nn1] | 0.004 | | 0.029 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 501 | 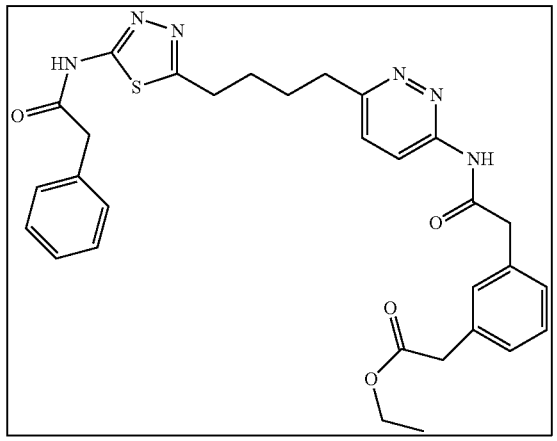 [SMILES: CCOC(=O)Cc1cccc(CC(=O)Nc2ccc(CCCCc3nnc(NC(=O)Cc4ccccc4)s3)nn2)c1] | 0.004 | | 0.069 |
| 502 | 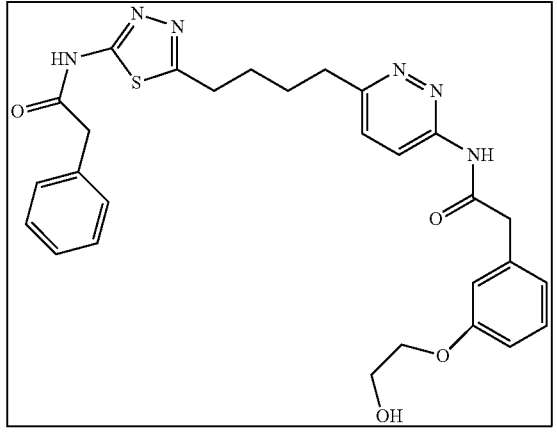 [SMILES: O=C(Cc1cccc(OCCO)c1)Nc1ccc(CCCCc2nnc(NC(=O)Cc3ccccc3)s2)nn1] | 0.007 | | 0.075 |
| 503 | 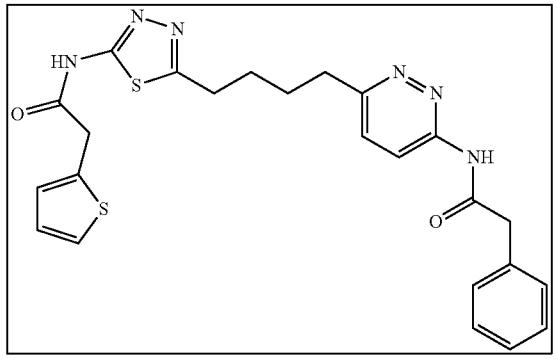 [SMILES: O=C(Cc1ccccc1)Nc1ccc(CCCCc2nnc(NC(=O)Cc3cccs3)s2)nn1] | 0.008 | | 0.15 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 504 | 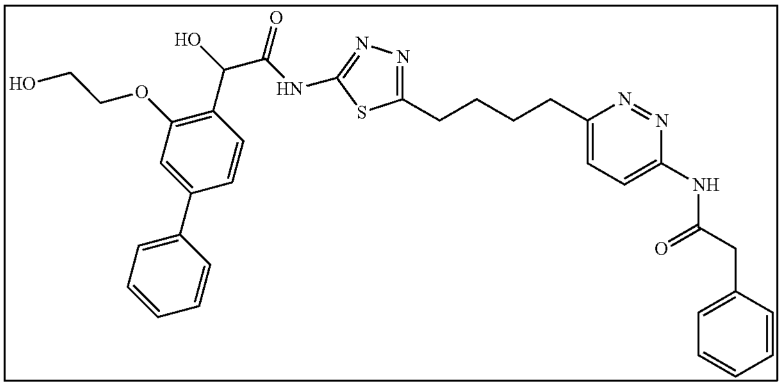 [SMILES: O=C(Cc1ccccc1)Nc1ccc(CCCCc2nnc(NC(=O)C(O)c3ccc(-c4ccccc4)cc3OCCO)s2)nn1] | | 0.007 | 0.12 |
| 505 | 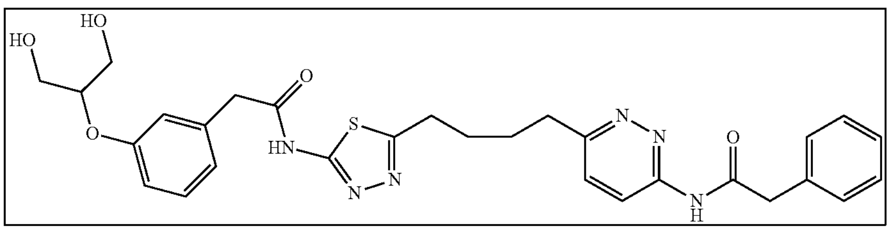 [SMILES: O=C(Cc1ccccc1)Nc1ccc(CCCCc2nnc(NC(=O)Cc3cccc(OC(CO)CO)c3)s2)nn1] | | 0.008 | 0.24 |
| 506 | 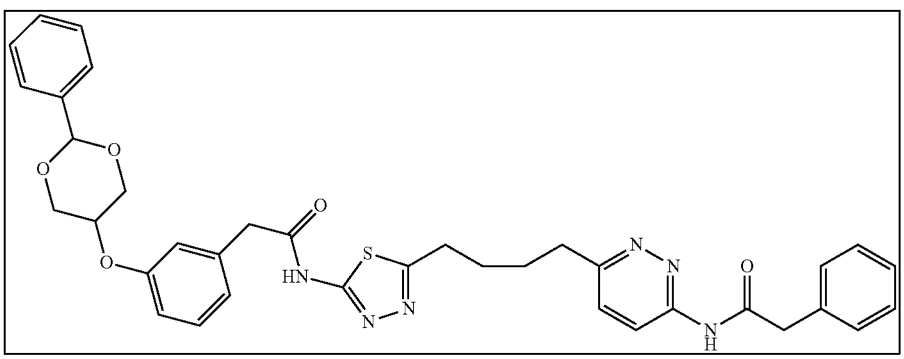 [SMILES: O=C(Cc1ccccc1)Nc1ccc(CCCCc2nnc(NC(=O)Cc3cccc(OC4COC(c5ccccc5)OC4)c3)s2)nn1] | | 0.010 | 0.17 |
| 507 | 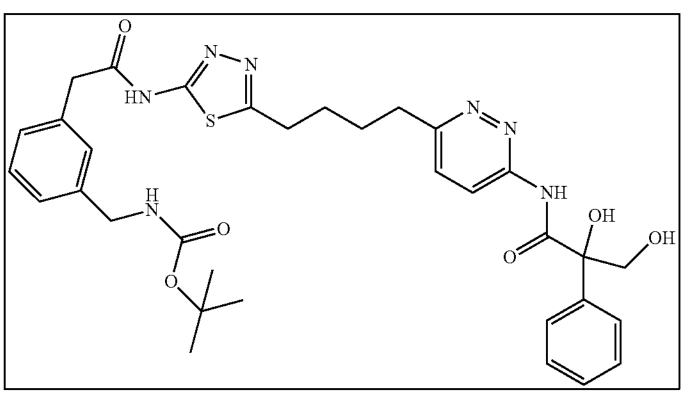 [SMILES: CC(C)(C)OC(=O)NCc1cccc(CC(=O)Nc2nnc(CCCCc3ccc(NC(=O)C(O)(CO)c4ccccc4)nn3)s2)c1] | | 0.013 | 0.041 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 508 | 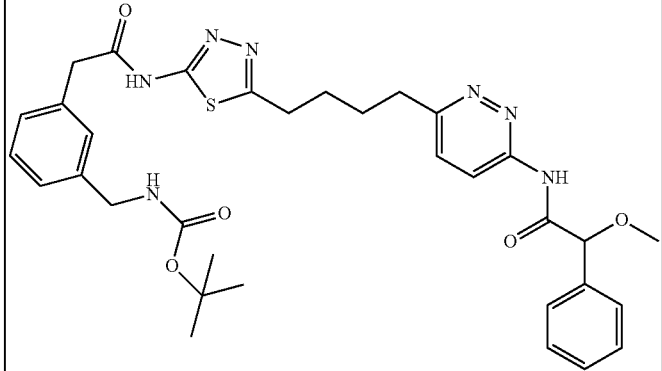 | | 0.011 | 0.020 |
| 509 | 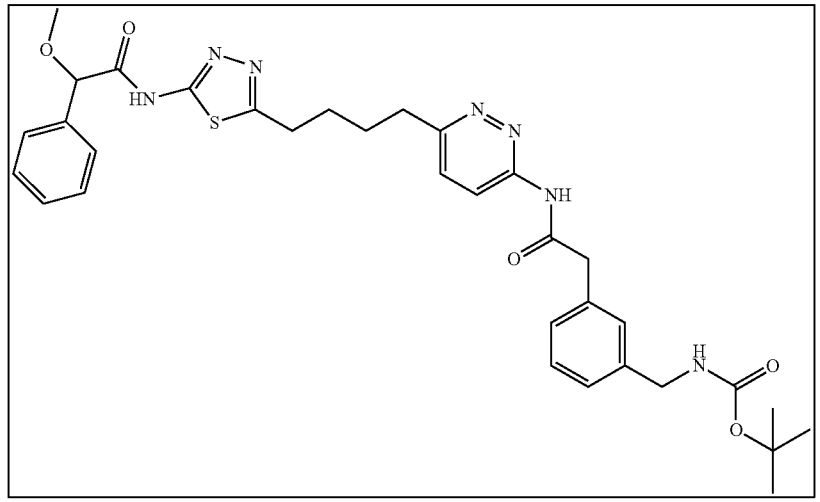 [SMILES: COC(C(=O)Nc1nnc(CCCCc2ccc(NC(=O)Cc3cccc(CNC(=O)OC(C)(C)C)c3)nn2)s1)c1ccccc1] | | 0.010 | 0.009 |
| 510 | 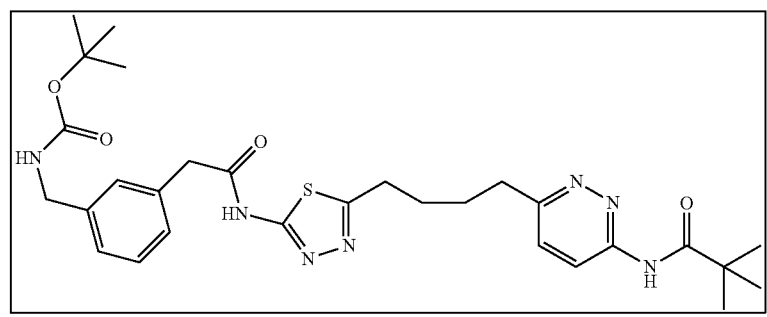 [SMILES: CC(C)(C)OC(=O)NCc1cccc(CC(=O)Nc2nnc(CCCCc3ccc(NC(=O)C(C)(C)C)nn3)s2)c1] | | 0.022 | 0.094 |
| 511 | 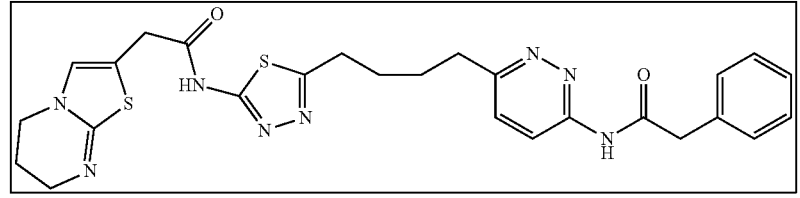 [SMILES: O=C(Cc1ccccc1)Nc1ccc(CCCCc2nnc(NC(=O)CC3=CN4CCCN=C4S3)s2)nn1] | | 0.58 | 1.1 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 512 | 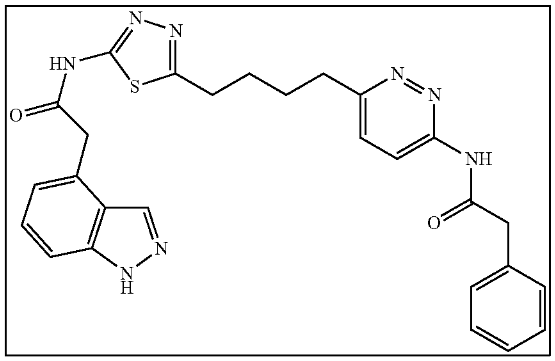 [SMILES: O=C(Cc1ccccc1)Nc1ccc(CCCCc2nnc(NC(=O)Cc3cccc4[nH]ncc34)s2)nn1] | 0.005 | | 0.046 |
| 513 | 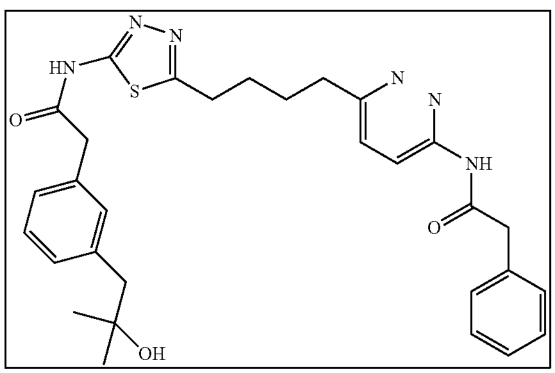 [SMILES: CC(C)(O)Cc1cccc(CC(=O)Nc2nnc(CCCC/C(N)=C/C=C(\N)NC(=O)Cc3ccccc3)s2)c1] | 0.007 | | 0.022 |
| 514 | 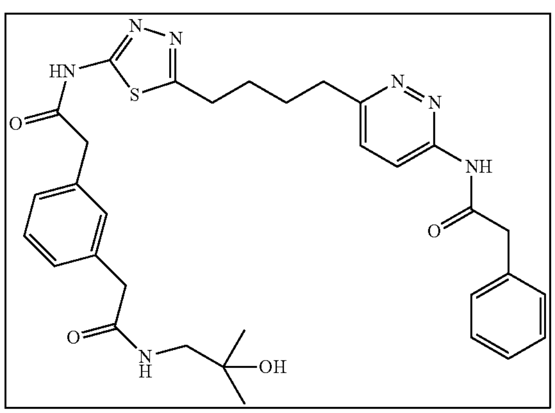 [SMILES: CC(C)(O)CNC(=O)Cc1cccc(CC(=O)Nc2nnc(CCCCc3ccc(NC(=O)Cc4ccccc4)nn3)s2)c1] | 0.009 | | 0.063 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
| --- | --- | --- | --- | --- |
| 515 | 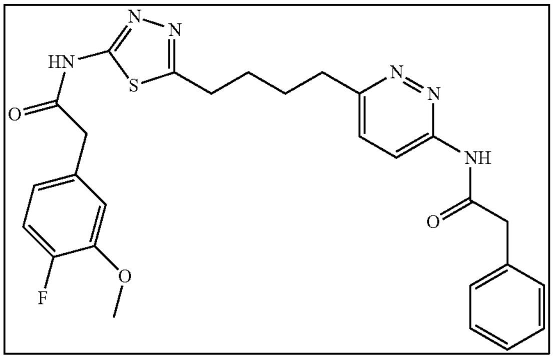 [SMILES: COc1cc(CC(=O)Nc2nnc(CCCCc3ccc(NC(=O)Cc4ccccc4)nn3)s2)ccc1F] | 0.007 | | 0.059 |
| 516 | 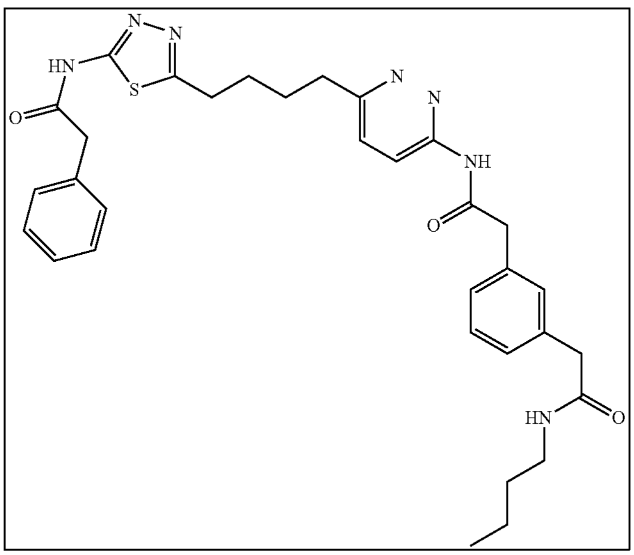 [SMILES: CCCCNC(=O)Cc1cccc(CC(=O)N/C(N)=C/C=C(\N)CCCCc2nnc(NC(=O)Cc3ccccc3)s2)c1] | 0.003 | | 0.028 |
| 517 | 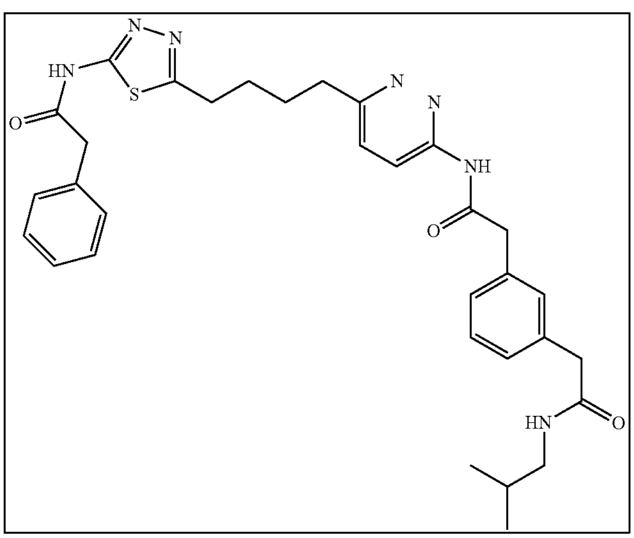 [SMILES: CC(C)CNC(=O)Cc1cccc(CC(=O)N/C(N)=C/C=C(\N)CCCCc2nnc(NC(=O)Cc3ccccc3)s2)c1] | 0.003 | | 0.046 |

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 518 | 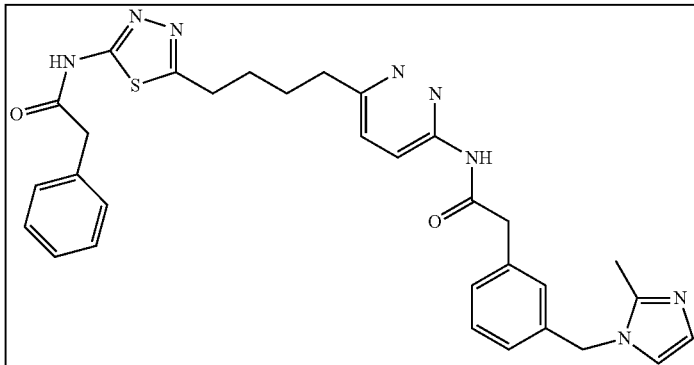 | | 0.004 | 0.063 |
| 519 | 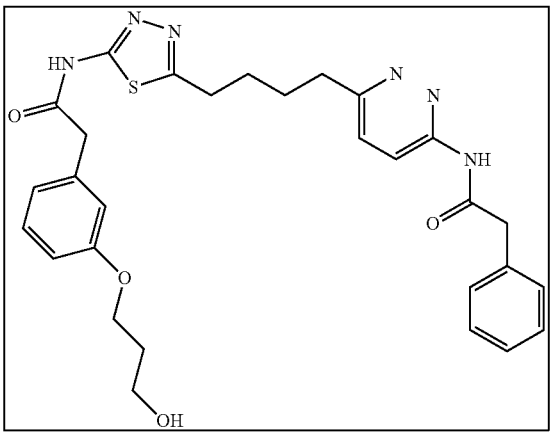 [SMILES: N/C(=C\C=C(/N)NC(=O)Cc1ccccc1)CCCCc1nnc(NC(=O)Cc2cccc(OCCCO)c2)s1] | | 0.009 | 0.059 |
| 520 | 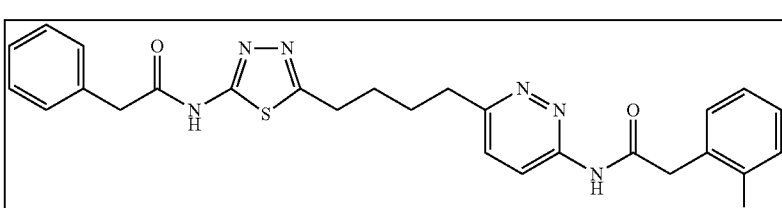 | | 0.007 | 0.056 |
| 521 | 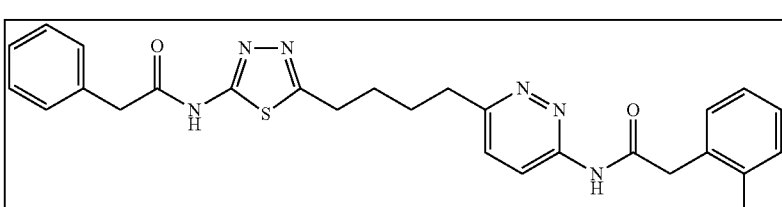 | | 0.006 | 0.052 |
| 522 | 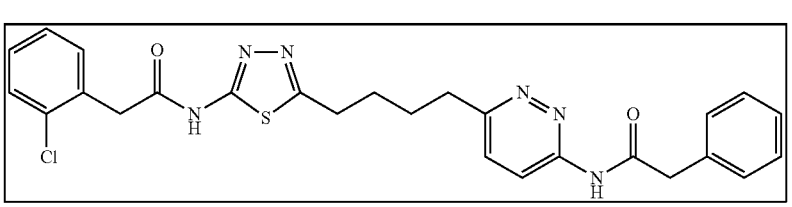 | | 0.023 | 0.060 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 523 | 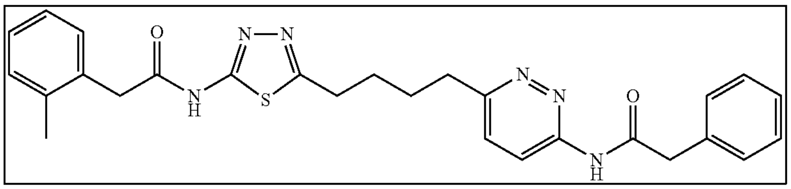 | | 0.021 | 0.055 |
| 524 | 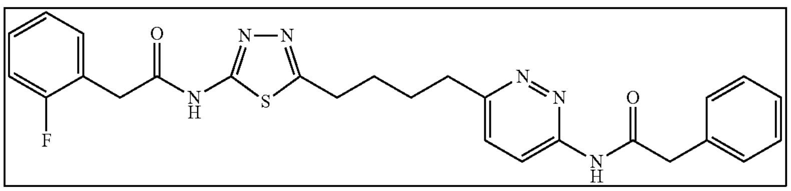 [SMILES: Cc1ccccc1CC(=O)Nc1nnc(CCCCc2ccc(NC(=O)Cc3ccccc3)nn2)s1] | | | |
| 525 | 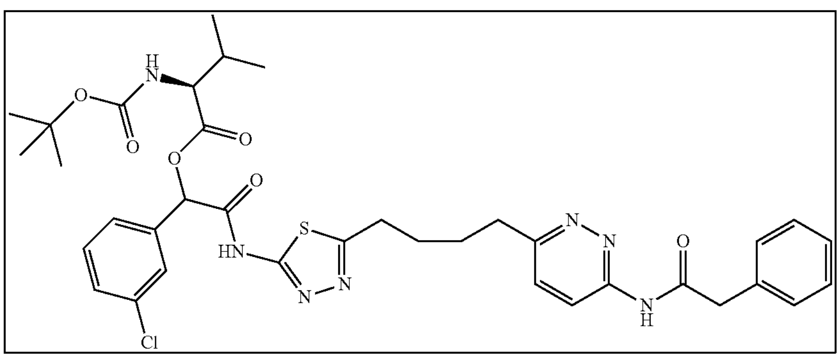 [SMILES: CC(C)[C@H](NC(=O)OC(C)(C)C)C(=O)OC(C(=O)Nc1nnc(CCCCc2ccc(NC(=O)Cc3ccccc3)nn2)s1)c1cccc(Cl)c1] | | | |
| 526 | 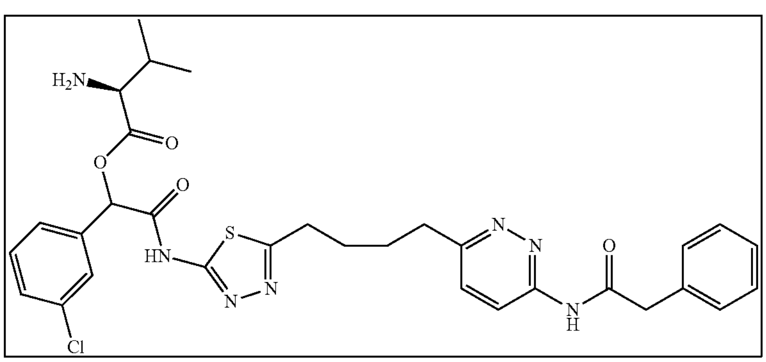 [SMILES: CC(C)[C@H](N)C(=O)OC(C(=O)Nc1nnc(CCCCc2ccc(NC(=O)Cc3ccccc3)nn2)s1)c1cccc(Cl)c1] | | | |

TABLE 3-continued
| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 528 | 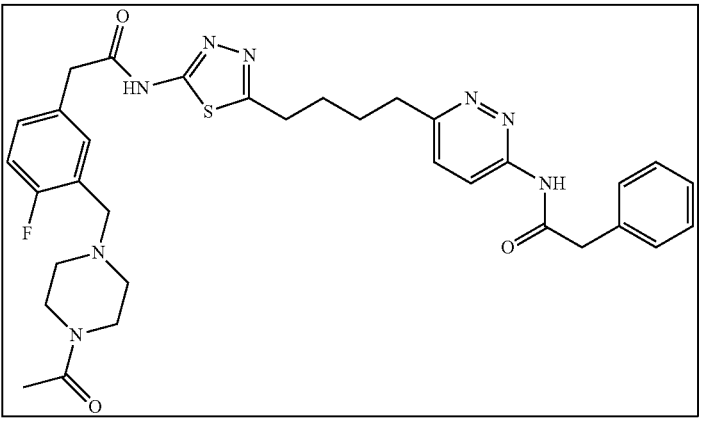 [SMILES: CC(=O)N1CCN(Cc2cc(CC(=O)Nc3nnc(CCCCc4ccc(NC(=O)Cc5ccccc5)nn4)s3)ccc2F)CC1] | | 0.007 | 0.044 |
| 529 | 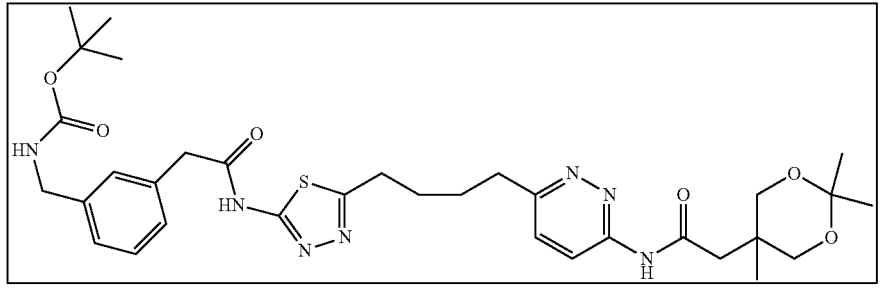 [SMILES: CC1(CC(=O)Nc2ccc(CCCCc3nnc(NC(=O)Cc4cccc(CNC(=O)OC(C)(C)C)c4)s3)nn2)COC(C)(C)OC1] | | 0.032 | 0.16 |
| 530 | 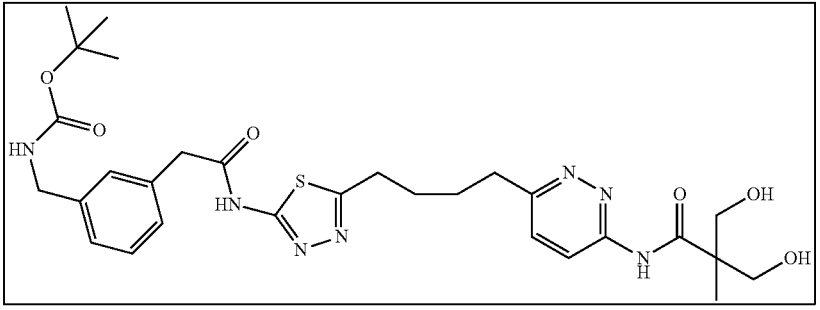 [SMILES: CC(C)(C)OC(=O)NCc1cccc(CC(=O)Nc2nnc(CCCCc3ccc(NC(=O)C(C)(CO)CO)nn3)s2)c1] | | 0.055 | 0.28 |
| 531 | 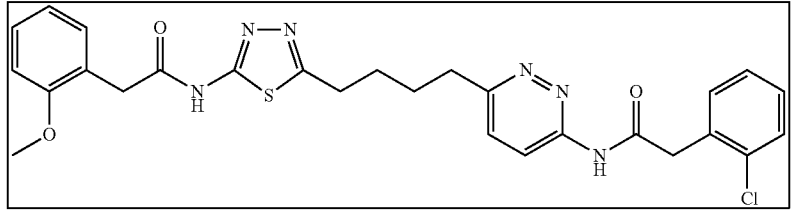 [SMILES: COc1ccccc1CC(=O)Nc1nnc(CCCCc2ccc(NC(=O)Cc3ccccc3F)nn2)s1] | | 0.006 | 0.042 |
| 532 | 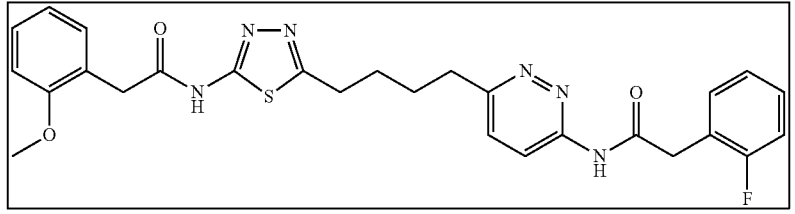 | | 0.006 | 0.059 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 533 | 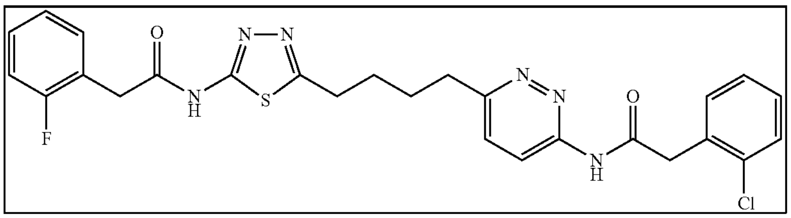 | 0.007 | 0.041 | |
| 534 | 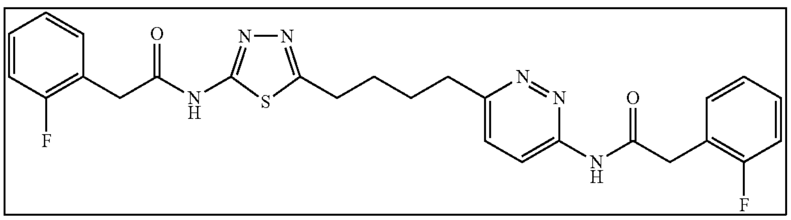 | 0.008 | 0.044 | |
| 535 | 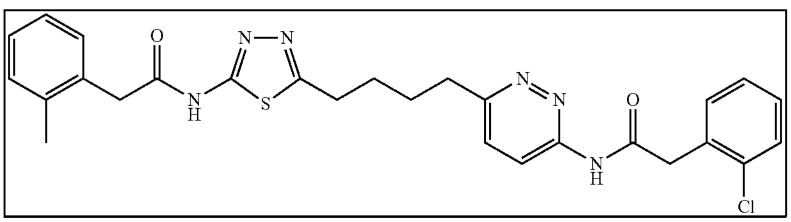 [SMILES: Cc1ccccc1CC(=O)Nc1nnc(CCCCc2ccc(NC(=O)Cc3ccccc3Cl)nn2)s1] | 0.007 | 0.090 | |
| 536 | 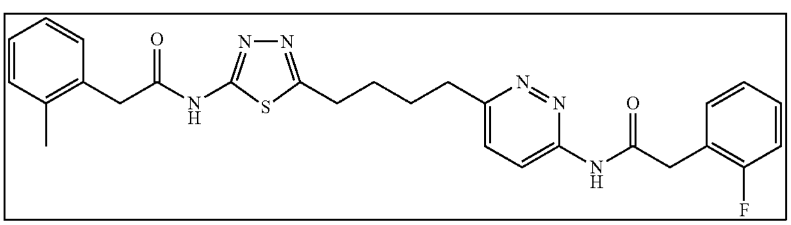 [SMILES: Cc1ccccc1CC(=O)Nc1nnc(CCCCc2ccc(NC(=O)Cc3ccccc3F)nn2)s1] | 0.006 | 0.071 | |
| 537 | 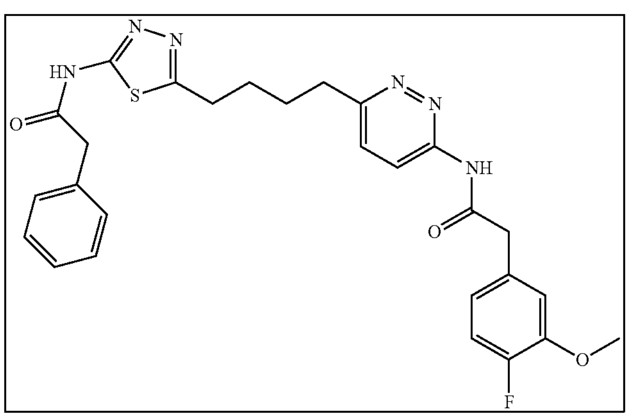 [SMILES: COc1cc(CC(=O)Nc2ccc(CCCCc3nnc(NC(=O)Cc4ccccc4)s3)nn2)ccc1F] | 0.007 | 0.076 | |

TABLE 3-continued
| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 538 | 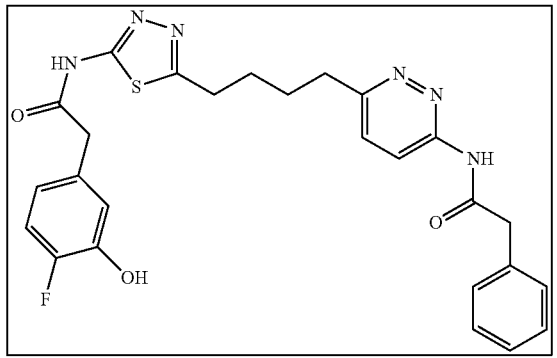 [SMILES: O=C(Cc1ccccc1)Nc1ccc(CCCCc2nnc(NC(=O)Cc3ccc(F)c(O)c3)s2)nn1] | | 0.004 | 0.030 |
| 539 | 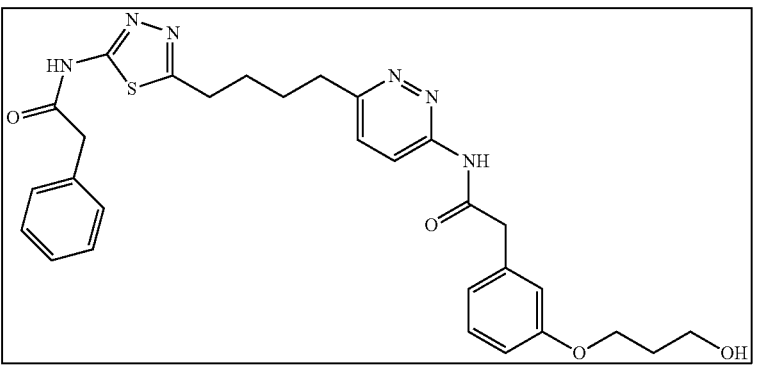 [SMILES: O=C(Cc1cccc(OCCCO)c1)Nc1ccc(CCCCc2nnc(NC(=O)Cc3ccccc3)s2)nn1] | | 0.009 | 0.045 |
| 540 | 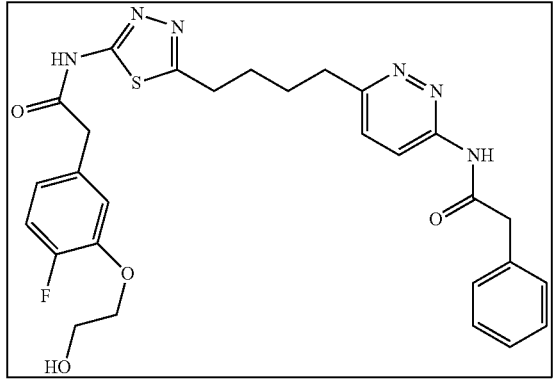 [SMILES: O=C(Cc1ccccc1)Nc1ccc(CCCCc2nnc(NC(=O)Cc3ccc(F)c(OCCO)c3)s2)nn1] | | 0.007 | 0.050 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 541 | 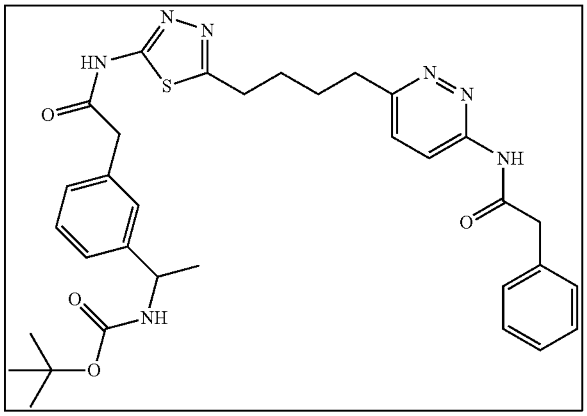 [SMILES: CC(NC(=O)OC(C)(C)C)c1cccc(CC(=O)Nc2nnc(CCCCc3ccc(NC(=O)Cc4ccccc4)nn3)s2)c1] | 0.004 | | 0.006 |
| 542 | 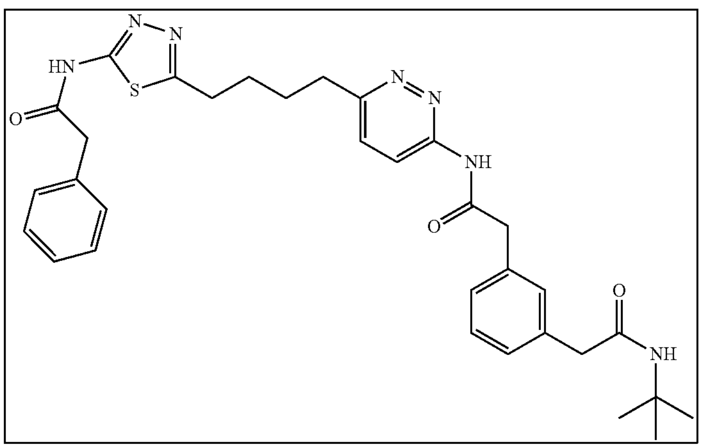 [SMILES: CC(C)(C)NC(=O)Cc1cccc(CC(=O)Nc2ccc(CCCCc3nnc(NC(=O)Cc4ccccc4)s3)nn2)c1] | 0.004 | | 0.043 |
| 543 | 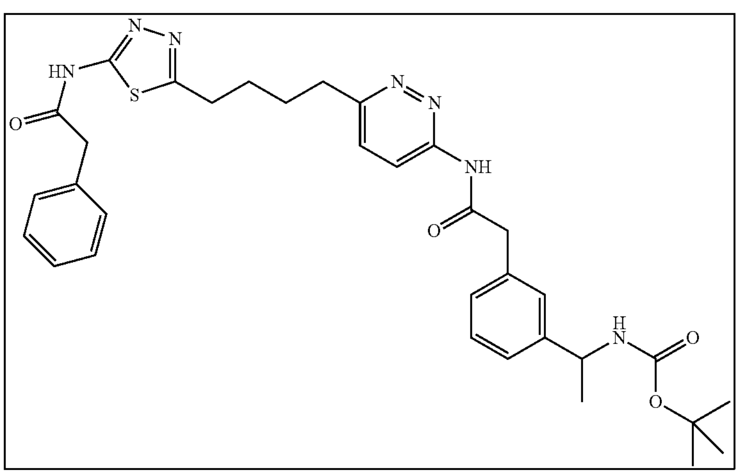 [SMILES: CC(NC(=O)OC(C)(C)C)c1cccc(CC(=O)Nc2ccc(CCCCc3nnc(NC(=O)Cc4ccccc4)s3)nn2)c1] | 0.004 | | 0.005 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 544 | 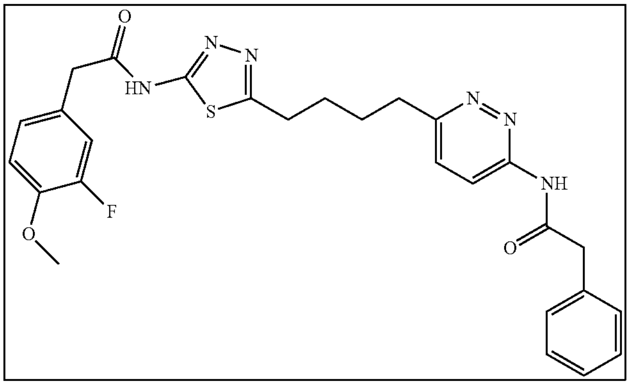 [SMILES: COc1ccc(CC(=O)Nc2nnc(CCCCc3ccc(NC(=O)Cc4ccccc4)nn3)s2)cc1F] | 0.006 | | 0.044 |
| 545 | 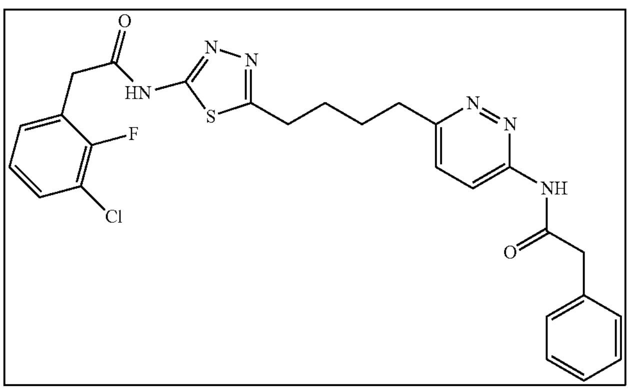 [SMILES: O=C(Cc1ccccc1)Nc1ccc(CCCCc2nnc(NC(=O)Cc3cccc(Cl)c3F)s2)nn1] | 0.006 | | 0.046 |
| 546 | 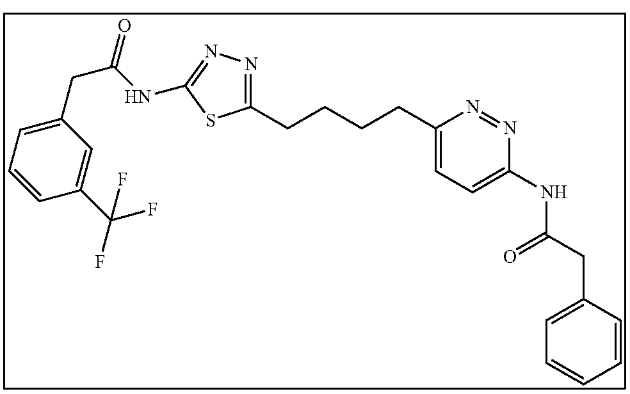 [SMILES: O=C(Cc1ccccc1)Nc1ccc(CCCCc2nnc(NC(=O)Cc3cccc(C(F)(F)F)c3)s2)nn1] | 0.005 | | 0.027 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 547 | 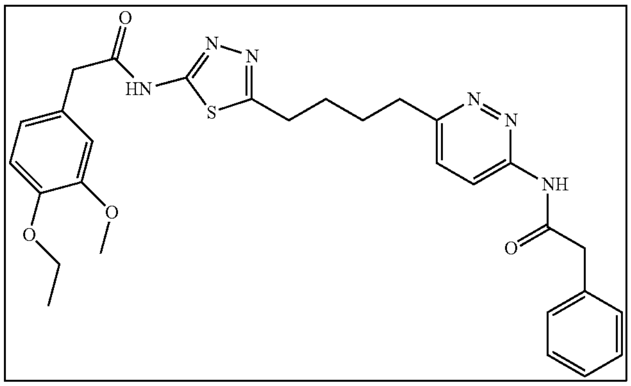 [SMILES: CCOc1ccc(CC(=O)Nc2nnc(CCCCc3ccc(NC(=O)Cc4ccccc4)nn3)s2)cc1OC] | 0.006 | | 0.031 |
| 548 | 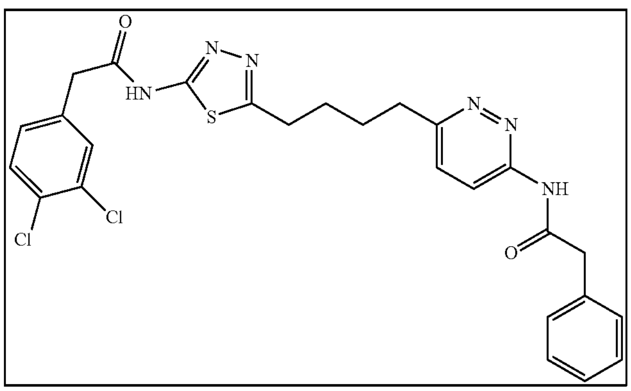 [SMILES: O=C(Cc1ccccc1)Nc1ccc(CCCCc2nnc(NC(=O)Cc3ccc(Cl)c(Cl)c3)s2)nn1] | 0.010 | | 0.085 |
| 549 | 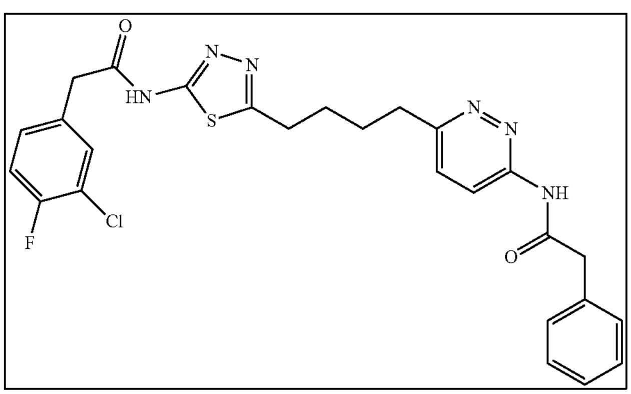 [SMILES: O=C(Cc1ccccc1)Nc1ccc(CCCCc2nnc(NC(=O)Cc3ccc(F)c(Cl)c3)s2)nn1] | 0.006 | | 0.045 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 550 | 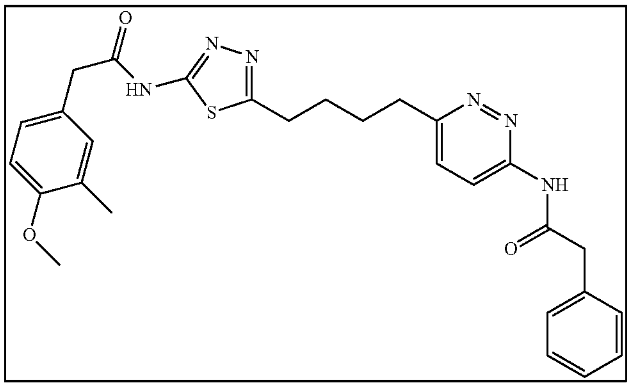 | | 0.005 | 0.036 |
| 551 | 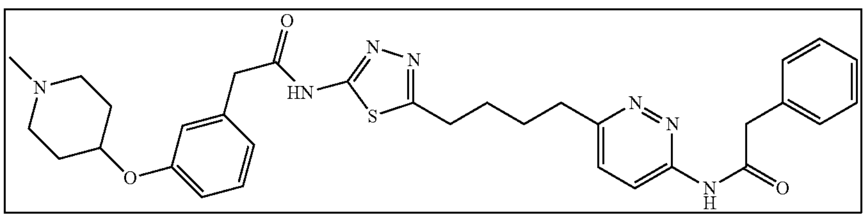 [SMILES: CN1CCC(Oc2cccc(CC(=O)Nc3nnc(CCCCc4ccc(NC(=O)Cc5ccccc5)nn4)s3)c2)CC1] | | 0.010 | 0.127 |
| 552 | 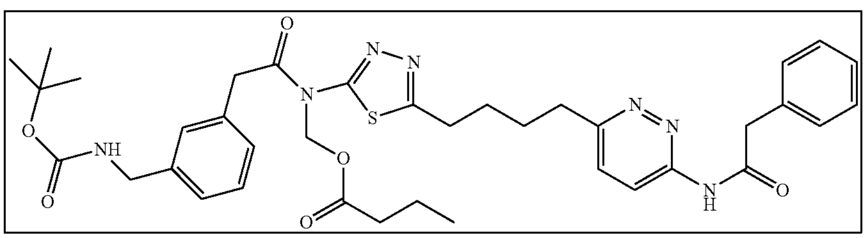 [SMILES: CCCC(=O)OCN(C(=O)Cc1cccc(CNC(=O)OC(C)(C)C)c1)c1nnc(CCCCc2ccc(NC(=O)Cc3ccccc3)nn2)s1] | | >20 | 0.005 |
| 553 | 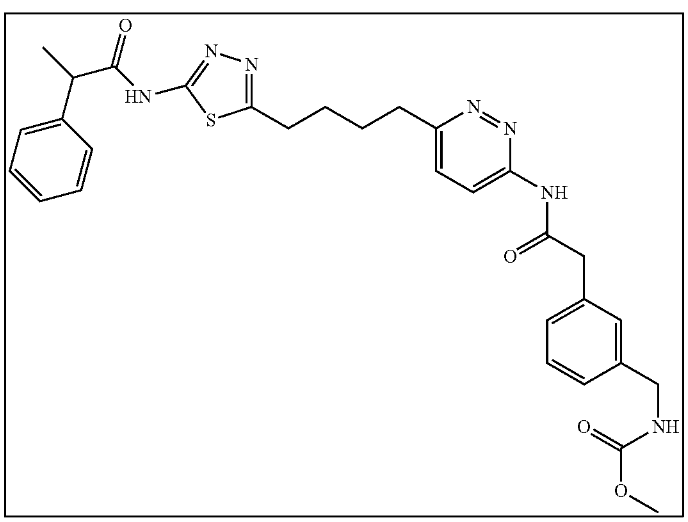 [SMILES: COC(=O)NCc1cccc(CC(=O)Nc2ccc(CCCCc3nnc(NC(=O)C(C)c4ccccc4)s3)nn2)c1] | | 0.005 | 0.019 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 554 | 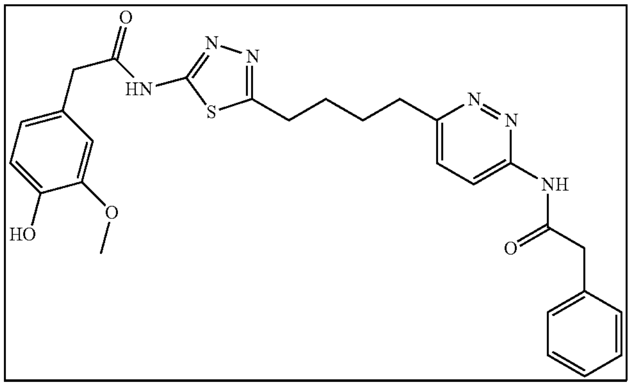 [SMILES: COc1cc(CC(=O)Nc2nnc(CCCCc3ccc(NC(=O)Cc4ccccc4)nn3)s2)ccc1O] | 0.008 | | 0.172 |
| 555 | 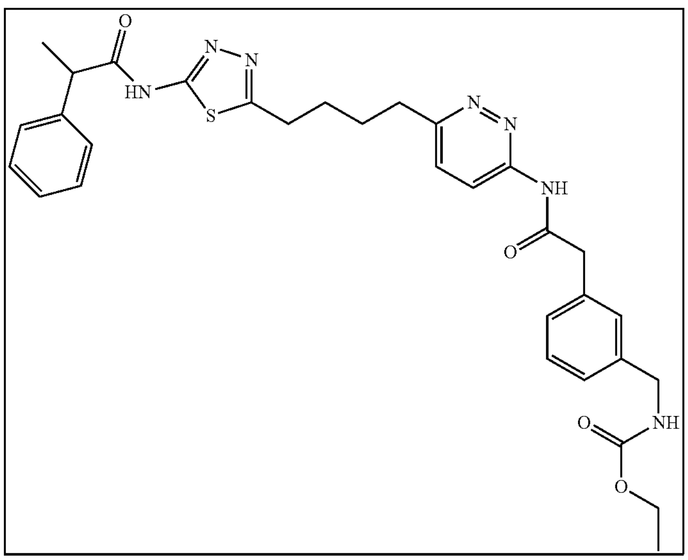 [SMILES: CCOC(=O)NCc1cccc(CC(=O)Nc2ccc(CCCCc3nnc(NC(=O)C(C)c4ccccc4)s3)nn2)c1] | 0.004 | | 0.010 |
| 556 | 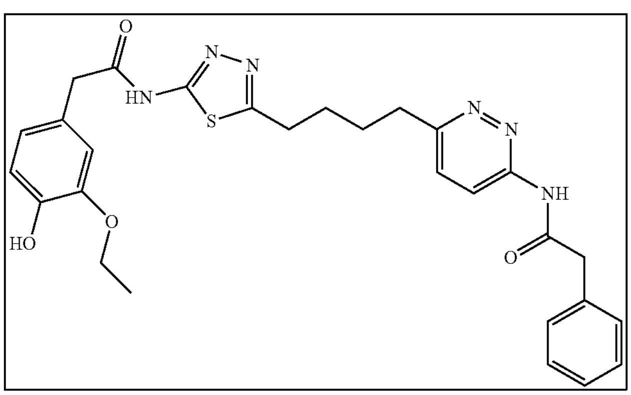 [SMILES: CCOc1cc(CC(=O)Nc2nnc(CCCCc3ccc(NC(=O)Cc4ccccc4)nn3)s2)ccc1O] | 0.005 | | 0.12 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 557 | 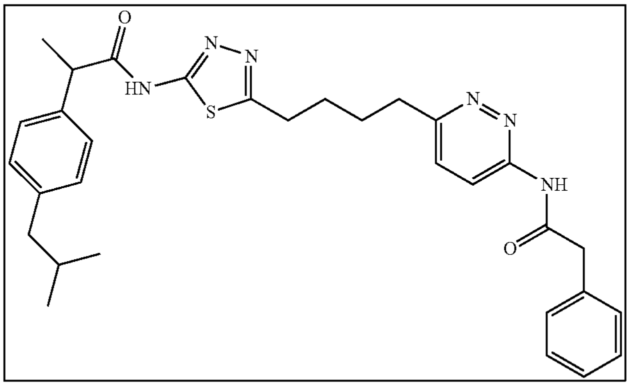 [SMILES: CC(C)Cc1ccc(C(C)C(=O)Nc2nnc(CCCCc3ccc(NC(=O)Cc4ccccc4)nn3)s2)cc1] | | 0.025 | 0.12 |
| 558 | 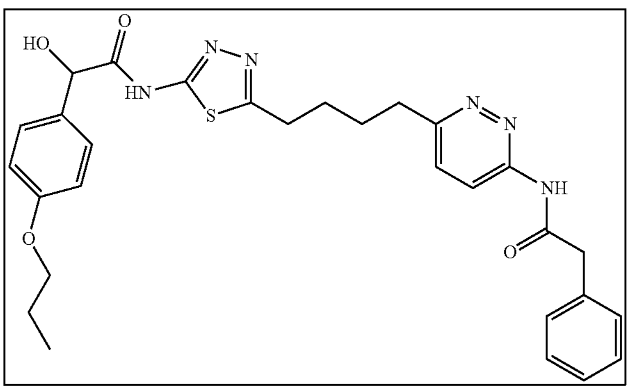 [SMILES: CCCOc1ccc(C(O)C(=O)Nc2nnc(CCCCc3ccc(NC(=O)Cc4ccccc4)nn3)s2)cc1] | | 0.006 | 0.028 |
| 559 | 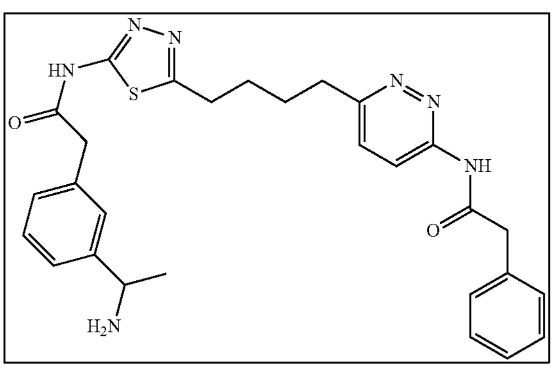 [SMILES: CC(N)c1cccc(CC(=O)Nc2nnc(CCCCc3ccc(NC(=O)Cc4ccccc4)nn3)s2)c1] | | 0.012 | 0.066 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 560 | 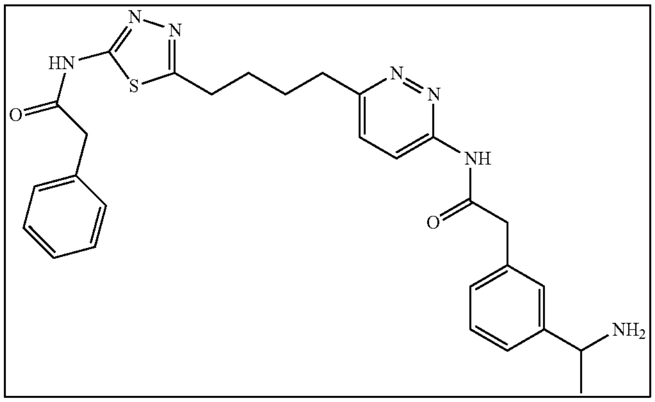 [SMILES: CC(N)c1cccc(CC(=O)Nc2ccc(CCCCc3nnc(NC(=O)Cc4ccccc4)s3)nn2)c1] | 0.010 | | 0.037 |
| 561 | 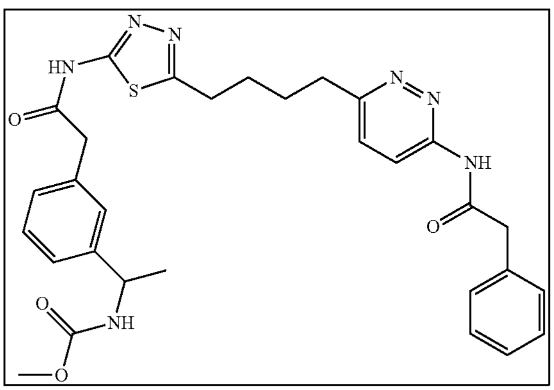 [SMILES: COC(=O)NC(C)c1cccc(CC(=O)Nc2nnc(CCCCc3ccc(NC(=O)Cc4ccccc4)nn3)s2)c1] | 0.004 | | 0.004 |
| 562 | 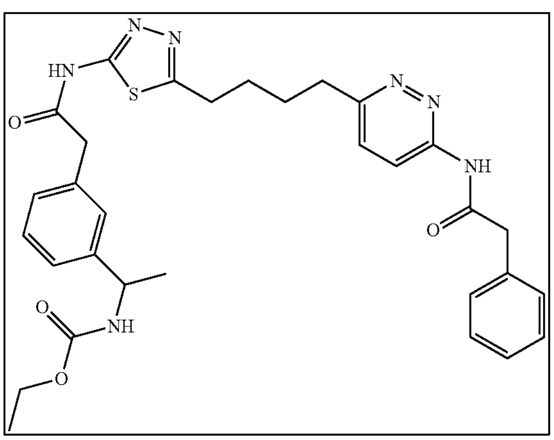 [SMILES: CCOC(=O)NC(C)c1cccc(CC(=O)Nc2nnc(CCCCc3ccc(NC(=O)Cc4ccccc4)nn3)s2)c1] | 0.003 | | 0.002 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 563 | 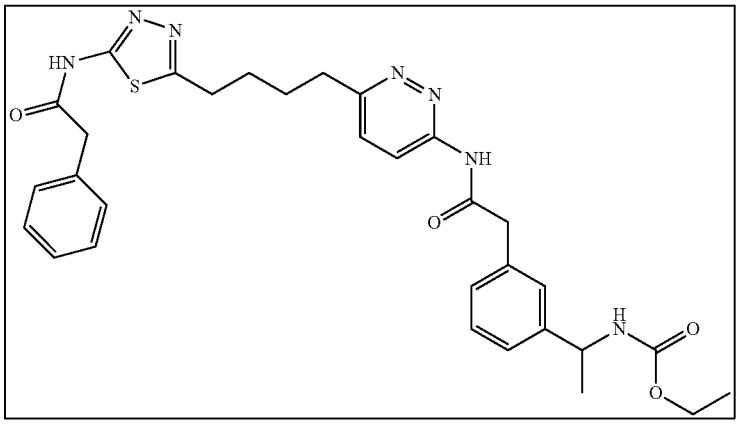 [SMILES: CCOC(=O)NC(C)c1cccc(CC(=O)Nc2ccc(CCCCc3nnc(NC(=O)Cc4ccccc4)s3)nn2)c1] | 0.003 | | 0.003 |
| 564 | 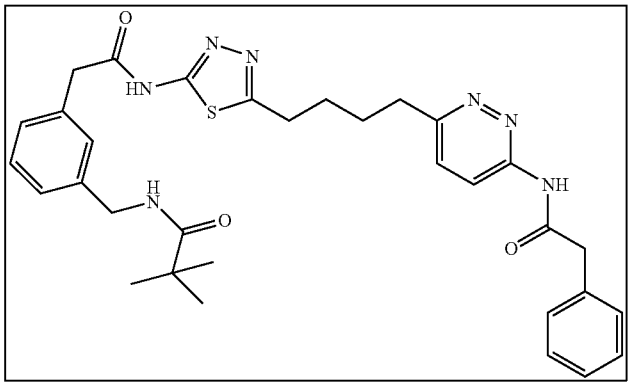 [SMILES: CC(C)(C)C(=O)NCc1cccc(CC(=O)Nc2nnc(CCCCc3ccc(NC(=O)Cc4ccccc4)nn3)s2)c1] | 0.004 | | 0.002 |
| 565 | 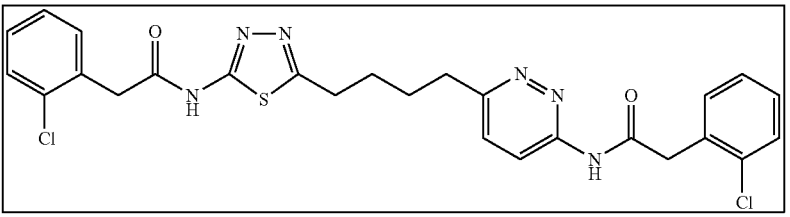 | 0.005 | | 0.013 |
| 566 | 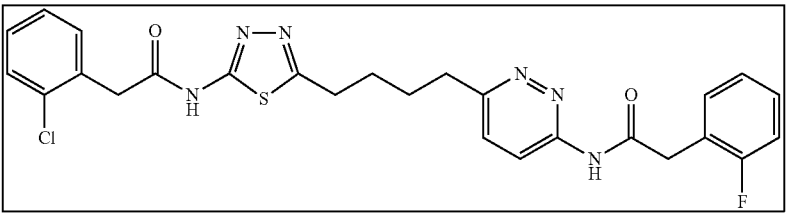 [SMILES: O=C(Cc1ccccc1F)Nc1ccc(CCCCc2nnc(NC(=O)Cc3ccccc3Cl)s2)nn1] | 0.006 | | 0.015 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 567 | 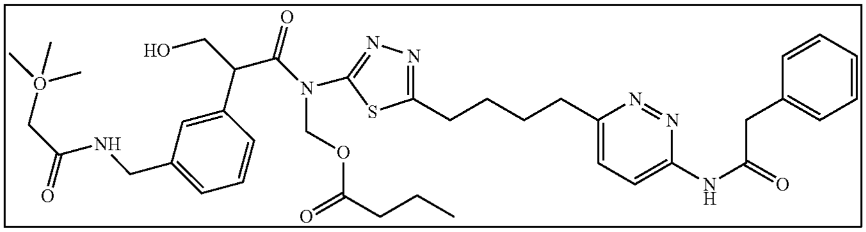 | | 0.43 | 0.021 |
| 568 | 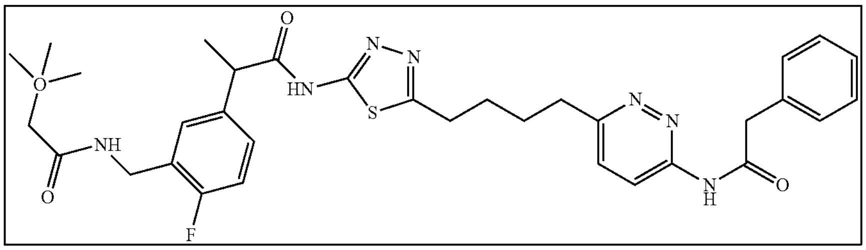 | | 0.009 | 0.028 |
| 569 | 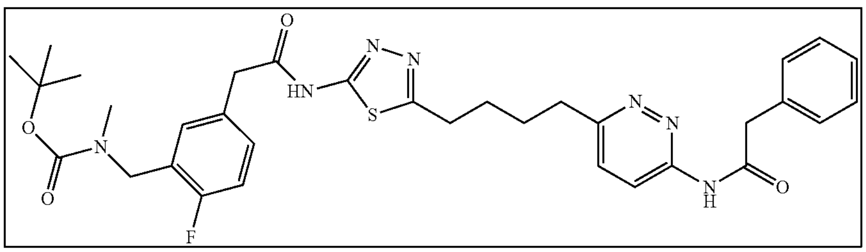 [SMILES: CN(Cc1cc(CC(=O)Nc2nnc(CCCCc3ccc(NC(=O)Cc4ccccc4)nn3)s2)ccc1F)C(=O)OC(C)(C)C] | | 0.006 | 0.011 |
| 570 | 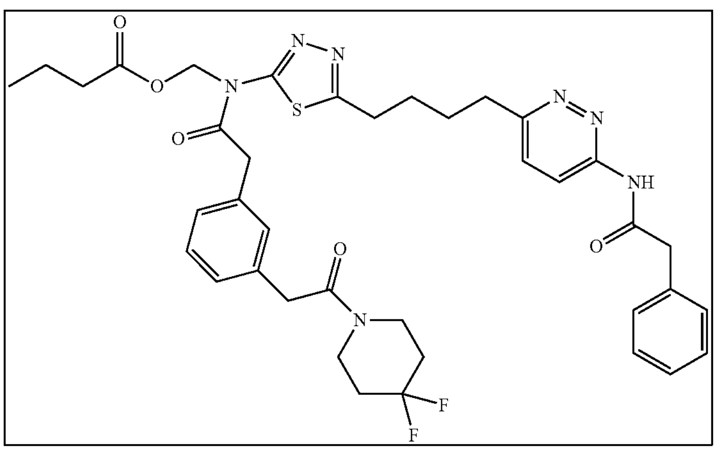 [SMILES: CCCC(=O)OCN(C(=O)Cc1cccc(CC(=O)N2CCC(F)(F)CC2)c1)c1nnc(CCCCc2ccc(NC(=O)Cc3ccccc3)nn2)s1] | | 0.43 | 0.009 |
| 571 | 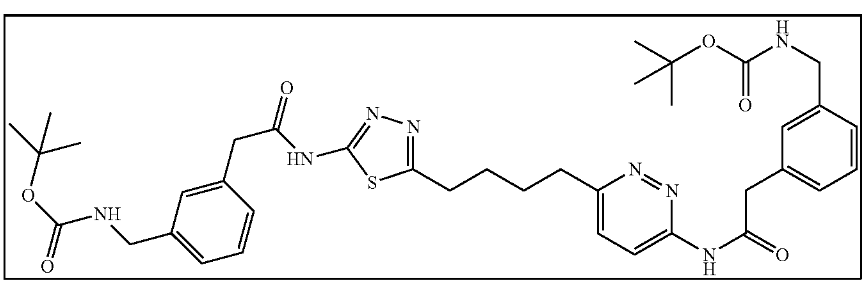 [SMILES: CC(C)(C)OC(=O)NCc1cccc(CC(=O)Nc2ccc(CCCCc3nnc(NC(=O)Cc4cccc(CNC(=O)OC(C)(C)C)c4)s3)nn2)c1] | | 0.011 | 0.010 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 572 | 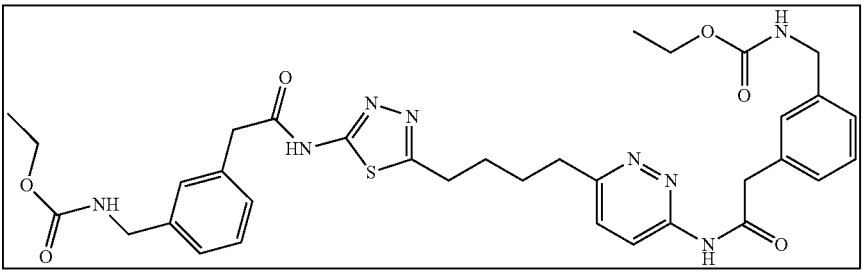 [SMILES: CCOC(=O)NCc1cccc(CC(=O)Nc2ccc(CCCCc3nnc(NC(=O)Cc4cccc(CNC(=O)OCC)c4)s3)nn2)c1] | 0.003 | | 0.004 |
| 573 | 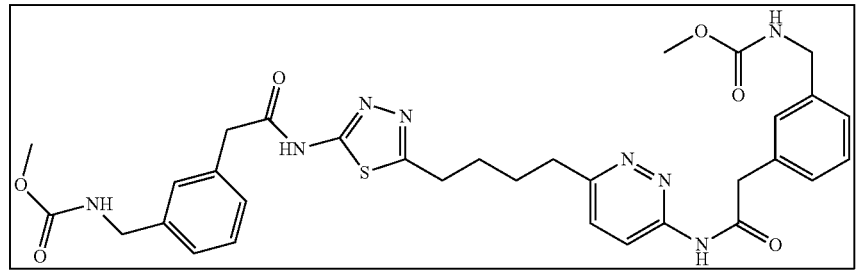 [SMILES: COC(=O)NCc1cccc(CC(=O)Nc2ccc(CCCCc3nnc(NC(=O)Cc4cccc(CNC(=O)OC)c4)s3)nn2)c1] | 0.004 | | 0.015 |
| 574 | 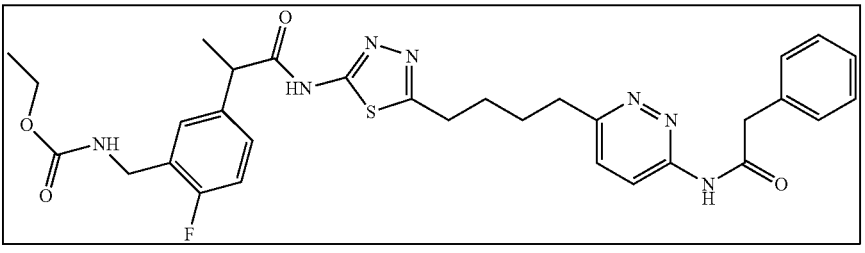 [SMILES: CCOC(=O)NCc1cc(C(C)C(=O)Nc2nnc(CCCCc3ccc(NC(=O)Cc4ccccc4)nn3)s2)ccc1F] | 0.006 | | 0.028 |
| 575 | 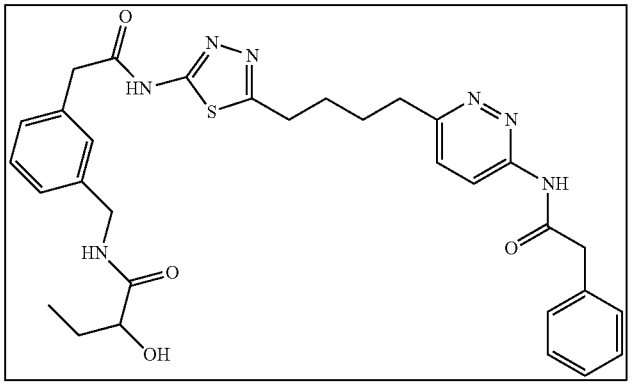 [SMILES: CCC(O)C(=O)NCc1cccc(CC(=O)Nc2nnc(CCCCc3ccc(NC(=O)Cc4ccccc4)nn3)s2)c1] | 0.007 | | 0.040 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 576 | 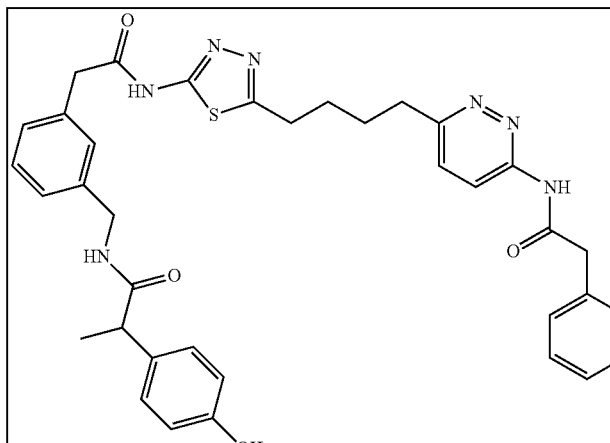 | 0.003 | | 0.013 |
| 577 | 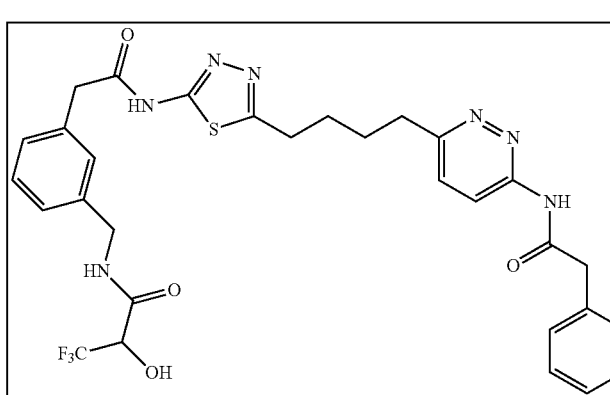 | 0.004 | | 0.034 |
| 578 | 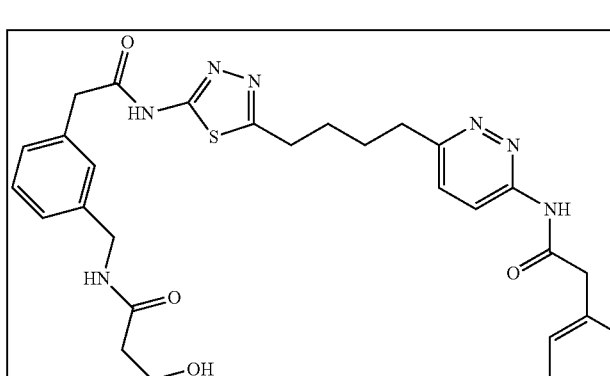 | 0.004 | | 0.022 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 579 | 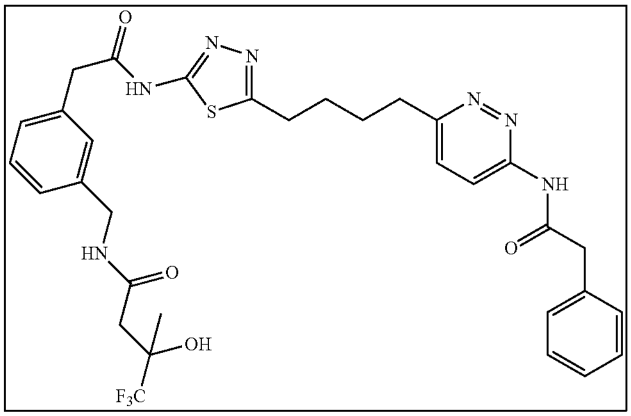 [SMILES: CC(O)(CC(=O)NCc1cccc(CC(=O)Nc2nnc(CCCCc3ccc(NC(=O)Cc4ccccc4)nn3)s2)c1)C(F)(F)F] | 0.004 | | 0.009 |
| 580 | 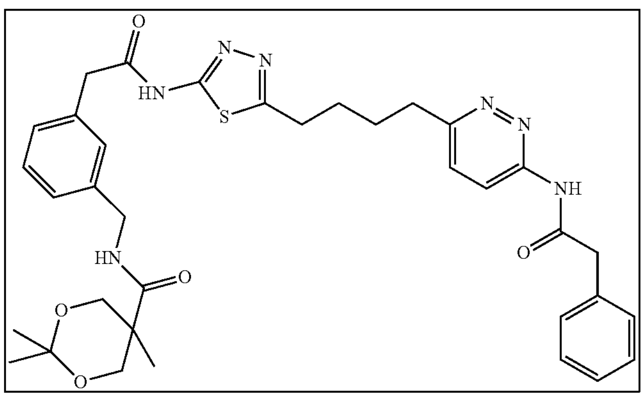 [SMILES: CC1(C)OCC(C)(C(=O)NCc2cccc(CC(=O)Nc3nnc(CCCCc4ccc(NC(=O)Cc5ccccc5)nn4)s3)c2)CO1] | 0.005 | | 0.013 |
| 581 | 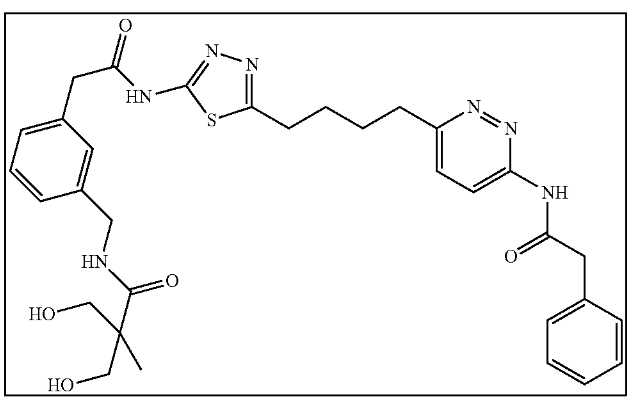 [SMILES: CC(CO)(CO)C(=O)NCc1cccc(CC(=O)Nc2nnc(CCCCc3ccc(NC(=O)Cc4ccccc4)nn3)s2)c1] | 0.011 | | 0.24 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 582 | 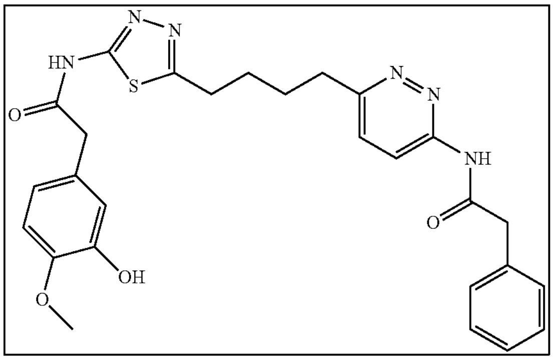 [SMILES: COc1ccc(CC(=O)Nc2nnc(CCCCc3ccc(NC(=O)Cc4ccccc4)nn3)s2)cc1O] | | 0.005 | 0.046 |
| 583 | 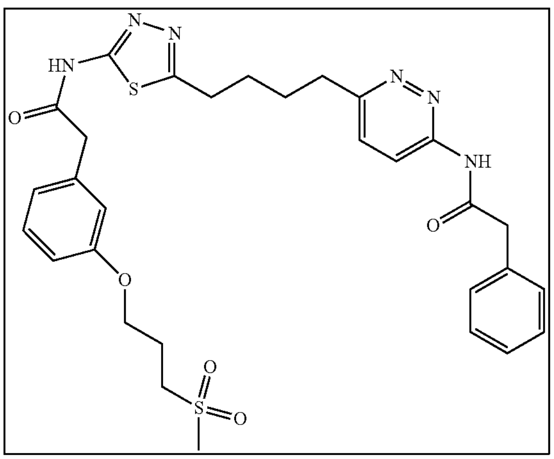 [SMILES: CS(=O)(=O)CCCOc1cccc(CC(=O)Nc2nnc(CCCCc3ccc(NC(=O)Cc4ccccc4)nn3)s2)c1] | | 0.005 | 0.042 |
| 584 | 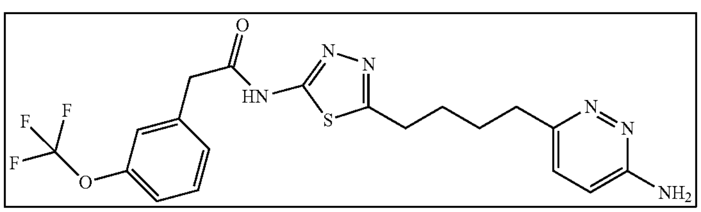 [SMILES: Nc1ccc(CCCCc2nnc(NC(=O)Cc3cccc(OC(F)(F)F)c3)s2)nn1] | | 0.22 | 1.4 |
| 585 | 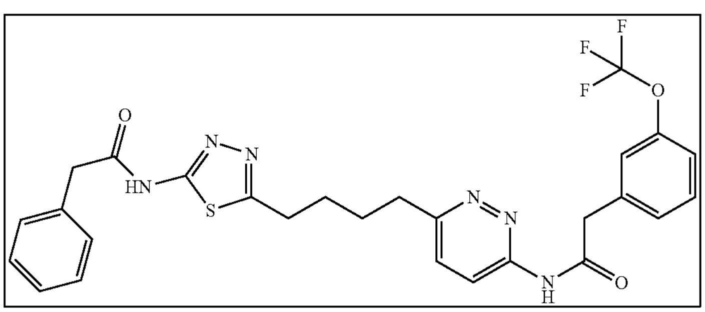 [SMILES: O=C(Cc1cccc(OC(F)(F)F)c1)Nc1ccc(CCCCc2nnc(NC(=O)Cc3ccccc3)s2)nn1] | | 0.006 | 0.070 |

TABLE 3-continued
| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 586 | 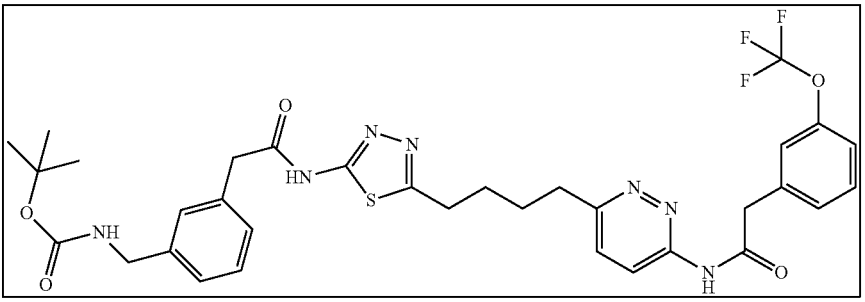 [SMILES: CC(C)(C)OC(=O)NCc1cccc(CC(=O)Nc2nnc(CCCCc3ccc(NC(=O)Cc4cccc(OC(F)(F)F)c4)nn3)s2)c1] | 0.013 | | 0.031 |
| 587 | 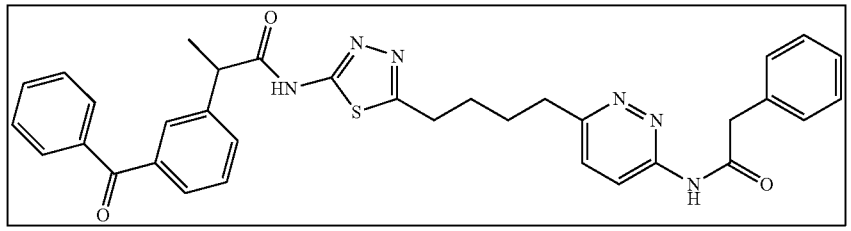 [SMILES: CC(C(=O)Nc1nnc(CCCCc2ccc(NC(=O)Cc3ccccc3)nn2)s1)c1cccc(C(=O)c2ccccc2)c1] | 0.007 | | 0.057 |
| 588 | 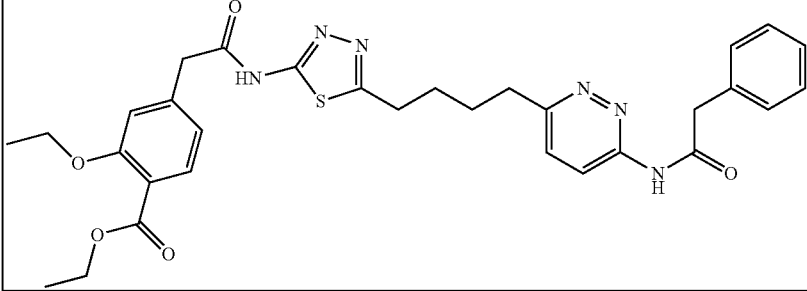 | 0.008 | | 0.27 |
| 589 | 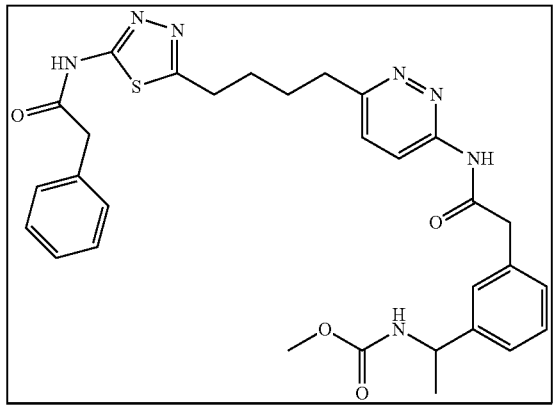 [SMILES: COC(=O)NC(C)c1cccc(CC(=O)Nc2ccc(CCCCc3nnc(NC(=O)Cc4ccccc4)s3)nn2)c1] | 0.004 | | 0.025 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 590 | 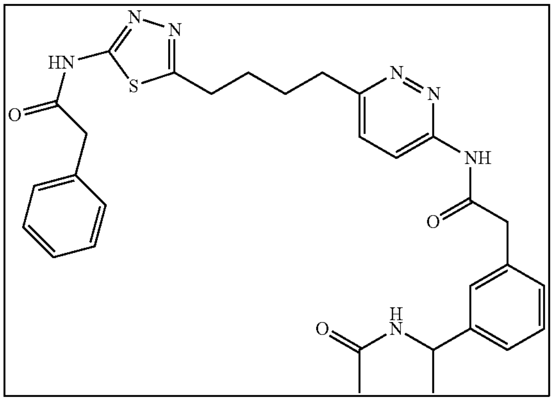 [SMILES: CC(=O)NC(C)c1cccc(CC(=O)Nc2ccc(CCCCc3nnc(NC(=O)Cc4ccccc4)s3)nn2)c1] | | 0.007 | 0.087 |
| 591 | 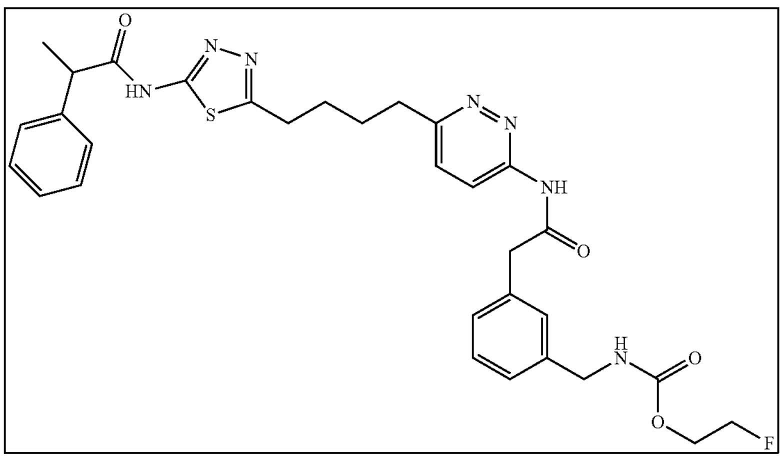 [SMILES: CC(C(=O)Nc1nnc(CCCCc2ccc(NC(=O)Cc3cccc(CNC(=O)OCCF)c3)nn2)s1)c1ccccc1] | | 0.004 | 0.033 |
| 592 | 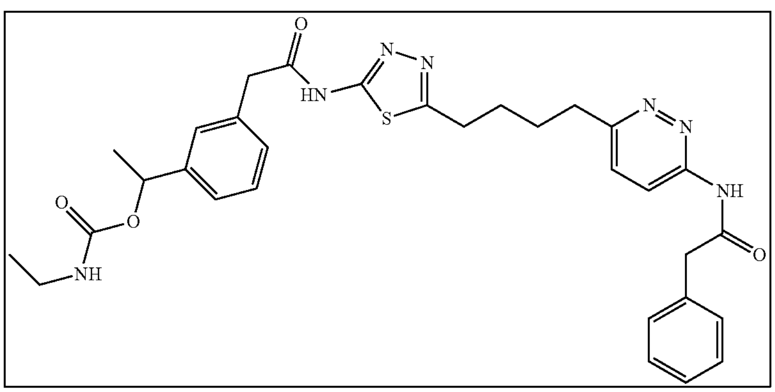 [SMILES: CCNC(=O)OC(C)c1cccc(CC(=O)Nc2nnc(CCCCc3ccc(NC(=O)Cc4ccccc4)nn3)s2)c1] | | 0.004 | 0.011 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 593 | 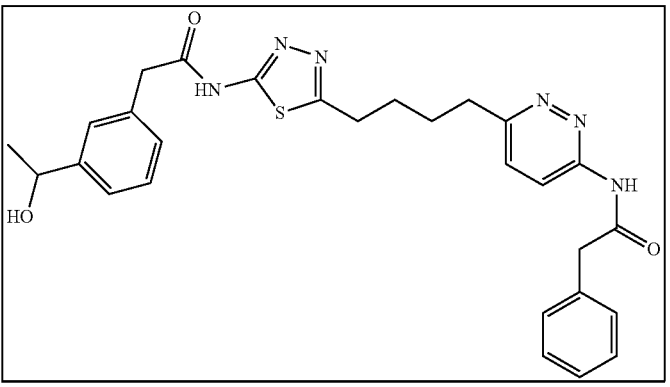 [SMILES: CC(O)c1cccc(CC(=O)Nc2nnc(CCCCc3ccc(NC(=O)Cc4ccccc4)nn3)s2)c1] | 0.005 | | 0.033 |
| 594 | 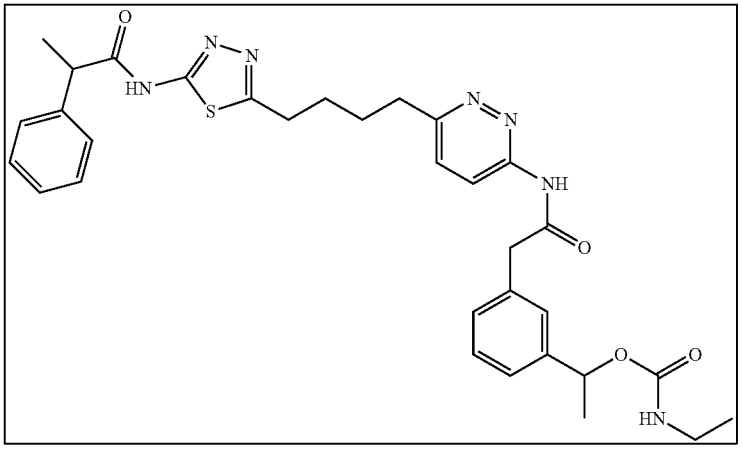 [SMILES: CCNC(=O)OC(C)c1cccc(CC(=O)Nc2ccc(CCCCc3nnc(NC(=O)C(C)c4ccccc4)s3)nn2)c1] | 0.007 | | 0.050 |
| 595 | 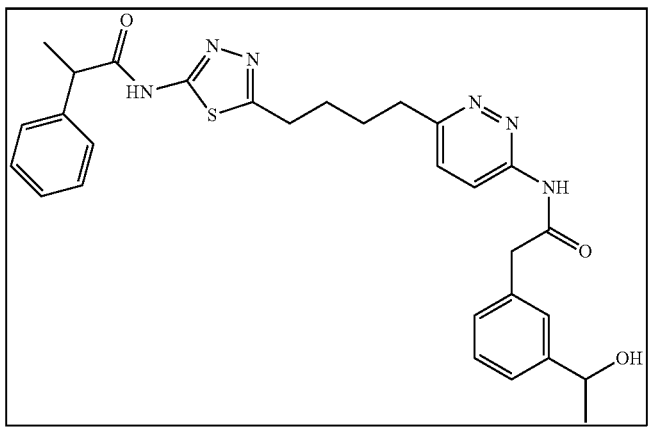 [SMILES: CC(O)c1cccc(CC(=O)Nc2ccc(CCCCc3nnc(NC(=O)C(C)c4ccccc4)s3)nn2)c1] | 0.007 | | 0.059 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 596 | 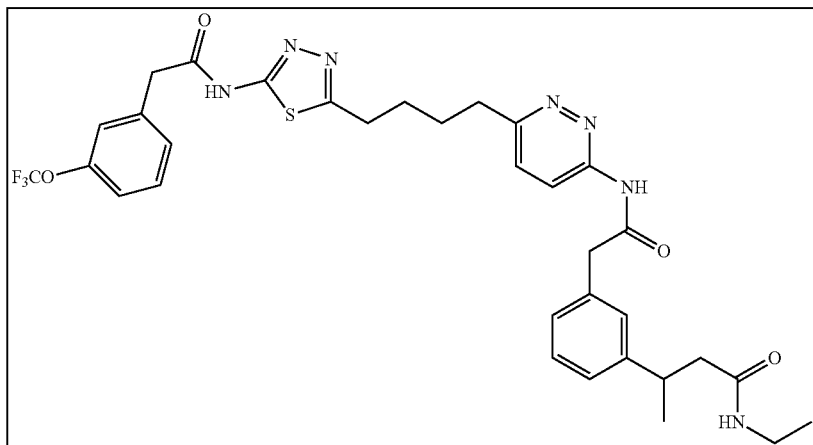 |  | 0.015 | 0.33 |
| 597 | 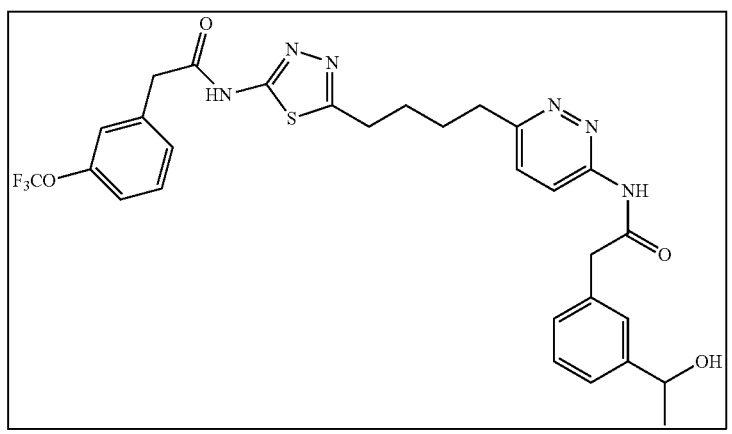 [SMILES: CC(O)c1cccc(CC(=O)Nc2ccc(CCCCc3nnc(NC(=O)Cc4cccc(OC(F)(F)F)c4)s3)nn2)c1] |  | 0.005 | 0.017 |
| 598 | 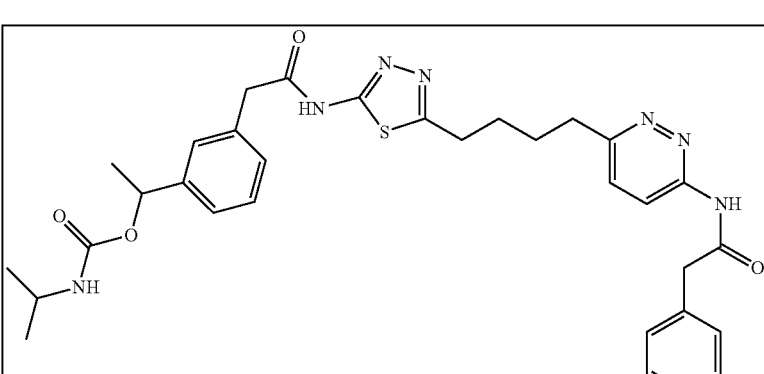 |  | 0.005 | 0.004 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 599 | 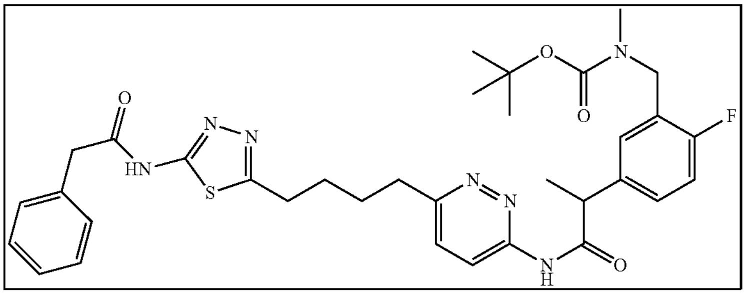 [SMILES: CC(C(=O)Nc1ccc(CCCCc2nnc(NC(=O)Cc3ccccc3)s2)nn1)c1ccc(F)c(CN(C)C(=O)OC(C)(C)C)c1] | | 0.010 | 0.039 |
| 600 | 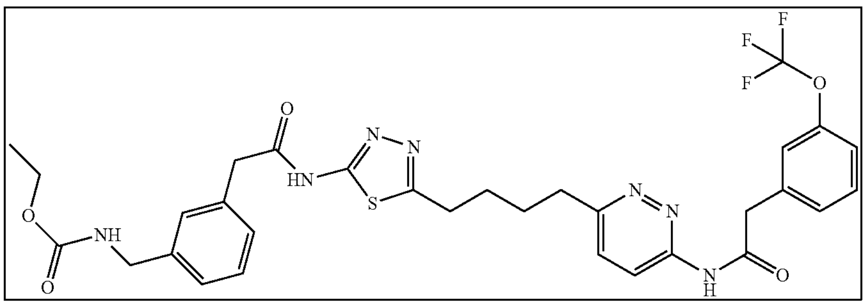 [SMILES: CCOC(=O)NCc1cccc(CC(=O)Nc2nnc(CCCCc3ccc(NC(=O)Cc4cccc(OC(F)(F)F)c4)nn3)s2)c1] | | 0.005 | 0.008 |
| 601 | 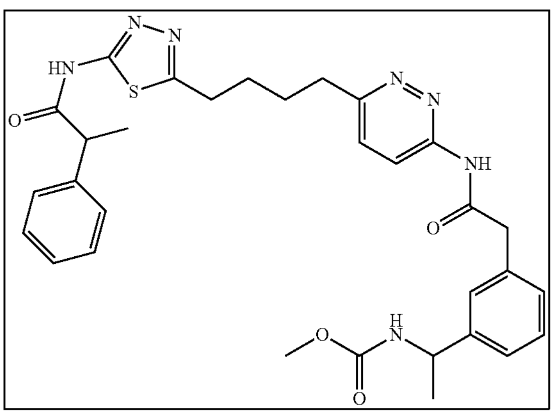 [SMILES: COC(=O)NC(C)c1cccc(CC(=O)Nc2ccc(CCCCc3nnc(NC(=O)C(C)c4ccccc4)s3)nn2)c1] | | 0.006 | 0.036 |
| 602 | 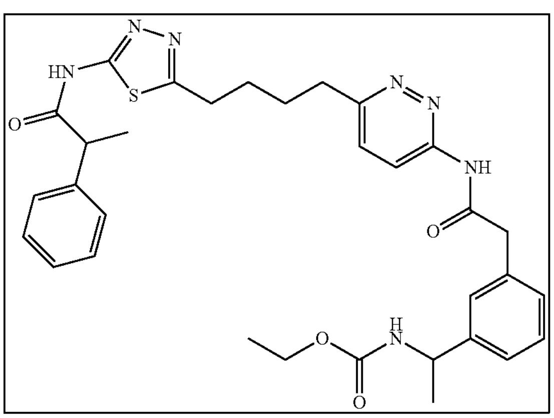 [SMILES: CCOC(=O)NC(C)c1cccc(CC(=O)Nc2ccc(CCCCc3nnc(NC(=O)C(C)c4ccccc4)s3)nn2)c1] | | 0.006 | 0.036 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 603 | 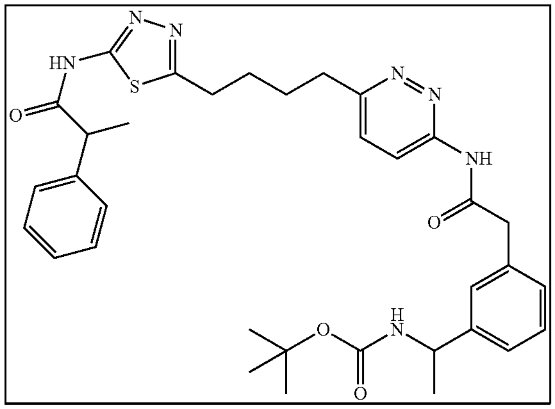 [SMILES: CC(NC(=O)OC(C)(C)C)c1cccc(CC(=O)Nc2ccc(CCCCc3nnc(NC(=O)C(C)c4ccccc4)s3)nn2)c1] | | 0.009 | 0.023 |
| 604 | 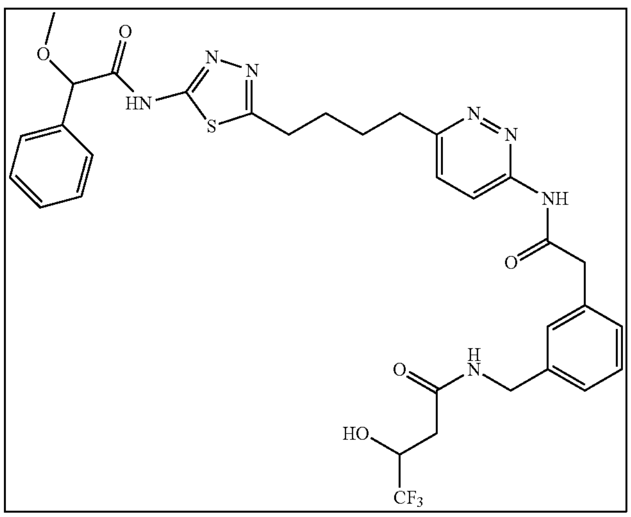 [SMILES: COC(C(=O)Nc1nnc(CCCCc2ccc(NC(=O)Cc3cccc(CNC(=O)CC(O)C(F)(F)F)c3)nn2)s1)c1ccccc1] | | 0.015 | 0.042 |
| 605 | 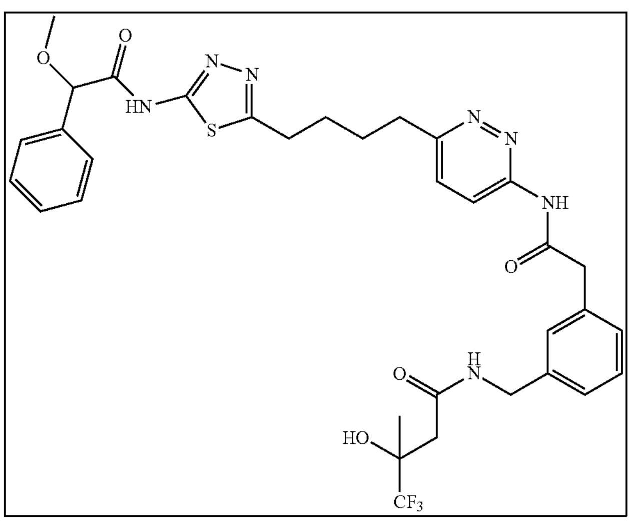 [SMILES: COC(C(=O)Nc1nnc(CCCCc2ccc(NC(=O)Cc3cccc(CNC(=O)CC(C)(O)C(F)(F)F)c3)nn2)s1)c1ccccc1] | | 0.013 | 0.018 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 606 | 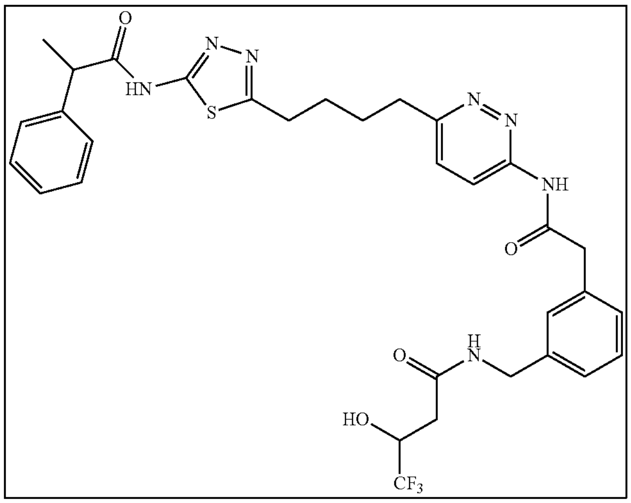 [SMILES: CC(C(=O)Nc1nnc(CCCCc2ccc(NC(=O)Cc3cccc(CNC(=O)CC(O)C(F)(F)F)c3)nn2)s1)c1ccccc1] | | 0.007 | 0.045 |
| 607 | 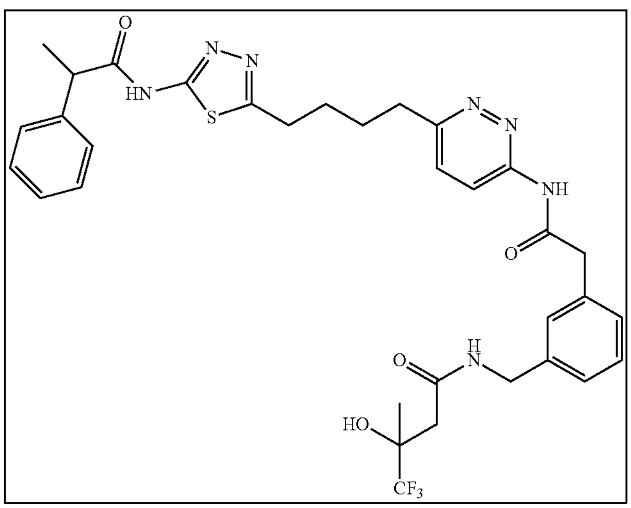 [SMILES: CC(C(=O)Nc1nnc(CCCCc2ccc(NC(=O)Cc3cccc(CNC(=O)CC(C)(O)C(F)(F)F)c3)nn2)s1)c1ccccc1] | | 0.007 | 0.047 |
| 608 | 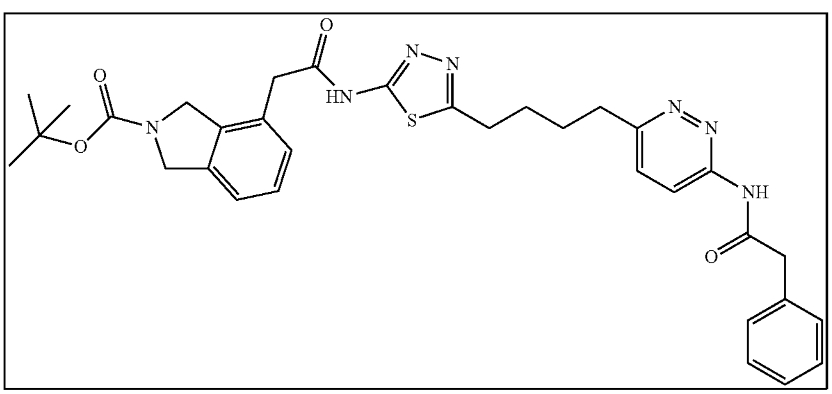 [SMILES: CC(C)(C)OC(=O)N1Cc2cccc(CC(=O)Nc3nnc(CCCCc4ccc(NC(=O)Cc5ccccc5)nn4)s3)c2C1] | | 0.007 | 0.037 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 609 | 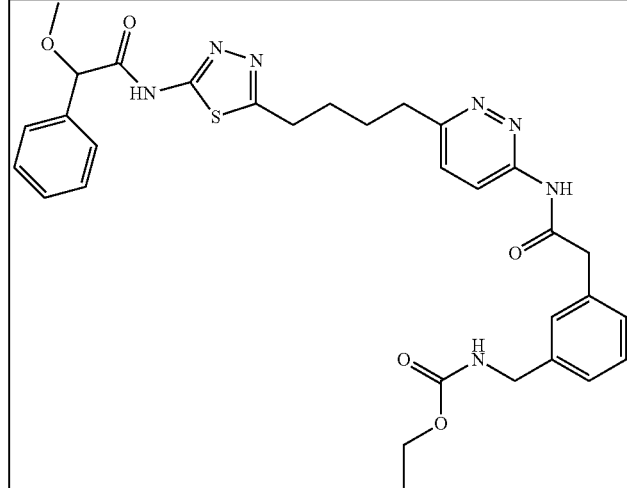 | 0.009 | | 0.014 |
| 610 | 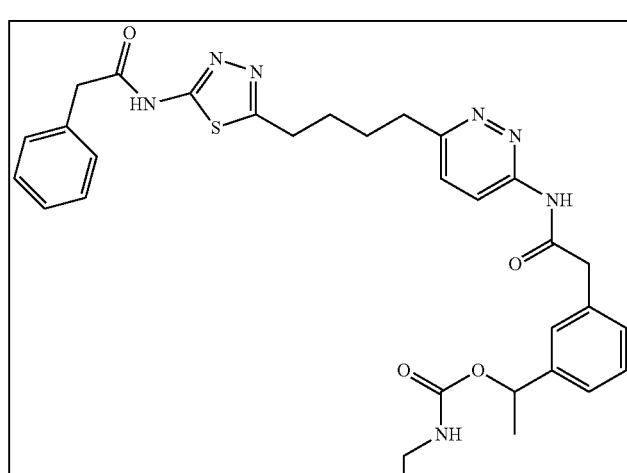 | 0.005 | | 0.011 |
| 611 | 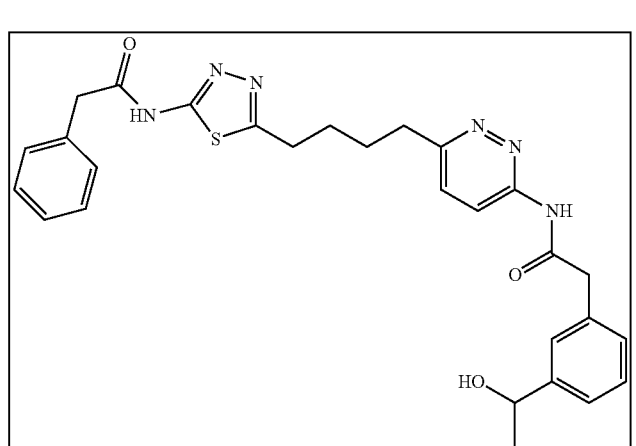 [SMILES: CC(O)c1cccc(CC(=O)Nc2ccc(CCCCc3nnc(NC(=O)Cc4ccccc4)s3)nn2)c1] | 0.006 | | 0.040 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 612 | 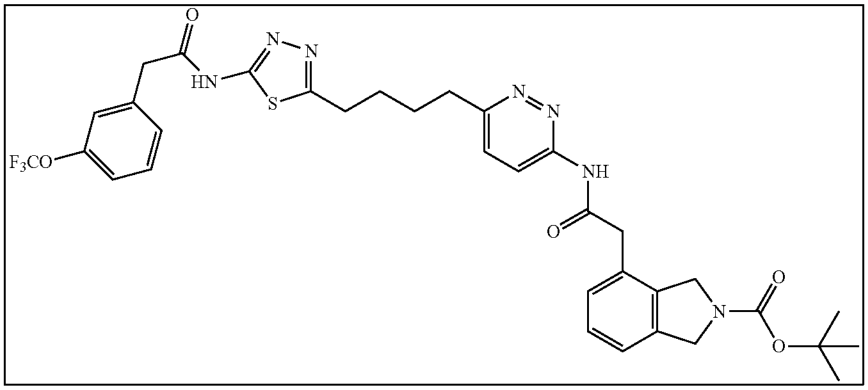 [SMILES: CC(C)(C)OC(=O)N1Cc2cccc(CC(=O)Nc3ccc(CCCCc4nnc(NC(=O)Cc5cccc(OC(F)(F)F)c5)s4)nn3)c2C1] | 0.065 | | 0.10 |
| 613 | 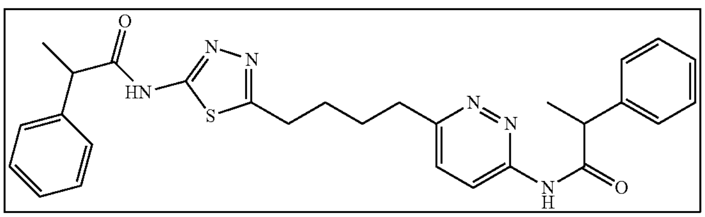 [SMILES: CC(C(=O)Nc1ccc(CCCCc2nnc(NC(=O)C(C)c3ccccc3)s2)nn1)c1ccccc1] | 0.019 | | 0.45 |
| 614 | 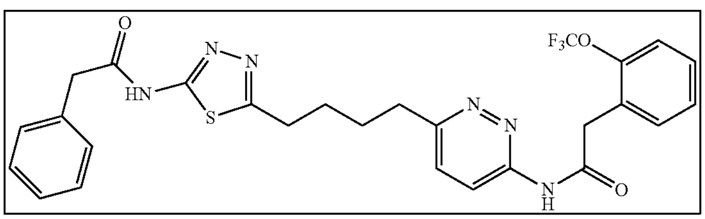 [SMILES: O=C(Cc1ccccc1OC(F)(F)F)Nc1ccc(CCCCc2nnc(NC(=O)Cc3ccccc3)s2)nn1] | 0.008 | | 0.082 |
| 615 | 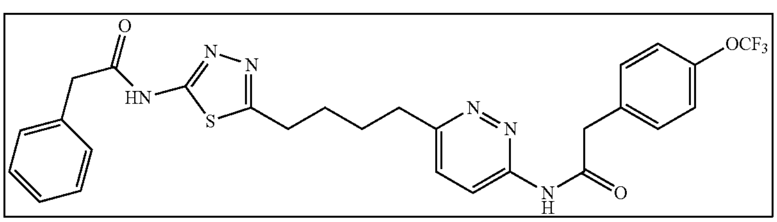 [SMILES: O=C(Cc1ccc(OC(F)(F)F)cc1)Nc1ccc(CCCCc2nnc(NC(=O)Cc3ccccc3)s2)nn1] | 0.009 | | 0.012 |
| 616 | 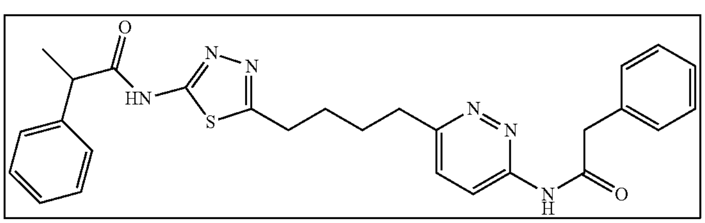 [SMILES: CC(C(=O)Nc1nnc(CCCCc2ccc(NC(=O)Cc3ccccc3)nn2)s1)c1ccccc1] | 0.008 | | 0.13 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 617 | 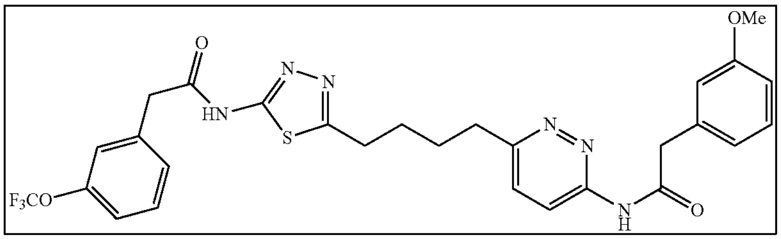 [SMILES: COc1cccc(CC(=O)Nc2ccc(CCCCc3nnc(NC(=O)Cc4cccc(OC(F)(F)F)c4)s3)nn2)c1] | | 0.005 | 0.040 |
| 618 | 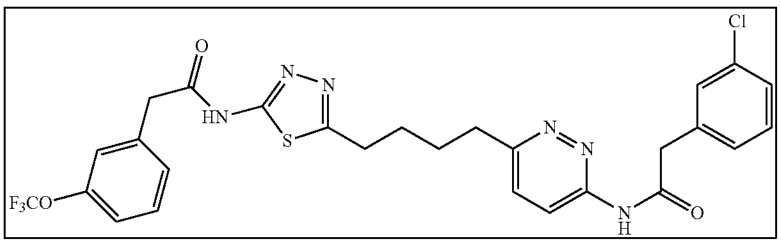 [SMILES: O=C(Cc1cccc(Cl)c1)Nc1ccc(CCCCc2nnc(NC(=O)Cc3cccc(OC(F)(F)F)c3)s2)nn1] | | 0.008 | 0.035 |
| 619 | 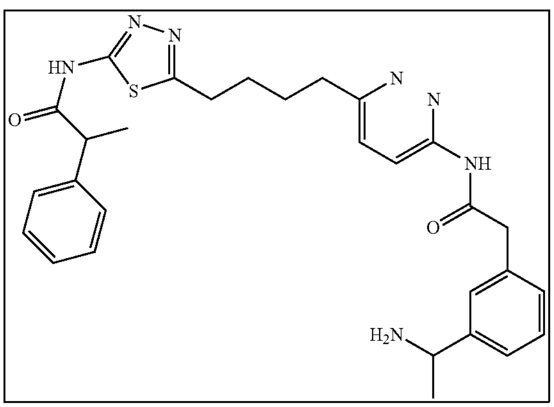 [SMILES: CC(N)c1cccc(CC(=O)N/C(N)=C/C=C(\N)CCCCc2nnc(NC(=O)C(C)c3ccccc3)s2)c1] | | 0.013 | 0.15 |
| 620 | 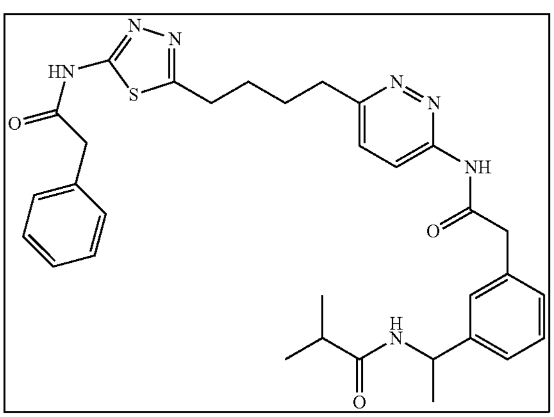 [SMILES: CC(C)C(=O)NC(C)c1cccc(CC(=O)Nc2ccc(CCCCc3nnc(NC(=O)Cc4ccccc4)s3)nn2)c1] | | 0.005 | 0.011 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 621 | 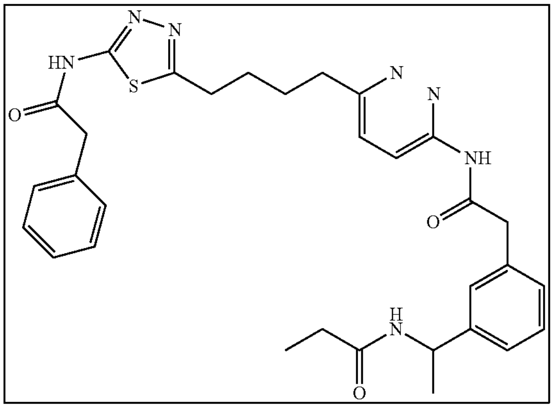 [SMILES: CCC(=O)NC(C)c1cccc(CC(=O)N/C(N)=C/C=C(\N)CCCCc2nnc(NC(=O)Cc3ccccc3)s2)c1] | 0.005 | | 0.020 |
| 622 | 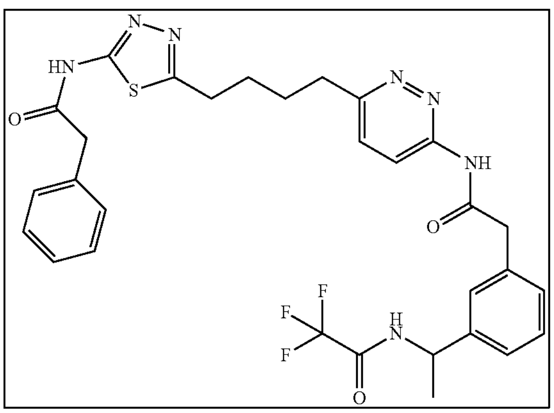 [SMILES: CC(NC(=O)C(F)(F)F)c1cccc(CC(=O)Nc2ccc(CCCCc3nnc(NC(=O)Cc4ccccc4)s3)nn2)c1] | 0.004 | | 0.010 |
| 623 | 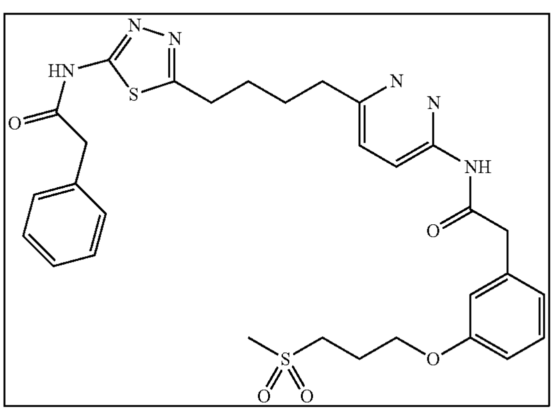 [SMILES: CS(=O)(=O)CCCOc1cccc(CC(=O)N/C(N)=C/C=C(\N)CCCCc2nnc(NC(=O)Cc3ccccc3)s2)c1] | 0.003 | | 0.026 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 624 | 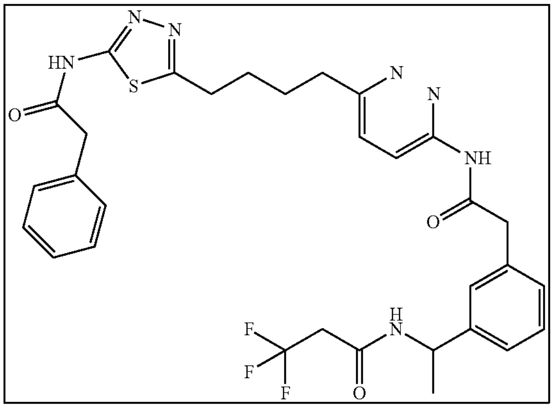 [SMILES: CC(NC(=O)CC(F)(F)F)c1cccc(CC(=O)N/C(N)=C/C=C(\N)CCCCc2nnc(NC(=O)Cc3ccccc3)s2)c1] | 0.004 | | 0.009 |
| 625 | 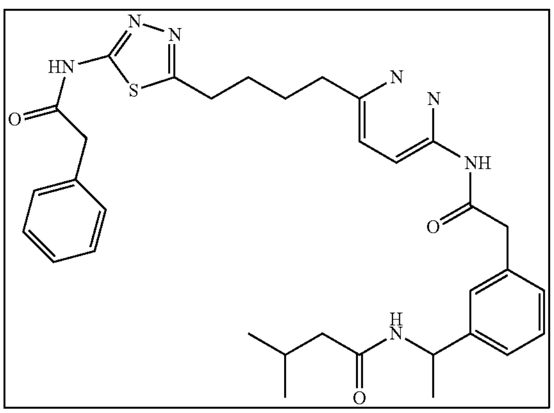 [SMILES: CC(C)CC(=O)NC(C)c1cccc(CC(=O)N/C(N)=C/C=C(\N)CCCCc2nnc(NC(=O)Cc3ccccc3)s2)c1] | 0.004 | | 0.006 |
| 626 | 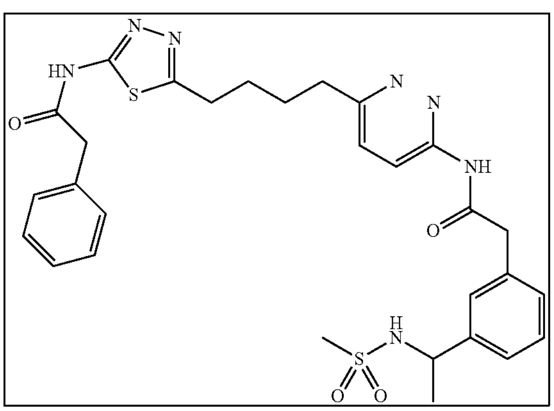 [SMILES: CC(NS(C)(=O)=O)c1cccc(CC(=O)N/C(N)=C/C=C(\N)CCCCc2nnc(NC(=O)Cc3ccccc3)s2)c1] | 0.004 | | 0.017 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 627 | 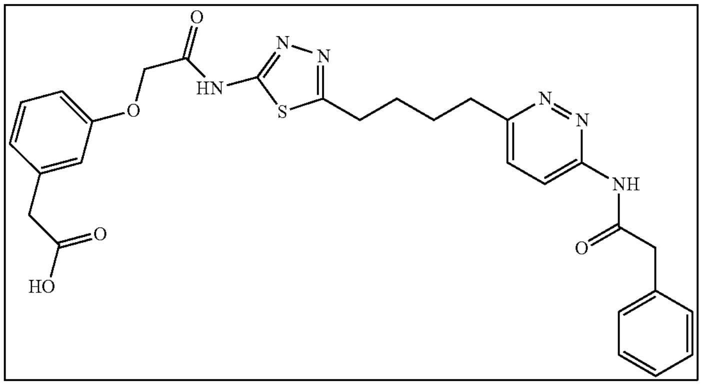 [SMILES: O=C(O)Cc1cccc(OCC(=O)Nc2nnc(CCCCc3ccc(NC(=O)Cc4ccccc4)nn3)s2)c1] | | 0.028 | 0.85 |
| 628 | 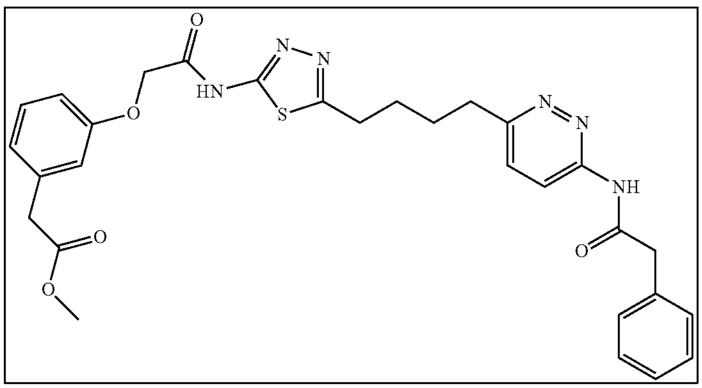 [SMILES: COC(=O)Cc1cccc(OCC(=O)Nc2nnc(CCCCc3ccc(NC(=O)Cc4ccccc4)nn3)s2)c1] | | 0.027 | 0.17 |
| 629 | 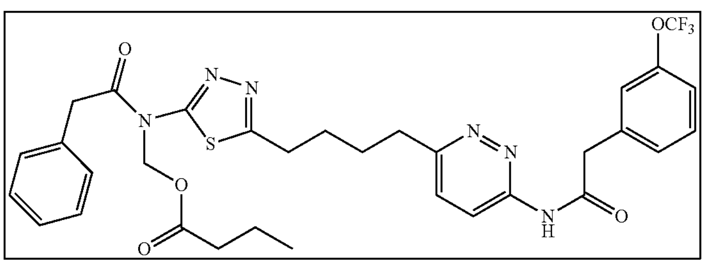 [SMILES: CCCC(=O)OCN(C(=O)Cc1ccccc1)c1nnc(CCCCc2ccc(NC(=O)Cc3cccc(OC(F)(F)F)c3)nn2)s1] | | >20 | 0.065 |
| 630 | 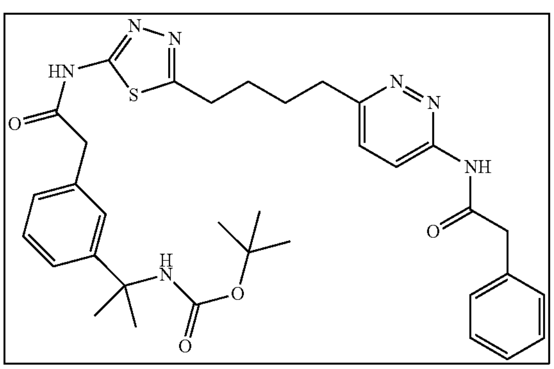 [SMILES: CC(C)(C)OC(=O)NC(C)(C)c1cccc(CC(=O)Nc2nnc(CCCCc3ccc(NC(=O)Cc4ccccc4)nn3)s2)c1] | | 0.004 | 0.009 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 631 | 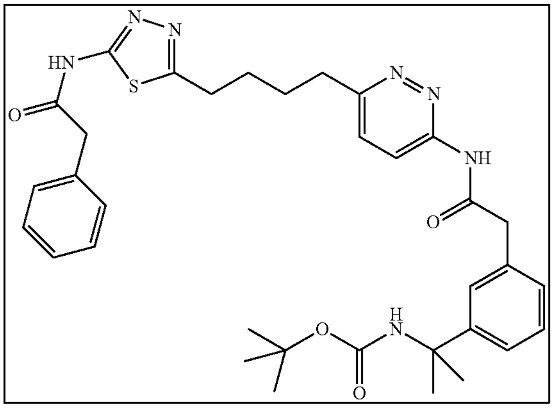 [SMILES: CC(C)(C)OC(=O)NC(C)(C)c1cccc(CC(=O)Nc2ccc(CCCCc3nnc(NC(=O)Cc4ccccc4)s3)nn2)c1] | | 0.005 | 0.006 |
| 632 | 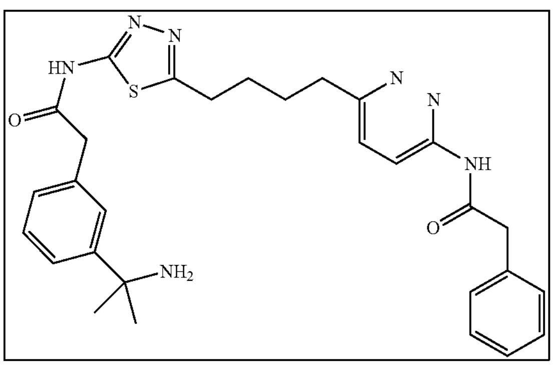 [SMILES: CC(C)(N)c1cccc(CC(=O)Nc2nnc(CCCC/C(N)=C/C=C(\N)NC(=O)Cc3ccccc3)s2)c1] | | 0.010 | 0.20 |
| 633 | 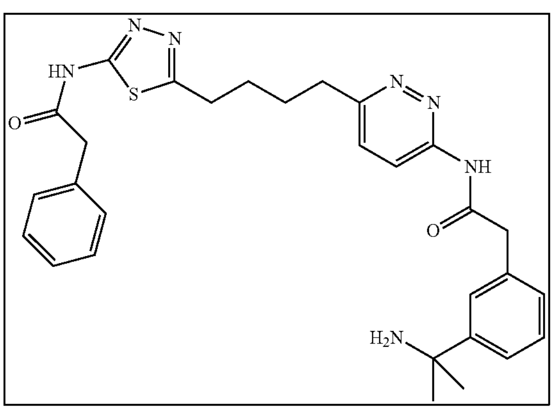 [SMILES: CC(C)(N)c1cccc(CC(=O)Nc2ccc(CCCCc3nnc(NC(=O)Cc4ccccc4)s3)nn2)c1] | | 0.007 | 0.13 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 634 | 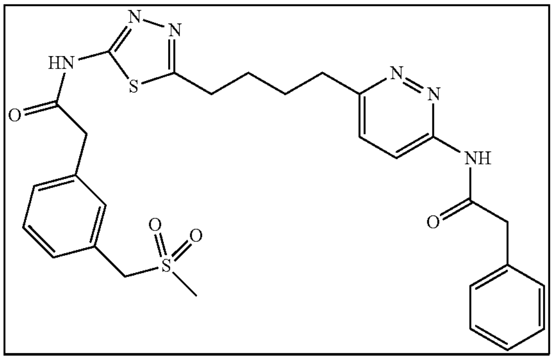 [SMILES: CS(=O)(=O)Cc1cccc(CC(=O)Nc2nnc(CCCCc3ccc(NC(=O)Cc4ccccc4)nn3)s2)c1] | | 0.006 | 0.048 |
| 635 | 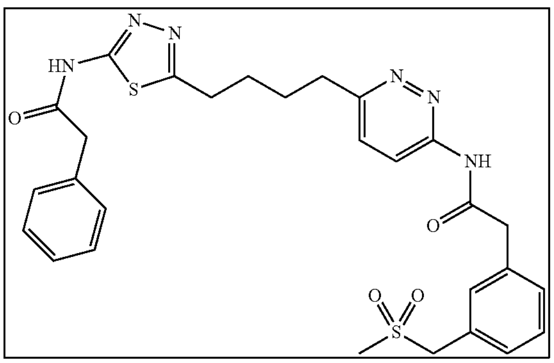 [SMILES: CS(=O)(=O)Cc1cccc(CC(=O)Nc2ccc(CCCCc3nnc(NC(=O)Cc4ccccc4)s3)nn2)c1] | | 0.005 | 0.030 |
| 636 | 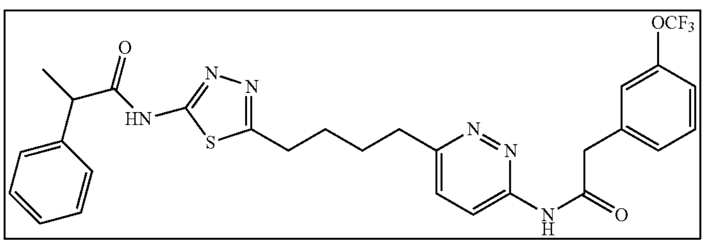 [SMILES: CC(C(=O)Nc1nnc(CCCCc2ccc(NC(=O)Cc3cccc(OC(F)(F)F)c3)nn2)s1)c1ccccc1] | | 0.008 | 0.059 |
| 637 | 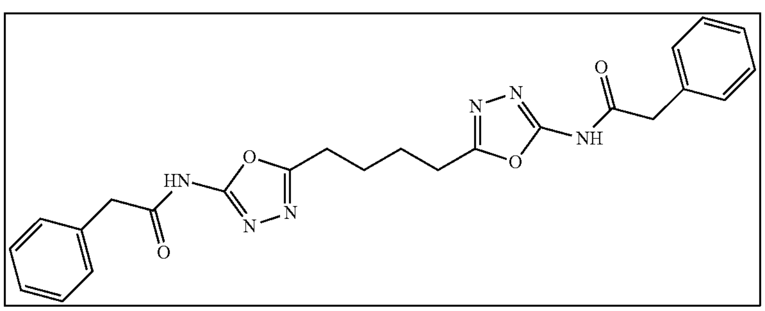 [SMILES: O=C(Cc1ccccc1)Nc1nnc(CCCCc2nnc(NC(=O)Cc3ccccc3)o2)o1] | | >20 | >50 |
| 638 | 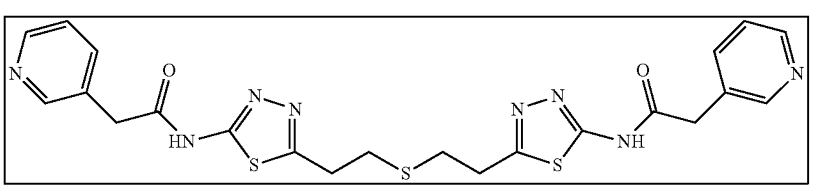 [SMILES: O=C(Cc1cccnc1)Nc1nnc(CCSCCc2nnc(NC(=O)Cc3cccnc3)s2)s1] | | 0.48 | 5.7 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 639 | 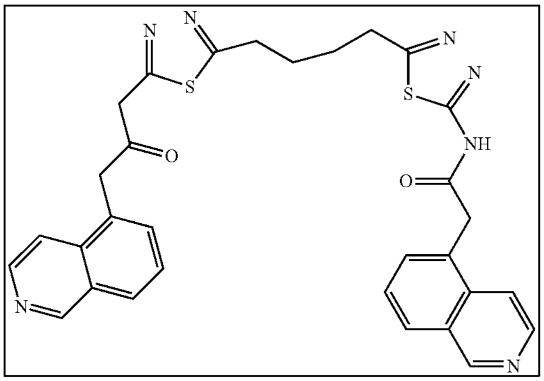 [SMILES: N=C(CCCCC(=N)SC(=N)NC(=O)Cc1cccc2cnccc12)SC(=N)CC(=O)Cc1cccc2cnccc12] | | 0.17 | 23 |
| 640 | 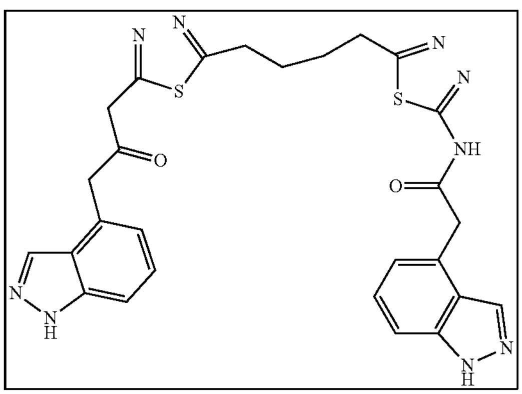 [SMILES: N=C(CCCCC(=N)SC(=N)NC(=O)Cc1cccc2[nH]ncc12)SC(=N)CC(=O)Cc1cccc2[nH]ncc12] | | 0.12 | 0.070 |
| 641 | 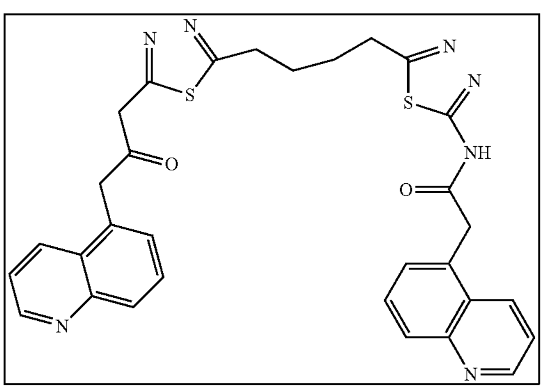 [SMILES: N=C(CCCCC(=N)SC(=N)NC(=O)Cc1cccc2ncccc12)SC(=N)CC(=O)Cc1cccc2ncccc12] | | 0.14 | 0.50 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 644 | 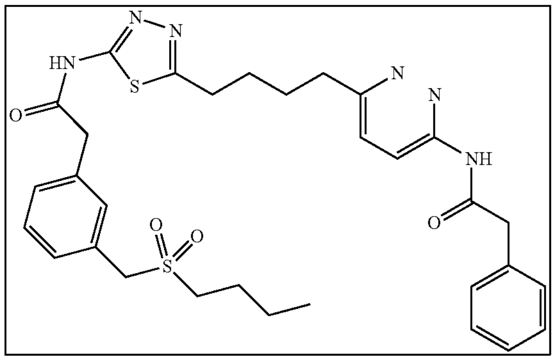 [SMILES: CCCCS(=O)(=O)Cc1cccc(CC(=O)Nc2nnc(CCCC/C(N)=C/C=C(\N)NC(=O)Cc3ccccc3)s2)c1] | 0.003 | | 0.013 |
| 645 | 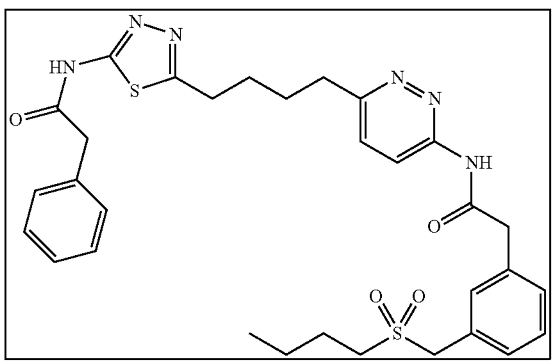 [SMILES: CCCCS(=O)(=O)Cc1cccc(CC(=O)Nc2ccc(CCCCc3nnc(NC(=O)Cc4ccccc4)s3)nn2)c1] | 0.002 | | 0.015 |
| 646 | 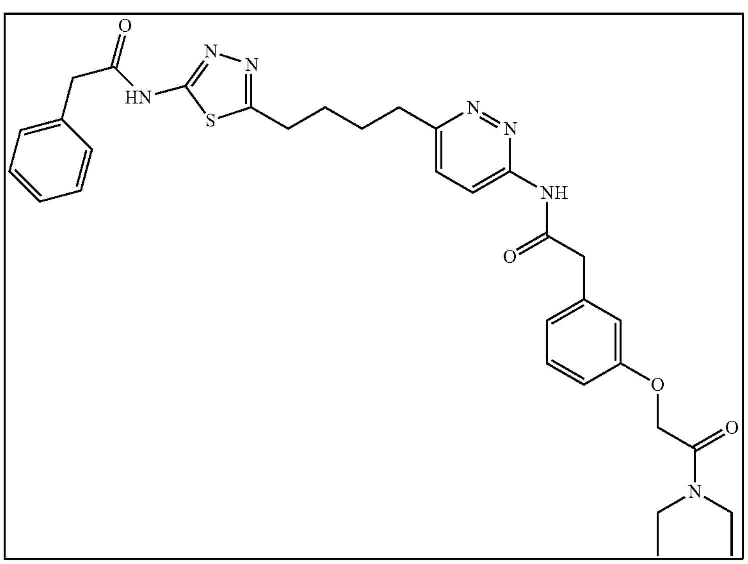 [SMILES: CCN(CC)C(=O)COc1cccc(CC(=O)Nc2ccc(CCCCc3nnc(NC(=O)Cc4ccccc4)s3)nn2)c1] | 0.007 | | 0.037 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 647 | 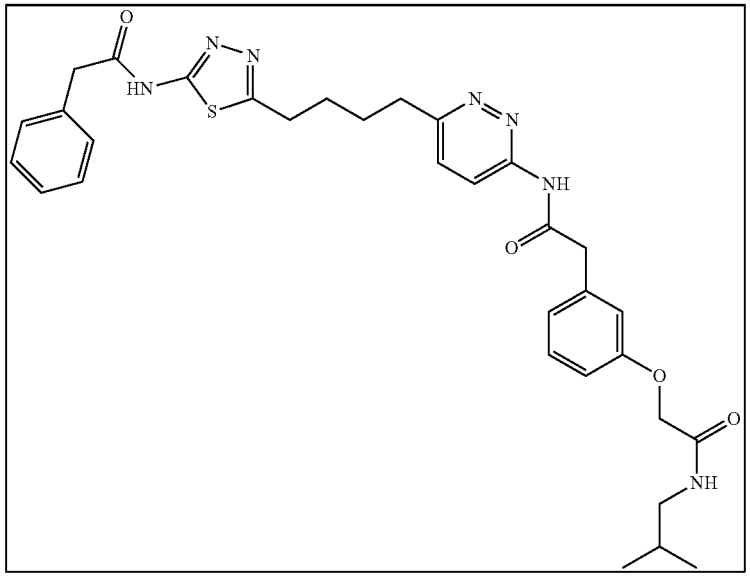 [SMILES: CC(C)CNC(=O)COc1cccc(CC(=O)Nc2ccc(CCCCc3nnc(NC(=O)Cc4ccccc4)s3)nn2)c1] | 0.004 | | 0.018 |
| 648 | 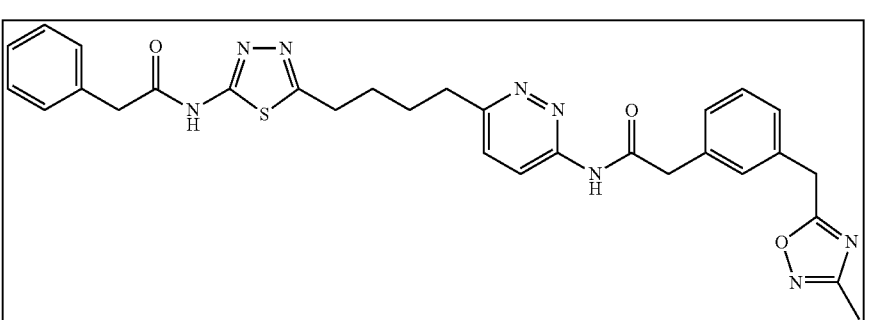 | 0.004 | | 0.011 |
| 649 | 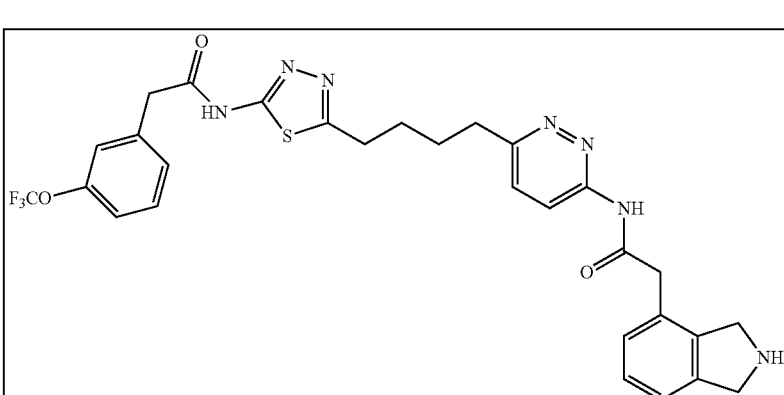 | 0.004 | | 0.034 |

TABLE 3-continued
| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 650 | 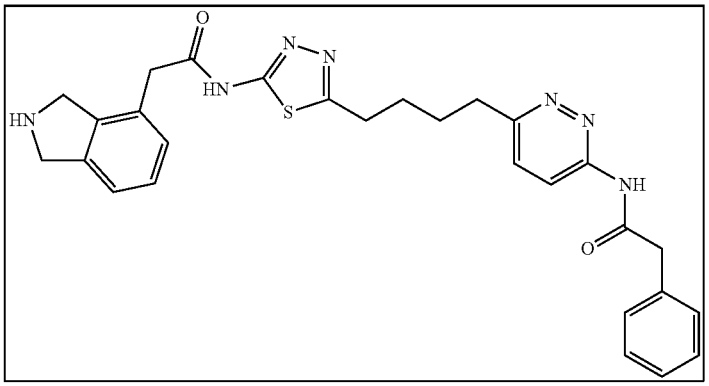 [SMILES: O=C(Cc1ccccc1)Nc1ccc(CCCCc2nnc(NC(=O)Cc3cccc4c3CNC4)s2)nn1] | 0.013 | | 0.14 |
| 651 | 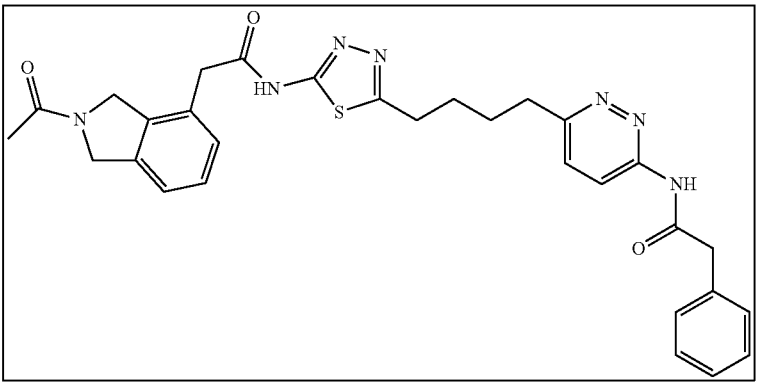 [SMILES: CC(=O)N1Cc2cccc(CC(=O)Nc3nnc(CCCCc4ccc(NC(=O)Cc5ccccc5)nn4)s3)c2C1] | 0.006 | | 0.037 |
| 652 | 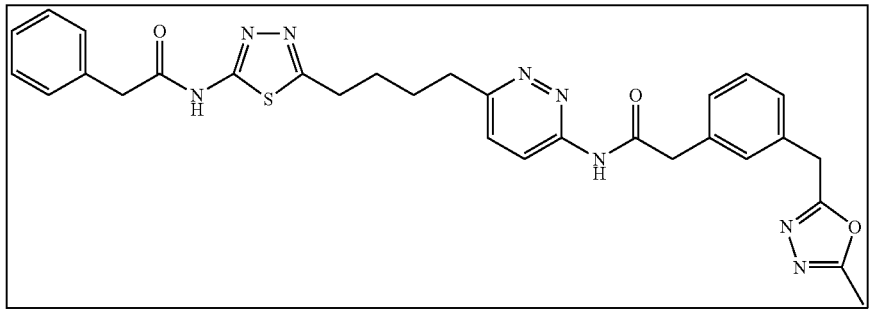 [SMILES: Cc1nnc(Cc2cccc(CC(=O)Nc3ccc(CCCCc4nnc(NC(=O)Cc5ccccc5)s4)nn3)c2)o1] | 0.004 | | 0.039 |
| 653 | 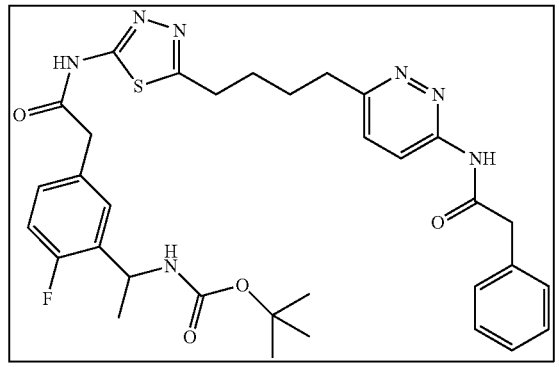 [SMILES: CC(NC(=O)OC(C)(C)C)c1cc(CC(=O)Nc2nnc(CCCCc3ccc(NC(=O)Cc4ccccc4)nn3)s2)ccc1F] | 0.005 | | 0.010 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 654 | 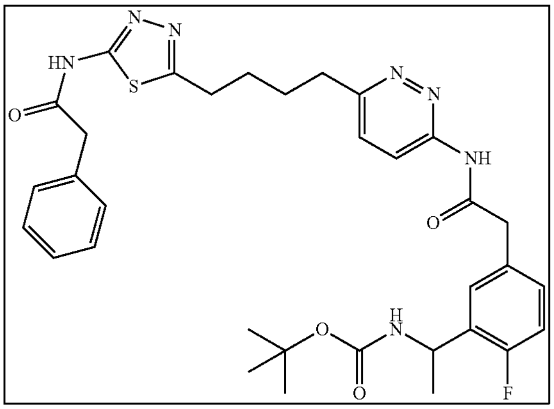 [SMILES: CC(NC(=O)OC(C)(C)C)c1cc(CC(=O)Nc2ccc(CCCCc3nnc(NC(=O)Cc4ccccc4)s3)nn2)ccc1F] | 0.005 | | 0.007 |
| 655 | 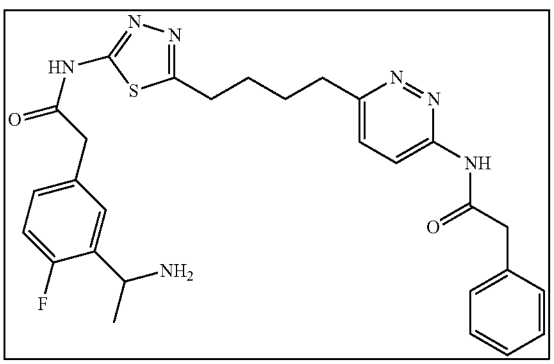 [SMILES: CC(N)c1cc(CC(=O)Nc2nnc(CCCCc3ccc(NC(=O)Cc4ccccc4)nn3)s2)ccc1F] | 0.019 | | 0.35 |
| 656 | 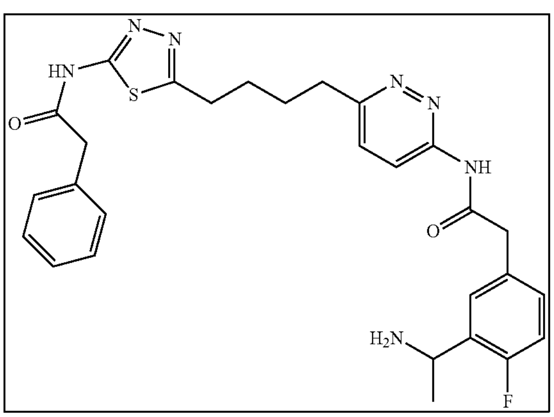 [SMILES: CC(N)c1cc(CC(=O)Nc2ccc(CCCCc3nnc(NC(=O)Cc4ccccc4)s3)nn2)ccc1F] | 0.018 | | 0.40 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 657 | 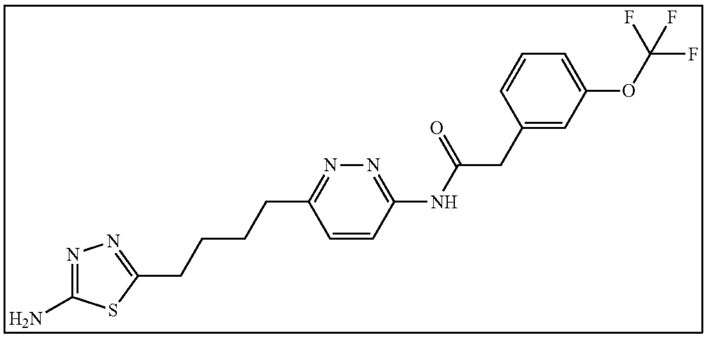 [SMILES: Nc1nnc(CCCCc2ccc(NC(=O)Cc3cccc(OC(F)(F)F)c3)nn2)s1] | 0.24 | | 1.5 |
| 658 | 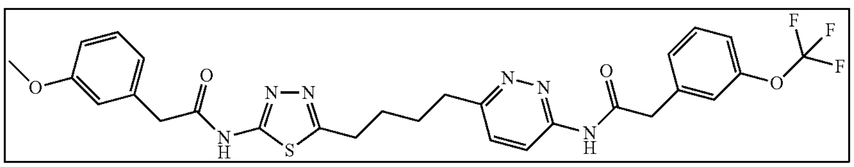 [SMILES: COc1cccc(CC(=O)Nc2nnc(CCCCc3ccc(NC(=O)Cc4cccc(OC(F)(F)F)c4)nn3)s2)c1] | 0.005 | | 0.040 |
| 659 | 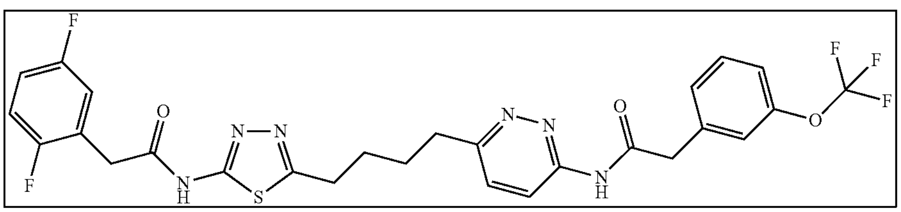 [SMILES: O=C(Cc1cccc(OC(F)(F)F)c1)Nc1ccc(CCCCc2nnc(NC(=O)Cc3cc(F)ccc3F)s2)nn1] | 0.010 | | 0.058 |
| 660 | 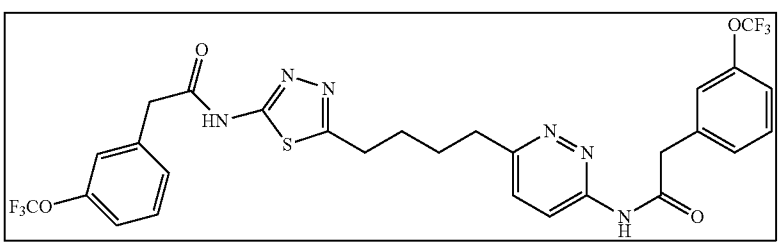 [SMILES: O=C(Cc1cccc(OC(F)(F)F)c1)Nc1ccc(CCCCc2nnc(NC(=O)Cc3cccc(OC(F)(F)F)c3)s2)nn1] | 0.025 | | 0.037 |
| 661 | 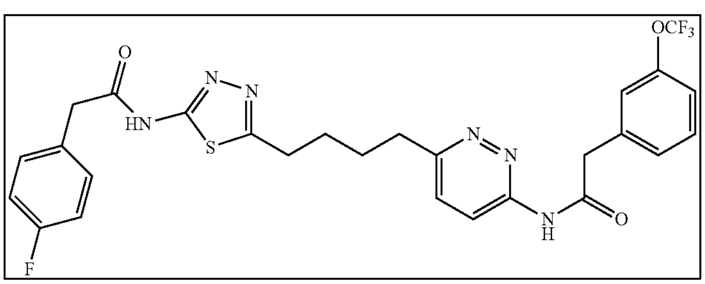 [SMILES: O=C(Cc1cccc(OC(F)(F)F)c1)Nc1ccc(CCCCc2nnc(NC(=O)Cc3ccc(F)cc3)s2)nn1] | 0.007 | | 0.12 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 662 | 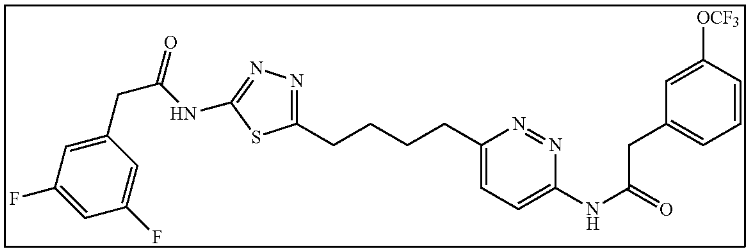 [SMILES: O=C(Cc1cccc(OC(F)(F)F)c1)Nc1ccc(CCCCc2nnc(NC(=O)Cc3cc(F)cc(F)c3)s2)nn1] | 0.007 | | 0.055 |
| 663 | 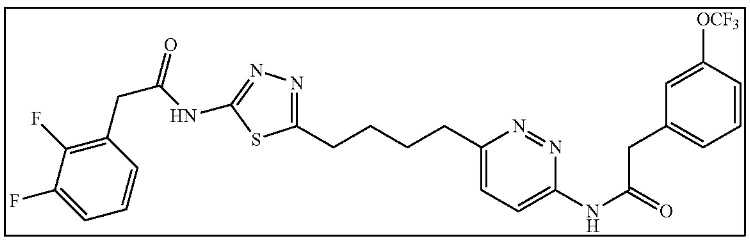 [SMILES: O=C(Cc1cccc(OC(F)(F)F)c1)Nc1ccc(CCCCc2nnc(NC(=O)Cc3cccc(F)c3F)s2)nn1] | 0.007 | | 0.089 |
| 664 | 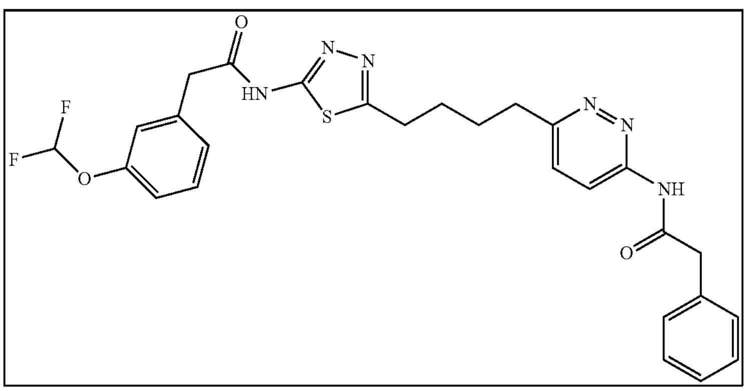 [SMILES: O=C(Cc1ccccc1)Nc1ccc(CCCCc2nnc(NC(=O)Cc3cccc(OC(F)F)c3)s2)nn1] | 0.005 | | 0.060 |
| 665 | 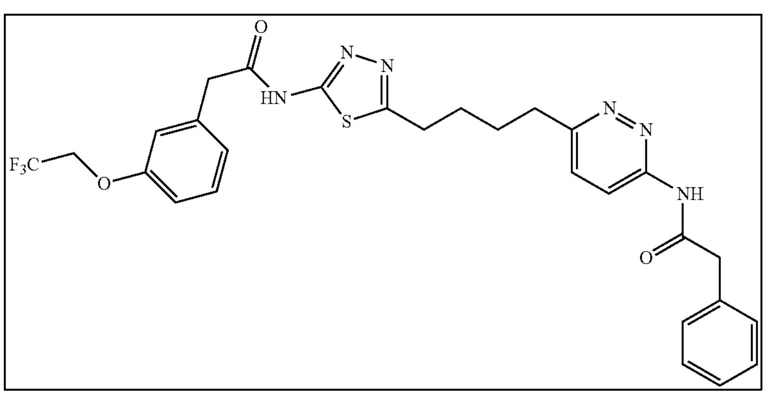 [SMILES: O=C(Cc1ccccc1)Nc1ccc(CCCCc2nnc(NC(=O)Cc3cccc(OCC(F)(F)F)c3)s2)nn1] | 0.005 | | 0.10 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 666 | 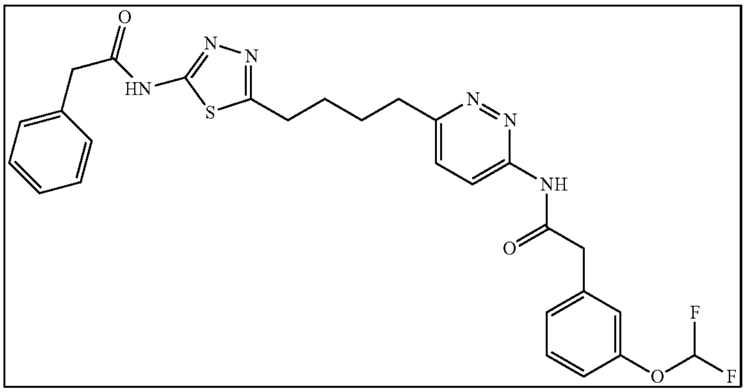 [SMILES: O=C(Cc1cccc(OC(F)F)c1)Nc1ccc(CCCCc2nnc(NC(=O)Cc3ccccc3)s2)nn1] | 0.004 | | 0.058 |
| 667 | 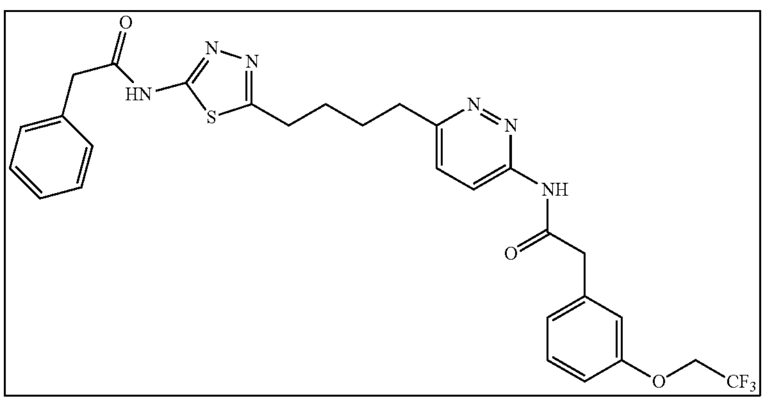 [SMILES: O=C(Cc1cccc(OCC(F)(F)F)c1)Nc1ccc(CCCCc2nnc(NC(=O)Cc3ccccc3)s2)nn1] | 0.004 | | 0.11 |
| 668 | 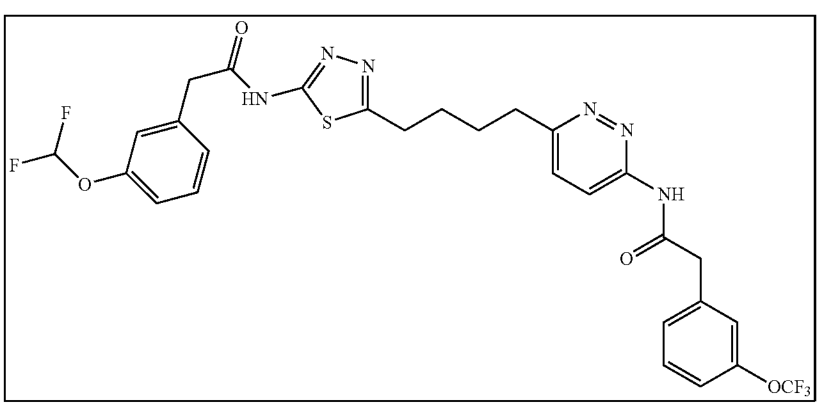 [SMILES: O=C(Cc1cccc(OC(F)(F)F)c1)Nc1ccc(CCCCc2nnc(NC(=O)Cc3cccc(OC(F)F)c3)s2)nn1] | 0.009 | | 0.026 |

TABLE 3-continued
| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 669 | 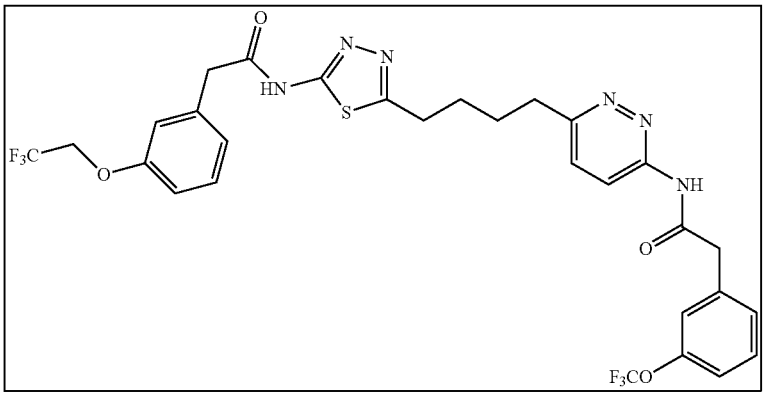 [SMILES: O=C(Cc1cccc(OC(F)(F)F)c1)Nc1ccc(CCCCc2nnc(NC(=O)Cc3cccc(OCC(F)(F)F)c3)s2)nn1] | | 0.021 | 0.026 |
| 670 | 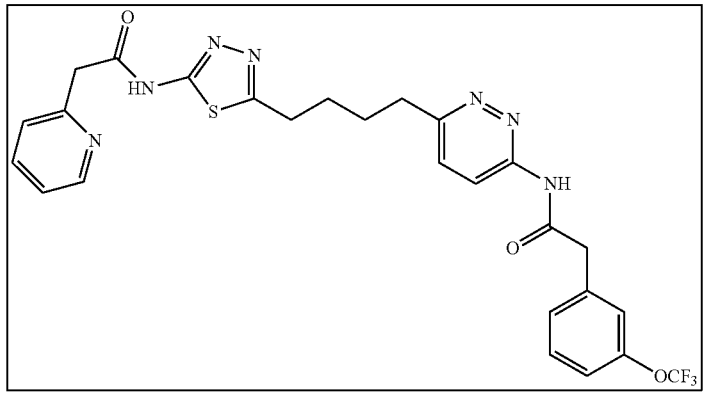 [SMILES: O=C(Cc1cccc(OC(F)(F)F)c1)Nc1ccc(CCCCc2nnc(NC(=O)Cc3ccccn3)s2)nn1] | | 0.005 | 0.030 |
| 671 | 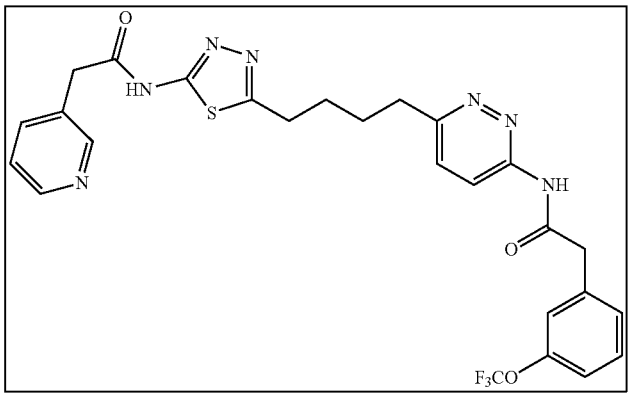 [SMILES: O=C(Cc1cccc(OC(F)(F)F)c1)Nc1ccc(CCCCc2nnc(NC(=O)Cc3cccnc3)s2)nn1] | | 0.004 | 0.035 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 672 | 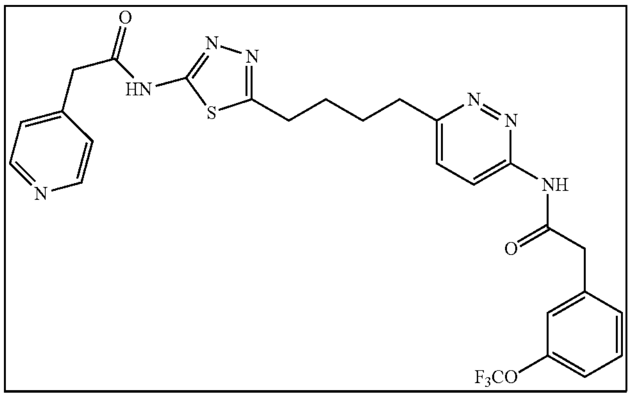 [SMILES: O=C(Cc1cccc(OC(F)(F)F)c1)Nc1ccc(CCCCc2nnc(NC(=O)Cc3ccncc3)s2)nn1] | 0.010 | | 0.045 |
| 673 | 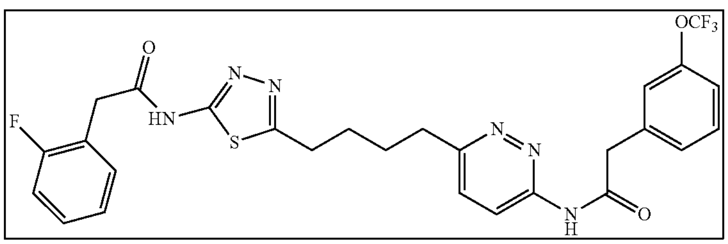 [SMILES: O=C(Cc1cccc(OC(F)(F)F)c1)Nc1ccc(CCCCc2nnc(NC(=O)Cc3ccccc3F)s2)nn1] | 0.006 | | 0.033 |
| 674 | 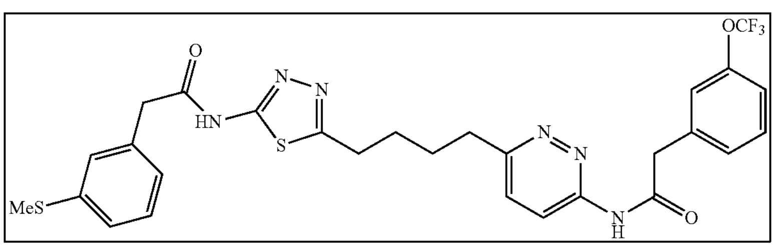 [SMILES: CSc1cccc(CC(=O)Nc2nnc(CCCCc3ccc(NC(=O)Cc4cccc(OC(F)(F)F)c4)nn3)s2)c1] | 0.008 | | 0.024 |
| 675 | 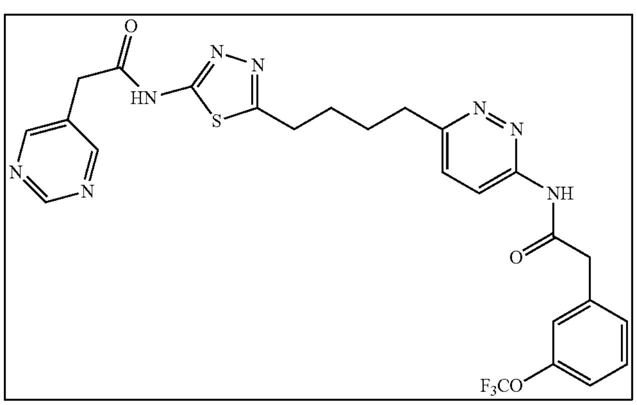 [SMILES: O=C(Cc1cccc(OC(F)(F)F)c1)Nc1ccc(CCCCc2nnc(NC(=O)Cc3cncnc3)s2)nn1] | | | 0.040 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 676 | 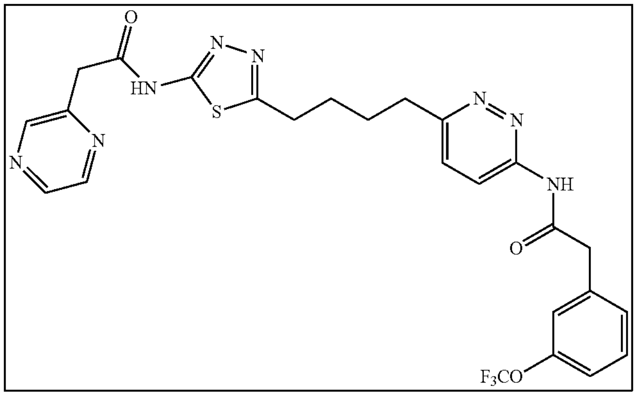 [SMILES: O=C(Cc1cccc(OC(F)(F)F)c1)Nc1ccc(CCCCc2nnc(NC(=O)Cc3cnccn3)s2)nn1] | | | 0.030 |
| 677 | 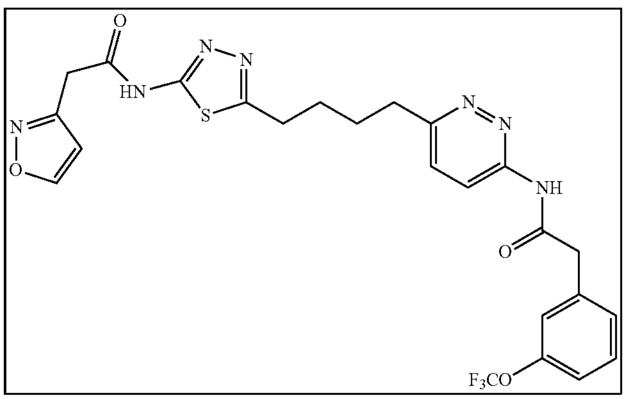 [SMILES: O=C(Cc1cccc(OC(F)(F)F)c1)Nc1ccc(CCCCc2nnc(NC(=O)Cc3ccon3)s2)nn1] | | | 0.056 |
| 678 | 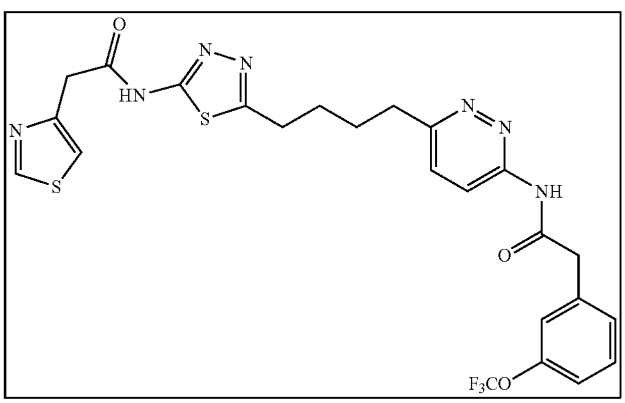 [SMILES: O=C(Cc1cccc(OC(F)(F)F)c1)Nc1ccc(CCCCc2nnc(NC(=O)Cc3cscn3)s2)nn1] | | | 0.026 |
| 679 | 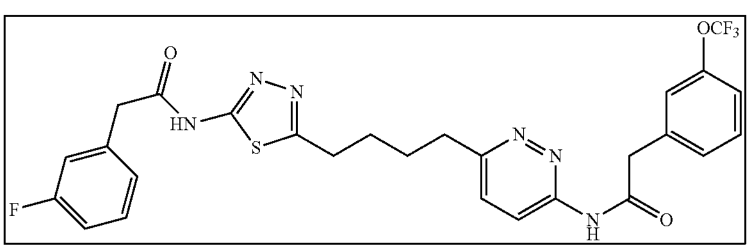 [SMILES: O=C(Cc1cccc(OC(F)(F)F)c1)Nc1ccc(CCCCc2nnc(NC(=O)Cc3cccc(F)c3)s2)nn1] | | | 0.036 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 680 | 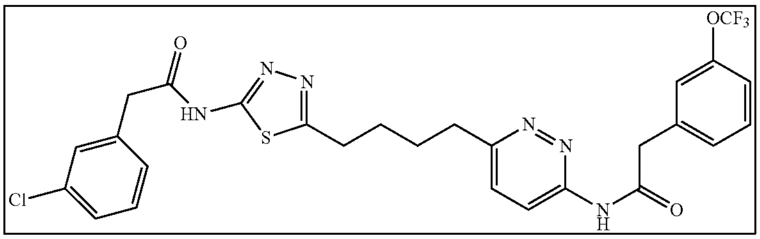 [SMILES: O=C(Cc1cccc(OC(F)(F)F)c1)Nc1ccc(CCCCc2nnc(NC(=O)Cc3cccc(Cl)c3)s2)nn1] | | | 0.033 |
| 681 | 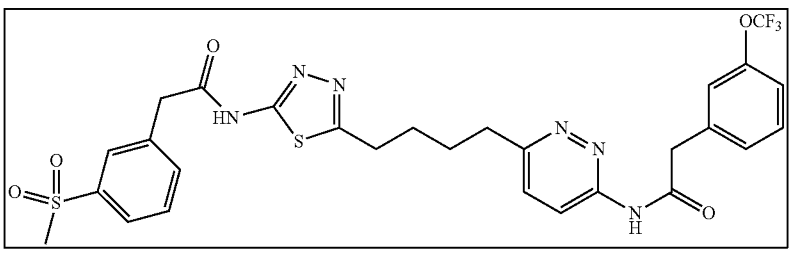 [SMILES: CS(=O)(=O)c1cccc(CC(=O)Nc2nnc(CCCCc3ccc(NC(=O)Cc4cccc(OC(F)(F)F)c4)nn3)s2)c1] | | | 0.019 |
| 682 | 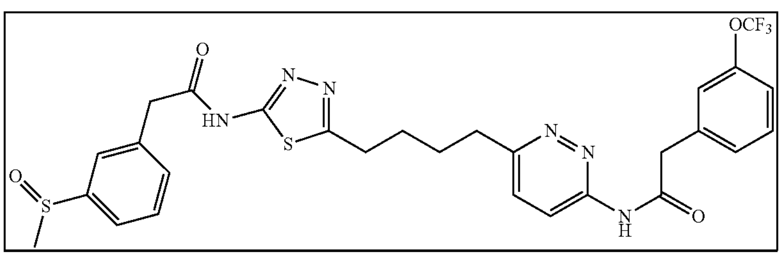 [SMILES: CS(=O)c1cccc(CC(=O)Nc2nnc(CCCCc3ccc(NC(=O)Cc4cccc(OC(F)(F)F)c4)nn3)s2)c1] | | | 0.017 |
| 683 | 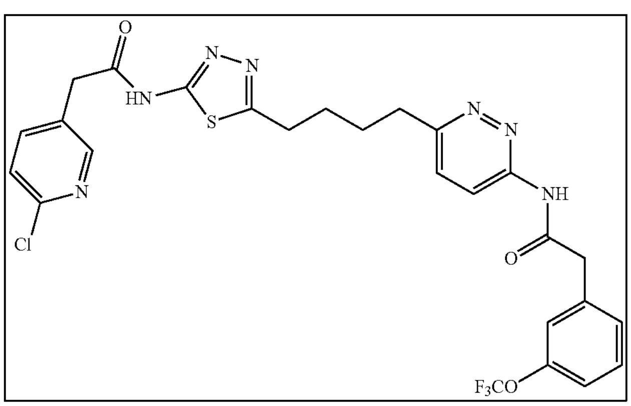 [SMILES: O=C(Cc1cccc(OC(F)(F)F)c1)Nc1ccc(CCCCc2nnc(NC(=O)Cc3ccc(Cl)nc3)s2)nn1] | | | 0.024 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
| --- | --- | --- | --- | --- |
| 684 | 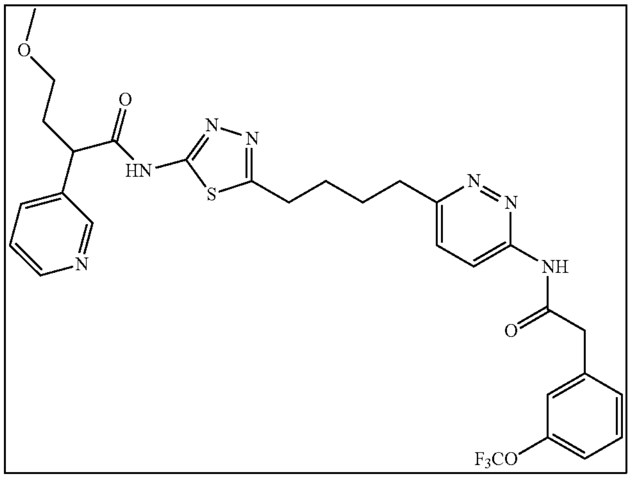 [SMILES: COCCC(C(=O)Nc1nnc(CCCCc2ccc(NC(=O)Cc3cccc(OC(F)(F)F)c3)nn2)s1)c1cccnc1] | | | 0.042 |
| 685 | 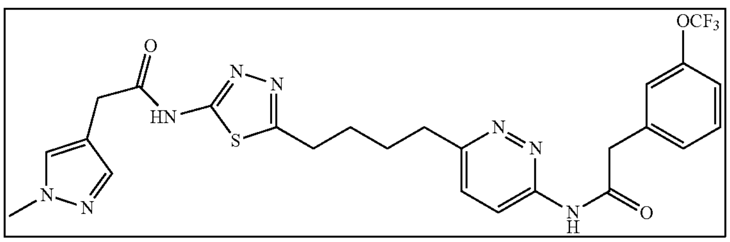 [SMILES: Cn1cc(CC(=O)Nc2nnc(CCCCc3ccc(NC(=O)Cc4cccc(OC(F)(F)F)c4)nn3)s2)cn1] | | | 0.022 |
| 686 | 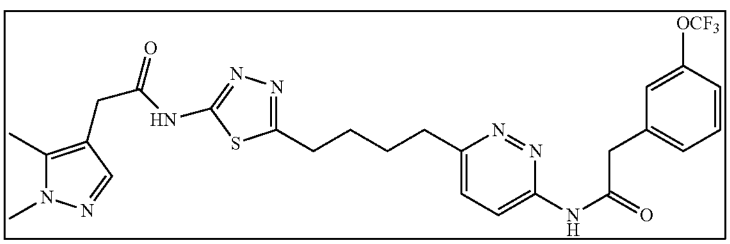 [SMILES: Cc1c(CC(=O)Nc2nnc(CCCCc3ccc(NC(=O)Cc4cccc(OC(F)(F)F)c4)nn3)s2)cnn1C] | | | 0.010 |
| 687 | 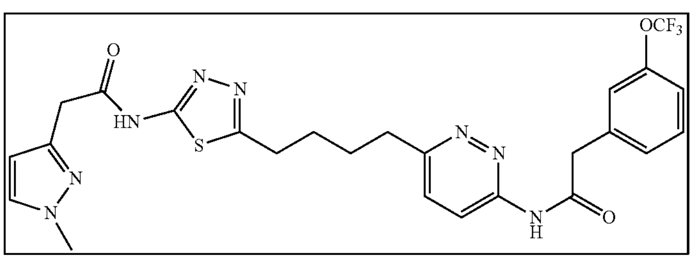 [SMILES: Cn1ccc(CC(=O)Nc2nnc(CCCCc3ccc(NC(=O)Cc4cccc(OC(F)(F)F)c4)nn3)s2)n1] | | | 0.011 |
| 688 | 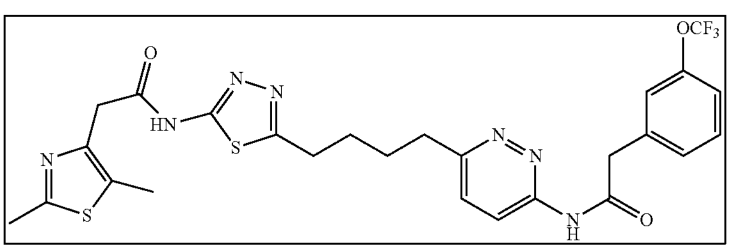 [SMILES: Cc1nc(CC(=O)Nc2nnc(CCCCc3ccc(NC(=O)Cc4cccc(OC(F)(F)F)c4)nn3)s2)c(C)s1] | | | 0.012 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 689 | 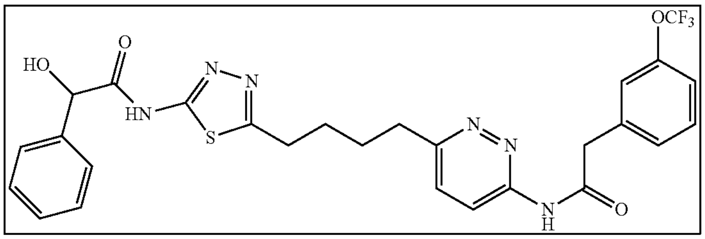 [SMILES: O=C(Cc1cccc(OC(F)(F)F)c1)Nc1ccc(CCCCc2nnc(NC(=O)C(O)c3ccccc3)s2)nn1] | | | 0.013 |
| 690 | 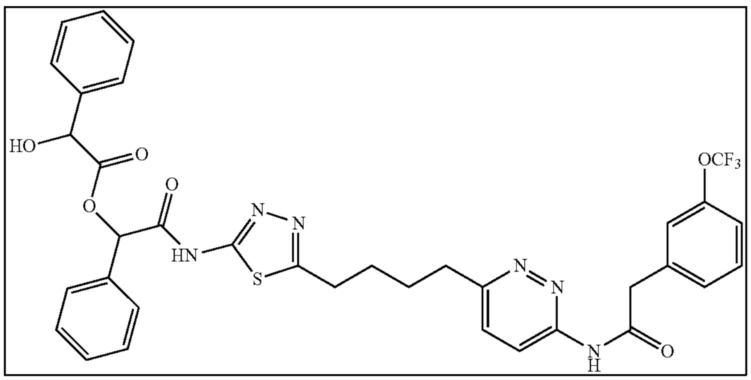 [SMILES: O=C(Cc1cccc(OC(F)(F)F)c1)Nc1ccc(CCCCc2nnc(NC(=O)C(OC(=O)C(O)c3ccccc3)c3ccccc3)s2)nn1] | | | 0.017 |
| 692 | 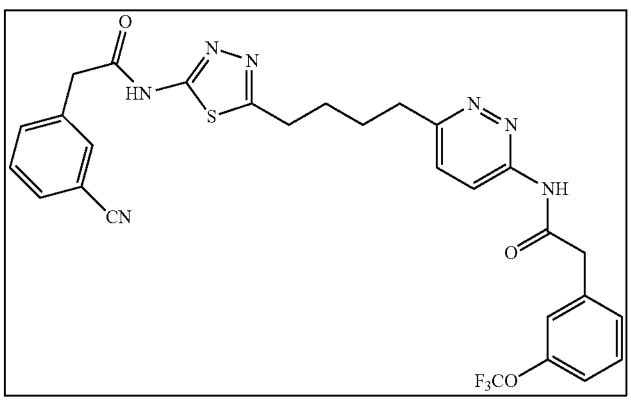 [SMILES: N#Cc1cccc(CC(=O)Nc2nnc(CCCCc3ccc(NC(=O)Cc4cccc(OC(F)(F)F)c4)nn3)s2)c1] | | | 0.020 |
| 693 | 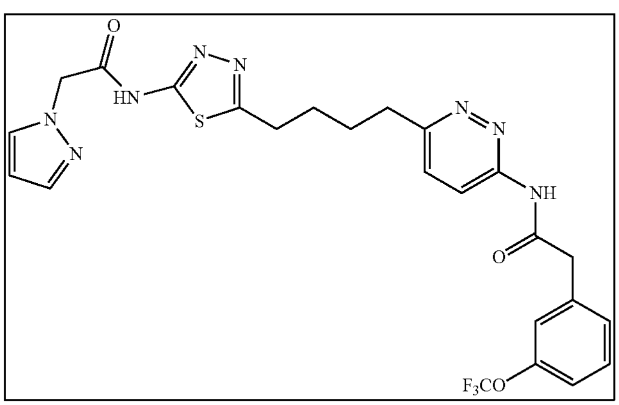 [SMILES: O=C(Cc1cccc(OC(F)(F)F)c1)Nc1ccc(CCCCc2nnc(NC(=O)Cn3cccn3)s2)nn1] | | | 0.070 |

TABLE 3-continued

| Cmpd ID | Structure | GAC Delta N2 IC50 60 min preinc (µM) | GAC Delta N2 IC50 no preinc (µM) | Cell prolif P493 72 h IC50 (µM) |
|---|---|---|---|---|
| 694 | 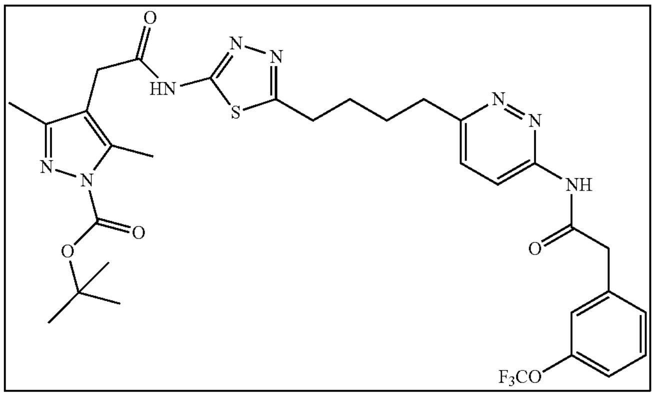 [SMILES: Cc1nn(C(=O)OC(C)(C)C)c(C)c1CC(=O)Nc1nnc(CCCCc2ccc(NC(=O)Cc3cccc(OC(F)(F)F)c3)nn2)s1] | | | 0.029 |
| 695 | 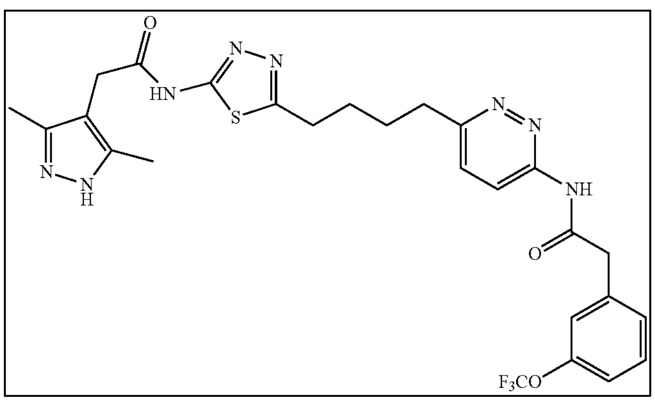 [SMILES: Cc1n[nH]c(C)c1CC(=O)Nc1nnc(CCCCc2ccc(NC(=O)Cc3cccc(OC(F)(F)F)c3)nn2)s1] | | | 0.030 |
| 696 | 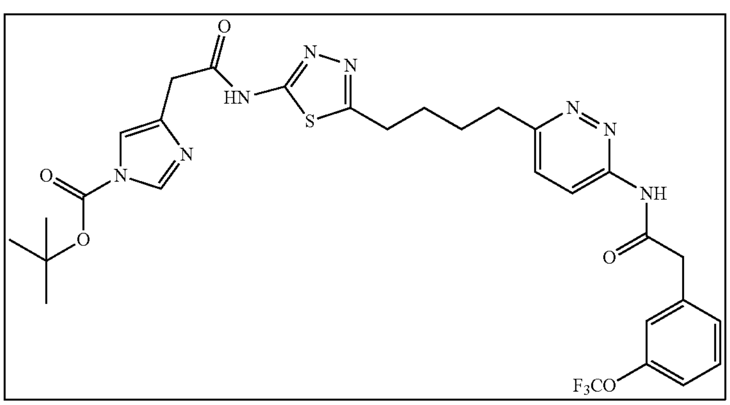 [SMILES: CC(C)(C)OC(=O)n1cnc(CC(=O)Nc2nnc(CCCCc3ccc(NC(=O)Cc4cccc(OC(F)(F)F)c4)nn3)s2)c1] | | | 0.034 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 697 | 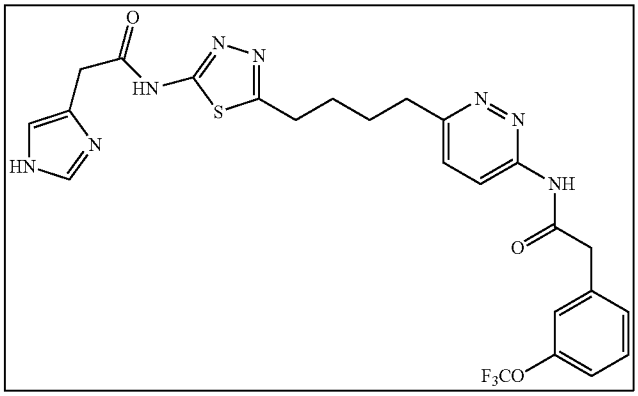 [SMILES: O=C(Cc1cccc(OC(F)(F)F)c1)Nc1ccc(CCCCc2nnc(NC(=O)Cc3c[nH]cn3)s2)nn1] | | | 0.050 |
| 698 | 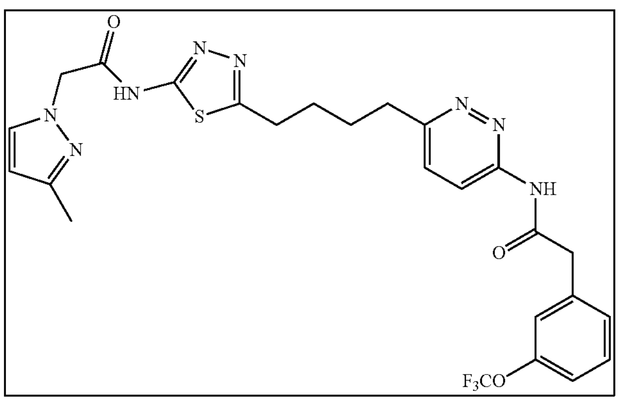 [SMILES: Cc1ccn(CC(=O)Nc2nnc(CCCCc3ccc(NC(=O)Cc4cccc(OC(F)(F)F)c4)nn3)s2)n1] | | | 0.098 |
| 699 | 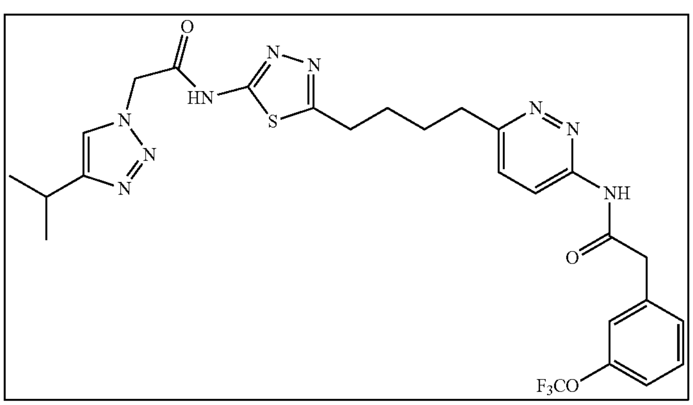 [SMILES: CC(C)c1cn(CC(=O)Nc2nnc(CCCCc3ccc(NC(=O)Cc4cccc(OC(F)(F)F)c4)nn3)s2)nn1] | | | 0.12 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 700 | 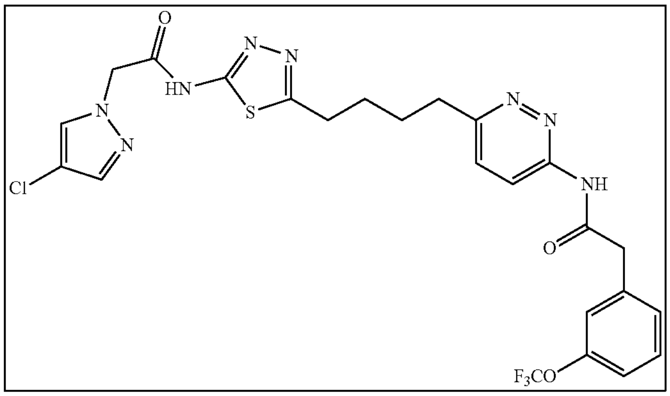 [SMILES: O=C(Cc1cccc(OC(F)(F)F)c1)Nc1ccc(CCCCc2nnc(NC(=O)Cn3cc(Cl)cn3)s2)nn1] | | | 0.17 |
| 701 | 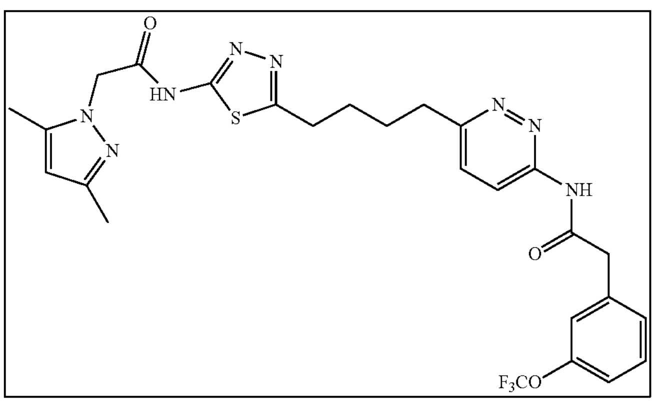 [SMILES: Cc1cc(C)n(CC(=O)Nc2nnc(CCCCc3ccc(NC(=O)Cc4cccc(OC(F)(F)F)c4)nn3)s2)n1] | | | 0.11 |
| 702 | 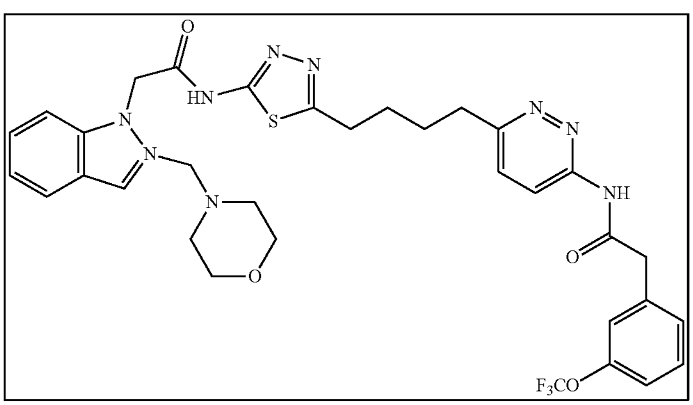 | | | 0.31 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 703 | 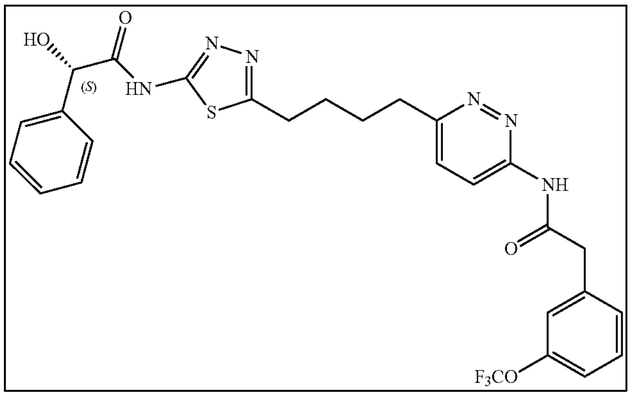 | | | 0.012 |
| 704 | 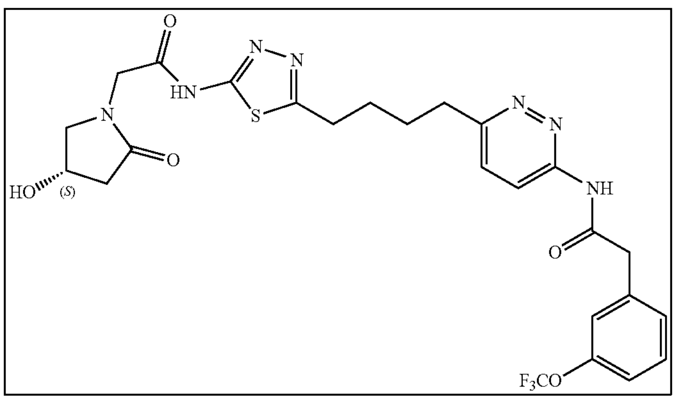 | | | 0.88 |
| 705 | 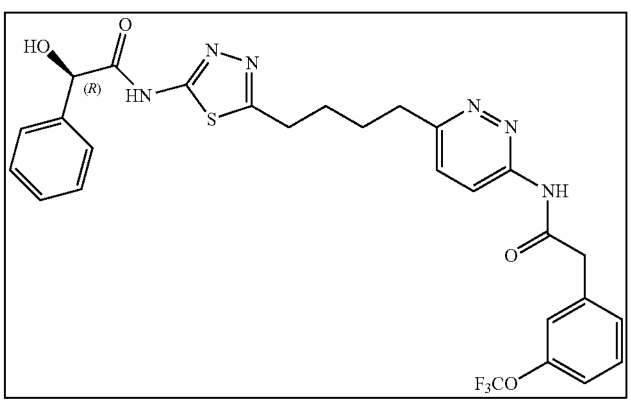 | | | 0.032 |
| 706 | 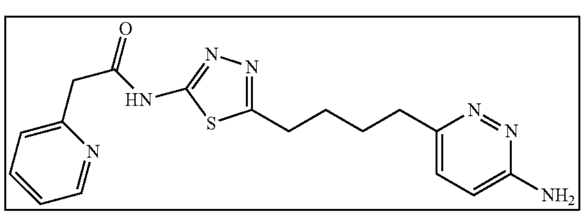 [SMILES: Nc1ccc(CCCCc2nnc(NC(=O)Cc3ccccn3)s2)nn1] | | | 14 |

TABLE 3-continued

| Cmpd ID | Structure | GAC Delta N2 IC50 60 min preinc (μM) | GAC Delta N2 IC50 no preinc (μM) | Cell prolif P493 72 h IC50 (μM) |
|---|---|---|---|---|
| 707 | 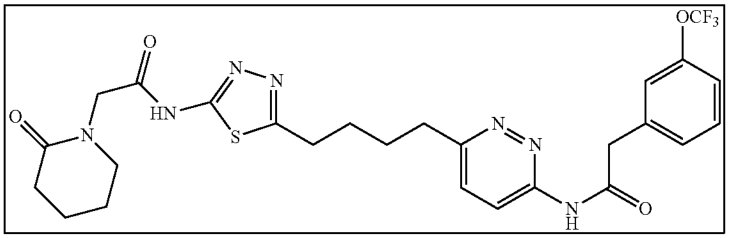 [SMILES: O=C(Cc1cccc(OC(F)(F)F)c1)Nc1ccc(CCCCc2nnc(NC(=O)CN3CCCCC3=O)s2)nn1] | | | 0.085 |
| 708 | 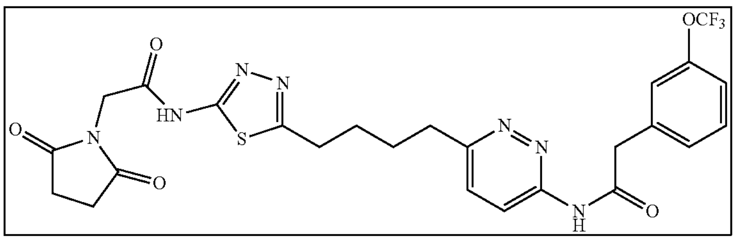 [SMILES: O=C(Cc1cccc(OC(F)(F)F)c1)Nc1ccc(CCCCc2nnc(NC(=O)CN3C(=O)CCC3=O)s2)nn1] | | | 2.8 |
| 709 | 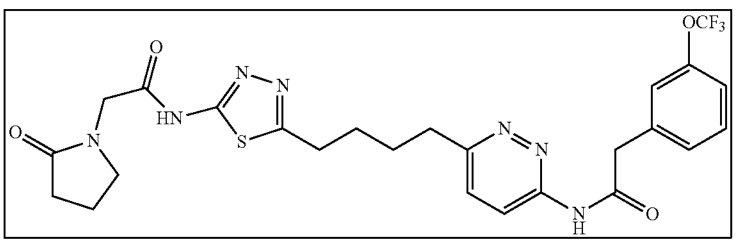 [SMILES: O=C(Cc1cccc(OC(F)(F)F)c1)Nc1ccc(CCCCc2nnc(NC(=O)CN3CCCC3=O)s2)nn1] | | | 0.14 |

Example 3: Xenograft Efficacy Studies

Certain compounds were assayed for in vivo efficacy in xenograft models as follows.

Female scid/bg mice, approximately 6 weeks of age, were implanted subcutaneously on the right flank with $5 \times 10^6$ HCT116 cells per mouse in a volume of 100 uL of sterile PBS. When tumors reached a volume of 50-100 mm$^3$, mice were randomized to groups of n=10 to receive either vehicle or test compound delivered twice daily by intraperitoneal injection. Tumors were measured three times per week using Vernier calipers and tumor volume calculated using the formula: Volume=(Length×Width$^2$/2), where length and width are the longest perpendicular sides of the tumor. Dosing continued twice daily until control tumors reached a size of 2000 mm$^3$. Statistical comparisons were made using a 2-way ANOVA with Bonferroni post-test.

FIG. 1 shows that intraperitoneal administration of compound 188 to mice results in reduced tumor size in this HCT116 colon carcinoma xenograft model.

Example 4: Caco-2 Permeability Assay

Caco-2 cells are commonly used in a confluent monolayer on a cell culture insert filter. When cultured in this format and under specific conditions, the cells become differentiated and polarized such that their phenotype, morphologically and functionally resembles the enterocytes lining the small intestine. The cell monolayer provides a physical and biochemical barrier to the passage of small molecules, and is widely used across the pharmaceutical industry as an in vitro model of the human small intestinal mucosa to predict the absorption of orally administered drugs (Hidalgo et al., Gastroenterology, 1989; Artursson, J. Pharm. Sci., 1990). The correlation between the in vitro apparent permeability (P ¬app) across Caco-2 monolayers and the in vivo absorption is well established (Artursson et al., Biochem. Biophys. Res. Comm., 1991).

The present assay was used to determine the bidirectional permeability of the compounds of the invention through Caco-2 cell monolayers. Caco-2 cells were grown in confluent monolayers where the media of both the apical (A) and basolateral (B) sides were at pH 7.4. Compounds were dosed at 1 μM in the presence of 200 μM Lucifer Yellow, on the apical side (A→B) or the basolateral side (B→A) for assessment, in duplicate. Samples from both A and B sides were taken after 120 minutes exposure, and compound concentration (reported as percent recovery) was determined using a generic LC-MS/MS method with a minimum four-point calibration curve.

The absorption potential of compounds were classified as either Low (P-app $<1 \times 10^{-6}$ cm/s) or High (P-app$>1 \times 10^{-6}$ cm/s). The efflux ratio was calculated as (Papp B→A)/(Papp A→B), with efflux ratios being significant when greater than or equal to 3 when the Papp (B→A) was greater than or equal to 1×10$^{-6}$ cm/s. Results for certain compounds of the invention are shown in Table 4.

TABLE 4

Caco-2 Permeability Results

| Cmpd | Direction | Recovery (%) | Papp (avg.) | Efflux Ratio | Permeability Classi-fication | Sig-nificant Efflux |
|---|---|---|---|---|---|---|
| 533 | A→B | 41 | 4.94 | 7.6 | High | Yes |
| | B→A | 52 | 37.5 | | | |
| 585 | A→B | 42 | 7.52 | 3.1 | High | Yes |
| | B→A | 53 | 23.4 | | | |
| 616 | A→B | 65 | 8.23 | 6.0 | High | Yes |
| | B→A | 76 | 49.5 | | | |
| 295 | A→B | 89 | 8.17 | 7.3 | High | Yes |
| | B→A | 96 | 59.8 | | | |
| 318 | A→B | 73 | 2.45 | 18 | High | Yes |
| | B→A | 82 | 44.5 | | | |
| 339 | A→B | 73 | 2.39 | 17 | High | Yes |
| | B→A | 80 | 41.6 | | | |
| 354 | A→B | 117 | 1.38 | 33 | High | Yes |
| | B→A | 101 | 45.0 | | | |
| 436 | A→B | 44 | 3.75 | 6.6 | High | Yes |
| | B→A | 57 | 24.7 | | | |
| 660 | A→B | 56 | 0.61 | 3.9 | Low | Yes |
| | B→A | 68 | 2.37 | | | |
| 670 | A→B | 70 | 9.64 | 6.2 | High | Yes |
| | B→A | 72 | 59.6 | | | |
| 679 | A→B | 34 | 7.59 | 2.6 | High | No |
| | B→A | 42 | 19.6 | | | |
| 447 | A→B | 71 | 7.76 | 3.5 | High | Yes |
| | B→A | 56 | 27.2 | | | |
| 703 | A→B | 51 | 6.26 | 6.6 | High | Yes |
| | B→A | 66 | 41.0 | | | |
| 705 | A→B | 60 | 8.52 | 6.0 | High | Yes |
| | B→A | 67 | 51.0 | | | |

Example 5: Solubility

Ca. 1 mg portions of test article were combined with 120 μL solvent in wells of a 96×2 mL polypropylene plate. The plate was vigorously vortex mixed at room temperature (ca. 20 C) for 18 hr and each well checked visually for undissolved solid; wells containing no visible solid were charged with additional solid test article and vortex mixed another 6 hr at room temperature after which all wells showed visible solid. The contents of all wells were then filtered through a 0.45 μm GHP filter plate to yield clear filtrates. 5 μL of each filtrate was diluted into 100 μL DMF and vortex mixed to yield HPLC samples. Duplicate quantitation standards for each test article were prepared by diluting weighed portions of solid test article in measured volumes of DMF. 2 μL of each HPLC sample and quantitation standard were analyzed by HPLC using the method outlined in Table 5. Dissolved test article concentrations were calculated by peak area ratio against the appropriate quantitation standards. Solubility results are presented in Table 6.

TABLE 5

Outline of HPLC Method

| | |
|---|---|
| Instrument | Shimadzu Prominence UFLC with Diode Array UV/Vis Detector |
| Column | VWR Sonoma C8(2), 3.5 μm, 2.1 × 50 mm |
| Column Temp | 40° C. |
| Mobile Phase A | 0.1% (v/v) formic acid in water |
| Mobile Phase B | 0.1% (v/v) formic acid in acetonitrile |
| Flow Rate | 0.4 mL/min |

| Gradient | Time (min) | % Mobile Phase B |
|---|---|---|
| | 0 | 20 |
| | 8 | 100 |
| | 8.5 | 100 |
| | 8.6 | 20 |
| | 9.6 | END |

TABLE 6

Measured Solubilities

| | Solubility (mg/mL) | | | |
|---|---|---|---|---|
| Solvent | 1 | 295 | 402 | 585 |
| water | <0.002 | <0.002 | <0.004 | <0.002 |
| 0.9% NaCl | <0.002 | <0.002 | <0.004 | <0.002 |
| 0.1M HCl | <0.002 | 0.003 | <0.004 | <0.002 |
| 50 mM Cit pH 2.3 | <0.002 | <0.002 | <0.004 | <0.002 |
| 50 mM Cit pH 3.3 | <0.002 | <0.002 | <0.004 | <0.002 |
| 50 mM Cit pH 4.4 | <0.002 | <0.002 | <0.004 | <0.002 |
| 50 mM Cit pH 5.4 | <0.002 | <0.002 | <0.004 | <0.002 |
| PBS | <0.002 | <0.002 | <0.004 | <0.002 |
| 0.1M NaOH | 14.420 | 0.268 | <0.004 | 0.192 |
| 10% PS80/ 50 mM cit | 0.050 | 0.027 | 0.153 | 0.261 |
| 10% CrEL/ 50 mM cit | 0.076 | 0.055 | 0.157 | 0.228 |
| 20% SBECD/ 50 mM cit | 0.046 | 0.090 | 0.019 | 0.125 |
| 20% HPBCD/ 50 mM cit | 0.042 | 0.167 | 0.056 | 0.327 |
| Labrasol | 0.258 | 0.918 | 31.032 | 5.004 |
| Capryol PGMC | 0.042 | 1.540 | 11.210 | 1.780 |
| Capryol 90 | 0.081 | 0.215 | 13.676 | 1.744 |
| canola oil | <0.002 | <0.002 | 0.529 | 0.072 |
| PEG400 | 0.451 | 1.644 | 30.179 | 3.944 |
| PG | 0.048 | 0.234 | 1.365 | 1.422 |
| EtOH | 0.040 | 0.083 | 2.958 | 1.991 |

| | Solubility (mg/mL) | | |
|---|---|---|---|
| Solvent | 670 | 447 | 703 |
| water | 0.007 | <0.004 | <0.004 |
| 0.9% NaCl | <0.002 | 0.005 | <0.004 |
| 0.1M HCl | 0.005 | <0.004 | <0.004 |
| 50 mM Cit pH 2.3 | 0.066 | <0.004 | <0.004 |
| 50 mM Cit pH 3.3 | 0.003 | <0.004 | <0.004 |
| 50 mM Cit pH 4.4 | <0.002 | <0.004 | <0.004 |
| 50 mM Cit pH 5.4 | <0.002 | <0.004 | <0.004 |
| PBS | <0.002 | <0.004 | <0.004 |
| 0.1M NaOH | 0.227 | 0.192 | 0.656 |
| 10% PS80/ 50 mM cit | 1.204 | 0.851 | 0.378 |
| 10% CrEL/ 50 mM cit | 0.458 | 0.732 | 0.309 |

TABLE 6-continued

| | Measured Solubilities | | |
|---|---|---|---|
| 20% SBECD/ 50 mM cit | 5.256 | 2.718 | 0.476 |
| 20% HPBCD/ 50 mM cit | 9.685 | 2.177 | 0.651 |
| Labrasol | 5.042 | 77.164 | 20.727 |
| Capryol PGMC | 1.519 | 7.916 | 3.683 |
| Capryol 90 | 1.974 | 11.114 | 7.409 |
| canola oil | 0.012 | 0.071 | 0.014 |
| PEG400 | 9.901 | 57.334 | 22.419 |
| PG | 2.569 | 8.265 | 4.698 |
| EtOH | 0.964 | 3.921 | 2.645 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A compound of formula I,

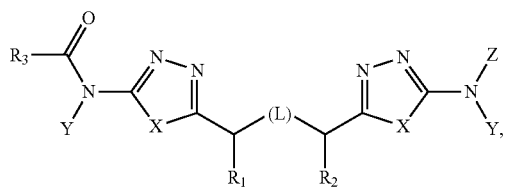

(I)

or a pharmaceutically acceptable salt thereof, wherein:
L represents $CH_2CH_2$;
X, independently for each occurrence, represents S or $CH=CH$;
each Y represents H;
Z represents $R_3(CO)$;
$R_1$ and $R_2$ each represent H; and
$R_3$, independently for each occurrence, represents substituted or unsubstituted arylalkyl, cycloalkyl, heterocycloalkyl, or heteroarylalkyl.

2. The compound of claim 1, wherein one occurrence of X is S and the other is $CH=CH$.

3. The compound of claim 1, wherein each occurrence of $R_3$ is not identical.

4. The compound of claim 2, wherein each occurrence of $R_3$ is not identical.

5. The compound of claim 1, wherein each $R_3$ is independently substituted or unsubstituted arylalkyl or heteroarylalkyl.

6. The compound of claim 2, wherein each $R_3$ is independently substituted or unsubstituted arylalkyl or heteroarylalkyl.

7. The compound of claim 3, wherein each $R_3$ is independently substituted or unsubstituted arylalkyl or heteroarylalkyl.

8. The compound of claim 4, wherein each $R_3$ is independently substituted or unsubstituted arylalkyl or heteroarylalkyl.

9. A pharmaceutical composition comprising one or more pharmaceutically acceptable excipients and a compound of claim 1.

10. A method of therapeutically treating cancer or an immunological or neurological disease, comprising administering to a patient a compound of claim 1.

11. The method of claim 10, for therapeutically treating cancer, wherein the cancer is renal cell carcinoma.

12. The method of claim 10, for therapeutically treating cancer, wherein the cancer is triple negative breast cancer.

13. The method of claim 10, for therapeutically treating cancer, wherein the cancer is colorectal cancer.

14. The method of claim 10, for therapeutically treating cancer, wherein the cancer is acute myeloid leukemia.

15. The method of claim 10, for therapeutically treating cancer, wherein the cancer is breast cancer.

16. The method of claim 10, for therapeutically treating cancer, wherein the cancer is lung cancer.

17. The method of claim 10, for therapeutically treating cancer, wherein the cancer is melanoma.

18. The method of claim 10, for therapeutically treating cancer, wherein the cancer is ovarian cancer.

19. The method of claim 10, for therapeutically treating cancer, wherein the cancer is selected from breast cancer, renal cell carcinoma, lung cancer, melanoma, colorectal cancer, acute myeloid leukemia, Non-Hodgkin lymphoma, multiple myeloma, acute lymphoblastic leukemia, ovarian cancer, head and neck cancer, bladder cancer, pancreatic cancer, sarcoma, and prostate cancer.

20. The method of claim 19, wherein the cancer is selected from breast cancer, renal cell carcinoma, lung cancer, melanoma, colorectal cancer, ovarian cancer, head and neck cancer, bladder cancer, and prostate cancer.

21. A method of therapeutically treating cancer, comprising administering to a patient a compound of claim 1.

* * * * *